US010100058B2

(12) United States Patent
Elzein et al.

(10) Patent No.: US 10,100,058 B2
(45) Date of Patent: Oct. 16, 2018

(54) FUSED HETEROCYCLIC COMPOUNDS AS CAM KINASE INHIBITORS

(71) Applicant: Gilead Sciences, Inc., Foster City, CA (US)

(72) Inventors: Elfatih Elzein, Mountain House, CA (US); Rao V. Kalla, Cupertino, CA (US); Dmitry Koltun, Foster City, CA (US); Xiaofen Li, Mountain View, CA (US); Eric Q. Parkhill, San Francisco, CA (US); Thao Perry, San Jose, CA (US); Scott Preston Simonovich, Oakland, CA (US); Jeff Zablocki, Los Altos, CA (US); Christopher Allen Ziebenhaus, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/825,993

(22) Filed: Nov. 29, 2017

(65) Prior Publication Data

US 2018/0148457 A1 May 31, 2018

Related U.S. Application Data

(60) Provisional application No. 62/428,397, filed on Nov. 30, 2016.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .......................... C07D 487/04; C07D 519/00
USPC ................................................. 514/210.18
See application file for complete search history.

(56) References Cited

U.S. PATENT DOCUMENTS

| | | | |
|---|---|---|---|
| 7,550,470 B2 | 6/2009 | Fraley | |
| 2006/0025426 A1 | 2/2006 | Fraley | |
| 2006/0074082 A1 | 4/2006 | Castelhano et al. | |
| 2007/0082900 A1* | 4/2007 | Guzi | A61K 31/519 514/234.5 |
| 2015/0284383 A1 | 10/2015 | Lynch et al. | |

FOREIGN PATENT DOCUMENTS

| | | |
|---|---|---|
| WO | WO-2010/048314 A1 | 4/2010 |
| WO | WO-2011/087999 A1 | 7/2011 |
| WO | WO-2014/138212 A8 | 11/2015 |
| WO | WO-2016/037106 A1 | 3/2016 |

OTHER PUBLICATIONS

Di Carlo, et al. (2014) "CaMKII-dependent Phosphorylation of Cardiac Ryanodine Receptors Regulates Cell Death in Cardian Ischemia/Reperfusion Injury", Journal of Molecular and Cellular Cardiology, 74 pp. 274-283.
Ling et al., (2013) "Ca2+/Cadmodulin-Dependent Protein Kinase II δ Mediates Myocardial Ischemia/Reperfusion Injury Through Nuclear Factor-κB", Circres Aha Journals , pp. 935-944.
America Chemical Society Chart (2016) OSIA Biamide pp. 1-4.
Vila-Petroff, et al. (2007) "CaMKII Inhibition Protects Against Necrosis and Apoptosis in Irreversible Ischemia-Reperfusion Injury" Caridovascular Research, 73 pp. 689-698.
Yang, et al. (2006) "Calmodulin Kinase II Inhibition Protects Against Myocardial cell Apoptosis in Vivo" Am J Physiol Heart Circ Physiol 291: H3065-H3075.
Zhang, et al. (2005) "Calmodulin Kinase II Inhibition Protects Against Structural Hear Disease" Nature Medicine 11 (4) pp. 409-417.
Zhang, et al. (2016) "CaMKII is a RIP3 Substrate Mediating Ischmia-and Oxidative Stress-Induced Myocardial Necroptosis" Nature Medicine 22 (2) pp. 175-182.

* cited by examiner

*Primary Examiner* — Kristin A Vajda

(57) ABSTRACT

The present disclosure relates to compounds that are CaM Kinase inhibitors and to their use in the treatment of various disease states, including atrial fibrillation and myocardial infarction. In particular embodiments, the general structure of the compounds is given by Formula I:

(I)

wherein $R^1$, $R^2$, $R^3$, $R^4$, $R^5$, $R^6$, $R^9$ and $R^{10}$ are as described herein, to methods for the preparation and use of the compounds and to pharmaceutical compositions containing the same.

33 Claims, No Drawings

FUSED HETEROCYCLIC COMPOUNDS AS CAM KINASE INHIBITORS

CROSS-REFERENCE TO RELATED APPLICATIONS

This application claims the benefit under 35 U.S.C. § 119(e) to U.S. Provisional Application No. 62/428,397, filed on Nov. 30, 2016, the entirety of which is incorporated herein by reference.

FIELD

The present disclosure relates to novel compounds and their uses in the treatment of cardiovascular diseases and hypertension. The disclosure also relates to methods for preparing the compounds and to pharmaceutical compositions comprising such compounds.

BACKGROUND

Atrial fibrillation (AF) is the most prevalent arrhythmia, the incidence of which increases with age. It is estimated that 8% of all people over the age of 80 experience this type of abnormal heart rhythm and AF accounts for one-third of hospital admissions for cardiac rhythm disturbances. Over 2.2 million people are believed to have AF in the United States alone (Fuster, et al. *Circulation* 2006 114: e257-354). Although atrial fibrillation is often asymptomatic it may cause palpitations or chest pain. Prolonged atrial fibrillation often results in the development of congestive heart failure and/or stroke. Heart failure develops as the heart attempts to compensate for the reduced cardiac efficiency while stroke may occur when thrombi form in the atria, pass into the blood stream and lodge in the brain. Pulmonary emboli may also develop in this manner.

Calmodulin-dependent protein kinase II (CaMKII) enzymes transmit calcium ion ($Ca^{2+}$) signals released inside the cell by regulating signal transduction pathways through phosphorylation. There are four isoforms of CaMKII: α, β, γ and δ, with CaMKIIδ as the predominant isoform expressed in the heart. When calcium ions bind to CaM, the resulting activated Ca2+/CaM complex phosphorylates other proteins within the cell. Specifically, activated CaMKIIδ phosphorylates a number of key $Ca^{2+}$ handling proteins in cardiac myocytes, including ryanodine receptor 2 (RyR2), phospholamban (PLB), the sarcoplasmic/endoplasmic reticulum $Ca^{2+}$-ATPase (SERCA) and the L-type $Ca^{2+}$ channel (LTCC).

An increase in $Ca^{2+}$/CaMKII activity has been implicated as a contributory cause of cardiac arrhythmias, diastolic heart failure (Ai, et al. *Circ. Res.* 2005, 97:1314-22) and in the induction and maintenance of atrial fibrillation (Dobrev, et al., Trends Cardiovasc Med., 2010, 20(1), 30-4). Thus, there is a need to discover CAMKII inhibitors for the treatment of cardiac diseases including atrial fibrillation and heart failure.

SUMMARY

Accordingly, the present disclosure provides novel compounds that function as CaM kinase inhibitors. In one embodiment, the disclosure provides compounds of Formula I:

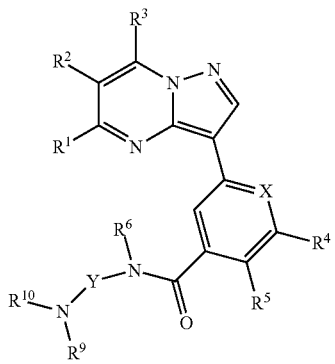

wherein
$R^1$ is aryl, heteroaryl or heterocyclic; wherein the aryl, heteroaryl or heterocyclic group is optionally substituted with one, two or three groups independently selected from the group consisting of halo, hydroxy, $C_1$-$C_6$ alkyl, $C_1$-$C_6$haloalkyl, $C_1$-$C_6$ alkoxy, —$OC_1$-$C_6$ haloalkyl, —$SC_1$-$C_6$ alkyl, —$NHSO_2R^a$, and $C_0$-$C_6$ alkylene-$NR^aR^b$;
$R^2$ and $R^3$ are each independently selected from the group consisting of H, halo and $C_1$-$C_6$ alkyl;
X is CH or N;
$R^4$ is is H, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkyl$C_3$-$C_6$ cycloalkyl, —$NR^aR^b$, $C_1$-$C_6$ alkyl$NR^aR^b$, $C_1$-$C_6$ alkyl-O—$C_1$-$C_6$ alkyl$NR^aR^b$, —$OC_2$-$C_6$ alkyl$NR^aR^b$, —$C(O)NR^aR^b$, —$NR^aC(O)NR^aR^b$, —$NR^aC(O)R^a$, —$NR^aC(O)OR^a$, aryl, heteroaryl, mono, bicyclic, bridged or spirocyclic carbocyclic or heterocyclic group, —O—$C_0$-$C_3$ alkylheterocyclic, or $C_1$-$C_6$ alkylheterocyclic, wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$OC_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkyl$NR^aCHR^aC(O)NHR^a$, —$C(O)R^a$, —$COOR^a$, —$NHC(O)NHR^a$, —$NHC(O)R^a$, —$NHC(O)OR^a$, $C(O)NR^aR^b$, —$NR^aR^b$, —$NHC_1$-$C_3$alkyl$NR^aR^b$, $SO_2R^a$, —$NHSO_2R^a$, $SO_2NR^aR^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group combine to form a mono, bicyclic, spirocyclic, or bridged carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, $C_1$-$C_6$ alkyl, $C_3$-$C_8$ cycloalkyl, $C_1$-$C_6$ haloalkyl, $C_1$-$C_6$ alkylOH, —$OC_1$-$C_6$ alkyl, —$OC_1$-$C_6$ haloalkyl, $C_1$-$C_6$ alkyl $C_3$-$C_6$ cycloalkyl, $C_1$-$C_6$ alkyl-O—$C_1$-$C_6$ alkyl, $C_0$-$C_3$ alkyl$NR^aCHR^aC(O)NHR^a$, $C(O)NR^aR^b$, —$SO_2R^a$, and $SO_2NR^aR^b$;
$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$C(O)C_1$-$C_6$ alkyl, —$C(O)OC_1$-$C_6$ alkyl, $C_0$-$C_3$ alkyl$NR^aR^a$, $C_1$-$C_3$alkyl$C(O)NH_2$, $C_1$-$C_3$alkyl$C(O)NHC_1$-$C_3$alkyl, $C_1$-$C_6$ alkyl$C_3$-$C_6$ cycloalkyl, $SO_2C_1$-$C_3$alkyl, $SO_2C_3$-$C_6$cycloalkyl, —$C_1$-$C_3$ alkylSO$_2$NR$^c$R$^d$, aryl, heteroaryl, heterocyclic, $C_1$-$C_6$ alkylheterocyclic, wherein the cycloalkyl, aryl, heteroaryl or heterocyclic group is optionally substituted with one to four groups independently selected from —OH, oxo, halo, cyano, NH$_2$, NHC$_1$-C$_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-C$_6$ cycloalkyl, $C_1$-$C_6$ alkyl-O—$C_1$-$C_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-C$_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-C$_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

R$^c$ and R$^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkylC$_3$-$C_6$ cycloalkyl, SO$_2$C$_1$-$C_6$ alkyl, and $C_1$-$C_6$ alkyl-O—$C_1$-$C_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-C$_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl;

R$^e$ and R$^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —OC$_1$-C$_6$ haloalkyl, and $C_1$-$C_6$ alkylOH;

R$^5$ is H, halo, cyano, NH$_2$, NHC$_1$-$C_6$ alkyl, N(C$_1$-$C_6$ alkyl)$_2$, $C_1$-$C_6$ alkyl, $C_3$-$C_8$ cycloalkyl, $C_1$-$C_6$ alkylC$_3$-C$_8$ cycloalkyl, $C_1$-$C_6$ haloalkyl, —OC$_1$-$C_6$ haloalkyl, $C_1$-$C_6$ alkyl-OH, or $C_1$-$C_6$ alkoxy;

R$^6$ is H, $C_1$-$C_6$ alkyl, $C_3$-$C_8$ cycloalkyl, $C_2$-$C_6$ haloalkyl, $C_2$-$C_6$ alkyl-OH, or $C_1$-$C_6$ alkoxy; or R$^6$ combines with Y, R$^9$, or R$^{10}$ to form an optionally substituted 4-8 membered nitrogen containing heterocyclic group;

Y is —(CR$^7$R$^8$)$_n$, wherein n is 2 or 3;

each R$^7$ or R$^8$ is independently selected from H, $C_1$-$C_6$ alkyl, $C_1$-$C_3$ alkylOH, $C_1$-$C_3$ alkylNH$_2$ and $C_1$-$C_3$alkyl-O-heterocyclic; or one R$^7$ or R$^8$ group combines with the R$^6$ group to form an optionally substituted nitrogen containing heterocyclic group; or one R$^7$ group combines with another R$^7$ or an R$^8$ group to form an optionally substituted monocyclic or bicyclic, bridged or spirocyclic ring system having from 4 to 10 carbon atoms in the ring; wherein the optional substituents include 1 or 2 groups independently selected from halo, —OH, NH$_2$, cyano, $C_1$-$C_6$ alkyl, $C_1$-$C_6$ haloalkyl, $C_1$-$C_6$ alkylOH, and $C_3$-$C_8$ cycloalkyl;

each R$^9$ and R$^{10}$ is independently H, $C_1$-$C_6$ alkyl, $C_2$-$C_6$ haloalkyl, $C_2$-$C_6$ alkylOH, $C_3$-$C_8$ cycloalkyl, $C_1$-$C_6$ alkylC$_3$-$C_8$ cycloalkyl, —C(O)OR$^{13}$, —C(O)NR$^{13}$R$^{14}$ or heterocyclic, wherein the alkyl, cycloalkyl or heterocyclic group is optionally substituted with one or two groups independently selected from the group consisting of halo, $C_1$-$C_6$ alkyl, $C_1$-$C_6$ haloalkyl, $C_1$-$C_6$ alkylOH, $C_3$-$C_8$ cycloalkyl, —OR$^{12}$, —NR$^{13}$R$^{14}$, —C(O)NR$^{13}$R$^{14}$, —NR$^{13}$COR$^{14}$, —SO$_2$NR$^{13}$R$^{14}$, —NR$^{13}$SO$_2$R$^{14}$, —NR$^2$SO$_2$NR$^{13}$R$^{14}$, —NR$^{12}$C(O)NR$^{13}$R$^{14}$, —NR$^{13}$CO$_2$R$^{14}$, and —OC(O)NR$^{13}$R$^{14}$; or R$^9$ and R$^{10}$ together with the nitrogen atom to which they are attached form a mono, bicyclic, bridged or spirocyclic heterocyclic ring optionally substituted with one or two groups independently selected from the group consisting of halo, —OH, —NH$_2$, —NH—C$_1$-$C_6$ alkyl, —$C_1$-$C_6$ alkyl, —$C_1$-$C_6$ alkylOH, $C_3$-$C_8$ cycloalkyl, aryl, and heterocyclic; wherein the cycloalkyl, aryl or heterocyclic group is optionally substituted with halo, —OH, —NH$_2$, —NH—C$_1$-$C_6$ alkyl, —$C_1$-$C_6$ alkyl, and —$C_1$-$C_6$ alkylOH; or R$^9$ and/or R$^{10}$ combines with Y to form a mono, bicyclic, bridged or spirocyclic nitrogen containing heterocycle optionally substituted with one or two groups independently selected from the group consisting of —$C_1$-$C_6$ alkyl, —$C_1$-$C_6$ alkylOH, $C_3$-$C_8$ cycloalkyl, —OH, —NH$_2$, and —NH—$C_1$-$C_6$ alkyl;

each R$^{12}$, R$^{13}$ and R$^{14}$ is independently H, $C_1$-$C_6$ alkyl, $C_3$-$C_8$ cycloalkyl, or heterocyclic, wherein the $C_1$-$C_6$ alkyl, $C_3$-$C_8$ cycloalkyl group, or heterocyclic, group is optionally substituted with one or two groups independently selected from the group consisting of —OH, —NH$_2$, —N(CH$_3$)$_2$, and $C_1$-$C_6$ haloalkyl; or R$^{13}$ and R$^{14}$ together with the atom to which they are attached form a heterocyclic ring;

or a pharmaceutically acceptable salt, stereoisomer or mixture of stereoisomer thereof.

Some embodiments provide a method of using the compounds of Formula I, II, III, IV, V, VI or VII, or additional Formula(s) described throughout, in the treatment of a disease or condition in a mammal that is amenable to treatment by a CaM Kinase inhibitor. Such diseases or conditions include arrhythmias, including atrial fibrillation, myocardial infarction and heart failure. It is contemplated that the compounds of the disclosure and their pharmaceutically acceptable salt, ester, stereoisomer, mixture of stereoisomers, isotopic analogs, and/or tautomer forms are potentially of use as medicaments for the treatment of the aforementioned diseases.

In certain embodiments, the disclosure provides pharmaceutical compositions comprising a therapeutically effective amount of a compound of the disclosure (e.g. a compound of Formula I or additional formulas described throughout), and at least one pharmaceutically acceptable excipient.

The aspects or embodiments of this disclosure are described throughout. In addition, specific embodiments of the invention are as disclosed herein.

DETAILED DESCRIPTION

Definitions and General Parameters

As used in the present specification, the following words and phrases are generally intended to have the meanings as set forth below, except to the extent that the context in which they are used indicates otherwise. Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. A prefix such as "$C_{u-v}$" or ($C_u$-$C_v$) indicates that the following group has from u to v carbon atoms. For example, "$C_{1-6}$ alkyl" indicates that the alkyl group has from 1 to 6 carbon atoms.

"Alkyl" refers to any group derived from a linear or branched saturated hydrocarbon. Alkyl groups include, but are not limited to, methyl, ethyl, propyls such as propan-1- yl, propan-2-yl (iso-propyl), butyls such as butan-1-yl, butan-2-yl (sec-butyl), 2-methyl-propan-1-yl (isobutyl), 2-methyl-propan-2-yl (t-butyl), pentyls, hexyls, octyls, decyls, and the like. Unless otherwise specified, an alkyl group has from 1 to about 10 carbon atoms, for example from 1 to 10 carbon atoms, for example from 1 to 6 carbon atoms, for example from 1 to 4 carbon atoms. An optionally substituted alkyl may have the optional substituents as defined or substituted for the particular alkyl group.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like. The term "substituted alkylene" refers to an alkylene group as defined above having 1 to 5 substituents (in some embodiments, 1, 2 or 3 substituents) as defined for substituted alkyl.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to about 10 carbon atoms, for example from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡CH), propargyl (—CH$_2$C≡CH), (E)-pent-3-en-1-ynyl, and the like. Unless otherwise specified, an alkynyl group has from 2 to about 10 carbon atoms, for example from 2 to 10 carbon atoms, for example from 2 to 6 carbon atoms, for example from 2 to 4 carbon atoms.

"Aryl" refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like. Unless otherwise specified, an aryl group has from 5 to about 20 carbon atoms, for example from 5 to 20 carbon atoms, for example from 5 to 14 carbon atoms, for example from 5 to 10 carbon atoms.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is substituted alkylene and Z is substituted alkenyl or substituted alkynyl, where substituted alkyl, substituted alkenyl and substituted alkynyl are as defined herein.

The term "$C_{1-6}$ haloalkyl" refers to an alkyl group having from 1 to 6 carbon atoms covalently bonded to from 1 to 7, or from 1 to 6, or from 1 to 3, halogen(s), where alkyl and halogen are defined herein. Similarly, the term "$C_{1-3}$ haloalkyl" refers to an alkyl group having from 1 to 3 carbon atoms covalently bonded to from 1 to 7, or from 1 to 6, or from 1 to 3, halogen(s), where alkyl and halogen are defined herein. In some embodiments, $C_{1-3}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, 3-fluoropropyl.

The term "$C_{1-3}$ hydroxyalkyl" refers to an alkyl group having a carbon atom covalently bonded to a hydroxy, where alkyl and hydroxy are defined herein. In some embodiments, $C_{1-3}$ hydroxyalkyl includes, by way of example, 2-hydroxyethyl.

The term "$C_{1-3}$ cyanoalkyl" refers to an alkyl group having a carbon atom covalently bonded to a cyano, where alkyl and cyano are defined herein. In some embodiments, $C_{1-3}$ cyanoalkyl includes, by way of example, 2-cyanoethyl.

The term "cycloalkyl" refers to cyclic alkyl groups of from 3 to 20 carbon atoms, from 3 to 10 carbon atoms, or from 3 to 8 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "$C_a$-$C_b$ alkyl$C_d$-$C_e$ cycloaklyl" and similar terms refer to an alkyl group further substituted with a cycloalkyl group each having the indicated number of carbon atoms, wherein the designations a, b, c, and d, for this purpose are independently from 0 to 8.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents) as otherwise described.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

"Aryl" refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like. Unless otherwise specified, an aryl group has from 5 to about 20 carbon atoms, for example from 5 to 20 carbon atoms, for example from 5 to 14 carbon atoms, for example from 5 to 10 carbon atoms.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)— heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical or biradical group having a single ring or multiple condensed rings, having from 1 to 20 carbon atoms and from 1 to 10 heteroatoms, and preferably from 1 to 4 heteroatoms, selected from nitrogen, sulfur, phosphorus, and/or oxygen within the ring. In some embodiments, the heterocyclyl," "heterocycle," or "heterocyclic" group is linked to the remainder of the molecule through one or more of the heteroatoms within the ring. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like.

Unless otherwise constrained by the definition for the heterocyclic substituent, such heterocyclic groups can be optionally substituted with 1 to 5 substituents (in some embodiments, 1, 2 or 3 substituents), selected from the group consisting of stated groups such as for examples, alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, and the like. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine.

The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

The term "heteroaryloxy" refers to the group heteroaryl-O—.

The term "amino" refers to the group —NH$_2$.

The term "substituted amino" refers to the group —NRR where each R is independently selected from the group consisting of H, alkyl, cycloalkyl, aryl, heteroaryl and heterocyclyl provided that both R groups are not H; or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group —N=.

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF$_3$, amino, substituted amino, cyano or —S(O)$_n$R$^z$, in which R$^z$ is alkyl, aryl or heteroaryl and n is 0, 1 or 2.

The term "acyl" denotes the group —C(O)R, in which R is H, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl; and n is 0, 1 or 2.

The term "aminocarbonyl" refers to the group —C(O)NRR where each R is independently H, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "acylamino" refers to the group —NRC(O)R where each R is independently H, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "alkoxycarbonylamino" refers to the group —N(R$^y$)C(O)OR in which R is alkyl and R$^y$ is H or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "aminocarbonylamino" refers to the group —NR$^x$C(O)NRR, wherein R$^x$ is H or alkyl and each R is H, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —S(O)$_2$R, in which R is alkyl, cycloalkyl, heterocyclyl, aryl or heteroaryl. "Substituted sulfone" refers to a group —S(O)$_2$R, in which R is substituted alkyl, substituted cycloalkyl, substituted heterocyclyl, substituted aryl or substituted heteroaryl, as defined herein.

The term "aminosulfonyl" refers to the group —S(O)$_2$NRR, wherein each R is independently H, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^z$, in which R$^z$ is alkyl, aryl or heteroaryl and n is 0, 1 or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a H of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given formula (e.g. the compound of Formula I, II, III, IV, V, VI or VII is intended to encompass the compounds of the disclosure, and the pharmaceutically acceptable salts, pharmaceutically acceptable esters, isomers, tautomers, solvates, isotopes, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or levorotary) that they rotate the plane of polarized light at the wavelength of the sodium D line.

Some of the compounds of the present disclosure exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of Formula I, II, III, IV, V, VI or VII and a solvent.

The term "hydrate" refers to the complex formed by the combining of a compound of Formula I, II, III, IV, V, VI or VII and water.

The term "prodrug" refers to compounds of Formula I, II, III, IV, V, VI or VII that include chemical groups which, in vivo, can be converted and/or can be split off from the remainder of the molecule to provide for the active drug, a pharmaceutically acceptable salt thereof or a biologically active metabolite thereof.

Any formula or structure given herein, including Formula I, II, III, IV, V, VI or VII compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include, for example, isotopes of hydrogen (H), carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I, II, III, IV, V, VI or VII in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "treatment" or "treating" means any administration of a compound of the invention or embodiment thereof, to a mammal, particularly a human, having a disease for purposes, including:
 (i) preventing the disease, that is, causing the clinical symptoms of the disease not to develop;
 (ii) inhibiting the disease, that is, arresting the development of clinical symptoms; and/or
 (iii) relieving the disease that is, causing the regression of clinical symptoms.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein monosubstituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroaryl, cycloalkyl, cycloalkenyl, heterocyclyl and the like. The above-mentioned amines refer to the compounds wherein one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to $NH(heteroaryl)_2$, wherein "heteroaryl" is as defined herein and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Myocardial infarction" is the irreversible necrosis of heart muscle secondary to prolonged ischemia. Increasing myocardial contractility, the intrinsic ability of the myocardium to contract, after myocardial infarction exacerbates cardiac injury and pump dysfunction. All factors that cause an increase in contractility work by causing an increase in intracellular [$Ca^{2+}$] during contraction.

"Arrhythmia" refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia and the ventricular tachycardias (VTs), including idiopathic ventricular tachycardia, ventricular fibrillation, pre-excitation syndrome and Torsade de Pointes (TdP).

"Atrial fibrillation" or "AF" occurs when the heart's two upper chambers (the right and left atria) quiver instead of beating and contracting rhythmically. Electrocardiographically, AF is characterized by a highly disorganized atrial electrical activity that often results in fast beating of the heart's two lower chambers (the right and left ventricles). Symptoms experienced by patients with AF include palpitation, fatigue, and dyspnea (shortness of breath).

There are three known types of AF based on the presentation and duration of the arrhythmia: a) Paroxysmal AF: recurrent AF (>2 episodes) that starts and terminates spontaneously within 7 days (paroxysmal AF starts and stops spontaneously); b) Persistent AF: sustained AF that lasts longer than 7 days or requires termination by pharmacologic or electrical cardioversion (electrical shock); and c) Permanent AF: long standing AF (for >1 year duration) in which normal sinus rhythm cannot be maintained even after treatment, or when the patient and physician have decided to allow AF to continue without further efforts to restore sinus rhythm.

Nomenclature

Names of compounds of the present disclosure are provided using ACD/Name software for naming chemical compounds (Advanced Chemistry Development, Inc., Toronto, Canada). Other compounds or radicals may be named with common names or systematic or non-systematic names. The naming and numbering of the compounds of the disclosure is illustrated with a representative compound of Formula I:

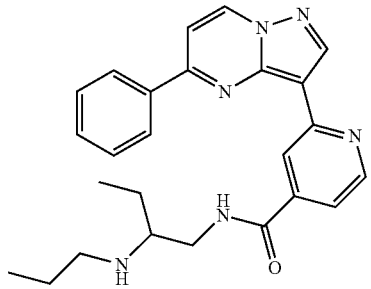 [SMILES: CCCNC(CC)CNC(=O)c1ccnc(-c2cnn3ccc(-c4ccccc4)nc23)c1]

2-(5-phenylpyrazolo[1,5-a]pyrimidin-3-yl)-N-(2-(propylamino)butyl)isonicotinamide Compounds Accordingly, one embodiment of the present disclosure provides novel compounds that function as CaM kinase inhibitors. In one embodiment of the compound of formula (I):

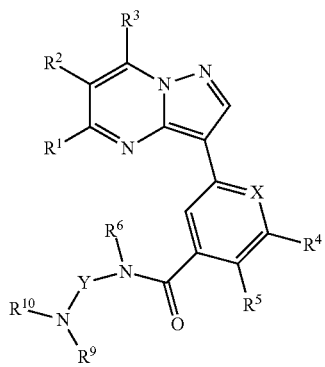

wherein, $R^1$ is aryl, heteroaryl or heterocyclic; wherein the aryl, heteroaryl or heterocyclic group is optionally substituted with one, two or three groups independently selected from the group consisting of halo, hydroxy, $C_1$-$C_6$ alkyl, $C_1$-$C_6$ haloalkyl, $C_1$-$C_6$ alkoxy, —$OC_1$-$C_6$haloalkyl, —$SC_1$-$C_6$alkyl, —$NHSO_2R^a$, and $C_0$-$C_6$ alkylene-$NR^aR^b$;

$R^2$ and $R^3$ are each H;

X is CH or N;

$R^4$ is H, $NR^aR^b$, —$OC_2$-$C_6$ alkyl$NR^aR^b$, $C_1$-$C_6$ alkylN-$R^aR^b$, —$C(O)NR^aR^b$, or $NR^aC(O)NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$C(O)C_1$-$C_6$ alkyl, —$C(O)OC_1$-$C_6$ alkyl, $C_0$-$C_3$ alkyl$NR^cR^d$, $C_1$-$C_3$alkylC(O)$NH_2$, $C_1$-$C_3$alkylC(O)$NHC_1$-$C_3$alkyl $C_1$-$C_6$ alkyl$C_3$-$C_6$ cycloalkyl, $SO_2C_1$-$C_3$alkyl, $SO_2C_3$-$C_6$cycloalkyl, —$C_1$-$C_3$ alkylSO$_2$$NR^cR^d$, aryl, heteroaryl, heterocyclic, or $C_1$-$C_6$ alkylheterocyclic, wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^eR^f$, —$SO_2R^e$, $SO_2NR^eR^f$ and $C_1$-$C_6$ alkyl-O—$C_1$-$C_6$ alkyl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH;

$R^5$ is H, halo, cyano, $NH_2$, $NHC_1$-$C_6$ alkyl, $N(C_1$-$C_6$ alkyl)$_2$, $C_1$-$C_6$ alkyl, $C_3$-$C_8$ cycloalkyl, $C_1$-$C_6$ alkyl$C_3$-$C_8$ cycloalkyl, $C_1$-$C_6$ haloalkyl, —$OC_1$-$C_6$ haloalkyl, $C_1$-$C_6$ alkyl-OH, or $C_1$-$C_6$ alkoxy;

$R^6$ is H, $C_1$-$C_6$ alkyl, or $C_3$-$C_8$ cycloalkyl; or $R^6$ combines with Y, $R^9$, or $R^{10}$ to form an optionally substituted 4-8 membered nitrogen containing heterocyclic group; and Y, R9 and R10 are as described previously.

In one embodiment, the disclosure provides compounds of Formula II:

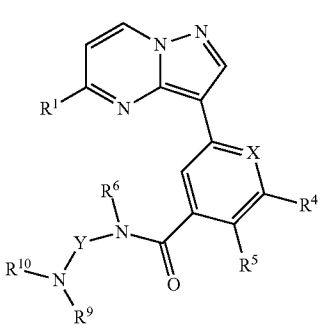

wherein $R^1$ is aryl, heteroaryl or heterocyclic; wherein the aryl, heteroaryl, or heterocyclic group is optionally substituted with one or two groups independently selected from the group consisting of halo, hydroxy, $C_1$-$C_6$ alkyl, $C_1$-$C_6$ haloalkyl, $C_1$-$C_6$ alkoxy, —$OC_1$-$C_6$ haloalkyl, —$SC_1$-$C_6$ alkyl, $NHSO_2R^a$ and $C_0$-$C_6$ alkylene-$NR^aR^b$;

X is CH or N;

$R^4$ is H, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkyl$C_3$-$C_6$ cycloalkyl, —$NR^aR^b$, $C_1$-$C_6$ alkyl$NR^aR^b$, $C_1$-$C_6$alkyl-O—$C_1$-$C_6$ alkylN-$R^aR^b$, —$OC_2$-$C_6$ alkyl$NR^aR^b$, $C(O)NR^aR^b$, —$NR^aC(O)NR^aR^b$, —$NR^aC(O)R^a$, —$NR^aC(O)OR^a$, aryl, heteroaryl, mono, bicyclic, bridged or spirocyclic carbocyclic or heterocyclic group, —O—$C_0$-$C_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —O$C_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkylNR$^a$CHR$^a$C(O)NHR$^a$, —C(O)R$^a$, —COOR$^a$, —NHC(O)NHR$^a$, —NHC(O)R$^a$, —NHC(O)OR$^a$, C(O)NR$^a$R$^b$, —NR$^a$R$^b$, —NH$C_1$-$C_3$alkylNR$^a$R$^b$, SO$_2$R$^a$, —NHSO$_2$R$^a$, SO$_2$NR$^a$R$^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group optionally combine to form a mono, bicyclic, bridged or spirocyclic carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, $C_1$-$C_6$ alkyl, $C_3$-$C_8$ cycloalkyl, $C_1$-$C_6$ haloalkyl, $C_1$-$C_6$ alkylOH, —O$C_1$-$C_6$ alkyl, —O$C_1$-$C_6$ haloalkyl, $C_1$-$C_6$ alkyl $C_3$-$C_6$ cycloalkyl, $C_1$-$C_6$ alkyl-O—$C_1$-$C_6$ alkyl, $C_0$-$C_3$ alkylNR$^a$CHR$^a$C(O)NHR$^a$, C(O)NR$^a$R$^b$, —SO$_2$R$^a$, and SO$_2$NR$^a$R$^b$;

R$^a$ and R$^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkylNR$^c$R$^d$, $C_1$-$C_3$alkylC(O)NH$_2$, $C_1$-$C_3$alkylC(O)NH$C_1$-$C_3$alkyl, $C_1$-$C_6$ alkyl$C_3$-$C_6$ cycloalkyl, SO$_2$$C_1$-$C_3$alkyl, SO$_2$$C_3$-$C_6$cycloalkyl, aryl, heterocyclic, or $C_1$-$C_6$ alkylheterocyclic; wherein the cycloalkyl, aryl or heterocyclic group is optionally substituted with one to four groups independently selected from —OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or R$^a$ and R$^b$ combine with a nitrogen atom to which they are attached to form a monocyclic, bicyclic, bridged or spirocyclic heterocyclic group optionally substituted with a group selected from OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

R$^c$ and R$^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, SO$_2$$C_1$-$C_6$ alkyl, and $C_1$-$C_6$ alkyl-O—$C_1$-$C_6$ alkyl; or R$^c$ and R$^d$ combine to form mono or bicyclic, bridged or spirocyclic heterocycle optionally substituted with a group selected from OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl; wherein R$^e$ and R$^f$ are independently selected from $C_1$-$C_6$ alkyl, $C_1$-$C_6$ alkylOH, and $C_1$-$C_6$ alkyl aryl;

R$^e$ and R$^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —O$C_1$-$C_6$ haloalkyl, and $C_1$-$C_6$ alkylOH;

R$^5$ is H, halo, cyano, NH$_2$, NH$C_1$-$C_6$ alkyl, N($C_1$-$C_6$ alkyl)$_2$, $C_1$-$C_6$ alkyl, or $C_1$-$C_6$ alkyl$C_3$-$C_8$ cycloalkyl;

R$^6$ is H, $C_1$-$C_6$ alkyl, $C_3$-$C_8$ cycloalkyl, $C_1$-$C_6$ haloalkyl, $C_1$-$C_6$ alkyl-OH, or $C_1$-$C_6$ alkoxy; or R$^6$ combines with Y to form a 4-8 membered nitrogen containing heterocyclic group;

Y is —(CR$^7$R$^8$)$_n$ wherein n is 2 or 3;

each R$^7$ or R$^8$ is independently selected from H, $C_1$-$C_6$ alkyl, $C_1$-$C_6$ alkylOH, $C_1$-$C_3$ alkyl-O-heteroaryl, $C_1$-$C_3$ alkyl-O-heterocyclyl, $C_1$-$C_3$ alkyl-O-aryl, $C_1$-$C_3$ alkylNH$_2$; or one R$^7$ or R$^8$ group combines with the R$^6$ group to form a nitrogen containing heterocyclic group; or one R$^7$ group combines with another R$^7$ or R$^8$ group to form an optionally substituted monocyclic or bicyclic ring system having from 4 to 10 carbon atoms in the ring;

each R$^9$ and R$^{10}$ is independently H, $C_1$-$C_6$ alkyl, $C_3$-$C_8$ cycloalkyl, or heterocyclic, wherein the alkyl, cycloalkyl or heterocyclic group is optionally substituted with one or two groups independently selected from the group consisting of halo, $C_1$-$C_6$ alkyl, $C_1$-$C_6$ haloalkyl, $C_1$-$C_6$ alkylOH, $C_3$-$C_8$ cycloalkyl, —OR$^{12}$, —NR$^{13}$R$^{14}$, —C(O)NR$^{13}$R$^{14}$, —NR$^{13}$COR$^{14}$, —SO$_2$NR$^{13}$R$^{14}$, —NR$^{13}$SO$_2$R$^{14}$, —NR$^{12}$SO$_2$NR$^{13}$R$^{14}$, —NR$^{12}$C(O)NR$^{13}$R$^{14}$, —NR$^{13}$CO$_2$R$^{14}$, and —OC(O)NR$^{13}$R$^{14}$; or R$^9$ and R$^{10}$ together with the nitrogen atom to which they are attached form a mono, bicyclic, bridged or spirocyclic heterocyclic ring optionally substituted with one or two groups independently selected from the group consisting of halo, —OH, —NH$_2$, —NH—$C_1$-$C_6$ alkyl, —$C_1$-$C_6$ alkyl, —$C_1$-$C_6$ alkylOH, $C_3$-$C_8$ cycloalkyl, aryl, and heterocyclic; wherein the cycloalkyl, aryl or heterocyclic group is optionally substituted with halo, —OH, —NH$_2$, —NH—$C_1$-$C_6$ alkyl, —$C_1$-$C_6$ alkyl, and —$C_1$-$C_6$ alkylOH; or R$^9$ and/or R$^{10}$ combines with Y to form a monocyclic, bicyclic, bridged or spirocyclic nitrogen containing heterocycle optionally substituted with one or two groups independently selected from the group consisting of —$C_1$-$C_6$ alkyl, —$C_1$-$C_6$ alkylOH, $C_3$-$C_8$ cycloalkyl, —OH, —NH$_2$, and —NH—$C_1$-$C_6$ alkyl;

each R$^{12}$, R$^{13}$ and R$^{14}$ is independently H, $C_1$-$C_6$ alkyl, $C_3$-$C_8$ cycloalkyl, or heterocyclic, wherein the $C_1$-$C_6$ alkyl, $C_3$-$C_8$ cycloalkyl group, or heterocyclic, is optionally substituted with one or two groups independently selected from the group consisting of —OH, —NH$_2$, —N(CH$_3$)$_2$, $C_1$-$C_6$ haloalkyl; or R$^{13}$ and R$^{14}$ together with the atom to which they are attached form a heterocyclic ring;

or a pharmaceutically acceptable salt, stereoisomer or mixture of stereoisomer thereof.

In one embodiment of the compound of formula (II),

R$^1$ is aryl, heteroaryl or heterocyclic; wherein the aryl, heteroaryl or heterocyclic group is optionally substituted with one, two or three groups independently selected from the group consisting of halo, hydroxy, $C_1$-$C_6$ alkyl, $C_1$-$C_6$haloalkyl, $C_1$-$C_6$ alkoxy, —O$C_1$-$C_6$ haloalkyl, —S$C_1$-$C_6$ alkyl, —NHSO$_2$R$^a$, and $C_0$-$C_6$ alkylene-NR$^a$R$^b$;

R$^2$ and R$^3$ are each H;

X is CH or N;

R$^4$ is H, NR$^a$R$^b$, —OC$_2$-$C_6$ alkylNR$^a$R$^b$, $C_1$-$C_6$ alkylN-R$^a$R$^b$, —C(O)NR$^a$R$^b$, or NR$^a$C(O)NR$^a$R$^b$;

R$^a$ and R$^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkylNR$^c$R$^d$, $C_1$-$C_3$alkylC(O)NH$_2$, $C_1$-$C_3$alkylC(O)NHC$_1$-$C_3$alkyl, $C_1$-$C_6$ alkylC$_3$-$C_6$ cycloalkyl, SO$_2$C$_1$-$C_3$alkyl, SO$_2$C$_3$-$C_6$cycloalkyl, —C$_1$-$C_3$ alkylSO$_2$NR$^c$R$^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, $C_1$-$C_6$ alkyl-O—$C_1$-$C_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

R$^c$ and R$^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkylC$_3$-$C_6$ cycloalkyl, SO$_2$C$_1$-$C_6$ alkyl, and $C_1$-$C_6$ alkyl-O—$C_1$-$C_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl;

R$^e$ and R$^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —OC$_1$-$C_6$ haloalkyl, and $C_1$-$C_6$ alkylOH;

R$^5$ is H, halo, cyano, NH$_2$, NHC$_1$-$C_6$ alkyl, N(C$_1$-$C_6$ alkyl)$_2$, $C_1$-$C_6$ alkyl, $C_3$-$C_8$ cycloalkyl, $C_1$-$C_6$ alkylC$_3$-$C_8$ cycloalkyl, $C_1$-$C_6$ haloalkyl, —OC$_1$-$C_6$ haloalkyl, $C_1$-$C_6$ alkyl-OH, or $C_1$-$C_6$ alkoxy;

R$^6$ is H, $C_1$-$C_6$ alkyl, or $C_3$-$C_8$ cycloalkyl; or R$^6$ combines with Y, R$^9$, or R$^{10}$ to form an optionally substituted 4-8 membered nitrogen containing heterocyclic group; and Y, R$^9$ and R$^{10}$ are as described previously.

In one embodiment of the compound of formula (II),
R$^1$ is aryl, heteroaryl or heterocyclic; wherein the aryl, heteroaryl or heterocyclic group is optionally substituted with one, two or three groups independently selected from the group consisting of halo, hydroxy, $C_1$-$C_6$ alkyl, $C_1$-$C_6$haloalkyl, $C_1$-$C_6$ alkoxy, —OC$_1$-$C_6$ haloalkyl, —SC$_1$-$C_6$ alkyl, —NHSO$_2$R$^a$, and C$_0$-$C_6$ alkylene-NR$^a$R$^b$;

R$^2$ and R$^3$ are each H;
X is N;
R$^4$ is H, NR$^a$R$^b$, $C_1$-$C_6$ alkylNR$^a$R$^b$, —C(O)NR$^a$R$^b$, or NR$^a$C(O)NR$^a$R$^b$;
R$^a$ and R$^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)C$_1$-$C_6$ alkyl, —C(O)OC$_1$-$C_6$ alkyl, C$_0$-$C_3$ alkylNR$^c$R$^d$, $C_1$-$C_3$alkylC(O)NH$_2$, $C_1$-$C_3$alkylC(O)NHC$_1$-$C_3$alkyl, $C_1$-$C_6$ alkylC$_3$-$C_6$ cycloalkyl, SO$_2$C$_1$-$C_3$alkyl, SO$_2$C$_3$-$C_6$cycloalkyl, —C$_1$-$C_3$ alkylSO$_2$NR$^c$R$^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, $C_1$-$C_6$ alkyl-O—$C_1$-$C_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

R$^c$ and R$^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkylC$_3$-$C_6$ cycloalkyl, SO$_2$C$_1$-$C_6$ alkyl, and $C_1$-$C_6$ alkyl-O—$C_1$-$C_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl;

R$^e$ and R$^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —OC$_1$-$C_6$ haloalkyl, and $C_1$-$C_6$ alkylOH;

R$^5$ is H;
R$^6$ is H.

In one embodiment of the present disclosure is provided the compound of Formula (III)

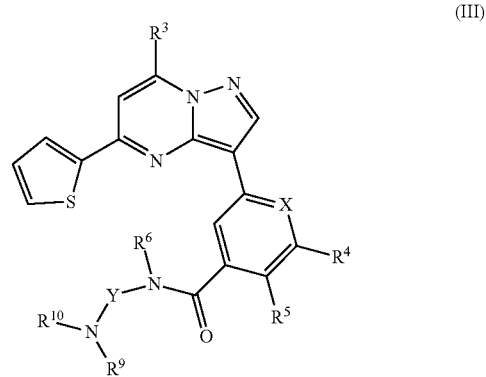

wherein
R$^3$ is selected from the group consisting of H, halo, or $C_1$-$C_6$ alkyl;
X is CH or N;
R$^4$ is H, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkylC$_3$-$C_6$ cycloalkyl, —NR$^a$R$^b$, $C_1$-$C_6$ alkylNR$^a$R$^b$, $C_1$-$C_6$alkyl-O—$C_1$-$C_6$ alkylNR$^a$R$^b$, —OC$_2$-$C_6$ alkylNR$^a$R$^b$, —C(O)NR$^a$R$^b$, —NR$^a$C(O)NR$^a$R$^b$, —NR$^a$C(O)R$^a$, —NR$^a$C(O)OR$^a$, aryl, heteroaryl, mono, bicyclic, bridged or spirocyclic carbocyclic or heterocyclic group, —O—C$_0$-$C_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —OC$_1$-$C_6$ haloalkyl, $C_1$-$C_6$ alkyl C$_3$-$C_8$ cycloalkyl, $C_1$-$C_6$ alkyl-O—$C_1$-$C_6$ alkyl, C$_0$-$C_3$ alkylNR$^a$CHR$^a$C(O)NHR$^a$, —C(O)R$^a$, —COOR$^a$, —NHC(O)NHR$^a$, —NHC(O)R$^a$, —NHC(O)OR$^a$, C(O)NR$^a$R$^b$, —NR$^a$R$^b$, —NHC$_1$-C$_3$alkylNR$^a$R$^b$, SO$_2$R$^a$, —NHSO$_2$R$^a$, SO$_2$NR$^a$R$^b$, aryl, heteroaryl, mono, bicyclic, bridged or spirocyclic carbocyclic or heterocyclic group, and C$_1$-C$_6$ alkylheterocyclic; or two substituents on the aryl, heteroaryl, mono, bicyclic, bridged or spirocyclic carbocyclic or heterocyclic group combines to form a mono, bicyclic, bridged or spirocyclic carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, C$_1$-C$_6$ alkyl, C$_3$-C$_8$ cycloalkyl, C$_1$-C$_6$ haloalkyl, C$_1$-C$_6$ alkylOH, —OC$_1$-C$_6$ alkyl, —OC$_1$-C$_6$ haloalkyl, C$_1$-C$_6$ alkyl C$_3$-C$_6$ cycloalkyl, C$_1$-C$_6$ alkyl-O—C$_1$-C$_6$ alkyl, C$_0$-C$_3$ alkylNR$^a$CHR$^a$C(O)NHR$^a$, C(O)NR$^a$R$^b$, —SO$_2$R$^a$, and SO$_2$NR$^a$R$^b$;

R$^a$ and R$^b$ are each independently H, OH, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —C(O)C$_1$-C$_6$ alkyl, —C(O)OC$_1$-C$_6$ alkyl, C$_0$-C$_3$ alkylNR$^c$R$^d$, C$_1$-C$_3$alkylC(O)NH$_2$, C$_1$-C$_3$alkylC(O)NHC$_1$-C$_3$alkyl, C$_1$-C$_6$ alkylC$_3$-C$_6$ cycloalkyl, SO$_2$C$_1$-C$_3$alkyl, SO$_2$C$_3$-C$_6$cycloalkyl, aryl, heterocyclic, or C$_1$-C$_6$ alkylheterocyclic; wherein the cycloalkyl, aryl or heterocyclic group is optionally substituted with one to four groups independently selected from —OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, C$_1$-C$_6$ alkyl-O—C$_1$-C$_6$ alkyl, and heterocyclyl; or R$^a$ and R$^b$ combine with a nitrogen atom to which they are attached to form a monocyclic, bicyclic, bridged or spirocyclic heterocyclic group optionally substituted with a group selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^c$R$^d$, —SO$_2$R$^c$, SO$_2$NR$^c$R$^d$ and C$_1$-C$_6$ alkyl-O—C$_1$-C$_6$ alkyl;

R$^c$ and R$^d$ are independently selected from H, C$_1$-C$_6$ alkyl, C$_3$-C$_8$ cycloalkyl, C$_2$-C$_6$ haloalkyl, C$_2$-C$_6$ alkylOH, C$_1$-C$_6$ alkylC$_3$-C$_6$ cycloalkyl, SO$_2$C$_1$-C$_6$ alkyl, and C$_1$-C$_6$ alkyl-O—C$_1$-C$_6$ alkyl; or R$^c$ and R$^d$ combine to form mono or bicyclic, bridged or spirocyclic heterocycle optionally substituted with a group selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^e$R$^f$, —SO$_2$R$^e$, SO$_2$NR$^e$R$^f$ and C$_1$-C$_6$ alkyl-O—C$_1$-C$_6$ alkyl; wherein R$^e$ and R$^f$ are independently selected from C$_1$-C$_6$ alkyl, C$_1$-C$_6$ alkylOH, and C$_1$-C$_6$ alkyl aryl;

R$^e$ and R$^f$ are at each occurrence independently selected from the group consisting of: C$_1$-C$_6$ alkyl, C$_3$-C$_8$ cycloalkyl, C$_2$-C$_6$ haloalkyl, C$_1$-C$_6$ haloalkyl, —OC$_1$-C$_6$ haloalkyl, and C$_1$-C$_6$ alkylOH;

R$^5$ is H, halo, cyano, NH$_2$, NHC$_1$-C$_6$ alkyl, N(C$_1$-C$_6$ alkyl)$_2$, C$_1$-C$_6$ alkyl, or C$_1$-C$_6$ alkylC$_3$-C$_8$ cycloalkyl;

R$^6$ is H, amino, C$_1$-C$_6$ alkyl, C$_3$-C$_8$ cycloalkyl, C$_2$-C$_6$ haloalkyl, C$_2$-C$_6$ alkyl-OH, or C$_1$-C$_6$ alkoxy; or R$^6$ combines with Y to form a 4-8 membered nitrogen containing heterocyclic group;

Y is —(CR$^7$R$^8$)$_n$, wherein n is 2 or 3;

each R$^7$ or R$^8$ is independently selected from H, C$_1$-C$_6$ alkyl, C$_1$-C$_6$ alkylOH, C$_1$-C$_3$ alkyl-O-heteroaryl, C$_1$-C$_3$ alkyl-O-heterocyclyl, C$_1$-C$_3$ alkyl-O-aryl, C$_1$-C$_3$ alkylNH$_2$; or one R$^7$ or R$^8$ group combines with the R$^6$ group to form a nitrogen containing heterocyclic group; or one R$^7$ group combines with an another R$^7$ or R$^8$ group to form an optionally substituted monocyclic or bicyclic ring system having from 4 to 10 carbon atoms in the ring;

each R$^9$ and R$^{10}$ is independently H, C$_1$-C$_6$ alkyl, C$_3$-C$_8$ cycloalkyl, or heterocyclic, wherein the alkyl, cycloalkyl or heterocyclic group is optionally substituted with one or two groups independently selected from the group consisting of halo, C$_1$-C$_6$ alkyl, C$_1$-C$_6$ haloalkyl, C$_1$-C$_6$ alkylOH, C$_3$-C$_8$ cycloalkyl, —OR$^{12}$, —NR$^{13}$R$^{14}$, —C(O)NR$^{13}$R$^{14}$, —NR$^{13}$COR$^{14}$, —SO$_2$NR$^{13}$R$^{14}$, —NR$^{13}$SO$_2$R$^{14}$, —NR$^{12}$SO$_2$NR$^{13}$R$^{14}$, —NR$^{12}$C(O)NR$^{13}$R$^{14}$, —NR$^{13}$CO$_2$R$^{14}$, and —OC(O)NR$^{13}$R$^{14}$; or R$^9$ and R$^{10}$ together with the nitrogen atom to which they are attached form a mono, bicyclic bridged or spirocyclic heterocyclic ring optionally substituted with one or two groups independently selected from the group consisting of halo, —OH, —NH$_2$, —NH—C$_1$-C$_6$ alkyl, —C$_1$-C$_6$ alkyl, —C$_1$-C$_6$ alkylOH, C$_3$-C$_8$ cycloalkyl, aryl, and heterocyclic; wherein the cycloalkyl, aryl or heterocyclic group is optionally substituted with halo, —OH, —NH$_2$, —NH—C$_1$-C$_6$ alkyl, —C$_1$-C$_6$ alkyl, and —C$_1$-C$_6$ alkylOH; or R$^9$ and/or R$^{10}$ combines with Y to form a monocyclic, bicyclic, bridged or spirocyclic nitrogen containing heterocycle optionally substituted with one or two groups independently selected from the group consisting of —C$_1$-C$_6$ alkyl, —C$_1$-C$_6$ alkylOH, C$_3$-C$_8$ cycloalkyl, —OH, —NH$_2$, and —NH—C$_1$-C$_6$ alkyl;

each R$^{12}$, R$^{13}$ and R$^{14}$ is independently H, C$_1$-C$_6$ alkyl, C$_3$-C$_8$ cycloalkyl, or heterocyclic, wherein the C$_1$-C$_6$ alkyl, C$_3$-C$_8$ cycloalkyl group, or heterocyclic, is optionally substituted with one or two groups independently selected from the group consisting of —OH, —NH$_2$, —N(CH$_3$)$_2$, C$_1$-C$_6$ haloalkyl; or R$^{13}$ and R$^{14}$ together with the atom to which they are attached form a heterocyclic ring;

or a pharmaceutically acceptable salt, stereoisomer or mixture of stereoisomer thereof.

In certain embodiments of the compounds of formula (III), R$^4$ is H. In some embodiments, R$^5$ is H. In certain embodiments of the compounds of formula (III), X is N and in certain embodiments, X is CH.

In one embodiment of the compound of formula (III),

R$^3$ is H;

X is CH or N;

R$^4$ is H, NR$^a$R$^b$, —OC$_2$-C$_6$ alkylNR$^a$R$^b$, C$_1$-C$_6$ alkylNR$^a$R$^b$, —C(O)NR$^a$R$^b$, or NR$^a$C(O)NR$^a$R$^b$;

R$^a$ and R$^b$ are each independently H, OH, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —C(O)C$_1$-C$_6$ alkyl, —C(O)OC$_1$-C$_6$ alkyl, C$_0$-C$_3$ alkylNR$^c$R$^d$, C$_1$-C$_3$alkylC(O)NH$_2$, C$_1$-C$_3$alkylC(O)NHC$_1$-C$_3$alkyl, C$_1$-C$_6$ alkylC$_3$-C$_6$ cycloalkyl, SO$_2$C$_1$-C$_3$alkyl, SO$_2$C$_3$-C$_6$cycloalkyl, —C$_1$-C$_3$ alkylSO$_2$NR$^c$R$^d$, aryl, heteroaryl, heterocyclic, or C$_1$-C$_6$ alkylheterocyclic; wherein the cycloalkyl, aryl, heteroaryl or heterocyclic group is optionally substituted with one to four groups independently selected from —OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, C$_1$-C$_6$ alkyl-O—C$_1$-C$_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

R$^c$ and R$^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, SO$_2$$C_1$-$C_6$ alkyl, and $C_1$-$C_6$ alkyl-O—$C_1$-$C_6$ alkyl; or R$^c$ and R$^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl;

R$^e$ and R$^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —O$C_1$-$C_6$ haloalkyl, and $C_1$-$C_6$ alkylOH;

R$^5$ is H, halo, cyano, $NH_2$, $NHC_1$-$C_6$ alkyl, N($C_1$-$C_6$ alkyl)$_2$, $C_1$-$C_6$ alkyl, $C_3$-$C_8$ cycloalkyl, $C_1$-$C_6$ alkyl$C_3$-$C_8$ cycloalkyl, $C_1$-$C_6$ haloalkyl, —O$C_1$-$C_6$ haloalkyl, $C_1$-$C_6$ alkyl-OH, or $C_1$-$C_6$ alkoxy;

R$^6$ is H, $C_1$-$C_6$ alkyl, or $C_3$-$C_8$ cycloalkyl; or R$^6$ combines with Y, R$^9$, or R$^{10}$ to form an optionally substituted 4-8 membered nitrogen containing heterocyclic group.

In one embodiment of the compound of formula (III),
X is N;
R$^4$ is H, NR$^a$R$^b$, $C_1$-$C_6$ alkylNR$^a$R$^b$, —C(O)NR$^a$R$^b$, or NR$^a$C(O)NR$^a$R$^b$;
R$^a$ and R$^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkylNR$^c$R$^d$, $C_1$-$C_3$alkylC(O)NH$_2$, $C_1$-$C_3$alkylC(O)NHC$_1$-$C_3$alkyl, $C_1$-$C_6$ alkyl$C_3$-$C_6$ cycloalkyl, SO$_2$$C_1$-$C_3$alkyl, SO$_2$$C_3$-$C_6$cycloalkyl, —$C_1$-$C_3$ alkylSO$_2$NR$^c$R$^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

R$^c$ and R$^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, SO$_2$$C_1$-$C_6$ alkyl, and $C_1$-$C_6$ alkyl-O—$C_1$-$C_6$ alkyl; or R$^c$ and R$^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl;

R$^e$ and R$^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —O$C_1$-$C_6$ haloalkyl, and $C_1$-$C_6$ alkylOH;

R$^5$ is H;
R$^6$ is H.

In another embodiment, the disclosure provides compounds of Formula (IV):

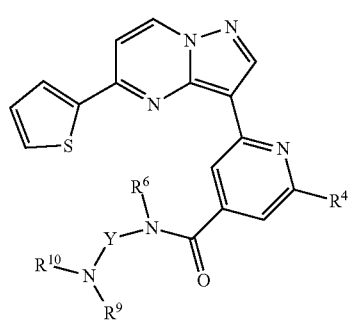

(IV)

wherein
R$^4$ is H, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkyl$C_3$-$C_6$ cycloalkyl, —NR$^a$R$^b$, $C_1$-$C_6$ alkylNR$^a$R$^b$, $C_1$-$C_6$alkyl-O—$C_1$-$C_6$ alkylNR$^a$R$^b$, —O$C_2$-$C_6$ alkylNR$^a$R$^b$, —C(O)NR$^a$R$^b$, —NR$^a$C(O)NR$^a$R$^b$, —NR$^a$C(O)R$^a$, —NR$^a$C(O)OR$^a$, aryl, heteroaryl, mono, bicyclic, bridged or spirocyclic carbocyclic or heterocyclic group, —O—$C_0$-$C_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —O$C_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkylNR$^a$CHR$^a$C(O)NHR$^a$, —C(O)R$^a$, —COOR$^a$, —NHC(O)NHR$_a$, —NHC(O)R$^a$, —NHC(O)OR$^a$, C(O)NR$^a$R$^b$, —NR$^a$R$^b$, —NHC$_1$-$C_3$alkylNR$^a$R$^b$, SO$_2$R$^a$, —NHSO$_2$R$^a$, SO$_2$NR$^a$R$^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group combines to form a mono, bicyclic, bridged or spirocyclic carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, $C_1$-$C_6$ alkyl, $C_3$-$C_8$ cycloalkyl, $C_1$-$C_6$ haloalkyl, $C_1$-$C_6$ alkylOH, —O$C_1$-$C_6$ alkyl, —O$C_1$-$C_6$ haloalkyl, $C_1$-$C_6$ alkyl $C_3$-$C_6$ cycloalkyl, $C_1$-$C_6$ alkyl-O—$C_1$-$C_6$ alkyl, $C_0$-$C_3$ alkylNR$^a$CHR$^a$C(O)NHR$^a$, C(O)NR$^a$R$^b$, —SO$_2$R$^a$, and SO$_2$NR$^a$R$^b$;

R$^a$ and R$^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkylNR$^c$R$^d$, $C_1$-$C_3$alkylC(O)NH$_2$, $C_1$-$C_3$alkylC(O)NHC$_1$-$C_3$alkyl, $C_1$-$C_6$ alkyl$C_3$-$C_6$ cycloalkyl, SO$_2$$C_1$-$C_3$alkyl, SO$_2$$C_3$-$C_6$cycloalkyl, aryl, heterocyclic, or $C_1$-$C_6$ alkylheterocyclic; wherein the cycloalkyl, aryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a monocyclic, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

R$^c$ and R$^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, SO$_2$$C_1$-$C_6$ alkyl, and $C_1$-$C_6$ alkyl-O—$C_1$-$C_6$ alkyl; or R$^c$ and R$^d$ combine to form mono or bicyclic, bridged or spirocyclic heterocycle optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl; wherein R$^e$ and R$^f$ are independently selected from $C_1$-$C_6$ alkyl, $C_1$-$C_6$ alkylOH, and $C_1$-$C_6$ alkyl aryl;

R$^e$ and R$^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —OC$_1$-$C_6$ haloalkyl, and $C_1$-$C_6$ alkylOH;

$R^6$ is H, $C_1$-$C_6$ alkyl, $C_3$-$C_8$ cycloalkyl, $C_2$-$C_6$ haloalkyl, $C_2$-$C_6$ alkyl-OH, or $C_1$-$C_6$ alkoxy; or $R^6$ combines with Y to form a 4-8 membered nitrogen containing heterocyclic group;

Y is —(CR$^7$R$^8$)$_n$ wherein n is 2 or 3;

each $R^7$ or $R^8$ is independently selected from H, $C_1$-$C_6$ alkyl, $C_1$-$C_6$ alkylOH, $C_1$-$C_3$ alkyl-O-heteroaryl, $C_1$-$C_3$ alkyl-O-heterocyclyl, $C_1$-$C_3$ alkyl-O-aryl, $C_1$-$C_3$ alkyl$NH_2$; or one $R^7$ or $R^8$ group combines with the $R^6$ group to form a nitrogen containing heterocyclic group; or one $R^7$ group combines with an another $R^7$ or $R^8$ group to form an optionally substituted monocyclic or bicyclic ring system having from 4 to 10 carbon atoms in the ring;

each $R^9$ and $R^{10}$ is independently H, $C_1$-$C_6$ alkyl, $C_3$-$C_8$ cycloalkyl, or heterocyclic, wherein the alkyl, cycloalkyl or heterocyclic group is optionally substituted with one or two groups independently selected from the group consisting of halo, $C_1$-$C_6$ alkyl, $C_1$-$C_6$ haloalkyl, $C_1$-$C_6$ alkylOH, $C_3$-$C_8$ cycloalkyl, —OR$^{12}$, —NR$^{13}$R$^{14}$, —C(O)NR$^{13}$R$^{14}$, —NR$^{13}$COR$^{14}$, —SO$_2$NR$^{13}$R$^{14}$, —NR$^{13}$SO$_2$R$^{14}$, —NR$^{12}$SO$_2$NR$^{13}$R$^{14}$, —NR$^{12}$C(O)NR$^{13}$R$^{14}$, —NR$^{13}$CO$_2$R$^{14}$, and —OC(O)NR$^{13}$R$^{14}$; or $R^9$ and $R^{10}$ together with the nitrogen atom to which they are attached form a mono, bicyclic bridged or spirocyclic heterocyclic ring optionally substituted with one or two groups independently selected from the group consisting of halo, —OH, —NH$_2$, —NH—$C_1$-$C_6$ alkyl, —$C_1$-$C_6$ alkyl, —$C_1$-$C_6$ alkylOH, $C_3$-$C_8$ cycloalkyl, aryl, and heterocyclic; wherein the cycloalkyl, aryl or heterocyclic group is optionally substituted with halo, —OH, —NH$_2$, —NH—$C_1$-$C_6$ alkyl, —$C_1$-$C_6$ alkyl, and —$C_1$-$C_6$ alkylOH; or $R^9$ and/or $R^{10}$ combines with Y to form a monocyclic, bicyclic, bridged or spirocyclic nitrogen containing heterocycle optionally substituted with one or two groups independently selected from the group consisting of —$C_1$-$C_6$ alkyl, —$C_1$-$C_6$ alkylOH, $C_3$-$C_8$ cycloalkyl, —OH, —NH$_2$, and —NH—$C_1$-$C_6$ alkyl;

each $R^{12}$, $R^{13}$ and $R^{14}$ is independently H, $C_1$-$C_6$ alkyl, $C_3$-$C_8$ cycloalkyl, or heterocyclic, wherein the $C_1$-$C_6$ alkyl, $C_3$-$C_8$ cycloalkyl group, or heterocyclic, is optionally substituted with one or two groups independently selected from the group consisting of —OH, —NH$_2$, —N(CH$_3$)$_2$, $C_1$-$C_6$ haloalkyl; or $R^{13}$ and $R^{14}$ together with the atom to which they are attached form a heterocyclic ring;

or a pharmaceutically acceptable salt, stereoisomer or mixture of stereoisomer thereof.

In one embodiment of the compound of formula (IV), $R^4$ is H, NR$^a$R$^b$, —OC$_2$-$C_6$ alkylNR$^a$R$^b$, $C_1$-$C_6$ alkylNR$^a$R$^b$, —C(O)NR$^a$R$^b$, or NR$^a$C(O)NR$^a$R$^b$;

R$^a$ and R$^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkylNR$^c$R$^d$, $C_1$-$C_3$alkylC(O)NH$_2$, $C_1$-$C_3$alkylC(O)NHC$_1$-$C_3$alkyl, $C_1$-$C_6$ alkyl$C_3$-$C_6$ cycloalkyl, SO$_2$$C_1$-$C_3$alkyl, SO$_2$$C_3$-$C_6$cycloalkyl, —$C_1$-$C_3$ alkylSO$_2$NR$^c$R$^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

R$^c$ and R$^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, SO$_2$$C_1$-$C_6$ alkyl, and $C_1$-$C_6$ alkyl-O—$C_1$-$C_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl;

R$^e$ and R$^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —OC$_1$-$C_6$ haloalkyl, and $C_1$-$C_6$ alkylOH;

$R^6$ is H, $C_1$-$C_6$ alkyl, or $C_3$-$C_8$ cycloalkyl; or $R^6$ combines with Y, $R^9$, or $R^{10}$ to form an optionally substituted 4-8 membered nitrogen containing heterocyclic group.

In one embodiment of the compound of formula (IV), $R^4$ is H, NR$^a$R$^b$, $C_1$-$C_6$ alkylNR$^a$R$^b$, —C(O)NR$^a$R$^b$, or NR$^a$C(O)NR$^a$R$^b$;

R$^a$ and R$^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkylNR$^c$R$^d$, $C_1$-$C_3$alkylC(O)NH$_2$, $C_1$-$C_3$alkylC(O)NHC$_1$-$C_3$alkyl, $C_1$-$C_6$ alkyl$C_3$-$C_6$ cycloalkyl, SO$_2$$C_1$-$C_3$alkyl, SO$_2$$C_3$-$C_6$cycloalkyl, —$C_1$-$C_3$ alkylSO$_2$NR$^c$R$^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^eR^f$, —$SO_2R^e$, $SO_2NR^eR^f$ and $C_1$-$C_6$ alkyl-O—$C_1$-$C_6$ alkyl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH;

$R^6$ is H.

In another embodiment, the disclosure provides compounds of Formula V:

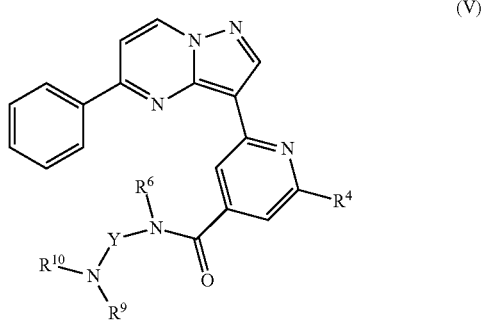

(V)

wherein $R^4$ is H, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkyl$C_3$-$C_6$ cycloalkyl, —$NR^aR^b$, $C_1$-$C_6$ alkyl$NR^aR^b$, $C_1$-$C_6$alkyl O $C_1$ $C_6$ alkyl$NR^aR^b$, $OC_2$ $C_6$ alkyl$NR^aR^b$, C(O)$NR^aR^b$, —$NR^aC(O)NR^aR^b$, —$NR^aC(O)R^a$, —$NR^aC(O)OR^a$, aryl, heteroaryl, mono, bicyclic, bridged or spirocyclic carbocyclic or heterocyclic group, —O—$C_0$-$C_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$OC_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkyl$NR^aCHR^aC(O)NHR^a$, —C(O)$R^a$, —$COOR^a$, —$NHC(O)NHR^a$, —$NHC(O)R^a$, —$NHC(O)OR^a$, C(O)$NR^aR^b$, —$NR^aR^b$, —$NHC_1$-$C_3$alkyl$NR^aR^b$, $SO_2R^a$, —$NHSO_2R^a$, $SO_2NR^aR^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group combines to form a mono, bicyclic, bridged or spirocyclic carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, $C_1$-$C_6$ alkyl, $C_3$-$C_8$ cycloalkyl, $C_1$-$C_6$ haloalkyl, $C_1$-$C_6$ alkylOH, —$OC_1$-$C_6$ alkyl, —$OC_1$-$C_6$ haloalkyl, $C_1$-$C_6$ alkyl $C_3$-$C_6$ cycloalkyl, $C_1$-$C_6$ alkyl-O—$C_1$-$C_6$ alkyl, $C_0$-$C_3$ alkyl$NR^aCHR^aC(O)NHR^a$, C(O)$NR^aR^b$, —$SO_2R^a$, and $SO_2NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)$OC_1$-$C_6$ alkyl, $C_0$-$C_3$ alkyl$NR^cR^d$, $C_1$-$C_3$alkylC(O)$NH_2$, $C_1$-$C_3$alkylC(O)$NHC_1$-$C_3$alkyl, $C_1$-$C_6$ alkyl$C_3$-$C_6$ cycloalkyl, $SO_2C_1$-$C_3$alkyl, $SO_2C_3$-$C_6$cycloalkyl, aryl, heterocyclic, or $C_1$-$C_6$ alkylheterocyclic; wherein the cycloalkyl, aryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a monocyclic, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono or bicyclic, bridged or spirocyclic heterocycle optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^eR^f$, —$SO_2R^e$, $SO_2NR^eR^f$ and $C_1$-$C_6$ alkyl-O—$C_1$-$C_6$ alkyl; wherein $R^e$ and $R^f$ are independently selected from $C_1$-$C_6$ alkyl, $C_1$-$C_6$ alkylOH, and $C_1$-$C_6$ alkyl aryl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH;

$R^6$ is H, $C_1$-$C_6$ alkyl, $C_3$-$C_8$ cycloalkyl, $C_1$-$C_6$ haloalkyl, $C_1$-$C_6$ alkyl-OH, or $C_1$-$C_6$ alkoxy; or $R^6$ combines with Y to form a 4-8 membered nitrogen containing heterocyclic group;

Y is —$(CR^7R^8)_n$ wherein n is 2 or 3;

each $R^7$ or $R^8$ is independently selected from H, $C_1$-$C_6$ alkyl, $C_1$-$C_6$ alkylOH, $C_1$-$C_3$ alkyl-O-heteroaryl, $C_1$-$C_3$ alkyl-O-heterocyclyl, $C_1$-$C_3$ alkyl-O-aryl, $C_1$-$C_3$ alkyl$NH_2$; or one $R^7$ or $R^8$ group combines with the $R^6$ group to form a nitrogen containing heterocyclic group; or one $R^7$ group combines with an another $R^7$ or $R^8$ group to form an optionally substituted monocyclic or bicyclic ring system having from 4 to 10 carbon atoms in the ring;

each $R^9$ and $R^{10}$ is independently H, $C_1$-$C_6$ alkyl, $C_3$-$C_8$ cycloalkyl, or heterocyclic, wherein the alkyl, cycloalkyl or heterocyclic group is optionally substituted with one or two groups independently selected from the group consisting of halo, $C_1$-$C_6$ alkyl, $C_1$-$C_6$ haloalkyl, $C_1$-$C_6$ alkylOH, $C_3$-$C_8$ cycloalkyl, —$OR^{12}$, —$NR^{13}R^{14}$, —$C(O)NR^{13}R^{14}$, —$NR^{13}COR^4$, —$SO_2NR^{13}R^{14}$, —$NR^{13}SO_2R^{14}$, —$NR^{12}SO_2NR^{13}R^{14}$, —$NR^{12}C(O)NR^{13}R^{14}$, —$NR^{13}CO_2R^{14}$, and —$OC(O)NR^{13}R^{14}$; or $R^9$ and $R^{10}$ together with the nitrogen atom to which they are attached form a mono, bicyclic bridged or spirocyclic heterocyclic ring optionally substituted with one or two groups independently selected from the group consisting of halo, —OH, —$NH_2$, —NH—$C_1$-$C_6$ alkyl, —$C_1$-$C_6$ alkyl, —$C_1$-$C_6$ alkylOH, $C_3$-$C_8$ cycloalkyl, aryl, and heterocyclic; wherein the cycloalkyl, aryl or heterocyclic group is optionally substituted with halo, —OH, —$NH_2$, —NH—$C_1$-$C_6$ alkyl, —$C_1$-$C_6$ alkyl, and —$C_1$-$C_6$ alkylOH; or $R^9$ and/or $R^{10}$ combines with Y to form a monocyclic, bicyclic, bridged or spirocyclic nitrogen containing heterocycle optionally substituted with one or two groups independently selected from the group consisting of —$C_1$-$C_6$ alkyl, —$C_1$-$C_6$ alkylOH, $C_3$-$C_8$ cycloalkyl, —OH, —$NH_2$, and —NH—$C_1$-$C_6$ alkyl; each $R^{12}$, $R^{13}$ and $R^{14}$ is independently H, $C_1$-$C_6$ alkyl, $C_3$-$C_8$ cycloalkyl, or heterocyclic, wherein the $C_1$-$C_6$ alkyl, $C_3$-$C_8$ cycloalkyl group, or heterocyclic, is optionally substituted with one or two groups independently selected from the group consisting of —OH, —$NH_2$, —$N(CH_3)_2$, $C_1$-$C_6$ haloalkyl; or $R^{13}$ and $R^{14}$ together with the atom to which they are attached form a heterocyclic ring;

or a pharmaceutically acceptable salt, stereoisomer or mixture of stereoisomer thereof.

In one embodiment of the compound of formula (V), $R^4$ is H, $NR^aR^b$, —$OC_2$-$C_6$ alkyl$NR^aR^b$, $C_1$-$C_6$ alkylN-$R^aR^b$, —$C(O)NR^aR^b$, or $NR^aC(O)NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$C(O)C_1$-$C_6$ alkyl, —$C(O)OC_1$-$C_6$ alkyl, $C_0$-$C_3$ alkyl$NR^cR^d$, $C_1$-$C_3$alkyl$C(O)NH_2$, $C_1$-$C_3$alkyl$C(O)NHC_1$-$C_3$alkyl, $C_1$-$C_6$ alkyl$C_3$-$C_6$ cycloalkyl, $SO_2C_1$-$C_3$alkyl, $SO_2C_3$-$C_6$cycloalkyl, —$C_1$-$C_3$ alkyl$SO_2NR^cR^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^eR^f$, —$SO_2R^e$, $SO_2NR^eR^f$ and $C_1$-$C_6$ alkyl-O—$C_1$-$C_6$ alkyl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH;

$R^6$ is H, $C_1$-$C_6$ alkyl, or $C_3$-$C_8$ cycloalkyl; or $R^6$ combines with Y, $R^9$, or $R^{10}$ to form an optionally substituted 4-8 membered nitrogen containing heterocyclic group.

In one embodiment of the compound of formula (V), $R^4$ is H, $NR^aR^b$, $C_1$-$C_6$ alkyl$NR^aR^b$, —$C(O)NR^aR^b$, or $NR^aC(O)NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$C(O)C_1$-$C_6$ alkyl, —$C(O)OC_1$-$C_6$ alkyl, $C_0$-$C_3$ alkyl$NR^cR^d$, $C_1$-$C_3$alkyl$C(O)NH_2$, $C_1$-$C_3$alkyl$C(O)NHC_1$-$C_3$alkyl, $C_1$-$C_6$ alkyl$C_3$-$C_6$ cycloalkyl, $SO_2C_1$-$C_3$alkyl, $SO_2C_3$-$C_6$cycloalkyl, —$C_1$-$C_3$ alkyl$SO_2NR^cR^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^eR^f$, —$SO_2R^e$, $SO_2NR^eR^f$ and $C_1$-$C_6$ alkyl-O—$C_1$-$C_6$ alkyl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH;

$R^6$ is H.

In another embodiment, the disclosure provides compounds of Formula VI:

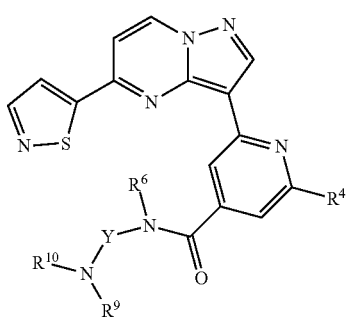

(VI)

wherein
$R^4$ is H, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkyl$C_3$-$C_6$ cycloalkyl, —NR$^a$R$^b$, $C_1$-$C_6$ alkylNR$^a$R$^b$, $C_1$-$C_6$alkyl-O—$C_1$-$C_6$ alkylNR$^a$R$^b$, —OC$_2$-$C_6$alkylNR$^a$R$^b$, —C(O)NR$^a$R$^b$, —NR$^a$C(O)NR$^a$R$^b$, —NR$^a$C(O)R$^a$, —NR$^a$C(O)OR$^a$, aryl, heteroaryl, mono, bicyclic, bridged or spirocyclic carbocyclic or heterocyclic group, —O—$C_0$-$C_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —OC$_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkylNR$^a$CHR$^a$C(O)NHR$^a$, —C(O)R$^a$, —COOR$^a$, —NHC(O)NHR$^a$, —NHC(O)R$^a$, —NHC(O)OR$^a$, C(O)NR$^a$R$^b$, —NR$^a$R$^b$, —NHC$_1$-$C_3$alkylNR$^a$R$^b$, SO$_2$R$^a$, —NHSO$_2$R$^a$, SO$_2$NR$^a$R$^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group combines to form a mono, bicyclic, bridged or spirocyclic carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, $C_1$-$C_6$ alkyl, $C_3$-$C_8$ cycloalkyl, $C_1$-$C_6$ haloalkyl, $C_1$-$C_6$ alkylOH, —OC$_1$-$C_6$ alkyl, —OC$_1$-$C_6$ haloalkyl, $C_1$-$C_6$ alkyl $C_3$-$C_6$ cycloalkyl, $C_1$-$C_6$ alkyl-O—$C_1$-$C_6$ alkyl, $C_0$-$C_3$ alkylNR$^a$CHR$^a$C(O)NHR$^a$, C(O)NR$^a$R$^b$, —SO$_2$R$^a$, and SO$_2$NR$^a$R$^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)C$_1$-$C_6$ alkyl, —C(O)OC$_1$-$C_6$ alkyl, $C_0$-$C_3$ alkylNR$^c$R$^d$, $C_1$-$C_3$alkylC(O)NH$_2$, $C_1$-$C_3$alkylC(O)NHC$_1$-$C_3$alkyl, $C_1$-$C_6$ alkylC$_3$-$C_6$ cycloalkyl, SO$_2$C$_1$-$C_3$alkyl, SO$_2$C$_3$-$C_6$cycloalkyl, aryl, heterocyclic, or $C_1$-$C_6$ alkylheterocyclic; wherein the cycloalkyl, aryl or heterocyclic group is optionally substituted with one to four groups independently selected from —OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a monocyclic, bicyclic, bridged or spirocyclic heterocyclic group optionally substituted with a group selected from OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkylC$_3$-$C_6$ cycloalkyl, SO$_2$C$_1$-$C_6$ alkyl, and $C_1$-$C_6$ alkyl-O—$C_1$-$C_6$ alkyl; or $R^c$ and $R^d$ combine to form mono or bicyclic, bridged or spirocyclic heterocycle optionally substituted with a group selected from OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl; wherein $R^e$ and $R^f$ are independently selected from $C_1$-$C_6$ alkyl, $C_1$-$C_6$ alkylOH, and $C_1$-$C_6$ alkyl aryl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —OC$_1$-$C_6$ haloalkyl, and $C_1$-$C_6$ alkylOH;

$R^6$ is H, $C_1$-$C_6$ alkyl, $C_3$-$C_8$ cycloalkyl, $C_1$-$C_6$ haloalkyl, $C_1$-$C_6$ alkyl-OH, or $C_1$-$C_6$ alkoxy; or $R^6$ combines with Y to form a 4-8 membered nitrogen containing heterocyclic group;

Y is —(CR$^7$R$^8$)$_n$ wherein n is 0, 1, 2 or 3;

each $R^7$ or $R^8$ is independently selected from H, $C_1$-$C_6$ alkyl, $C_1$-$C_6$ alkylOH, $C_1$-$C_3$ alkyl-O-heteroaryl, $C_1$-$C_3$ alkyl-O-heterocyclyl, $C_1$-$C_3$ alkyl-O-aryl, $C_1$-$C_3$ alkylNH$_2$; or one $R^7$ or $R^8$ group combines with the $R^6$ group to form a nitrogen containing heterocyclic group; or one $R^7$ group combines with an another $R^7$ or $R^8$ group to form an optionally substituted monocyclic or bicyclic ring system having from 4 to 10 carbon atoms in the ring;

each $R^9$ and $R^{10}$ is independently H, $C_1$-$C_6$ alkyl, $C_3$-$C_8$ cycloalkyl, or heterocyclic, wherein the alkyl, cycloalkyl or heterocyclic group is optionally substituted with one or two groups independently selected from the group consisting of halo, $C_1$-$C_6$ alkyl, $C_1$-$C_6$ haloalkyl, $C_1$-$C_6$ alkylOH, $C_3$-$C_8$ cycloalkyl, —OR$^{12}$, —NR$^{13}$R$^{14}$, —C(O)NR$^{13}$R$^{14}$, —NR$^{13}$COR$^{14}$, —SO$_2$NR$^{13}$R$^{14}$, —NR$^{13}$SO$_2$R$^{14}$, —NR$^2$SO$_2$NR$^{13}$R$^{14}$, —NR$^{12}$C(O)NR$^{13}$R$^{14}$, —NR$^{13}$CO$_2$R$^{14}$, and —OC(O)NR$^{13}$R$^{14}$; or $R^9$ and $R^{10}$ together with the nitrogen atom to which they are attached form a mono, bicyclic bridged or spirocyclic heterocyclic ring optionally substituted with one or two groups independently selected from the group consisting of halo, —OH, —NH$_2$, —NH—$C_1$-$C_6$ alkyl, —$C_1$-$C_6$ alkyl, —$C_1$-$C_6$ alkylOH, $C_3$-$C_8$ cycloalkyl, aryl, and heterocyclic; wherein the cycloalkyl, aryl or heterocyclic group is optionally substituted with halo, —OH, —NH$_2$, —NH—$C_1$-$C_6$ alkyl, —$C_1$-$C_6$ alkyl, and —$C_1$-$C_6$ alkylOH; or $R^9$ and/or $R^{10}$ combines with Y to form a monocyclic, bicyclic, bridged or spirocyclic nitrogen containing heterocycle optionally substituted with one or two groups independently selected from the group consisting of —$C_1$-$C_6$ alkyl, —$C_1$-$C_6$ alkylOH, $C_3$-$C_8$ cycloalkyl, —OH, —NH$_2$, and —NH—$C_1$-$C_6$ alkyl;

each $R^{12}$, $R^{13}$ and $R^{14}$ is independently H, $C_1$-$C_6$ alkyl, $C_3$-$C_8$ cycloalkyl, or heterocyclic, wherein the $C_1$-$C_6$ alkyl, $C_3$-$C_8$ cycloalkyl group, or heterocyclic, is optionally substituted with one or two groups independently selected from the group consisting of —OH, —NH$_2$, —N(CH$_3$)$_2$, C$_1$-C$_6$ haloalkyl; or R$^{13}$ and R$^{14}$ together with the atom to which they are attached form a heterocyclic ring;

or a pharmaceutically acceptable salt, stereoisomer or mixture of stereoisomer thereof.

In one embodiment of the compound of formula (VI);
R$^4$ is H, NR$^a$R$^b$, —OC$_2$-C$_6$ alkylNR$^a$R$^b$, C$_1$-C$_6$ alkylN-R$^a$R$^b$, —C(O)NR$^a$R$^b$, or NR$^a$C(O)NR$^a$R$^b$;

R$^a$ and R$^b$ are each independently H, OH, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —C(O)C$_1$-C$_6$ alkyl, —C(O)OC$_1$-C$_6$ alkyl, C$_0$-C$_3$ alkylNR$^c$R$^d$, C$_1$-C$_3$alkylC(O)NH$_2$, C$_1$-C$_3$alkylC(O)NHC$_1$-C$_3$alkyl, C$_1$-C$_6$ alkylC$_3$-C$_6$ cycloalkyl, SO$_2$C$_1$-C$_3$alkyl, SO$_2$C$_3$-C$_6$cycloalkyl, —C$_1$-C$_3$ alkylSO$_2$NR$^c$R$^d$, aryl, heteroaryl, heterocyclic, or C$_1$-C$_6$ alkylheterocyclic; wherein the cycloalkyl, aryl, heteroaryl or heterocyclic group is optionally substituted with one to four groups independently selected from —OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, C$_1$-C$_6$ alkyl-O—C$_1$-C$_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^c$R$^d$, —SO$_2$R$^c$, SO$_2$NR$^c$R$^d$ and C$_1$-C$_6$ alkyl-O—C$_1$-C$_6$ alkyl;

R$^c$ and R$^d$ are independently selected from H, C$_1$-C$_6$ alkyl, C$_3$-C$_8$ cycloalkyl, C$_2$-C$_6$ haloalkyl, C$_2$-C$_6$ alkylOH, C$_1$-C$_6$ alkylC$_3$-C$_6$ cycloalkyl, SO$_2$C$_1$-C$_6$ alkyl, and C$_1$-C$_6$ alkyl-O—C$_1$-C$_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^e$R$^f$, —SO$_2$R$^e$, SO$_2$NR$^e$R$^f$ and C$_1$-C$_6$ alkyl-O—C$_1$-C$_6$ alkyl;

R$^e$ and R$^f$ are at each occurrence independently selected from the group consisting of: C$_1$-C$_6$ alkyl, C$_3$-C$_8$ cycloalkyl, C$_2$-C$_6$ haloalkyl, C$_1$-C$_6$ haloalkyl, —OC$_1$-C$_6$ haloalkyl, and C$_1$-C$_6$ alkylOH;

R$^6$ is H, C$_1$-C$_6$ alkyl, or C$_3$-C$_8$ cycloalkyl; or R$^6$ combines with Y, R$^9$, or R$^{10}$ to form an optionally substituted 4-8 membered nitrogen containing heterocyclic group.

In one embodiment of the compound of formula (VI);
R$^4$ is H, NR$^a$R$^b$, C$_1$-C$_6$ alkylNR$^a$R$^b$, —C(O)NR$^a$R$^b$, or NR$^a$C(O)NR$^a$R$^b$;

R$^a$ and R$^b$ are each independently H, OH, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —C(O)C$_1$-C$_6$ alkyl, —C(O)OC$_1$-C$_6$ alkyl, C$_0$-C$_3$ alkylNR$^c$R$^d$, C$_1$-C$_3$alkylC(O)NH$_2$, C$_1$-C$_3$alkylC(O)NHC$_1$-C$_3$alkyl, C$_1$-C$_6$ alkylC$_3$-C$_6$ cycloalkyl, SO$_2$C$_1$-C$_3$alkyl, SO$_2$C$_3$-C$_6$cycloalkyl, —C$_1$-C$_3$ alkylSO$_2$NR$^c$R$^d$, aryl, heteroaryl, heterocyclic, or C$_1$-C$_6$ alkylheterocyclic; wherein the cycloalkyl, aryl, heteroaryl or heterocyclic group is optionally substituted with one to four groups independently selected from —OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, C$_1$-C$_6$ alkyl-O—C$_1$-C$_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^c$R$^d$, —SO$_2$R$^c$, SO$_2$NR$^c$R$^d$ and C$_1$-C$_6$ alkyl-O—C$_1$-C$_6$ alkyl;

R$^c$ and R$^d$ are independently selected from H, C$_1$-C$_6$ alkyl, C$_3$-C$_8$ cycloalkyl, C$_2$-C$_6$ haloalkyl, C$_2$-C$_6$ alkylOH, C$_1$-C$_6$ alkylC$_3$-C$_6$ cycloalkyl, SO$_2$C$_1$-C$_6$ alkyl, and C$_1$-C$_6$ alkyl-O—C$_1$-C$_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^e$R$^f$, —SO$_2$R$^e$, SO$_2$NR$^e$R$^f$ and C$_1$-C$_6$ alkyl-O—C$_1$-C$_6$ alkyl;

R$^e$ and R$^f$ are at each occurrence independently selected from the group consisting of: C$_1$-C$_6$ alkyl, C$_3$-C$_8$ cycloalkyl, C$_2$-C$_6$ haloalkyl, C$_1$-C$_6$ haloalkyl, —OC$_1$-C$_6$ haloalkyl, and C$_1$-C$_6$ alkylOH;

R$^6$ is H.

Accordingly, the present disclosure provides novel compounds that function as CaM kinase inhibitors. In one embodiment, the disclosure provides compounds of Formula VII:

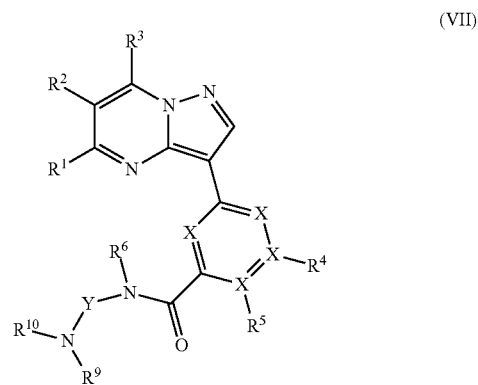

(VII)

wherein

R$^1$ is aryl, heteroaryl or heterocyclic; wherein the aryl, heteroaryl or heterocyclic group is optionally substituted with one, two or three groups independently selected from the group consisting of halo, hydroxy, C$_1$-C$_6$ alkyl, C$_1$-C$_6$ haloalkyl, C$_1$-C$_6$ alkoxy, —OC$_1$-C$_6$haloalkyl, —SC$_1$-C$_6$alkyl, —NHSO$_2$R$^a$, and C$_0$-C$_6$ alkylene-NR$^a$R$^b$;

R$^2$ and R$^3$ are each independently selected from the group consisting of H, halo and C$_1$-C$_6$ alkyl;

each X is independently CH or N; provided that there are no more than 3 nitrogen atoms in the ring;

R$^4$ is absent when X to which it is attached is N; or R$^4$ is H, halo, cyano, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ haloalkoxy, C$_1$-C$_6$ alkylC$_3$-C$_6$ cycloalkyl, —NR$^a$R$^b$, C$_1$-C$_6$ alkylNR$^a$R$^b$, C$_1$-C$_6$ alkyl-O—C$_1$-C$_6$ alkylN-R$^a$R$^b$, —OC$_2$-C$_6$ alkylNR$^a$R$^b$, —C(O)NR$^a$R$^b$, —NR$^a$C(O)NR$^a$R$^b$, —NR$^a$C(O)R$^a$, —NR$^a$C(O)OR$^a$, aryl, heteroaryl, mono, bicyclic, bridged or spirocyclic carbocyclic or heterocyclic group, —O—C$_0$-C$_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —O$C_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkylNR$^a$CHR$^a$C(O)NHR$^a$, —C(O)R$^a$, —COOR$^a$, —NHC(O)NHR$^a$, —NHC(O)R$^a$, —NHC(O)OR$^a$, C(O)NR$^a$R$^b$, —NR$^a$R$^b$, —NHC$_1$-$C_3$alkylNR$^a$R$^b$, SO$_2$R$^a$, —NHSO$_2$R$^a$, SO$_2$NR$^a$R$^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group combines to form a mono, bicyclic, spirocyclic, or bridged carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, $C_1$-$C_6$ alkyl, $C_3$-$C_8$ cycloalkyl, $C_1$-$C_6$ haloalkyl, $C_1$-$C_6$ alkylOH, —O$C_1$-$C_6$ alkyl, —O$C_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkylNR$^a$CHR$^a$C(O)NHR$^a$, C(O)NR$^a$R$^b$, —SO$_2$R$^a$, and SO$_2$NR$^a$R$^b$;

R$^a$ and R$^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkylNR$^c$R$^d$, $C_1$-$C_3$alkylC(O)NH$_2$, $C_1$-$C_3$alkylC(O)NH$C_1$-$C_3$alkyl, $C_1$-$C_6$ alkyl$C_3$-$C_6$ cycloalkyl, SO$_2$$C_1$-$C_3$alkyl, SO$_2$$C_3$-$C_6$cycloalkyl, —$C_1$-$C_3$ alkylSO$_2$NR$^c$R$^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^c$R$^d$, —SO$_2$R$^c$, SO$_2$NR$^c$R$^d$ and $C_1$-$C_6$ alkyl-O—$C_1$-$C_6$ alkyl;

R$^c$ and R$^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, SO$_2$$C_1$-$C_6$ alkyl, and $C_1$-$C_6$ alkyl-O—$C_1$-$C_6$ alkyl; or R$^c$ and R$^d$ combine to form mono, bicyclic, bridged or spirocyclic heterocyclic group optionally substituted with a group selected from OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)NR$^e$R$^f$, —SO$_2$R$^e$, SO$_2$NR$^e$R$^f$ and $C_1$-$C_6$ alkyl-O—$C_1$-$C_6$ alkyl;

R$^e$ and R$^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —O$C_1$-$C_6$ haloalkyl, and $C_1$-$C_6$ alkylOH;

R$^5$ is H, halo, cyano, NH$_2$, NH$C_1$-$C_6$ alkyl, N($C_1$-$C_6$ alkyl)$_2$, $C_1$-$C_6$ alkyl, $C_3$-$C_8$ cycloalkyl, $C_1$-$C_6$ alkyl$C_3$- $C_8$ cycloalkyl, $C_1$-$C_6$ haloalkyl, —O$C_1$-$C_6$ haloalkyl, $C_1$-$C_6$ alkyl-OH, or $C_1$-$C_6$ alkoxy;

R$^6$ is H, $C_1$-$C_6$ alkyl, $C_3$-$C_8$ cycloalkyl, $C_2$-$C_6$ haloalkyl, $C_2$-$C_6$ alkyl-OH, or $C_1$-$C_6$ alkoxy; or R$^6$ combines with Y, R$^9$, or R$^{10}$ to form an optionally substituted 4-8 membered nitrogen containing heterocyclic group;

Y is —(CR$^7$R$^8$)$_n$ wherein n is 2 or 3;

each R$^7$ or R$^8$ is independently selected from H, $C_1$-$C_6$ alkyl, $C_1$-$C_3$ alkylOH, $C_1$-$C_3$ alkylNH$_2$ and $C_1$-$C_3$alkyl-O-heterocyclic; or one R$^7$ or R$^8$ group combines with the R$^6$ group to form an optionally substituted nitrogen containing heterocyclic group; or one R$^7$ group combines with another R$^7$ or an R$^8$ group to form an optionally substituted monocyclic or bicyclic, bridged or spirocyclic ring system having from 4 to 10 carbon atoms in the ring; wherein the optional substituents include 1 or 2 groups independently selected from halo, —OH, NH$_2$, cyano, $C_1$-$C_6$ alkyl, $C_1$-$C_6$ haloalkyl, $C_1$-$C_6$ alkylOH, and $C_3$-$C_8$ cycloalkyl;

each R$^9$ and R$^{10}$ is independently H, $C_1$-$C_6$ alkyl, $C_3$-$C_8$ cycloalkyl, $C_2$-$C_6$ haloalkyl, $C_2$-$C_6$ alkylOH, $C_3$-$C_8$ cycloalkyl, $C_1$-$C_6$ alkyl$C_3$-$C_8$ cycloalkyl, —C(O)OR$^{13}$, —C(O)NR$^{13}$R$^{14}$ or heterocyclic, wherein the alkyl, cycloalkyl or heterocyclic group is optionally substituted with one or two groups independently selected from the group consisting of halo, $C_1$-$C_6$ alkyl, $C_1$-$C_6$ haloalkyl, $C_1$-$C_6$ alkylOH, $C_3$-$C_8$ cycloalkyl, —OR$^{12}$, —NR$^{13}$R$^{14}$, —C(O)NR$^{13}$R$^{14}$, —NR$^{13}$COR$^{14}$, —SO$_2$NR$^{13}$R$^{14}$, —NR$^{13}$SO$_2$R$^{14}$, —NR$^{12}$SO$_2$NR$^{13}$R$^{14}$, —NR$^{12}$C(O)NR$^{13}$R$^{14}$, —NR$^{13}$CO$_2$R$^{14}$, and —OC(O)NR$^{13}$R$^{14}$; or R$^9$ and R$^{10}$ together with the nitrogen atom to which they are attached form a mono, bicyclic, bridged or spirocyclic heterocyclic ring optionally substituted with one or two groups independently selected from the group consisting of halo, —OH, —NH$_2$, —NH—$C_1$-$C_6$ alkyl, —$C_1$-$C_6$ alkyl, —$C_1$-$C_6$ alkylOH, $C_3$-$C_8$ cycloalkyl, aryl, and heterocyclic; wherein the cycloalkyl, aryl or heterocyclic group is optionally substituted with halo, —OH, —NH$_2$, —NH—$C_1$-$C_6$ alkyl, —$C_1$-$C_6$ alkyl, and —$C_1$-$C_6$ alkylOH; or R$^9$ and/or R$^{10}$ combines with Y to form a mono, bicyclic, bridged or spirocyclic nitrogen containing heterocycle optionally substituted with one or two groups independently selected from the group consisting of —$C_1$-$C_6$ alkyl, —$C_1$-$C_6$ alkylOH, $C_3$-$C_8$ cycloalkyl, —OH, —NH$_2$, and —NH—$C_1$-$C_6$ alkyl;

each R$^{12}$, R$^{13}$ and R$^{14}$ is independently H, $C_1$-$C_6$ alkyl, $C_3$-$C_8$ cycloalkyl, or heterocyclic, wherein the $C_1$-$C_6$ alkyl, $C_3$-$C_8$ cycloalkyl group, or heterocyclic, group is optionally substituted with one or two groups independently selected from the group consisting of —OH, —NH$_2$, —N(CH$_3$)$_2$, $C_1$-$C_6$ haloalkyl; or R$^{13}$ and R$^{14}$ together with the atom to which they are attached form a heterocyclic ring;

or a pharmaceutically acceptable salt, stereoisomer or mixture of stereoisomer thereof.

In one embodiment of the compound of formula (VII):
R$^4$ is H, NR$^a$R$^b$, —O$C_2$-$C_6$ alkylNR$^a$R$^b$, $C_1$-$C_6$ alkylN-R$^a$R$^b$, —C(O)NR$^a$R$^b$, or NR$^a$C(O)NR$^a$R$^b$;
only one X group is N;
R$^a$ and R$^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkylNR$^c$R$^d$, $C_1$-$C_3$alkylC(O)NH$_2$, $C_1$-$C_3$alkylC(O)NH$C_1$-$C_3$alkyl, $C_1$-$C_6$ alkyl$C_3$-$C_6$ cycloalkyl, SO$_2$$C_1$-$C_3$alkyl, SO$_2$$C_3$-$C_6$cycloalkyl, —$C_1$-$C_3$ alkylSO$_2$NR$^c$R$^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^eR^f$, —$SO_2R^e$, $SO_2NR^eR^f$ and $C_1$-$C_6$ alkyl-O—$C_1$-$C_6$ alkyl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH;

$R^6$ is H, $C_1$-$C_6$ alkyl, or $C_3$-$C_8$ cycloalkyl; or $R^6$ combines with Y, $R^9$, or $R^{10}$ to form an optionally substituted 4-8 membered nitrogen containing heterocyclic group.

In one embodiment of the compound of formula (VII):

$R^4$ is H, $NR^aR^b$, $C_1$-$C_6$ alkyl$NR^aR^b$, —C(O)$NR^aR^b$, or $NR^aC(O)NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)$OC_1$-$C_6$ alkyl, $C_0$-$C_3$ alkyl$NR^cR^d$, $C_1$-$C_3$alkylC(O)$NH_2$, $C_1$-$C_3$alkylC(O)$NHC_1$-$C_3$alkyl, $C_1$-$C_6$ alkyl$C_3$-$C_6$ cycloalkyl, $SO_2C_1$-$C_3$alkyl, $SO_2C_3$-$C_6$cycloalkyl, —$C_1$-$C_3$ alkyl$SO_2NR^cR^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^eR^f$, —$SO_2R^e$, $SO_2NR^eR^f$ and $C_1$-$C_6$ alkyl-O—$C_1$-$C_6$ alkyl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH;

$R^6$ is H.

In certain embodiments of any one of compounds of formula I to VII, the group $R^4$ is H or halo. In one embodiment of the compound of formula (VII) only two of the X groups are N.

In certain embodiments of any one of the compounds of formula I to VII, the group $R^4$ is selected from the group consisting of halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkyl$C_3$-$C_6$ cycloalkyl, —$NR^aR^b$, $C_1$-$C_6$ alkyl$NR^aR^b$, $C_1$-$C_6$alkyl-O—$C_1$-$C_6$ alkyl$NR^aR^b$, —$OC_2$-$C_6$ alkyl$NR^aR^b$, —C(O)$NR^aR^b$, —$NR^aC(O)NR^aR^b$, —$NR^aC(O)R^a$, and —$NR^aC(O)OR^a$, wherein $R^a$ and $R^b$ are as described previously.

In certain embodiments of any one of compounds of formula I to VII, the group $R^4$ is aryl, heteroaryl, mono, bicyclic, bridged or spirocyclic carbocyclic or heterocyclic group, —O—$C_0$-$C_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$OC_1$-$C_6$ haloalkoxy, $C_1$-$C_6$ alkyl $C_3$-$C_8$ cycloalkyl, $C_1$-$C_6$ alkyl-O—$C_1$-$C_6$ alkyl, $C_0$-$C_3$ alkyl$NR^aCHR^aC(O)NHR^a$, —C(O)$R^a$, —$COOR^a$, —NHC(O)$NHR^a$, —NHC(O)$R^a$, —NHC(O)$OR^a$, C(O)$NR^aR^b$, —$NR^aR^b$, —$NHC_1$-$C_3$alkyl$NR^aR^b$, $SO_2R^a$, —$NHSO_2R^a$, $SO_2NR^aR^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group combines to form a mono, bicyclic, spirocyclic, or bridged carbocyclic or heterocyclic ring wherein said heteroaryl, mono, bicyclic, bridged or spirocyclic carbocyclic or heterocyclic group is optionally substituted with one to four groups independently selected from the group consisting of OH, halo, cyano, $C_1$-$C_6$ alkyl, $C_3$-$C_8$ cycloalkyl, $C_1$-$C_6$ haloalkyl, $C_1$-$C_6$ alkylOH, —$OC_1$-$C_6$ alkyl, —$OC_1$-$C_6$ haloalkyl, $C_1$-$C_6$ alkyl $C_3$-$C_6$ cycloalkyl, $C_1$-$C_6$ alkyl-O—$C_1$-$C_6$ alkyl, $C_0$-$C_3$ alkyl$NR^aCHR^aC(O)NHR^a$, C(O)$NR^aR^b$, —$SO_2R^a$, and $SO_2NR^aR^b$; wherein $R^a$ and $R^b$ are as described previously.

In certain embodiments of any one of compounds of formula I to VII, the group $R^4$ is $NR^aR^b$, $C_1$-$C_6$ alkyl$NR^aR^b$, —C(O)$NR^aR^b$, or $NR^a$-C(O)$NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)$OC_1$-$C_6$ alkyl, $C_0$-$C_3$ alkyl$NR^cR^d$, $C_1$-$C_3$alkylC(O)$NH_2$, $C_1$-$C_3$alkylC(O)$NHC_1$-$C_3$alkyl, $C_1$-$C_6$ alkyl$C_3$-$C_6$ cycloalkyl, $SO_2C_1$-$C_3$alkyl, $SO_2C_3$-$C_6$cycloalkyl, —$C_1$-$C_3$ alkyl$SO_2NR^cR^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-C$_6$ cycloalkyl, C$_1$-C$_6$ alkyl-O—C$_1$-C$_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^c$R$^d$, —SO$_2$R$^c$, SO$_2$NR$^c$R$^d$ and C$_1$-C$_6$ alkyl-O—C$_1$-C$_6$ alkyl;

R$^c$ and R$^d$ are independently selected from H, C$_1$-C$_6$ alkyl, C$_3$-C$_8$ cycloalkyl, C$_2$-C$_6$ haloalkyl, C$_2$-C$_6$ alkylOH, C$_1$-C$_6$ alkylC$_3$-C$_6$ cycloalkyl, SO$_2$C$_1$-C$_6$ alkyl, and C$_1$-C$_6$ alkyl-O—C$_1$-C$_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^e$R$^f$, —SO$_2$R$^e$, SO$_2$NR$^e$R$^f$ and C$_1$-C$_6$ alkyl-O—C$_1$-C$_6$ alkyl;

R$^e$ and R$^f$ are at each occurrence independently selected from the group consisting of: C$_1$-C$_6$ alkyl, C$_3$-C$_8$ cycloalkyl, C$_2$-C$_6$ haloalkyl, C$_1$-C$_6$ haloalkyl, —OC$_1$-C$_6$ haloalkyl, and C$_1$-C$_6$ alkylOH; and R$^6$ is H.

In certain embodiments of any one of compounds of formula I to VII, the group R$^4$ is is aryl, heteroaryl, mono, bicyclic, bridged or spirocyclic carbocyclic or heterocyclic group, —O—C$_0$-C$_3$ alkylheterocyclyl, or C$_1$-C$_6$ alkylheterocyclic; wherein the alkyl, cycloalkyl, aryl, heteroaryl, carbocyclic or heterocyclic group is optionally substituted with one to four groups independently selected from —OH, oxo, halo, cyano, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —OC$_1$-C$_6$ haloalkyl, C$_1$-C$_6$ alkyl C$_3$-C$_8$ cycloalkyl, C$_1$-C$_6$ alkyl-O—C$_1$-C$_6$ alkyl, C$_0$-C$_3$ alkylNR$^a$CHR$^a$C(O)NHR$^a$, —C(O)R$^a$, —COOR$^a$, —NHC(O)NHR$^a$, —NHC(O)R$^a$, —NHC(O)OR$^a$, C(O)NR$^a$R$^b$, —NR$^a$R$^b$, —NHC$_1$-C$_3$alkylNR$^a$R$^b$, SO$_2$R$^a$, —NHSO$_2$R$^a$, SO$_2$NR$^a$R$^b$, aryl, heteroaryl, mono, bicyclic, bridged or spirocyclic carbocyclic or heterocyclic group, and C$_1$-C$_6$ alkylheterocyclic.

In certain embodiments of the compounds of any of formula I-VII, R$^4$ is any one of the groups selected from:

—NH$_2$, NHCH$_3$, CF$_3$, —C(CH$_3$)$_3$,

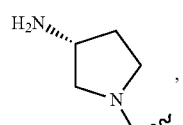

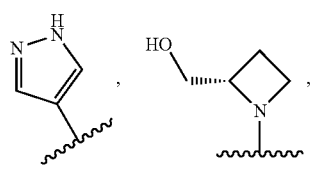

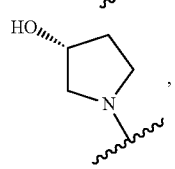

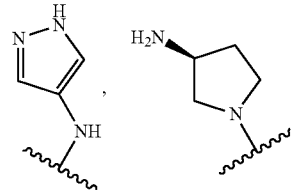

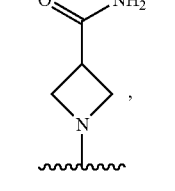

-continued

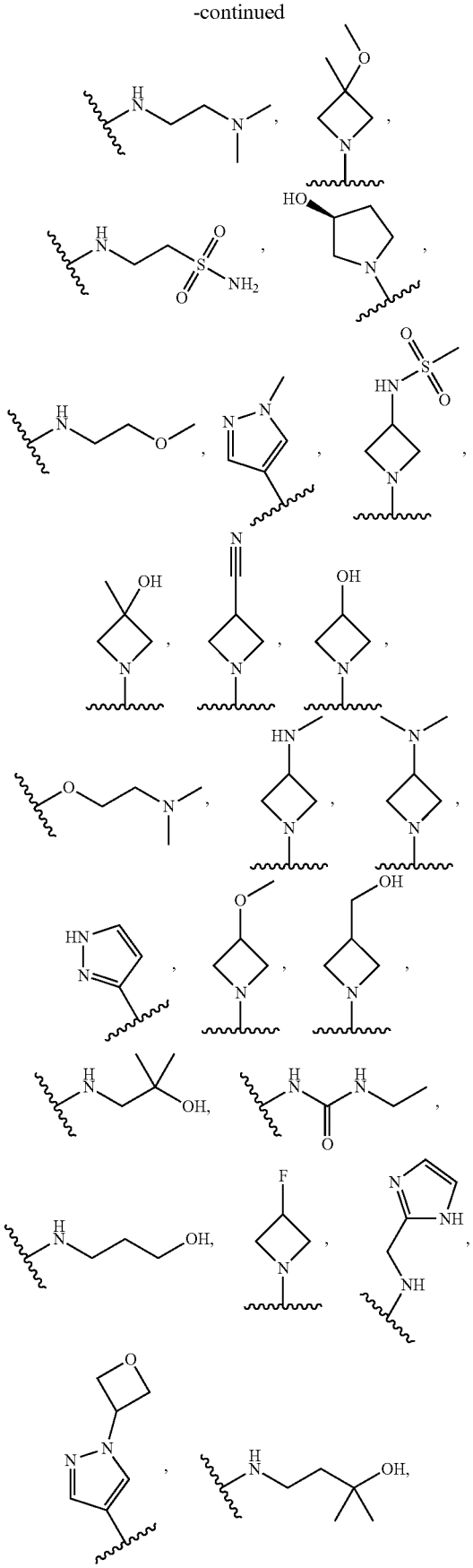

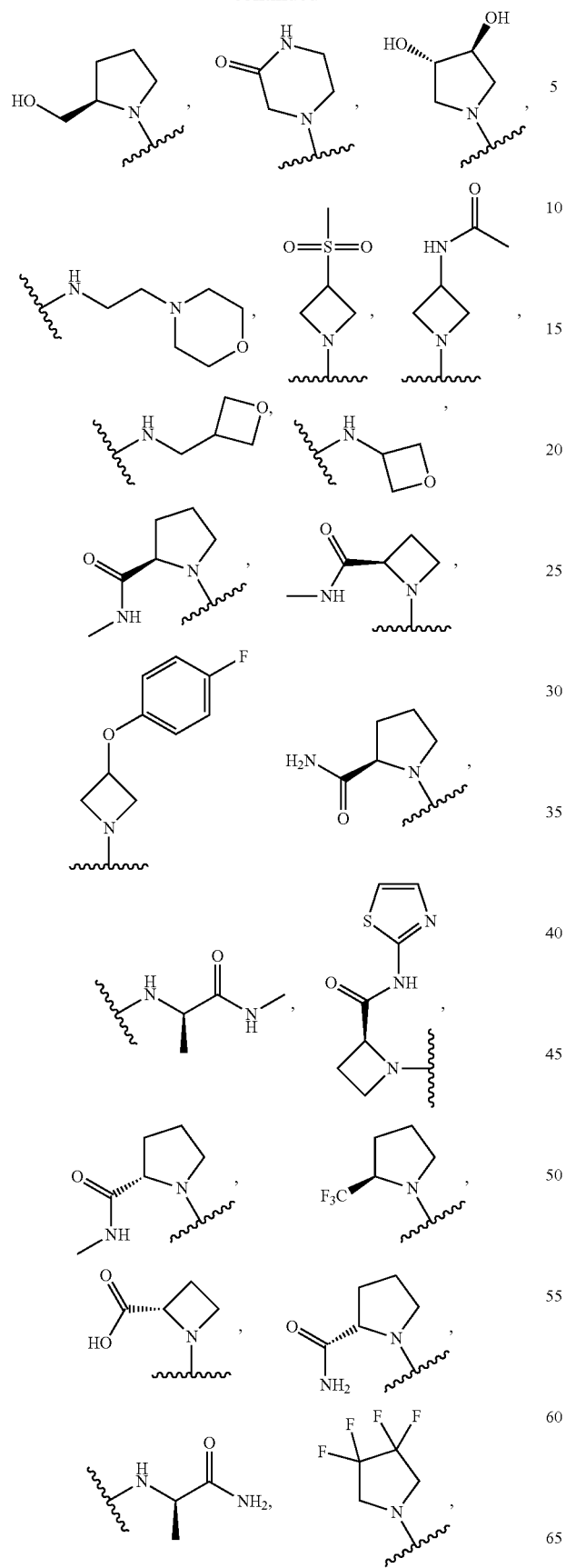
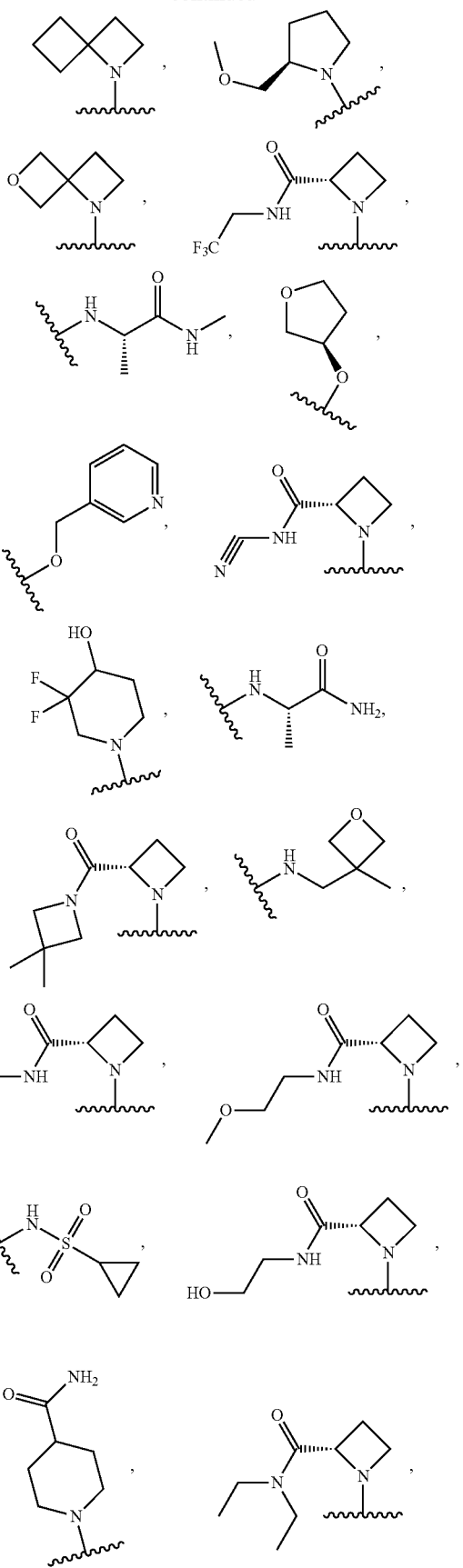

-continued

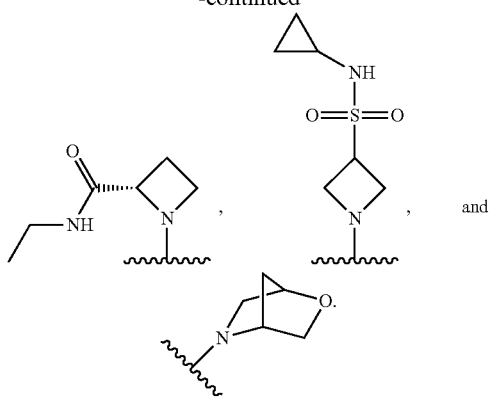

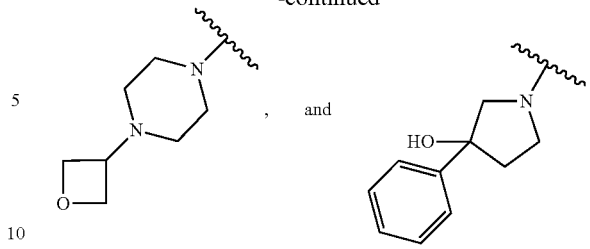

In certain embodiments of the compounds of formula I to VII, the group $R^4$ is selected from the group consisting of:

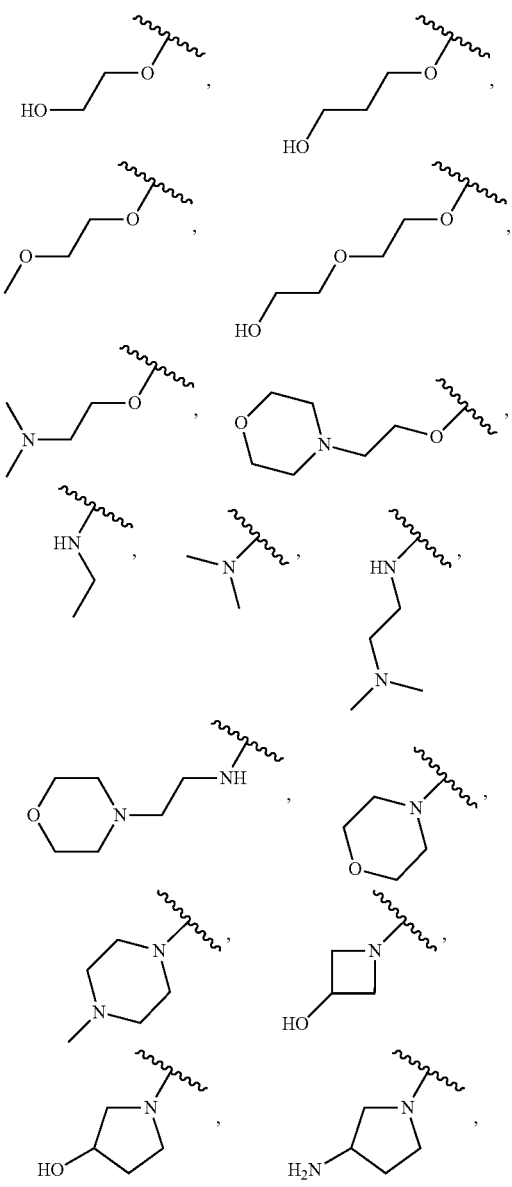

In certain embodiments of compounds of any one of formula I to VII, the group $R^6$ is H.

In yet another embodiment, the disclosure provides a compound or groups of compounds selected from the group consisting of:

N-(2-(diethylamino)ethyl)-2-(5-(thiophen-2-yl)pyrazolo[1,5-a]pyrimidin-3-yl)isonicotinamide;

N-(2-(diethylamino)propyl)-2-(5-(thiophen-2-yl)pyrazolo[1,5-a]pyrimidin-3-yl)isonicotinamide;

N-((hexahydro-1H-pyrrolizin-7a-yl)methyl)-2-(5-(thiophen-2-yl)pyrazolo[1,5-a]pyrimidin-3-yl)isonicotinamide;

(S)—N-(2-(diethylamino)propyl)-2-(5-(thiophen-2-yl)pyrazolo[1,5-a]pyrimidin-3-yl)isonicotinamide;

N-(((2S,4S)-4-fluoropyrrolidin-2-yl)methyl)-2-(5-(thiophen-2-yl)pyrazolo[1,5-a]pyrimidin-3-yl)isonicotinamide;

N-(((2S,4S)-1-ethyl-4-fluoropyrrolidin-2-yl)methyl)-2-(5-(thiophen-2-yl)-3H-imidazo[4,5-b]pyridin-3-yl)isonicotinamide;

(S)—N-(azetidin-2-ylmethyl)-2-(5-(thiophen-2-yl)pyrazolo[1,5-a]pyrimidin-3-yl)isonicotinamide;

(R)—N-(azetidin-2-ylmethyl)-2-(5-(thiophen-2-yl)pyrazolo[1,5-a]pyrimidin-3-yl)isonicotinamide;

N-(2-(dimethylamino)ethyl)-2-(5-(thiophen-2-yl)pyrazolo[1,5-a]pyrimidin-3-yl)isonicotinamide;

(S)—N-((2-propylpyrrolidin-2-yl)methyl)-2-(5-(thiophen-2-yl)pyrazolo[1,5-a]pyrimidin-3-yl)isonicotinamide;

(S)—N-((2-ethylpyrrolidin-2-yl)methyl)-2-(5-(thiophen-2-yl)pyrazolo[1,5-a]pyrimidin-3-yl)isonicotinamide;

(S)—N-((2-methylpyrrolidin-2-yl)methyl)-2-(5-(thiophen-2-yl)pyrazolo[1,5-a]pyrimidin-3-yl)isonicotinamide;

N—((R)-1-((S)-pyrrolidin-2-yl)ethyl)-2-(5-(thiophen-2-yl)pyrazolo[1,5-a]pyrimidin-3-yl)isonicotinamide;

(R)—N-(2-((2,2-difluoroethyl)amino)propyl)-2-(5-(thiophen-2-yl)pyrazolo[1,5-a]pyrimidin-3-yl)isonicotinamide;

(R)—N-(1-((2,2-difluoroethyl)(ethyl)amino)propan-2-yl)-2-(5-(thiophen-2-yl)pyrazolo[1,5-a]pyrimidin-3-yl)isonicotinamide;

N-(azepan-2-ylmethyl)-2-(5-(thiophen-2-yl)pyrazolo[1,5-a]pyrimidin-3-yl)isonicotinamide;

(R)—N-((2-isobutylpyrrolidin-2-yl)methyl)-2-(5-(thiophen-2-yl)pyrazolo[1,5-a]pyrimidin-3-yl)isonicotinamide;

(R)—N-((2-(cyclopropylmethyl)pyrrolidin-2-yl)methyl)-2-(5-(thiophen-2-yl)pyrazolo[1,5-a]pyrimidin-3-yl)isonicotinamide;

N-(piperidin-2-ylmethyl)-2-(5-(thiophen-2-yl)pyrazolo[1,5-a]pyrimidin-3-yl)isonicotinamide;

(S)—N-(2-(ethylamino)propyl)-2-(5-(thiophen-2-yl)pyrazolo[1,5-a]pyrimidin-3-yl)isonicotinamide;

(S)—N-(2-((2-hydroxyethyl)amino)propyl)-2-(5-(thiophen-2-yl)pyrazolo[1,5-a]pyrimidin-3-yl)isonicotinamide;

(S)—N-(2-aminopropyl)-2-(5-(thiophen-2-yl)pyrazolo[1,5-a]pyrimidin-3-yl)isonicotinamide;

(S)—N-(2-(propylamino)propyl)-2-(5-(thiophen-2-yl)pyrazolo[1,5-a]pyrimidin-3-yl)isonicotinamide;
(S)—N-(2-((2-fluoroethyl)amino)propyl)-2-(5-(thiophen-2-yl)pyrazolo[1,5-a]pyrimidin-3-yl)isonicotinamide;
N-(2-aminobutyl)-2-(5-(thiophen-2-yl)pyrazolo[1,5-a]pyrimidin-3-yl)isonicotinamide;
(S)—N-(2-((cyclopropyl methyl)amino)propyl)-2-(5-(thiophen-2-yl)pyrazolo[1,5-a]pyrimidin-3-yl)isonicotinamide;
(S)—N-(2-((2,2-difluoroethyl)amino)propyl)-2-(5-(thiophen-2-yl)pyrazolo[1,5-a]pyrimidin-3-yl)isonicotinamide;
(S)-2-(5-(thiophen-2-yl)pyrazolo[1,5-a]pyrimidin-3-yl)-N-(2-((2,2,2-trifluoroethyl)amino)propyl)isonicotinamide;
(R)—N-(2-(ethylamino)butyl)-2-(5-(thiophen-2-yl)pyrazolo[1,5-a]pyrimidin-3-yl)isonicotinamide;
(S)—N-(2-(ethylamino)butyl)-2-(5-(thiophen-2-yl)pyrazolo[1,5-a]pyrimidin-3-yl)isonicotinamide;
N-(2-isopropylamino)butyl)-2-(5-(thiophen-2-yl)pyrazolo[1,5-a]pyrimidin-3-yl)isonicotinamide;
(S)—N-(2-(isopropylamino)propyl)-2-(5-(thiophen-2-yl)pyrazolo[1,5-a]pyrimidin-3-yl)isonicotinamide;
(R)—N-(2-(ethylamino)propyl)-2-(5-(thiophen-2-yl)pyrazolo[1,5-a]pyrimidin-3-yl)isonicotinamide;
(S)—N-(pyrrolidin-2-ylmethyl)-2-(5-(thiophen-2-yl)pyrazolo[1,5-a]pyrimidin-3-yl)isonicotinamide;
(S)—N-((1-methylpyrrolidin-2-yl)methyl)-2-(5-(thiophen-2-yl)pyrazolo[1,5-a]pyrimidin-3-yl)isonicotinamide;
(S)—N-((1-ethylpyrrolidin-2-yl)methyl)-2-(5-(thiophen-2-yl)pyrazolo[1,5-a]pyrimidin-3-yl)isonicotinamide;
N-(2-(diethylamino)propyl)-2-(5-phenylpyrazolo[1,5-a]pyrimidin-3-yl)isonicotinamide;
(S)—N-(2-(diethylamino)propyl)-2-(5-phenylpyrazolo[1,5-a]pyrimidin-3-yl)isonicotinamide;
N-(2-(dimethylamino)ethyl)-2-(5-phenylpyrazolo[1,5-a]pyrimidin-3-yl)isonicotinamide;
2-(5-phenylpyrazolo[1,5-a]pyrimidin-3-yl)-N-(piperidin-2-ylmethyl)isonicotinamide;
N-((3,3-dimethylazetidin-2-yl)methyl)-2-(5-phenylpyrazolo[1,5-a]pyrimidin-3-yl)isonicotinamide;
(S)—N-(2-(ethylamino)propyl)-2-(5-phenylpyrazolo[1,5-a]pyrimidin-3-yl)isonicotinamide;
(R)—N-((2-ethylpyrrolidin-2-yl)methyl)-2-(5-phenylpyrazolo[1,5-a]pyrimidin-3-yl)isonicotinamide;
(S)—N-(2-aminopropyl)-2-(5-phenylpyrazolo[1,5-a]pyrimidin-3-yl)isonicotinamide;
N-((2S)-2-(sec-butylamino)propyl)-2-(5-phenylpyrazolo[1,5-a]pyrimidin-3-yl)isonicotinamide;
N-(2-aminobutyl)-2-(5-phenylpyrazolo[1,5-a]pyrimidin-3-yl)isonicotinamide;
N-(2-amino-3-methylbutyl)-2-(5-phenylpyrazolo[1,5-a]pyrimidin-3-yl)isonicotinamide;
N-(2 aminopentyl)-2-(5-phenylpyrazolo[1,5-a]pyrimidin-3-yl)isonicotinamide;
(S)-2-(5-phenylpyrazolo[1,5-a]pyrimidin-3-yl)-N-(2-((pyrimidin-2-ylmethyl)amino)propyl) isonicotinamide;
N-(2-((cyclopropylmethyl)amino)butyl)-2-(5-phenylpyrazolo[1,5-a]pyrimidin-3-yl)isonicotinamide;
2-(5-phenylpyrazolo[1,5-a]pyrimidin-3-yl)-N-(2-(propylamino)butyl)isonicotinamide;
N-(2-((cyclopropyl methyl)amino)-3-methylbutyl)-2-(5-phenylpyrazolo[1,5-a]pyrimidin-3-yl)isonicotinamide;
N-(3-methyl-2-(propylamino)butyl)-2-(5-phenylpyrazolo[1,5-a]pyrimidin-3-yl)isonicotinamide;
N-(2-(ethylamino)butyl)-2-(5-phenylpyrazolo[1,5-a]pyrimidin-3-yl)isonicotinamide;
N-(2-(ethylamino)-3-methylbutyl)-2-(5-phenylpyrazolo[1,5-a]pyrimidin-3-yl)isonicotinamide;
N-((1S,2S)-2-aminocyclopentyl)-2-(5-phenylpyrazolo[1,5-a]pyrimidin-3-yl)isonicotinamide;
(R)—N-(2-amino-3-hydroxypropyl)-2-(5-phenylpyrazolo[1,5-a]pyrimidin-3-yl)isonicotinamide;
(R)—N-(2-(diethylamino)-3-hydroxypropyl)-2-(5-phenylpyrazolo[1,5-a]pyrimidin-3-yl)isonicotinamide;
(R)—N-(2-(ethylamino)-3-hydroxypropyl)-2-(5-phenylpyrazolo[1,5-a]pyrimidin-3-yl)isonicotinamide;
N-(2-(diethylamino)pentyl)-2-(5-phenylpyrazolo[1,5-a]pyrimidin-3-yl)isonicotinamide;
N-(2-(diethylamino)-3-methylbutyl)-2-(5-phenylpyrazolo[1,5-a]pyrimidin-3-yl)isonicotinamide;
N-(1-aminopropan-2-yl)-2-(5-phenylpyrazolo[1,5-a]pyrimidin-3-yl)isonicotinamide;
N-((1R,2S)-2-aminocyclopentyl)-2-(5-phenylpyrazolo[1,5-a]pyrimidin-3-yl)isonicotinamide;
N-(2-amino-2-methylpropyl)-2-(5-phenylpyrazolo[1,5-a]pyrimidin-3-yl)isonicotinamide;
N-(2-aminoethyl)-N-ethyl-2-(5-phenylpyrazolo[1,5-a]pyrimidin-3-yl)isonicotinamide;
(R)—N-(2-amino-3-(pyrimidin-2-yloxy)propyl)-2-(5-phenylpyrazolo[1,5-a]pyrimidin-3-yl)isonicotinamide;
N-(2-(ethyl amino)-2-methylpropyl)-2-(5-phenylpyrazolo[1,5-a]pyrimidin-3-yl)isonicotinamide;
(2-(5-phenylpyrazolo[1,5-a]pyrimidin-3-yl)pyridin-4-yl)(1,8-diazaspiro[5.5]undecan-1-yl)methanone;
(R)—N-(2-(ethylamino)-3-(pyrimidin-2-yloxy)propyl)-2-(5-phenylpyrazolo[1,5-a]pyrimidin-3-yl)isonicotinamide;
(R)—N-(2-(diethylamino)-3-(pyrimidin-2-yloxy)propyl)-2-(5-phenylpyrazolo[1,5-a]pyrimidin-3-yl)isonicotinamide;
N-((1R,2R)-2-aminocyclopentyl)-2-(5-phenylpyrazolo[1,5-a]pyrimidin-3-yl)isonicotinamide;
N-((1S,2R) 2 aminocyclopentyl)-2-(5-phenylpyrazolo[1,5-a]pyrimidin-3-yl)isonicotinamide;
N-(2-(isopropylamino)-3-methylbutyl)-2-(5-phenylpyrazolo[1,5-a]pyrimidin-3-yl)isonicotinamide;
(R)—N-(2-(ethylamino)propyl)-2-(5-phenylpyrazolo[1,5-a]pyrimidin-3-yl)isonicotinamide;
(S)—N-((2-ethylpyrrolidin-2-yl)methyl)-2-(5-phenylpyrazolo[1,5-a]pyrimidin-3-yl)isonicotinamide;
((5S)-3,6-diazabicyclo[3.2.2]nonan-3-yl)(2-(5-(thiophen-2-yl)pyrazolo[1,5-a]pyrimidin-3-yl)pyridin-4-yl)methanone;
((1S)-3,9-diazabicyclo[3.3.2]decan-3-yl)(2-(5-(thiophen-2-yl)pyrazolo[1,5-a]pyrimidin-3-yl)pyridin-4-yl)methanone;
(S)-(2-(aminomethyl)-4,4-difluoropyrrolidin-1-yl)(2-(5-(thiophen-2-yl)pyrazolo[1,5-a]pyrimidin-3-yl)pyridin-4-yl)methan one;
(R)-(2-(aminomethyl)pyrrolidin-1-yl)(2-(5-(thiophen-2-yl)pyrazolo[1,5-a]pyrimidin-3-yl)pyridin-4-yl)methanone;
((5S)-3,6-diazabicyclo[3.2.2]nonan-3-yl)(2-(5-(thiophen-2-yl)pyrazolo[1,5-a]pyrimidin-3-yl)pyridin-4-yl)methanone;
((1R)-3-oxa-7,9-diazabicyclo[3.3.2]decan-7-yl)(2-(5-(thiophen-2-yl)pyrazolo[1,5-a]pyridin-3-yl)pyridin-4-yl)methanone;
((1R,6S)-3,9-diazabicyclo[4.2.1]nonan-9-yl)(2-(5-(thiophen-2-yl)pyrazolo[1,5-a]pyrimidin-3-yl)pyridin-4-yl)methanone;
(S)-(3-aminopiperidin-1-yl)(2-(5-(thiophen-2-yl)pyrazolo[1,5-a]pyrimidin-3-yl)pyridin-4-yl)methanone;
(R)-(2-methylpiperazin-1-yl)(2-(5-(thiophen-2-yl)pyrazolo[1,5-a]pyrimidin-3-yl)pyridin-4-yl)methanone;

(S)-(3-aminopyrrolidin-1-yl)(2-(5-(thiophen-2-yl)pyrazolo[1,5-a]pyrimidin-3-yl)pyridin-4-yl)methanone;
((4aR,8R,8aS)-8-aminooctahydroquinolin-1(2H)-yl)(2-(5-(thiophen-2-yl)pyrazolo[1,5-a]pyrimidin-3-yl)pyridin-4-yl)methanone;
(S)-(3-aminopyrrolidin-1-yl)(2-(5-phenylpyrazolo[1,5-a]pyrimidin-3-yl)pyridin-4-yl)methanone;
((1S,5R,6S)-6-amino-8-azabicyclo[3.2.1]octan-8-yl)(2-(5-phenylpyrazolo[1,5-a]pyrimidin-3-yl)pyridin-4-yl)methanone;
(2-(5-phenylpyrazolo[1,5-a]pyrimidin-3-yl)pyridin-4-yl)(2,6-diazaspiro[4.5]decan-6-yl)methanone;
((S)-2-((S)-1-aminoethyl)piperidin-1-yl)(2-(5-phenylpyrazolo[1,5-a]pyrimidin-3-yl)pyridin-4-yl)methanone;
((1S,6R)-3,10-diazabicyclo[4.3.1]decan-10-yl)(2-(5-phenylpyrazolo[1,5-a]pyrimidin-3-yl)pyridin-4-yl)methanone;
(hexahydropyrrolo[3,4-b]pyrrol-1(2H)-yl)(2-(5-phenylpyrazolo[1,5-a]pyrimidin-3-yl)pyridin-4-yl)methanone;
(2-(5-phenylpyrazolo[1,5-a]pyrimidin-3-yl)pyridin-4-yl)((R)-2-((S)-pyrrolidin-2-yl)piperidin-1-yl)methanone;
((4aR,7S,7aR)-7-aminooctahydro-1H-cyclopenta[b]pyridin-1-yl)(2-(5-phenylpyrazolo[1,5-a]pyrimidin-3-yl)pyridin-4-yl)methan one;
(octahydro-1H-pyrrolo[2,3-c]pyridin-1-yl)(2-(5-phenylpyrazolo[1,5-a]pyrimidin-3-yl)pyridin-4-yl)methanone;
((4aR,7R,7aR)-7-aminooctahydro-1H-cyclopenta[b]pyridin-1-yl)(2-(5-phenylpyrazolo[1,5-a]pyrimidin-3-yl)pyridin-4-yl)methanone;
(2-(5-phenylpyrazolo[1,5-a]pyrimidin-3-yl)pyridin-4-yl)(1,7-diazaspiro[4.5]decan-1-yl)methanone;
((4aS,8R,8aR)-8-aminooctahydroquinolin-1(2H)-yl)(2-(5-phenylpyrazolo[1,5-a]pyrimidin-3-yl)pyridin-4-yl)methanone;
((4aS,7S,7aS)-7-aminooctahydro-1H-cyclopenta[b]pyridin-1-yl)(2-(5-phenylpyrazolo[1,5-a]pyrimidin-3-yl)pyridin-4-yl)methanone;
((1R,5S)-3,8-diazabicyclo[3.2.1]octan-3-yl)(2-(5-phenylpyrazolo[1,5-a]pyrimidin-3-yl)pyridin-4-yl)methanone;
((4aR,8aR)-octahydro-1,7-naphthyridin-1(2H)-yl)(2-(5-(thiophen-2-yl)pyrazolo[1,5-a]pyrimidin-3-yl)pyridin-4-yl)methanone;
(S)-2-amino-N-(2-(diethylamino)propyl)-6-(5-(thiophen-2-yl)pyrazolo[1,5-a]pyrimidin-3-yl)isonicotinamide;
(S)-2-chloro-N-(2-(diethylamino)propyl)-6-(5-(thiophen-2-yl)pyrazolo[1,5-a]pyrimidin-3-yl)isonicotinamide;
(S)—N-(2-(diethylamino)propyl)-2-isopropyl-6-(5-(thiophen-2-yl)pyrazolo[1,5-a]pyrimidin-3-yl)isonicotinamide;
(S)—N-(2-(diethylamino)propyl)-2-ethyl-6-(5-(thiophen-2-yl)pyrazolo[1,5-a]pyrimidin-3-yl)isonicotinamide;
(R)=(2-(aminomethyl)piperidin-1-yl)(2-(dimethylamino)-6-(5-(thiophen-2-yl)pyrazolo[1,5-a]pyrimidin-3-yl)pyridin-4-yl)methanone;
(S)—N-(2-(diethylamino)propyl)-2-(5-(thiophen-2-yl)pyrazolo[1,5-a]pyrimidin-3-yl)-6-(trifluoromethyl)isonicotinamide;
(S)—N-(2-(diethylamino)propyl)-2-(dimethylamino)-6-(5-(thiophen-2-yl)pyrazolo[1,5-a]pyrimidin-3-yl)isonicotinamide;
(S)-(3-aminopyrrolidin-1-yl)(2-(dimethylamino)-6-(5-(thiophen-2-yl)pyrazolo[1,5-a]pyrimidin-3-yl)pyridin-4-yl)methanone;
(S)-(3-aminopyrrolidin-1-yl)(2-methoxy-6-(5-(thiophen-2-yl)pyrazolo[1,5-a]pyrimidin-3-yl)pyridin-4-yl)methanone;
(R)-(2-(aminomethyl)piperidin-1-yl)(2-chloro-6-(5-(thiophen-2-yl)pyrazolo[1,5-a]pyrimidin-3-yl)pyridin-4-yl)methanone;
(S)—N-(2-(diethylamino)propyl)-2-methoxy-6-(5-(thiophen-2-yl)pyrazolo[1,5-a]pyrimidin-3-yl)isonicotinamide;
(S)-(2-(aminomethyl)piperidin-1-yl)(2-chloro-6-(5-(thiophen-2-yl)pyrazolo[1,5-a]pyrimidin-3-yl)pyridin-4-yl)methanone;
(S)-2-amino-N-(2-(diethylamino)propyl)-6-(5-phenylpyrazolo[1,5-a]pyrimidin-3-yl)isonicotinamide;
(R)-(2-(aminomethyl)piperidin-1-yl)(2-methyl-6-(5-phenylpyrazolo[1,5-a]pyrimidin-3-yl)pyridin-4-yl)methanone;
(R)-(2-(aminomethyl)piperidin-1-yl)(2-(5-phenylpyrazolo[1,5-a]pyrimidin-3-yl)-6-(trifluoromethyl)pyridin-4-yl)methanone;
(R)-(2-(aminomethyl)piperidin-1-yl)(2-cyclopropyl-6-(5-phenylpyrazolo[1,5-a]pyrimidin-3-yl)pyridin-4-yl)methanone;
(R)-(2-(aminomethyl)piperidin-1-yl)(2-(dimethylamino)-6-(5-phenylpyrazolo[1,5-a]pyrimidin-3-yl)pyridin-4-yl)methanone;
(S)-2-ethyl-N-(2-(ethylamino)propyl)-6-(5-phenylpyrazolo[1,5-a]pyrimidin-3-yl)isonicotinamide;
(S)—N-(2-(ethylamino)propyl)-2-methyl-6-(5-phenylpyrazolo[1,5-a]pyrimidin-3-yl)isonicotinamide;
(S)-2-amino-N-(2-(ethylamino)propyl)-6-(5-phenylpyrazolo[1,5-a]pyrimidin-3-yl)isonicotinamide;
(S)—N-(2-(ethylamino)propyl)-2-isopropyl-6-(5-phenylpyrazolo[1,5-a]pyrimidin-3-yl)isonicotinamide;
(S)-2-cyclopropyl-N-(2-(ethylamino)propyl)-6-(5-phenylpyrazolo[1,5-a]pyrimidin-3-yl)isonicotinamide;
(S)-2-chloro-N-(2-(ethylamino)propyl)-6-(5-phenylpyrazolo[1,5-a]pyrimidin-3-yl)isonicotinamide;
(S)-(3-aminopyrrolidin-1-yl)(2-(dimethylamino)-6-(5-phenylpyrazolo[1,5-a]pyrimidin-3-yl)pyridin-4-yl)methanone;
(S)-(3-aminopyrrolidin-1-yl)(2-methoxy-6-(5-phenylpyrazolo[1,5-a]pyrimidin-3-yl)pyrindin-4-yl)methanone;
(R)-(2-(aminomethyl)piperidin-1-yl)(2-chloro-6-(5-phenylpyrazolo[1,5-a]pyrimidin-3-yl)pyridin-4-yl)methanone;
(2-amino-6-(5-phenylpyrazolo[1,5-a]pyrimidin-3-yl)pyridin-4-yl)((1S,6R)-3,9-diazabicyclo[4.2.1]nonan-9-yl)methanone;
(2-amino-6-(5-(thiophen-2-yl)pyrazolo[1,5-a]pyrimidin-3-yl)pyridin-4-yl)((1S,6R)-3,9-diazabicyclo[4.2.1]nonan-9-yl)methanone;
(R)-(2-(aminomethyl)piperidin-1-yl)(2-(tert-butyl)-6-(5-phenylpyrazolo[1,5-a]pyrimidin-3-yl)pyridin-4-yl)methanone;
(R)-(2-(aminomethyl)pyrrolidin-1-yl)(2-methyl-6-(5-phenylpyrazolo[1,5-a]pyrimidin-3-yl)pyridin-4-yl)methanone;
(R)-(2-(aminomethyl)piperidin-1-yl)(2-methoxy-6-(5-phenylpyrazolo[1,5-a]pyrimidin-3-yl)pyridin-4-yl)methanone;
(S)-(2-(aminomethyl)piperidin-1-yl)(2-chloro-6-(5-phenylpyrazolo[1,5-a]pyrimidin-3-yl)pyridin-4-yl)methanone;
(S)-(2-(aminomethyl)piperidin-1-yl)(2-methoxy-6-(5-phenylpyrazolo[1,5-a]pyrimidin-3-yl)pyridin-4-yl)methanone;

(S)-(2-(aminomethyl)piperidin-1-yl)(2-(dimethylamino)-6-(5-phenylpyrazolo[1,5-a]pyrimidin-3-yl)pyridin-4-yl)methanone;

(R)-(2-(aminomethyl)piperidin-1-yl)(5-methyl-2-(5-phenylpyrazolo[1,5-a]pyrimidin-3-yl)pyridin-4-yl)methanone;

(R)-(2-(aminomethyl)piperidin-1-yl)(5-chloro-2-(5-phenylpyrazolo[1,5-a]pyrimidin-3-yl)pyridin-4-yl)methanone;

(R)-(5-amino-2-(5-phenylpyrazolo[1,5-a]pyrimidin-3-yl)pyridin-4-yl)(2-(aminomethyl)piperidin-1-yl)methanone;

(R)-(2-(aminomethyl)piperidin-1-yl)(5-(methylamino)-2-(5-phenylpyrazolo[1,5-a]pyrimidin-3-yl)pyridin-4-yl)methanone;

((R)-2-((R)-1-aminoethyl)piperidin-1-yl)(5-methyl-2-(5-phenylpyrazolo[1,5-a]pyrimidin-3-yl)pyridin-4-yl)methanone;

(S)—N-(2-(diethylamino)propyl)-2-(3-methoxyazetidin-1-yl)-6-(5-(thiophen-2-yl)pyrazolo[1,5-a]pyrimidin-3-yl)isonicotinamide;

(S)-2-(3-cyanoazetidin-1-yl)-N-(2-(diethylamino)propyl)-6-(5-(thiophen-2-yl)pyrazolo[1,5-a]pyrimidin-3-yl)isonicotinamide;

(S)—N-(2-(diethylamino)propyl)-2-(3-ethoxyazetidin-1-yl)-6-(5-(thiophen-2-yl)pyrazolo[1,5-a]pyrimidin-3-yl)isonicotinamide;

(S)—N-(2-(diethylamino)propyl)-2-(3-(difluoromethoxy)azetidin-1-yl)-6-(5-(thiophen-2-yl)pyrazolo[1,5-a]pyrimidin-3-yl)isonicotinamide;

(S)—N-(2-(diethylamino)propyl)-2-(3-hydroxyazetidin-1-yl)-6-(5-(thiophen-2-yl)pyrazolo[1,5-a]pyrimidin-3-yl)isonicotinamide;

(S)-2-(azetidin-1-yl)-N-(2-(diethylamino)propyl)-6-(5-(thiophen-2-yl)pyrazolo[1,5-a]pyrimidin-3-yl)isonicotinamide;

(S)—N-(2-(diethylamino)propyl)-2-(5-(thiophen-2-yl)pyrazolo[1,5-a]pyriniidin-3-yl)-6-(3-(trifluoromethyl)azetidin-1-yl)isonicotinamide;

(S)—N-(2-(diethylamino)propyl)-2-(3,3-difluoroazetidin-1-yl)-6-(5-(thiophen-2-yl)pyrazolo[1,5-a]pyrimidin-3-yl)isonicotinamide;

(S)—N-(2-(diethylamino)propyl)-2-(3-(methylsulfonyl)azetidin-1-yl)-6-(5-(thiophen-2-yl)pyrazolo[1,5-a]pyrimidin-3-yl)isonicotinamide;

(S)—N-(2-(diethylamino)propyl)-2-(3-(N-methylsulfamoyl)azetidin-1-yl)-6-(5-(thiophen-2-yl)pyrazolo[1,5-a]pyrimidin-3-yl)isonicotinamide;

(S)-2-(3-(N-cyclopropylsulfamoyl)azetidin-1-yl)-N-(2-(diethylamino)propyl)-6-(5-(thiophen-2-yl)pyrazolo[1,5-a]pyrimidin-3-yl)isonicotinamide;

(S)—N-(2-(diethylamino)propyl)-2-(3,3-dimethylazetidin-1-yl)-6-(5-(thiophen-2-yl)pyrazolo[1,5-a]pyrimidin-3-yl)isonicotinamide;

(S)—N-(2-(diethylamino)propyl)-2-(3-fluoroazetidin-1-yl)-6-(5-(thiophen-2-yl)pyrazolo[1,5-a]pyrimidin-3-yl)isonicotinamide;

(S)-2-(3-(cyclopropanesulfonamido)azetidin-1-yl)-N-(2-(diethylamino)propyl)-6-(5-(thiophen-2-yl)pyrazolo[1,5-a]pyrimidin-3-yl)isonicotinamide;

(S)—N-(2-(diethylamino)propyl)-2-(5,6-dihydroimidazo[1,2-a]pyrazin-7(8H)-yl)-6-(5-(thiophen-2-yl)pyrazolo[1,5-a]pyrimidin-3-yl)isonicotinamide;

N—((S)-2-(diethylamino)propyl)-2-(3,3-difluoro-4-hydroxypiperidin-1-yl)-6-(5-(thiophen-2-yl)pyrazolo[1,5-a]pyrimidin-3-yl)isonicotinamide;

(S)—N-(2-(diethylamino)propyl)-2-((2-(dimethylamino)ethyl)amino)-6-(5-(thiophen-2-yl)pyrazolo[1,5-a]pyrimidin-3-yl)isonicotinamide;

(S)—N-(2-(diethylamino)propyl)-2-((2-(dimethylamino)ethyl)amino)-6-(5-phenylpyrazolo[1,5-a]pyrimidin-3-yl)isonicotinamide;

N-((1-aminocyclobutyl)methyl)-2-(3-methoxyazetidin-1-yl)-6-(5-phenylpyrazolo[1,5-a]pyrimidin-3-yl)isonicotinamide;

(S)—N-(2-(diethylamino)propyl)-2-(3-methoxyazetidin-1-yl)-6-(5-phenylpyrazolo[1,5-a]pyrimidin-3-yl)isonicotinamide;

N-((hexahydro-1H-pyrrolizin-7a-yl)methyl)-2-(3-methoxyazetidin-1-yl)-6-(5-phenylpyrazolo[1,5-a]pyrimidin-3-yl)isonicotinamide;

(S)—N-(2-(diethylamino)propyl)-2-(4-hydroxypiperidin-1-yl)-6-(5-(thiophen-2-yl)pyrazolo[1,5-a]pyrimidin-3-yl)isonicotinamide;

(S)—N-(2-(diethylamino)propyl)-2-(4-hydroxy-4-methylpiperidin-1-yl)-6-(5-(thiophen-2-yl)pyrazolo[1,5-a]pyrimidin-3-yl)isonicotinamide;

(S)—N-(2-(diethylamino)propyl)-2-(((3-(pyrrolidin-1-yl)oxetan-3-yl)methyl)amino)-6-(5-(thiophen-2-yl)pyrazolo[1,5-a]pyrimidin-3-yl)isonicotinamide;

(S)—N-(2-(diethylamino)propyl)-2-(3-methoxyazetidin-1-yl)-6-(5-(thiophen-3-yl)pyrazolo[1,5-a]pyrimidin-3-yl)isonicotinamide;

(S)—N-(2-(diethylamino)propyl)-2-(3-methoxyazetidin-1-yl)-6-(5-(pyrimidin-5-yl)pyrazolo[1,5-a]pyrimidin-3-yl)isonicotinamide;

(S)—N-(2-(diethylamino)propyl)-2-(1,1-dioxidoisothiazolidin-2-yl)-6-(5-(thiophen-2-yl)pyrazolo[1,5-a]pyrimidin-3-yl)isonicotinamide;

(S)—N-(2-aminopropyl)-2-(3-hydroxyazetidin-1-yl)-6-(5-(thiophen-2-yl)pyrazolo[1,5-a]pyrimidin-3-yl)isonicotinamide;

(S)—N-(2-(ethylamino)propyl)-2-(3-hydroxyazetidin-1-yl)-6-(5-(thiophen-2-yl)pyrazolo[1,5-a]pyrimidin-3-yl)isonicotinamide;

N-((1-aminocyclobutyl)methyl)-2-(3-methoxyazetidin-1-yl)-6-(5-(thiophen-2-yl)pyrazolo[1,5-a]pyrimidin-3-yl)isonicotinamide;

(S)—N-(2-aminopropyl)-2-(3-methoxyazetidin-1-yl)-6-(5-(thiophen-2-yl)pyrazolo[1,5-a]pyrimidin-3-yl)isonicotinamide;

(S)—N (2 aminopropyl)-2-(3-methoxyazetidin-1-yl)-6-(5-phenylpyrazolo[1,5-a]pyrimidin-3-yl)isonicotinamide;

(S)—N-(2-(ethylamino)propyl)-2-(3-methoxyazetidin-1-yl)-6-(5-(thiophen-2-yl)pyrazolo[1,5-a]pyrimidin-3-yl)isonicotinamide;

(S)—N-(2-(ethylamino)propyl)-2-(3-methoxyazetidin-1-yl)-6-(5-phenylpyrazolo[1,5-a]pyrimidin-3-yl)isonicotinamide;

(S)—N-(2-(diethylamino)propyl)-2-(3-((isoxazol-3-ylmethyl)sulfonamido)azetidin-1-yl)-6-(5-(thiophen-2-yl)pyrazolo[1,5-a]pyrimidin-3-yl)isonicotinamide;

(S)—N-(2-(diethylamino)propyl)-2-(5-(isothiazol-5-yl)pyrazolo[1,5-a]pyrimidin-3-yl)-6-(3-methoxyazetidin-1-yl)isonicotinamide;

(S)—N-(2-(diethylamino)propyl)-2-((N-methyl methyl)sulfonamido)-6-(5-(thiophen-2-yl)pyrazolo[1,5-a]pyrimidin-3-yl)isonicotinamide;

(S)—N-(2-(diethylamino)propyl)-2-((1-methylethyl)sulfonamido)-6-(5-(thiophen-2-yl)pyrazolo[1,5-a]pyrimidin-3-yl)isonicotinamide;

(S)—N-(2-(diethylamino)propyl)-2-(ethylsulfonamido)-6-(5-(thiophen-2-yl)pyrazolo[1,5-a]pyrimidin-3-yl)isonicotinamide;
(S)-2-(cyclopropanesulfonamido)-N-(2-(diethylamino)propyl)-6-(5-(thiophen-2-yl)pyrazolo[1,5-a]pyrimidin-3-yl)isonicotinamide;
(S)—N-(2-(diethylamino)propyl)-2-(methylsulfonamido)-6-(5-(thiophen-2-yl)pyrazolo[1,5-a]pyrimidin-3-yl)isonicotinamide;
(S)—N-(2-(diethylamino)propyl)-2-(3-(ethyl sulfonamido)azetidin-1-yl)-6-(5-(thiophen-2-yl)pyrazolo[1,5-a]pyrimidin-3-yl)isonicotinamide;
(S)—N-(2-(diethylamino)propyl)-2-(3-((1-methyl ethyl)sulfonamido)azetidin-1-yl)-6-(5-(thiophen-2-yl)pyrazolo[1,5-a]pyrimidin-3-yl)isonicotinamide;
(S)—N-(2-(diethylamino)propyl)-2-(2-oxoimidazolidin-1-yl)-6-(5-(thiophen-2-yl)pyrazolo[1,5-a]pyrimidin-3-yl)isonicotinamide;
(S)—N-(2-(diethylamino)propyl)-2-(3-ethylureido)-6-(5-(thiophen-2-yl)pyrazolo[1,5-a]pyrimidin-3-yl)isonicotinamide;
(S)-ethyl (4-((2-(diethylamino)propyl)carbamoyl)-6-(5-(thiophen-2-yl)pyrazolo[1,5-a]pyrimidin-3-yl)pyridin-2-yl)carbamate;
(S)-isopropyl (4-((2-(diethylamino)propyl)carbamoyl)-6-(5-(thiophen-2-yl)pyrazolo[1,5-a]pyrimidin-3-yl)pyridin-2-yl)carbamate;
(S)—N-(2-(diethylamino)propyl)-2-propionamido-6-(5-(thiophen-2-yl)pyrazolo[1,5-a]pyrimidin-3 yl)isonicotinamide;
(S)—N-(2-(diethylamino)propyl)-2-isobutyramido-6-(5-(thiophen-2-yl)pyrazolo[1,5-a]pyrimidin-3-yl)isonicotinamide;
(S)-2-(cyclopropanecarboxamido)-N-(2-(diethylamino)propyl)-6-(5-(thiophen-2-yl)pyrazolo[1,5-a]pyrimidin-3-yl)isonicotinamide;
(S)—N-(2-(diethylamino)propyl)-2-(((3-methyloxetan-3-yl)methyl)amino)-6-(5-(thiophen-2-yl)pyrazolo[1,5-a]pyrimidin-3-yl)isonicotinamide;
(S)—N-(2-(diethylamino)propyl)-2-((oxetan-3-ylmethyl)amino)-6-(5-(thiophen-2-yl)pyrazolo[1,5-a]pyrimidin-3-yl)isonicotinamide;
(S)—N-(2-(diethylamino)propyl)-2-(oxetan-3-ylamino)-6-(5-(thiophen-2-yl)pyrazolo[1,5-a]pyrimidin-3-yl)isonicotinamide;
(S)—N-(1-(4-((2-(diethylamino)propyl)carbamoyl)-6-(5-(thiophen-2-yl)pyrazolo[1,5-a]pyrimidin-3-yl)pyridin-2-yl)azetidin-3-yl)oxazole-2-carboxamide;
(S)—N-(2-(diethylamino)propyl)-2-(3-(3,3-dimethylureido)azetidin-1-yl)-6-(5-(thiophen-2-yl)pyrazolo[1,5-a]pyrimidin-3-yl)isonicotinamide;
(S)-2-(3-(cyclopropanecarboxamido)azetidin-1-yl)-N-(2-(diethylamino)propyl)-6-(5-(thiophen-2-yl)pyrazolo[1,5-a]pyrimidin-3-yl)isonicotinamide;
(S)—N-(2-(diethylamino)propyl)-2-(3-(methylsulfonamido)azetidin-1-yl)-6-(5-(thiophen-2-yl)pyrazolo[1,5-a]pyrimidin-3-yl)isonicotinamide;
(S)-2-(3-acetamidoazetidin-1-yl)-N-(2-(diethylamino)propyl)-6-(5-(thiophen-2-yl)pyrazolo[1,5-a]pyrimidin-3-yl)isonicotinamide;
N—((S)-2-(diethylamino)propyl)-2-(((R)-1-hydroxypropan-2-yl)amino)-6-(5-(thiophen-2-yl)pyrazolo[1,5-a]pyrimidin-3-yl)isonicotinamide;
N—((S)-2-(diethylamino)propyl)-2-(((S)-1-hydroxypropan-2-yl)amino)-6-(5-(thiophen-2-yl)pyrazolo[1,5-a]pyrimidin-3-yl)isonicotinamide;
N—((S)-2-(diethylamino)propyl)-2-(((S)-2-hydroxypropyl)amino)-6-(5-(thiophen-2-yl)pyrazolo[1,5-a]pyrimidin-3-yl)isonicotinamide;
N—((S)-2-(diethylamino)propyl)-2-(((R)-2-hydroxypropyl)amino)-6-(5-(thiophen-2-yl)pyrazolo[1,5-a]pyrimidin-3-yl)isonicotinamide;
N—((S)-2-(diethylamino)propyl)-2-(((S)-tetrahydrofuran-3-yl)amino)-6-(5-(thiophen-2-yl)pyrazolo[1,5-a]pyrimidin-3-yl)isonicotinamide;
(S)-2-(4-acetylpiperazin-1-yl)-N-(2-(diethylamino)propyl)-6-(5-(thiophen-2-yl)pyrazolo[1,5-a]pyrimidin-3-yl)isonicotinamide;
(S)—N-(2-(diethylamino)propyl)-2-(3-(methylamino)azetidin-1-yl)-6-(5-(thiophen-2-yl)pyrazolo[1,5-a]pyrimidin-3-yl)isonicotinamide;
(S)—N-(2-(diethylamino)propyl)-2-(3-(dimethylamino)azetidin-1-yl)-6-(5-(thiophen-2-yl)pyrazolo[1,5-a]pyrimidin-3-yl)isonicotinamide;
(S)—N-(2-(diethylamino)propyl)-2-(piperazin-1-yl)-6-(5-(thiophen-2-yl)pyrazolo[1,5-a]pyrimidin-3-yl)isonicotinamide;
(S)-2-(3-carbamoylazetidin-1-yl)-N-(2-(diethylamino)propyl)-6-(5-(thiophen-2-yl)pyrazolo[1,5-a]pyrimidin-3-yl)isonicotinamide;
N—((S)-2-(diethylamino)propyl)-2-((S)-3-methoxypyrrolidin-1-yl)-6-(5-(thiophen-2-yl)pyrazolo[1,5-a]pyrimidin-3-yl)isonicotinamide;
(S)—N-(2-(diethylamino)propyl)-2-(3-(4-fluorophenoxy)azetidin-1-yl)-6-(5-(thiophen-2-yl)pyrazolo[1,5-a]pyrimidin-3-yl)isonicotinamide;
(S)—N-(2-(diethylamino)propyl)-2-morpholino-6-(5-(thiophen-2-yl)pyrazolo[1,5-a]pyrimidin-3-yl)isonicotinamide;
(S)-2-(((1H-pyrazol-3-yl)methyl)amino)-N-(2-(diethylamino)propyl)-6-(5-(thiophen-2-yl)pyrazolo[1,5-a]pyrimidin-3-yl)isonicotinamide;
(S)-2-(cyclopropylamino)-N-(2-(diethylamino)propyl)-6-(5-(thiophen-2-yl)pyrazolo[1,5-a]pyrimidin-3-yl)isonicotinamide;
(S)—N-(2-(diethylamino)propyl)-2-(3-ethyl-3-hydroxyazetidin-1-yl)-6-(5-(thiophen-2-yl)pyrazolo[1,5-a]pyrimidin-3-yl)isonicotinamide;
(S)—N-(2-(diethylamino)propyl)-2-(3-(2-hydroxy propan-2-yl)azetidin-1-yl)-6-(5-(thiophen-2-yl)pyrazolo[1,5-a]pyrimidin-3-yl)isonicotinamide;
(S)—N-(2-(diethylamino)propyl)-2-(3-(hydroxymethyl)azetidin-1-yl)-6-(5-(thiophen-2-yl)pyrazolo[1,5-a]pyrimidin-3-yl)isonicotinamide;
(S)-2-(3-cyclopropyl-3-hydroxyazetidin-1-yl)-N-(2-(diethylamino)propyl)-6-(5-(thiophen-2-yl)pyrazolo[1,5-a]pyrimidin-3-yl)isonicotinamide;
(S)—N-(2-(diethylamino)propyl)-2-((3-methoxypropyl)amino)-6-(5-(thiophen-2-yl)pyrazolo[1,5-a]pyrimidin-3-yl)isonicotinamide;
(S)—N-(2-(diethylamino)propyl)-2-(3-hydroxy-3-(trifluoromethyl)azetidin-1-yl)-6-(5-(thiophen-2-yl)pyrazolo[1,5-a]pyrimidin-3-yl)isonicotinamide;
(S)—N-(2-(diethylamino)propyl)-2-((3-hydroxypropyl)amino)-6-(5-(thiophen-2-yl)pyrazolo[1,5-a]pyrimidin-3-yl)isonicotinamide;
(S)—N-(2-(diethylamino)propyl)-2-((3-hydroxy-3-methylbutyl)amino)-6-(5-(thiophen-2-yl)pyrazolo[1,5-a]pyrimidin-3-yl)isonicotinamide;
(S)—N-2-(diethylamino)propyl)-2-(tetrahydro-2H-pyran-4-yl)amino)-6-(5-(thiophen-2-yl)pyrazolo[1,5-a]pyrimidin-3-yl)isonicotinamide;

(S)—N-(2-(diethylamino)propyl)-2-((2-morpholinoethyl)amino)-6-(5-(thiophen-2-yl)pyrazolo[1,5-a]pyrimidin-3-yl)isonicotinamide;

(S)—N-(2-(diethylamino)propyl)-2-((2-(3,3-difluoroazetidin-1-yl)ethyl)amino)-6-(5-(thiophen-2-yl)pyrazolo[1,5-a]pyrimidin-3-yl)isonicotinamide;

(S)—N-(2-(diethylamino)propyl)-2-((2-methoxyethyl)amino)-6-(5-(thiophen-2-yl)pyrazolo[1,5-a]pyrimidin-3-yl)isonicotinamide;

(S)—N-(2-(diethylamino)propyl)-2-(3-hydroxy-3-methylazetidin-1-yl)-6-(5-(thiophen-2-yl)pyrazolo[1,5-a]pyrimidin-3-yl)isonicotinamide;

(S)—N-(2-(diethylamino)propyl)-2-(3-methoxy-3-methylazetidin-1-yl)-6-(5-(thiophen-2-yl)pyrazolo[1,5-a]pyrimidin-3-yl)isonicotinamide;

(S)—N-(2-(diethylamino)propyl)-2-(methylamino)-6-(5-(thiophen-2-yl)pyrazolo[1,5-a]pyrimidin-3-yl)isonicotinamide;

(S)—N-(2-(diethylamino)propyl)-2-((2-hydroxyethyl)amino)-6-(5-(thiophen-2-yl)pyrazolo[1,5-a]pyrimidin-3-yl)isonicotinamide;

(S)—N-(2-(diethylamino)propyl)-2-(3,3,4,4-tetrafluoropyrrolidin-1-yl)-6-(5-(thiophen-2-yl)pyrazolo[1,5-a]pyrimidin-3-yl)isonicotinamide;

(S)-2-((1H-pyrazol-4-yl)amino)-N-(2-(diethylamino)propyl)-6-(5-(thiophen-2-yl)pyrazolo[1,5-a]pyrimidin-3-yl)isonicotinamide;

(S)—N-(2-(diethylamino)propyl)-2-(3,3-difluoropyrrolidin-1-yl)-6-(5-(thiophen-2-yl)pyrazolo[1,5-a]pyrimidin-3-yl)isonicotinamide;

(S)—N-(2-(diethylamino)propyl)-2-(2-oxa-6-azaspiro[3.4]octan-6-yl)-6-(5-(thiophen-2-yl)pyrazolo[1,5-a]pyrimidin-3-yl)isonicotinamide;

(S)—N-(2-(diethylamino)propyl)-2-(6-oxa-1-azaspiro[3.3]heptan-1-yl)-6-(5-(thiophen-2-yl)pyrazolo[1,5-a]pyrimidin-3-yl)isonicotinamide;

2-(((R)-1-amino-1-oxopropan-2-yl)amino)-N—((S)-2-(diethylamino)propyl)-6-(5-(thiophen-2-yl)pyrazolo[1,5-a]pyrimidin-3-yl)isonicotinamide;

2-(((S)-1-amino-1-oxopropan-2-yl)amino)-N—((S)-2-(diethylamino)propyl)-6-(5-(thiophen-2-yl)pyrazolo[1,5-a]pyrimidin-3-yl)isonicotinamide;

(S)-2-(((1H-imidazol-2-yl)methyl)amino)-N-(2-(diethylamino)propyl)-6-(5-(thiophen-2-yl)pyrazolo[1,5-a]pyrimidin-3-yl)isonicotinamide;

(S)-2-((2-amino-2-oxoethyl)amino)-N-(2-(diethylamino)propyl)-6-(5-(thiophen-2-yl)pyrazolo[1,5-a]pyrimidin-3-yl)isonicotinamide;

N—((S)-2-(diethylamino)propyl)-2-(((R)-1-(methylamino)-1-oxopropan-2-yl)amino)-6-(5-(thiophen-2-yl)pyrazolo[1,5-a]pyrimidin-3-yl)isonicotinamide;

N—((S)-2-(diethylamino)propyl)-2-(((S)-1-(methylamino)-1-oxopropan-2-yl)amino)-6-(5-(thiophen-2-yl)pyrazolo[1,5-a]pyrimidin-3-yl)isonicotinamide;

(S)-2-((1H-imidazol-2-yl)amino)-N-(2-(diethylamino)propyl)-6-(5-(thiophen-2-yl)pyrazolo[1,5-a]pyrimidin-3-yl)isonicotinamide;

(S)—N-(2-(diethylamino)propyl)-2-((2-sulfamoylethyl)amino)-6-(5-(thiophen-2-yl)pyrazolo[1,5-a]pyrimidin-3-yl)isonicotinamide;

N—((S)-2-(diethylamino)propyl)-2-((3S,4S)-3,4-dihydroxypyrrolidin-1-yl)-6-(5-(thiophen-2-yl)pyrazolo[1,5-a]pyrimidin-3-yl)isonicotinamide;

(S)-2-(3,3-bis(hydroxymethyl)azetidin-1-yl)-N-(2-(diethylamino)propyl)-6-(5-(thiophen-2-yl)pyrazolo[1,5-a]pyrimidin-3-yl)isonicotinamide;

(S)—N-(2-(ethylamino)propyl)-2-(3-hydroxy-3-methylazetidin-1-yl)-6-(5-(thiophen-2-yl)pyrazolo[1,5-a]pyrimidin-3-yl)isonicotinamide;

(S)—N-(2-(diethylamino)propyl)-2-((2-(methylamino)-2-oxoethyl)amino)-6-(5-(thiophen-2-yl)pyrazolo[1,5-a]pyrimidin-3-yl)isonicotinamide;

(S)—N-(2-(diethylamino)propyl)-2-(4-methoxypiperidin-1-yl)-6-(5-(thiophen-2-yl)pyrazolo[1,5-a]pyrimidin-3-yl)isonicotinamide;

(S)—N-(2-(diethylamino)propyl)-2-(3-(dimethylamino)-3-methylazetidin-1-yl)-6-(5-(thiophen-2-yl)pyrazolo[1,5-a]pyrimidin-3-yl)isonicotinamide;

(S)—N-(2-(diethylamino)propyl)-2-(5,5-difluoro-2-azaspiro[3.3]heptan-2-yl)-6-(5-(thiophen-2-yl)pyrazolo[1,5-a]pyrimidin-3-yl)isonicotinamide;

(S)—N-(2-(diethylamino)propyl)-2-(1-azaspiro[3.3]heptan-1-yl)-6-(5-(thiophen-2-yl)pyrazolo[1,5-a]pyrimidin-3-yl)isonicotinamide;

N—((S)-2-(diethylamino)propyl)-2-(5-(thiophen-2-yl)pyrazolo[1,5-a]pyrimidin-3-yl)-6-((R)-2-(trifluoromethyl)pyrrolidin-1-yl)isonicotinamide;

(S)—N-(2-(diethylamino)propyl)-2-(5-(thiophen-2-yl)pyrazolo[1,5-a]pyrimidin-3-yl)-6-(1H-1,2,4-triazol-1-yl)isonicotinamide;

2-((1S,4S)-2-oxa-5-azabicyclo[2.2.1]heptan-5-yl)-N—((S)-2-(diethylamino)propyl)-6-(5-(thiophen-2-yl)pyrazolo[1,5-a]pyrimidin-3-yl)isonicotinamide;

N-(2-(diethylamino)ethyl)-2-(3-methoxyazetidin-1-yl)-6-(5-(thiophen-2-yl)pyrazolo[1,5-a]pyrimidin-3-yl)isonicotinamide;

(S)-2-(3-methoxyazetidin-1-yl)-N-(pyrrolidin-2-ylmethyl)-6-(5-(thiophen-2-yl)pyrazolo[1,5-a]pyrimidin-3-yl)isonicotinamide;

(S)—N-((1-ethylpyrrolidin-2-yl)methyl)-2-(3-methoxyazetidin-1-yl)-6-(5-(thiophen-2-yl)pyrazolo[1,5-a]pyrimidin-3-yl)isonicotinamide;

(S)-2-(3-methoxyazetidin-1-yl)-N-((1-methylpyrrolidin-2-yl)methyl)-6-(5-(thiophen-2-yl)pyrazolo[1,5-a]pyrimidin-3-yl)isonicotinamide;

N-(2-(diethylamino)ethyl)-2-(3-hydroxy-3-methylazetidin-1-yl)-6-(5-(thiophen-2-yl)pyrazolo[1,5-a]pyrimidin-3-yl)isonicotinamide;

N-(2-(diethylamino)ethyl)-2-((2-hydroxyethyl)amino)-6-(5-(thiophen-2-yl)pyrazolo[1,5-a]pyrimidin-3-yl)isonicotinamide;

(S)-2-(diethylamino)-N-(2-(diethylamino)propyl)-6-(5-(thiophen-2-yl)pyrazolo[1,5-a]pyrimidin-3-yl)isonicotinamide;

(S)—N-(2-(diethylamino)propyl)-2-(ethylamino)-6-(5-(thiophen-2-yl)pyrazolo[1,5-a]pyrimidin-3-yl)isonicotinamide;

(S)—N-(2-(diethylamino)propyl)-2-(3-methoxyazetidin-1-yl)-6-(5-(pyridin-4-yl)pyrazolo[1,5-a]pyrimidin-3-yl)isonicotinamide;

(S)-2-(4-carbamoylpiperidin-1-yl)-N-(2-(diethylamino)propyl)-6-(5-(thiophen-2-yl)pyrazolo[1,5-a]pyrimidin-3-yl)isonicotinamide;

N—((S)-2-(diethylamino)propyl)-2-((S)-2-(hydroxymethyl)morpholino)-6-(5-(thiophen-2-yl)pyrazolo[1,5-a]pyrimidin-3-yl)isonicotinamide;

N—((S)-2-(diethylamino)propyl)-2-((S)-2-(methoxymethyl)azetidin-1-yl)-6-(5-(thiophen-2-yl)pyrazolo[1,5-a]pyrimidin-3-yl)isonicotinamide;

N—((S)-2-(diethylamino)propyl)-2-((R)-2-(methoxymethyl)azetidin-1-yl)-6-(5-(thiophen-2-yl)pyrazolo[1,5-a]pyrimidin-3-yl)isonicotinamide;

N—((S)-2-(diethylamino)propyl)-2-((R)-2-(hydroxymethyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(hydroxymethyl)azetidin-1-yl)-6-(5-(thiophen-2-yl)pyrazolo[1,5-a]pyrimidin-3-yl)isonicotinamide;

2-((R)-2-carbamoylpyrrolidin-1-yl)-N—((S)-2-(diethylamino)propyl)-6-(5-(thiophen-2-yl)pyrazolo[1,5-a]pyrimidin-3-yl)isonicotinamide;

2-((S)-2-carbamoylpyrrolidin-1-yl)-N—((S)-2-(diethylamino)propyl)-6-(5-(thiophen-2-yl)pyrazolo[1,5-a]pyrimidin-3-yl)isonicotinamide;

N—((S)-2-(diethylamino)propyl)-2-((S)-2-(hydroxymethyl)pyrrolidin-1-yl)-6-(5-(thiophen-2-yl)pyrazolo[1,5-a]pyrimidin-3-yl)isonicotinamide;

N—((S)-2-(diethylamino)propyl)-2-((R)-2-(hydroxymethyl)pyrrolidin-1-yl)-6-(5-(thiophen-2-yl)pyrazolo[1,5-a]pyrimidin-3-yl)isonicotinamide;

N—((S)-2-(diethylamino)propyl)-2-((R)-2-(methoxymethyl)pyrrolidin-1-yl)-6-(5-(thiophen-2-yl)pyrazolo[1,5-a]pyrimidin-3-yl)isonicotinamide;

N—((S)-2-(diethylamino)propyl)-2-((S)-2-(methoxymethyl)pyrrolidin-1-yl)-6-(5-(thiophen-2-yl)pyrazolo[1,5-a]pyrimidin-3-yl)isonicotinamide;

N—((S)-2-(diethylamino)propyl)-2-((S)-2-(methylcarbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(ethylcarbamoyl)azetidin-1-yl)-6-(5-(thiophen-2-yl)pyrazolo[1,5-a]pyrimidin-3-yl)isonicotinamide;

2-((S)-2-(cyclopropylcarbamoyl)azetidin-1-yl)-N—((S)-2-(diethylamino)propyl)-6-(5-(thiophen-2-yl)pyrazolo[1,5-a]pyrimidin-3-yl)isonicotinamide;

2-((S)-2-((cyclopropylmethyl)carbamoyl)azetidin-1-yl)-N—((S)-2-(diethylamino)propyl)-6-(5-(thiophen-2-yl)pyrazolo[1,5-a]pyrimidin-3-yl)isonicotinamide;

N—((S)-2-(diethylamino)propyl)-2-((S)-2-(dimethylcarbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(diethylcarbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-((2-fluoroethyl)carbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-((2,2-difluoroethyl)carbamoyl)azetidin-1-yl)-6-(5-(thiophen-2-yl)pyrazolo[1,5-a]pyrimidin-3-yl)isonicotinamide;

N—((S)-2-(diethylamino)propyl)-2-(5-(thiophen-2-yl)pyrazolo[1,5-a]pyrimidin-3-yl)-6-((S)-2-((2,2,2-trifluoroethyl)carbamoyl)azetidin-1-yl)isonicotinamide;

N—((S)-2-(diethylamino)propyl)-2-((S)-2-(3-fluoroazetidine-1-carbonyl)azetidin-1-yl)-6-(5-(thiophen-2-yl)pyrazolo[1,5-a]pyrimidin-3-yl)isonicotinamide;

2-((2S)-2-(3-azabicyclo[3.1.0]hexane-3-carbonyl)azetidin-1-yl)-N—((S)-2-(diethylamino)propyl)-6-(5-(thiophen-2-yl)pyrazolo[1,5-a]pyrimidin-3-yl)isonicotinamide;

N—((S)-2-(diethylamino)propyl)-2-((S)-2-(3-(methylsulfonamido)azetidine-1-carbonyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(methoxy(methyl)carbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(pyrrolidine-1-carbonyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(methoxycarbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((R)-2-(methylcarbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(thiazol-2-ylcarbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(3,3-dimethylazetidine-1-carbonyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(morpholine-4-carbonyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(3,3-difluoroazetidine-1-carbonyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(3-methoxyazetidine-1-carbonyl)azetidin-1-yl)-6-(5-(thiophen-2-yl)pyrazolo[1,5-a]pyrimidin-3-yl)isonicotinamide;

(S)-1-(4-(((S)-2-(diethylamino)propyl)carbamoyl)-6-(5-(thiophen-2-yl)pyrazolo[1,5-a]pyrimidin-3-yl)pyridin-2-yl)azetidine-2-carboxylic acid;

N—((S)-2-(diethylamino)propyl)-2-((S)-2-((2-hydroxyethyl)carbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(hydroxy(methyl)carbamoyl)azetidin-1-yl)-6-(5-(thiophen-2-yl)pyrazolo[1,5-a]pyrimidin-3-yl)isonicotinamide;

2-((S)-2-carbamoylazetidin-1-yl)-N—((S)-2-(diethylamino)propyl)-6-(5-(thiophen-2-yl)pyrazolo[1,5-a]pyrimidin-3-yl)isonicotinamide;

2-((S)-2-((cyanomethyl)carbamoyl)azetidin-1-yl)-N—((S)-2-(diethylamino)propyl)-6-(5-(thiophen-2-yl)pyrazolo[1,5-a]pyrimidin-3-yl)isonicotinamide;

N—((S)-2-(diethylamino)propyl)-2-((S)-2-((2-methoxyethyl)carbamoyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(3-(methylsulfonyl)azetidine-1-carbonyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(1,1-dioxidothiomorpholine-4-carbonyl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(3-hydroxyazetidine-1-carbonyl)azetidin-1-yl)-6-(5-(thiophen-2-yl)pyrazolo[1,5-a]pyrimidin-3-yl)isonicotinamide;

N—((S)-2-(ethylamino)propyl)-2-((S)-2-(methylcarbamoyl)azetidin-1-yl)-6-(5-(thiophen-2-yl)pyrazolo[1,5-a]pyrimidin-3-yl)isonicotinamide;

N—((S)-2-(diethylamino)propyl)-2-(5-(isothiazol-5-yl)pyrazolo[1,5-a]pyrimidin-3-yl)-6-((S)-2-(methylcarbamoyl)azetidin-1-yl)isonicotinamide;

N—((S)-2-(diethylamino)propyl)-2-((S)-2-(3-methyl-1,2,4-oxadiazol-5-yl)azetidin-1-yl)-6-(5-(thiophen-2-yl)pyrazolo[1,5-a]pyrimidin-3-yl)isonicotinamide;

N—((S)-2-(diethylamino)propyl)-2-((S)-2-(methylcarbamoyl)azetidin-1-yl)-6-(5-phenylpyrazolo[1,5-a]pyrimidin-3-yl)isonicotinamide;

N—((S)-2-(diethylamino)propyl)-2-((S)-3-(methylcarbamoyl)pyrrolidin-1-yl)-6-(5-(thiophen-2-yl)pyrazolo[1,5-a]pyrimidin-3-yl)isonicotinamide;

N—((S)-2-(diethylamino)propyl)-2-((R)-3-(methylcarbamoyl)pyrrolidin-1-yl)-6-(5-(thiophen-2-yl)pyrazolo[1,5-a]pyrimidin-3-yl)isonicotinamide;

2-((R)-3-cyanopyrrolidin-1-yl)-N—((S)-2-(diethylamino)propyl)-6-(5-(thiophen-2-yl)pyrazolo[1,5-a]pyrimidin-3-yl)isonicotinamide;

2-((S)-3-cyanopyrrolidin-1-yl)-N—((S)-2-(diethylamino)propyl)-6-(5-(thiophen-2-yl)pyrazolo[1,5-a]pyrimidin-3-yl)isonicotinamide;

(S)—N-(2-(diethylamino)propyl)-2-(3-oxopiperazin-1-yl)-6-(5-(thiophen-2-yl)pyrazolo[1,5-a]pyrimidin-3-yl)isonicotinamide;

N—((S)-2-(diethylamino)propyl)-2-((S)-3-hydroxypyrrolidin-1-yl)-6-(5-(thiophen-2-yl)pyrazolo[1,5-a]pyrimidin-3-yl)isonicotinamide;

N—((S)-2-(diethylamino)propyl)-2-((R)-3-hydroxypyrrolidin-1-yl)-6-(5-(thiophen-2-yl)pyrazolo[1,5-a]pyrimidin-3-yl)isonicotinamide;

2-((S)-3-aminopyrrolidin-1-yl)-N—((S)-2-(diethylamino)propyl)-6-(5-(thiophen-2-yl)pyrazolo[1,5-a]pyrimidin-3-yl)isonicotinamide 2-((R)-3-aminopyrrolidin-1-yl)-N—((S)-2-(diethylamino)propyl)-6-(5-(thiophen-2-yl)pyrazolo[1,5-a]pyrimidin-3-yl)isonicotinamide;

N—((S)-2-(diethylamino)propyl)-2-((S)-2-(methylcarbamoyl)pyrrolidin-1-yl)-6-(5-(thiophen-2-yl)pyrazolo[1,5-a]pyrimidin-3-yl)isonicotinamide;

N—((S)-2-(diethylamino)propyl)-2-((R)-2-(methylcarbamoyl)pyrrolidin-1-yl)-6-(5-(thiophen-2-yl)pyrazolo[1,5-a]pyrimidin-3-yl)isonicotinamide;

(2-((2-(1H-imidazol-1-yl)ethyl)(methyl)amino)-6-(5-(thiophen-2-yl)pyrazolo[1,5-a]pyrimidin-3-yl)pyridin-4-yl)((1S,5S)-3,6-diazabicyclo[3.2.2]nonan-3-yl)methanone;

((1S,5S)-3,6-diazabicyclo[3.2.2]nonan-3-yl)(2-((2-hydroxy-2-methylpropyl)amino)-6-(5-(thiophen-2-yl)pyrazolo[1,5-a]pyrimidin-3-yl)pyridin-4-yl)methanone;

((1S,5S)-3,6-diazabicyclo[3.2.2]nonan-3-yl)(2-((2-methoxyethyl)amino)-6-(5-(thiophen-2-yl)pyrazolo[1,5-a]pyrimidin-3-yl)pyridin-4-yl)methanone;

((1S,5S)-3,6-diazabicyclo[3.2.2]nonan-3-yl)(2-(4-(oxetan-3-yl)piperazin-1-yl)-6-(5-(thiophen-2-yl)pyrazolo[1,5-a]pyrimidin-3-yl)pyridin-4-yl)methanone;

((1S,5S)-3,6-diazabicyclo[3.2.2]nonan-3-yl)(2-(3-methoxyazetidin-1-yl)-6-(5-(thiophen-2-yl)pyrazolo[1,5-a]pyrimidin-3-yl)pyridin-4-yl)methanone;

((1S,6R)-3,9-diazabicyclo[4.2.1]nonan-9-yl)(2-(3-methoxyazetidin-1-yl)-6-(5-(thiophen-2-yl)pyrazolo[1,5-a]pyrimidin-3-yl)pyridin-4-yl)methanone;

(S)-(3-aminopyrrolidin-1-yl)(2-(3-methoxyazetidin-1-yl)-6-(5-(thiophen-2-yl)pyrazolo[1,5-a]pyrimidin-3-yl)pyridin-4-yl)methanone;

(S)-(3-aminopyrrolidin-1-yl)(2-(3-methoxyazetidin-1-yl)-6-(5-phenylpyrazolo[1,5-a]pyrimidin-3-yl)pyridin-4-yl)methanone;

((1S,5S)-3,6-diazabicyclo[3.2.2]nonan-3-yl)(2-(3-methoxyazetidin-1-yl)-6-(5-phenylpyrazolo[1,5-a]pyrimidin-3-yl)pyridin-4-yl)methanone;

((1S,6R)-3,9-diazabicyclo[4.2.1]nonan-9-yl)(2-(3-methoxyazetidin-1-yl)-6-(5-phenylpyrazolo[1,5-a]pyrimidin-3-yl)pyridin-4-yl)methanone;

(S)—N-(2-(diethylamino)propyl)-2-(1-methyl-1H-pyrazol-4-yl)-6-(5-(thiophen-2-yl)pyrazolo[1,5-a]pyrimidin-3-yl)isonicotinamide;

(S)—N-(2-(diethylamino)propyl)-2-(3,5-dimethyl-1H-pyrazol-4-yl)-6-(5-(thiophen-2-yl)pyrazolo[1,5-a]pyrimidin-3-yl)isonicotinamide;

(S)—N-(2-(diethylamino)propyl)-2-(3-methyl-1H-pyrazol-4-yl)-6-(5-(thiophen-2-yl)pyrazolo[1,5-a]pyrimidin-3-yl)isonicotinamide;

(S)—N-(2-(diethylamino)propyl)-2-(5-(thiophen-2-yl)pyrazolo[1,5-a]pyrimidin-3-yl)-6-(3-(trifluoromethyl)-1H-pyrazol-4-yl)isonicotinamide;

(S)—N-(2-(diethylamino)propyl)-2-(isoxazol-4-yl)-6-(5-(thiophen-2-yl)pyrazolo[1,5-a]pyrimidin-3-yl)isonicotinamide;

(S)—N-(2-(diethylamino)propyl)-2-(1H-pyrazol-3-yl)-6-(5-(thiophen-2-yl)pyrazolo[1,5-a]pyrimidin-3-yl)isonicotinamide;

(S)—N-(2-(diethylamino)propyl)-2,6-bis(5-(thiophen-2-yl)pyrazolo[1,5-a]pyrimidin-3-yl)isonicotinamide;

(S)—N-(2-(diethylamino)propyl)-2-(thiazol-2-yl)-6-(5-(thiophen-2-yl)pyrazolo[1,5-a]pyrimidin-3-yl)isonicotinamide;

(S)—N-(2-(diethylamino)propyl)-2-(oxazol-2-yl)-6-(5-(thiophen-2-yl)pyrazolo[1,5-a]pyrimidin-3-yl)isonicotinamide;

(S)—N-(2-(diethylamino)propyl)-2-(1H-pyrazol-4-yl)-6-(5-(thiophen-2-yl)pyrazolo[1,5-a]pyrimidin-3-yl)isonicotinamide;

(S)-2-(1-(2-cyanoethyl)-1H-pyrazol-4-yl)-N-(2-(diethylamino)propyl)-6-(5-(thiophen-2-yl)pyrazolo[1,5-a]pyrimidin-3-yl)isonicotinamide;

(S)—N-(2-(diethylamino)propyl)-2-(1-(oxetan-3-yl)-1H-pyrazol-4-yl)-6-(5-(thiophen-2-yl)pyrazolo[1,5-a]pyrimidin-3-yl)isonicotinamide;

N—((S)-2-(diethylamino)propyl)-2-(((R)-tetrahydrofuran-2-yl)methoxy)-6-(5-(thiophen-2-yl)pyrazolo[1,5-a]pyrimidin-3-yl)isonicotinamide;

N—((S)-2-(diethylamino)propyl)-2-((S)-2-methoxypropoxy)-6-(5-(thiophen-2-yl)pyrazolo[1,5-a]pyrimidin-3-yl)isonicotinamide;

N—((S)-2-(diethylamino)propyl)-2-(((S)-tetrahydrofuran-3-yl)oxy)-6-(5-(thiophen-2-yl)pyrazolo[1,5-a]pyrimidin-3-yl)isonicotinamide;

N—((S)-2-(diethylamino)propyl)-2-(((R)-tetrahydrofuran-3-yl)oxy)-6-(5-(thiophen-2-yl)pyrazolo[1,5-a]pyrimidin-3-yl)isonicotinamide;

(S)—N-(2-(diethylamino)propyl)-2-(2-(dimethylamino)ethoxy)-6-(5-(thiophen-2-yl)pyrazolo[1,5-a]pyrimidin-3-yl)isonicotinamide;

(S)—N-(2-(diethylamino)propyl)-2-(2-methoxyethoxy)-6-(5-(thiophen-2-yl)pyrazolo[1,5-a]pyrimidin-3-yl)isonicotinamide;

(S)—N-(2-(diethylamino)propyl)-2-((3-methyloxetan-3-yl)methoxy)-6-(5-(thiophen-2-yl)pyrazolo[1,5-a]pyrimidin-3-yl)isonicotinamide;

(S)—N-(2-(diethylamino)propyl)-2-(2-(pyrazin-2-yl)ethoxy)-6-(5-(thiophen-2-yl)pyrazolo[1,5-a]pyrimidin-3-yl)isonicotinamide;

(S)—N-(2-(diethylamino)propyl)-2-(3-methoxypropoxy)-6-(5-(thiophen-2-yl)pyrazolo[1,5-a]pyrimidin-3-yl)isonicotinamide;

(S)—N-(2-(diethylamino)propyl)-2-(2-morpholinoethoxy)-6-(5-(thiophen-2-yl)pyrazolo[1,5-a]pyrimidin-3-yl)isonicotinamide;

(S)—N-(2-(diethylamino)propyl)-2-(2-hydroxy-2-methylpropoxy)-6-(5-(thiophen-2-yl)pyrazolo[1,5-a]pyrimidin-3-yl)isonicotinamide;

(S)—N-(2-(diethylamino)propyl)-2-(pyridin-3-ylmethoxy)-6-(5-(thiophen-2-yl)pyrazolo[1,5-a]pyrimidin-3-yl)isonicotinamide; and (S)-3-(((4-((2-(diethylamino)propyl)carbamoyl)-6-(5-(thiophen-2-yl)pyrazolo[1,5-a]pyrimidin-3-yl)pyridin-2-yl)oxy)methyl)pyridine 1-oxide or a pharmaceutically acceptable salt, stereoisomer or mixture of stereoisomer thereof.

Further Embodiments

In some embodiments, the compounds provided by the present disclosure are effective in the treatment of conditions or diseases known to respond to administration of Calmodulin kinase II (CAM K) inhibitors, including but not limited to cardiovascular diseases such as atrial arrhythmia.

Accordingly, provided herein is a method for treating or preventing arrhythmia in a human subject comprising administering a compound as disclosed herein or a pharmaceutical composition comprising a therapeutically effective amount of a compound as disclosed herein and a pharmaceutically acceptable excipient to the subject.

Also provided herein is a method for treating or preventing atrial fibrillation in a human subject comprising administering a compound as disclosed herein or a pharmaceutical composition comprising a therapeutically effective amount of a compound as disclosed herein and a pharmaceutically acceptable excipient to the subject.

Also provided herein is a method of treating myocardial infarction in a human subject comprising administering a compound as disclosed herein or a pharmaceutical composition comprising a therapeutically effective amount of a compound as disclosed herein and a pharmaceutically acceptable excipient to the subject.

Also provided herein is a compound of any of the embodiments or combination of embodiments provided herein useful for the manufacture of a medicament for the treatment of arrhythmias.

Pharmaceutical Compositions and Administration

Compounds provided in accordance with the present disclosure are usually administered in the form of pharmaceutical compositions. This disclosure therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers. Diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Preferably, for parenteral administration, sterile injectable solutions are prepared containing a therapeutically effective amount, e.g., 0.1 to 700 mg, of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of compounds in accordance with the disclosure. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g, or alternatively, or 100 mg to 500 mg, of a compound described herein, and for parenteral administration, preferably from 0.1 mg to 700 mg, or alternatively, 0.1 mg to 100 mg, of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Methods of Use

In addition to the methods of use of disclosed heretofore, the compounds of the present disclosure (i.e. compounds of formula I, II, III, IV, V, VI or VII) are also useful as treatment or adjunct treatment for cardiovascular and non-cardiovascular (pre or post operative) procedures that may be impacted by conditions mediated by CAM K levels. One such example is the need to have peri-operative cardioprotection in non-cardiac surgery. Another example is use as a treatment or adjunct treatment (in combination with other agents) or amelioration of the cardiovascular side effects of chemotherapy. For example, anthracycline chemotherapeutics can cause cardiovascular toxicities that may limit the use or usefulness of such therapies. Also, in the US it has been reported that as many as 50+ million people undergo non-cardiac surgery each year with up to 2 million people having cardiac complications attendant to non-cardiac surgeries. Beta blockers are used per guideline to reduce the incidences of cardiac complications in such procedures. However, beta blockers are reported to substantially increase the risk of hypertension, stroke or death. Thus, the use of a cardioprotective agent such as a compound of the present disclosure singly or in combination with other useful agents disclosed herein provides a means to effect non-cardiac surgery and also reduce the risk of peril-operative cardiac risks.

Combination Therapy

Patients being treated by administration of the CaM kinase inhibitors of the disclosure often exhibit diseases or conditions that benefit from treatment with other therapeutic agents. These diseases or conditions can be of cardiovascular nature or can be related to pulmonary disorders, metabolic disorders, gastrointestinal disorders and the like. Thus, one aspect of the disclosure is a method of treating a cardiovascular disease or disease related to pulmonary disorders, metabolic disorders, gastrointestinal disorders and the like comprising administering a compound of the disclosure (i.e. compound of formula I, II, III, IV, V, VI or VII) in combination with one or more compounds useful for the treatment of such diseases to a subject, particularly a human subject, in human in need thereof.

Cardiovascular Agent Combination Therapy

Cardiovascular related diseases or conditions that can benefit from a combination treatment of the late sodium channel blockers of the disclosure with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular diseases or conditions related thereto include anti-anginals, heart failure agents, antithrombotic agents, antiarrhythmic agents, antihypertensive agents, and lipid lowering agents. Anti arrhythmic agents include late INa inhibitor compounds such as ranolazine and eleclazine. Ranolazine is disclosed in U.S. Pat. No. 6,617,328, the entirety of which is incorporated herein by reference. Eleclazine is disclosed in U.S. Pat. No. 8,586,732, the entirety of which is incorporated herein by reference. Other cardiovascular agents which may be combined with compounds of the present invention for beneficial outcomes include ASK-1 inhibitors. An example of an ASK-1 inhibitor is selonsertib. Selonsertib is disclosed in U.S. Pat. No. 8,742,126, the entirety of which is incorporated herein by reference.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral®), atenolol (Tenormin®), betaxolol (Kerlone®), bisoprolol/hydrochlorothiazide (Ziac®), bisoprolol (Zebeta®), carteolol (Cartrol®), esmolol (Brevibloc®), labetalol (Normodyne®, Trandate®), metoprolol (Lopressor®, Toprol® XL), nadolol (Corgard®), propranolol (Inderal®), sotalol (Betapace®), and timolol (Blocadren®).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc®, Lotrel®), bepridil (Vascor®), diltiazem (Cardizem®, Tiazac®), felodipine (Plendil®), nifedipine (Adalat®, Procardia®), nimodipine (Nimotop®), nisoldipine (Sular®), verapamil (Calan®, Isoptin®, Verelan®), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn®), furosemide (Lasix®), bumetanide (Bumex®), spironolactone (Aldactone®), and eplerenone (Inspra®).

Angiotensin converting enzyme (ACE) inhibitors reduce the workload on the heart by expanding the blood vessels and decreasing resistance to blood flow. Examples of ACE inhibitors include benazepril (Lotensin®), captopril (Capoten®), enalapril (Vasotec®), fosinopril (Monopril®), lisinopril (Prinivil®, Zestril®), moexipril (Univasc®), perindopril (Aceon®), quinapril (Accupril®), ramipril (Altace®), and trandolapril (Mavik®).

Vasodilators reduce pressure on the blood vessels by making them relax and expand. Examples of vasodilators include hydralazine, diazoxide, prazosin, clonidine, methyldopa, and riociguat. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (Plavix®), prasugrel (Effient®), dipyridamole, cilostazol, persantine sulfinpyrazone, dipyridamole, indomethacin, and glycoprotein llb/llla inhibitors, such as abciximab, tirofiban, and eptifibatide (Integrelin®). Beta blockers and calcium channel blockers also have a platelet-inhibiting effect.

Anticoagulants prevent blood clots from growing larger and prevent the formation of new clots. Examples of anticoagulants include bivalirudin (Angiomax®), warfarin (Coumadin®), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress®), doxazosin mesylate (Cardura®), prazosin hydrochloride (Minipress®), prazosin, polythiazide (Minizide®), and terazosin hydrochloride (Hytrin®); beta-adrenergic antagonists, such as propranolol (Inderal®), nadolol (Corgard®), timolol (Blocadren®), metoprolol (Lopressor®), and pindolol (Visken®); central alpha-adrenoceptor agonists, such as clonidine hydrochloride (Catapres®), clonidine hydrochloride and chlorthalidone (Clorpres®, Combipres®), guanabenz Acetate (Wytensin®), guanfacine hydrochloride (Tenex®), methyldopa (Aldomet®), methyldopa and chlorothiazide (Aldoclor®), methyldopa and hydrochlorothiazide (Aldoril®); combined alpha/beta-adrenergic antagonists, such as labetalol (Normodyne®, Trandate®), carvedilol (Coreg®); adrenergic neuron blocking agents, such as guanethidine (Ismelin®), reserpine (Serpasil®); central nervous system-acting antihypertensives, such as clonidine (Catapres®), methyldopa (Aldomet®), guanabenz (Wytensin®); anti-angiotensin II agents; ACE inhibitors, such as perindopril (Aceon®) captopril (Capoten®), enalapril (Vasotec®), lisinopril (Prinivil®, Zestril®); angiotensin-II receptor antagonists, such as candesartan (Atacand®), eprosartan (Teveten®), irbesartan (Avapro®), losartan (Cozaar®), telmisartan (Micardis®), valsartan (Diovan®); calcium channel blockers, such as verapamil (Calan®, Isoptin®), diltiazem (Cardizem®), nifedipine (Adalat®, Procardia®); diuretics; direct vasodilators, such as nitroprusside (Nipride®), diazoxide (Hyperstat® IV), hydralazine (Apresoline®), minoxidil (Loniten®), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip®), ciprofibrate (Modalim®), and statins, such as atorvastatin (Lipitor®), fluvastatin (Lescol®), lovastatin (Mevacor®, Altocor®), mevastatin, pitavastatin (Livalo®, Pitava®) pravastatin (Lipostat®), rosuvastatin (Crestor®), and simvastatin (Zocor®).

In this disclosure, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient a compound as disclosed herein (e.g., Formula I, II, III, IV, V or VI) in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire®, Bricanyl®), albuterol (Proventil®), salmeterol (Serevent®, Serevent Diskus®), theophylline, ipratropium bromide (Atrovent®), tiotropium (Spiriva®), methylprednisolone (Solu-Medrol®, Medrol®), magnesium, and potassium. Thus, one aspect of the disclosure is a method of treating a pulmonary disorder comprising administering a compound of the disclosure in combination with one or more compounds useful for the treatment of pulmonary disorders to a subject, particularly a human subject, in human in need thereof Metabolic Disorders Combination Therapy Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics. Thus, one aspect of the disclosure is a method of treating a metabolic disease comprising administering a compound of the disclosure in combination with one or more compounds useful for the treatment of metabolic diseases to a subject, particularly a human subject, in human in need thereof Peripheral Vascular Disorders Combination Therapy Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix®), lansoprazole (Prevacid®), esomeprazole (Nexium®), omeprazole (Prilosec®), rabeprazole; H2 blockers, such as cimetidine (Tagamet®), ranitidine (Zantac®), famotidine (Pepcid®), nizatidine (Axid®); prostaglandins, such as misoprostol (Cytotec®); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with a compound as disclosed herein (e.g., Formula III, III, IV, or V).

Antibiotics

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef®), cephalexin (Keflex®), cephradine (Velosef®), cefaclor (Ceclor®), cefuroxime axtel (Ceftin®), cefprozil (Cefzil®), loracarbef (Lorabid®), cefixime (Suprax®), cefpodoxime proxetil (Vantin®), ceftibuten (Cedax®), cefdinir (Omnicef®), ceftriaxone (Rocephin®), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors.

Antidepressant and Anti-Anxiety Agents

Antidepressant and anti-anxiety agents include those agents used to treat anxiety disorders, depression, and those used as sedatives and tranquilizers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft®, Lustral®, Apo-Sertral®, Asentra®, Gladem®, Serlift®, Stimuloton®); escitalopram (Lexapro®, Cipralex®); fluoxetine (Prozac®, Sarafem®, Fluctin®, Fontex®, Prodep®, Fludep®, Lovan®); venlafaxine (Effexor® XR, Efexor®); citalopram (Celexa®, Cipramil®, Talohexane®); paroxetine (Paxil®, Seroxat®, Aropax®); trazodone (Desyrel®); amitriptyline (Elavil®); and bupropion (Wellbutrin®, Zyban®).

Accordingly, one aspect of the disclosure provides for a composition comprising the late sodium channel blockers of the disclosure (i.e. compound of formula I, II, III, IV, V, VI or VII) and at least one therapeutic agent. In an alternative embodiment, the composition comprises the late sodium channel blockers of the disclosure and at least two therapeutic agents. In further alternative embodiments, the composition comprises the late sodium channel blockers of the disclosure and at least three therapeutic agents, the late sodium channel blockers of the disclosure and at least four therapeutic agents, or the late sodium channel blockers of the disclosure and at least five therapeutic agents.

The methods of combination therapy include co-administration of a single formulation containing the late sodium channel blockers of the disclosure (i.e. compound of formula I, II, III, IV, V, VI or VII) and therapeutic agent or agents, essentially contemporaneous administration of more than one formulation comprising the late sodium channel blocker of the disclosure and therapeutic agent or agents, and consecutive administration of a late sodium channel blocker of the disclosure and therapeutic agent or agents, in any order, wherein preferably there is a time period where the late sodium channel blocker of the disclosure and therapeutic agent or agents simultaneously exert their therapeutic effect.

Synthesis of Example Compounds

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula I-VII or other formulas or compounds disclosed herein, may be accomplished as described in the following examples. If available, reagents may be purchased commercially, e.g. from Sigma Aldrich or other chemical suppliers.

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, that conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I

The compounds of the disclosure including compounds of Formula I-VII may be prepared by first providing a suitably substituted pyridine, then attaching the desired substituents using suitable coupling conditions (e.g., Suzuki coupling, Mitsunobu reaction, alkylation, etc.), and then cyclizing the imidazole portion of the bicyclic core. Exemplary processes are shown in the schemes below for the synthesis of a compound of Formula I.

Scheme 1 shows the preparation of compounds of Formula I, where $R^1$ is H (or other formula as described herein). In Scheme 1, LG is a leaving group (e.g., halo), PG is a nitrogen protecting group, and alkyl, $R^1$, $R^2$, $R^3$ and $R^4$ are as defined herein. The schemes and processes to prepare compounds of formula I may be readily adapted to prepare compounds of formula VII by using the analogous coupling agent of formula F by one of ordinary skill in the art.

Scheme A

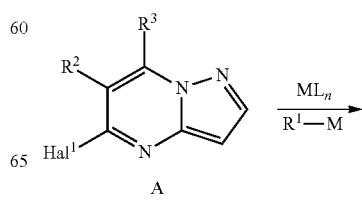

A

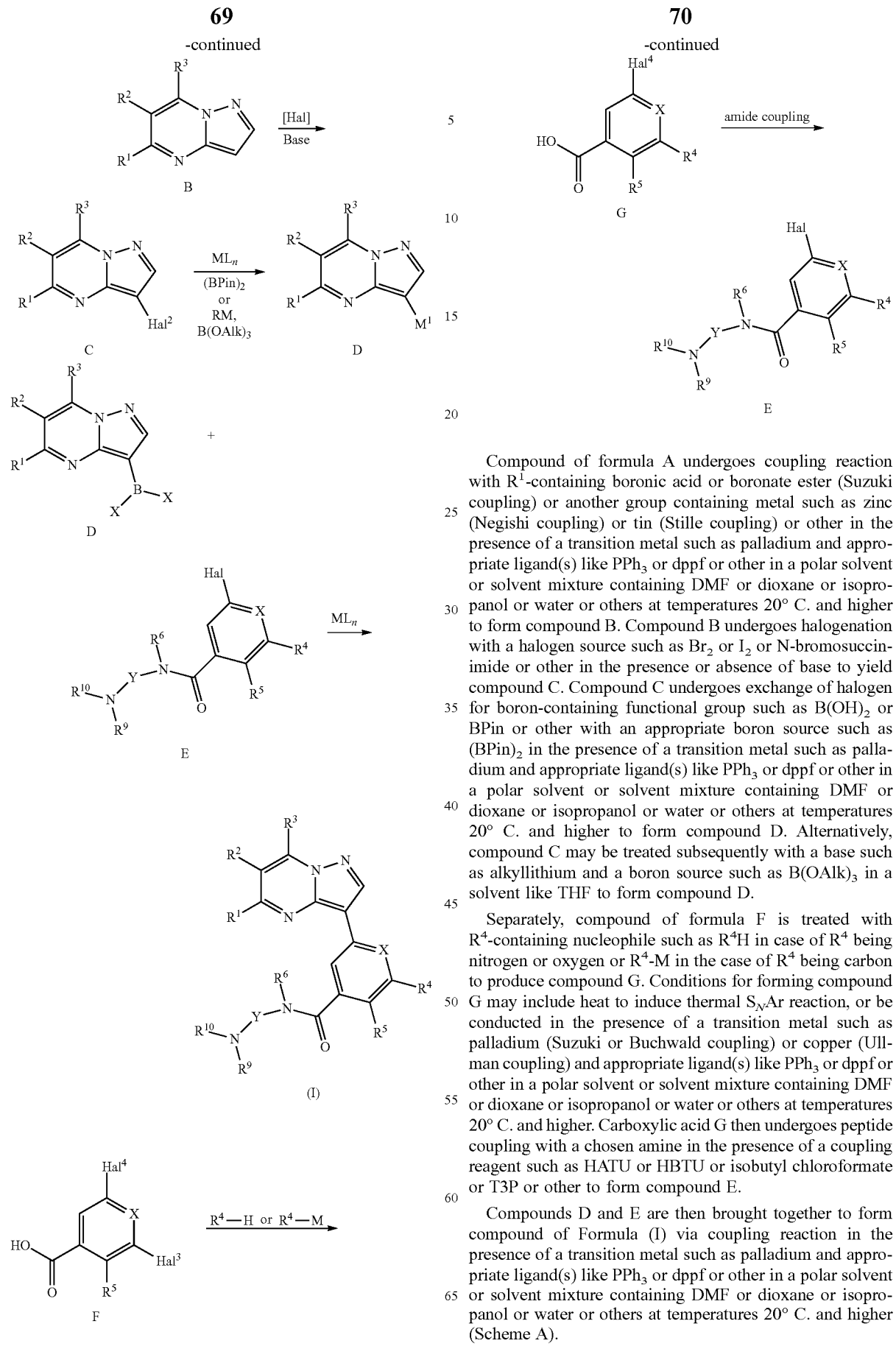

Compound of formula A undergoes coupling reaction with $R^1$-containing boronic acid or boronate ester (Suzuki coupling) or another group containing metal such as zinc (Negishi coupling) or tin (Stille coupling) or other in the presence of a transition metal such as palladium and appropriate ligand(s) like $PPh_3$ or dppf or other in a polar solvent or solvent mixture containing DMF or dioxane or isopropanol or water or others at temperatures 20° C. and higher to form compound B. Compound B undergoes halogenation with a halogen source such as $Br_2$ or $I_2$ or N-bromosuccinimide or other in the presence or absence of base to yield compound C. Compound C undergoes exchange of halogen for boron-containing functional group such as $B(OH)_2$ or BPin or other with an appropriate boron source such as $(BPin)_2$ in the presence of a transition metal such as palladium and appropriate ligand(s) like $PPh_3$ or dppf or other in a polar solvent or solvent mixture containing DMF or dioxane or isopropanol or water or others at temperatures 20° C. and higher to form compound D. Alternatively, compound C may be treated subsequently with a base such as alkyllithium and a boron source such as $B(OAlk)_3$ in a solvent like THF to form compound D.

Separately, compound of formula F is treated with $R^4$-containing nucleophile such as $R^4H$ in case of $R^4$ being nitrogen or oxygen or $R^4$-M in the case of $R^4$ being carbon to produce compound G. Conditions for forming compound G may include heat to induce thermal $S_NAr$ reaction, or be conducted in the presence of a transition metal such as palladium (Suzuki or Buchwald coupling) or copper (Ullman coupling) and appropriate ligand(s) like $PPh_3$ or dppf or other in a polar solvent or solvent mixture containing DMF or dioxane or isopropanol or water or others at temperatures 20° C. and higher. Carboxylic acid G then undergoes peptide coupling with a chosen amine in the presence of a coupling reagent such as HATU or HBTU or isobutyl chloroformate or T3P or other to form compound E.

Compounds D and E are then brought together to form compound of Formula (I) via coupling reaction in the presence of a transition metal such as palladium and appropriate ligand(s) like $PPh_3$ or dppf or other in a polar solvent or solvent mixture containing DMF or dioxane or isopropanol or water or others at temperatures 20° C. and higher (Scheme A).

Scheme B

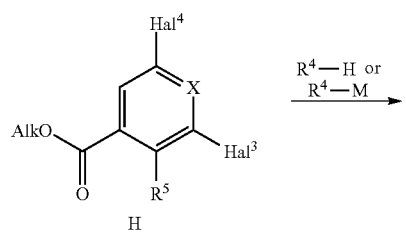

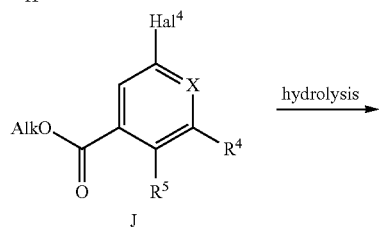

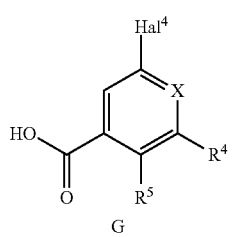

Alternatively, compound of formula G may be prepared from ester of formula H which is treated with $R^1$-containing nucleophile such as $R^1H$ in case of $R^1$ being nitrogen or oxygen or $R^1$-M in the case of $R^1$ being carbon to produce compound J. Conditions for forming compound J may include heat to induce thermal $S_NAr$ reaction, or be conducted in the presence of a transition metal such as palladium (Suzuki or Buchwald coupling) or copper (Ullman coupling) and appropriate ligand(s) like $PPh_3$ or dppf or other in a polar solvent or solvent mixture containing DMF or dioxane or isopropanol or water or others at temperatures 20° C. and higher. Compound J then undergoes acidic or basic hydrolysis to form acid G. Conditions may include alkali metal hydroxide or another aqueous base, or inorganic acid such as hydrochloric or sulphuric acid or another aqueous acid in a solvent or mixture of solvents such as water, methanol, THF, dioxane and others (Scheme B).

Scheme C

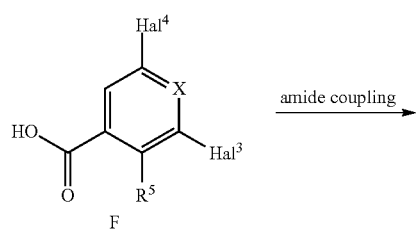

Alternatively, compound of formula F may first undergo peptide coupling with a chosen amine in the presence of a coupling reagent such as HATU or HBTU or isobutyl chloroformate or T3P or other to form compound K and then treated with $R^4$-containing nucleophile such as $R^4H$ in case of $R^4$ being nitrogen or oxygen or $R^4$-M in the case of $R^4$ being carbon to produce compound E. Conditions for forming compound E may include heat to induce thermal $S_NAr$ reaction, or be conducted in the presence of a transition metal such as palladium (Suzuki or Buchwald coupling) or copper (Ullman coupling) and appropriate ligand(s) like $PPh_3$ or dppf or other in a polar solvent or solvent mixture containing DMF or dioxane or isopropanol or water or others at temperatures 20° C. and higher (Scheme C).

Scheme D

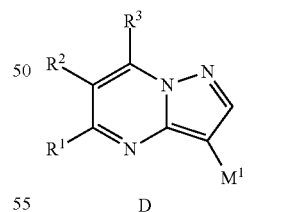

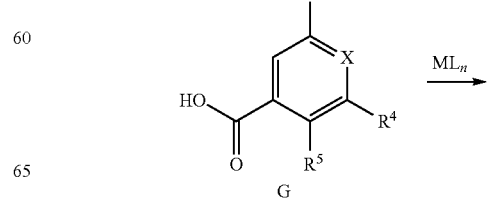

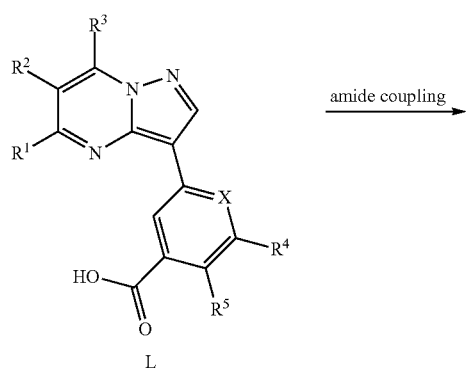

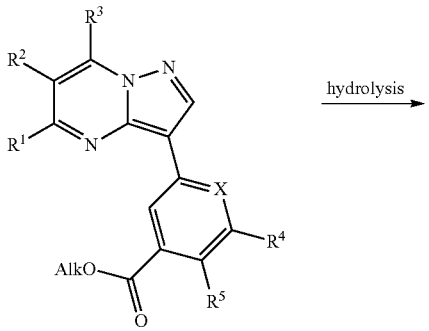

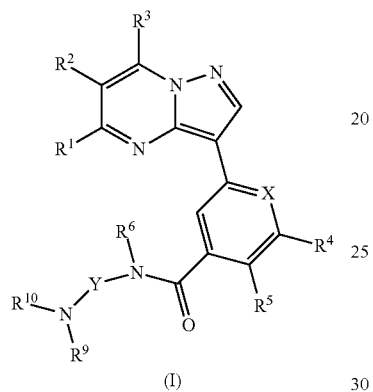

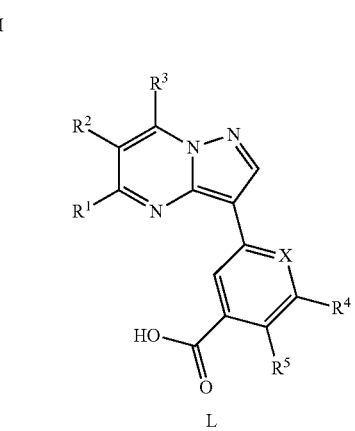

Alternatively, compound of formula D may undergo coupling with compound of formula G to form compound of formula L. Conditions for forming compound L may include a transition metal such as palladium and appropriate ligand(s) like PPh₃ or dppf or other in a polar solvent or solvent mixture containing DMF or dioxane or isopropanol or water or others at temperatures 20° C. and higher. Compound of formula L then undergoes peptide coupling with a chosen amine in the presence of a coupling reagent such as HATU or HBTU or isobutyl chloroformate or T3P or other to form compound of Formula (I) (Scheme D).

Alternatively, compound of formula D may undergo coupling with compound of formula J to form compound of formula M. Conditions for forming compound M may include a transition metal such as palladium and appropriate ligand(s) like PPh₃ or dppf or other in a polar solvent or solvent mixture containing DMF or dioxane or isopropanol or water or others at temperatures 20° C. and higher. Compound of formula M then undergoes acidic or basic hydrolysis to form acid L. Conditions may include alkali metal hydroxide or another aqueous base, or inorganic acid such as hydrochloric or sulphuric acid or another aqueous acid in a solvent or mixture of solvents such as water, methanol, THF, dioxane and others (Scheme E).

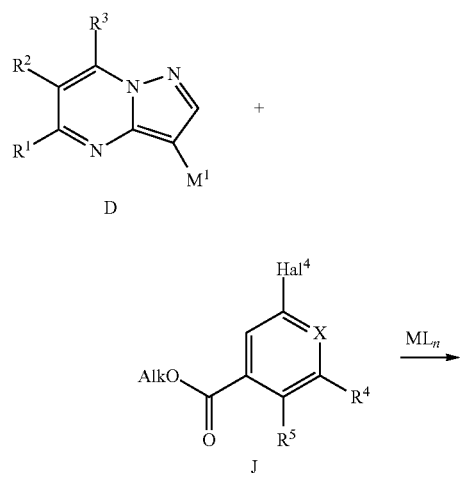

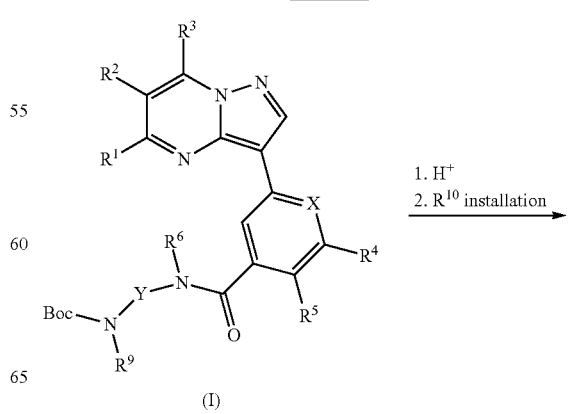

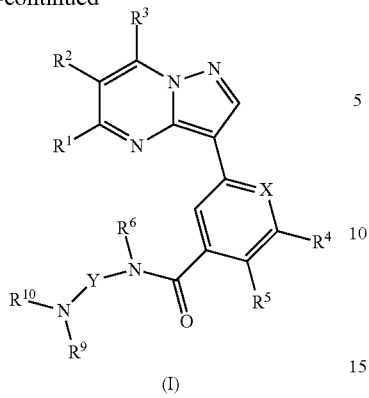

(I)

In the case of Compounds of Formula (I) where $R^{10}$=Boc the protecting group can be removed with aid of TFA or HCl or another strong acid and replaced with another $R^{10}$ group. Methods for $R^{10}$ installation may include but are not limited to alkylation with $R^{10}$ halides or triflates and such in the presence of the base and reductive amination with corresponding aldehyde or ketone and a reducing agent such as $NaBH_4$, $NaBH_3CN$, $NaBH(OAc)_3$, and others (Scheme F).

Scheme G.

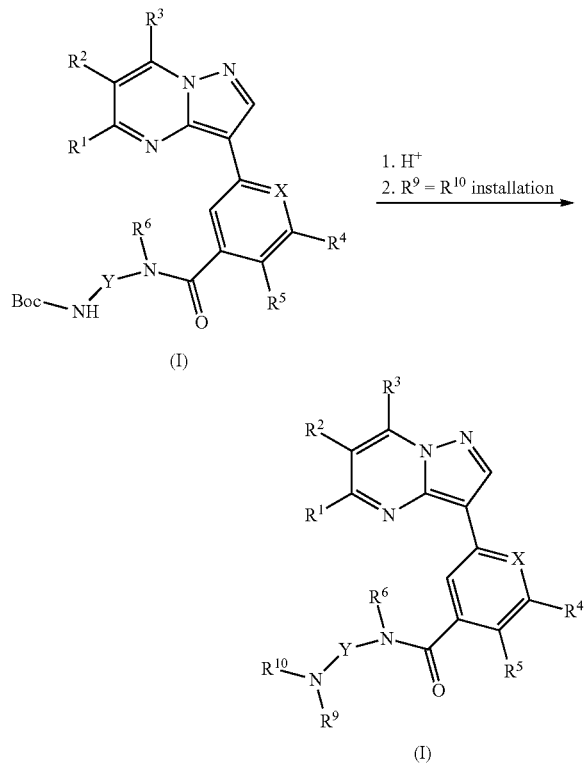

When compounds of Formula (I) where $R^9=R^{10}$ are needed, they can be prepared by double derivatization strategy. Compounds of Formula (I) where $R^{10}$=Boc and $R^9$=H can be used as starting materials and the protecting group can be removed with aid of TFA or HCl or another strong acid and replaced with $R^9$ (same as $R^{10}$) group. Methods for $R^9/R^{10}$ installation may include but are not limited to alkylation with $R^9/R^{10}$ halides or triflates and such in the presence of the base and reductive amination with corresponding aldehyde or ketone and a reducing agent such as $NaBH_4$, $NaBH_3CN$, $NaBH(OAc)_3$, and others (Scheme G).

Example 1

N-(2-(diethylamino)ethyl)-2-(5-(thiophen-2-yl)pyrazolo[1,5-a]pyrimidin-3-yl)isonicotinamide

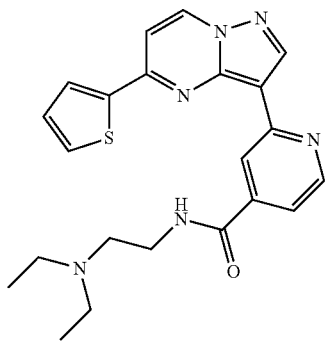

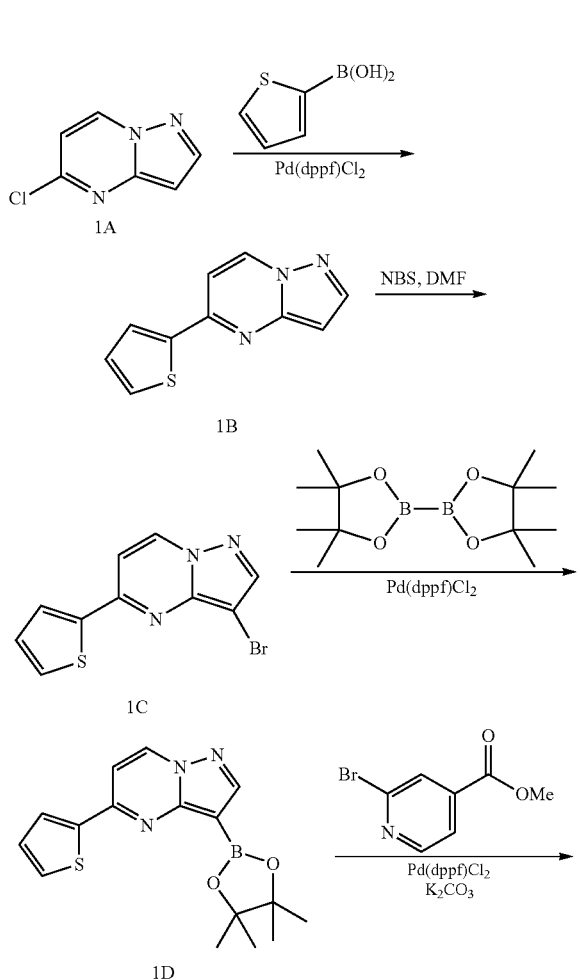

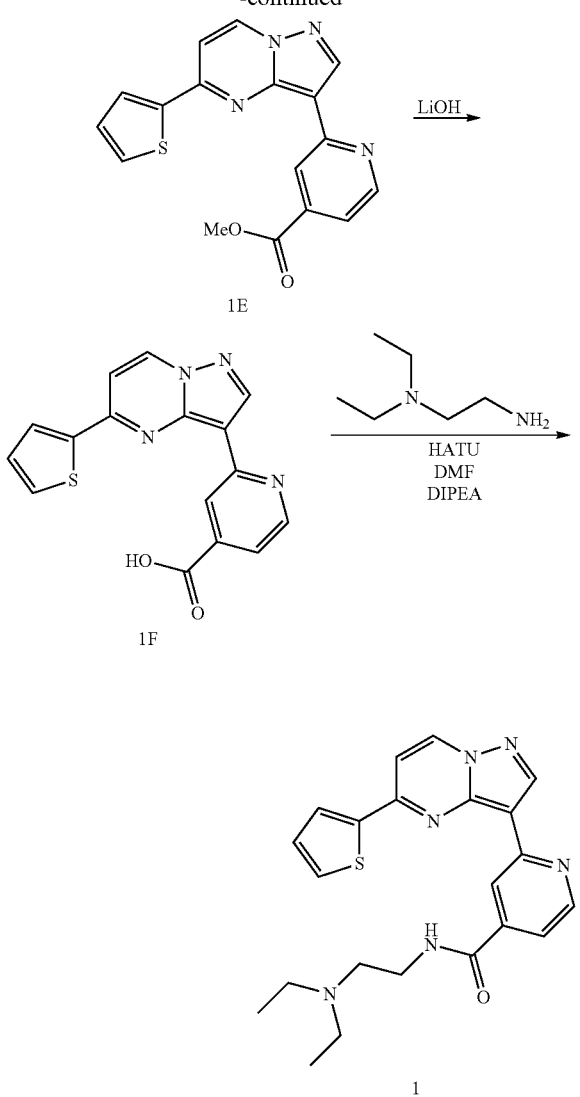

Synthesis of 3-bromo-5-(thiophen-2-yl)pyrazolo[1,5-a]pyrimidine (1C)

The product 1B (200 mg) was dissolved in DMF (5 mL), NBS was added (212 mg) and mixture was stirred overnight. Concentrated, dissolved in $CH_2Cl_2$ and passed through silica with aid of 2:1 hexanes/ethyl acetate. Concentrated the filtrate and the obtained product (yield 59 mg) is used for next step without additional purification.

Synthesis of 3-(4,4,5,5-tetramethyl-1,3,2-dioxaborolan-2-yl)-5-(thiophen-2-yl)pyrazolo[1,5-a]pyrimidine (1D)

The product 1C (200 mg), bis(pinacolato)diboron (288 mg), KOAc (209 mg) and $Pd(dppf)_2Cl_2$ (58 mg) were stirred in 1,4-dioxane (15 mL) at 80° C. overnight. Filtered the reaction mixture through Celite and washed with EtOAc. The filtrate was concentrated and the mixture was used directly for next step.

Synthesis of methyl 2-(5-(thiophen-2-yl)pyrazolo[1,5-a]pyrimidin-3-yl)isonicotinate (1E)

The product 1D (1.0 eq), methyl 2-bromoisonicotinate (1.5 eq), $K_2CO_3$ (3 eq) and $Pd(dppf)_2Cl_2$ (5 mol %) in DMF (3.5 mL) and $H_2O$ (0.3 mL) were put in microwave vial and irradiated at 120° C. for 20 min. Diluted the reaction mixture with EtOAc, filtered through Celite and washed with EtOAc. The filtrate was concentrated and purified by HPLC.

Synthesis of 2-(5-(thiophen-2-yl)pyrazolo[1,5-a]pyrimidin-3-yl)isonicotinic Acid (1F)

Product 1E from previous step (60 mg) was stirred in MeOH (2.5 mL) and 2N LiOH in $H_2O$ (1 mL) at ambient temperature for 2 h. Purified by reverse-phase HPLC.

Synthesis of N-(2-(diethylamino)ethyl)-2-(5-(thiophen-2-yl)pyrazolo[1,5-a]pyrimidin-3-yl)isonicotinamide (1)

To a vial containing product 1F from step V (50 mg), diisopropylethyl (108 uL) and HATU (88.4 mg) were dissolved in DMF (2 mL), and N,N-diethylethylenediamine as a TFA salt (23.4 mg) was added. Stirred overnight and subjected to reverse-phase chromatography and the product was isolated as a TFA salt, 29.8 mg.

LC/MS (M+H): 421.2; $^1$H-NMR (□, 400 MHz, $CD_3OD$) 9.20 (dd, 1H, J=1.6, 0.8 Hz), 8.95 (dd, 1H, J=7.6 Hz), 8.80 (s, 1H), 8.71 (dd, 1H, J=5.2, 0.8 Hz), 8.02 (dd, 1H, J=4.0, 1.2 Hz), 7.76 (dd, 1H, J=5.2, 1.2 Hz), 7.61 (d, 1H, J=7.6 Hz), 7.55 (dd, 1H, J=5.2, 1.6 Hz), 7.26 (dd, 1H, J=5.0, 3.8 Hz), 3.85 (t, 2H, J=6.2 Hz), 3.42-23.47 (m, 4H), 1.40 (t, 6H, J=7.2 Hz).

Synthesis of 5-(thiophen-2-yl)pyrazolo[1,5-a]pyrimidine (1B)

5-Chloropyrazolo[1,5-a]pyrimidine 1A (602 mg) was placed in a 100 mL pressure vessel. 2-Thienylboronic acid (602 mg) and $K_2CO_3$ (1.2 g) were suspended in a mixture of toluene (30 mL), isopropanol (15 mL), and water (15 mL). The solution was degassed by passing nitrogen for 15 min, and $Pd(dppf)Cl_2$—$CH_2Cl_2$ complex was added (160 mg). The reaction mixture was heated at 100° C. for 24 h. Then, the reaction mixture was cooled to room temperature and the organic layer was decanted off, filtered, and concentrated to ~10% of the original volume. At this time, ethyl acetate and hexanes were added in small portions to cause formation of precipitate. Solids filtered and dissolved in 5% MeOH/$CH_2Cl_2$ and filtered through a plug of silica with aid of 10% MeOH in $CH_2Cl_2$. Concentrated the filtrate and the obtained product (yield 256 mg) is used for next step without additional purification.

Example 2

N-(2-(diethylamino)propyl)-2-(5-(thiophen-2-yl)pyrazolo[1,5-a]pyrimidin-3-yl)isonicotinamide

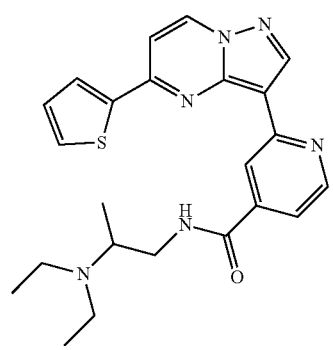

Compound 2 was synthesized following the same procedure as shown in Example 1 and using the commercially available N-(2-(diethylamino)propyl). LC/MS (M+H): 435.2; $^1$H-NMR (CD$_3$OD) δ 9.03 (dd, 1H, J=2.0, 0.8 Hz), 8.89 (d, 1H, J=7.6 Hz), 8.75 (s, 1H), 8.64 (dd, 1H, J=5.2, 0.8 Hz), 7.96 (dd, 1H, J=4.0, 1.2 Hz), 7.73 (dd, 1H, J=5.2, 1.2 Hz), 7.54 (d, 1H, J=7.6 Hz), 7.48 (dd, 1H, J=5.0, 1.8 Hz), 7.23 (dd, 1H, J=5.2, 3.6 Hz), 3.43-3.52 (m, 2H), 3.14-3.25 (m, 1H), 2.65-2.74 (m, 2H), 2.53-2.62 (m, 2H), 1.07-1.16 (m, 9H);

Example 3

N-((hexahydro-1H-pyrrolizin-7a-yl)methyl)-2-(5-(thiophen-2-yl)pyrazolo[1,5-a]pyrimidin-3-yl)isonicotinamide

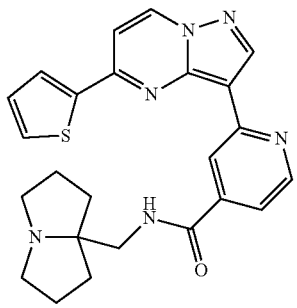

Compound 3 synthesized following the same process as shown in Example 1 and using commercially available (tetrahydro-1H-pyrrolizin-7a(5H)-yl)methanas a TFA salt as its TFA salt. LC/MS (M+H): 445.1; 1H NMR (400 MHL, DMSO-d6) δ 9.71 (s, 1H), 9.26 (d, J=7.4 Hz, 1H), 9.10 (t, J=6.1 Hz, 1H), 8.97-8.86 (m, 1H), 8.82 (s, 1H), 8.77 (dd, J=5.1, 0.9 Hz, 1H), 8.18 (dd, J=3.8, 1.1 Hz, 1H), 7.94 (dd, J=5.0, 1.1 Hz, 1H), 7.76 (d, J=7.4 Hz, 1H), 7.56 (dd, J=5.1, 1.7 Hz, 1H), 7.31 (dd, J=5.0, 3.7 Hz, 1H), 3.72 (d, J=6.1 Hz, 2H), 3.60 (dt, J=12.3, 6.0 Hz, 2H), 3.32-3.16 (m, 2H), 2.20 (dt, J=10.5, 4.7 Hz, 2H), 2.10 (ddt, J=11.8, 8.6, 4.8 Hz, 2H), 2.03-1.88 (m, 4H).

Example 4

(S)—N-(2-(diethylamino)propyl)-2-(5-(thiophen-2-yl)pyrazolo[1,5-a]pyrimidin-3-yl)isonicotinamide

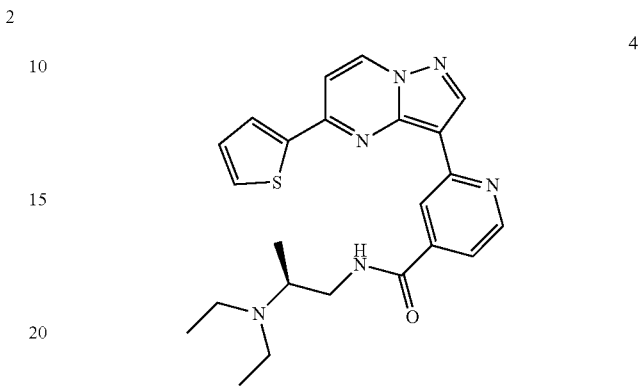

Compound 4 was synthesized following the same process as shown in Example 1 and using the commercially available (S)—N2,N2-diethylpropane-1,2-diamine LC/MS (M+H): 435.2; $^1$H NMR (400 MHz, Methanol-d$_4$) δ 9.13 (s, 1H), 8.88 (d, J=7.4 Hz, 1H), 8.76 (s, 1H), 8.68 (dd, J=5.6, 0.8 Hz, 1H), 7.95 (dd, J=3.8, 1.1 Hz, 1H), 7.74 (dd, J=5.0, 1.1 Hz, 1H), 7.71 (dd, J=5.7, 1.8 Hz, 1H), 7.56 (d, J=7.4 Hz, 1H), 7.23 (dd, J=5.0, 3.8 Hz, 1H), 3.98 (dd, J=14.1, 5.8 Hz, 1H), 3.89 (q, J=6.4 Hz, 1H), 3.61 (dd, J=14.2, 6.3 Hz, 1H), 3.52 (p, J=7.0 Hz, 1H), 3.46-3.34 (m, 1H), 3.28-3.18 (m, 1H), 1.55-1.44 (m, 4H), 1.40 (t, J=7.2 Hz, 3H).

Example 5

N-(((2S,4S)-4-fluoropyrrolidin-2-yl)methyl)-2-(5-(thiophen-2-yl)pyrazolo[1,5-a]pyrimidin-3-yl)isonicotinamide

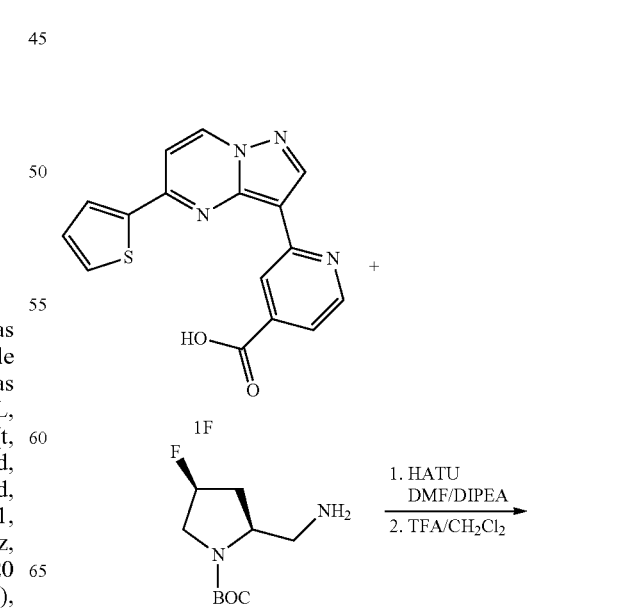

-continued

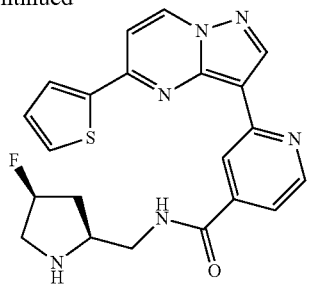

5

Compound 5 was synthesized following the same process as shown in Example 1 and using the commercially available tert-butyl (2S,4S)-2-(aminomethyl)-4-fluoropyrrolidine-1-carboxylate and the product obtained was deported using TFA/DCM as solvent to get the final compound as its TFA salt. LC/MS (M+H): 423.1

Example 6

N-(((2S,4S)-1-ethyl-4-fluoropyrrolidin-2-yl)methyl)-2-(5-(thiophen-2-yl)-3H-imidazo[4,5-b]pyridin-3-yl)isonicotinamide

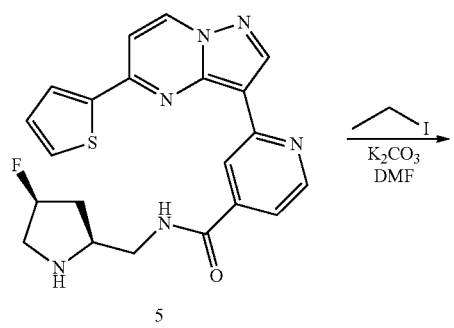

6

Compound 6 was synthesized by alkylating product 5 with ethyl iodide in the presence of a potassium carbonate. The product was obtained by HPLC purification as TFA salt. LC/MS (M+H): 451.1; $^1$H-NMR (DMSO) δ 9.20 (s, 1H), 9.17 (t, 1H, J=1.2 Hz), 8.80 (t, 1H, J=6.0 Hz), 8.72 (d, 1H, J=5.2 Hz), 8.26 (d, 1H, J=8.4 Hz), 7.97 (d, 1H, J=8.4 Hz), 7.90 (dd, 1H, J=3.8, 1.0 Hz), 7.77 (dd, 1H, J=5.2, 1.6 Hz), 7.68 (dd, 1H, J=5.2, 1.4 Hz), 7.19 (dd, 1H, J=5.2, 1.2 Hz), 5.14 (dt, 1H, J=55.2, 1.2 Hz), 3.54-3.60 (m, 1H), 3.20-3.27 (m, 2H), 2.86-2.93 (m, 1H), 2.65-2.70 (m, 1H), 2.22-2.40 (m, 3H), 1.83-1.96 (m, 1H), 1.04 (t, 3H, J=3.2 Hz);

Example 7

(S)—N-(azetidin-2-ylmethyl)-2-(5-(thiophen-2-yl)pyrazolo[1,5-a]pyrimidin-3-yl)isonicotinamide

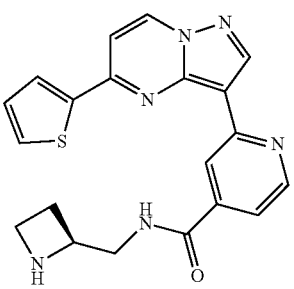

7

Compound 7 was synthesized following the same process as shown in Example 5 and using the commercially available tert-butyl (S)-2-(aminomethyl)azetidine-1-carboxylate, as a TFA salt. LC/MS (M+H): 391.1

Example 8

(R)—N-(azetidin-2-ylmethyl)-2-(5-(thiophen-2-yl)pyrazolo[1,5-a]pyrimidin-3-yl)isonicotinamide

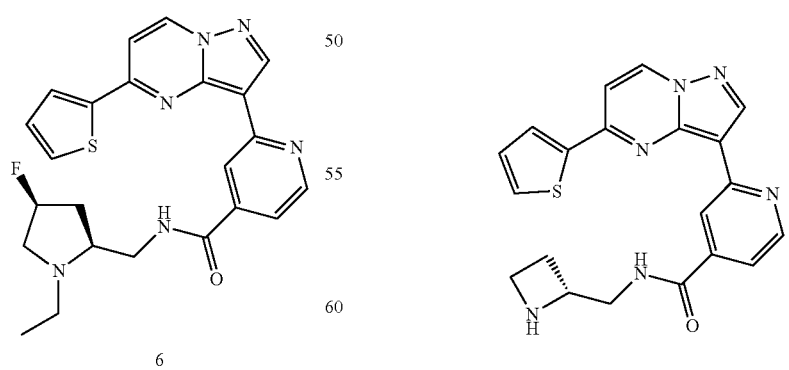

8

Compound 8 was synthesized following the same process as shown in Example 5 and using the commercially available tert-butyl (R)-2-(aminomethyl)azetidine-1-carboxylate, as a TFA salt. LC/MS (M+H): 391.1

Example 9

N-(2-(dimethylamino)ethyl)-2-(5-(thiophen-2-yl)pyrazolo[1,5-a]pyrimidin-3-yl)isonicotinamide

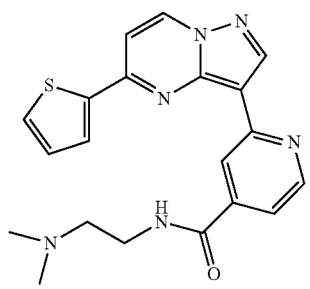

Compound 9 was synthesized following the same process as shown in Example 1 and using the commercially available N1,N1-dimethylethane-1,2-diamine. LC/MS (M+H): 393.1

Example 10

(S)—N-((2-propylpyrrolidin-2-yl)methyl)-2-(5-(thiophen-2-yl)pyrazolo[1,5-a]pyrimidin-3-yl)isonicotinamide

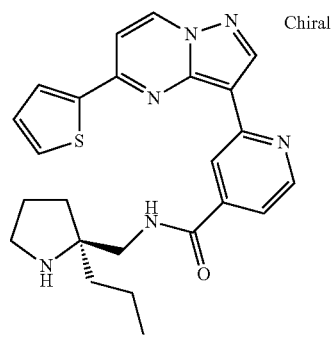

Compound 10 was synthesized following the same process as shown in Example 5 and using the commercially available tert-butyl (S)-2-(aminomethyl)-2-propylpyrrolidine-1-carboxylate as a TFA salt. LC/MS (M+H): 447.2; 1H NMR (400 MHz, Methanol-d4) δ 8.96 (d, J=7.4 Hz, 1H), 8.80 (s, 1H), 8.77 (d, J=0.8 Hz, 1H), 8.70 (dd, J=5.3, 0.9 Hz, 1H), 8.00 (dd, J=3.8, 1.1 Hz, 1H), 7.78 (dd, J=5.1, 1.1 Hz, 1H), 7.63 (d, J=7.4 Hz, 1H), 7.48 (dd, J=5.3, 1.6 Hz, 1H), 7.27 (dd, J=5.1, 3.8 Hz, 1H), 4.06 (s, 2H), 3.40-3.24 (m, 3H), 1.32-1.07 (m, 4H).

Example 11

(S)—N-((2-ethylpyrrolidin-2-yl)methyl)-2-(5-(thiophen-2-yl)pyrazolo[1,5-a]pyrimidin-3-yl)isonicotinamide

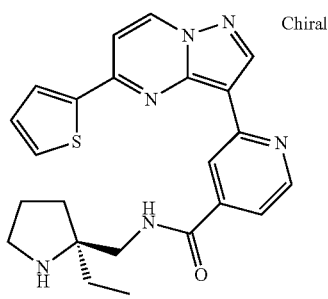

Compound 11 was synthesized following the same process as shown in Example 5 and using the commercially available tert-butyl (S)-2-(aminomethyl)-2-ethylpyrrolidine-1-carboxylate as a TFA salt. LC/MS (M+H): 433.1.

Example 12

(S)—N-((2-methylpyrrolidin-2-yl)methyl)-2-(5-(thiophen-2-yl)pyrazolo[1,5-a]pyrimidin-3-yl)isonicotinamide

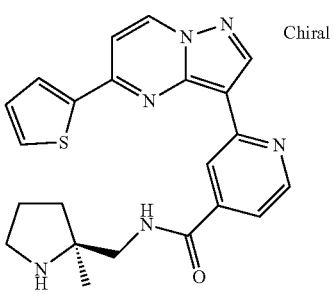

Compound 12 is synthesized following the same process as shown in Example 5 and using the commercially available tert-butyl (S)-2-(aminomethyl)-2-methylpyrrolidine-1-carboxylate as a TFA salt. LC/MS (M+H): 419.1.

Example 13

N—((R)-1-((S)-pyrrolidin-2-yl)ethyl)-2-(5-(thiophen-2-yl)pyrazolo[1,5-a]pyrimidin-3-yl)isonicotinamide

Compound 13 was synthesized following the same process as shown in Example 5 and using the commercially available tert-butyl (R)-2-((S)-1-aminoethyl)pyrrolidine-1-carboxylate as a TFA salt. LC/MS (M+H): 419.1.

Example 14

(S)—N-(2-((2,2-difluoroethyl)amino)propyl)-2-(5-(thiophen-2-yl)pyrazolo[1,5-a]pyrimidin-3-yl)isonicotinamide

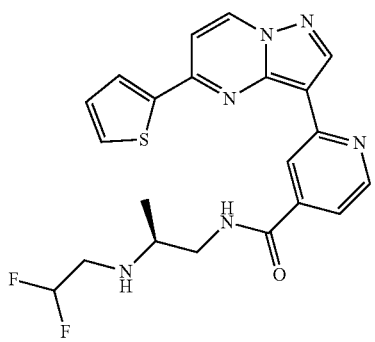 [SMILES: C[C@@H](CNC(=O)c1ccnc(-c2cnn3ccc(-c4cccs4)nc23)c1)NCC(F)F]

Compound 14 was synthesized following the same process as shown in Example 1 and using the commercially available (S)-N2-(2,2-difluoroethyl)propane-1,2-diamine 2×HCl as a TFA salt. LC/MS (M+H): 443.1.

Example 15

(S)—N-(2-((2,2-difluoroethyl)(ethyl)amino)propyl)-2-(5-(thiophen-2-yl)pyrazolo[1,5-a]pyrimidin-3-yl)isonicotinamide

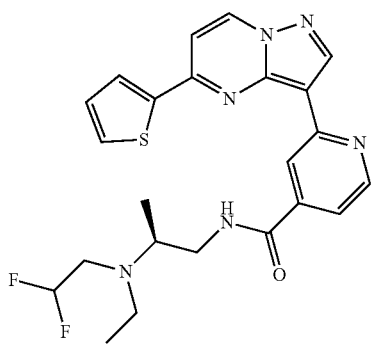 [SMILES: CCN(CC(F)F)[C@@H](C)CNC(=O)c1ccnc(-c2cnn3ccc(-c4cccs4)nc23)c1]

Compound 15 was synthesized following the same process as shown in Example 1 and using the commercially available (S)-N2-(2,2-difluoroethyl)-N2-ethylpropane-1,2-diamine 2×HCl as aTFA salt. LC/MS (M+H): 471.1

Example 16

N-(azepan-2-ylmethyl)-2-(5-(thiophen-2-yl)pyrazolo[1,5-a]pyrimidin-3-yl)isonicotinamide

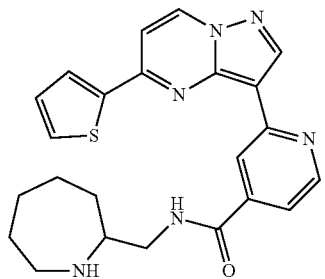

Compound 16 was synthesized following the same process as shown in Example 5 and using the commercially available tert-butyl 2-(aminomethyl)azepane-1-carboxylate, as a TFA salt. LC/MS (M+H): 433.1.

Example 17

(R)—N-((2-isobutylpyrrolidin-2-yl)methyl)-2-(5-(thiophen-2-yl)pyrazolo[1,5-a]pyrimidin-3-yl)isonicotinamide

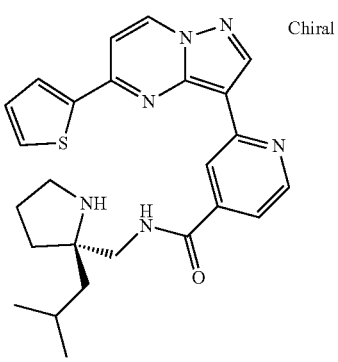

Compound 17 was synthesized following the same process as shown in Example 5 and using the commercially available tert-butyl (R)-2-(aminomethyl)-2-isobutylpyrrolidine-1-carboxylate, as a TFA salt. LC/MS (M+H): 461.2; 1H NMR (δ, 400 MHz, CD3OD), diagnostic signals: 9.13 (dd, J=1.7, 0.8 Hz, 1H), 8.88 (d, J=7.4 Hz, 1H), 8.78 (s, 1H), 8.71 (dd, J=6.0, 0.8 Hz, 1H), 7.93 (dd, J=3.8, 1.1 Hz, 1H), 7.86 (dd, J=6.0, 1.8 Hz, 1H), 7.75 (dd, J=5.0, 1.1 Hz, 1H), 7.56 (d, J=7.4 Hz, 1H), 7.21 (dd, J=5.0, 3.8 Hz, 1H), 3.89 (d, J=15.0 Hz, 1H), 3.78 (d, J=15.0 Hz, 1H), 3.63-3.50 (m, 1H), 3.48-3.36 (m, 1H), 2.42-2.05 (m, 4H), 2.05-1.83 (m, 2H), 1.68 (dd, J=13.9, 7.0 Hz, 1H), 1.07 (d, J=6.4 Hz, 6H).

Example 18

(R)—N-((2-(cyclopropylmethyl)pyrrolidin-2-yl)methyl)-2-(5-(thiophen-2-yl)pyrazolo[1,5-a]pyrimidin-3-yl)isonicotinamide

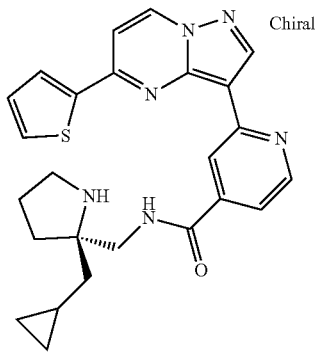

Compound 18 was synthesized following the same process as shown in Example 5 and using the commercially available tert-butyl (R)-2-(aminomethyl)-2-(cyclopropylmethyl)pyrrolidine-1-carboxylate, as a TFA salt. LC/MS (M+H): 459.1; 1H NMR (400 MHz, Methanol-d4) δ 9.13 (dd, J=1.7, 0.8 Hz, 1H), 8.89 (d, J=7.4 Hz, 1H), 8.78 (s, 1H), 8.71 (dd, J=5.9, 0.8 Hz, 1H), 7.94 (dd, J=3.8, 1.1 Hz, 1H), 7.85 (dd, J=5.9, 1.7 Hz, 1H), 7.75 (dd, J=5.1, 1.1 Hz, 1H), 7.57 (d, J=7.4 Hz, 1H), 7.22 (dd, J=5.0, 3.8 Hz, 1H), 3.96 (d, J=14.9 Hz, 1H), 3.89 (d, J=14.9 Hz, 1H), 3.60-3.50 (m, 1H), 3.50-3.40 (m, 1H), 2.37-2.09 (m, 4H), 1.95 (dd, J=14.4, 6.1 Hz, 1H), 1.67 (dd, J=14.4, 7.4 Hz, 1H), 0.90-0.88 (m, 1H), 0.76-0.51 (m, 2H), 0.37-0.14 (m, 2H).

Example 19

N-(piperidin-2-ylmethyl)-2-(5-(thiophen-2-yl)pyrazolo[1,5-a]pyrimidin-3-yl)isonicotinamide

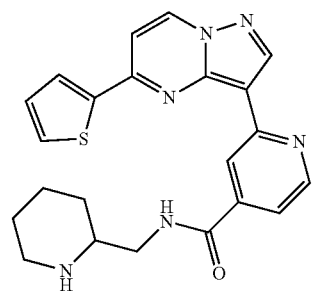

Compound 19 was synthesized following the same process as shown in Example 5 and using the commercially available tert-butyl 2-(aminomethyl)piperidine-1-carboxylate, as a TFA salt. LC/MS (M+H): 419.1.

Example 20

(S)—N-(2-(ethylamino)propyl)-2-(5-(thiophen-2-yl)pyrazolo[1,5-a]pyrimidin-3-yl)isonicotinamide

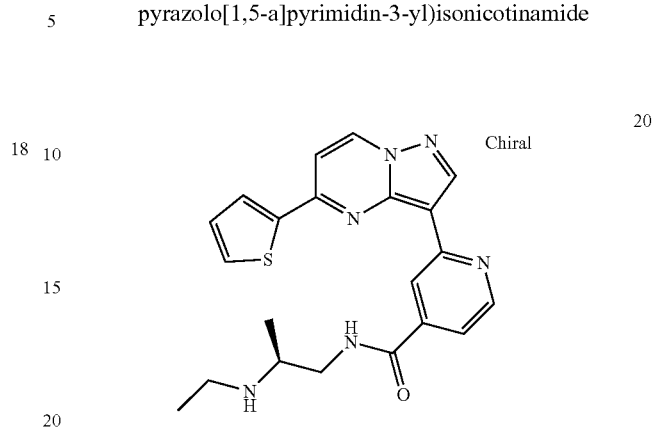

Compound 20 was synthesized following the same process as shown in Example 5 and using the commercially available tert-butyl (S)-(1-aminopropan-2-yl)(ethyl)carbamate, as a TFA salt. LC/MS (M+H): 407.1 1H NMR (400 MHz, Methanol-d4) δ 9.27 (dd, J=1.8, 0.8 Hz, 1H), 8.98 (d, J=7.4 Hz, 1H), 8.84 (s, 1H), 8.75 (dd, J=5.9, 0.8 Hz, 1H), 8.03 (dd, J=3.8, 1.1 Hz, 1H), 7.86 (dd, J=5.9, 1.8 Hz, 1H), 7.78 (dd, J=5.1, 1.1 Hz, 1H), 7.67 (d, J=7.4 Hz, 1H), 7.26 (dd, J=5.0, 3.8 Hz, 1H), 3.83 (dd, J=14.5, 4.9 Hz, 1H), 3.71 (dd, J=14.5, 5.5 Hz, 1H), 3.59 (hept, J=6.4 Hz, 1H), 3.24 (q, J=7.2 Hz, 2H), 1.45 (d, J=6.7 Hz, 3H), 1.37 (t, J=7.2 Hz, 3H).

Example 21

(S)—N-(2-((2-hydroxyethyl)amino)propyl)-2-(5-(thiophen-2-yl)pyrazolo[1,5-a]pyrimidin-3-yl)isonicotinamide

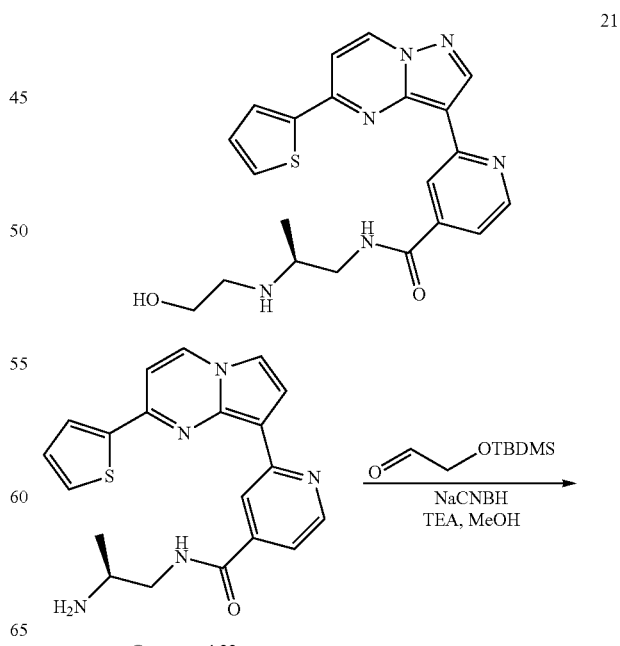

Compound 22

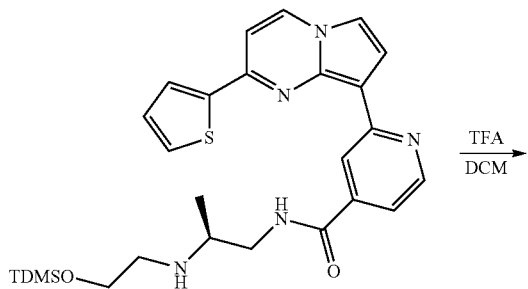

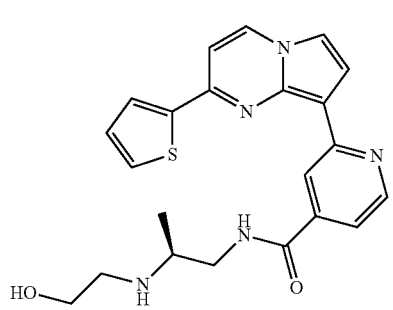

Synthesis of 21: To a solution of compound 22 (50 mg, 0.08 mmol) in MeOH was added (tert-Butyldimethylsilyloxy)acetaldehyde (31.41 µl, 0.16 mmol), Triethylamine (25.28 µl, 0.18 mmol), and then sodium cyanoborohydride (6.22 mg, 0.1 mmol) was added. The reaction was stirred for 16 h. Purified by reverse phase chromatography. The product was dissolved in 10 mL dichloromethane and 0.5 mL trifluoroacetic acid was added. After 16 h, the reaction was concentrated to afford the product as a TFA salt (24 mg). LC/MS (M+H): 423.

Example 22

(S)—N-(2-aminopropyl)-2-(5-(thiophen-2-yl)pyrazolo[1,5-a]pyrimidin-3-yl)isonicotinamide Compound 22 was synthesized following the same process as shown in Example 5 and using the commercially available tert-butyl (S)-(1-aminopropan-2-yl)carbamate, as a TFA salt. LC/MS (M+H):379.1

Example 23

(S)—N-(2-(propylamino)propyl)-2-(5-(thiophen-2-yl)pyrazolo[1,5-a]pyrimidin-3-yl)isonicotinamide

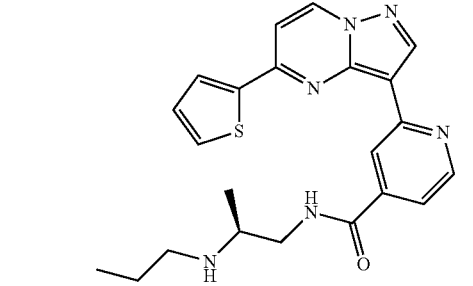

Compound 23 was synthesized following the same process as shown in Example 31 and using compound 22 and commercially available propionaldehyde, as a TFA salt. LC/MS (M+H): 421.2

Example 24

(S)—N-(2-((2-fluoroethyl)amino)propyl)-2-(5-(thiophen-2-yl)pyrazolo[1,5-a]pyrimidin-3-yl)isonicotinamide

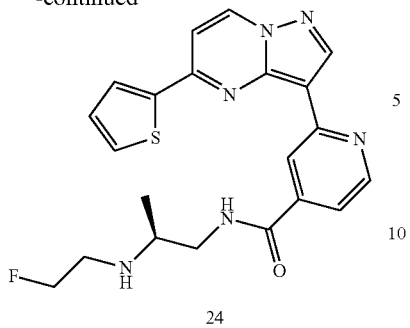

24

Synthesis of 24: To a solution of compound 22 (50 mg, 0.08 mmol) in DMF, 1-Bromo-2-fluoroethane (6.14 µl, 0.08 mmol), Triethylamine (28.73 µl, 0.21 mmol) and Cesium carbonate (10.23 mg, 0.16 mmol) were added and heated at 60° C. for 16 h. The reaction mixture was filtered through syringe filter. Purified on Gilson eluting with 20 mL/min ACN and water with 0.1% TFA (2" 5% ACN; 20" 5-60% ACN; 2" 60-95% ACN; 4" 95% ACN) on Luna column (150×21.30 mm, 5 u C12(2) 100 A). The title compound 24 was obtained as a TFA salt. LC/MS (M+H): 425.1; 1H NMR (400 MHz, Methanol-d4) δ 9.11 (s, 1H), 8.86 (d, J=7.4 Hz, 1H), 8.73 (s, 1H), 8.66 (d, J=5.6 Hz, 1H), 7.93 (dd, J=3.8, 1.1 Hz, 1H), 7.76-7.67 (m, 2H), 7.53 (d, J=7.4 Hz, 1H), 7.22 (dd, J=5.0, 3.8 Hz, 1H), 4.89 (t, J=4.7 Hz, 1H), 4.77 (t, J=4.7 Hz, 1H), 3.87-3.56 (m, 5H), 1.49 (d, J=6.6 Hz, 3H).

Example 25

N-(2-aminobutyl)-2-(5-(thiophen-2-yl)pyrazolo[1,5-a]pyrimidin-3-yl)isonicotinamide

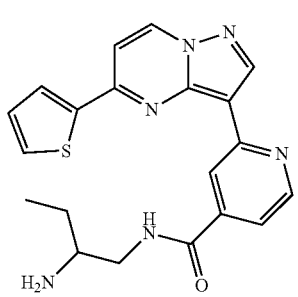

25

Compound 25 was synthesized following the same process as shown in Example 5 and using the commercially available tert-butyl (1-aminobutan-2-yl)carbamate, as a TFA salt. LC/MS (M+H): 387; 1H NMR (400 MHz, Methanol-d4) δ 9.19 (dd, J=1.8, 0.8 Hz, 1H), 8.95 (d, J=7.4 Hz, 1H), 8.80 (s, 1H), 8.71 (dd, J=5.6, 0.9 Hz, 1H), 8.01 (dd, J=3.8, 1.1 Hz, 1H), 7.78-7.71 (m, 2H), 7.62 (d, J=7.4 Hz, 1H), 7.25 (dd, J=5.0, 3.8 Hz, 1H), 3.78 (dd, J=14.6, 4.3 Hz, 1H), 3.73-3.60 (m, 1H), 3.42 (dd, J=6.8, 4.5 Hz, 1H), 1.81 (ddd, J=27.6, 14.4, 7.2 Hz, 2H), 1.14 (t, J=7.5 Hz, 3H).

Example 26

(S)—N-(2-((cyclopropylmethyl)amino)propyl)-2-(5-(thiophen-2-yl)pyrazolo[1,5-a]pyrimidin-3-yl)isonicotinamide

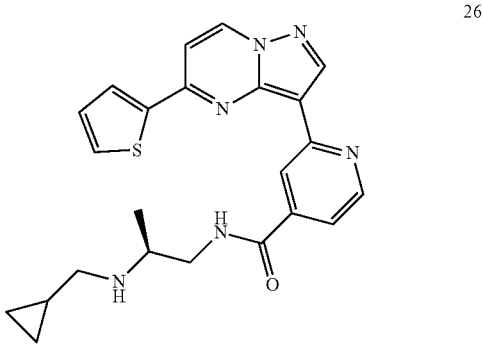 [SMILES: C[C@@H](CNC(=O)c1ccnc(-c2cnn3ccc(-c4cccs4)nc23)c1)NCC1CC1]

26

Compound 26 was synthesized following the same process as shown in Example 31 and using compound 22 and commercially available cyclopropane carbaldehyde, as a TFA salt.

LC/MS (M+H): 433.2

Example 27

(S)—N-(2-((2,2-difluoroethyl)amino)propyl)-2-(5-(thiophen-2-yl)pyrazolo[1,5-a]pyrimidin-3-yl)isonicotinamide

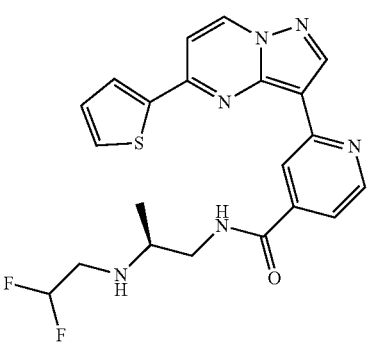

27

Compound 27 was synthesized following the same process as shown in Example 24 and using the commercially available 2,2-Difluoroethyl trifluoromethanesulfonate, as a TFA salt. LC/MS (M+H): 443.1

Example 28
(S)-2-(5-(thiophen-2-yl)pyrazolo[1,5-a]pyrimidin-3-yl)-N-(2-((2,2,2-trifluoroethyl)amino)propyl)isonicotinamide
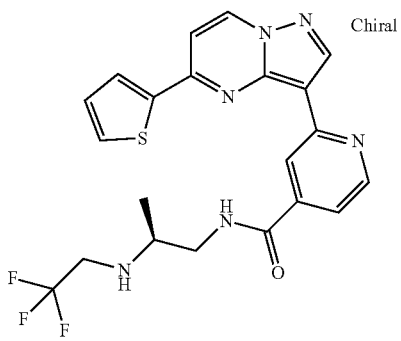
Compound 28 was synthesized following the same process as shown in Example 24 and using the commercially available 2,2,2-trifluoroethyl trifluoromethanesulfonate. LC/MS (M+H): 461.1
Example 29
(R)—N-(2-(ethylamino)butyl)-2-(5-(thiophen-2-yl)pyrazolo[1,5-a]pyrimidin-3-yl)isonicotinamide
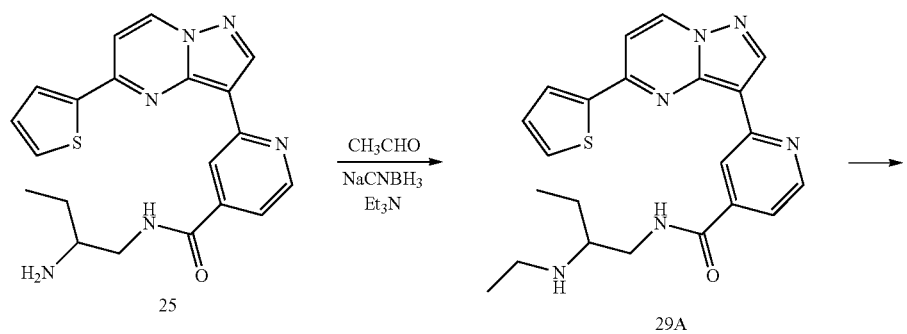
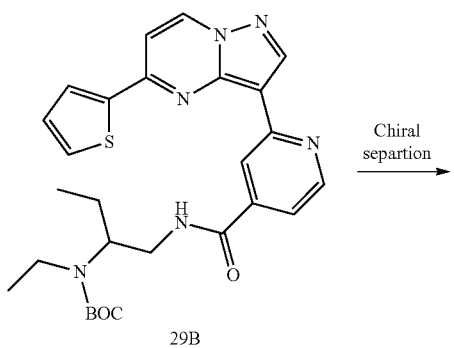

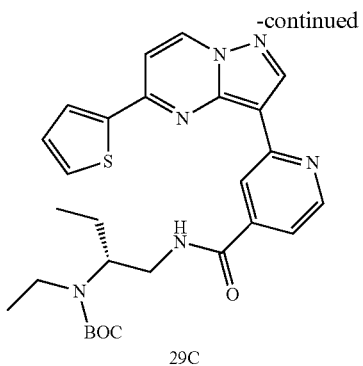

29C

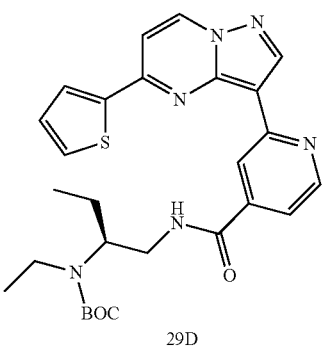

29D

TFA
CH₂Cl₂

TFA
CH₂Cl₂

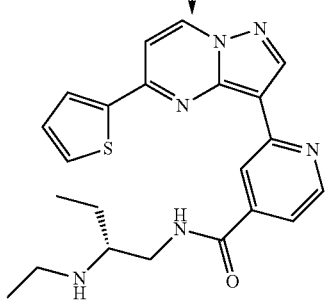

29

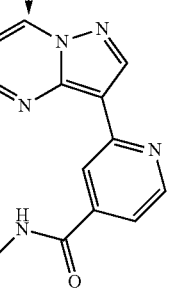

30

Synthesis of N-(2-(ethylamino)butyl)-2-(5-(thiophen-2-yl)pyrazolo[1,5-a]pyrimidin-3-yl)isonicotinamide (29A)

Compound 29A was synthesized following the same process as shown in Example 23 and using compound 25 and commercially available acetaldehyde, as a TFA salt.

Synthesis of tert-butyl ethyl(1-(2-(5-(thiophen-2-yl)pyrazolo[1,5-a]pyrimidin-3-yl)isonicotinamido)butan-2-yl)carbamate (29B)

To a solution of compound 29A (64 mg, 0.09 mmol) in 2 mL DCM was added Di-tert-butyl dicarbonate (23.62 mg, 0.11 mmol) and Hunig's base (55.13 µl, 0.32 mmol). After 16 hours, the rxn was concentrated and purified by reverse phase chromatography to afford 40 mg of product.

Separation of tert-butyl (R)-ethyl(1-(2-(5-(thiophen-2-yl)pyrazolo[1,5-a]pyrimidin-3-yl)isonicotinamido)butan-2-yl)carbamate (29C) and tert-butyl (S)-ethyl(1-(2-(5-(thiophen-2-yl)pyrazolo[1,5-a]pyrimidin-3-yl)isonicotinamido)butan-2-yl)carbamate (29D)

The enantiomer of compound 29B were separated using SFC to afford 19 mg of compound 29C and 20 mg of compound 29D. The R and S were arbitrarily assigned.

Synthesis of (R)—N-(2-(ethylamino)butyl)-2-(5-(thiophen-2-yl)pyrazolo[1,5-a]pyrimidin-3-yl)isonicotinamide (29)

Compound 29C (20 mg) was dissolved in 10 mL DCM and 0.5 mL trifluoroacetic acid was added to solution. The reaction was stirred for 16 h and then concentrated to afford 24 mg of compound 29 as a TFA salt.

LC/MS (M+H): 421.1

1H NMR (400 MHz, Methanol-d4) δ 9.19 (d, J=1.5 Hz, 1H), 8.92 (d, J=7.3 Hz, 1H), 8.80 (s, 1H), 8.71 (d, J=5.8 Hz, 1H), 7.98 (dd, J=3.8, 1.0 Hz, 1H), 7.84 (dd, J=5.8, 1.7 Hz, 1H), 7.76 (dd, J=5.0, 1.0 Hz, 1H), 7.60 (d, J=7.3 Hz, 1H), 7.23 (dd, J=5.0, 3.7 Hz, 1H), 3.92 (dd, J=15.0, 3.8 Hz, 1H), 3.73 (dd, J=15.0, 5.4 Hz, 1H), 3.39 (d, J=4.6 Hz, 1H), 3.30-3.18 (m, 2H), 2.00-1.67 (m, 2H), 1.38 (t, J=7.2 Hz, 3H), 1.15 (t, J=7.4 Hz, 3H).

Example 30

(S)—N-(2-(ethylamino)butyl)-2-(5-(thiophen-2-yl)pyrazolo[1,5-a]pyrimidin-3-yl)isonicotinamide

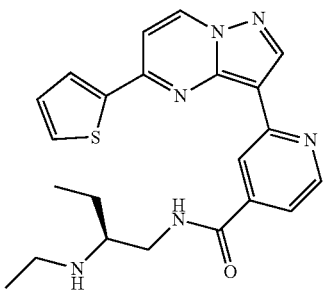

30

Compound 30 was synthesized by deprotection of 29D as shown in example 29, as a TFA salt. LC/MS (M+H): 421.1;

1H NMR (400 MHz, Methanol-d4) δ 9.26 (d, J=1.6 Hz, 1H), 8.98 (d, J=7.4 Hz, 1H), 8.84 (s, 1H), 8.75 (d, J=5.8 Hz, 1H), 8.03 (dd, J=3.8, 1.1 Hz, 1H), 7.86 (dd, J=5.8, 1.7 Hz, 1H), 7.78 (dd, J=5.1, 1.1 Hz, 1H), 7.66 (d, J=7.4 Hz, 1H), 7.26 (dd, J=5.0, 3.8 Hz, 1H), 3.93 (dd, J=15.0, 3.9 Hz, 1H), 3.73 (dd, J=15.0, 5.4 Hz, 1H), 3.38 (dd, J=8.9, 4.4 Hz, 1H), 3.30-3.20 (m, 2H), 1.98-1.72 (m, 1H), 1.38 (t, J=7.2 Hz, 3H), 1.15 (t, J=7.5 Hz, 3H).

Example 31

N-(2-(isopropylamino)butyl)-2-(5-(thiophen-2-yl)pyrazolo[1,5-a]pyrimidin-3-yl)isonicotinamide

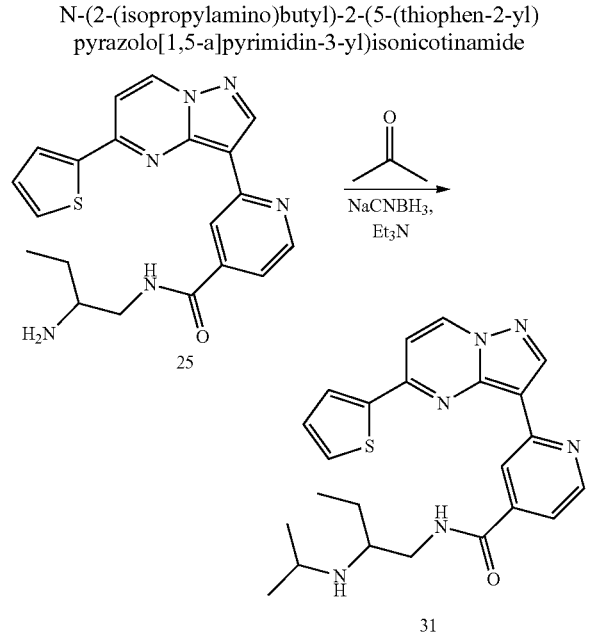

Synthesis of compound 31: Compound 31 was synthesized as shown in example 29. To a solution of compound 25 in methanol at ice temperature acetone, and triethylamine were added followed by sodium cyanoborohydride, and the reaction mixture was allowed to come to r.t. and stirred for 16 h. The reaction mixture was filtered through syringe filter, concentrated and the product was obtained by HPLC purification.
LC/MS (M+H): 435.2

Example 32

(S)—N-(2-(isopropylamino)propyl)-2-(5-(thiophen-2-yl)pyrazolo[1,5-a]pyrimidin-3-yl)isonicotinamide

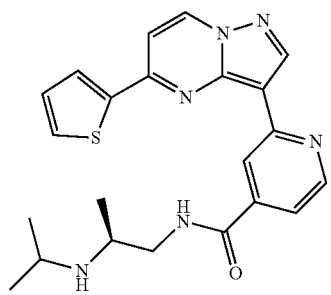

Compound 32 was synthesized as shown in the synthesis of compound 31 starting from compound 22, as a TFA salt. LC/MS (M+H): 421.1

Example 33

(R)—N-(2-(ethylamino)propyl)-2-(5-(thiophen-2-yl)pyrazolo[1,5-a]pyrimidin-3-yl)isonicotinamide

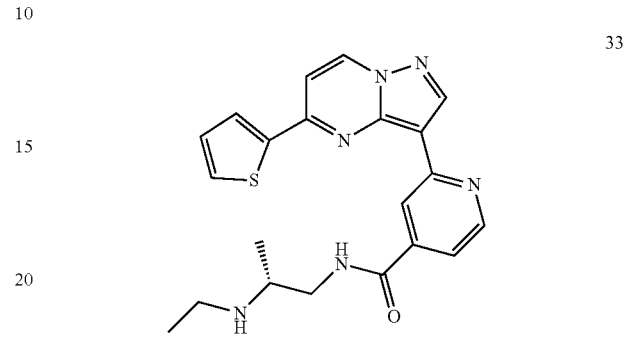

Compound 33 was synthesized as shown in example 5, starting from commercially available tert-butyl (R)-(1-aminopropan-2-yl)(ethyl)carbamate, as a TFA salt. LC/MS (M+H): 407.1; 1H NMR (400 MHz, Methanol-d4) δ 9.15 (dd, J=1.8, 0.8 Hz, 1H), 8.85 (d, J=7.4 Hz, 1H), 8.76 (s, 1H), 8.70 (dd, J=6.1, 0.8 Hz, 1H), 7.90 (dd, J=3.8, 1.1 Hz, 1H), 7.87 (dd, J=6.1, 1.8 Hz, 1H), 7.73 (dd, J=5.0, 1.1 Hz, 1H), 7.53 (d, J=7.4 Hz, 1H), 7.19 (dd, J=5.0, 3.8 Hz, 1H), 3.81 (dd, J=14.5, 5.0 Hz, 1H), 3.72 (dd, J=14.5, 5.6 Hz, 1H), 3.64-3.56 (m, 1H), 3.24 (q, J=7.2 Hz, 2H), 1.45 (d, J=6.7 Hz, 3H), 1.37 (t, J=7.2 Hz, 3H).

Example 34

(S)—N-(pyrrolidin-2-ylmethyl)-2-(5-(thiophen-2-yl)pyrazolo[1,5-a]pyrimidin-3-yl)isonicotinamide

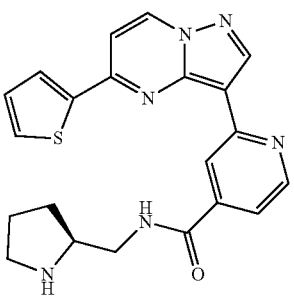

Compound 34 was synthesized following the same process as shown in Example 5 and using the commercially available tert-butyl (S)-2-(aminomethyl)pyrrolidine-1-carboxylate, as a TFA salt. LC/MS (M+H): 405.1.

Example 35

(S)—N-((1-methylpyrrolidin-2-yl)methyl)-2-(5-(thiophen-2-yl)pyrazolo[1,5-a]pyrimidin-3-yl)isonicotinamide

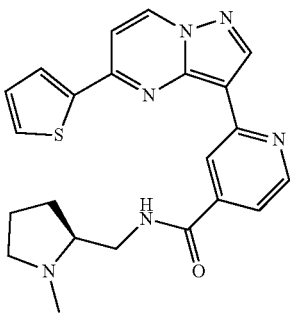

35

Compound 35 was synthesized following the same process as shown in Example 1 and using the commercially available (S)-(1-methylpyrrolidin-2-yl)methanamine LC/MS (M+H): 419.1

Example 36

(S)—N-((1-ethylpyrrolidin-2-yl)methyl)-2-(5-(thiophen-2-yl)pyrazolo[1,5-a]pyrimidin-3-yl)isonicotinamide

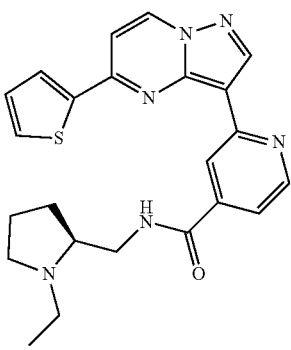

36

Compound 36 was synthesized following the same process as shown in Example 1 and using the commercially available (S)-(1-ethylpyrrolidin-2-yl)methanamine. LC/MS (M+H): 433.1; 1H NMR (400 MHz, Methanol-d4) δ 9.15 (d, J=0.9 Hz, 0H), 8.89 (d, J=7.4 Hz, 1H), 8.76 (s, 1H), 8.69 (dd, J=5.8, 0.8 Hz, 1H), 7.95 (dd, J=3.8, 1.1 Hz, 1H), 7.78-7.74 (m, 2H), 7.56 (d, J=7.4 Hz, 1H), 7.23 (dd, J=5.0, 3.8 Hz, 1H), 3.96 (d, J=9.7 Hz, 1H), 3.88-3.62 (m, 3H), 3.29-3.14 (m, 2H), 2.37 (d, J=7.3 Hz, 1H), 2.26-1.98 (m, 3H), 1.45 (t, J=7.2 Hz, 3H).

Example 37

N-(2-(diethylamino)propyl)-2-(5-phenylpyrazolo[1,5-a]pyrimidin-3-yl)isonicotinamide

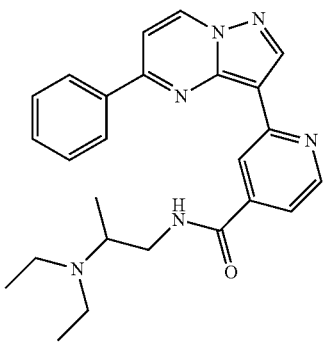

37

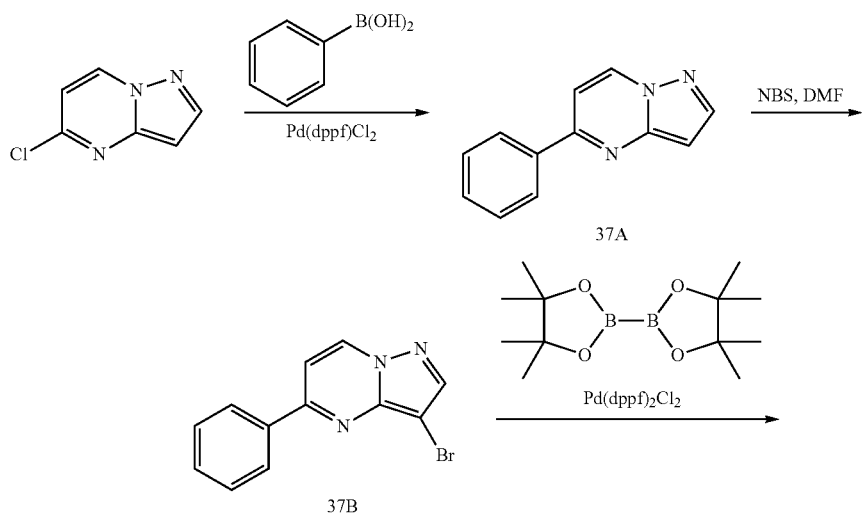

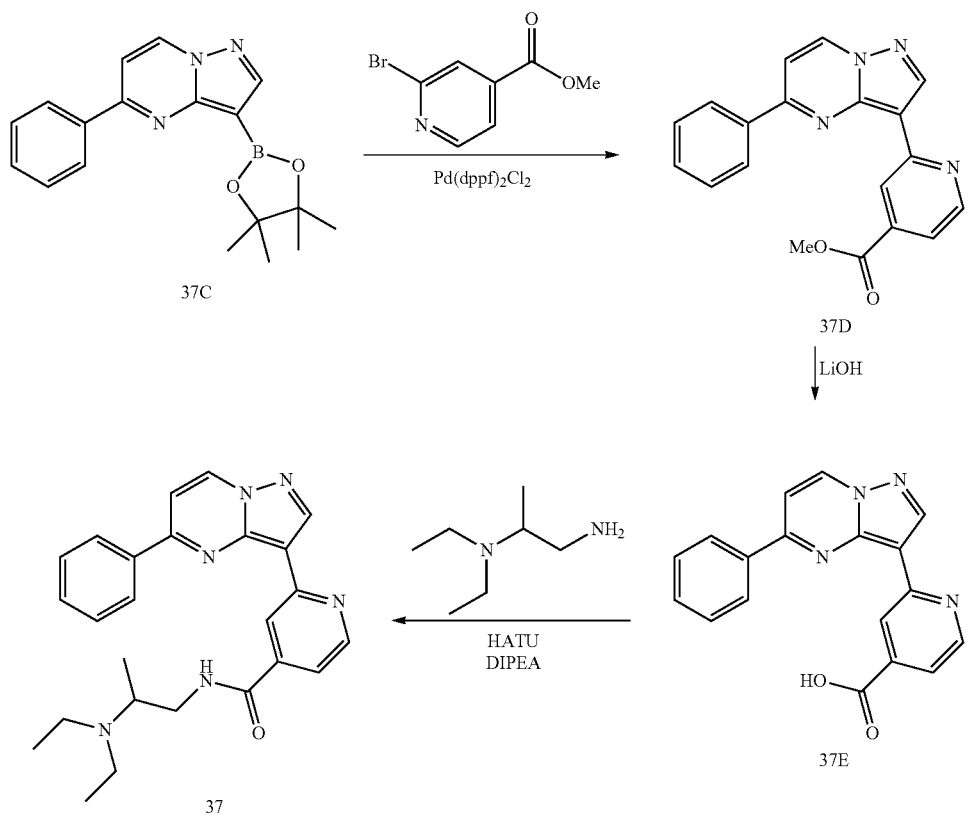

Compound 37 was synthesized following the same process as shown in Example 1 and starting with phenyl boronic acid and the commercially available N2,N2-diethylpropane-1,2-diamine, as a TFA salt. LC/MS (M+H): 429.2.

Example 38

(S)—N-(2-(diethylamino)propyl)-2-(5-phenylpyrazolo[1,5-a]pyrimidin-3-yl)isonicotinamide

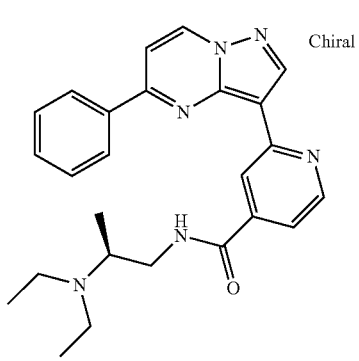

Compound 38 was synthesized following the same process as shown in Example 37 and using the commercially available (S)—N2,N2-diethylpropane-1,2-diamine, as a TFA salt. LC/MS (M+H): 429.2; 1H NMR (400 MHz, Methanol-$d_4$) δ 9.13 (dd, J=1.7, 0.8 Hz, 1H), 8.93 (d, J=7.4 Hz, 1H), 8.77 (s, 1H), 8.67 (dd, J=5.6, 0.8 Hz, 1H), 8.24 (dd, J=7.5, 1.4 Hz, 2H), 7.67 (dd, J=5.6, 1.7 Hz, 1H), 7.63 (d, J=7.4 Hz, 1H), 7.59-7.49 (m, 3H), 3.97 (dd, J=14.1, 5.8 Hz, 1H), 3.88 (h, J=6.5 Hz, 1H), 3.58 (dd, J=14.1, 6.3 Hz, 1H), 3.51 (dt, J=14.1, 7.0 Hz, 1H), 3.45-3.34 (m, 2H), 3.27-3.16 (m, 1H), 1.53-1.43 (m, 5H), 1.39 (t, J=7.2 Hz, 3H).

Example 39

N-(2-(dimethylamino)ethyl)-2-(5-phenylpyrazolo[1,5-a]pyrimidin-3-yl)isonicotinamide

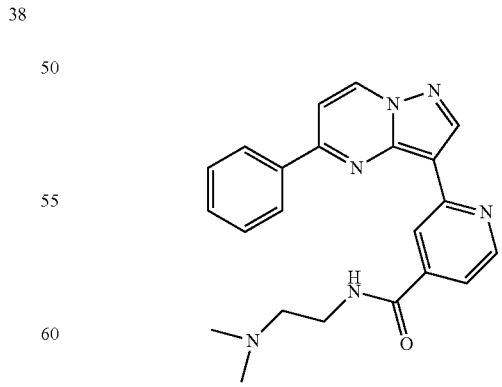

Compound 39 was synthesized following the same process as shown in Example 37 and using the commercially available N1,N1-dimethylethane-1,2-diamine, as a TFA salt. LC/MS (M+H): 387.1

Example 40

2-(5-phenylpyrazolo[1,5-a]pyrimidin-3-yl)-N-(piperidin-2-ylmethyl)isonicotinamide

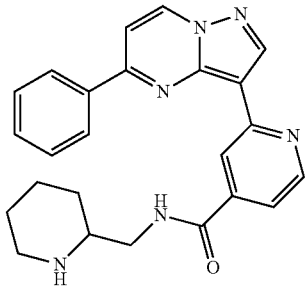

Compound 40 was synthesized following the same process as shown in Example 37 and example 5, and using the commercially available tert-butyl piperidine-1-carboxylate, as a TFA salt. LC/MS (M+H): 413.13

Example 41

N-((3,3-dimethylazetidin-2-yl)methyl)-2-(5-phenylpyrazolo[1,5-a]pyrimidin-3-yl)isonicotinamide

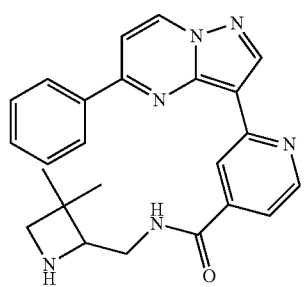

Compound 41 was synthesized following the same process as shown in Example 37 and example 5, and using the commercially available tert-butyl 3,3-dimethylazetidine-1-carboxylate, as a TFA salt. LC/MS (M+H): 413.1

Example 42

(S)—N-(2-(ethylamino)propyl)-2-(5-phenylpyrazolo[1,5-a]pyrimidin-3-yl)isonicotinamide

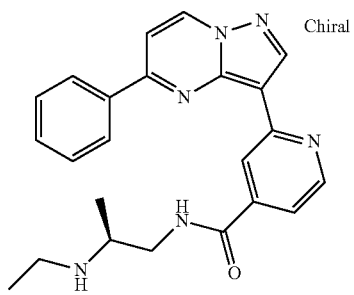

Compound 42 was synthesized following the same process as shown in Example 37 and example 5, and using the commercially available tert-butyl (S)-(1-aminopropan-2-yl)(ethyl)carbamate, as a TFA salt. LC/MS (M+H): 401.1

Example 43

(R)—N-((2-ethylpyrrolidin-2-yl)methyl)-2-(5-phenylpyrazolo[1,5-a]pyrimidin-3-yl)isonicotinamide

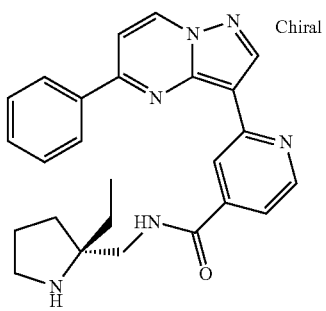

Compound 43 was synthesized following the same process as shown in Example 37 and example 5, and using the commercially available tert-butyl (R)-2-(aminomethyl)-2-ethylpyrrolidine-1-carboxylate, as a TFA salt. LC/MS (M+H): 427.2

Example 44

(S)—N-(2-aminopropyl)-2-(5-phenylpyrazolo[1,5-a]pyrimidin-3-yl)isonicotinamide

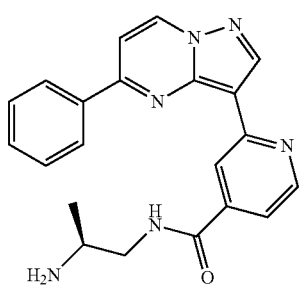

Compound 44 was synthesized following the same process as shown in Example 37 and example 5, and using the commercially available tert-butyl (S)-(1-aminopropan-2-yl)carbamate, as a TFA salt. LC/MS (M+H): 373.1

Example 45

N-((2S)-2-(sec-butylamino)propyl)-2-(5-phenylpyrazolo[1,5-a]pyrimidin-3-yl)isonicotinamide

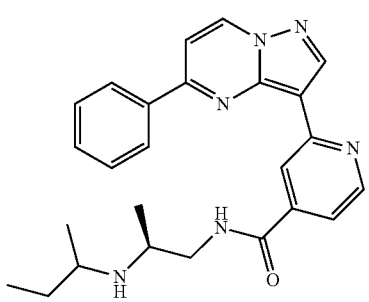

Compound 26 was synthesized following the same process as shown in Example 31 and using compound 22 and commercially available butan-2-one, as a TFA salt. LC/MS (M+H): 429.2

Example 46

N-(2-aminobutyl)-2-(5-phenylpyrazolo[1,5-a]pyrimidin-3-yl)isonicotinamide

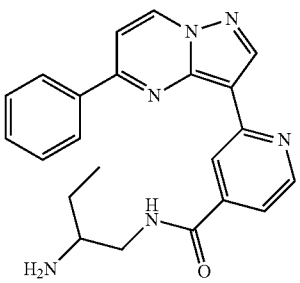

46

Compound 46 was synthesized following the same process as shown in Example 37 and example 5, and using the commercially available tert-butyl (1-aminobutan-2-yl)carbamate, as a TFA salt. LC/MS (M+H): 387.2

Example 47

N-(2-amino-3-methylbutyl)-2-(5-phenylpyrazolo[1,5-a]pyrimidin-3-yl)isonicotinamide

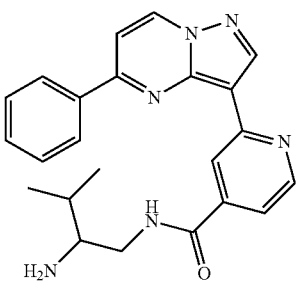

47

Compound 47 was synthesized following the same process as shown in Example 37 and example 5, and using the commercially available tert-butyl (1-amino-3-methylbutan-2-yl)carbamate, as a TFA salt. LC/MS (M+H): 401.2

Example 48

N-(2-aminopentyl)-2-(5-phenylpyrazolo[1,5-a]pyrimidin-3-yl)isonicotinamide

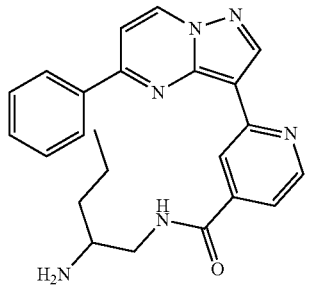

48

Compound 48 was synthesized following the same process as shown in Example 37 and example 5, and using the commercially available tert-butyl (1-aminopentan-2-yl)carbamate, as a TFA salt. LC/MS (M+H): 401.2

Example 49

(S)-2-(5-phenylpyrazolo[1,5-a]pyrimidin-3-yl)-N-(2-((pyrimidin-2-ylmethyl)amino)propyl) isonicotinamide

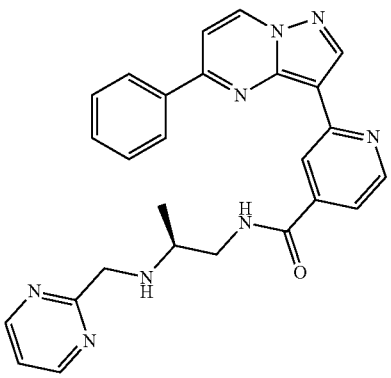

49

Compound 49 was synthesized following the same process as shown in Example 31 and starting with compound 44, and using the commercially available pyrimidine-2-carbaldehyde, as a TFA salt. LC/MS (M+H): 465

Example 50

N-(2-((cyclopropylmethyl)amino)butyl)-2-(5-phenylpyrazolo[1,5-a]pyrimidin-3-yl)isonicotinamide

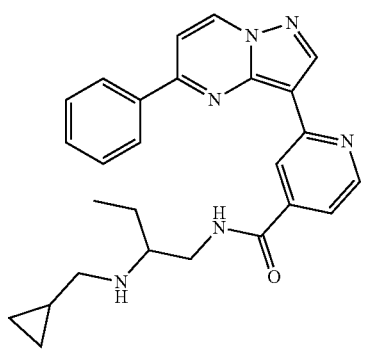

Compound 50 was synthesized following the same process as shown in Example 31 and starting with compound 46, and using the commercially available cyclopropane carbaldehyde, as a TFA salt. LC/MS (M+H): 441.2; 1H NMR (400 MHz, Methanol-d4) δ 9.22 (dd, J=1.8, 0.8 Hz, 1H), 9.01 (d, J=7.4 Hz, 1H), 8.84 (s, 1H), 8.76-8.69 (m, 1H), 8.32 (dd, J=6.7, 3.1 Hz, 1H), 7.79-7.73 (m, 1H), 7.73-7.67 (m, 1H), 7.58 (dd, J=5.0, 1.8 Hz, 3H), 3.90 (dd, J=15.1, 3.7 Hz, 1H), 3.69 (dd, J=15.1, 5.5 Hz, 1H), 3.46-3.35 (m, 1H), 3.22-3.05 (m, 2H), 1.92-1.75 (m, 2H), 1.19-1.11 (m, 4H), 0.79-0.65 (m, 1H), 0.60-0.40 (m, 2H).

Example 51

2-(5-phenylpyrazolo[1,5-a]pyrimidin-3-yl)-N-(2-(propylamino)butyl)isonicotinamide

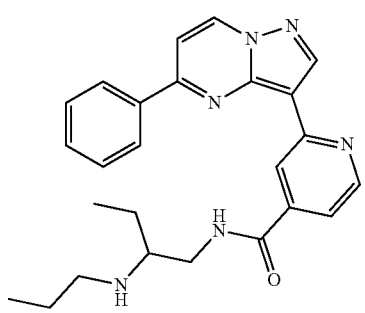

Compound 51 was synthesized following the same process as shown in Example 31 and starting with compound 47, and using the commercially available propionaldehyde, as a TFA salt. LC/MS (M+H): 429.2; 1H NMR (400 MHz, Methanol-d4) δ 9.19 (d, J=0.9 Hz, 0H), 8.98 (d, J=7.4 Hz, 1H), 8.81 (s, 1H), 8.70 (dd, J=5.6, 0.8 Hz, 1H), 8.28 (d, J=8.0 Hz, 2H), 7.73 (dd, J=5.6, 1.7 Hz, 1H), 7.68 (d, J=7.4 Hz, 1H), 7.60-7.49 (m, 3H), 3.91 (dd, J=15.1, 3.7 Hz, 1H), 3.71 (dd, J=15.1, 5.5 Hz, 1H), 3.44-3.33 (m, 1H), 3.27-3.08 (m, 2H), 2.01-1.65 (m, 4H), 1.14 (t, J=7.5 Hz, 3H), 1.06 (t, J=7.4 Hz, 3H).

Example 52

N-(2-((cyclopropylmethyl)amino)-3-methylbutyl)-2-(5-phenylpyrazolo[1,5-a]pyrimidin-3-yl)isonicotinamide

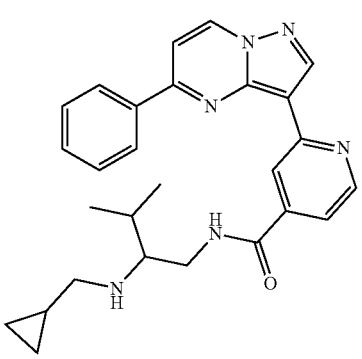

Compound 52 was synthesized following the same process as shown in Example 31 and starting with compound 46, and using the commercially available cyclopropane carbaldehyde, as a TFA salt. LC/MS (M+H): 455.2; 1H NMR (400 MHz, Methanol-d4) δ 9.20 (dd, J=1.8, 0.8 Hz, 1H), 8.99 (d, J=7.4 Hz, 1H), 8.82 (s, 1H), 8.71 (dd, J=5.5, 0.7 Hz, 1H), 8.33-8.25 (m, 2H), 7.72-7.66 (m, 2H), 7.60-7.53 (m, 3H), 3.88-3.67 (m, 2H), 3.37 (q, J=5.3 Hz, 1H), 3.20 (dd, J=12.9, 7.1 Hz, 1H), 3.08 (dd, J=12.9, 7.7 Hz, 1H), 2.35-2.16 (m, 1H), 1.17 (dd, J=15.7, 6.9 Hz, 6H), 0.78-0.62 (m, 2H), 0.48 (dd, J=4.9, 3.2 Hz, 2H).

Example 53

N-(3-methyl-2-(propylamino)butyl)-2-(5-phenylpyrazolo[1,5-a]pyrimidin-3-yl)isonicotinamide

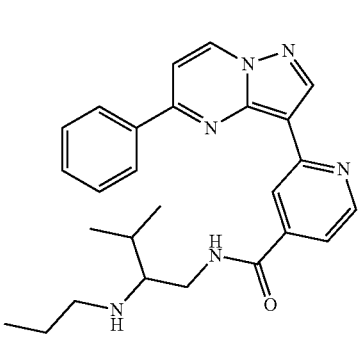

Compound 53 was synthesized following the same process as shown in Example 31 and starting with compound 46, and using the commercially available propionaldehyde, as a TFA salt. LC/MS (M+H): 443.2; 1H NMR (400 MHz, Methanol-d4) δ 9.18 (dd, J=1.7, 0.8 Hz, 1H), 8.98 (d, J=7.4 Hz, 1H), 8.81 (s, 1H), 8.70 (dd, J=5.5, 0.8 Hz, 1H), 8.35-8.26 (m, 2H), 7.71-7.66 (m, 2H), 7.70-7.65 (m, 1H), 7.63-7.48 (m, 3H), 3.87-3.67 (m, 2H), 3.18 (t, J=8.0 Hz, 2H), 2.23 (td, J=6.9, 5.2 Hz, 1H), 1.89-1.71 (m, 2H), 1.18 (d, J=6.9 Hz, 3H), 1.14 (d, J=6.9 Hz, 3H), 1.03 (t, J=7.4 Hz, 3H).

Example 54

N-(2-(ethylamino)butyl)-2-(5-phenylpyrazolo[1,5-a]pyrimidin-3-yl)isonicotinamide

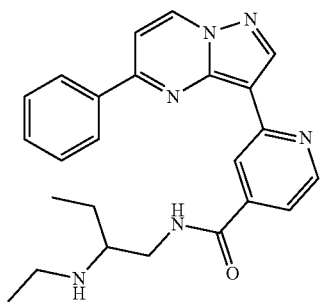

54

Compound 54 was synthesized following the same process as shown in Example 31 and starting with compound 47, and using the commercially available acetaldehyde, as a TFA salt. LC/MS (M+H): 415.2

Example 55

N-(2-(ethylamino)-3-methylbutyl)-2-(5-phenylpyrazolo[1,5-a]pyrimidin-3-yl)isonicotinamide

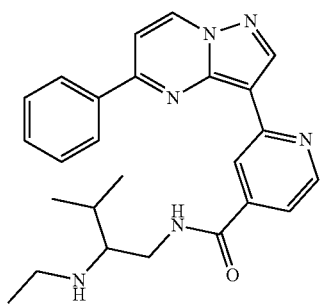

55

Compound 55 was synthesized following the same process as shown in Example 31 and starting with compound 46, and using the commercially available acetaldehyde, as a TFA salt. LC/MS (M+H): 429.2

Example 56

N-((1S,2S)-2-aminocyclopentyl)-2-(5-phenylpyrazolo[1,5-a]pyrimidin-3-yl)isonicotinamide

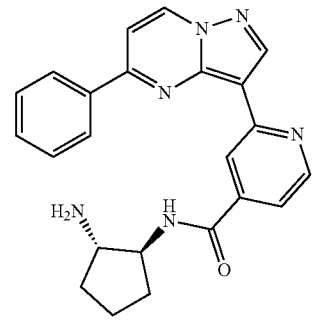

56

Compound 56 was synthesized following the same process as shown in Example 37 and example 5, and using the commercially available (1S,2S)-trans-N-Boc-1,2-cyclopentanediamine, as a TFA salt. LC/MS (M+H): 399.1

Example 57

(R)—N-(2-amino-3-hydroxypropyl)-2-(5-phenylpyrazolo[1,5-a]pyrimidin-3-yl)isonicotinamide

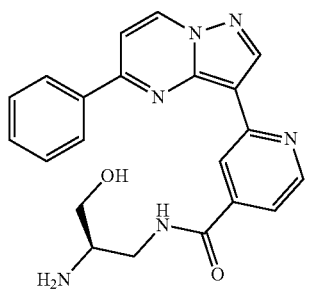

57

Compound 57 was synthesized following the same process as shown in Example 37 and example 5, and using the commercially available tert-butyl (R)-(1-amino-3-hydroxypropan-2-yl)carbamate, as a TFA salt. LC/MS (M+H): 389.1

Example 58

(R)—N-(2-(diethylamino)-3-hydroxypropyl)-2-(5-phenylpyrazolo[1,5-a]pyrimidin-3-yl)isonicotinamide

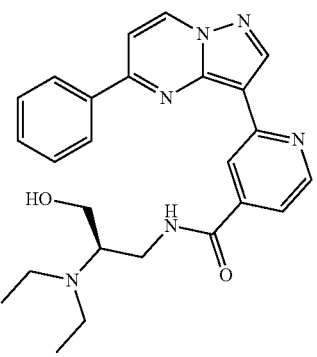

58

Compound 58 was synthesized following the same process as shown in Example 31 and starting with compound 57, and using the commercially available acetaldehyde, as a TFA salt. LC/MS (M+H): 435.2; 1H NMR (400 MHz, Methanol-$d_4$) δ 9.05 (dd, J=1.7, 0.9 Hz, 1H), 8.92 (d, J=7.4 Hz, 1H), 8.75 (s, 1H), 8.62 (d, J=5.2 Hz, 1H), 8.30 (dd, J=8.0, 1.7 Hz, 2H), 7.62 (d, J=7.4 Hz, 1H), 7.60-7.51 (m, 3H), 7.46 (dd, J=5.1, 1.7 Hz, 1H), 3.68 (dd, J=11.5, 6.3 Hz, 2H), 3.54 (dd, J=11.1, 6.9 Hz, 2H), 3.21-3.05 (m, 1H), 2.72 (q, J=7.1 Hz, 4H), 1.07 (t, J=7.1 Hz, 6H).

Example 59

(R)—N-(2-(ethylamino)-3-hydroxypropyl)-2-(5-phenylpyrazolo[1,5-a]pyrimidin-3-yl)isonicotinamide

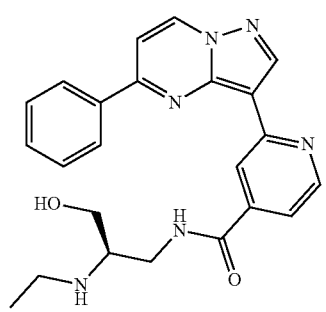

Compound 59 was synthesized following the same process as shown in Example 31 and starting with compound 57, and using the commercially available acetaldehyde, as a TFA salt. LC/MS (M+H): 417.2

Example 60

N-(2-(diethylamino)pentyl)-2-(5-phenylpyrazolo[1,5-a]pyrimidin-3-yl)isonicotinamide

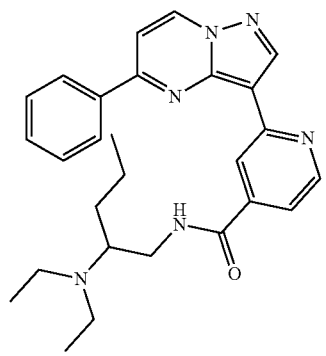

Compound 60 was synthesized following the same process as shown in Example 31 and starting with compound 48, and using the commercially available acetaldehyde, as a TFA salt. LC/MS (M+H): 457; 1H NMR (400 MHz, Methanol-d4) δ 9.17 (dd, J=1.8, 0.8 Hz, 1H), 8.93 (d, J=7.4 Hz, 1H), 8.80 (s, 1H), 8.68 (d, J=5.6 Hz, 1H), 8.31-8.18 (m, 2H), 7.74 (dd, J=5.7, 1.7 Hz, 1H), 7.65 (d, J=7.4 Hz, 1H), 7.60-7.47 (m, 3H), 4.06-3.90 (m, 1H), 3.77-3.63 (m, 2H), 3.64-3.49 (m, 1H), 3.37 (dd, J=15.5, 7.4 Hz, 2H), 3.28-3.15 (m, 1H), 1.89-1.71 (m, 1H), 1.71-1.60 (m, 1H), 1.60-1.53 (m, 1H), 1.47 (t, J=7.2 Hz, 3H), 1.37 (t, J=7.2 Hz, 3H), 1.05 (t, J=7.2 Hz, 3H).

Example 61

N-(2-(diethylamino)-3-methylbutyl)-2-(5-phenylpyrazolo[1,5-a]pyrimidin-3-yl)isonicotinamide

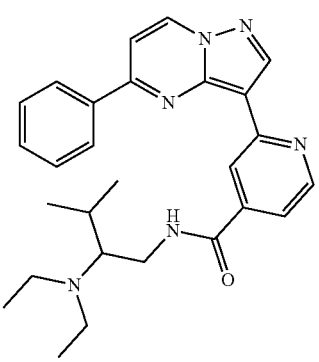

Compound 61 was synthesized following the same process as shown in Example 31 and starting with compound 46, and using the commercially available acetaldehyde, as a TFA salt. LC/MS (M+H): 457; 1H NMR (400 MHz, Methanol-d4) δ 9.07 (dd, J=1.8, 0.8 Hz, 1H), 8.86 (d, J=7.4 Hz, 1H), 8.73 (s, 1H), 8.64 (dd, J=5.7, 0.8 Hz, 1H), 8.20-8.12 (m, 2H), 7.69 (dd, J=5.7, 1.7 Hz, 1H), 7.57 (d, J=7.4 Hz, 1H), 7.55-7.45 (m, 3H), 3.98 (dd, J=15.4, 7.1 Hz, 1H), 3.72 (dd, J=15.4, 4.1 Hz, 1H), 3.69-3.53 (m, 2H), 3.47-3.33 (m, 3H), 2.34 (td, J=6.9, 4.4 Hz, 1H), 1.45 (t, J=7.1 Hz, 3H), 1.37 (t, J=7.2 Hz, 3H), 1.21 (t, J=6.6 Hz, 6H).

Example 62

N-(1-aminopropan-2-yl)-2-(5-phenylpyrazolo[1,5-a]pyrimidin-3-yl)isonicotinamide

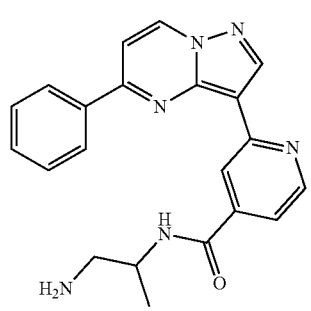

Compound 62 was synthesized following the same process as shown in Example 37 and example 5, and using the commercially available tert-butyl (2-aminopropyl)carbamate, as a TFA salt. LC/MS (M+H): 373.1

Example 63

N-((1R,2S)-2-aminocyclopentyl)-2-(5-phenylpyrazolo[1,5-a]pyrimidin-3-yl)isonicotinamide

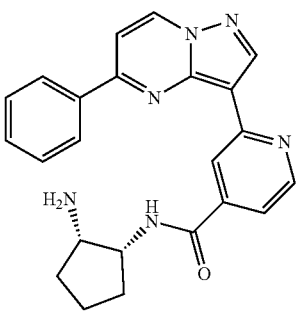

63

Compound 63 was synthesized following the same process as shown in Example 37 and example 5, and using the commercially available tert-butyl ((1R,2S)-2-aminocyclopentyl)carbamate, as a TFA salt LC/MS (M+H): 399.1

Example 64

N-(2-amino-2-methylpropyl)-2-(5-phenylpyrazolo[1,5-a]pyrimidin-3-yl)isonicotinamide

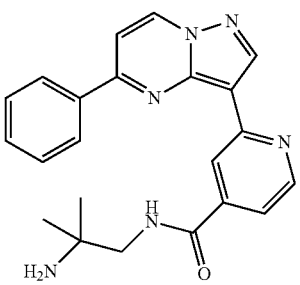

64

Compound 62 was synthesized following the same process as shown in Example 37 and example 5, and using the commercially available tert-butyl (1-amino-2-methylpropan-2-yl)carbamate, as a TFA salt. LC/MS (M+H): 393.1

Example 65

N-(2-aminoethyl)-N-ethyl-2-(5-phenylpyrazolo[1,5-a]pyrimidin-3-yl)isonicotinamide

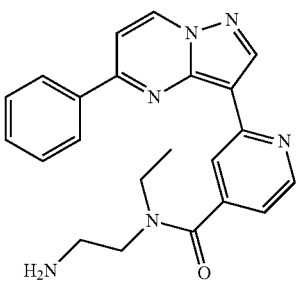

65

Compound 65 was synthesized following the same process as shown in Example 37 and example 5, and using the commercially available tert-butyl (2-(ethylamino)ethyl)carbamate, as a TFA salt. LC/MS (M+H): 387.2

Example 66

(R)—N-(2-amino-3-(pyrimidin-2-yloxy)propyl)-2-(5-phenylpyrazolo[1,5-a]pyrimidin-3-yl)isonicotinamide

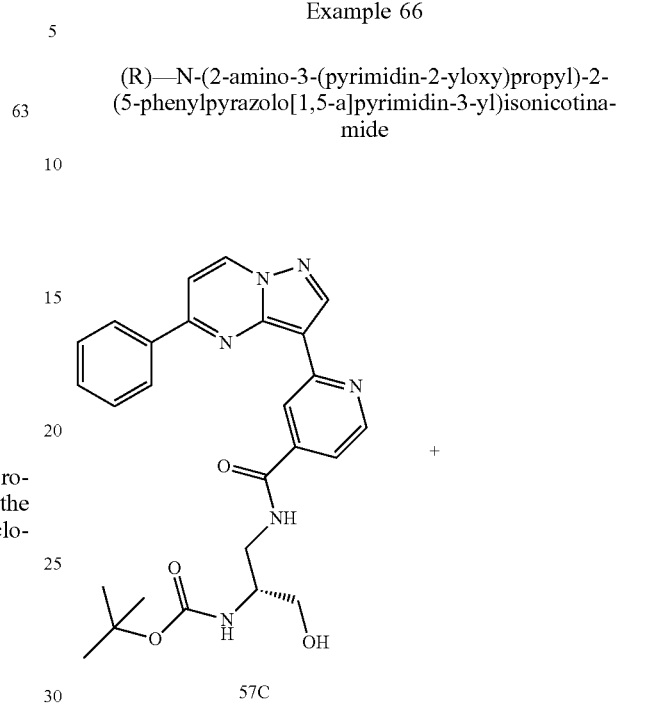

57C

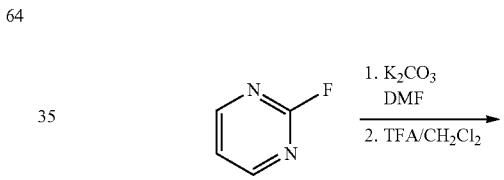

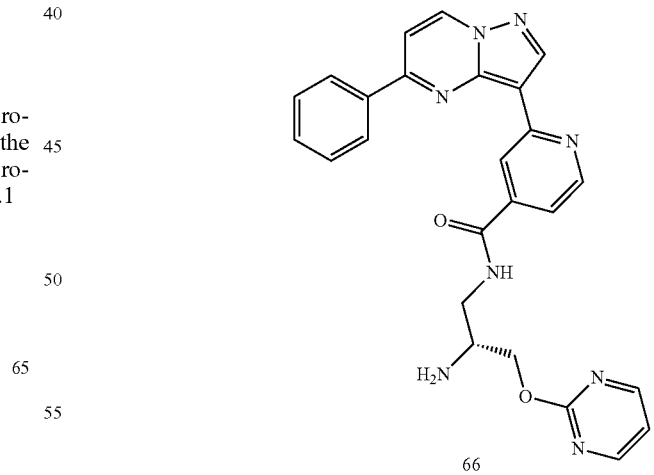

66

Compound 57C was synthesized by Example 37 and example 5, without TFA deprotection. Compound 57C heated in 1 mL DMF with 2-Fluoropyrimidine (20.08 mg, 0.2 mmol) and Potassium carbonate (56.58 mg, 0.41 mmol) at 60° C. for 4 h. Solution was diluted with water and the precipitate filtered and collected. The compound was dissolved in 10 mL dichloromethane and 0.5 mL trifluoroacetic acid was added. After 16 h, the rxn was concentrated to afford compound 66 as a TFA salt. LC/MS (M+H): 467.1

Example 67

N-(2-(ethylamino)-2-methylpropyl)-2-(5-phenylpyrazolo[1,5-a]pyrimidin-3-yl)isonicotinamide

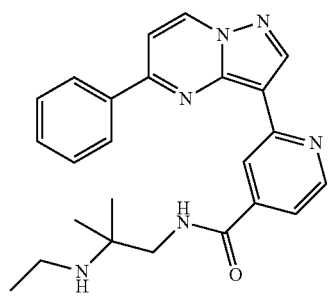

Compound 67 was synthesized following the same process as shown in Example 31 and starting with compound 64, and using the commercially available acetaldehyde, as a TFA salt. LC/MS (M+H): 415.2

Example 68

(2-(5-phenylpyrazolo[1,5-a]pyrimidin-3-yl)pyridin-4-yl)(1,8-diazaspiro[5.5]undecan-1-yl)methanone

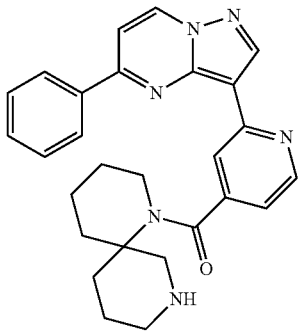

Compound 68 was synthesized following the same process as shown in Example 37 and example 5, and using the commercially available tert-butyl 1,8-diazaspiro[5.5]undecane-8-carboxylate, as a TFA salt. LC/MS (M+H): 453.2

Example 69

(R)—N-(2-(ethylamino)-3-(pyrimidin-2-yloxy)propyl)-2-(5-phenylpyrazolo[1,5-a]pyrimidin-3-yl)isonicotinamide

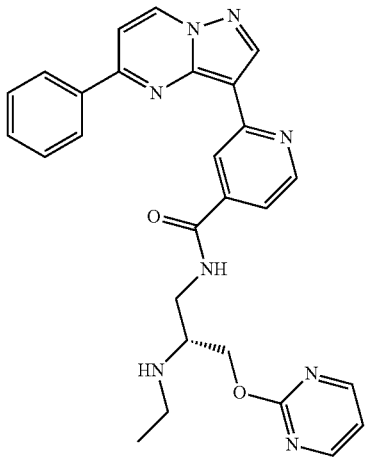

Compound 69 was synthesized following the same process as shown in Example 31 and starting with compound 66, and using the commercially available acetaldehyde, as a TFA salt. LC/MS (M+H): 495.2

Example 70

(R)—N-(2-(diethylamino)-3-(pyrimidin-2-yloxy)propyl)-2-(5-phenylpyrazolo[1,5-a]pyrimidin-3-yl)isonicotinamide

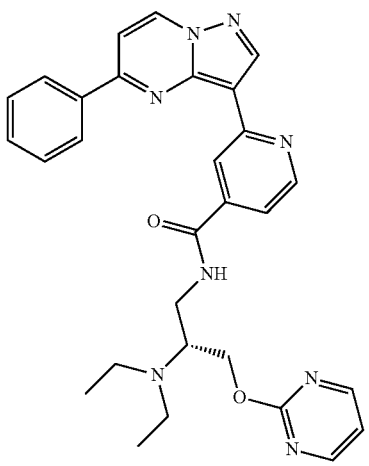

Compound 70 was synthesized following the same process as shown in Example 31 and starting with compound 66, and using the commercially available acetaldehyde, as a TFA salt. LC/MS (M+H): 523.2

Example 71

N-((1R,2R)-2-aminocyclopentyl)-2-(5-phenylpyrazolo[1,5-a]pyrimidin-3-yl)isonicotinamide

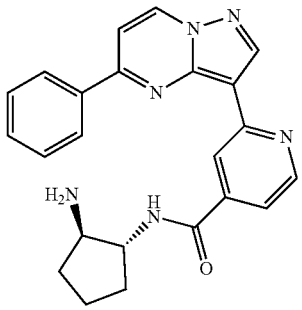

71

Compound 71 was synthesized following the same process as shown in Example 37 and example 5, and using the commercially available tert-butyl ((1R,2R)-2-aminocyclopentyl)carbamate, as a TFA salt. LC/MS (M+H): 399.1

Example 72

N-((1S,2R)-2-aminocyclopentyl)-2-(5-phenylpyrazolo[1,5-a]pyrimidin-3-yl)isonicotinamide

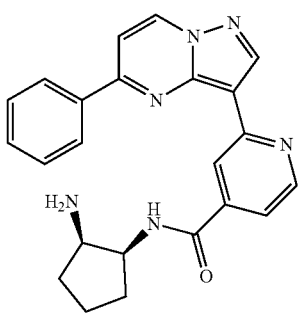

72

Compound 72 was synthesized following the same process as shown in Example 37 and example 5, and using the commercially tert-butyl ((1R,2S)-2-aminocyclopentyl)carbamate, as a TFA salt. LC/MS (M+H): 399.1

Example 73

N-(2-(isopropylamino)-3-methylbutyl)-2-(5-phenylpyrazolo[1,5-a]pyrimidin-3-yl)isonicotinamide

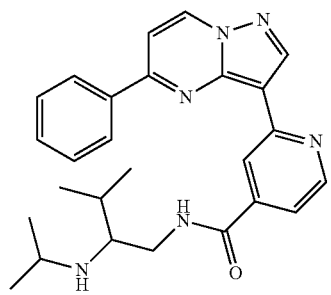

73

Compound 73 was synthesized following the same process as shown in Example 31 and starting with compound 46, and using commercially available propan-2-one, as a TFA salt. LC/MS (M+H): 443.2

Example 74

(R)—N-(2-(ethylamino)propyl)-2-(5-phenylpyrazolo[1,5-a]pyrimidin-3-yl)isonicotinamide

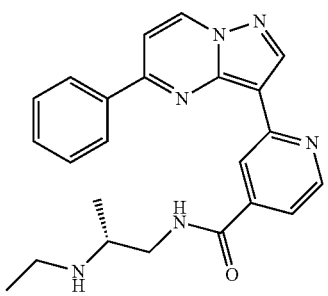

74

Compound 71 was synthesized following the same process as shown in Example 37 and example 5, and using the commercially available tert-butyl (R)-(1-aminopropan-2-yl)(ethyl)carbamate, as a TFA salt. LC/MS (M+H): 401.2

Example 75

(S)—N-((2-ethylpyrrolidin-2-yl)methyl)-2-(5-phenylpyrazolo[1,5-a]pyrimidin-3-yl)isonicotinamide

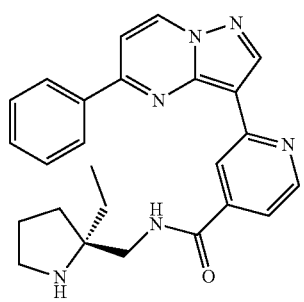

75

Compound 75 was synthesized following the same process as shown in Example 1 and using the intermediate 4 and the commercially available as a TFA salt. LC/MS (M+H): 427.1

Example 76

3,6-diazabicyclo[3.2.2]nonan-3-yl)(2-(5-(thiophen-2-yl)pyrazolo[1,5-a]pyrimidin-3-yl)pyridin-4-yl)methanone

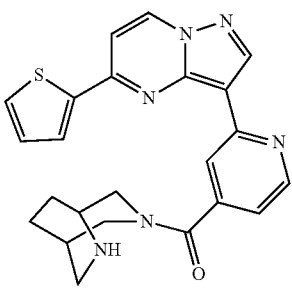

Compound 76 was synthesized following the same process as shown in Example 37 and example 5, and using the commercially available tert-butyl-3,6-diazabicyclo[3.2.2]nonane-6-carboxylate, as a TFA salt. LC/MS (M+H): 431.1; ¹H NMR (δ), 400 MHz, CDCl₃), diagnostic signals: 8.96 (d, 1H); 8.80 (m, 2H); 8.69 (d, 1H); 8.00 (d, 1H); 7.75 (br d, 1H); 7.63 (d, 1H); 7.35 (br d, 1H), 7.26 (dd, 1H). Aliphatic area of the spectrum contains approximately 13 protons by integration.

Example 77

((1S)-3,9-diazabicyclo[3.3.2]decan-3-yl)(2-(5-(thiophen-2-yl)pyrazolo[1,5-a]pyrimidin-3-yl)pyridin-4-yl)methanone

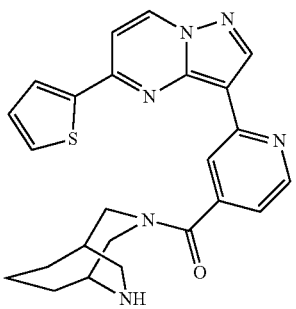

Compound 76 was synthesized following the same process as shown in Example 37 and example 5, and using the commercially available tert-butyl 3,9-diazabicyclo[3.3.2]decane-9-carboxylate, as a TFA salt. LC/MS (M+H): 445.2; ¹H-NMR (CD₃OD) δ 8.96 (d, 1H, J=7.6 Hz), 8.76-8.82 (m, 2H), 8.68 (d, 1H, J=4.8 Hz), 7.99 (d, 1H, J=4.0 Hz), 7.74-7.76 (m, 1H), 7.62 (d, 1H, J=7.6 Hz), 7.24-7.32 (m, 2H), 5.07-5.25 (m, 1H), 4.18-4.24 (m, 1H), 3.85-4.06 (m, 1H), 3.60-3.77 (m, 1H), 3.51-3.56 (m, 2H), 3.19-3.73 (m, 1H), 2.44-2.71 (m, 1H), 1.73-2.26 (m, 6H)

Example 78

(S)-(2-(aminomethyl)-4,4-difluoropyrrolidin-1-yl)(2-(5-(thiophen-2-yl)pyrazolo[1,5-a]pyrimidin-3-yl)pyridin-4-yl)methanone

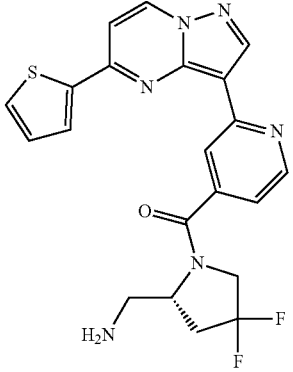

Compound 78 was synthesized following the same process as shown in Example 37 and example 5, and using the commercially available tert-butyl (S)-((4,4-difluoropyrrolidin-2-yl)methyl)carbamate, as a TFA salt. LC/MS (M+H): 441.1

Example 79

(R)-(2-(aminomethyl)pyrrolidin-1-yl)(2-(5-(thiophen-2-yl)pyrazolo[1,5-a]pyrimidin-3-yl)pyridin-4-yl)methanone

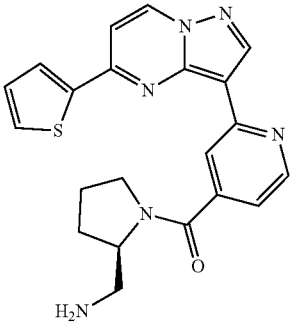

Compound 79 was synthesized following the same process as shown in Example 37 and example 5, and using the commercially available tert-butyl (R)-(pyrrolidin-2-ylmethyl)carbamate, as a TFA salt. LC/MS (M+H): 405.1; ¹H-NMR (CD₃OD) δ 9.03 (d, 1H, J=7.2 Hz), 9.00 (dd, 1H, J=1.6, 0.8 Hz), 8.85 (s, 1H), 8.75 (dd, 1H, J=5.8, 1.0 Hz), 8.06 (dd, 1H, J=4.0, 1.2 Hz), 7.81 (dd, 1H, J=5.2, 1.2 Hz), 7.72 (d, 1H, J=7.6 Hz), 7.66 (dd, 1H, J=5.8, 1.8 Hz), 7.28 (dd, 1H, J=5.0, 3.8 Hz), 4.53-4.60 (m, 1H), 3.79-3.85 (m, 1H), 3.64-3.70 (m, 1H), 3.24-3.38 (m, 2H), 2.32-2.38 (m, 1H), 1.88-2.10 (m, 3H);

Example 80

3,6-diazabicyclo[3.2.2]nonan-3-yl)(2-(5-(thiophen-2-yl)pyrazolo[1,5-a]pyrimidin-3-yl)pyridin-4-yl)methanone

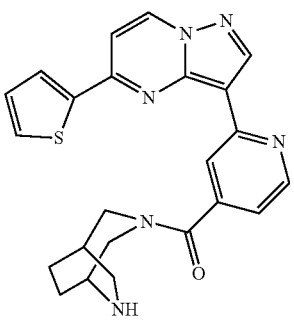

Compound 80 was synthesized following the same process as shown in Example 37 and example 5, and using the commercially tert-butyl 3,6-diazabicyclo[3.2.2]nonane-6-carboxylate, as a TFA salt. LC/MS (M+H): 431.1; $^1$H-NMR (CD$_3$OD) δ 8.97 (d, 1H, J=7.6 Hz), 8.80-8.81 (m, 2H), 8.69 (dd, 1H, J=5.4, 1.0 Hz), 8.00 (dd, 1H, J=3.6, 1.2 Hz), 7.75 (d, 1H, J=4.8 Hz), 7.63 (d, 1H, J=7.2 Hz), 7.35 (d, 1H, J=5.2 Hz), 7.26 (dd, 1H, J=5.0, 3.8 Hz), 5.00-5.12 (m, 1H), 3.96-4.14 (m, 2H), 3.61-3.78 (m, 1H), 3.40-3.48 (m, 3H), 1.83-2.78 (m, 5H);

Example 81

3-oxa-7,9-diazabicyclo[3.3.2]decan-7-yl)(2-(5-(thiophen-2-yl)pyrazolo[1,5-a]pyrimidin-3-yl)pyridin-4-yl)methanone

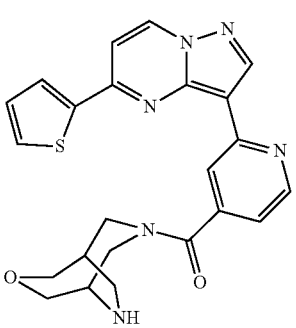

Compound 81 was synthesized following the same process as shown in Example 37 and example 5, and using the commercially available tert-butyl 3-oxa-7,9-diazabicyclo[3.3.2]decane-9-carboxylate, as a TFA salt. LC/MS (M+H): 447.2

Example 82

3,9-diazabicyclo[4.2.1]nonan-9-yl)(2-(5-(thiophen-2-yl)pyrazolo[1,5-a]pyrimidin-3-yl)pyridin-4-yl)methanone

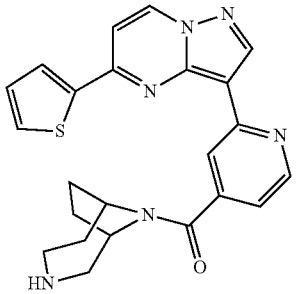

Compound 82 was synthesized following the same process as shown in Example 37 and example 5, and using the commercially available tert-butyl-3,9-diazabicyclo[4.2.1]nonane-3-carboxylate, as a TFA salt. LC/MS (M+H): 431.1

Example 83

(S)-(3-aminopiperidin-1-yl)(2-(5-(thiophen-2-yl)pyrazolo[1,5-a]pyrimidin-3-yl)pyridin-4-yl)methanone

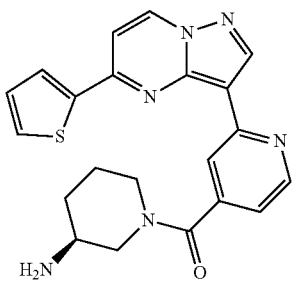

Compound 83 was synthesized following the same process as shown in Example 37 and example 5, and using the commercially available tert-butyl (S)-piperidin-3-ylcarbamate, as a TFA salt. LC/MS (M+H): 405.1

Example 84

(R)-(2-methylpiperazin-1-yl)(2-(5-(thiophen-2-yl)pyrazolo[1,5-a]pyrimidin-3-yl)pyridin-4-yl)methanone

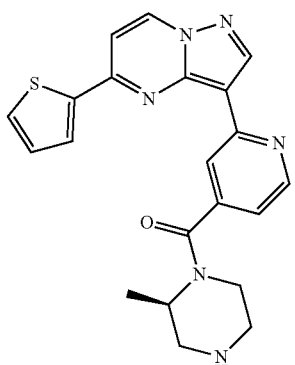

Compound 84 was synthesized following the same process as shown in Example 37 and example 5, and using the commercially available tert-butyl (R)-3-methylpiperazine-1-carboxylate, as a TFA salt. LC/MS (M+H): 405.1

Example 85

(S)-(3-aminopyrrolidin-1-yl)(2-(5-(thiophen-2-yl)pyrazolo[1,5-a]pyrimidin-3-yl)pyridin-4-yl)methanone

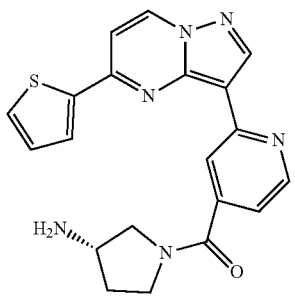

85

Compound 85 was synthesized following the same process as shown in Example 37 and example 5, and using the commercially available tert-butyl (S)-pyrrolidin-3-ylcarbamate, as a TFA salt. C/MS (M+H): 391.1

Example 86

((4aR,8R,8aS)-8-aminooctahydroquinolin-1(2H)-yl)(2-(5-(thiophen-2-yl)pyrazolo[1,5-a]pyrimidin-3-yl)pyridin-4-yl)methanone

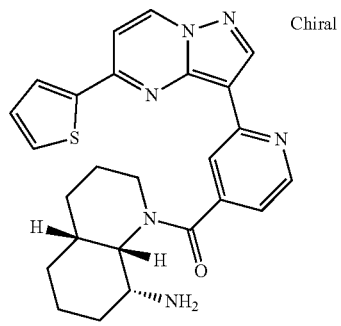

86 Chiral

Compound 86 was synthesized following the same process as shown in Example 94 using the commercially available (R)-5,6,7,8-tetrahydroquinolin-8-amine, as a TFA salt. LC/MS (M+H): 459.2; $^1$H NMR (400 MHz, Methanol-d$_4$) δ 9.00 (d, J=7.4 Hz, 1H), 8.94 (dd, J=1.7, 0.8 Hz, 1H), 8.89 (s, 1H), 8.75 (dd, J=6.1, 0.8 Hz, 1H), 8.03 (dd, J=3.8, 1.1 Hz, 1H), 7.81-7.75 (m, 2H), 7.69 (d, J=7.4 Hz, 1H), 7.24 (dd, J=5.0, 3.8 Hz, 1H), 4.81 (dd, J=11.4, 5.2 Hz, 1H), 3.98-3.79 (m, 1H), 3.54 (d, J=14.6 Hz, 1H), 2.42-2.15 (m, 3H), 2.04-1.50 (m, 11H).

Example 87

(S)-(3-aminopyrrolidin-1-yl)(2-(5-phenylpyrazolo[1,5-a]pyrimidin-3-yl)pyridin-4-yl)methanone

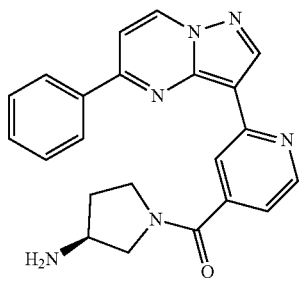

87

Compound 87 was synthesized following the same process as shown in Example 37 and example 5, and using the commercially available tert-butyl (S)-pyrrolidin-3-ylcarbamate, as a TFA salt.

Example 88

((1S,5R,6S)-6-amino-8-azabicyclo[3.2.1]octan-8-yl)(2-(5-phenylpyrazolo[1,5-a]pyrimidin-3-yl)pyridin-4-yl)methanone

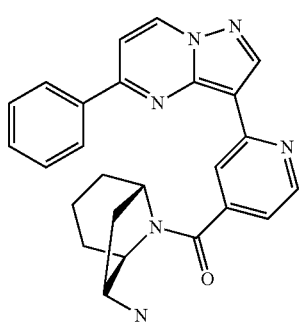

88

Compound 88 was synthesized following the same process as shown in Example 37 and example 5, and using the commercially available tert-butyl ((1S,5R,6S)-8-azabicyclo[3.2.1]octan-6-yl)-14-azanecarboxylate, as a TFA salt. LC/MS (M+H): 425.2

Example 89

(2-(5-phenylpyrazolo[1,5-a]pyrimidin-3-yl)pyridin-4-yl)(2,6-diazaspiro[4.5]decan-6-yl)methanone

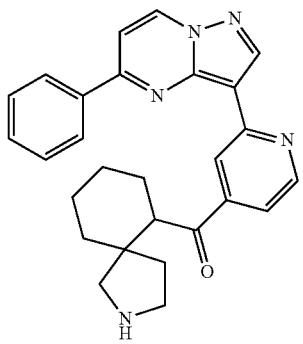

Compound 89 was synthesized following the same process as shown in Example 37 and example 5, and using the commercially available tert-butyl 2,6-diazaspiro[4.5]decane-2-carboxylate, as a TFA salt. LC/MS (M+H): 439

Example 90

((S)-2-((S)-1-aminoethyl)piperidin-1-yl)(2-(5-phenylpyrazolo[1,5-a]pyrimidin-3-yl)pyridin-4-yl)methanone

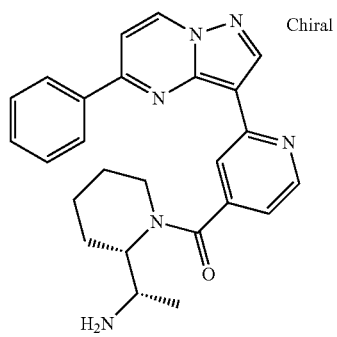

Compound 90 was synthesized following the same process as shown in Example 94 using the commercially available (S)-1-(pyridin-2-yl)ethan-1-amine, as a TFA salt. LC/MS (M+H): 427.2

Example 91

3,10-diazabicyclo[4.3.1]decan-10-yl)(2-(5-phenylpyrazolo[1,5-a]pyrimidin-3-yl)pyridin-4-yl)methanone

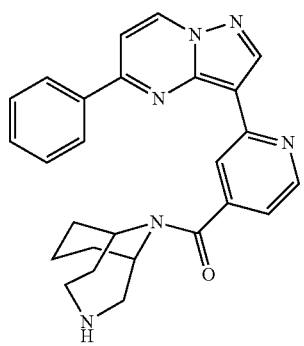

Compound 91 was synthesized following the same process as shown in Example 37 and example 5, and using the commercially available tert-butyl-3,10-diazabicyclo[4.3.1]decane-3-carboxylate, as a TFA salt. LC/MS (M+H): 439.2

Example 92

(hexahydropyrrolo[3,4-b]pyrrol-1(2H)-yl)(2-(5-phenylpyrazolo[1,5-a]pyrimidin-3-yl)pyridin-4-yl)methanone

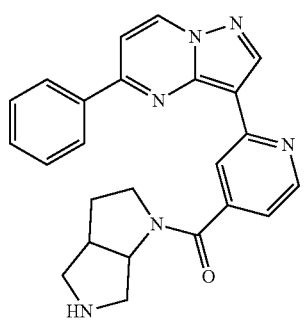

Compound 92 was synthesized following the same process as shown in Example 37 and example 5, and using the commercially available tert-butyl hexahydropyrrolo[3,4-b]pyrrole-5(1H)-carboxylate, as a TFA salt. LC/MS (M+H): 411.1

Example 93

(2-(5-phenylpyrazolo[1,5-a]pyrimidin-3-yl)pyridin-4-yl)((R)-2-((S)-pyrrolidin-2-yl)piperidin-1-yl)methanone

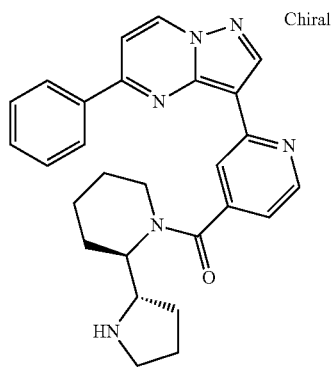

93

Compound 93 was synthesized following the same process as shown in Example 37 and example 5, and using the commercially available tert-butyl hexahydropyrrolo[3,4-b]pyrrole-5(1H)-carboxylate, as a TFA salt. LC/MS (M+H): 453.2

Example 94

((4aR,7S,7aR)-7-aminooctahydro-1H-cyclopenta[b]pyridin-1-yl)(2-(5-phenylpyrazolo[1,5-a]pyrimidin-3-yl)pyridin-4-yl)methanone

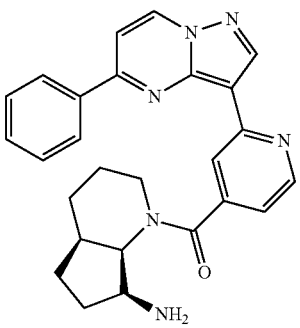

94

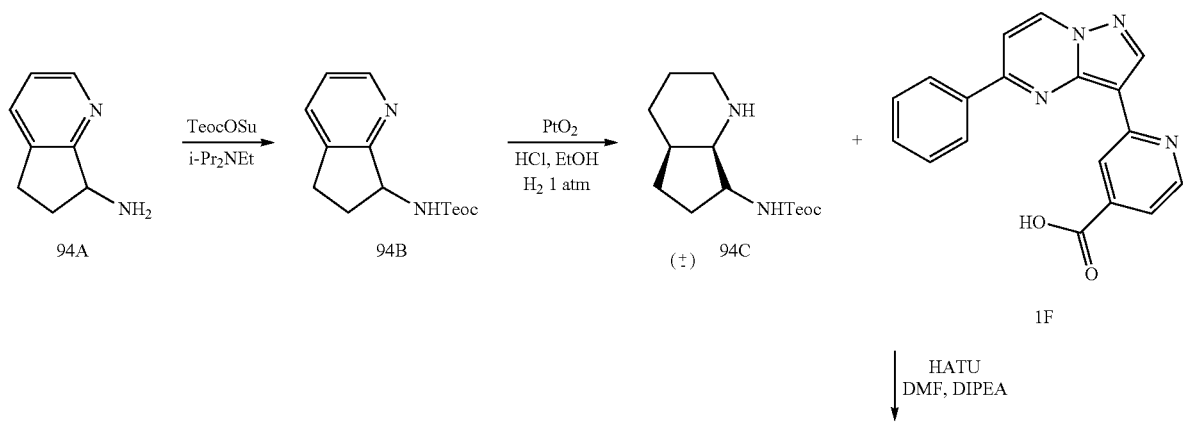

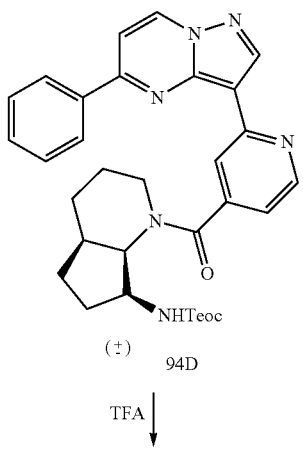

94D

TFA

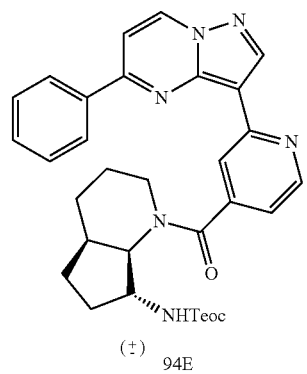

94E

TFA

-continued

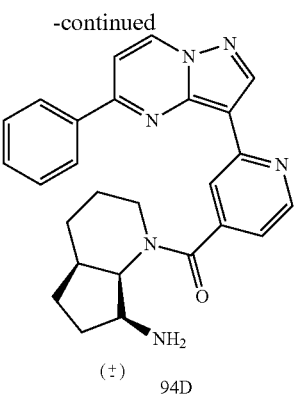

(±) 94D

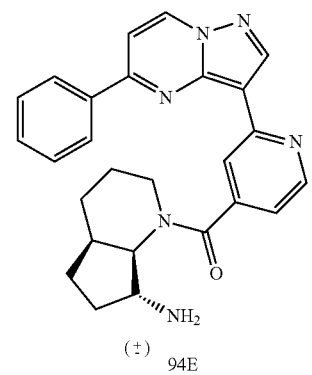

(±) 94E

Synthesis of 2-(trimethylsilyl)ethyl (6,7-dihydro-5H-cyclopenta[b]pyridin-7-yl)carbamate (94B)

A solution of 6,7-Dihydro-5H-cyclopenta[b]pyridin-7-amine HCl (200 mg, 1.17 mmol), Teoc-OSu (607.9 mg, 2.34 mmol), and Hunig's base (716.46 µl, 4.1 mmol) in dichloromethane (10 mL) was stirred for 16 h. The reaction was concentrated and purified reverse phase chromatography. 223 mg of product was collected.

Synthesis 2-(trimethylsilyl)ethyl ((4aR,7S,7aS)-octahydro-1H-cyclopenta[b]pyridin-7-yl)carbamate (94C)

To a solution of the compound 94B (223 mg) in 5 mL ethanol was added Platinum(iv) oxide (90.94 mg, 0.4 mmol) and 6M HCl (266.98 µl). The reaction was stirred at RT under 1 atm hydrogen for 16 h. The reaction was filtered through celite and concentrated to afford, 280 mg of product as an HCl salt.

Synthesis of 2-(trimethylsilyl)ethyl ((4aR,7S,7aR)-1-(2-(5-phenylpyrazolo[1,5-a]pyrimidin-3-yl)isonicotinoyl)octahydro-1H-cyclopenta[b]pyridin-7-yl)carbamate (94D and 94E)

Compound 94D and 94E were synthesized following the same process as shown in Example 37 and example 5, and using the compound 94C. Both cis and trans isomers were collected, the cis being the major product.

Synthesis ((4aR,7S,7aR)-7-aminooctahydro-1H-cyclopenta[b]pyridin-1-yl)(2-(5-phenylpyrazolo[1,5-a]pyrimidin-3-yl)pyridin-4-yl)methanone (94)

Compound 94D was dissolved in 10 mL DCM and 0.5 mL TFA was added. The reaction was stirred for 16 hours and then concentrated to afford compound 94 (47 mg) as a TFA salt. LC/MS (M+H): 439.2; $^1$H NMR (400 MHz, Methanol-$d_4$) δ 9.17 (d, J=7.4 Hz, 1H), 8.95 (s, 1H), 8.91 (dd, J=1.6, 0.8 Hz, 1H), 8.80 (d, J=6.0 Hz, 1H), 8.38-8.24 (m, 2H), 7.85 (d, J=7.4 Hz, 1H), 7.70 (dd, J=5.9, 1.6 Hz, 1H), 7.66-7.56 (m, 3H), 5.10-5.02 (m, 1H), 4.00 (q, J=9.2 Hz, 1H), 3.69 (d, J=14.0 Hz, 1H), 3.29-3.21 (m, 8H), 2.55-2.13 (m, 3H), 1.87-1.70 (m, 2H), 1.70-1.54 (m, 3H), 1.41 (qd, J=12.6, 4.7 Hz, 1H).

Example 95

(octahydro-1H-pyrrolo[2,3-c]pyridin-1-yl)(2-(5-phenylpyrazolo[1,5-a]pyrimidin-3-yl)pyridin-4-yl)methanone

95

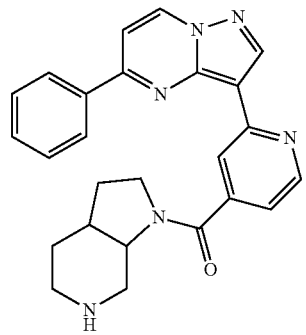

Compound 95 was synthesized following the same process as shown in Example 37 and example 5, and using the commercially available tert-butyl octahydro-6H-pyrrolo[2,3-c]pyridine-6-carboxylate, as a TFA salt. LC/MS (M+H): 425.2

Example 96

((4aR,7R,7aR)-7-aminooctahydro-1H-cyclopenta[b]pyridin-1-yl)(2-(5-phenylpyrazolo[1,5-a]pyrimidin-3-yl)pyridin-4-yl)methanone

96

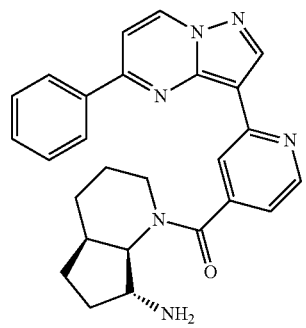

Compound 96 was synthesized following the same process as shown in Example 94, as a TFA salt. LC/MS (M+H): 439.3

Example 97

(2-(5-phenylpyrazolo[1,5-a]pyrimidin-3-yl)pyridin-4-yl)(1,7-diazaspiro[4.5]decan-1-yl)methanone

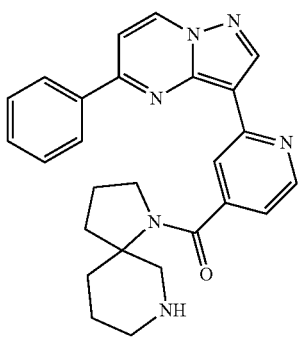

Compound 97 was synthesized following the same process as shown in Example 37 and example 5, and using the commercially available tert-butyl 1,7-diazaspiro[4.5]decane-7-carboxylate, as a TFA salt. LC/MS (M+H): 439.2

Example 98

((4aS,8R,8aR)-8-aminooctahydroquinolin-1(2H)-yl)(2-(5-phenylpyrazolo[1,5-a]pyrimidin-3-yl)pyridin-4-yl)methanone

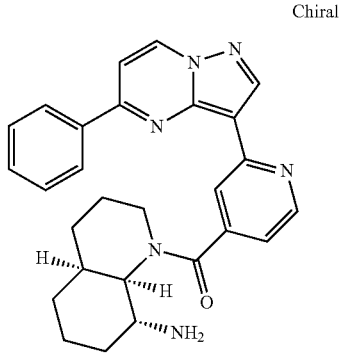

Compound 98 was synthesized following the same process as shown in Example 94 using the commercially available (S)-5,6,7,8-tetrahydroquinolin-8-amine, as a TFA salt.

LC/MS (M+H): 453.2; $^1$H NMR (400 MHz, Methanol-d$_4$) δ 9.13 (d, J=7.4 Hz, 1H), 9.03 (dd, J=1.7, 0.8 Hz, 1H), 8.95 (s, 1H), 8.78 (dd, J=5.9, 0.8 Hz, 1H), 8.33-8.26 (m, 2H), 7.82 (d, J=7.4 Hz, 1H), 7.74 (dd, J=5.9, 1.6 Hz, 1H), 7.66-7.49 (m, 3H), 4.77 (dd, J=11.4, 5.1 Hz, 1H), 3.90-3.81 (m, 1H), 3.56 (d, J=14.4 Hz, 1H), 3.29-3.18 (m, 1H), 2.35-2.17 (m, 3H), 2.00-1.52 (m, 8H), 1.44 (d, J=13.3 Hz, 2H).

Example 99

((4aS,7S,7aS)-7-aminooctahydro-1H-cyclopenta[b]pyridin-1-yl)(2-(5-phenylpyrazolo[1,5-a]pyrimidin-3-yl)pyridin-4-yl)methanone

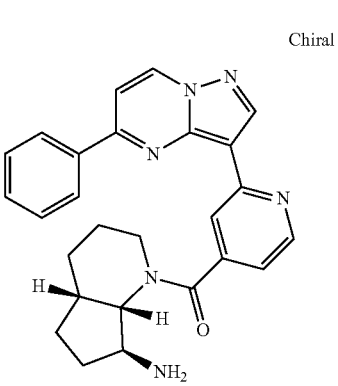

Compound 99 was synthesized following the same process as shown in Example 37 and example 5, and using the commercially available tert-butyl ((4aS,7S,7aS)-octahydro-1H-cyclopenta[b]pyridin-7-yl)carbamate, as a TFA salt. LC/MS (M+H): 439.2; $^1$H NMR (400 MHz, Methanol-d$_4$) δ 9.15 (d, J=7.4 Hz, 1H), 8.94 (s, 1H), 8.91 (s, 1H), 8.80 (d, J=5.9 Hz, 1H), 8.35-8.27 (m, 2H), 7.84 (d, J=7.4 Hz, 1H), 7.70 (dd, J=5.9, 1.6 Hz, 1H), 7.66-7.53 (m, 3H), 5.06 (dd, J=9.2, 7.4 Hz, 1H), 4.01 (q, J=9.4 Hz, 1H), 3.69 (d, J=14.0 Hz, 1H), 3.30-3.19 (m, 2H), 2.53-2.40 (m, 1H), 2.40-2.10 (m, 3H), 1.96-1.71 (m, 2H), 1.71-1.51 (m, 3H), 1.51-1.33 (m, 3H).

Example 100

((1R,5S)-3,8-diazabicyclo[3.2.1]octan-3-yl)(2-(5-phenylpyrazolo[1,5-a]pyrimidin-3-yl)pyridin-4-yl)methanone

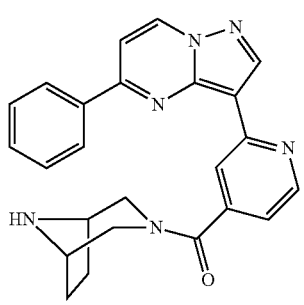

Compound 100 was synthesized following the same process as shown in Example 37 and example 5, and using the commercially available tert-butyl-3,8-diazabicyclo[3.2.1]octane-8-carboxylate, as a TFA salt. LC/MS (M+H): 411.1

Example 101

(((4aR,8aR)-octahydro-1,7-naphthyridin-1(2H)-yl)(2-(5-(thiophen-2-yl)pyrazolo[1,5-a]pyrimidin-3-yl)pyridin-4-yl)methanone

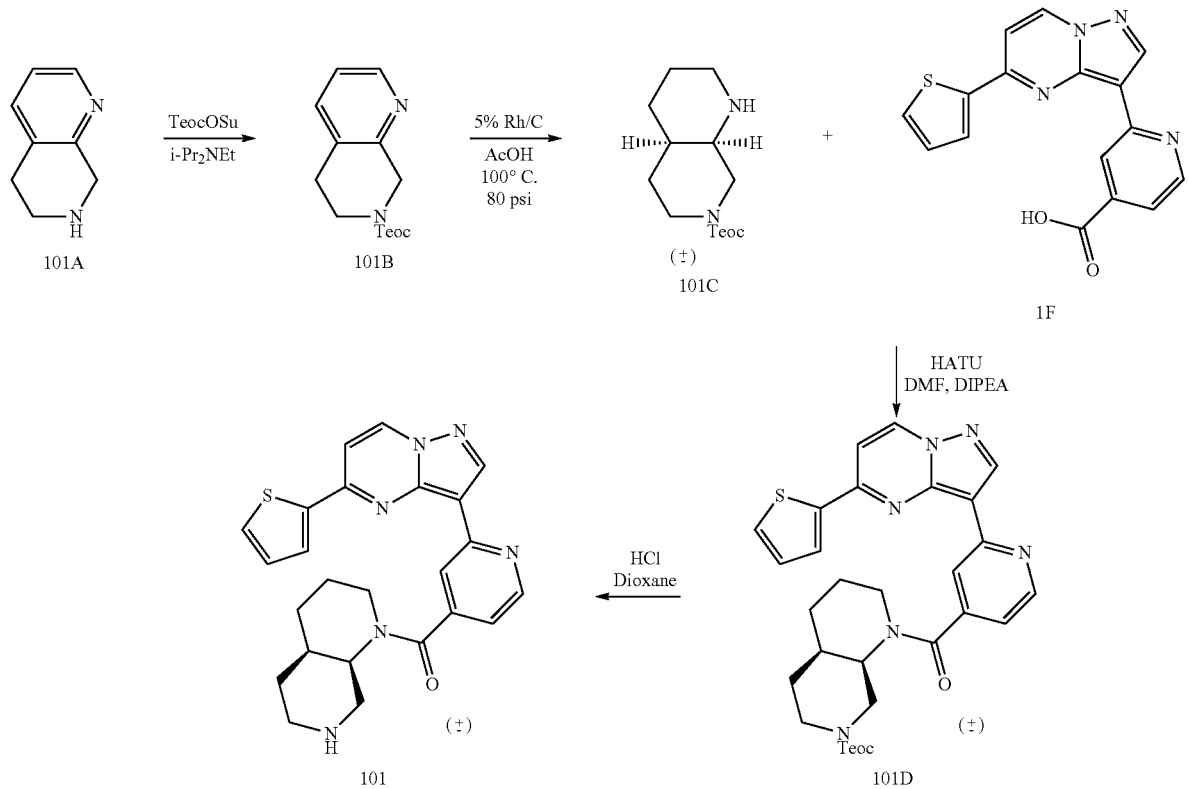

Synthesis of 101:

To a solution of 101A 5,6,7,8-tetrahydro-1,7-naphthyridine (250 mg, 1.207 mmol) and Teoc-O-Su (610 mg, 2.35 mmol) in dichloromethane (10 mL) at r.t. as Hunig's base (0.63 mL, 3.6 mmol) was added and the reaction mixture was stirred over weekend. The reaction mixture was washed with water, concentrated and absorbed onto silica, chromatographed with 10 to 100% gradient of ethyl acetate in hexanes, and product 101B was obtained. (161 mg, 47%). Compound 101B (12 mg) was dissolved in 1:1 mixture of ethanol and acetic acid and the solution was passed through H-Cube hydrogenation apparatus charged with 5% rhodium on carbon catalyst cartridge. After concentration, 20 mg of crude product 101C were obtained and used for next step without purification. Compound 101C was coupled with 1F as explained in Example 1 to get the product 101D. The Teoc group from product 101D was removed by treating it with 6N HCl in dioxane. The reaction mixture was concentrated and purified by HPLC to obtain the final product 101, as a TFA salt. LC/MS (M+H): 445.1; $^1$H NMR (δ, 400 MHz, Methanol-$d_4$), diagnostic signals: 8.87 (d, 1H, J=7.6 Hz), 8.72 (s, 1H), 8.66 (br s, 1H), 8.59 (d, 1H, J=6.0 Hz), 7.91 (d, 1H, J=3.6 Hz), 7.68 (d, 1H, J=5.2 Hz), 7.42 (d, 1H, J=7.2 Hz), 7.55 (dd, 1H, J=4.8, 1.2 Hz), 7.26 (dd, 1H, J=4.8, 4.0 Hz), 5.05 (dt, 1H, J=12.4, 5.2 Hz). Remaining area of the spectrum contains approximately 13 protons by integration.

Example 102

(S)-2-amino-N-(2-(diethylamino)propyl)-6-(5-(thiophen-2-yl)pyrazolo[1,5-a]pyrimidin-3-yl)isonicotinamide

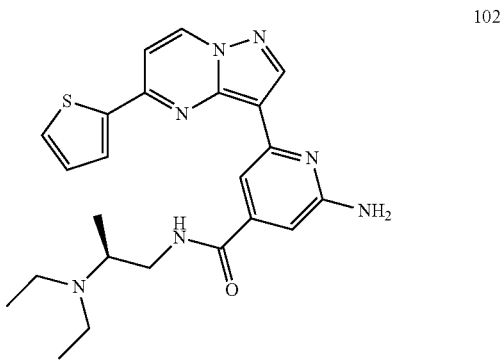 [SMILES: CCN(CC)[C@@H](C)CNC(=O)c1cc(N)nc(-c2cnn3ccc(-c4cccs4)nc23)c1]

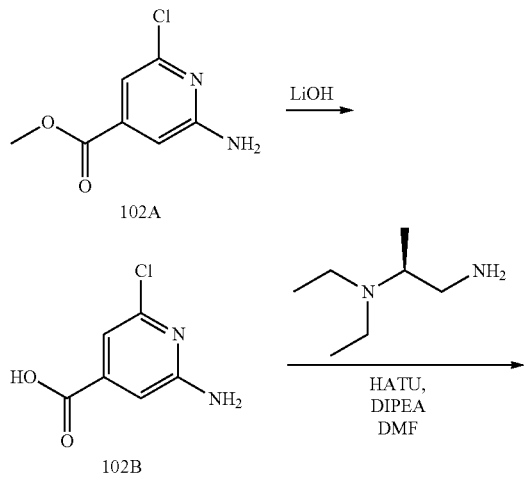

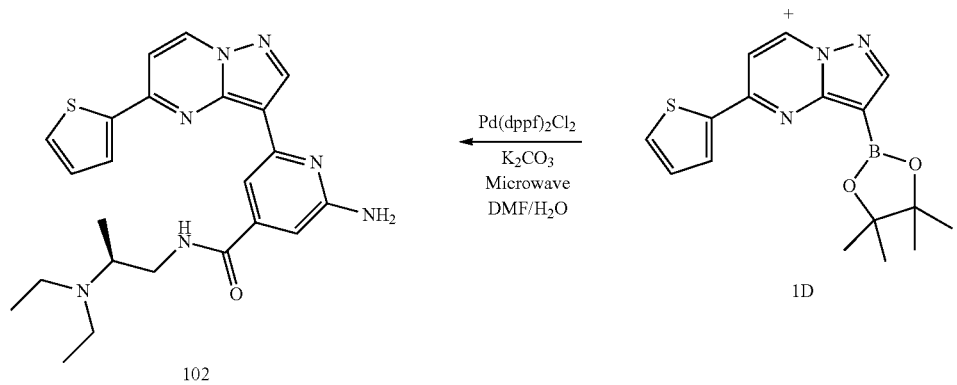

Compound 102 was synthesized following the procedures as described in Example 1, starting from the corresponding commercially available methyl 2-amino-6-chloroisonicotinate, as a TFA salt. LC/MS (M+H): 450.2; $^1$H NMR (MeOD, 400 MHz): δ 8.99 (dd, 1H), 8.77 (d, 1H), 8.13 (d, 1H), 8.04 (dd, 1H), 7.79 (dd, 1H), 7.68 (dd, 1H), 7.30-7.24 (m, 1H), 7.10 (d, 1H), 3.95 (dd, 1H), 3.87 (p, 1H), 3.54 (ddd, 2H), 3.40-3.33 (m, 2H), 3.23 (dd, 1H), 1.43 (dd, 9H).

Example 103

(S)-2-chloro-N-(2-(diethylamino)propyl)-6-(5-(thiophen-2-yl)pyrazolo[1,5-a]pyrimidin-3-yl)isonicotinamide

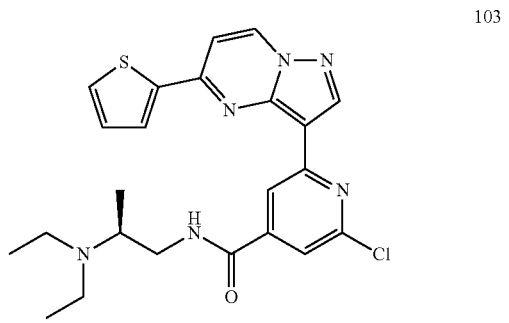 [SMILES: CCN(CC)[C@@H](C)CNC(=O)c1cc(Cl)nc(-c2cnn3ccc(-c4cccs4)nc23)c1]

Compound 103 was synthesized following the Example 102, starting from the corresponding commercially available methyl 2-chloro-6-chloroisonicotinate, as a TFA salt. LC/MS (M+H): 469.2; $^1$H NMR (MeOD, 400 MHz): δ 9.05 (d, 1H), 8.93 (d, 1H), 8.77 (s, 1H), 8.00 (dd, 1H), 7.74 (dd, 1H), 7.62-7.54 (m, 2H), 7.25 (dd, 1H), 3.75-4.0 (m, 2H), 3.55 (dd, 3H), 3.35-3.50 (m, 2H), 3.10 (bs, 1H), 1.47-1.35 (m, 8H).

Example 104

(S)—N-(2-(diethylamino)propyl)-2-isopropyl-6-(5-(thiophen-2-yl)pyrazolo[1,5-a]pyrimidin-3-yl)isonicotinamide

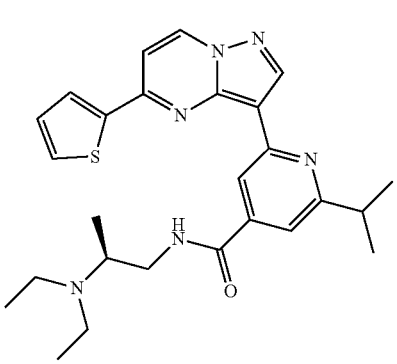

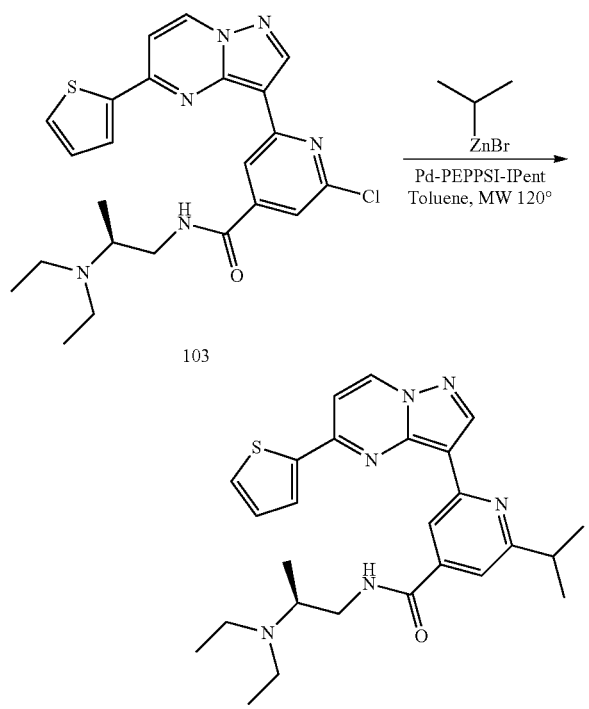

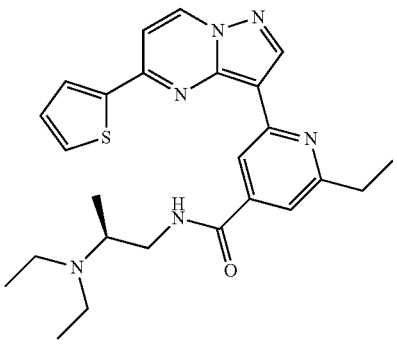

To a suspension of compound 103 (40 mg, 0.085 mmol), 0.5M 2-Propylzinc bromide solution 0.5 M in THF (341.15 µl), and Pd-PEPPSI"-IPent catalyst (6.75 mg, 0.01 mmol) in 3 mL toluene was microwaved at 120° for 15 minutes. The reaction mixture was concentrated and purified by HPLC to obtain the final product 104 as a TFA salt. LC/MS (M+H): 477.2; 1H NMR (400 MHz, Methanol-d4) δ 8.99 (d, J=7.4 Hz, 1H), 8.89 (d, J=1.4 Hz, 1H), 8.87 (d, J=1.5 Hz, 1H), 8.02 (dd, J=4.0, 1.1 Hz, 1H), 7.80 (dd, J=5.1, 1.2 Hz, 1H), 7.77 (d, J=1.6 Hz, 1H), 7.71-7.63 (m, 1H), 7.26 (dd, J=5.1, 3.8 Hz, 1H), 3.98 (dd, J=14.1, 5.9 Hz, 1H), 3.90 (d, J=6.5 Hz, 1H), 3.63 (dd, J=14.1, 6.1 Hz, 1H), 3.59-3.46 (m, 1H), 3.44-3.33 (m, 3H), 3.22 (dd, J=13.5, 7.0 Hz, 1H), 1.52 (dd, J=7.0, 1.4 Hz, 6H), 1.46 (d, J=6.6 Hz, 4H), 1.40 (t, J=7.2 Hz, 3H).

Example 105

(S)—N-(2-(diethylamino)propyl)-2-ethyl-6-(5-(thiophen-2-yl)pyrazolo[1,5-a]pyrimidin-3-yl)isonicotinamide Compound 105 was synthesized following the Example 104, starting from the corresponding commercially available diethylzinc, as a TFA salt. LC/MS (M+H): 463.2; 1H NMR (400 MHz, Methanol-d4) δ 9.02 (d, J=7.4 Hz, 1H), 8.96 (d, J=1.6 Hz, 1H), 8.93 (d, J=1.3 Hz, 1H), 8.03 (d, J=3.5 Hz, 1H), 7.89-7.79 (m, 2H), 7.72 (d, J=7.4 Hz, 1H), 7.26 (dd, J=5.1, 3.8 Hz, 1H), 4.05-3.84 (m, 2H), 3.65 (dd, J=14.0, 6.3 Hz, 1H), 3.52 (dd, J=13.6, 7.0 Hz, 1H), 3.45-3.34 (m, 2H), 3.30-3.02 (m, 3H), 1.53 (td, J=7.6, 1.3 Hz, 3H), 1.48-1.33 (m, 9H).

Example 106

(R)-(2-(aminomethyl)piperidin-1-yl)(2-(dimethylamino)-6-(5-(thiophen-2-yl)pyrazolo[1,5-a]pyrimidin-3-yl)pyridin-4-yl)methanone -continued

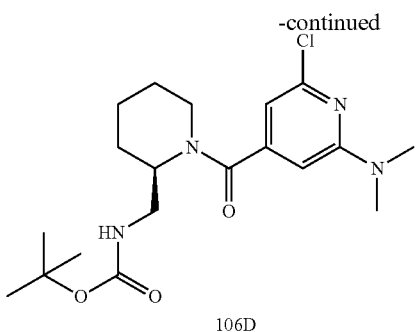
106D

+

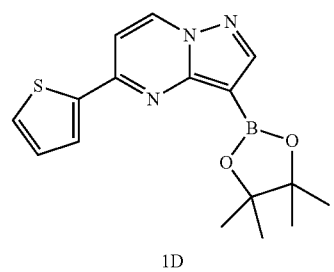
1D

Pd(dppf)₂Cl₂
K₂CO₃
Microwave
DMF/H₂O

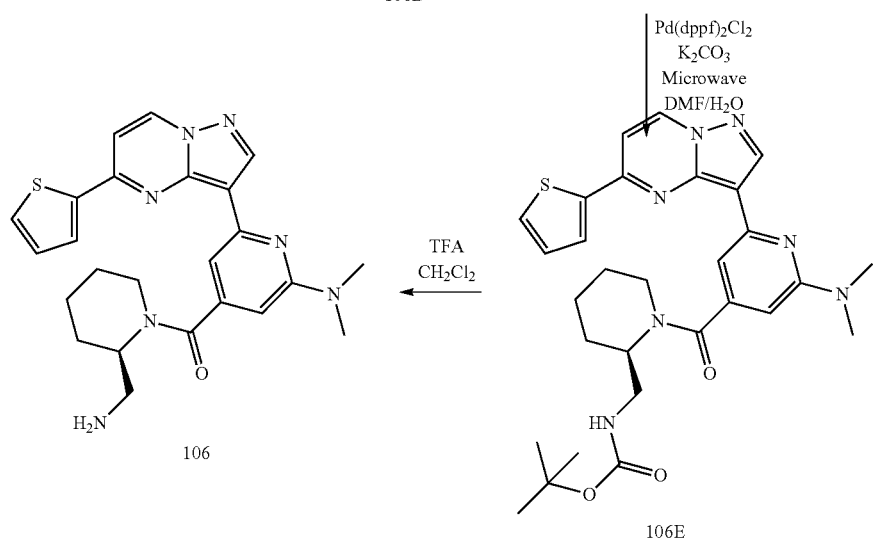

TFA
CH₂Cl₂

106 ← 106E

Compound 106 was synthesized following the Example 102, starting from the corresponding commercially available tert-butyl (R)-(piperidin-2-ylmethyl)carbamate, and methyl 2-chloro-6-(dimethylamino)isonicotinate, as a TFA salt. LC/MS (M+H): 462.2; ¹H NMR (400 MHz, Methanol-d₄) δ 9.03 (d, J=7.4 Hz, 1H), 8.82 (s, 1H), 8.06 (dd, J=3.8, 1.1 Hz, 1H), 7.83 (dd, J=5.0, 1.1 Hz, 1H), 7.72 (d, J=7.4 Hz, 1H), 7.58 (s, 1H), 7.30 (dd, J=5.1, 3.8 Hz, 1H), 6.96 (s, 1H), 5.16-5.01 (m, 1H), 3.74-3.55 (m, 2H), 3.48 (s, 7H), 3.23 (dd, J=13.3, 4.6 Hz, 1H), 2.10-1.85 (m, 2H), 1.85-1.60 (m, 4H).

Example 107

(S)—N-(2-(diethylamino)propyl)-2-(5-(thiophen-2-yl)pyrazolo[1,5-a]pyrimidin-3-yl)-6-(trifluoromethyl)isonicotinamide

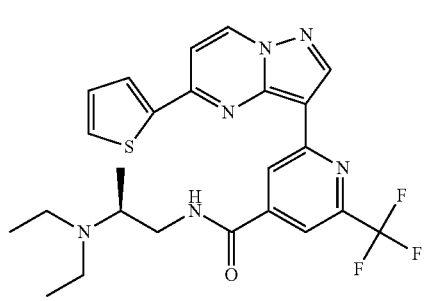
107

Compound 107 was synthesized following the Example 102, starting from the corresponding commercially available methyl 2-chloro-6-(trifluoromethyl)isonicotinate, as a TFA salt. LC/MS (M+H): 503.2; ¹H NMR (400 MHz, Methanol-d₄) δ 9.37-9.32 (m, 1H), 8.94 (d, J=7.4 Hz, 1H), 8.81 (s, 1H), 8.01 (dd, J=3.8, 1.1 Hz, 1H), 7.93 (d, J=1.4 Hz, 1H), 7.75 (dd, J=5.1, 1.1 Hz, 1H), 7.60 (d, J=7.4 Hz, 1H), 7.26 (dd, J=5.0, 3.8 Hz, 1H), 3.99 (dd, J=14.3, 5.8 Hz, 1H), 3.88 (h, J=6.6 Hz, 1H), 3.55 (ddd, J=26.2, 14.4, 6.7 Hz, 2H), 3.46-3.31 (m, 3H), 3.23 (dq, J=14.2, 7.2 Hz, 4H), 1.50-1.36 (m, 8H).

Example 108

(S)—N-(2-(diethylamino)propyl)-2-(dimethylamino)-6-(5-(thiophen-2-yl)pyrazolo[1,5-a]pyrimidin-3-yl)isonicotinamide

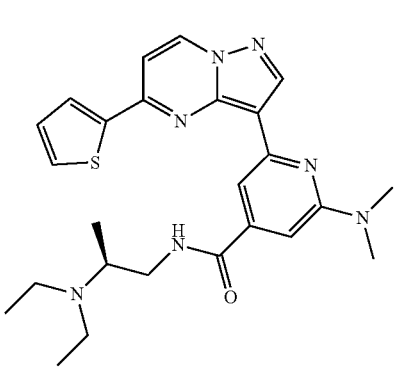
108

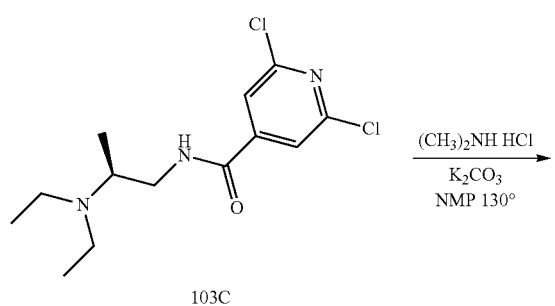

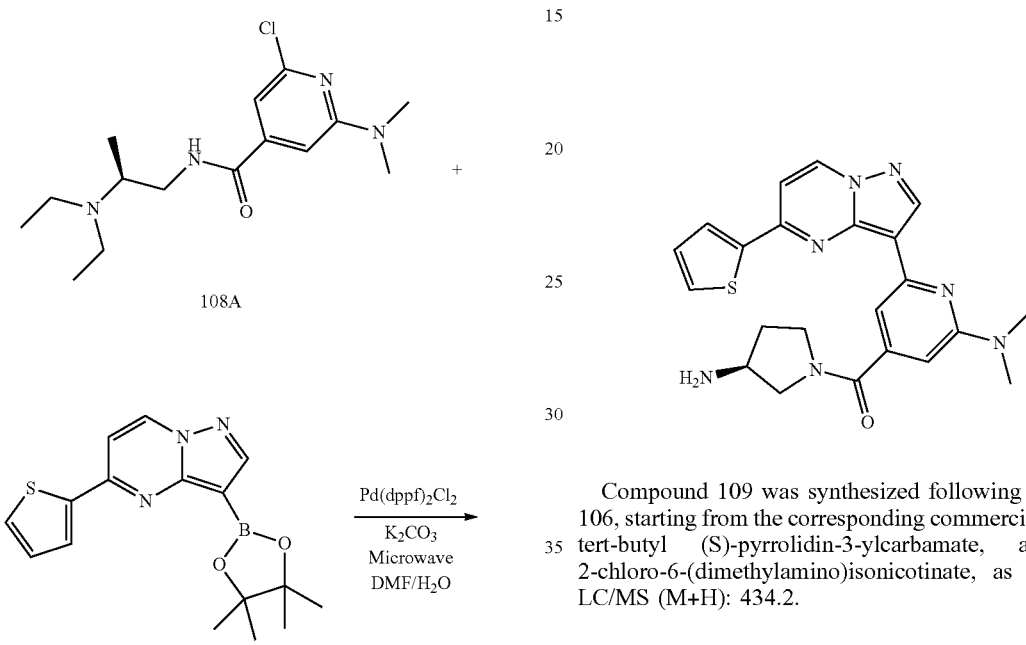

Synthesis of Compound 108A:

A mixture of Compound 103C (50 mg, 0.16 mmol), dimethylamine hydrochloride (26.8 mg, 0.33 mmol), and potassium carbonate (45.43 mg, 0.33 mmol) in 1 mL NMP was heated at 150° C. for 30 minutes. The reaction was filtered and purified by reverse phase chromatography.

Synthesis of Compound 108:

Compound 107 was synthesized following the Example 102, starting from Compound 108A and 1D, as a TFA salt.

LC/MS (M+H): 478.2; 1H NMR (400 MHz, Methanol-d4) δ 8.75 (d, J=7.4 Hz, 1H), 8.63 (s, 1H), 8.04 (d, J=1.2 Hz, 1H), 7.88 (dd, J=3.8, 1.1 Hz, 1H), 7.67 (dd, J=5.0, 1.1 Hz, 1H), 7.41 (d, J=7.4 Hz, 1H), 7.19 (dd, J=5.0, 3.8 Hz, 1H), 6.67 (d, J=1.2 Hz, 1H), 3.44 (d, J=7.0 Hz, 2H), 3.15 (s, 6H), 2.69 (d, J=7.1 Hz, 1H), 2.66-2.51 (m, 1H), 1.20-1.04 (m, 9H).

Example 109

(S)-(3-aminopyrrolidin-1-yl)(2-(dimethylamino)-6-(5-(thiophen-2-yl)pyrazolo[1,5-a]pyrimidin-3-yl)pyridin-4-yl)methanone

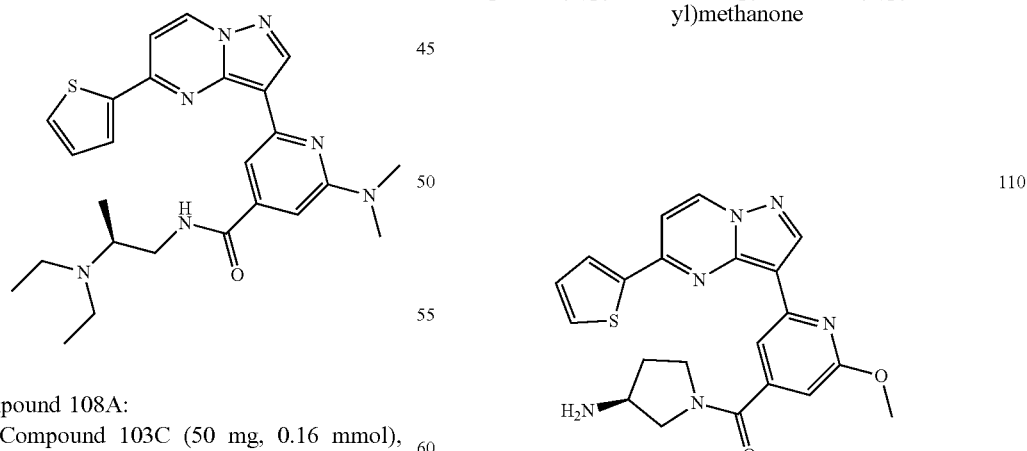

Compound 109 was synthesized following the Example 106, starting from the corresponding commercially available tert-butyl (S)-pyrrolidin-3-ylcarbamate, and methyl 2-chloro-6-(dimethylamino)isonicotinate, as a TFA salt. LC/MS (M+H): 434.2.

Example 110

(S)-(3-aminopyrrolidin-1-yl)(2-methoxy-6-(5-(thiophen-2-yl)pyrazolo[1,5-a]pyrimidin-3-yl)pyridin-4-yl)methanone Compound 110 was synthesized following the Example 106, starting from the corresponding commercially available tert-butyl (S)-pyrrolidin-3-ylcarbamate, and methyl 2-chloro-6-methoxyisonicotinate, as a TFA salt. LC/MS (M+H): 421.1.

Example 111

(R)-(2-(aminomethyl)piperidin-1-yl)(2-chloro-6-(5-(thiophen-2-yl)pyrazolo[1,5-a]pyrimidin-3-yl)pyridin-4-yl)methanone

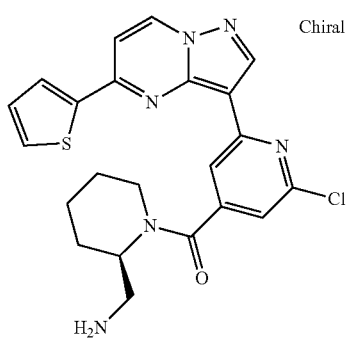

Compound 111 was synthesized following the Example 106, starting from the corresponding commercially available methyl 2,6-dichloroisonicotinate, as a TFA salt. LC/MS (M+H): 453; 1H NMR (400 MHz, Methanol-d4) δ 8.94 (d, J=7.4 Hz, 1H), 8.79 (s, 1H), 8.63-8.60 (m, 1H), 8.00-8.78 (m, 1H), 7.77-7.75 (m, 1H), 7.61-7.58 (m, 1H), 7.37-7.30 (m, 1H), 7.27-7.25 (m, 1H), 5.15-5.10 (m, 1H), 3.70-3.54 (m, 2H), 3.27-3.25 (m, 1H), 2.17-1.90 (m, 2H), 1.90-1.59 (m, 4H).

Example 112

(S)—N-(2-(diethylamino)propyl)-2-methoxy-6-(5-(thiophen-2-yl)pyrazolo[1,5-a]pyrimidin-3-yl)isonicotinamide

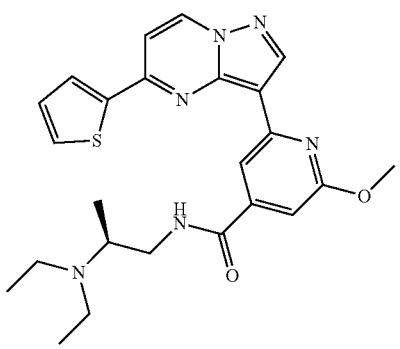

Compound 112 was synthesized following the Example 102, starting from the corresponding commercially available methyl 2-chloro-6-methoxyisonicotinate, as a TFA salt. LC/MS (M+H): 465.2; ¹H NMR (400 MHz, Methanol-d₄) δ 8.86 (d, J=7.4 Hz, 1H), 8.56 (d, J=1.4 Hz, 1H), 7.95 (d, J=3.8 Hz, 1H), 7.72 (d, J=5.0 Hz, 1H), 7.52 (d, J=7.4 Hz, 1H), 7.24 (t, J=4.4 Hz, 1H), 6.93 (d, J=1.4 Hz, 1H), 4.05 (d, J=1.4 Hz, 31H), 3.95 (dd, J=14.3, 6.0 Hz, 1H), 3.86 (h, J=6.8 Hz, 1H), 3.58-3.45 (m, 2H), 3.38 (h, J=6.6 Hz, 2H), 3.30 (d, J=4.9 Hz, 9H), 3.21 (dq, J=13.9, 7.2 Hz, 1H), 1.51-1.36 (m, 9H).

Example 113

(S)-(2-(aminomethyl)piperidin-1-yl)(2-chloro-6-(5-(thiophen-2-yl)pyrazolo[1,5-a]pyrimidin-3-yl)pyridin-4-yl)methanone

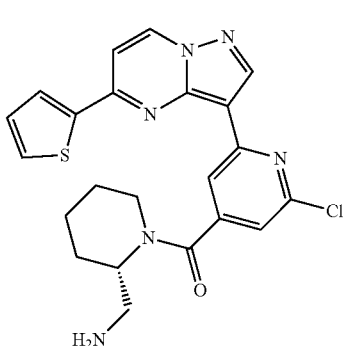

Compound 113 was synthesized following the Example 102, starting from the corresponding commercially available tert-butyl (S)-(piperidin-2-ylmethyl)carbamate, and methyl 2,6-dichloroisonicotinate, as a TFA salt. LC/MS (M+H): 453.1.

Example 114

(S)-2-amino-N-(2-(diethylamino)propyl)-6-(5-phenylpyrazolo[1,5-a]pyrimidin-3-yl)isonicotinamide

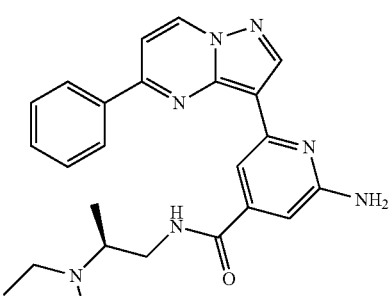

Compound 114 was synthesized following the Example 106, starting from the corresponding commercially available methyl 2-chloro-6-aminoisonicotinate and suing the intermediate 37C from example 37, as a TFA salt. LC/MS (M+H): 444.2; 1H NMR (400 MHz, Methanol-d4) δ 9.15 (d, J=7.4 Hz, 1H), 8.84 (d, J=1.3 Hz, 1H), 8.44-8.30 (m, 2H), 8.20 (d, J=1.4 Hz, 1H), 7.85 (d, J=7.4 Hz, 1H), 7.71-7.56 (m, 3H), 7.12 (t, J=2.0 Hz, 1H), 3.98 (dd, J=14.1, 5.5 Hz, 1H), 3.88 (q, J=6.4 Hz, 1H), 3.55 (ddd, J=20.7, 13.8, 6.7 Hz, 2H), 3.40 (q, J=7.3 Hz, 2H), 3.31-3.15 (m, 1H), 1.60-1.26 (m, 10H).

Example 115

(R)-(2-(aminomethyl)piperidin-1-yl)(2-methyl-6-(5-phenylpyrazolo[1,5-a]pyrimidin-3-yl)pyridin-4-yl)methanone

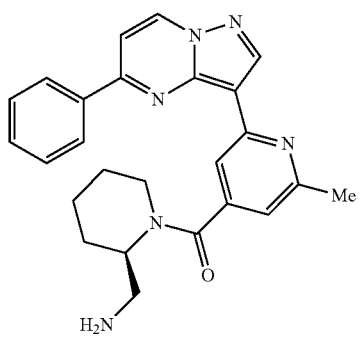

Compound 115 was synthesized following the Example 114, starting from the corresponding commercially available methyl 2-chloro-6-methylisonicotinate and tert-butyl (R)-(piperidin-2-ylmethyl)carbamate, as a TFA salt. LC/MS (M+H): 427.1; $^1$H NMR (400 MHz, Methanol-$d_4$) δ 9.13 (dd, J=7.4, 5.6 Hz, 1H), 8.96 (d, J=5.2 Hz, 1H), 8.75 (s, 1H), 8.32 (dd, J=6.6, 2.9 Hz, 2H), 7.81 (dd, J=7.4, 6.0 Hz, 1H), 7.62 (dd, J=5.1, 1.9 Hz, 3H), 7.45 (d, J=1.4 Hz, 1H), 5.09 (s, 1H), 3.78-3.51 (m, 2H), 3.24 (dd, J=13.4, 4.6 Hz, 1H), 2.80 (d, J=6.6 Hz, 3H), 1.97 (s, 2H), 1.67 (d, J=33.1 Hz, 4H).

Example 116

(R)-(2-(aminomethyl)piperidin-1-yl)(2-(5-phenylpyrazolo[1,5-a]pyrimidin-3-yl)-6-(trifluoromethyl)pyridin-4-yl)methanone

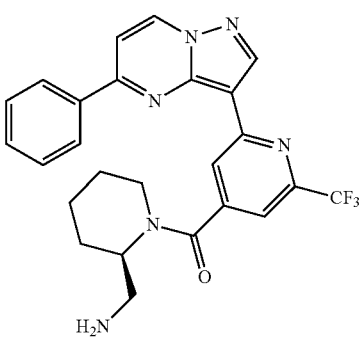

Compound 116 was synthesized following the Example 114, starting from the corresponding commercially available methyl 2-chloro-6-trifloromethylisonicotinate, as a TFA salt. LC/MS (M+H): 481.1; $^1$H NMR (400 MHz, Methanol-$d_4$) δ 9.14-8.99 (m, 2H), 8.91 (s, 1H), 8.31 (dd, J=6.5, 3.0 Hz, 2H), 7.83-7.67 (m, 2H), 7.62 (dd, J=5.0, 1.9 Hz, 3H), 5.13 (s, 1H), 3.74-3.56 (m, 2H), 3.31-3.18 (m, 2H), 2.16-1.87 (m, 3H), 1.85-1.50 (m, 5H).

Example 117

(R)-(2-(aminomethyl)piperidin-1-yl)(2-cyclopropyl-6-(5-phenylpyrazolo[1,5-a]pyrimidin-3-yl)pyridin-4-yl)methanone

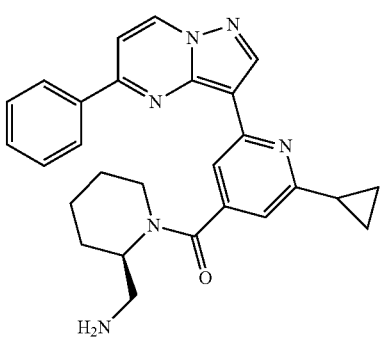

Compound 117 was synthesized following the Example 114, starting from the corresponding commercially available methyl 2-chloro-6-cyclopropylisonicotinate, as a TFA salt. LC/MS (M+H): 453.2; $^1$H NMR (400 MHz, Methanol-$d_4$) δ 9.08 (d, J=7.4 Hz, 1H), 8.89 (s, 1H), 8.57 (d, J=1.3 Hz, 1H), 8.30 (dd, J=6.7, 3.0 Hz, 2H), 7.74 (d, J=7.4 Hz, 1H), 7.68-7.54 (m, 2H), 7.25 (s, 1H), 5.09 (s, 1H), 3.76-3.44 (m, 3H), 3.23 (dd, J=13.5, 4.9 Hz, 2H), 2.39-2.21 (m, 1H), 1.96 (s, 2H), 1.66 (d, J=40.0 Hz, 4H), 1.23 (d, J=4.8 Hz, 4H).

Example 118

(R)-(2-(aminomethyl)piperidin-1-yl)(2-(dimethylamino)-6-(5-phenylpyrazolo[1,5-a]pyrimidin-3-yl)pyridin-4-yl)methanone

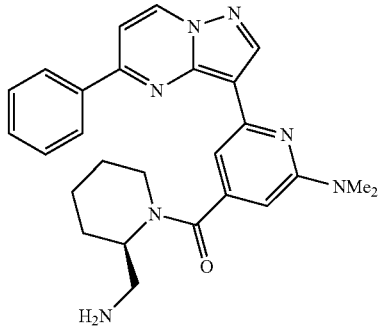

Compound 118 was synthesized following the Example 115, starting from the corresponding commercially available methyl 2-chloro-6-(dimethylamino)isonicotinate, as a TFA salt. LC/MS (M+H): 456.2; $^1$H NMR (400 MHz, Methanol-$d_4$) δ 9.17 (d, J=7.4 Hz, 1H), 8.89 (s, 1H), 8.26-8.12 (m, 2H), 7.73 (d, J=7.4 Hz, 1H), 7.69-7.56 (m, 4H), 6.97 (s, 1H), 5.08 (d, J=9.3 Hz, 1H), 3.77-3.51 (m, 2H), 3.41 (s, 7H), 3.23 (dd, J=13.3, 4.5 Hz, 1H), 2.07-1.85 (m, 2H), 1.85-1.59 (m, 4H).

Example 119

(S)-2-ethyl-N-(2-(ethylamino)propyl)-6-(5-phenylpyrazolo[1,5-a]pyrimidin-3-yl)isonicotinamide

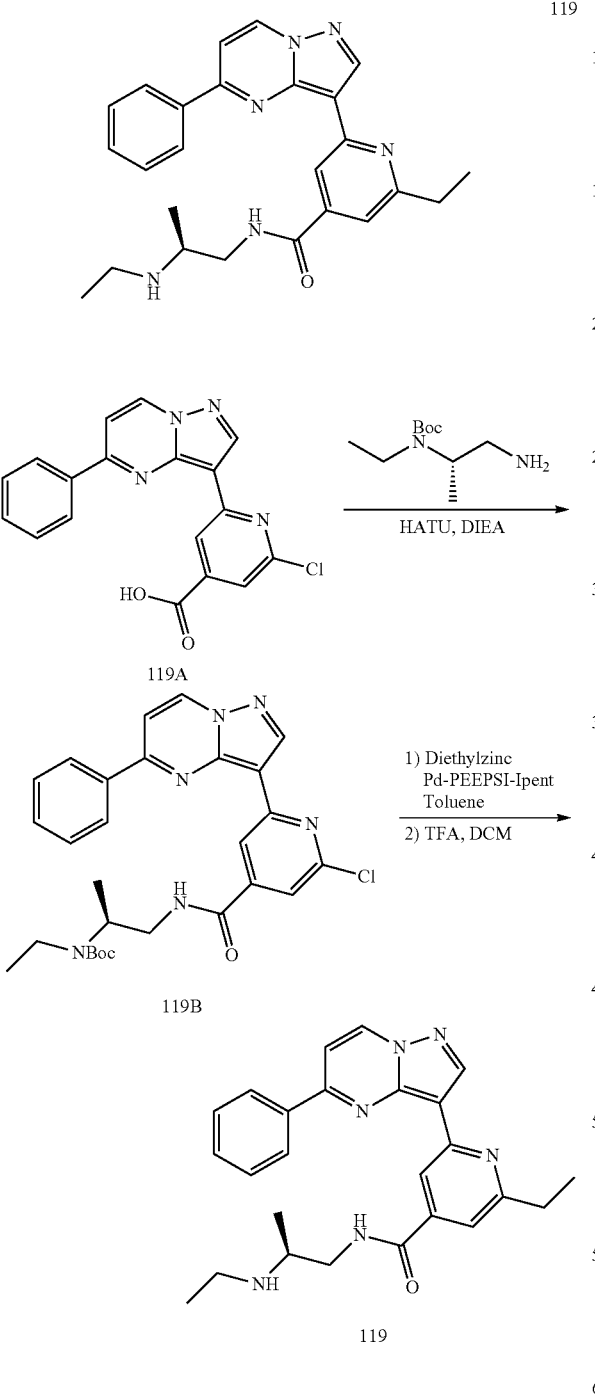

Compound 119B was synthesized following the Example 1, starting from the corresponding commercially available methyl 2,6-dichloroisonicotinate, phenylboronic acid, and tert-butyl (S)-(1-aminopropan-2-yl)(ethyl)carbamate.

To a suspension of compound 119B (50 mg, 0.09 mmol), 1M Diethylzinc 1.0M in HEX (184.47 µl), and Pd-PEPPSI"-IPent catalyst (6.75 mg, 0.01 mmol) in 3 mL toluene was microwaved at 120° for 15 minutes. The reaction mixture was concentrated and purified by HPLC. The product was dissolved in 10 mL of DCM and 0.5 mL TFA was added. The reaction was stirred at RT for 16 hours and then concentrated to afford Compound 119 (13 mg), as a TFA salt. LC/MS (M+H): 429.2

Example 120

(S)—N-(2-(ethylamino)propyl)-2-methyl-6-(5-phenylpyrazolo[1,5-a]pyrimidin-3-yl)isonicotinamide

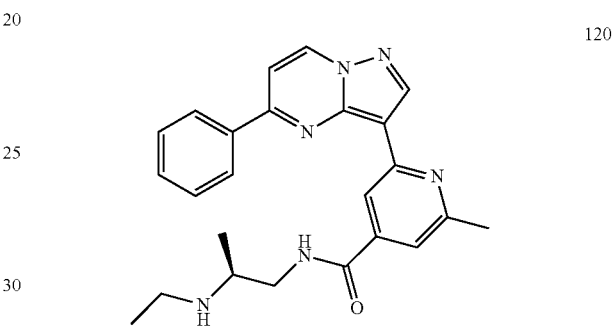

Compound 120 was synthesized following the Example 119, starting from the corresponding commercially available dimethylzinc, as a TFA salt. LC/MS (M+H): 415.2

Example 121

(S)-2-amino-N-(2-(ethylamino)propyl)-6-(5-phenylpyrazolo[1,5-a]pyrimidin-3-yl)isonicotinamide

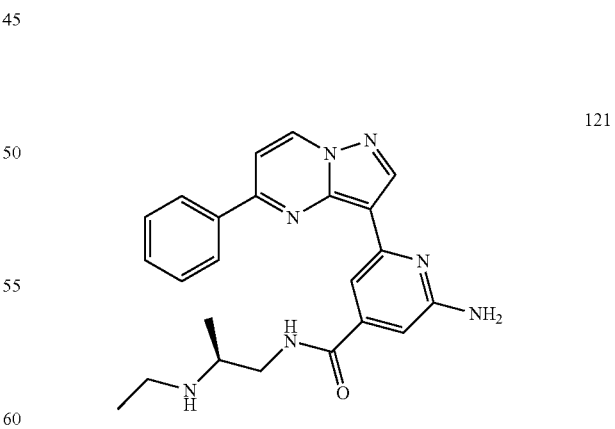

Compound 121 was synthesized following the Example 114, starting from the corresponding commercially available tert-butyl (S)-(1-aminopropan-2-yl)(ethyl)carbamate, and methyl 2-chloro-6-aminoisonicotinate, as a TFA salt. LC/MS (M+H):

Example 122

(S)—N-(2-(ethylamino)propyl)-2-isopropyl-6-(5-phenylpyrazolo[1,5-a]pyrimidin-3-yl)isonicotinamide

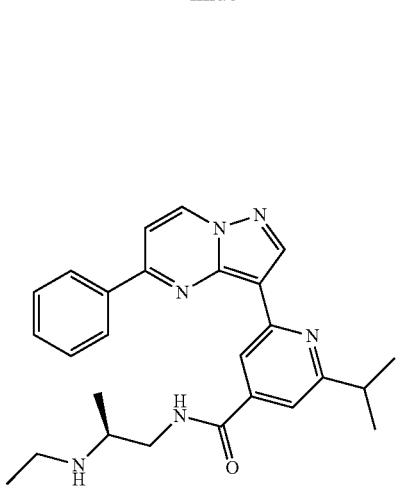

122

Compound 120 was synthesized following the Example 119, starting from the corresponding commercially available 2-propylzinc bromide, as a TFA salt. LC/MS (M+H): 443.2; 1H NMR (400 MHz, Methanol-d4) δ 9.14 (d, J=7.4 Hz, 1H), 9.02 (d, J=1.6 Hz, 1H), 8.99 (s, 1H), 8.39-8.24 (m, 2H), 7.90-7.76 (m, 2H), 7.64-7.59 (m, 3H), 3.83 (dd, J=14.5, 4.7 Hz, 1H), 3.69 (dd, J=14.5, 5.4 Hz, 1H), 3.65-3.52 (m, 1H), 3.53-3.36 (m, 1H), 3.30-3.15 (m, 2H), 1.51 (d, J=6.9 Hz, 6H), 1.44 (d, J=6.7 Hz, 3H), 1.36 (t, J=7.2 Hz, 3H).

Example 123

(S)-2-cyclopropyl-N-(2-(ethylamino)propyl)-6-(5-phenylpyrazolo[1,5-a]pyrimidin-3-yl)isonicotinamide

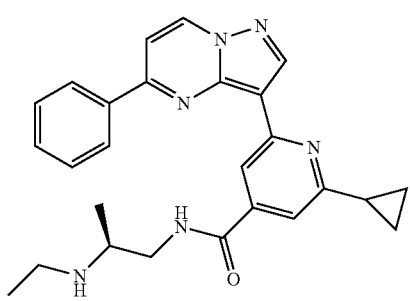

123

Compound 123 was synthesized following the Example 119, starting from the corresponding commercially available cyclopropylzinc bromide, as a TFA salt. LC/MS (M+H): 441.2

Example 124

(S)-2-chloro-N-(2-(ethylamino)propyl)-6-(5-phenylpyrazolo[1,5-a]pyrimidin-3-yl)isonicotinamide

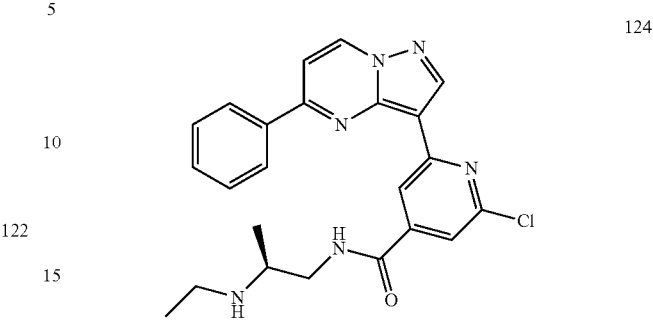

124

Compound 124 was synthesized following the Example 114, starting from the corresponding commercially available tert-butyl (S)-(1-aminopropan-2-yl)(ethyl)carbamate, and methyl 2,6-dichloro isonicotinate, as a TFA salt. LC/MS (M+H): 435.1

Example 125

(S)-(3-aminopyrrolidin-1-yl)(2-(dimethylamino)-6-(5-phenylpyrazolo[1,5-a]pyrimidin-3-yl)pyridin-4-yl)methanone

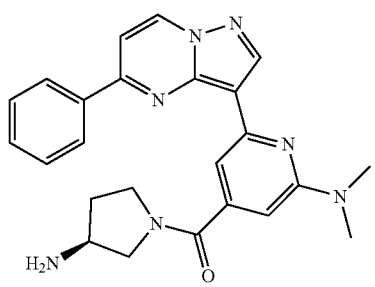

125

Compound 125 was synthesized following the Example 114, starting from the corresponding commercially available methyl 2-chloro-6-(dimethylamino)isonicotinate, and tert-butyl (S)-pyrrolidin-3-ylcarbamate, as a TFA salt. LC/MS (M+H): 428.2

Example 126

(S)-(3-aminopyrrolidin-1-yl)(2-methoxy-6-(5-phenylpyrazolo[1,5-a]pyrimidin-3-yl)pyridin-4-yl)methanone

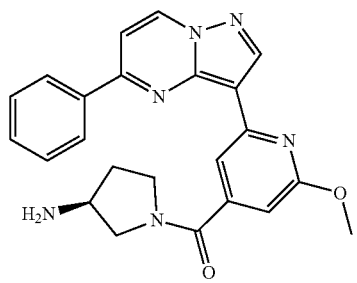

126

Compound 126 was synthesized following the Example 114, starting from the corresponding commercially available methyl 2-chloro-6-methoxyisonicotinate, and tert-butyl (S)-pyrrolidin-3-ylcarbamate, as a TFA salt. LC/MS (M+H): 415.1

Example 127

(R)-(2-(aminomethyl)piperidin-1-yl)(2-chloro-6-(5-phenylpyrazolo[1,5-a]pyrimidin-3-yl)pyridin-4-yl)methanone

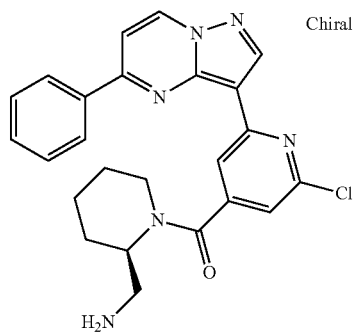

Compound 127 was synthesized following the Example 115, starting from the corresponding commercially available methyl 2,6-dichloroisonicotinate, as a TFA salt. LC/MS (M+H): 447; 1H NMR (400 MHz, Methanol-d4) δ 8.96 (d, J=7.4 Hz, 1H), 8.77 (s, 1H), 8.73-8.62 (m, 1H), 8.35-8.20 (m, 2H), 7.69-7.48 (m, 4H), 7.45-7.40 (m, 1H), 5.15-5.09 (m, 1H), 3.72-3.55 (m, 2H), 3.23-3.20 (m, 2H), 2.00-1.97 (m, 2H), 1.78-1.53 (m, 4H).

Example 128

(2-amino-6-(5-phenylpyrazolo[1,5-a]pyrimidin-3-yl)pyridin-4-yl)(-3,9-diazabicyclo[4.2.1]nonan-9-yl)methanone

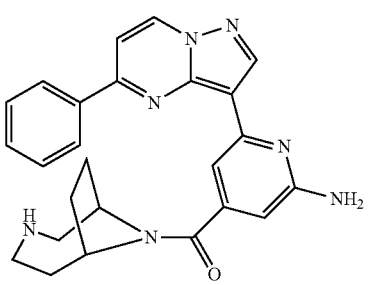

Compound 128 was synthesized following the Example 115, starting from the commercially available methyl 2-chloro-6-aminoisonicotinate, and tert-butyl (3,9-diazabicyclo[4.2.1]nonane-3-carboxylate, as a TFA salt. LC/MS (M+H): 440.2

Example 129

(2-amino-6-(5-(thiophen-2-yl)pyrazolo[1,5-a]pyrimidin-3-yl)pyridin-4-yl)(-3,9-diazabicyclo[4.2.1]nonan-9-yl)methanone

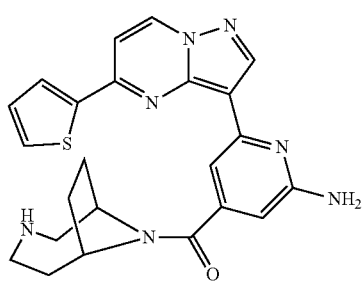

Compound 129 was synthesized following the Example 106, starting from the commercially available methyl 2-chloro-6-aminoisonicotinate and (1S,3S,6R)-314,9-diazabicyclo[4.2.1]nonane-3-carboxylate tert-butyl (3,9-diazabicyclo[4.2.1]nonane-3-carboxylate, as a TFA salt. LC/MS (M+H): 446.1

Example 130

(R)-(2-(aminomethyl)piperidin-1-yl)(2-(tert-butyl)-6-(5-phenylpyrazolo[1,5-a]pyrimidin-3-yl)pyridin-4-yl)methanone

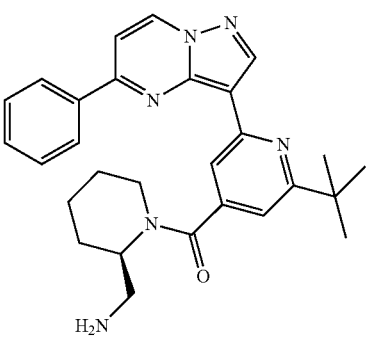

Compound 130 was synthesized following the Example 115, starting from the commercially available methyl 2-chloro-6-t-butylisonicotinate, as a TFA salt. LC/MS (M+H): 469.2

Example 131

(R)-(2-(aminomethyl)pyrrolidin-1-yl)(2-methyl-6-(5-phenylpyrazolo[1,5-a]pyrimidin-3-yl)pyridin-4-yl)methanone

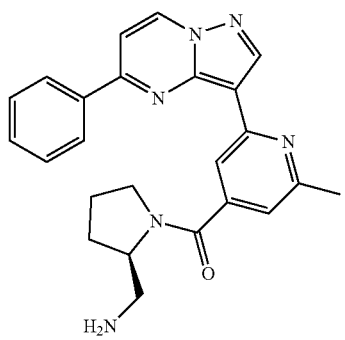

Compound 131 was synthesized following the Example 106, starting from the commercially available methyl 2-chloro-6-methylisonicotinate and tert-butyl (R)-(pyrrolidin-2-ylmethyl)carbamate, as a TFA salt. LC/MS (M+H): 413.1

Example 132

(R)-(2-(aminomethyl)piperidin-1-yl)(2-methoxy-6-(5-phenylpyrazolo[1,5-a]pyrimidin-3-yl)pyridin-4-yl)methanone

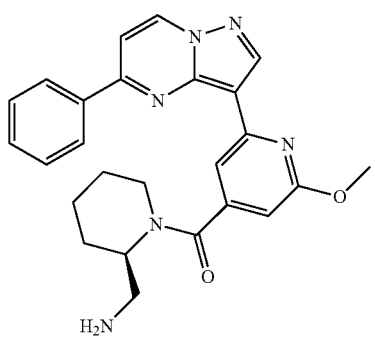

Compound 132 was synthesized following the Example 115, starting from the commercially available methyl 2-chloro-6-methoxyisonicotinate, as a TFA salt. LC/MS (M+H): 443.1

Example 133

(S)-(2-(aminomethyl)piperidin-1-yl)(2-chloro-6-(5-phenylpyrazolo[1,5-a]pyrimidin-3-yl)pyridin-4-yl)methanone

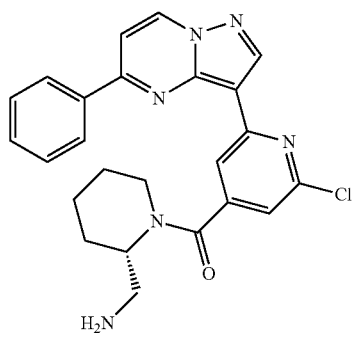

Compound 133 was synthesized following the Example 115, starting from the commercially available methyl 2,6-dichloroisonicotinate, and tert-butyl (S)-(piperidin-2-ylmethyl)carbamate, as a TFA salt. LC/MS (M+H): 447.1

Example 134

(S)-(2-(aminomethyl)piperidin-1-yl)(2-methoxy-6-(5-phenylpyrazolo[1,5-a]pyrimidin-3-yl)pyridin-4-yl)methanone

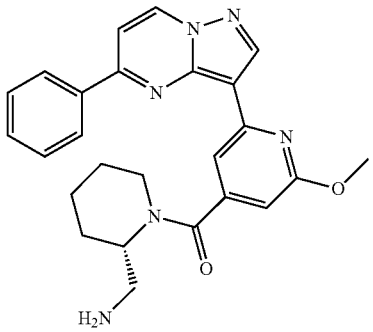

Compound 134 was synthesized following the Example 115, starting from the commercially available methyl 2-chloro-6-methoxyisonicotinate, and tert-butyl (S)-(piperidin-2-ylmethyl)carbamate, as a TFA salt. LC/MS (M+H): 443.2

Example 135

(S)-(2-(aminomethyl)piperidin-1-yl)(2-(dimethyl-amino)-6-(5-phenylpyrazolo[1,5-a]pyrimidin-3-yl)pyridin-4-yl)methanone

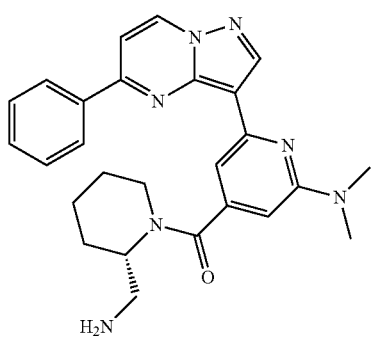

Compound 135 was synthesized following the Example 115, starting from the commercially available methyl 2-chloro-6-(dimethylamino)isonicotinate, and tert-butyl (S)-(piperidin-2-ylmethyl)carbamate, as a TFA salt. LC/MS (M+H): 456.2

Example 136

(R)-(2-(aminomethyl)piperidin-1-yl)(5-methyl-2-(5-phenylpyrazolo[1,5-a]pyrimidin-3-yl)pyridin-4-yl)methanone

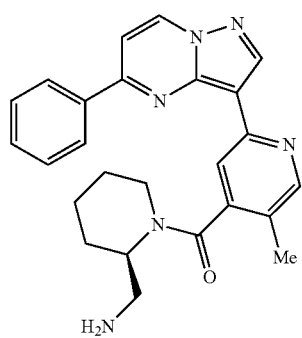

Compound 136 was synthesized following the Example 115, starting from the commercially available methyl 2-chloro-5-methylisonicotinate, as a TFA salt. LC/MS (M+H): 427.2; $^1$H NMR (400 MHz, Methanol-$d_4$) δ 9.10 (d, J=7.6 Hz, 1H), 8.86 (d, J=4.5 Hz, 1H), 8.62 (s, 1H), 8.31 (dd, J=6.6, 3.1 Hz, 2H), 7.77 (d, J=7.4 Hz, 1H), 7.68-7.52 (m, 4H), 5.25-5.09 (m, 1H), 3.61-3.36 (m, 4H), 2.43 (d, J=12.0 Hz, 4H), 1.99 (d, J=9.2 Hz, 2H), 1.73 (s, 4H).

Example 137

(R)-(2-(aminomethyl)piperidin-1-yl)(5-chloro-2-(5-phenylpyrazolo[1,5-a]pyrimidin-3-yl)pyridin-4-yl)methanone

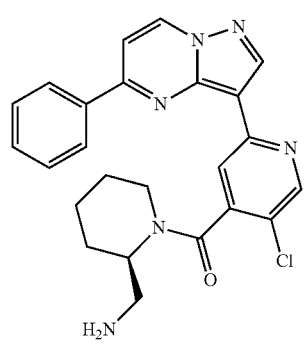

Compound 137 was synthesized following the Example 115, starting from the commercially available methyl 2,5-dichloroisonicotinate, as a TFA salt. LC/MS (M+H): 447.2

Example 138

(R)-(5-amino-2-(5-phenylpyrazolo[1,5-a]pyrimidin-3-yl)pyridin-4-yl)(2-(aminomethyl)piperidin-1-yl)methanone

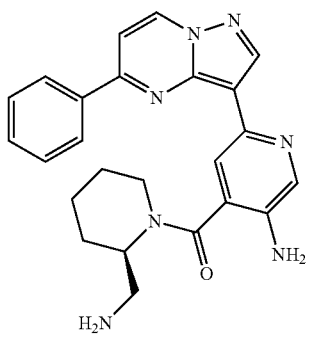

Compound 138 was synthesized following the Example 115, starting from the commercially available methyl 2-chloro-5-aminoisonicotinate, as a TFA salt. LC/MS (M+H): 428.2; $^1$H NMR (400 MHz, Methanol-$d_4$) δ 9.07 (d, J=7.4 Hz, 1H), 8.74 (s, 1H), 8.62 (s, 1H), 8.37-8.25 (m, 2H), 8.23 (d, J=0.6 Hz, 1H), 7.73 (d, J=7.4 Hz, 1H), 7.66-7.52 (m, 3H), 5.17-5.00 (m, 1H), 3.55 (d, J=11.6 Hz, 2H), 3.29-3.17 (m, 1H), 2.14-1.82 (m, 3H), 1.70 (d, J=19.8 Hz, 4H).

Example 139

(R)-(2-(aminomethyl)piperidin-1-yl)(5-(methylamino)-2-(5-phenylpyrazolo[1,5-a]pyrimidin-3-yl)pyridin-4-yl)methanone

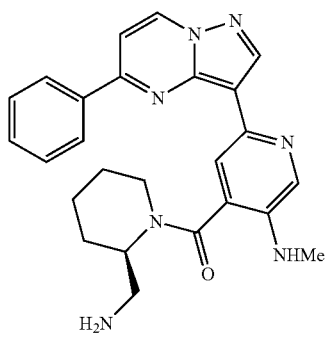

139

Compound 139 was synthesized following the Example 115, starting from the commercially available methyl 2-chloro-5-(methylamino)isonicotinate, as a TFA salt. LC/MS (M+H): 442.2; $^1$H NMR (400 MHz, Methanol-d$_4$) δ 9.09 (d, J=7.4 Hz, 1H), 8.77 (s, 1H), 8.60 (s, 1H), 8.38-8.19 (m, 2H), 8.06 (s, 1H), 7.76 (d, J=7.4 Hz, 1H), 7.69-7.54 (m, 3H), 5.08 (d, J=9.5 Hz, 1H), 3.59 (d, J=12.1 Hz, 2H), 3.26 (t, J=5.8 Hz, 1H), 2.98 (s, 4H), 1.95 (s, 3H), 1.64 (d, J=23.0 Hz, 4H).

Example 140

((R)-2-((R)-1-aminoethyl)piperidin-1-yl)(5-methyl-2-(5-phenylpyrazolo[1,5-a]pyrimidin-3-yl)pyridin-4-yl)methanone

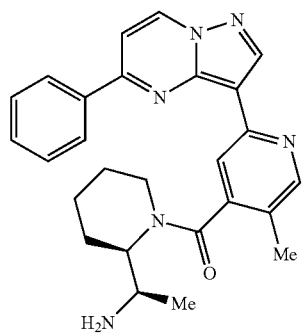

140

Compound 140 was synthesized following the same process as shown in Example 94 using the commercially available (R)-1-(pyridin-2-yl)ethan-1-amine and methyl 2-chloro-5-methylisonicotinate, as a TFA salt. LC/MS (M+H): 441.2; $^1$H NMR (δ, 400 MHz, Methanol-d$_4$), diagnostic signals: 9.30 (d, 1H), 8.83 (s, 1H), 8.65-8.59 (s, 1H), 8.56 (s, 1H), 8.42-8.26 (m, 2H), 7.80 (d, 1H), 7.61-7.55 (m, 3H), 4.72 (d, 1H), 3.98-3.79 (m, 1H), 3.33-3.20 (m, 2H), 2.33 (s, 3H), 2.01-1.91 (m, 1H), 1.70-1.40 (m, 6H), 1.34 (d, 3H).

Example 141

(S)—N-(2-(diethylamino)propyl)-2-(3-methoxyazetidin-1-yl)-6-(5-(thiophen-2-yl)pyrazolo[1,5-a]pyrimidin-3-yl)isonicotinamide

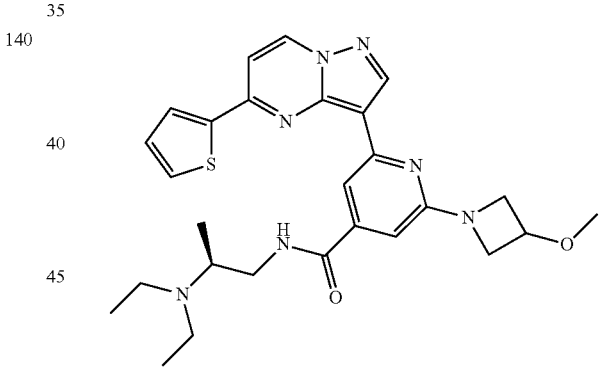

141

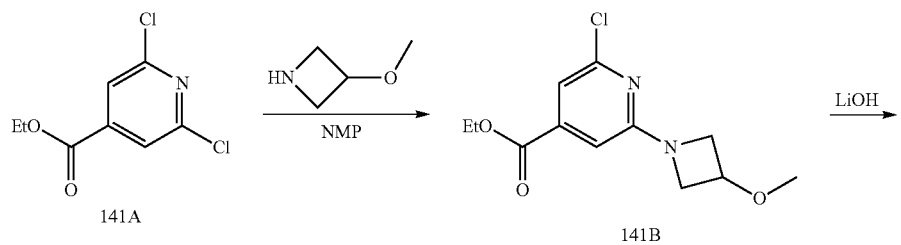

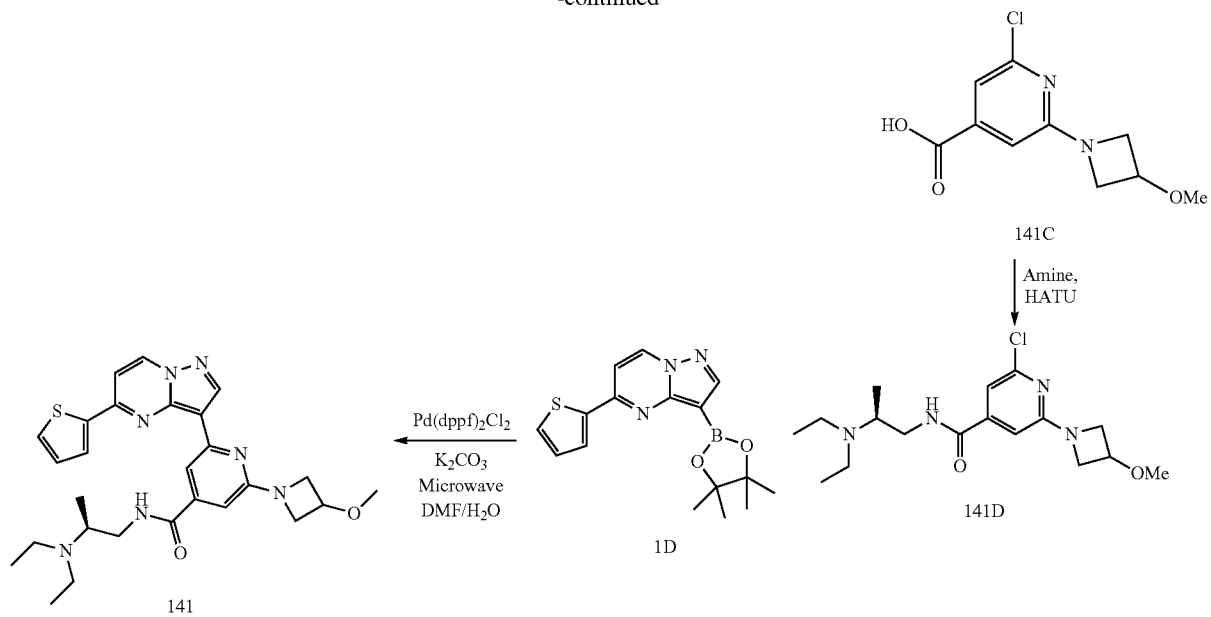

Synthesis of ethyl 2-chloro-6-(3-methoxyazetidin-1-yl)isonicotinate (141B)

Methyl-2,6-dichloro-pyridine-4-carboxylate 141A (416 mg) was combined with the 3-methoxy azetidine HCl (100 mg) and K₂CO₃ in N-Methyl-2-pyrrolidone (2 mL) in a sealed tube. The resulting reaction mixture was heated at 130° C. for 3 h and purified by reverse phase HPLC.

Synthesis of 2-chloro-6-(3-methoxyazetidin-1-yl)isonicotinic Acid (14C)

To the ester 141B (150 mg) in methanol (2 mL), 1M LiOH in methanol (2 mL) was added and heated at 80° C. for 60 min. LC/MS shows the complete conversion, acidified the reaction mixture with 1N HCl, concentrated and purified by reverse-phase HPLC. Concentrated and used for the next step.

Synthesis of (S)-2-chloro-N-(2-(diethylamino)propyl)-6-(3-methoxyazetidin-1-yl)isonicotinamide (141D)

To a mixture of the acid 141C and HATU in DMF (S)—N2,N2-diethylpropane-1,2-diamine and diisopropylethylamine were added and stirred at room temperature for 2 h. LC-MS shows the complete conversion, purified the reaction mixture using reverse phase HPLC, concentrated and the product 141D used for the next step

Synthesis of (S)—N-(2-(diethylamino)propyl)-2-(3-methoxyazetidin-1-yl)-6-(5-(thiophen-2-yl)pyrazolo[1,5-a]pyrimidin-3-yl)isonicotinamide (141)

The Suzuki reaction was performed as explained in Example 1, and the final product was obtained as TFA salt. LC/MS (M+H): 520.2; 1H NMR (400 MHz, Methanol-d4) δ 8.85 (d, J=7.4 Hz, 1H), 8.63 (s, 1H), 7.95 (dd, J=3.8, 1.1 Hz, 1H), 7.83 (d, J=1.4 Hz, 1H), 7.78 (dd, J=5.1, 1.1 Hz, 1H), 7.54 (d, J=7.4 Hz, 1H), 7.26 (dd, J=5.0, 3.8 Hz, 1H), 6.71 (d, J=1.4 Hz, 1H), 4.58-4.45 (m, 3H), 4.17 (d, J=6.5 Hz, 2H), 3.91 (ddd, J=18.7, 13.2, 6.1 Hz, 2H), 3.66-3.48 (m, 2H), 3.42-3.12 (m, 6H), 1.57-1.34 (m, 8H).

Example 142

(S)-2-(3-cyanoazetidin-1-yl)-N-(2-(diethylamino)propyl)-6-(5-(thiophen-2-yl)pyrazolo[1,5-a]pyrimidin-3-yl)isonicotinamide

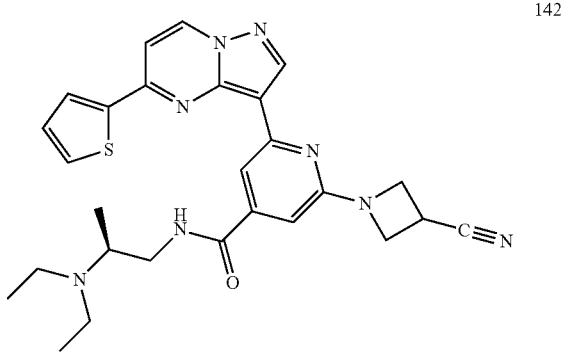 [SMILES: CCN(CC)[C@@H](C)CNC(=O)c1cc(-c2cnn3ccc(-c4cccs4)nc23)nc(N2CC(C#N)C2)c1]

Compound 142 was synthesized following the Example 141, starting from commercially available azetidine-3-carbonitrile, as a TFA salt. LC/MS (M+H): 515.2; 1H NMR (400 MHz, Methanol-d4) δ 8.85 (d, J=7.4 Hz, 1H), 8.69 (s, 1H), 8.37 (d, J=1.2 Hz, 1H), 7.95 (d, J=3.9 Hz, 1H), 7.70 (d, J=5.1 Hz, 1H), 7.52 (d, J=7.4 Hz, 1H), 7.22 (dd, J=5.1, 3.8 Hz, 1H), 6.63 (d, J=1.2 Hz, 1H), 4.42 (t, J=8.3 Hz, 1H), 4.26 (dd, J=7.9, 5.8 Hz, 2H), 3.92-3.37 (m, 3H), 3.16 (q, J=7.2 Hz, 2H), 2.18 (t, J=7.4 Hz, 1H), 1.37 (dd, J=25.0, 6.9 Hz, 7H), 0.87 (q, J=10.2, 8.3 Hz, 6H).

Example 143

(S)—N-(2-(diethylamino)propyl)-2-(3-ethoxyazetidin-1-yl)-6-(5-(thiophen-2-yl)pyrazolo[1,5-a]pyrimidin-3-yl)isonicotinamide

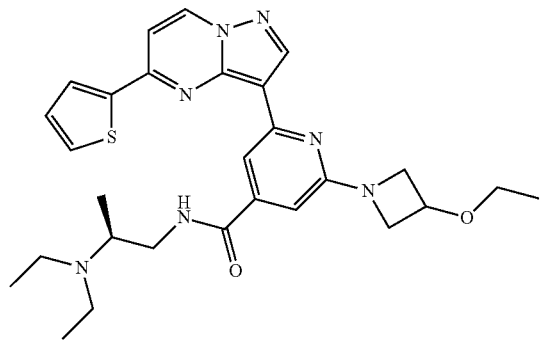

143

Compound 143 was synthesized following the Example 141, starting from commercially available 3-ethoxyazetidine, as a TFA salt. LC/MS (M+H): 534.2; 1H NMR (400 MHz, Methanol-d4) δ 8.76 (d, J=7.4 Hz, 1H), 8.58 (s, 1H), 8.14 (d, J=1.3 Hz, 1H), 7.89 (dd, J=3.8, 1.1 Hz, 1H), 7.67 (dd, J=5.1, 1.0 Hz, 1H), 7.42 (d, J=7.4 Hz, 1H), 7.19 (dd, J=5.1, 3.8 Hz, 1H), 6.50 (d, J=1.3 Hz, 1H), 4.46 (tt, J=6.2, 4.3 Hz, 1H), 4.25 (dd, J=8.7, 6.3 Hz, 2H), 3.89 (dd, J=8.9, 4.3 Hz, 2H), 3.76-3.38 (m, 4H), 3.17 (q, J=7.2 Hz, 2H), 1.41 (d, J=6.7 Hz, 3H), 1.33 (q, J=7.3 Hz, 3H), 1.28-1.11 (m, 10H).

Example 144

(S)—N-(2-(diethylamino)propyl)-2-(3-(difluoromethoxy)azetidin-1-yl)-6-(5-(thiophen-2-yl)pyrazolo[1,5-a]pyrimidin-3-yl)isonicotinamide

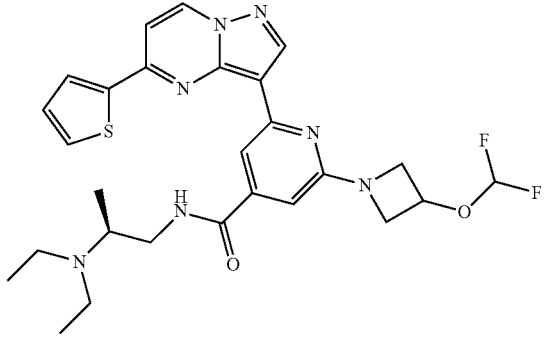

144

Compound 144 was synthesized following the Example 141, starting from commercially available 3-difluoromethoxyazetidine, as a TFA salt. LC/MS (M+H): 556.2; 1H NMR (400 MHz, Methanol-d4) δ 8.85 (d, J=7.4 Hz, 1H), 8.68 (s, 1H), 8.33 (d, J=1.2 Hz, 1H), 7.95 (dd, J=3.8, 1.1 Hz, 1H), 7.69 (dd, J=5.1, 1.0 Hz, 1H), 7.51 (d, J=7.4 Hz, 1H), 7.22 (dd, J=5.0, 3.8 Hz, 1H), 6.62 (d, J=1.3 Hz, 2H), 4.44 (dd, J=9.3, 6.5 Hz, 2H), 4.10 (dd, J=9.4, 4.4 Hz, 2H), 3.76 (dd, J=14.5, 4.7 Hz, 1H), 3.66-3.42 (m, 1H), 3.20 (qd, J=7.2, 2.3 Hz, 1H), 2.23 (t, J=7.4 Hz, 2H), 1.57 (s, 2H), 1.48-1.32 (m, 5H), 0.96-0.74 (m, 6H).

Example 145

(S)—N-(2-(diethylamino)propyl)-2-(3-hydroxyazetidin-1-yl)-6-(5-(thiophen-2-yl)pyrazolo[1,5-a]pyrimidin-3-yl)isonicotinamide

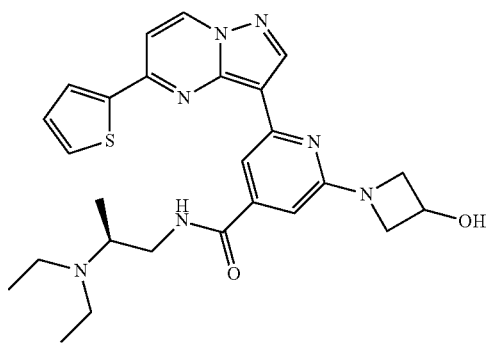

145

Compound 145 was synthesized following the Example 141, starting from commercially available azetidin-3-ol, as a TFA salt. LC/MS (M+H): 506.2

Example 146

(S)-2-(azetidin-1-yl)-N-(2-(diethylamino)propyl)-6-(5-(thiophen-2-yl)pyrazolo[1,5-a]pyrimidin-3-yl)isonicotinamide

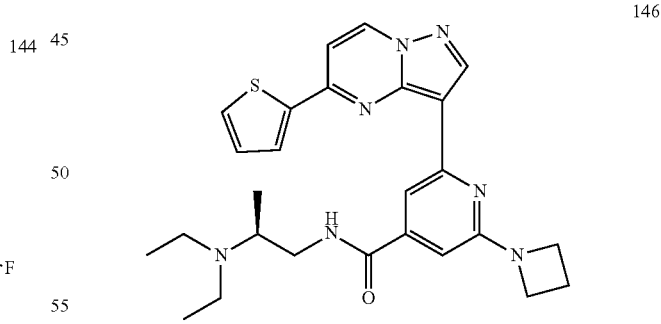

146

Compound 146 was synthesized following the Example 141, starting from commercially available azetidine, as a TFA salt. LC/MS (M+H): 490.2; $^1$H NMR (400 MHz, Methanol-d$_4$) δ 8.99 (d, J=7.4 Hz, 1H), 8.76 (s, 1H), 8.07-8.01 (m, 1H), 7.90 (s, 1H), 7.80 (d, J=4.9 Hz, 1H), 7.68 (d, J=7.4 Hz, 1H), 7.27 (dd, J=5.0, 3.9 Hz, 1H), 6.82 (s, 1H), 4.47 (t, J=7.6 Hz, 4H), 3.94 (dd, J=14.1, 5.5 Hz, 1H), 3.84 (q, J=6.4 Hz, 1H), 3.59-3.48 (m, 2H), 3.36 (q, J=7.0 Hz, 2H), 3.22 (dd, J=13.5, 6.8 Hz, 1H), 2.63 (p, J=7.5 Hz, 2H), 1.42 (dt, J=22.7, 6.7 Hz, 9H).

Example 147

(S)—N-(2-(diethylamino)propyl)-2-(5-(thiophen-2-yl)pyrazolo[1,5-a]pyrimidin-3-yl)-6-(3-(trifluoromethyl)azetidin-1-yl)isonicotinamide

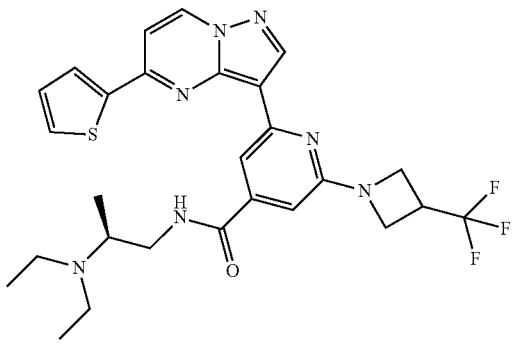

Compound 147 was synthesized following the Example 141, starting from commercially available 3-trifloromethyl-azetidine, as a TFA salt. LC/MS (M+H): 558.2; $^1$H NMR (400 MHz, Methanol-$d_4$) δ 8.92 (d, J=7.4 Hz, 1H), 8.72 (s, 1H), 8.16 (s, 1H), 8.08-7.96 (m, 1H), 7.76 (dd, J=5.0, 1.1 Hz, 1H), 7.59 (d, J=7.4 Hz, 1H), 7.25 (dd, J=5.0, 3.8 Hz, 1H), 6.74 (d, J=1.3 Hz, 1H), 4.59 (ddd, J=20.0, 10.1, 5.8 Hz, 2H), 4.35 (dd, J=23.4, 10.0 Hz, 2H), 3.94 (dd, J=14.2, 5.8 Hz, 1H), 3.85 (q, J=6.4 Hz, 1H), 3.52 (td, J=13.3, 12.7, 6.7 Hz, 2H), 3.36 (dt, J=9.9, 5.0 Hz, 2H), 3.21 (dd, J=13.4, 6.9 Hz, 1H), 1.50-1.35 (m, 8H).

Example 148

(S)—N-(2-(diethylamino)propyl)-2-(3,3-difluoroazetidin-1-yl)-6-(5-(thiophen-2-yl)pyrazolo[1,5-a]pyrimidin-3-yl)isonicotinamide

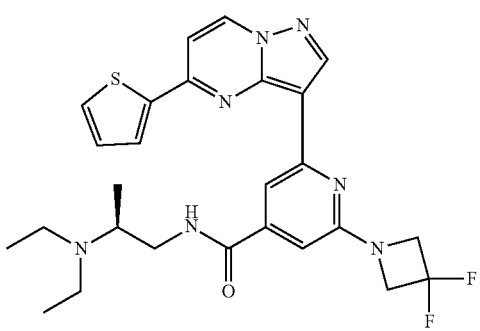

Compound 148 was synthesized following the Example 141, starting from commercially available 3,3-difluoroazetidine, as a TFA salt. LC/MS (M+H): 526.4; $^1$H NMR (400 MHz, Methanol-$d_4$) δ 8.88 (d, J=7.4 Hz, 1H), 8.72 (s, 1H), 8.42 (d, J=1.3 Hz, 1H), 7.97 (dd, J=3.8, 1.1 Hz, 1H), 7.72 (dd, J=5.1, 1.1 Hz, 1H), 7.54 (d, J=7.4 Hz, 1H), 7.24 (dd, J=5.1, 3.8 Hz, 1H), 6.72 (d, J=1.3 Hz, 1H), 4.50 (t, J=12.1 Hz, 4H), 3.95 (dd, J=14.3, 5.9 Hz, 1H), 3.85 (h, J=6.5 Hz, 1H), 3.58-3.47 (m, 2H), 3.45-3.32 (m, 2H), 3.21 (dq, J=14.2, 7.1 Hz, 2H), 1.51-1.36 (m, 8H).

Example 149

(S)—N-(2-(diethylamino)propyl)-2-(3-(methylsulfonyl)azetidin-1-yl)-6-(5-(thiophen-2-yl)pyrazolo[1,5-a]pyrimidin-3-yl)isonicotinamide

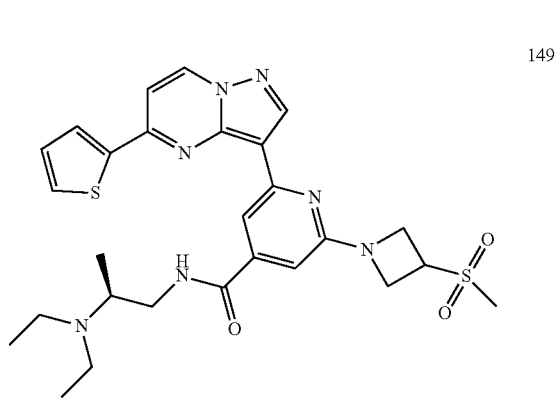 [SMILES: CCN(CC)[C@@H](C)CNC(=O)c1cc(-c2cnn3ccc(-c4cccs4)nc23)nc(N2CC(S(C)(=O)=O)C2)c1]

Compound 149 was synthesized following the Example 141, starting from commercially available 3-(methylsulfonyl)azetidine, as a TFA salt. LC/MS (M+H): 568.2; $^1$H NMR (400 MHz, Methanol-$d_4$) δ 8.91 (d, J=7.3 Hz, 1H), 8.79 (d, J=8.3 Hz, 1H), 8.48 (s, 1H), 7.99 (d, J=3.7 Hz, 1H), 7.74 (d, J=5.2 Hz, 1H), 7.65-7.54 (m, 3H), 7.29-7.19 (m, 2H), 5.26 (s, 2H), 4.40 (d, J=5.3 Hz, 2H), 4.33 (d, J=5.2 Hz, 2H), 3.98 (dd, J=14.2, 5.6 Hz, 1H), 3.88 (q, J=6.4 Hz, 1H), 3.56 (dd, J=13.7, 6.6 Hz, 2H), 3.39 (d, J=7.4 Hz, 2H), 3.24 (s, 1H), 1.45 (dd, J=25.6, 7.1 Hz, 10H).

Example 150

(S)—N-(2-(diethylamino)propyl)-2-(3-(N-methylsulfamoyl)azetidin-1-yl)-6-(5-(thiophen-2-yl)pyrazolo[1,5-a]pyrimidin-3-yl)isonicotinamide

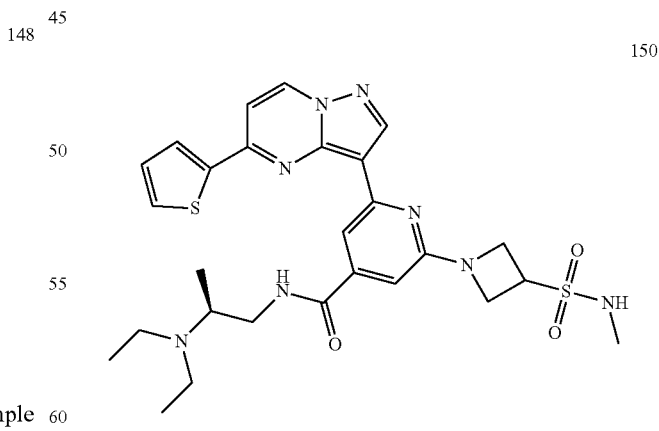

Compound 150 was synthesized following the Example 141, starting from commercially available N-methylazetidine-3-sulfonamide, as a TFA salt. LC/MS (M+H): 583.2; $^1$H NMR (400 MHz, Methanol-$d_4$) δ 8.87 (d, J=7.4 Hz, 1H), 7.96 (dd, J=3.8, 1.1 Hz, 1H), 7.71 (dd, J=5.0, 1.1 Hz, 1H), 7.53 (d, J=7.4 Hz, 1H), 7.23 (dd, J=5.0, 3.8 Hz, 1H), 6.60 (d, J=1.3 Hz, 1H), 4.47 (d, J=5.8 Hz, 3H), 4.03 (dd, J=9.2, 5.2 Hz, 2H), 3.94 (dd, J=14.2, 5.9 Hz, 2H), 3.59-3.39 (m, 4H), 3.30-3.21 (m, 10H), 2.26 (t, J=7.4 Hz, 2H), 1.59 (t, J=7.2 Hz, 3H), 1.48-1.35 (m, 9H), 1.28 (s, 31H), 1.12-1.01 (m, 5H), 0.93-0.82 (m, 8H).

Example 151

(S)-2-(3-(N-cyclopropylsulfamoyl)azetidin-1-yl)-N-(2-(diethylamino)propyl)-6-(5-(thiophen-2-yl)pyrazolo[1,5-a]pyrimidin-3-yl)isonicotinamide

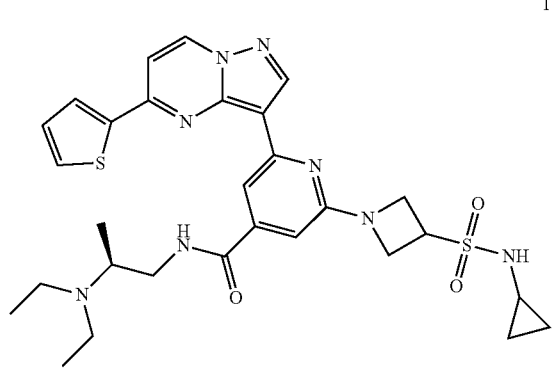

Compound 151 was synthesized following the Example 141, starting from commercially available N-cyclopropylazetidine-3-sulfonamide, as a TFA salt. LC/MS (M+H): 609.2; ¹H NMR (400 MHz, Methanol-d₄) δ 8.87 (d, J=7.4 Hz, 1H), 7.96 (dd, J=3.8, 1.1 Hz, 1H), 7.71 (dd, J=5.0, 1.1 Hz, 1H), 7.53 (d, J=7.4 Hz, 1H), 7.23 (dd, J=5.0, 3.8 Hz, 1H), 6.60 (d, J=1.3 Hz, 1H), 4.47 (d, J=5.8 Hz, 3H), 4.03 (dd, J=9.2, 5.2 Hz, 2H), 3.94 (dd, J=14.2, 5.9 Hz, 2H), 3.59-3.39 (m, 4H), 3.30-3.21 (m, 10H), 2.26 (t, J=7.4 Hz, 2H), 1.59 (t, J=7.2 Hz, 3H), 1.48-1.35 (m, 9H), 1.28 (s, 31H), 1.12-1.01 (m, 5H), 0.93-0.82 (m, 8H).

Example 152

(S)—N-(2-(diethylamino)propyl)-2-(3,3-dimethylazetidin-1-yl)-6-(5-(thiophen-2-yl)pyrazolo[1,5-a]pyrimidin-3-yl)isonicotinamide

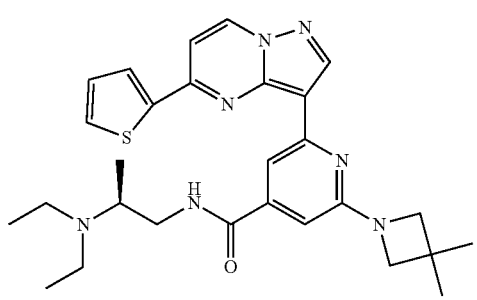

Compound 152 was synthesized following the Example 141, starting from commercially available 3,3-dimethylazetidine, as a TFA salt. LC/MS (M+H): 518.3; ¹H NMR (400 MHz, Methanol-d₄) δ 9.00 (dd, J=7.4, 2.4 Hz, 1H), 8.77 (d, J=1.3 Hz, 1H), 8.05 (dd, J=3.8, 1.3 Hz, 1H), 7.92-7.61 (m, 4H), 7.32-7.11 (m, 2H), 6.91 (d, J=1.4 Hz, 1H), 4.21 (s, 3H), 4.00-3.80 (m, 3H), 3.53 (ddd, J=36.6, 13.8, 6.5 Hz, 3H), 3.36 (dd, J=7.2, 4.2 Hz, 8H), 3.22 (dt, J=13.6, 7.0 Hz, 1H), 1.50-1.31 (m, 14H).

Example 153

(S)—N-(2-(diethylamino)propyl)-2-(3-fluoroazetidin-1-yl)-6-(5-(thiophen-2-yl)pyrazolo[1,5-a]pyrimidin-3-yl)isonicotinamide

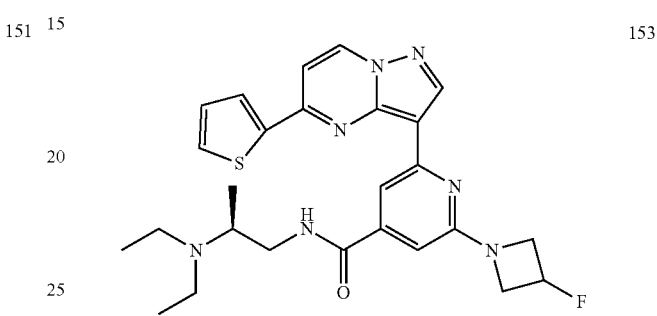

Compound 153 was synthesized following the Example 141, starting from commercially available 3-fluoroazetidine, as a TFA salt. LC/MS (M+H): 508.2; ¹H NMR (400 MHz, Methanol-d₄) δ 8.92 (d, J=7.4 Hz, 1H), 8.72 (s, 1H), 8.16 (s, 1H), 8.08-7.96 (m, 1H), 7.76 (dd, J=5.0, 1.1 Hz, 1H), 7.59 (d, J=7.4 Hz, 1H), 7.25 (dd, J=5.0, 3.8 Hz, 1H), 6.74 (d, J=1.3 Hz, 1H), 4.59 (ddd, J=20.0, 10.1, 5.8 Hz, 2H), 4.35 (dd, J=23.4, 10.0 Hz, 2H), 3.94 (dd, J=14.2, 5.8 Hz, 1H), 3.85 (q, J=6.4 Hz, 1H), 3.52 (td, J=13.3, 12.7, 6.7 Hz, 2H), 3.36 (dt, J=9.9, 5.0 Hz, 2H), 3.21 (dd, J=13.4, 6.9 Hz, 1H), 1.50-1.35 (m, 8H).

Example 154

(S)-2-(3-(cyclopropanesulfonamido)azetidin-1-yl)-N-(2-(diethylamino)propyl)-6-(5-(thiophen-2-yl)pyrazolo[1,5-a]pyrimidin-3-yl)isonicotinamide

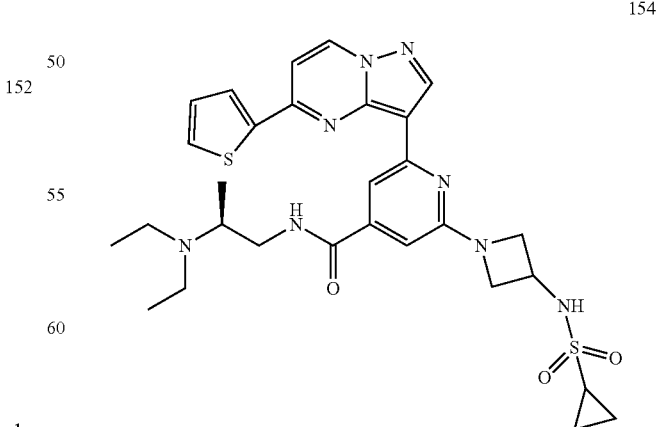

Compound 154 was synthesized following the Example 141, starting from commercially available N-cyclopropylazetidine-3-sulfonamide, as a TFA salt. LC/MS (M+H): 609.2; $^1$H NMR (400 MHz, Methanol-$d_4$) δ 8.62 (s, 1H), 7.92 (dd, J=3.8, 1.1 Hz, 1H), 7.85 (d, J=1.4 Hz, 1H), 7.72 (dd, J=5.0, 1.1 Hz, 1H), 7.53 (d, J=7.4 Hz, 1H), 7.22 (dd, J=5.0, 3.8 Hz, 1H), 6.76 (d, J=1.4 Hz, 1H), 4.69-4.54 (m, 3H), 4.28 (q, J=6.8 Hz, 4H), 4.17-4.07 (m, 4H), 3.98-3.79 (m, 6H), 3.54 (ddd, J=33.9, 13.9, 6.7 Hz, 2H), 3.42-3.31 (m, 2H), 2.67-2.43 (m, 5H), 1.49-1.33 (m, 9H), 1.17-1.04 (m, 6H), 1.08-0.98 (m, 11H), 0.99 (ddd, J=3.2, 1.7, 0.7 Hz, 2H).

Example 155

(S)—N-(2-(diethylamino)propyl)-2-(5,6-dihydroimidazo[1,2-a]pyrazin-7(8H)-yl)-6-(5-(thiophen-2-yl)pyrazolo[1,5-a]pyrimidin-3-yl)isonicotinamide

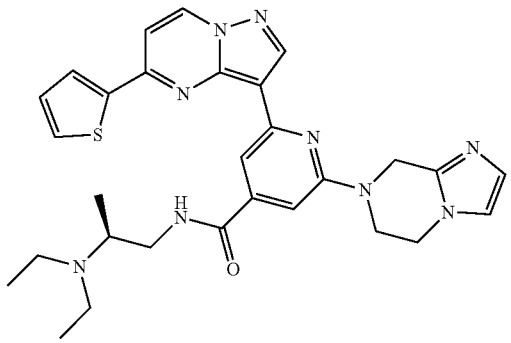

155

Compound 155 was synthesized following the Example 141, starting from commercially available 5,6,7,8-tetrahydroimidazo[1,2-a]pyrazine, as a TFA salt. LC/MS (M+H): 556.2; $^1$H NMR (400 MHz, Methanol-d4) δ 8.85 (d, J=7.4 Hz, 1H), 8.68 (s, 1H), 7.98-7.92 (m, 1H), 7.75-7.69 (m, 1H), 7.52 (d, J=7.4 Hz, 1H), 7.27-7.20 (m, 1H), 6.67 (d, J=1.3 Hz, 1H), 4.48 (s, 4H), 3.90 (ddd, J=37.1, 13.5, 6.2 Hz, 2H), 3.58-3.47 (m, 2H), 3.43-3.37 (m, 1H), 3.37-3.27 (m, 16H), 3.21 (dq, J=13.8, 7.1 Hz, 1H), 3.07 (d, J=1.3 Hz, 3H), 1.46 (t, J=7.5 Hz, 5H), 1.40 (t, J=7.2 Hz, 3H).

Example 156

N—((S)-2-(diethylamino)propyl)-2-(3,3-difluoro-4-hydroxypiperidin-1-yl)-6-(5-(thiophen-2-yl)pyrazolo[1,5-a]pyrimidin-3-yl)isonicotinamide

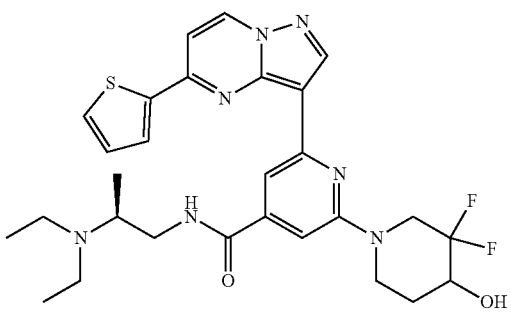

156

Compound 156 was synthesized following the Example 141, starting from commercially available 3,3-difluoropiperidin-4-ol, as a TFA salt. LC/MS (M+H): 570.2; $^1$H NMR (400 MHz, Methanol-$d_4$) δ 8.88 (d, J=7.4 Hz, 1H), 8.73 (s, 1H), 8.30 (d, J=1.1 Hz, 1H), 7.96 (dd, J=3.9, 1.1 Hz, 1H), 7.83-7.68 (m, 1H), 7.53 (d, J=7.4 Hz, 1H), 7.24 (dd, J=5.1, 3.7 Hz, 1H), 7.04 (d, J=1.1 Hz, 1H), 4.21 (ddd, J=19.4, 14.0, 5.9 Hz, 1H), 3.97 (td, J=15.3, 14.3, 6.0 Hz, 3H), 3.85 (q, J=6.3 Hz, 1H), 3.73 (s, 1H), 3.53 (dd, J=14.2, 6.1 Hz, 2H), 3.37 (dt, J=12.8, 6.8 Hz, 2H), 3.21 (dq, J=14.2, 7.1 Hz, 1H), 2.13-2.02 (m, 1H), 1.51-1.36 (m, 7H).

Example 157

(S)—N-(2-(diethylamino)propyl)-2-((2-(dimethylamino)ethyl)amino)-6-(5-(thiophen-2-yl)pyrazolo[1,5-a]pyrimidin-3-yl)isonicotinamide

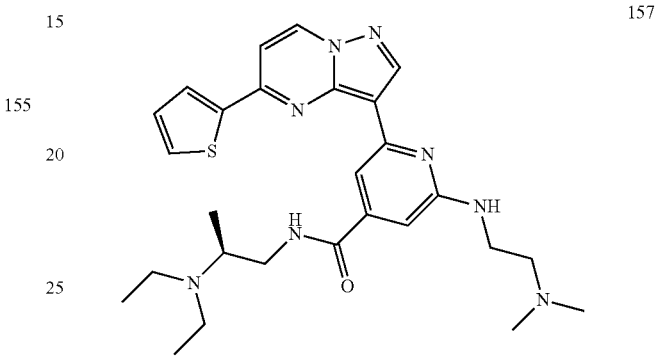

157

Compound 157 was synthesized following the Example 141, starting from commercially available N1,N1-dimethylethane-1,2-diamine, as a TFA salt. LC/MS (M+H): 521.3; 1H NMR (400 MHz, Methanol-d4) δ 8.92 (d, J=7.4 Hz, 1H), 8.78 (s, 1H), 8.24 (d, J=1.4 Hz, 1H), 8.00 (dd, J=3.8, 1.1 Hz, 1H), 7.76 (dd, J=5.1, 1.1 Hz, 1H), 7.58 (d, J=7.4 Hz, 1H), 7.27 (dd, J=5.0, 3.8 Hz, 1H), 6.85 (d, J=1.3 Hz, 1H), 4.06-3.81 (m, 4H), 3.67-3.46 (m, 4H), 3.48-3.14 (m, 10H), 1.57-1.36 (m, 8H).

Example 158

(S)—N-(2-(diethylamino)propyl)-2-((2-(dimethylamino)ethyl)amino)-6-(5-phenylpyrazolo[1,5-a]pyrimidin-3-yl)isonicotinamide

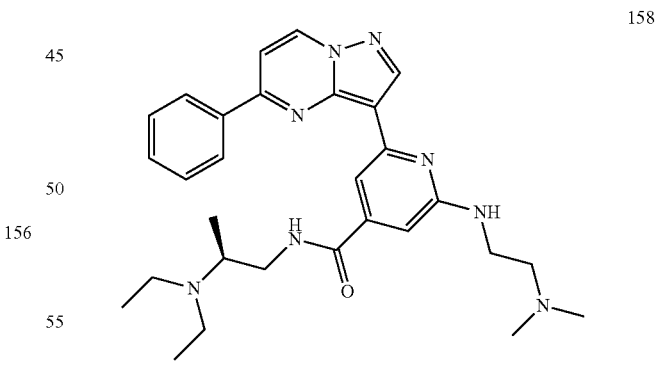

158

Compound 158 was synthesized following the Example 141, starting from commercially available N1,N1-dimethylethane-1,2-diamine and coupling with 5-phenyl-3-(4,4,5,5-tetramethyl-1,3,2-dioxaborolan-2-yl)pyrazolo[1,5-a]pyrimidine (37C), as a TFA salt. LC/MS (M+H): 515.3; 1H NMR (400 MHz, Methanol-d4) δ 9.02 (d, J=7.4 Hz, 1H), 8.84 (s, 1H), 8.43-8.27 (m, 3H), 7.69 (d, J=7.4 Hz, 1H), 7.61 (dd, J=5.0, 1.8 Hz, 3H), 6.87 (d, J=1.4 Hz, 1H), 4.04-3.91 (m, 3H), 3.87 (d, J=6.4 Hz, 1H), 3.54 (q, J=6.7, 6.1 Hz, 4H), 3.47-3.17 (m, 11H), 1.57-1.32 (m, 8H).

Example 159

N-((1-aminocyclobutyl)methyl)-2-(3-methoxyazetidin-1-yl)-6-(5-phenylpyrazolo[1,5-a]pyrimidin-3-yl)isonicotinamide

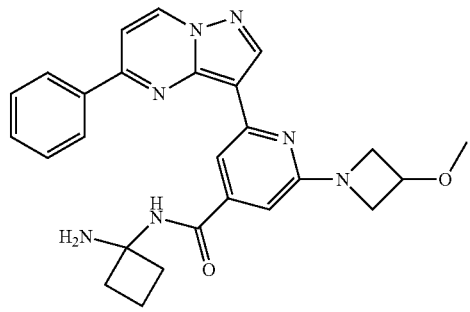

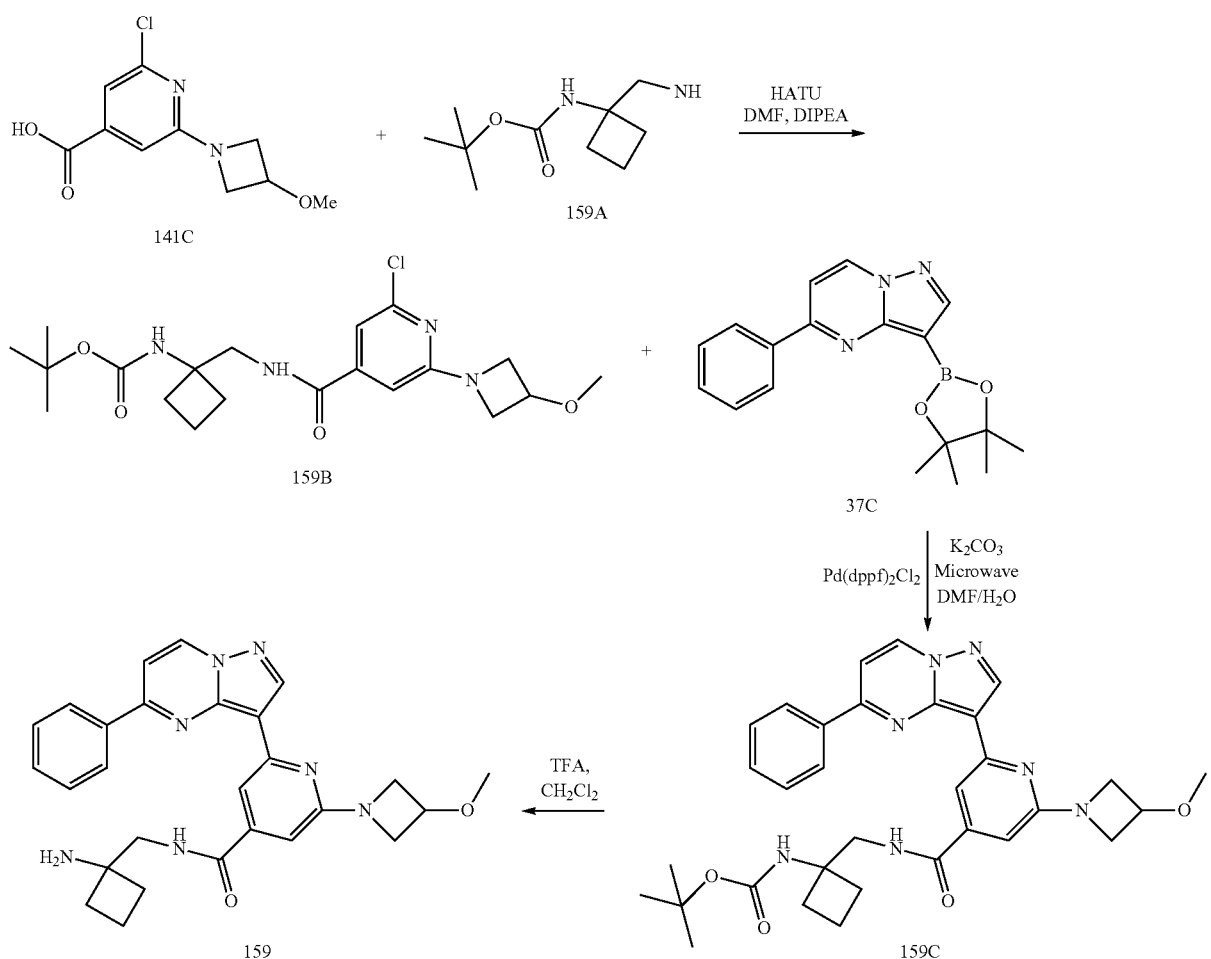

Compound 159C was synthesized following the Example 141, starting from commercially available tert-butyl (1-(aminomethyl)cyclobutyl)carbamate, and coupling with 5-phenyl-3-(4,4,5,5-tetramethyl-1,3,2-dioxaborolan-2-yl)pyrazolo[1,5-a]pyrimidine (37C). The final compound 159 was obtained by treating 159C with TFA in dichloromethane, as a TFA salt. LC/MS (M+H): 484.2

Example 160

(S)—N-(2-(diethylamino)propyl)-2-(3-methoxyazetidin-1-yl)-6-(5-phenylpyrazolo[1,5-a]pyrimidin-3-yl)isonicotinamide

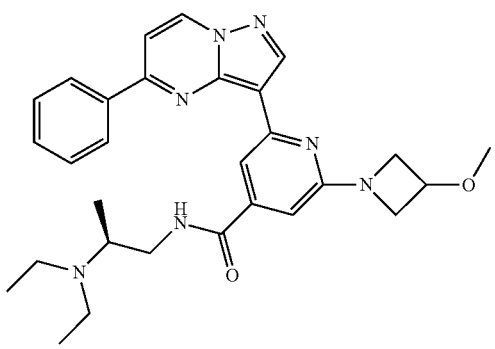

Compound 160 was synthesized following the Example 141, by coupling with 5-phenyl-3-(4,4,5,5-tetramethyl-1,3,2-dioxaborolan-2-yl)pyrazolo[1,5-a]pyrimidine (37C), as a TFA salt. LC/MS (M+H): 514.3 1H NMR (400 MHz, Methanol-d4) δ 9.08 (d, J=7.4 Hz, 1H), 8.82 (s, 1H), 8.40-8.26 (m, 2H), 8.09 (s, 1H), 7.73 (d, J=7.4 Hz, 1H), 7.64 (p, J=2.5 Hz, 3H), 6.82 (d, J=1.4 Hz, 1H), 4.59-4.45 (m, 3H), 4.19 (d, J=6.3 Hz, 2H), 3.94 (m, 2H), 3.57 (m, 2H), 3.45 (s, 3H), 3.30 (m, 1H), 1.59-1.35 (m, 9H).

Example 161

N-((hexahydro-1H-pyrrolizin-7a-yl)methyl)-2-(3-methoxyazetidin-1-yl)-6-(5-phenylpyrazolo[1,5-a]pyrimidin-3-yl)isonicotinamide

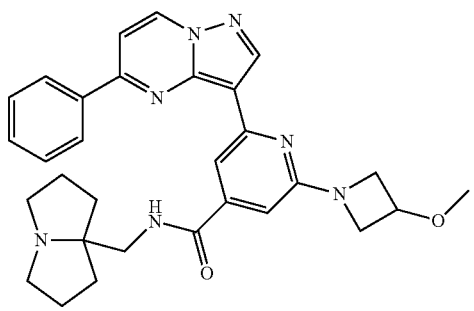

Compound 161 was synthesized following the Example 159, starting from commercially available (tetrahydro-1H-pyrrolizin-7a(5H)-yl)methanamine, as a TFA salt. LC/MS (M+H): 524.2

Example 162

(S)—N-(2-(diethylamino)propyl)-2-(4-hydroxypiperidin-1-yl)-6-(5-(thiophen-2-yl)pyrazolo[1,5-a]pyrimidin-3-yl)isonicotinamide

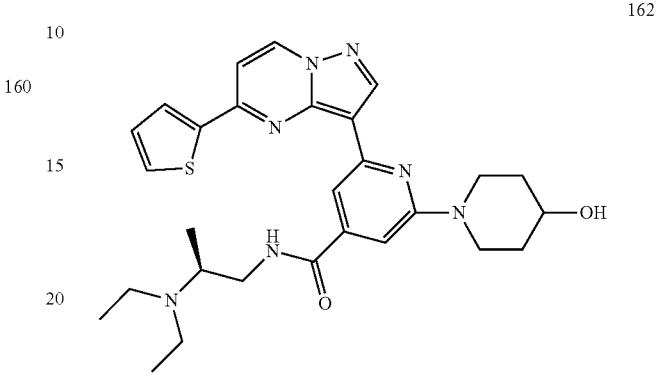

Compound 162 was synthesized following the Example 141, starting from commercially available piperidin-4-ol, as a TFA salt. LC/MS (M+H): 534; 1H NMR (400 MHz, Methanol-d4) δ 8.93 (d, J=7.4 Hz, 1H), 8.72 (s, 1H), 7.98 (dd, J=3.8, 1.1 Hz, 1H), 7.89 (d, J=1.2 Hz, 1H), 7.77 (dd, J=5.1, 1.1 Hz, 1H), 7.61 (d, J=7.4 Hz, 1H), 7.28-7.20 (m, 2H), 4.26-4.12 (m, 2H), 4.03-3.77 (m, 3H), 3.63-3.42 (m, 4H), 3.45-3.35 (m, z, 2H), 3.23-3.16 (m, 1H), 2.10-1.98 (m, 2H), 1.8-1.71 (m, 2H), 1.46-1.35 (m, 9H).

Example 163

(S)—N-(2-(diethylamino)propyl)-2-(4-hydroxy-4-methylpiperidin-1-yl)-6-(5-(thiophen-2-yl)pyrazolo[1,5-a]pyrimidin-3-yl)isonicotinamide

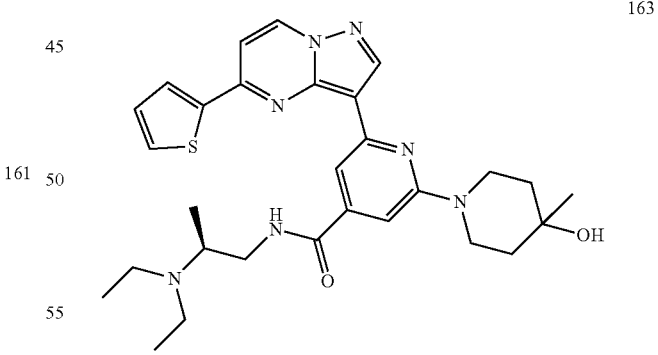

Compound 163 was synthesized following the Example 141, starting from commercially available 4-methylpiperidin-4-ol, as a TFA salt. LC/MS (M+H): 548; 1H NMR (400 MHz, Methanol-d4) δ 8.93 (d, J=7.5 Hz, 1H), 8.72 (s, 1H), 7.99 (dd, J=3.8, 1.1 Hz, 1H), 7.87 (s, 1H), 7.78 (dd, J=5.0, 1.0 Hz, 1H), 7.61 (d, J=7.5 Hz, 1H), 7.29-7.20 (m, 2H), 4.20-4.11 (m, 2H), 3.97-3.80 (m, 2H), 3.72-3.60 (m, 2H), 3.61-3.50 (m, 2H), 3.40-3.30 (m, 2H), 3.24-3.15 (m, 1H), 1.90-1.78 (m, 4H), 1.48-1.27 (m, 12H).

Example 164

(S)—N-(2-(diethylamino)propyl)-2-(((3-(pyrrolidin-1-yl)oxetan-3-yl)methyl)amino)-6-(5-(thiophen-2-yl)pyrazolo[1,5-a]pyrimidin-3-yl)isonicotinamide

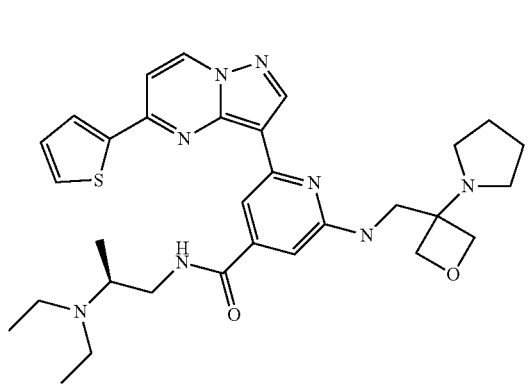

Compound 164 was synthesized following the Example 141, starting from commercially available (3-(pyrrolidin-1-yl)oxetan-3-yl)methanamine, as a TFA salt. LC/MS (M+H): 589

Example 165

(S)—N-(2-(diethylamino)propyl)-2-(3-methoxyazetidin-1-yl)-6-(5-(thiophen-3-yl)pyrazolo[1,5-a]pyrimidin-3-yl)isonicotinamide

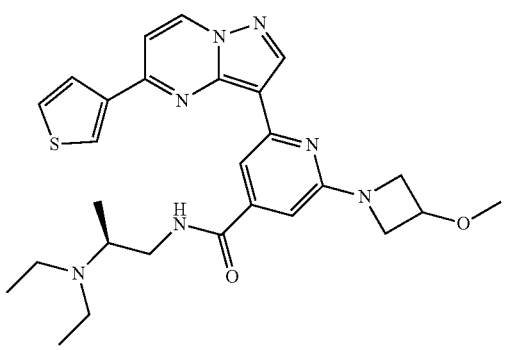

Compound 165 was synthesized as a TFA salt following the Example 141, by coupling with the corresponding boronic ester, which was prepared as shown in Example 1, starting from 3-thiophene analog. LC/MS (M+H): 520.2; $^1$H-NMR (CD$_3$OD) δ 8.99 (d, 1H, J=7.6 Hz), 8.76 (s, 1H), 8.43 (dd, 1H, J=3.0, 1.4 Hz), 8.11 (d, 1H, J=1.6 Hz), 7.97 (d, 1H, J=5.2, 1.2 Hz), 7.61-7.64 (m, 2H), 6.79 (d, 1H, J=1.6 Hz), 4.46-4.53 (m, 3H), 4.16-4.18 (m, 2H), 3.94 (dd, 1H, J=11.0, 6.0 Hz), 3.81-3.89 (m, 1H), 3.16-3.58 (m, 2H), 3.10 (s, 3H), 3.31-3.38 (m, 2H), 3.17 3.26 (m, 1H), 1.42-1.47 (m, 6H), 1.39 (t, 3H, J=7.2 Hz);

Example 166

(S)—N-(2-(diethylamino)propyl)-2-(3-methoxyazetidin-1-yl)-6-(5-(pyrimidin-5-yl)pyrazolo[1,5-a]pyrimidin-3-yl)isonicotinamide

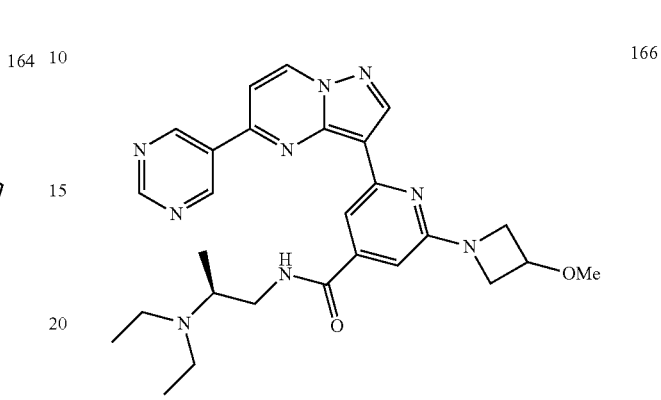

Compound 166 was synthesized as a TFA salt following the Example 141, by coupling with the corresponding boronic ester, which was prepared as shown in Example 1, starting from 5-bromo pyrimidine. LC/MS (M+H): 516.3

Example 167

(S)—N-(2-(diethylamino)propyl)-2-(1,1-dioxidoisothiazolidin-2-yl)-6-(5-(thiophen-2-yl)pyrazolo[1,5-a]pyrimidin-3-yl)isonicotinamide

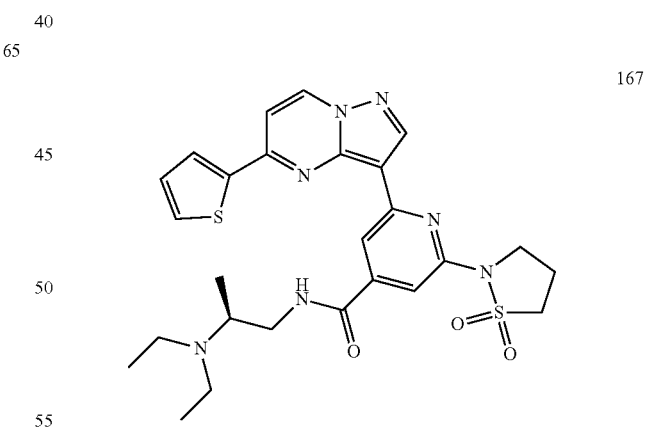

Compound 167 was synthesized following the Example 141, starting from commercially available isothiazolidine 1,1-dioxide, as a TFA salt. LC/MS (M+H): 554.2; $^1$H-NMR (CD$_3$OD) δ 8.83 (d, 1H, J=7.6 Hz), 8.70 (s, 1H), 8.55 (d, 1H, J=1.2 Hz), 7.95 (dd, 1H, J=3.8, 1.0 Hz), 7.72 (dd, 1H, J=4.8, 1.2 Hz), 7.50 (d, 1H, J=7.6 Hz), 7.35 (d, 1H, J=1.2 Hz), 7.24 (dd, 1H, J=5.0, 3.8 Hz), 4.12 (t, 2H, J=6.6 Hz), 3.95 (dd, 1H, J=14.2, 5.8), 3.83-3.91 (m, 1H), 3.50-3.58 (m, 4H), 3.36-3.41 (m, 2H), 3.20-3.27 (m, 1H), 2.51-2.58 (m, 2H), 1.45-1.49 (m, 6H), 1.41 (t, 3H, J=7.4 Hz);

Example 168

(S)—N-(2-aminopropyl)-2-(3-hydroxyazetidin-1-yl)-6-(5-(thiophen-2-yl)pyrazolo[1,5-a]pyrimidin-3-yl)isonicotinamide

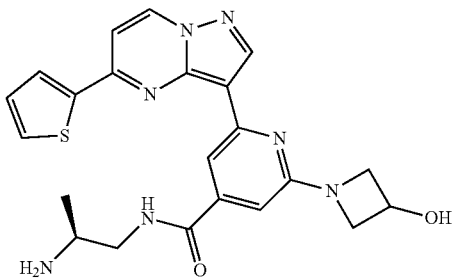

168

Compound 168 was synthesized following the Example 141, starting from commercially available 3-hydroxy azetidine and tert-butyl (S)-(1-aminopropan-2-yl)carbamate, as a TFA salt. LC/MS (M+H): 450.1

Example 169

(S)—N-(2-(ethylamino)propyl)-2-(3-hydroxyazetidin-1-yl)-6-(5-(thiophen-2-yl)pyrazolo[1,5-a]pyrimidin-3-yl)isonicotinamide

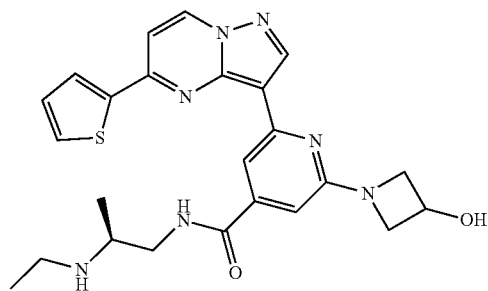

169

Compound 169 was synthesized following the Example 141, starting from commercially available 3-hydroxy azetidine and tert-butyl (S)-(1-aminopropan-2-yl)(ethyl)carbamate, as a TFA salt. LC/MS (M+H): 478.2

Example 170

N-((1-aminocyclobutyl)methyl)-2-(3-methoxyazetidin-1-yl)-6-(5-(thiophen-2-yl)pyrazolo[1,5-a]pyrimidin-3-yl)isonicotinamide

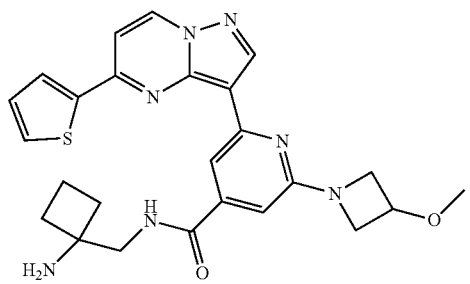

170

Compound 170 was synthesized following the Example 159, by coupling with the boronic ester 3-(4,4,5,5-tetramethyl-1,3,2-dioxaborolan-2-yl)-5-(thiophen-2-yl)pyrazolo[1,5-a]pyrimidine (1D), as a TFA salt. LC/MS (M+H): 490.2

Example 171

(S)—N-(2-aminopropyl)-2-(3-methoxyazetidin-1-yl)-6-(5-(thiophen-2-yl)pyrazolo[1,5-a]pyrimidin-3-yl)isonicotinamide

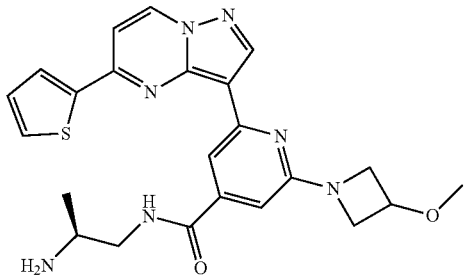

171

Compound 171 was synthesized following the Example 141, starting from commercially available tert-butyl (S)-(1-aminopropan-2-yl)carbamate, as a TFA salt. LC/MS (M+H): 464.1

Example 172

(S)—N-(2-aminopropyl)-2-(3-methoxyazetidin-1-yl)-6-(5-phenylpyrazolo[1,5-a]pyrimidin-3-yl)isonicotinamide

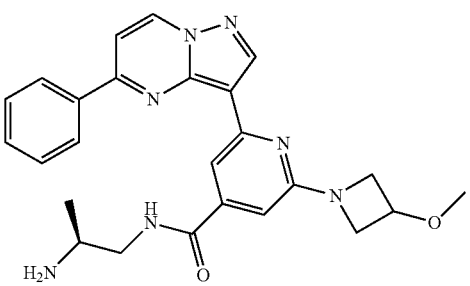

172

Compound 172 was synthesized following the Example 159, starting from commercially available tert-butyl (S)-(1-aminopropan-2-yl)carbamate, as a TFA salt. LC/MS (M+H): 458.2

Example 173

(S)—N-(2-(ethylamino)propyl)-2-(3-methoxyazetidin-1-yl)-6-(5-(thiophen-2-yl)pyrazolo[1,5-a]pyrimidin-3-yl)isonicotinamide

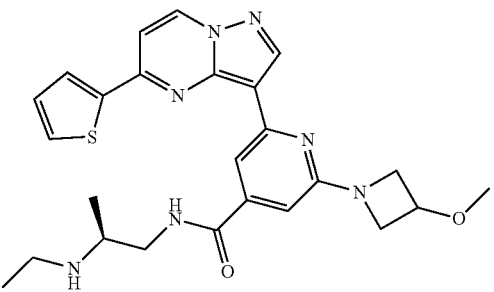

173

Compound 173 was synthesized following the Example 159, starting from commercially available tert-butyl (S)-(1-aminopropan-2-yl)(ethyl)carbamate, as a TFA salt. LC/MS (M+H): 492.2

Example 174

(S)—N-(2-(ethylamino)propyl)-2-(3-methoxyazetidin-1-yl)-6-(5-phenylpyrazolo[1,5-a]pyrimidin-3-yl)isonicotinamide

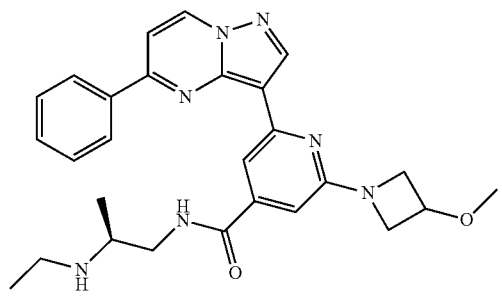

174

Compound 173 was synthesized following the Example 159, starting from commercially available tert-butyl (S)-(1-aminopropan-2-yl)(ethyl)carbamate, by coupling with the boronic ester 3-(4,4,5,5-tetramethyl-1,3,2-dioxaborolan-2-yl)-5-(thiophen-2-yl)pyrazolo[1,5-a]pyrimidine (1D), as a TFA salt. LC/MS (M+H): 486.2

Example 175

(S)—N-(2-(diethylamino)propyl)-2-(3-((isoxazol-3-ylmethyl)sulfonamido)azetidin-1-yl)-6-(5-(thiophen-2-yl)pyrazolo[1,5-a]pyrimidin-3-yl)isonicotinamide

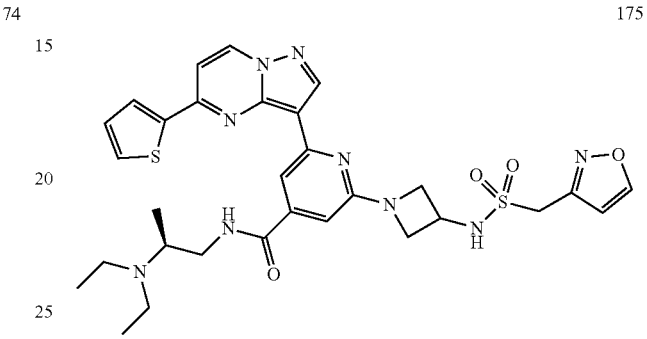

175

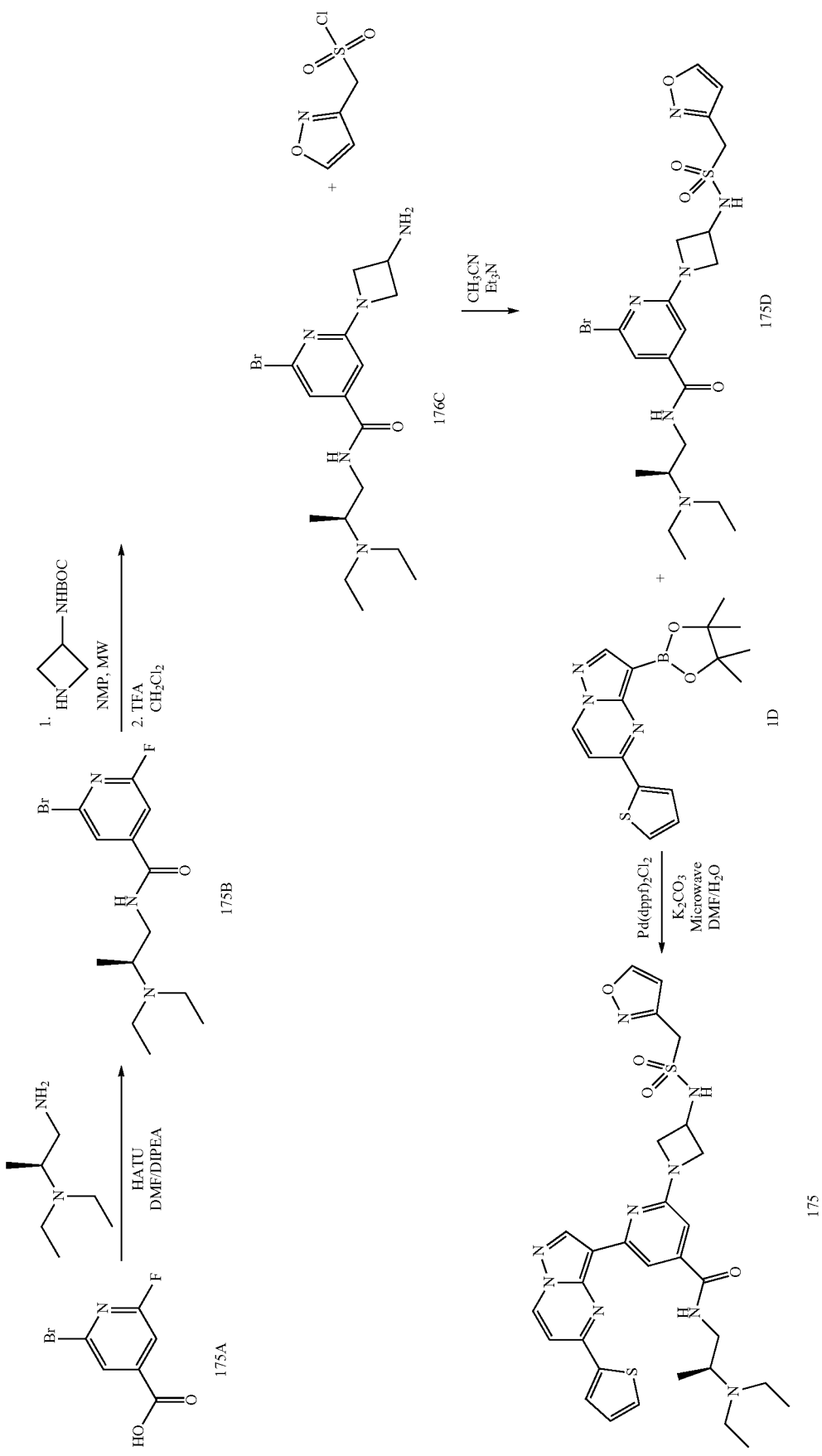

Compound 175 was synthesized as shown above and following the methods explained in Example 1, starting from the corresponding commercially available starting materials, as a TFA salt. LC/MS (M+H): 550.2; $^1$H-NMR (CD$_3$OD) δ 8.89-8.92 (m, 1H), 8.70-8.74 (m, 2H), 8.16-8.20 (m, 1H), 7.98-7.99 (m, 1H), 7.73-7.74 (m, 1H), 7.57 (d, 1H, J=7.2 Hz), 7.24 (dd, 1H, J=5.0, 3.8 Hz), 6.66-6.71 (m, 2H), 4.59 (s, 2H), 4.50-4.53 (m, 3H), 4.11-4.13 (m, 2H), 3.94 (dd, 1H, J=14.4, 5.6), 3.82-3.87 (m, 1H), 3.47-3.56 (m, 2H), 3.33-3.38 (m, 2H), 3.19-3.24 (m, 1H), 1.44-1.48 (m, 6H), 1.39 (t, 3H, J=7.2 Hz);

Example 176

(S)—N-(2-(diethylamino)propyl)-2-(5-(isothiazol-5-yl)pyrazolo[1,5-a]pyrimidin-3-yl)-6-(3-methoxyazetidin-1-yl)isonicotinamide

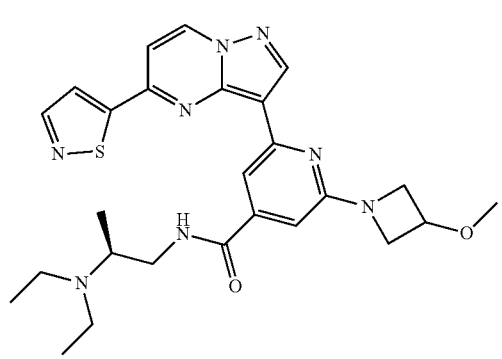

176

Compound 176 was synthesized following the Example 141 starting with compound 176-1, as the boronic ester, as a TFA salt.

LC/MS (M+H): 521.2; $^1$H-NMR (CD$_3$OD) δ 8.95 (d, 1H, J=7.2 Hz), 8.68 (s, 1H), 8.60 (d, 1H, J=2.0 Hz), 8.03 (d, 1H, J=1.2 Hz), 7.98 (d, 1H, J=1.6 Hz), 7.50 (d, 1H, J=7.6 Hz), 6.47 (d, 1H, J=1.2 Hz), 4.38-4.43 (m, 1H), 4.26-4.30 (m, 2H), 3.92 (dd, 2H, J=9.0, 4.2 Hz), 3.41-3.53 (m, 2H), 3.38 (s, 3H), 3.22-3.27 (m, 1H), 2.73-2.82 (m, 2H), 2.60-2.69 (m, 2H), 1.08-1.17 (m, 9H).

The boronic ester 176-1 was prepared in the following manner:

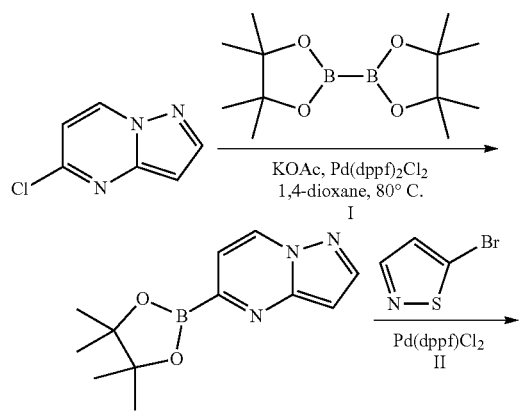

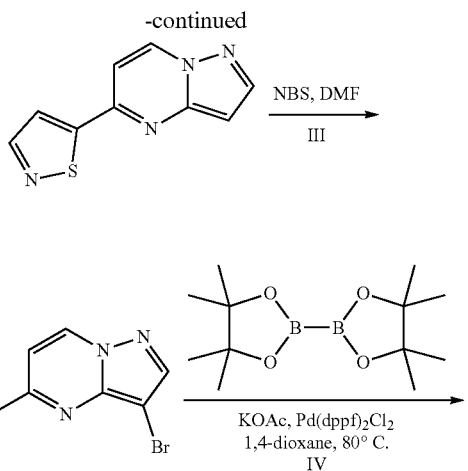

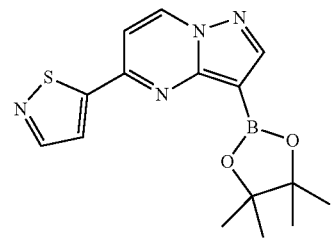

Step I.

5-Chloropyrazolo[1,5-a]pyrimidine (400 mg, 1 eq.), bis (pinacolato)diboron (1.06 g, 1.6 eq), KOAc (767 mg, 3 eq) and Pd(dppf)$_2$Cl$_2$ (213 mg, 10%) were stirred in 1,4-dioxane (10 mL) at 80° C. for 1 h. Filtered the reaction mixture through celite and washed with EtOAc. The filtrate was concentrated and the crude mixture was used directly for next step.

Step II.

Crude product from step I (2.6 mmol, 6 eq.), 5-bromoisothiazole (71.2 mg, 1 eq.), and K$_2$CO$_3$ (180 mg, 3 eq.) were suspended in a mixture of toluene (8 mL), isopropanol (5 mL), and water (2 mL). The solution was degassed by passing nitrogen for 15 min, and Pd(dppf)Cl$_2$—CH$_2$Cl$_2$ complex was added (35 mg, 10 mol %). Heated overnight at 90° C. Then, the reaction mixture was cooled, filtered through celite. And washed with EtOAc. The filtrate was concentrated and purified through silica gel column (EtOAc/Hexanes=3/2) to provide 75 mg of.

Step III.

The product from step II (23 mg, 1 eq.) was dissolved in DMF (3 mL), NBS added (22 mg, 1.2 eq.) and mixture stirred overnight. The product was purified by HPLC to form 17 mg.

Step IV.

The product from step III (36 mg, 1.0 eq), bis(pinacolato) diboron (52 mg, 1.6 eq), KOAc (38 mg, 3 eq) and Pd(dppf)$_2$Cl$_2$ (10.5 mg, 10%) were stirred in 1,4-dioxane (5 mL) at 80° C. overnight. Filtered the reaction mixture through celite and washed with EtOAc. The filtrate was concentrated and the crude mixture was used directly for next step.

Example 177

(S)—N-(2-(diethylamino)propyl)-2-((N-methylmethyl)sulfonamido)-6-(5-(thiophen-2-yl)pyrazolo[1,5-a]pyrimidin-3-yl)isonicotinamide

177

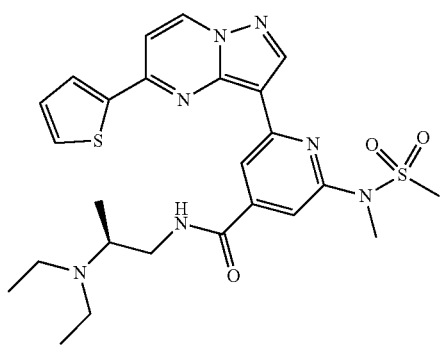

Synthesis of methyl 2-chloro-6-(N-methylmethyl-sulfonamido)isonicotinate (177B)

A mixture of 177A (200 mg, 0.971 mmol), N-methyl-methanesulfonamide (105.95 mg, 0.971 mmol), pd$_2$(dba)$_3$ (43.86 mg, 0.049 mmol), xanphos (56.17 mg, 0.097 mmol), and potassium phosphate (309.09 mg, 1.456 mmol) in dioxane (6 mL) were stirred at 100° C. for 3 h. Diluted the reaction mixture with EtOAc and filtered through celite. The filtrate was concentrated and purified with prep-HPLC to get the product 177B (120 mg). The following steps were performed as shown in Example 1 to provide the compound 177, as a TFA salt. LC/MS (M+H): 542.2; $^1$H-NMR (CD$_3$OD) δ 8.90 (d, 1H, J=7.2 Hz), 8.85 (d, 1H, J=1.2 Hz), 8.75 (s, 1H), 7.98 (dd, 1H, J=3.6, 1.2 Hz), 7.73 (dd, 1H, J=5.2, 1.2 Hz), 7.55-7.57 (m, 2H), 7.24 (dd, 1H, J=5.0, 3.8 Hz), 3.97 (dd, 1H, J=14.4, 6.0 Hz), 3.83-3.91 (m, 1H), 3.47-3.58 (m, 5H), 3.34-3.43 (m, 2H), 3.18-3.26 (m, 4H), 1.45-1.49 (m, 6H), 1.40 (t, 3H, J=7.2 Hz);

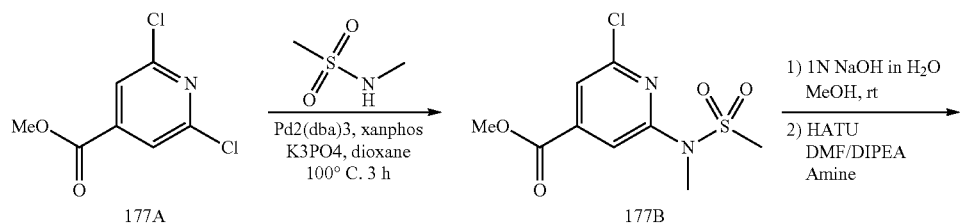

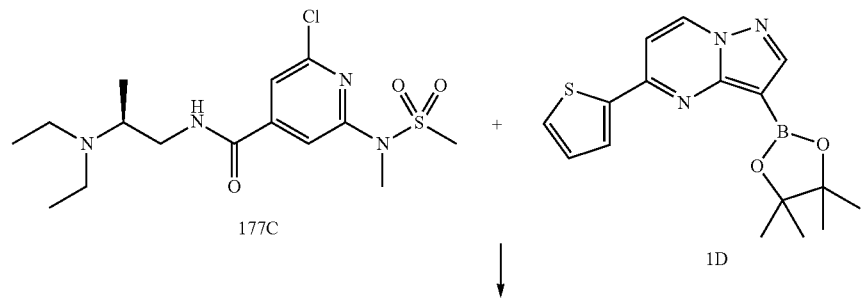

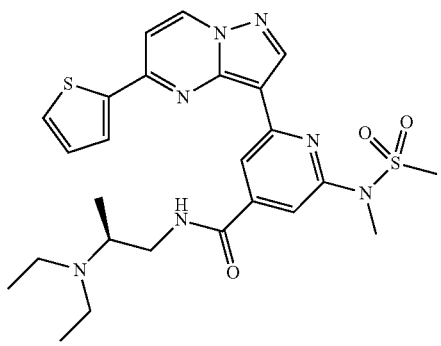

177

Example 178

(S)—N-(2-(diethylamino)propyl)-2-((1-methylethyl)
sulfonamido)-6-(5-(thiophen-2-yl)pyrazolo[1,5-a]
pyrimidin-3-yl)isonicotinamide

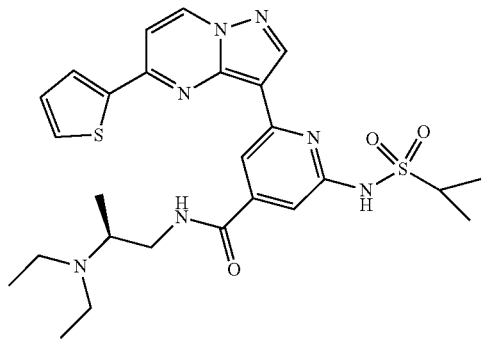

178

Compound 178 was synthesized as shown in the Example 177, starting from commercially available propane-2-sulfonamide, as a TFA salt. LC/MS (M+H): 556.2

Example 179

(S)—N-(2-(diethylamino)propyl)-2-(ethylsulfonamido)-6-(5-(thiophen-2-yl)pyrazolo[1,5-a]pyrimidin-3-yl)isonicotinamide

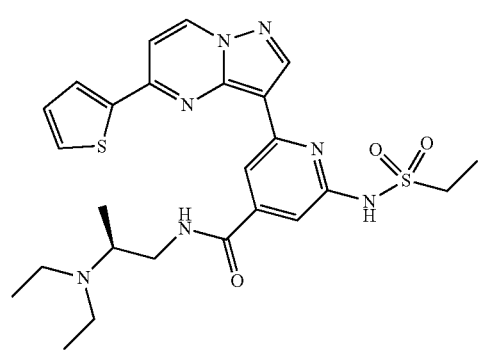

179

Compound 179 was synthesized as shown in the Example 177, starting from commercially available ethanesulfonamide, as a TFA salt. LC/MS (M+H): 542.2

Example 180

(S)-2-(cyclopropanesulfonamido)-N-(2-(diethylamino)propyl)-6-(5-(thiophen-2-yl)pyrazolo[1,5-a]pyrimidin-3-yl)isonicotinamide

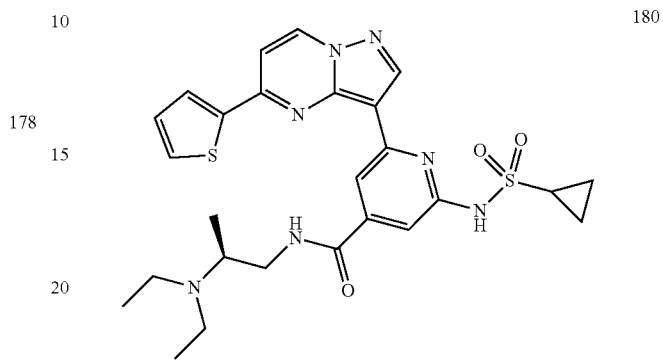

180

Compound 180 was synthesized as shown in the Example 177, starting from commercially available cyclopropanesulfonamide, as a TFA salt. LC/MS (M+H): 554.2; $^1$H-NMR (CD$_3$OD) δ 8.89 (d, 1H, J=7.6 Hz), 8.76 (s, 1H), 8.65 (s, 1H), 7.98 (dd, 1H, J=3.8, 1.0 Hz), 7.73 (dd, 1H, J=5.0, 1.0 Hz), 7.55 (d, 1H, J=7.6 Hz), 7.28 (d, 1H, J=1.2 Hz), 7.24 (dd, 1H, J=5.0, 3.8 Hz), 3.96 (dd, 1H, J=14.2, 5.8 Hz), 3.82-3.90 (m, 1H), 3.47-3.57 (m, 2H), 3.35-3.40 (m, 2H), 3.18-3.25 (m, 1H), 3.08-3.14 (m, 1H), 1.45-1.48 (m, 6H), 1.40 (t, 3H, J=7.2 Hz), 1.22-1.27 (m, 2H), 1.04-1.10 (m, 2H);

Example 181

(S)—N-(2-(diethylamino)propyl)-2-(methylsulfonamido)-6-(5-(thiophen-2-yl)pyrazolo[1,5-a]pyrimidin-3-yl)isonicotinamide

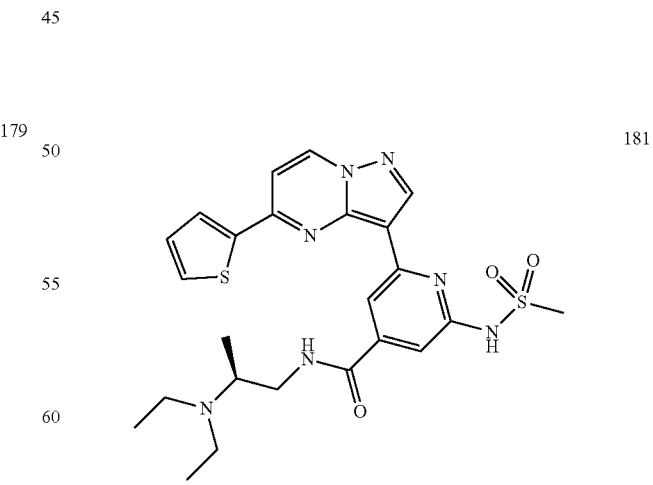

181

Compound 181 was synthesized as shown in the Example 177, starting from commercially available methanesulfonamide, as a TFA salt. LC/MS (M+H): 528.1

Example 182

(S)—N-(2-(diethylamino)propyl)-2-(3-(ethylsulfonamido)azetidin-1-yl)-6-(5-(thiophen-2-yl)pyrazolo[1,5-a]pyrimidin-3-yl)isonicotinamide

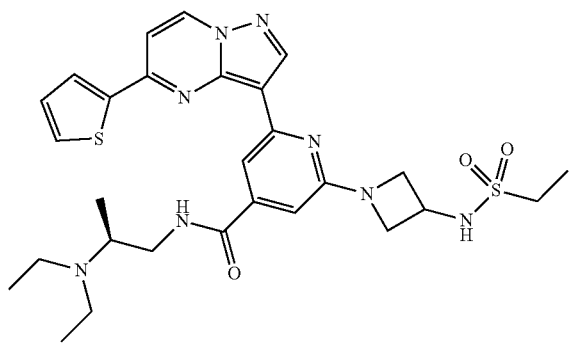
182

Compound 182 was synthesized as shown in the Example 175, starting from commercially available ethanesulfonyl chloride, as a TFA salt. LC/MS (M+H): 597.2; $^1$H-NMR (CD$_3$OD) δ 8.92 (d, 1H, J=7.2 Hz), 8.72 (s, 1H), 8.20 (s, 1H), 7.99 (dd, 1H, J=4.0, 1.2 Hz), 7.74 (dd, 1H, J=5.0, 1.0 Hz), 7.59 (d, 1H, J=7.2 Hz), 7.25 (dd, 1H, J=5.0, 3.8 Hz), 6.70 (s, 1H), 4.49-4.59 (m, 3H), 4.12-4.16 (m, 2H), 3.94 (dd, 1H, J=14.2, 5.8), 3.82-3.87 (m, 1H), 3.47-3.55 (m, 2H), 3.33-3.38 (m, 2H), 3.17-3.26 (m, 1H), 3.11 (q, 2H, J=7.2 Hz), 1.40-1.48 (m, 9H), 1.36 (t, 3H, J=7.2 Hz);

Example 183

(S)—N-(2-(diethylamino)propyl)-2-(3-((1-methylethyl)sulfonamido)azetidin-1-yl)-6-(5-(thiophen-2-yl)pyrazolo[1,5-a]pyrimidin-3-yl)isonicotinamide

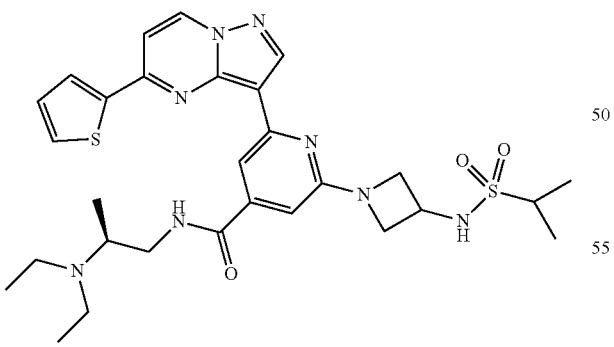
183

Compound 183 was synthesized as shown in the Example 175, starting from commercially available propane-2-sulfonyl chloride, as a TFA salt. LC/MS (M+H): 611.2; $^1$H-NMR (CD$_3$OD) δ 8.91 (d, 1H, J=7.6 Hz), 8.72 (s, 1H), 8.21 (s, 1H), 7.99 (dd, 1H, J=3.6, 1.2 Hz), 7.73 (dd, 1H, J=5.0, 1.0 Hz), 7.58 (d, 1H, J=7.2 Hz), 7.25 (dd, 1H, J=5.2, 3.6 Hz), 6.69 (s, 1H), 4.54-4.57 (m, 3H), 4.11-4.13 (m, 2H), 3.94 (dd, 1H, J=14.2, 5.8), 3.82-3.87 (m, 1H), 3.47-3.55 (m, 2H), 3.33-3.38 (m, 2H), 3.19-3.27 (m, 2H), 1.40-1.48 (m, 9H), 1.37 (d, 6H, J=6.8 Hz);

Example 184

(S)—N-(2-(diethylamino)propyl)-2-(2-oxoimidazolidin-1-yl)-6-(5-(thiophen-2-yl)pyrazolo[1,5-a]pyrimidin-3-yl)isonicotinamide

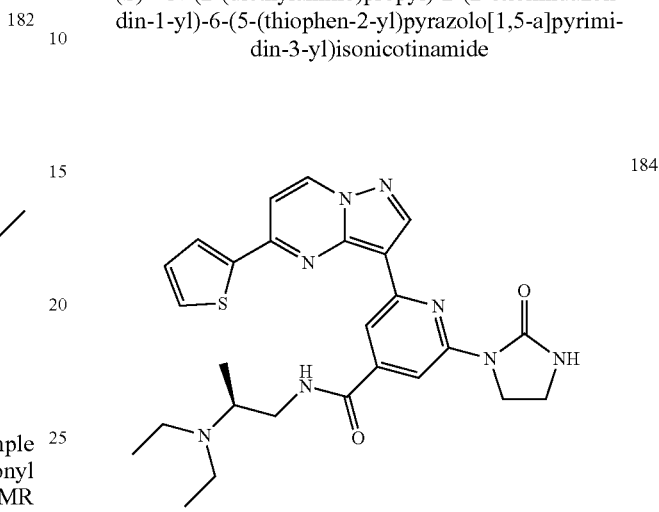
184

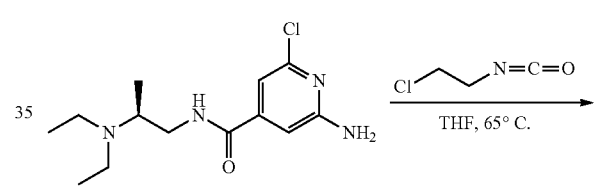
102C

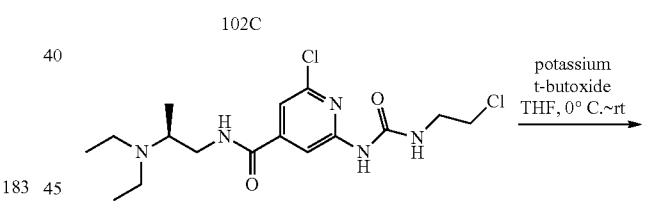
184A

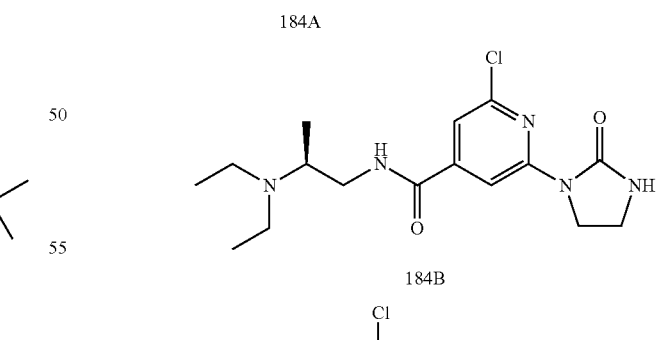
184B

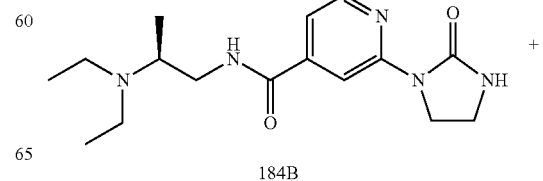
184B

189
-continued

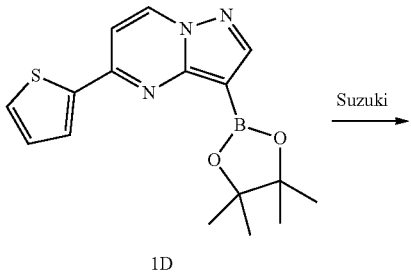

1D

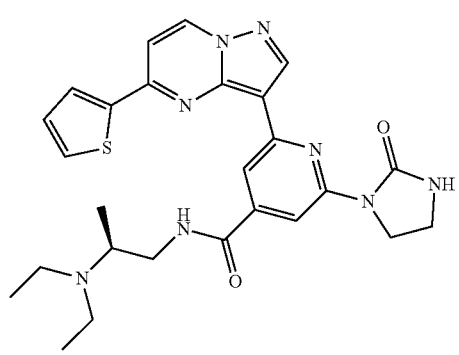

184

Synthesis of (S)-2-chloro-6-(3-(2-chloroethyl) ureido)-N-(2-(diethylamino)propyl)isonicotinamide (184A)

A solution of 102C (62 mg, 0.218 mmol) and 1-chloro-2-isocyanato ethane (114.86 mg, 1.09 mmol) in THF (5 mL) was heated at 65° C. overnight. The reaction mixture was concentrated and purified by prep-HPLC to give the product 184A (74 mg).

Synthesis of (S)-2-chloro-N-(2-(diethylamino)propyl)-6-(2-oxoimidazolidin-1-yl)isonicotinamide (184B)I To a stirred solution of 184A (74 mg, 0.19 mmol) in THF (5 mL) was added potassium t-butoxide (0.057 mL, 1.0M in THF). The resulting mixture was stirred at rt for 2 h. After concentration, the residue was purified by prep-HPLC to give the product 184B (31 mg).

Synthesis of 184

Product 184B was coupled with boronic ester 1D as shown in Example 1 to provide the product 184, as a TFA salt. LC/MS (M+H): 519.2

190

Example 185

(S)—N-(2-(diethylamino)propyl)-2-(3-ethylureido)-6-(5-(thiophen-2-yl)pyrazolo[1,5-a]pyrimidin-3-yl)isonicotinamide

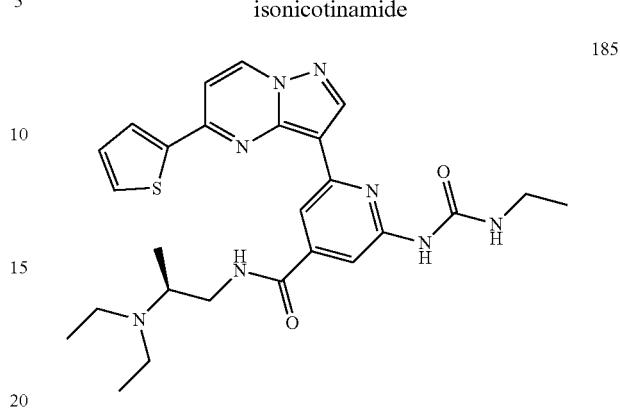

185

Compound 185 was synthesized as shown in the Example 184, by starting from the commercially available isocyanato ethane, as a TFA salt. LC/MS (M+H): 521.2; $^1$H-NMR (CD$_3$OD) δ 8.93 (d, 1H, J=7.2 Hz), 8.63 (s, 1H), 8.52 (d, 1H, J=1.6 Hz), 8.01 (d, 1H, J=3.6 Hz), 7.73 (dd, 1H, J=5.0, 1.0 Hz), 7.58 (d, 1H, J=7.6 Hz), 7.41 (s, 1H), 7.25 (dd, 1H, J=5.0, 3.8 Hz), 3.96 (dd, 1H, J=14.2, 5.8 Hz), 3.83-3.88 (m, 1H), 3.47-3.56 (m, 2H), 3.34-3.39 (m, 4H), 3.20-3.25 (m, 1H), 1.45-1.48 (m, 6H), 1.40 (t, 3H, J=7.2 Hz) 1.24 (t, 3H, J=7.2 Hz).

Example 186

(S)-ethyl (4-((2-(diethylamino)propyl)carbamoyl)-6-(5-(thiophen-2-yl)pyrazolo[1,5-a]pyrimidin-3-yl)pyridin-2-yl)carbamate

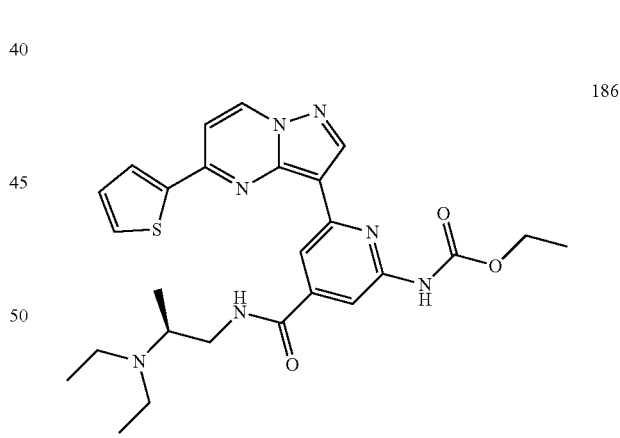

186

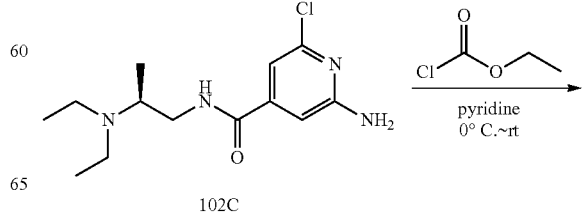

102C

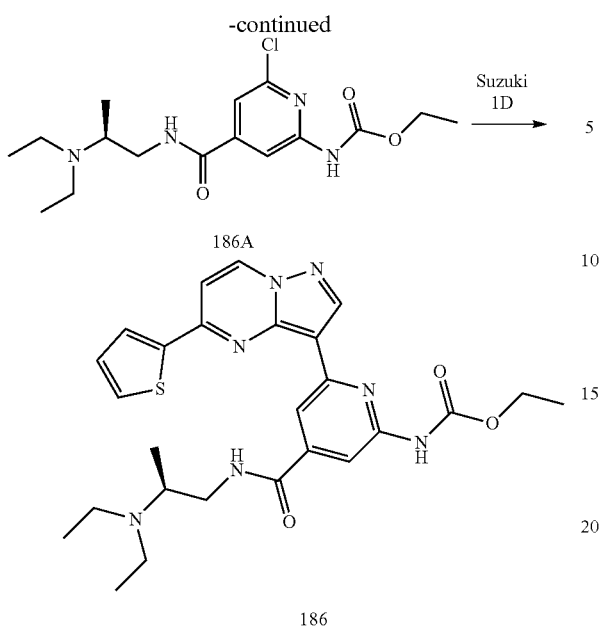

Synthesis of ethyl (S)-(6-chloro-4-((2-(diethylamino)propyl)carbamoyl)pyridin-2-yl)carbamate (186A)

To a stirred solution of 102C (50 mg, 0.176 mmol) in pyridine (2 mL) was added ethyl carbonochloridate (30.5 mg, 0.281 mmol) slowly at 0° C. The resulting mixture was warmed to room temperature and stirred for 3 h. Concentrated and the residue was purified by prep-HPLC to afford product 186A (30.5 mg).

Synthesis of 186

Product 186A was coupled with boronic ester 1D as shown in Example 1 to provide the product 186, as a TFA salt. LC/MS (M+H): 522.2

Example 187

(S)-isopropyl (4-((2-(diethylamino)propyl)carbamoyl)-6-(5-(thiophen-2-yl)pyrazolo[1,5-a]pyrimidin-3-yl)pyridin-2-yl)carbamate

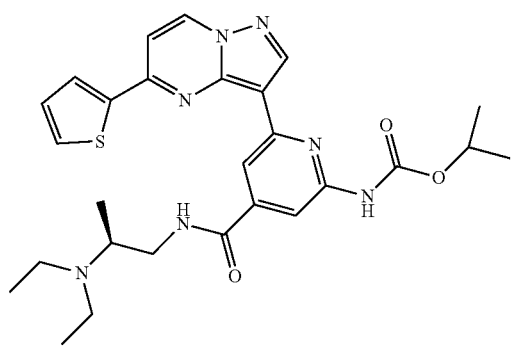

187

Compound 187 was synthesized as shown in Example 186, by starting from commercially available isopropyl carbonochloridate, as a TFA salt. LC/MS (M+H): 536.2; $^1$H-NMR (CD$_3$OD) δ 8.89 (d, 1H, J=7.6 Hz), 8.79 (s, 1H), 8.70 (d, 1H, J=1.2 Hz), 8.07 (d, 1H, J=1.6 Hz), 7.98 (dd, 1H, J=3.8, 1.0 Hz), 7.73 (dd, 1H, J=5.0, 1.0 Hz), 7.55 (d, 1H, J=7.6 Hz), 7.24 (dd, 1H, J=5.2, 4.0 Hz), 5.01-5.07 (m, 1H), 3.96 (dd, 1H, J=14.0, 6.0 Hz), 3.83-3.91 (m, 1H), 3.47-3.58 (m, 2H), 3.35-3.43 (m, 2H), 3.18-3.26 (m, 1H), 1.44-1.49 (m, 6H), 1.41 (t, 3H, J=7.2 Hz) 1.35 (d, 6H, J=6.4 Hz);

Example 188

(S)—N-(2-(diethylamino)propyl)-2-propionamido-6-(5-(thiophen-2-yl)pyrazolo[1,5-a]pyrimidin-3-yl)isonicotinamide

188

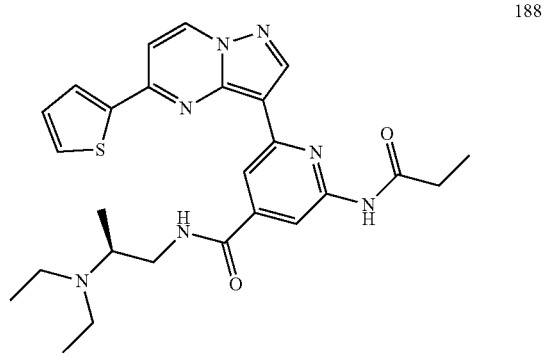 [SMILES: CCC(=O)Nc1cc(C(=O)NC[C@H](C)N(CC)CC)cc(-c2cnn3ccc(-c4cccs4)nc23)n1]

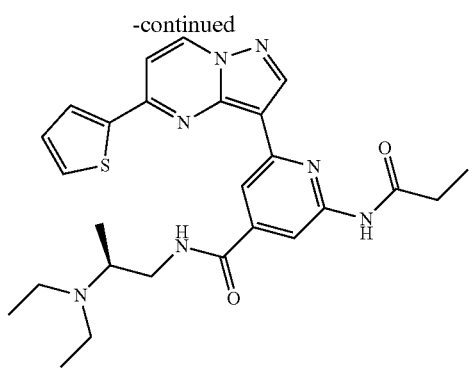

188

Synthesis of (S)-2-chloro-N-(2-(diethylamino)propyl)-6-propionamidoisonicotinamide (188A)

To a stirred solution of 102C (42 mg, 0.147 mmol) in DMF (3 mL) was added excess propionyl chloride (10 eq.) The resulting mixture was stirred at rt for 1 h and purified with prep-HPLC to get the product 188A (16.1 mg).

Synthesis of 188

Product 188A was coupled with boronic ester 1D as shown in Example 1 to provide the product 188, as a TFA salt. LC/MS (M+H): 506.2; $^1$H-NMR (CD$_3$OD) δ 8.91 (d, 1H, J=7.6 Hz), 8.78 (s, 1H), 8.77 (d, 1H, J=1.2 Hz), 8.26 (d, 1H, J=1.6 Hz), 8.00 (dd, 1H, J=4.0, 1.2 Hz), 7.74 (dd, 1H, J=5.0, 1.0 Hz), 7.57 (d, 1H, J=7.6 Hz), 7.25 (dd, 1H, J=5.0, 3.8 Hz), 3.97 (dd, 1H, J=14.4, 6.0 Hz), 3.83-3.91 (m, 1H), 3.47-3.58 (m, 2H), 3.35-3.41 (m, 2H), 3.18-3.25 (m, 1H), 3.53 (q, 2H, J=7.6 Hz), 1.39-1.49 (m, 6H), 1.41 (t, 3H, J=7.6 Hz) 1.25 (t, 3H, J=7.6 Hz);

Example 1.89

(S)—N-(2-(diethylamino)propyl)-2-isobutyramido-6-(5-(thiophen-2-yl)pyrazolo[1,5-a]pyrimidin-3-yl)isonicotinamide

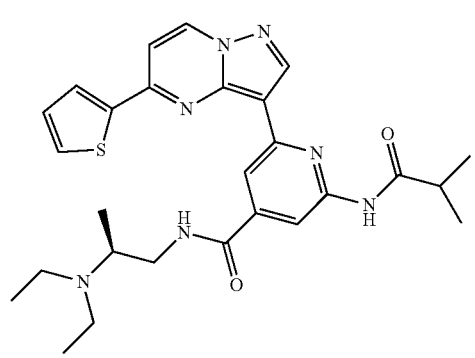

189

Compound 189 was synthesized as shown in the Example 188 and starting with the commercially available isobutyryl chloride, as a TFA salt. LC/MS (M+H): 520.2; 1H-NMR (CD$_3$OD) δ 8.90 (d, 1H, J=7.2 Hz), 8.78 (s, 1H), 8.76 (d, 1H, J=1.6 Hz), 8.24 (d, 1H, J=1.6 Hz), 8.00 (dd, 1H, J=3.8, 1.0 Hz), 7.73 (dd, 1H, J=5.0, 1.0 Hz), 7.56 (d, 1H, J=7.2 Hz), 7.24 (dd, 1H, J=5.0, 3.8 Hz), 3.97 (dd, 1H, J=14.4, 6.0 Hz), 3.83-3.91 (m, 1H), 3.47-3.59 (m, 2H), 3.35-3.41 (m, 2H), 3.18-3.27 (m, 1H), 2.74-2.83 (m, 1H), 1.45-1.49 (m, 6H), 1.41 (t, 3H, J=7.6 Hz) 1.25 (d, 6H, J=6.8 Hz);

Example 190

(S)-2-(cyclopropanecarboxamido)-N-(2-(diethylamino)propyl)-6-(5-(thiophen-2-yl)pyrazolo[1,5-a]pyrimidin-3-yl)isonicotinamide

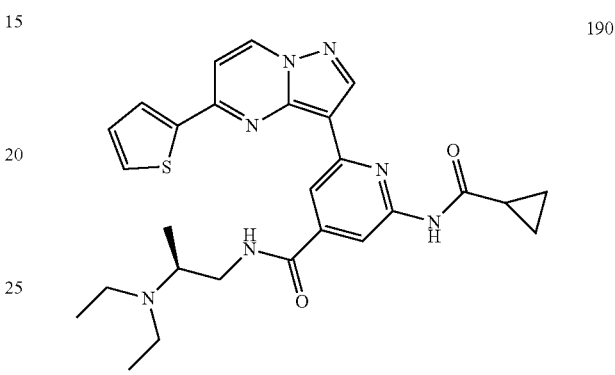

190

Compound 190 was synthesized as shown in the Example 188 and starting with the commercially available cyclopropanecarbonyl chloride, as a TFA salt. LC/MS (M+H): 518.2; $^1$H-NMR (CD$_3$OD) δ 8.91 (d, 1H, J=7.6 Hz), 8.80 (s, 1H), 8.77 (d, 1H, J=1.2 Hz), 8.22 (d, 1H, J=1.6 Hz), 7.99 (dd, 1H, J=3.8, 1.0 Hz), 7.73 (dd, 1H, J=5.0, 1.0 Hz), 7.56 (d, 1H, J=7.2 Hz), 7.25 (dd, 1H, J=5.0, 3.8 Hz), 3.95 (dd, 1H, J=14.4, 6.0 Hz), 3.83-3.90 (m, 1H), 3.47-3.57 (m, 2H), 3.32-3.42 (m, 2H), 3.17-3.26 (m, 1H), 1.93-2.00 (m, 1H), 1.44-1.48 (m, 6H), 1.40 (t, 3H, J=7.2 Hz), 1.01-1.04 (m, 2H), 0.88-0.98 (m, 2H);

Example 191

(S)—N-(2-(diethylamino)propyl)-2-(((3-methyloxetan-3-yl)methyl)amino)-6-(5-(thiophen-2-yl)pyrazolo[1,5-a]pyrimidin-3-yl)isonicotinamide

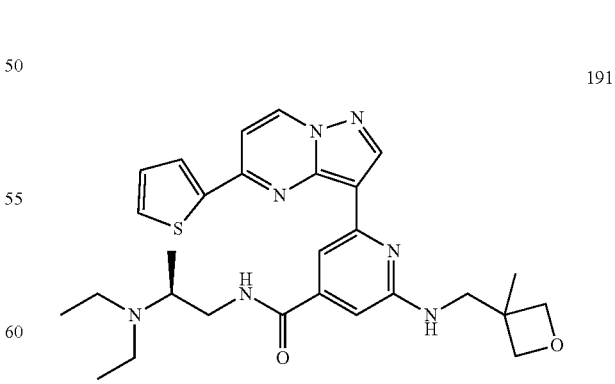

191

Compound 191 was synthesized following the Example 141, starting from commercially available (3-methyloxetan-3-yl)methanamine, as a TFA salt. LC/MS (M+H): 534.2; $^1$H NMR (400 MHz, Methanol-d$_4$) δ 9.05-8.95 (m, 1H), 8.78 (s, 1H), 8.09-8.00 (m, 1H), 7.87-7.75 (m, 2H), 7.75-7.64 (m, 1H), 7.28 (dd, J=5.0, 3.8 Hz, 1H), 6.95 (d, J=1.5 Hz, 1H), 4.43 (d, J=8.8 Hz, 2H), 4.16 (d, J=8.8 Hz, 2H), 3.89 (ddd, J=31.1, 13.3, 6.0 Hz, 2H), 3.68 (s, 2H), 3.53 (ddd, J=36.7, 13.7, 6.7 Hz, 2H), 3.36 (dd, J=7.4, 3.0 Hz, 1H), 3.22 (dq, J=14.2, 7.3 Hz, 1H), 1.48-1.34 (m, 12H).

Example 192

(S)—N-(2-(diethylamino)propyl)-2-((oxetan-3-yl methyl)amino)-6-(5-(thiophen-2-yl)pyrazolo[1,5-a]pyrimidin-3-yl)isonicotinamide

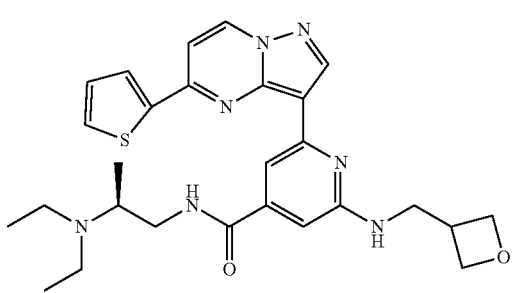

192

Compound 191 was synthesized following the Example 141, starting from commercially available oxetan-3-ylmethanamine, as a TFA salt. LC/MS (M+H): 520.2; $^1$H NMR (400 MHz, Methanol-d$_4$) δ 9.02 (dd, J=7.4, 5.0 Hz, 1H), 8.42 (d, J=9.0 Hz, 1H), 8.00 (dd, J=3.9, 1.1 Hz, 1H), 7.76-7.67 (m, 2H), 7.46 (dd, J=17.4, 1.8 Hz, 1H), 7.37 (dd, J=10.7, 1.9 Hz, 1H), 7.23 (td, J=4.4, 3.8, 1.1 Hz, 1H), 4.47-4.38 (m, 1H), 4.24 (d, J=13.6 Hz, 1H), 3.85 (ddd, J=33.0, 13.3, 6.0 Hz, 2H), 3.56 (s, 1H), 3.52 (s, 1H), 3.44 (d, J=5.6 Hz, 1H), 3.41 (s, 2H), 3.38-3.27 (m, 5H), 3.19 (dt, J=20.1, 7.0 Hz, 1H), 1.48-1.27 (m, 10H), 1.16 (s, 1H), 1.03 (s, 3H).

Example 193

(S)—N-(2-(diethylamino)propyl)-2-(oxetan-3-ylamino)-6-(5-(thiophen-2-yl)pyrazolo[1,5-a]pyrimidin-3-yl)isonicotinamide

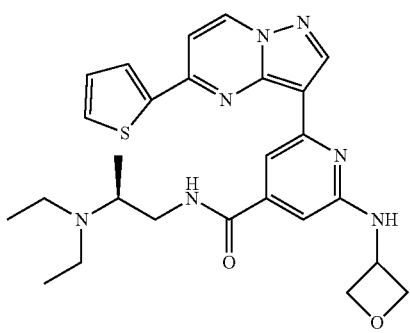

193

Compound 193 was synthesized following the Example 141, starting from commercially available oxetan-3-amine, as a TFA salt. LC/MS (M+H): 506.2; $^1$H NMR (400 MHz, Methanol-d$_4$) δ 9.05 (d, J=7.4 Hz, 1H), 8.61 (s, 1H), 8.05 (dd, J=3.8, 1.1 Hz, 1H), 7.84 (d, J=1.6 Hz, 1H), 7.81-7.71 (m, 2H), 7.29-7.21 (m, 2H), 5.11 (t, J=11.7 Hz, 1H), 4.93 (dd, J=12.6, 6.4 Hz, 1H), 4.52 (dq, J=10.5, 4.8 Hz, 1H), 3.97-3.68 (m, 4H), 3.54 (dd, J=13.6, 6.4 Hz, 1H), 3.50-3.31 (m, 3H), 3.21 (dq, J=14.1, 6.9 Hz, 1H), 1.46-1.29 (m, 7H).

Example 194

(S)—N-(1-(4-((2-(diethylamino)propyl)carbamoyl)-6-(5-(thiophen-2-yl)pyrazolo[1,5-a]pyrimidin-3-yl)pyridin-2-yl)azetidin-3-yl)oxazole-2-carboxamide

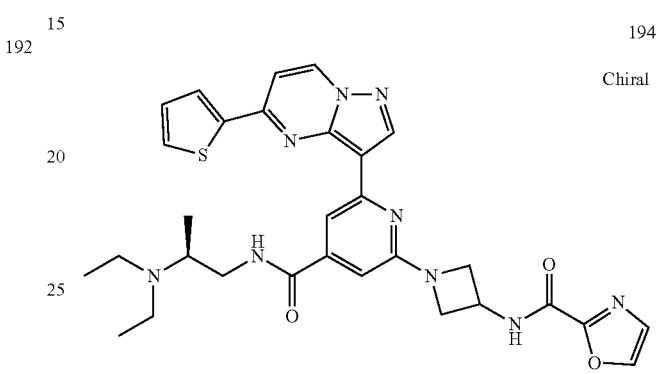

194
Chiral

Compound 194 was synthesized as shown in the Example 175, starting from commercially available oxazole-2-carbonyl chloride, as a TFA salt. LC/MS (M+H): 600.396; 1H NMR (400 MHz, Methanol-d4) δ 8.88 (d, J=7.4 Hz, 1H), 8.67 (s, 1H), 8.12 (d, J=0.8 Hz, 1H), 7.98 (d, J=1.3 Hz, 1H), 7.95 (dd, J=3.8, 1.1 Hz, 1H), 7.74 (dd, J=5.0, 1.1 Hz, 1H), 7.55 (d, J=7.4 Hz, 1H), 7.40 (d, J=0.8 Hz, 1H), 7.23 (dd, J=5.0, 3.8 Hz, 1H), 6.75 (d, J=1.4 Hz, 1H), 5.03 (tt, J=7.5, 5.5 Hz, 1H), 4.67 (t, J=8.4 Hz, 2H), 4.40 (dd, J=9.1, 5.5 Hz, 2H), 3.95 (dd, J=14.1, 5.7 Hz, 1H), 3.87 (q, J=6.4 Hz, 1H), 3.54 (ddd, J=21.7, 13.9, 6.8 Hz, 2H), 3.43-3.34 (m, 2H), 3.23 (dq, J=14.3, 7.1 Hz, 1H), 1.46 (t, J=6.6 Hz, 6H), 1.40 (t, J=7.2 Hz, 3H).

Example 195

(S)—N-(2-(diethylamino)propyl)-2-(3-(3,3-dimethylureido)azetidin-1-yl)-6-(5-(thiophen-2-yl)pyrazolo[1,5-a]pyrimidin-3-yl)isonicotinamide

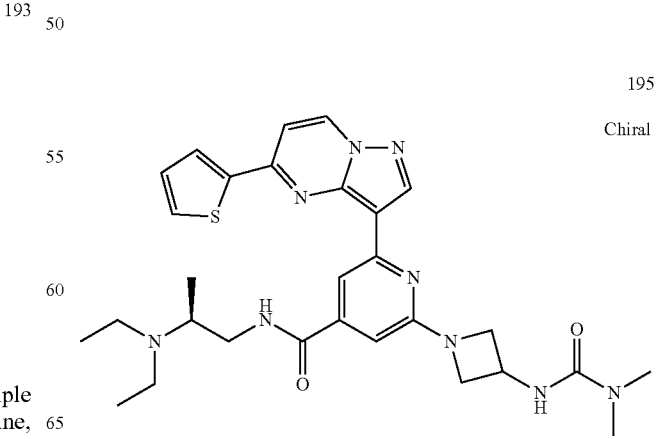

195
Chiral

Compound 195 was synthesized as shown in the Example 175, starting from commercially available dimethylcarbamic chloride, as a TFA salt. LC/MS (M+H): 576.230; 1H NMR (400 MHz, Methanol-d4) δ 8.91 (d, J=7.4 Hz, 1H), 8.73 (s, 1H), 8.24 (s, 1H), 7.99 (dd, J=3.8, 1.1 Hz, 1H), 7.74 (dd, J=5.1, 1.1 Hz, 1H), 7.58 (d, J=7.4 Hz, 1H), 7.25 (dd, J=5.1, 3.8 Hz, 1H), 6.68-6.62 (m, 1H), 4.70 (p, J=6.3 Hz, 3H), 4.49 (t, J=8.1 Hz, 2H), 4.14-4.06 (m, 2H), 3.95 (dd, J=14.3, 5.9 Hz, 1H), 3.85 (q, J=6.4 Hz, 1H), 3.53 (ddd, J=13.3, 6.6, 3.4 Hz, 2H), 3.43-3.35 (m, 3H), 3.21 (dq, J=15.5, 8.6, 7.6 Hz, 1H), 2.94 (s, 6H), 1.50-1.44 (m, 6H), 1.41 (t, J=7.2 Hz, 3H).

Example 196

(S)-2-(3-(cyclopropanecarboxamido)azetidin-1-yl)-N-(2-(diethylamino)propyl)-6-(5-(thiophen-2-yl)pyrazolo[1,5-a]pyrimidin-3-yl)isonicotinamide

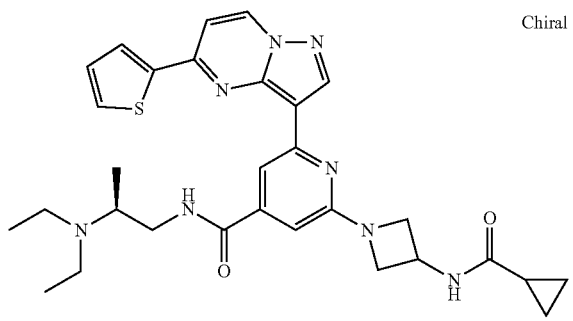

196

Chiral

Compound 196 was synthesized as shown in the Example 175, starting from commercially available cyclopropanecarbonyl chloride, as a TFA salt. LC/MS (M+H): 573.373; ¹H NMR (400 MHz, Methanol-d₄) δ 8.92 (d, J=7.4 Hz, 1H), 8.73 (s, 1H), 8.21-8.15 (m, 1H), 8.00 (dd, J=3.8, 1.1 Hz, 1H), 7.75 (dd, J=5.0, 1.0 Hz, 1H), 7.59 (d, J=7.5 Hz, 1H), 7.26 (dd, J=5.1, 3.8 Hz, 1H), 6.71 (d, J=1.4 Hz, 1H), 4.56 (t, J=8.2 Hz, 2H), 4.14 (dd, J=8.8, 5.4 Hz, 2H), 3.95 (dd, J=14.2, 5.8 Hz, 1H), 3.85 (q, J=6.4 Hz, 1H), 3.58-3.46 (m, 2H), 3.37 (dt, J=8.8, 4.4 Hz, 3H), 3.22 (dq, J=14.0, 7.1 Hz, 1H), 1.64 (ddd, J=12.6, 8.0, 4.6 Hz, 1H), 1.47 (dd, J=8.6; 6.9 Hz, 6H), 1.40 (t, J=7.2 Hz, 3H), 0.94-0.86 (m, 2H), 0.81 (dt, J=8.0, 3.1 Hz, 2H).

Example 197

(S)—N-(2-(diethylamino)propyl)-2-(3-(methylsulfonamido)azetidin-1-yl)-6-(5-(thiophen-2-yl)pyrazolo[1,5-a]pyrimidin-3-yl)isonicotinamide

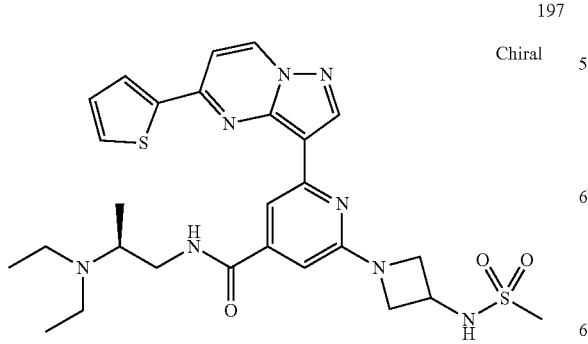

197

Chiral

Compound 197 was synthesized as shown in the Example 175, starting from commercially available methanesulfonyl chloride, as a TFA salt. LC/MS (M+H): 583.354; ¹H NMR (400 MHz, Methanol-d₄) δ 8.89 (d, J=7.4 Hz, 1H), 8.67 (s, 1H), 8.05 (d, J=1.3 Hz, 1H), 7.96 (dd, J=3.8, 1.1 Hz, 1H), 7.73 (dd, J=5.1, 1.1 Hz, 1H), 7.56 (d, J=7.4 Hz, 1H), 7.24 (dd, J=5.0, 3.8 Hz, 1H), 6.72 (d, J=1.4 Hz, 1H), 4.65-4.51 (m, 3H), 4.20 (dd, J=8.4, 4.7 Hz, 2H), 3.95 (dd, J=14.1, 5.7 Hz, 1H), 3.86 (q, J=6.4 Hz, 1H), 3.54 (ddd, J=19.4, 13.8, 6.7 Hz, 2H), 3.43-3.34 (m, 2H), 3.23 (dq, J=14.2, 7.1 Hz, 1H), 3.04 (s, 3H), 1.46 (t, J=7.3 Hz, 6H), 1.40 (t, J=7.2 Hz, 3H).

Example 198

(S)-2-(3-acetamidoazetidin-1-yl)-N-(2-(diethylamino)propyl)-6-(5-(thiophen-2-yl)pyrazolo[1,5-a]pyrimidin-3-yl)isonicotinamide

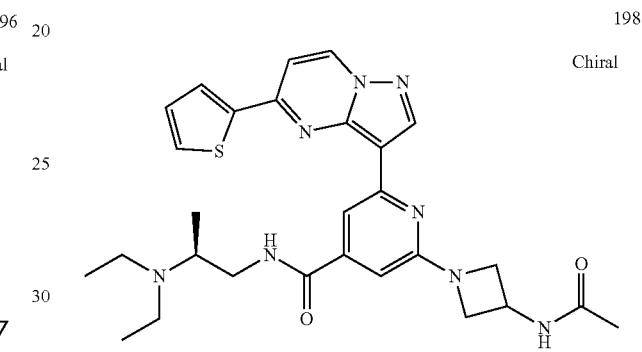

198

Chiral

Compound 198 was synthesized as shown in the Example 175, starting from commercially available acetyl chloride, as a TFA salt. LC/MS (M+H): 547.388; 1H NMR (400 MHz, Methanol-d4) δ 8.93 (d, J=7.4 Hz, 1H), 8.73 (d, J=1.0 Hz, 1H), 8.15 (s, 1H), 8.00 (d, J=3.8 Hz, 1H), 7.76 (d, J=5.0 Hz, 1H), 7.60 (d, J=7.4 Hz, 1H), 7.26 (t, J=4.4 Hz, 1H), 6.72 (s, 1H), 4.57 (t, J=8.3 Hz, 3H), 4.17-4.11 (m, 2H), 3.95 (dd, J=14.1, 5.7 Hz, 2H), 3.85 (q, J=6.4 Hz, 2H), 3.58-3.50 (m, 3H), 3.41-3.33 (m, 5H), 3.22 (dd, J=13.5, 6.9 Hz, 2H), 2.01 (d, J=1.1 Hz, 3H), 1.46 (t, J=7.6 Hz, 7H), 1.40 (t, J=7.2 Hz, 4H).

Example 199

N—((S)-2-(diethylamino)propyl)-2-(((R)-1-hydroxypropan-2-yl)amino)-6-(5-(thiophen-2-yl)pyrazolo[1,5-a]pyrimidin-3-yl)isonicotinamide

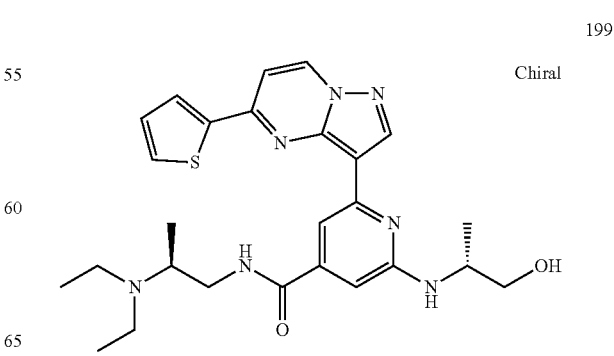

199

Chiral

Compound 199 was synthesized as shown in the Example 141, starting from commercially available (R)-2-aminopropan-1-ol, as a TFA salt. LC/MS (M+H): 508.242; 1H NMR (400 MHz, Methanol-d4) δ 8.99 (d, J=7.4 Hz, 1H), 8.75 (s, 1H), 8.05 (d, J=3.7 Hz, 1H), 7.97 (s, 1H), 7.81 (d, J=5.1 Hz, 1H), 7.68 (d, J=7.4 Hz, 1H), 7.28 (dd, J=5.1, 3.8 Hz, 1H), 7.05 (s, 1H), 4.35 (s, 1H), 3.95 (dd, J=14.1, 5.5 Hz, 1H), 3.85 (dt, J=11.6, 5.6 Hz, 2H), 3.68 (dd, J=10.9, 7.5 Hz, 1H), 3.54 (td, J=13.6, 6.5 Hz, 3H), 3.37 (q, J=7.1 Hz, 3H), 3.23 (dd, J=13.4, 6.8 Hz, 1H), 1.49-1.36 (m, 13H).

Example 200

N—((S)-2-(diethylamino)propyl)-2-(((S)-1-hydroxypropan-2-yl)amino)-6-(5-(thiophen-2-yl)pyrazolo[1,5-a]pyrimidin-3-yl)isonicotinamide

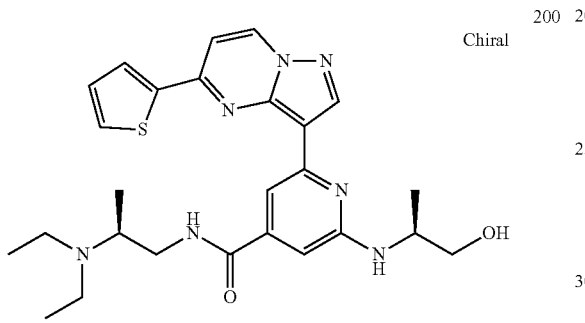

Compound 200 was synthesized as shown in the Example 141, starting from commercially available (S)-2-aminopropan-1-ol, as a TFA salt. LC/MS (M+H): 508.270; 1H NMR (400 MHz, Methanol-d4) δ 9.00 (d, J=7.4 Hz, 1H), 8.75 (s, 1H), 8.06 (dd, J=3.8, 1.1 Hz, 1H), 7.94 (s, 1H), 7.83 (dd, J=5.1, 1.1 Hz, 1H), 7.69 (d, J=7.4 Hz, 1H), 7.29 (dd, J=5.0, 3.8 Hz, 1H), 7.10 (s, 1H), 4.37 (s, 1H), 3.95 (dd, J=14.1, 5.6 Hz, 1H), 3.86 (q, J=6.7, 6.2 Hz, 2H), 3.67 (dd, J=10.8, 7.8 Hz, 1H), 3.60-3.44 (m, 3H), 3.37 (q, J=7.2 Hz, 3H), 3.23 (dd, J=13.4, 7.0 Hz, 1H), 1.50-1.36 (m, 14H).

Example 201

N—((S)-2-(diethylamino)propyl)-2-(((S)-2-hydroxypropyl)amino)-6-(5-(thiophen-2-yl)pyrazolo[1,5-a]pyrimidin-3-yl)isonicotinamide

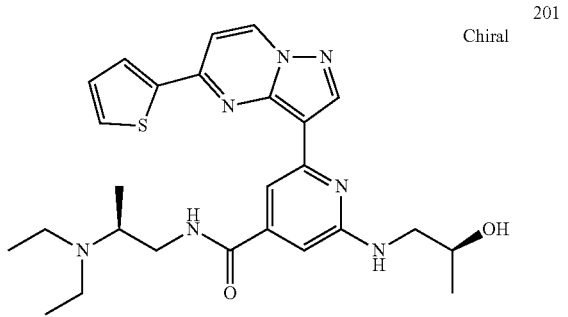 [SMILES: CCN(CC)[C@@H](C)CNC(=O)c1cc(NC[C@H](C)O)nc(-c2cnn3ccc(-c4cccs4)nc23)c1]

Compound 201 was synthesized as shown in the Example 141, starting from commercially available (S)-1-aminopropan-2-ol, as a TFA salt. LC/MS (M+H): 508.244; 1H NMR (400 MHz, Methanol-d4) δ 8.98 (d, J=7.4 Hz, 1H), 8.72 (s, 1H), 8.08 (s, 1H), 8.03 (dd, J=3.9, 1.1 Hz, 1H), 7.78 (dd, J=5.0, 1.1 Hz, 1H), 7.66 (d, J=7.4 Hz, 1H), 7.27 (dd, J=5.1, 3.8 Hz, 1H), 7.01 (s, 1H), 4.15 (td, J=6.4, 3.4 Hz, 1H), 3.95 (dd, J=14.1, 5.6 Hz, 1H), 3.86 (h, J=6.6 Hz, 1H), 3.71 (d, J=13.8 Hz, 1H), 3.54 (dt, J=13.1, 6.5 Hz, 4H), 3.38 (q, J=7.2 Hz, 3H), 3.22 (dt, J=14.2, 7.1 Hz, 1H), 1.46 (dt, J=7.3, 3.9 Hz, 7H), 1.41 (t, J=7.2 Hz, 3H), 1.29 (d, J=6.3 Hz, 4H).

Example 202

N—((S)-2-(diethylamino)propyl)-2-(((R)-2-hydroxypropyl)amino)-6-(5-(thiophen-2-yl)pyrazolo[1,5-a]pyrimidin-3-yl)isonicotinamide

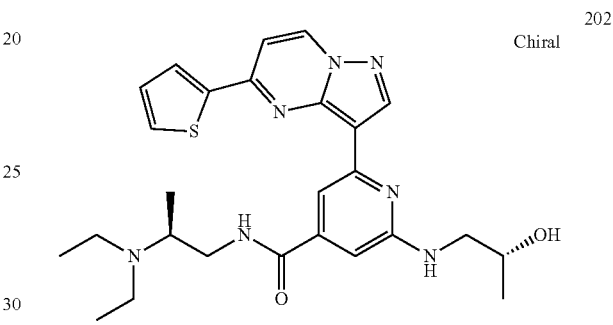

Compound 202 was synthesized as shown in the Example 141, starting from commercially available (R)-1-aminopropan-2-ol, as a TFA salt. LC/MS (M+H): 508.278; 1H NMR (400 MHz, Methanol-d4) δ 9.00 (d, J=7.4 Hz, 1H), 8.73 (s, 1H), 8.07-8.00 (m, 2H), 7.80 (dd, J=5.1, 1.1 Hz, 1H), 7.68 (d, J=7.4 Hz, 1H), 7.28 (dd, J=5.0, 3.8 Hz, 1H), 7.14-7.06 (m, 1H), 4.17 (td, J=6.3, 3.0 Hz, 1H), 3.95 (dd, J=14.1, 5.6 Hz, 1H), 3.86 (h, J=6.5 Hz, 1H), 3.75 (dd, J=14.1, 3.1 Hz, 1H), 3.61-3.45 (m, 3H), 3.38 (q, J=7.3 Hz, 2H), 3.23 (dt, J=14.1, 7.1 Hz, 1H), 1.46 (dd, J=7.0, 2.2 Hz, 6H), 1.40 (t, J=7.3 Hz, 3H), 1.29 (d, J=6.3 Hz, 3H).

Example 203

N—((S)-2-(diethylamino)propyl)-2-(((S)-tetrahydrofuran-3-yl)amino)-6-(5-(thiophen-2-yl)pyrazolo[1,5-a]pyrimidin-3-yl)isonicotinamide

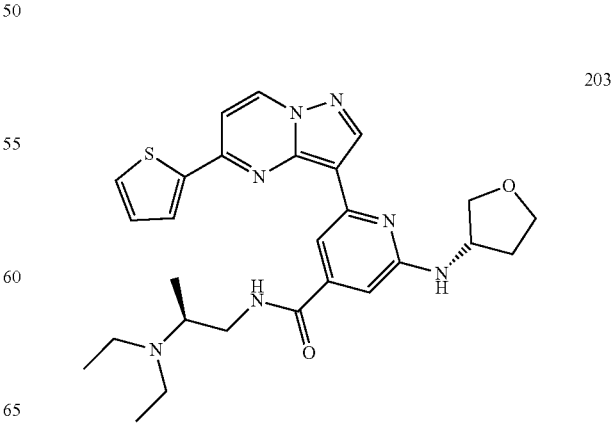

Compound 203 was synthesized as shown in the Example 141, starting from commercially available (S)-tetrahydrofuran-3-amine, as a TFA salt. LC/MS (M+H): 521.2

Example 204

(S)-2-(4-acetylpiperazin-1-yl)-N-(2-(diethylamino)propyl)-6-(5-(thiophen-2-yl)pyrazolo[1,5-a]pyrimidin-3-yl)isonicotinamide

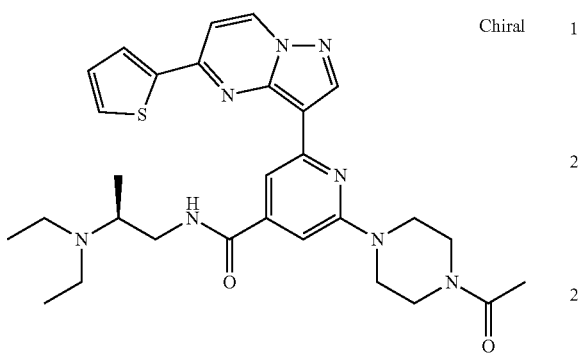

Compound 204 was synthesized as shown in the Example 141, starting from commercially available 1-(piperazin-1-yl)ethan-1-one, as a TFA salt. LC/MS (M+H): 561.408; 1H NMR (400 MHz, Methanol-d4) δ 8.87 (d, J=7.4 Hz, 1H), 8.73 (s, 1H), 8.24 (d, J=1.1 Hz, 1H), 7.96 (dd, J=3.8, 1.1 Hz, 1H), 7.74 (dd, J=5.0, 1.1 Hz, 1H), 7.53 (d, J=7.4 Hz, 1H), 7.25 (dd, J=5.1, 3.8 Hz, 1H), 7.01 (d, J=1.2 Hz, 1H), 3.96 (dd, J=14.2, 5.9 Hz, 1H), 3.91-3.70 (m, 10H), 3.54 (dt, J=12.8, 6.4 Hz, 2H), 3.44-3.34 (m, 2H), 3.22 (dq, J=14.1, 7.3 Hz, 1H), 2.19 (s, 3H), 1.48 (t, J=6.9 Hz, 7H), 1.41 (t, J=7.3 Hz, 4H).

Example 205

(S)—N-(2-(diethylamino)propyl)-2-(3-(methylamino)azetidin-1-yl)-6-(5-(thiophen-2-yl)pyrazolo[1,5-a]pyrimidin-3-yl)isonicotinamide

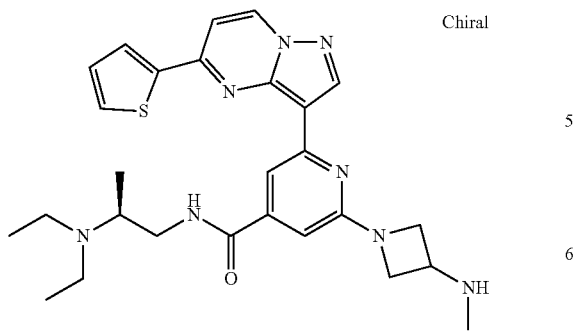

Compound 205 was synthesized as shown in the Example 141, starting from commercially available N-methylazetidin-3-amine, as a TFA salt. LC/MS (M+H): 519.243; 1H NMR (400 MHz, Methanol-d4) δ 8.91 (d, J=7.4 Hz, 1H), 8.73 (s, 1H), 8.42 (d, J=1.3 Hz, 1H), 7.99 (dd, J=3.8, 1.1 Hz, 1H), 7.73 (dd, J=5.0, 1.1 Hz, 1H), 7.57 (d, J=7.5 Hz, 1H), 7.25 (dd, J=5.0, 3.8 Hz, 1H), 6.69 (d, J=1.3 Hz, 1H), 4.53-4.44 (m, 2H), 4.22 (d, J=7.8 Hz, 3H), 3.96 (dd, J=14.2, 5.7 Hz, 1H), 3.87 (p, J=6.2 Hz, 1H), 3.54 (dd, J=14.0, 6.2 Hz, 2H), 3.38 (d, J=7.5 Hz, 3H), 2.81 (s, 3H), 1.51-1.44 (m, 7H), 1.41 (t, J=7.2 Hz, 3H).

Example 206

(S)—N-(2-(diethylamino)propyl)-2-(3-(dimethylamino)azetidin-1-yl)-6-(5-(thiophen-2-yl)pyrazolo[1,5-a]pyrimidin-3-yl)isonicotinamide

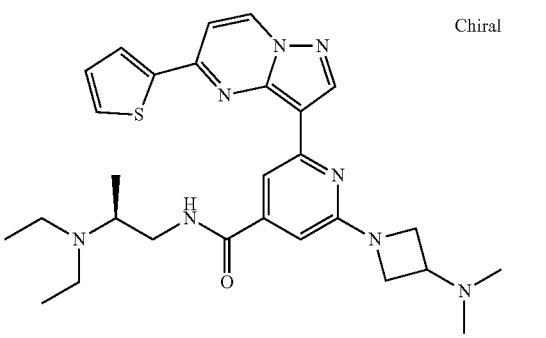

Compound 206 was synthesized as shown in the Example 141, starting from commercially available N,N-dimethylazetidin-3-amine, as a TFA salt. LC/MS (M+H): 533.209; 1H NMR (400 MHz, Methanol-d4) δ 8.90 (d, J=7.4 Hz, 1H), 8.74 (s, 1H), 8.42 (d, J=1.3 Hz, 1H), 7.98 (dd, J=3.8, 1.1 Hz, 1H), 7.73 (dd, J=5.1, 1.1 Hz, 1H), 7.56 (d, J=7.4 Hz, 1H), 7.25 (dd, J=5.1, 3.8 Hz, 1H), 6.72 (d, J=1.3 Hz, 1H), 4.54-4.45 (m, 2H), 4.31 (qd, J=5.2, 2.6 Hz, 3H), 3.96 (dd, J=14.1, 5.8 Hz, 1H), 3.87 (q, J=6.3 Hz, 1H), 3.54 (td, J=13.6, 6.6 Hz, 2H), 3.44-3.34 (m, 2H), 3.23 (dq, J=14.1, 7.1 Hz, 1H), 2.99 (s, 7H), 1.47 (dt, J=7.3, 3.9 Hz, 7H), 1.41 (t, J=7.2 Hz, 3H).

Example 207

(S)—N-(2-(diethylamino)propyl)-2-(piperazin-1-yl)-6-(5-(thiophen-2-yl)pyrazolo[1,5-a]pyrimidin-3-yl)isonicotinamide

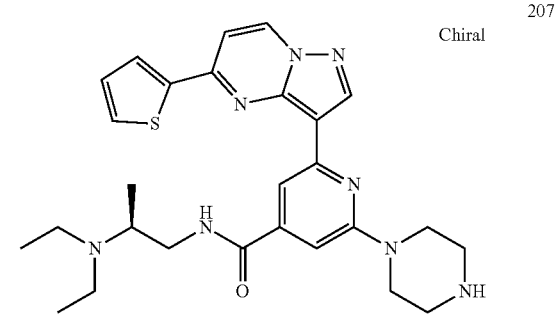 [SMILES: CCN(CC)[C@@H](C)CNC(=O)c1cc(-c2cnn3ccc(-c4cccs4)nc23)nc(N2CCNCC2)c1]

Compound 207 was synthesized as shown in the Example 141, starting from commercially available piperazine, as a TFA salt. LC/MS (M+H): 519.193; 1H NMR (400 MHz, Methanol-d4) δ 8.91 (d, J=7.4 Hz, 1H), 8.78 (s, 1H), 8.41 (d, J=1.1 Hz, 1H), 7.99 (dd, J=3.8, 1.1 Hz, 1H), 7.73 (dd, J=5.0, 1.1 Hz, 1H), 7.57 (d, J=7.4 Hz, 1H), 7.26 (dd, J=5.1, 3.8 Hz, 1H), 7.09 (d, J=1.2 Hz, 1H), 4.04-3.93 (m, 6H), 3.87 (h, J=6.4 Hz, 1H), 3.59-3.49 (m, 2H), 3.43-3.35 (m, 7H), 3.23 (dq, J=14.0, 7.1 Hz, 1H), 1.51-1.44 (m, 7H), 1.41 (t, J=7.2 Hz, 3H).

Example 208

(S)-2-(3-carbamoylazetidin-1-yl)-N-(2-(diethylamino)propyl)-6-(5-(thiophen-2-yl)pyrazolo[1,5-a]pyrimidin-3-yl)isonicotinamide

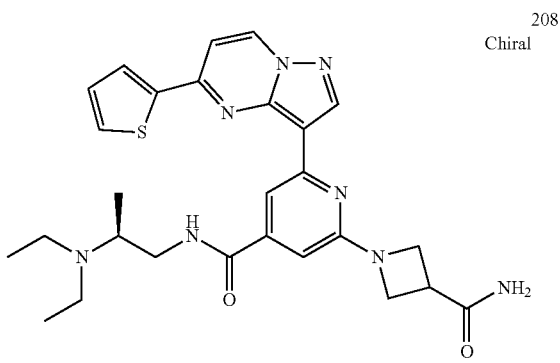 [SMILES: CCN(CC)[C@@H](C)CNC(=O)c1cc(-c2cnn3ccc(-c4cccs4)nc23)nc(N2CC(C(N)=O)C2)c1]

Compound 208 was synthesized as shown in the Example 141, starting from commercially available azetidine-3-carboxamide, as a TFA salt. LC/MS (M+H): 533.250; 1H NMR (400 MHz, Methanol-d4) δ 8.94 (d, J=7.4 Hz, 1H), 8.73 (s, 1H), 8.14 (s, 1H), 8.01 (dd, J=3.8, 1.1 Hz, 1H), 7.76 (dd, J=5.0, 1.1 Hz, 1H), 7.61 (d, J=7.4 Hz, 1H), 7.26 (dd, J=5.1, 3.8 Hz, 1H), 6.74 (d, J=1.3 Hz, 1H), 4.47 (t, J=8.5 Hz, 2H), 4.40 (t, J=7.1 Hz, 2H), 3.95 (dd, J=14.2, 5.8 Hz, 1H), 3.85 (h, J=6.4 Hz, 1H), 3.70 (s, 1H), 3.58-3.48 (m, 2H), 3.42-3.34 (m, 3H), 3.22 (dq, J=14.1, 7.1 Hz, 1H), 1.46 (dd, J=8.1, 7.0 Hz, 7H), 1.40 (t, J=7.3 Hz, 4H).

Example 209

N—((S)-2-(diethylamino)propyl)-2-((S)-3-methoxypyrrolidin-1-yl)-6-(5-(thiophen-2-yl)pyrazolo[1,5-a]pyrimidin-3-yl)isonicotinamide

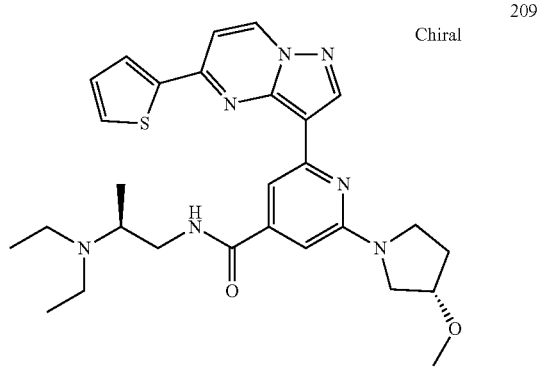 [SMILES: CCN(CC)[C@@H](C)CNC(=O)c1cc(-c2cnn3ccc(-c4cccs4)nc23)nc(N2CC[C@H](OC)C2)c1]

Compound 209 was synthesized as shown in the Example 141, starting from commercially available (S)-3-methoxypyrrolidine, as a TFA salt. LC/MS (M+H): 534.225; 1H NMR (400 MHz, Methanol-d4) δ 8.93 (d, J=7.4 Hz, 1H), 8.73 (s, 1H), 8.01 (dd, J=3.8, 1.1 Hz, 1H), 7.82 (dd, J=5.0, 1.1 Hz, 1H), 7.78 (s, 1H), 7.62 (d, J=7.4 Hz, 1H), 7.28 (dd, J=5.0, 3.8 Hz, 1H), 6.98 (s, 1H), 4.35-4.29 (m, 1H), 3.98-3.76 (m, 6H), 3.54 (ddd, J=27.0, 13.7, 6.6 Hz, 2H), 3.45 (s, 3H), 3.38 (dt, J=9.7, 6.2 Hz, 2H), 3.22 (dt, J=13.8, 6.9 Hz, 1H), 2.28 (dtd, J=13.4, 9.1, 4.6 Hz, 1H), 1.46 (dd, J=7.1, 5.1 Hz, 6H), 1.40 (t, J=7.2 Hz, 3H).

Example 210

(S)—N-(2-(diethylamino)propyl)-2-(3-(4-fluorophenoxy)azetidin-1-yl)-6-(5-(thiophen-2-yl)pyrazolo[1,5-a]pyrimidin-3-yl)isonicotinamide

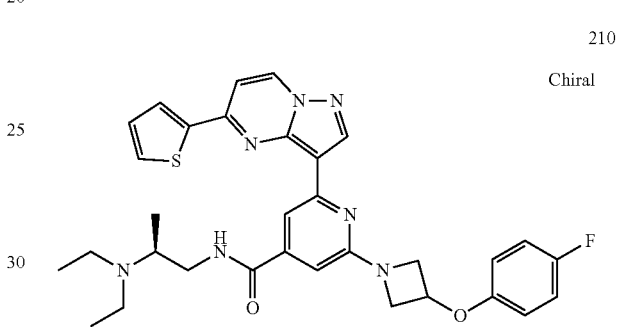

Compound 210 was synthesized as shown in the Example 141, starting from commercially available 3-(4-fluorophenoxy)azetidine, as a TFA salt. LC/MS (M+H): 600.160.

Example 211

(S)—N-(2-(diethylamino)propyl)-2-morpholino-6-(5-(thiophen-2-yl)pyrazolo[1,5-a]pyrimidin-3-yl)isonicotinamide

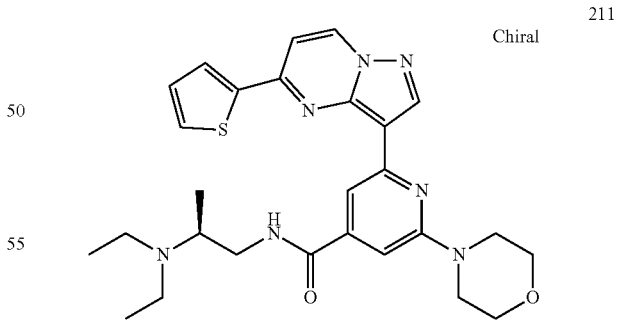

Compound 211 was synthesized as shown in the Example 141, starting from commercially available morpholine, as a TFA salt. LC/MS (M+H): 520.183; 1H NMR (400 MHz, Methanol-d4) δ 8.92-8.87 (m, 1H), 8.75 (d, J=1.6 Hz, 1H), 7.98 (dd, J=3.8, 1.1 Hz, 1H), 7.74 (ddd, J=5.0, 2.1, 1.1 Hz, 1H), 7.56 (d, J=7.4 Hz, 1H), 7.25 (dd, J=5.1, 3.8 Hz, 1H), 7.05-6.98 (m, 1H), 3.96 (dd, J=14.3, 5.9 Hz, 1H), 3.87 (q, J=5.9, 5.2 Hz, 5H), 3.71 (t, J=4.5 Hz, 4H), 3.53 (dd, J=13.1, 7.2 Hz, 2H), 3.44-3.35 (m, 2H), 3.22 (dq, J=14.1, 7.1 Hz, 1H), 1.47 (t, J=7.3 Hz, 6H), 1.41 (t, J=7.2 Hz, 3H).

Example 212

(S)-2-(((1H-pyrazol-3-yl)methyl)amino)-N-(2-(diethylamino)propyl)-6-(5-(thiophen-2-yl)pyrazolo[1,5-a]pyrimidin-3-yl)isonicotinamide

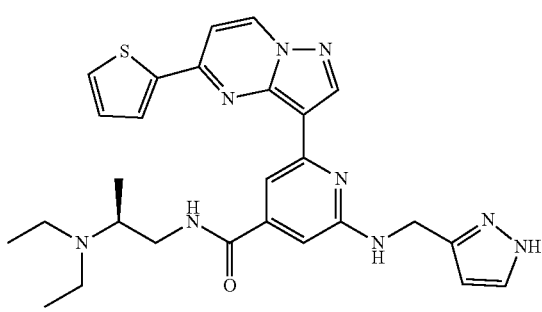

212

Compound 212 was synthesized as shown in the Example 141, starting from commercially available (1H-pyrazol-3-yl)methanamine, as a TFA salt. LC/MS (M+H): 530.2; $^1$H NMR (MeOD, 400 MHz): δ 8.98 (d, 1H), 8.77 (s, 1H), 8.06 (s, 1H), 8.01 (d, 1H), 7.75-7.70 (m, 1H), 7.67-7.55 (m, 2H), 7.26-7.21 (m, 1H), 7.01 (s, 1H), 6.40 (d, 1H), 3.94 (dd, 1H), 3.88-3.81 (m, 1H), 3.53 (dd, 3H), 3.42-3.32 (m, 3H), 3.10 (bs, 2H), 1.48-1.36 (m, 7H).

Example 213

(S)-2-(cyclopropylamino)-N-(2-(diethylamino)propyl)-6-(5-(thiophen-2-yl)pyrazolo[1,5-a]pyrimidin-3-yl)isonicotinamide

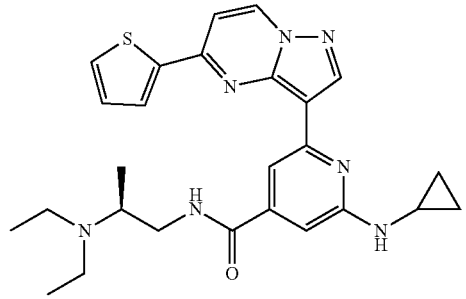

213

Compound 213 was synthesized as shown in the Example 141, starting from commercially available cyclopropylamine, as a TFA salt. LC/MS (M+H): 490.2; $^1$H NMR (MeOD, 400 MHz): δ 9.05 (d, 1H), 8.80 (s, 1H), 8.05 (dd, 1H), 7.92 (s, 1H), 7.79 (dd, 1H), 7.71 (d, 1H), 7.27 (dd, 1H), 7.18 (d, 1H), 3.90 (ddd, 2H), 3.58-3.43 (m, 2H), 3.36 (q, 2H), 3.23 (dd, 2H), 3.00-3.10 (m, 1H), 1.47-1.32 (m, 8H), 1.07 (d, 2H), 0.78 (s, 2H).

Example 214

(S)—N-(2-(diethylamino)propyl)-2-(3-ethyl-3-hydroxyazetidin-1-yl)-6-(5-(thiophen-2-yl)pyrazolo[1,5-a]pyrimidin-3-yl)isonicotinamide

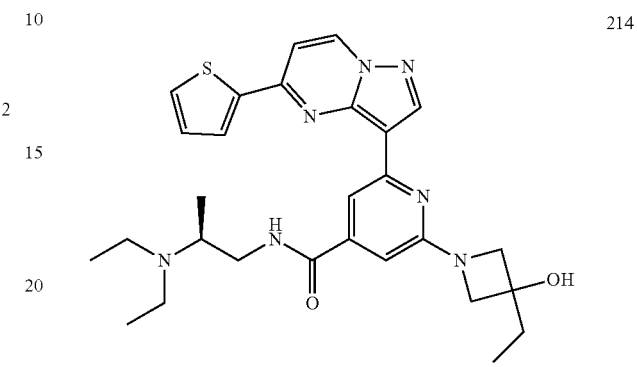

214

Compound 214 was synthesized as shown in the Example 141, starting from commercially available 3-ethylazetidin-3-ol, as a TFA salt. LC/MS (M+H): 534.3; $^1$H NMR (MeOD, 400 MHz): δ 9.00 (d, 1H), 8.77 (s, 1H), 8.07-8.01 (m, 1H), 7.95 (s, 1H), 7.80 (d, 1H), 7.68 (d, 1H), 7.26 (dd, 1H), 6.87 (s, 1H), 4.36 (d, 2H), 4.23 (d, 2H), 3.94 (dd, 1H), 3.88-3.82 (m, 1H), 3.51 (dd, 2H), 3.36 (q, 2H), 3.22 (dd, 1H), 1.92 (q, 2H), 1.47-1.37 (m, 9H), 1.07 (t, 3H).

Example 215

(S)—N-(2-(diethylamino)propyl)-2-(3-(2-hydroxypropan-2-yl)azetidin-1-yl)-6-(5-(thiophen-2-yl)pyrazolo[1,5-a]pyrimidin-3-yl)isonicotinamide

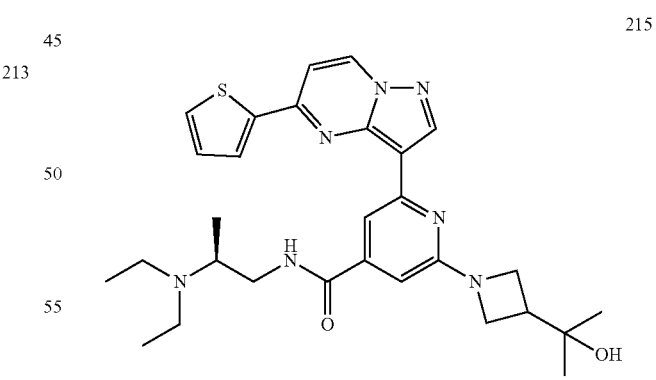

215

Compound 215 was synthesized as shown in the Example 141, starting from commercially available 2-(azetidin-3-yl)propan-2-ol, as a TFA salt. LC/MS (M+H): 548.3; $^1$H NMR (MeOD, 400 MHz): δ 8.95 (d, 1H), 8.75 (s, 1H), 8.10-8.12 (m, 1H), 8.01 (s, 1H), 7.75 (d, 1H), 6.70-6.72 (m, 1H), 4.23 (s, 3H), 3.80-3.95 (m, 2H), 3.42-3.58 (m, 2H), 3.10-3.40 (m, 2H), 2.95 (s, 3H), 1.45 (d, 9H), 1.25 (s, 6H).

Example 216

(S)—N-(2-(diethylamino)propyl)-2-(3-(hydroxymethyl)azetidin-1-yl)-6-(5-(thiophen-2-yl)pyrazolo[1,5-a]pyrimidin-3-yl)isonicotinamide

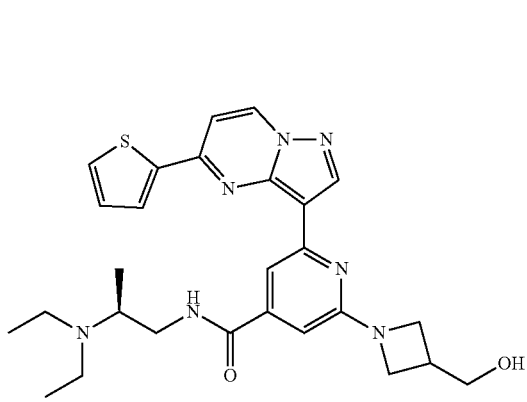

Compound 216 was synthesized as shown in the Example 141, starting from commercially available azetidin-3-yl-methanol, as a TFA salt. LC/MS (M+H): 520.2; $^1$H NMR (MeOD, 400 MHz): δ 8.90 (d, 1H), 8.73 (s, 1H), 8.38 (s, 1H), 7.98 (d, 1H), 7.73 (d, 1H), 7.56 (d, 1H), 7.25 (t, 1H), 6.67 (s, 1H), 4.44 (d, 2H), 4.17 (bs, 2H), 4.12 (d, 2H), 3.95 (dd, 1H), 3.89-3.82 (m, 1H), 3.53 (dd, 2H), 3.41-3.33 (m, 2H), 3.21 (dd, 1H), 3.10-3.19 (m, 1H), 1.47 (dd, 6H), 1.40 (t, 3H).

Example 217

(S)-2-(3-cyclopropyl-3-hydroxyazetidin-1-yl)-N-(2-(diethylamino)propyl)-6-(5-(thiophen-2-yl)pyrazolo[1,5-a]pyrimidin-3-yl)isonicotinamide

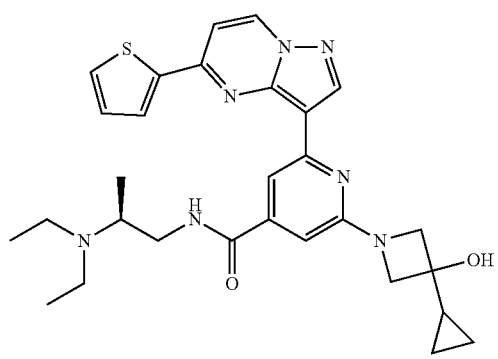

Compound 217 was synthesized as shown in the Example 141, starting from commercially available 3-cyclopropylazetidin-3-ol, as a TFA salt. LC/MS (M+H): 546.3

Example 218

(S)—N-(2-(diethylamino)propyl)-2-((3-methoxypropyl)amino)-6-(5-(thiophen-2-yl)pyrazolo[1,5-a]pyrimidin-3-yl)isonicotinamide

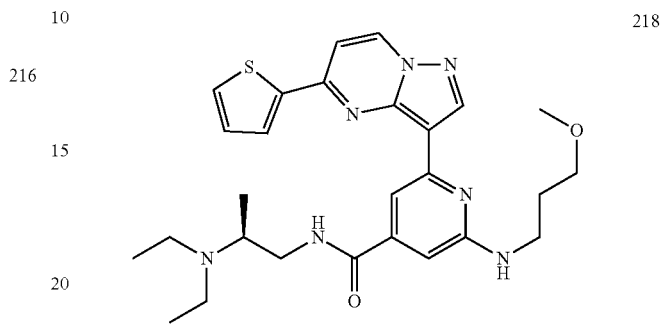

Compound 218 was synthesized as shown in the Example 141, starting from commercially available 3-methoxypropan-1-amine, as a TFA salt. LC/MS (M+H): 522.3; $^1$H NMR (MeOD, 400 MHz): δ 9.02 (d, 1H), 8.75 (s, 1H), 8.06 (d, 1H), 7.85-7.95 (m, 1H), 7.80 (d, 1H), 7.70 (d, J=7.4 Hz, 1H), 7.31-7.25 (m, 1H), 7.04-7.10 (m, 1H), 3.95 (dd, 1H), 3.85 (q, 1H), 3.75 (s, 2H), 3.58-3.47 (m, 4H), 3.37 (q, 2H), 3.30 (s, 3H), 3.20-3.22 (m, 1H), 2.11-2.02 (m, 2H), 1.50-1.35 (m, 9H).

Example 219

(S)—N-(2-(diethylamino)propyl)-2-(3-hydroxy-3-(trifluoromethyl)azetidin-1-yl)-6-(5-(thiophen-2 yl)pyrazolo[1,5-a]pyrimidin-3-yl)isonicotinamide

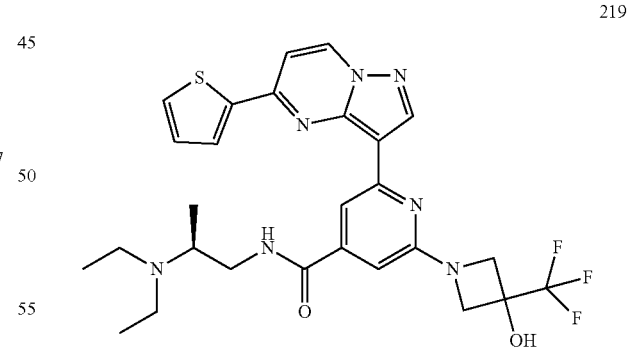

Compound 219 was synthesized as shown in the Example 141, starting from commercially available 3-(trifluoromethyl)azetidin-3-ol, as a TFA salt. LC/MS (M+H): 574.2; $^1$H NMR (MeOD, 400 MHz): δ 8.90 (d, 1H), 8.73 (s, 1H), 8.38 (s, 1H), 7.98 (d, 1H), 7.73 (d, 1H), 7.56 (d, 1H), 7.25 (t, 1H), 6.67 (s, 1H), 4.44 (d, 2H), 4.12 (d, 2H), 3.95 (dd, 1H), 3.89-3.82 (m, 1H), 3.53 (dd, 2H), 3.41-3.33 (m, 2H), 3.21 (dd, 1H), 1.47 (dd, 6H), 1.40 (t, 3H).

Example 220

(S)—N-(2-(diethylamino)propyl)-2-((3-hydroxypropyl)amino)-6-(5-(thiophen-2-yl)pyrazolo[1,5-a]pyrimidin-3-yl)isonicotinamide

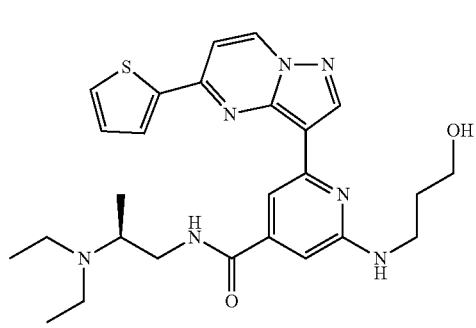

Compound 220 was synthesized as shown in the Example 141, starting from commercially available 3-aminopropan-1-ol, as a TFA salt. LC/MS (M+H): 508.2; $^1$H NMR (MeOD, 400 MHz): δ 9.02 (d, 1H), 8.77 (s, 1H), 8.06 (d, 1H), 7.85-7.95 (m, 1H), 7.81 (d, 1H), 7.70 (d, J=7.4 Hz, 1H), 7.31-7.25 (m, 1H), 7.05-7.10 (m, 1H), 3.95 (dd, 1H), 3.85 (q, 1H), 3.75 (s, 2H), 3.58-3.47 (m, 4H), 3.37 (q, 2H), 3.20-3.25 (m, 1H), 2.11-2.02 (m, 2H), 1.49-1.35 (m, 9H).

Example 221

(S)—N-(2-(diethylamino)propyl)-2-((3-hydroxy-3-methylbutyl)amino)-6-(5-(thiophen-2-yl)pyrazolo[1,5-a]pyrimidin-3-yl)isonicotinamide

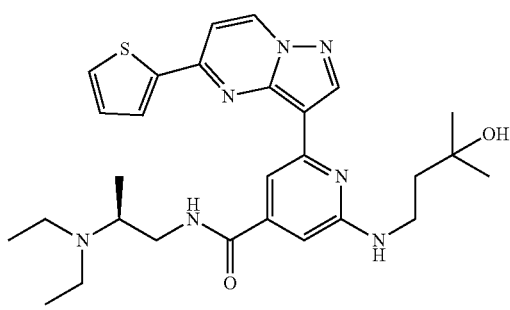

Compound 221 was synthesized as shown in the Example 141, starting from commercially available 4-amino-2-methylbutan-2-ol, as a TFA salt. LC/MS (M+H): 536.3; 1H NMR (MeOD, 400 MHz): δ 9.01 (d, 1H), 8.76 (s, 1H), 8.04 (d, 2H), 7.79 (d, 1H), 7.69 (d, 1H), 7.27 (dd, 1H), 7.03 (s, 1H), 3.95 (dd, 1H), 3.85 (d, 1H), 3.73 (s, 2H), 3.54-3.48 (m, 1H), 3.37 (d, 1H), 1.94 (t, 2H), 1.48-1.35 (m, 11H), 1.31 (s, 6H), 1.25 (s, 1H).

Example 222

(S)—N-(2-(diethylamino)propyl)-2-((tetrahydro-2H-pyran-4-yl)amino)-6-(5-(thiophen-2-yl)pyrazolo[1,5-a]pyrimidin-3-yl)isonicotinamide

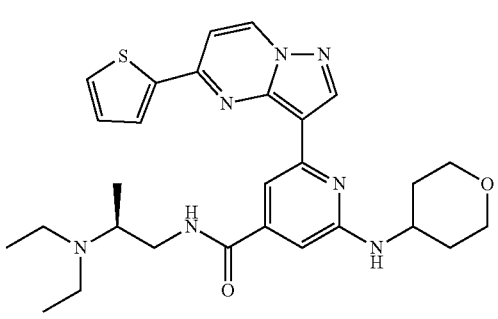

Compound 222 was synthesized as shown in the Example 141, starting from commercially available tetrahydro-2H-pyran-4-amine, as a TFA salt. LC/MS (M+H): 534.3; $^1$H NMR (MeOD, 400 MHz): δ 8.92 (s, 1H), 8.70 (s, 1H), 8.13 (d, 1H), 7.99 (d, 1H), 7.72 (d, 1H), 7.57 (d, 1H), 7.24 (dd, 1H), 6.75 (s, 1H), 3.82-4.05 (m, 4H), 3.62 (t, 2H), 3.36-3.55 (m, 6H), 3.10-3.25 (m, 2H), 2.10 (dd, 1H), 1.62 (bs, 1H), 1.39-1.49 (m, 9H).

Example 223

(S)—N-(2-(diethylamino)propyl)-2-((2-morpholinoethyl)amino)-6-(5-(thiophen-2-yl)pyrazolo[1,5-a]pyrimidin-3-yl)isonicotinamide

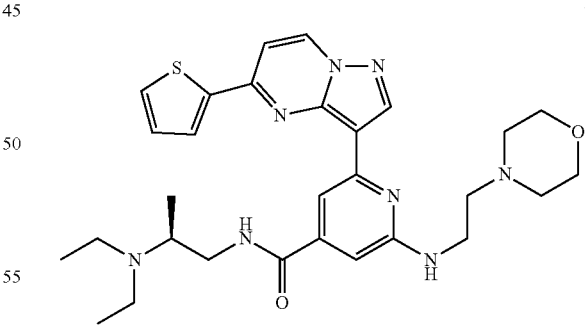

Compound 223 was synthesized as shown in the Example 141, starting from commercially available 2-morpholinoethan-1-amine, as a TFA salt. LC/MS (M+H): 563.3; $^1$H NMR (MeOD, 400 MHz): δ 8.92 (d, 1H), 8.75 (s, 1H), 8.17 (d, 1H), 8.00-7.96 (m, 1H), 7.75-7.71 (m, 1H), 7.58 (d, 1H), 7.25 (d, 1H), 6.80 (d, 1H), 4.01-3.92 (m, 2H), 3.80 (s, 5H), 3.54-3.43 (m, 7H), 3.37 (d, 2H), 3.24 (d, 1H), 1.49-1.36 (m, 11H).

Example 224

(S)—N-(2-(diethylamino)propyl)-2-((2-(3,3-difluoroazetidin-1-yl)ethyl)amino)-6-(5-(thiophen-2-yl)pyrazolo[1,5-a]pyrimidin-3-yl)isonicotinamide

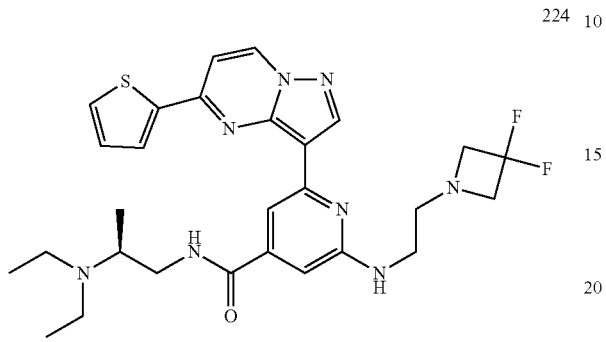

Compound 224 was synthesized as shown in the Example 141, starting from commercially available 3,3-difloroazetidine, as a TFA salt. LC/MS (M+H): 569.3; $^1$H NMR (MeOD, 400 MHz): δ 8.93 (d, 1H), 8.77 (s, 1H), 8.18 (d, 1H), 8.00 (dd, 1H), 7.74 (dd, 1H), 7.59 (d, 1H), 7.26 (dd, 1H), 6.84 (d, 1H), 4.63 (t, 3H), 3.95 (dd, 1H), 3.86 (t, 3H), 3.64 (t, 2H), 3.52 (dd, 2H), 3.32-3.40 (m, 4H), 3.23 (dd, 1H), 1.50-1.34 (m, 8H).

Example 225

(S)—N-(2-(diethylamino)propyl)-2-((2-methoxyethyl)amino) 6 (5 (thiophen-2-yl)pyrazolo[1,5-a]pyrimidin-3-yl)isonicotinamide

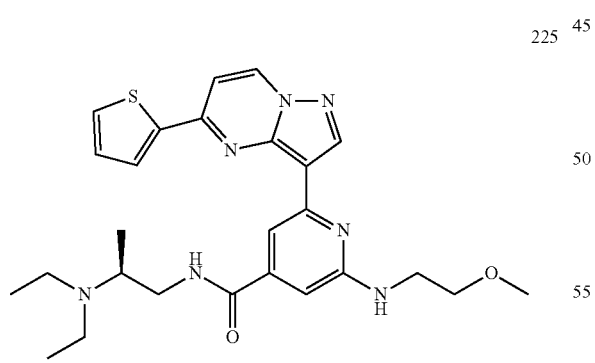

Compound 225 was synthesized as shown in the Example 141, starting from commercially available 2-methoxyethylamine, as a TFA salt. LC/MS (M+H): 508.2; $^1$H NMR (MeOD, 400 MHz): δ 9.00 (d, 1H), 8.76 (s, 1H), 8.05 (dd, 1H), 7.87 (s, 1H), 7.83 (dd, 1H), 7.69 (d, 1H), 7.28 (dd, 1H), 7.14 (d, 1H), 3.97-3.82 (m, 4H), 3.76 (dd, 2H), 3.53 (ddd, 3H), 3.36 (dd, 2H), 3.30 (s, 3H), 3.22 (dd, 1H), 1.46-1.37 (m, 8H).

Example 226

(S)—N-(2-(diethylamino)propyl)-2-(3-hydroxy-3-methylazetidin-1-yl)-6-(5-(thiophen-2-yl)pyrazolo[1,5-a]pyrimidin-3-yl)isonicotinamide

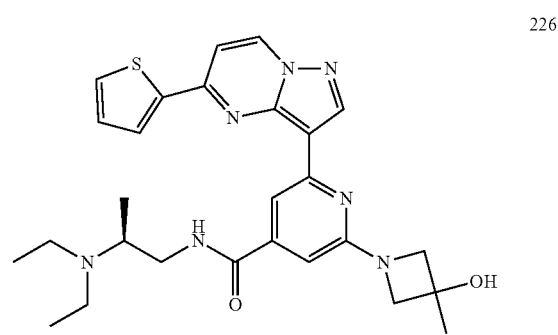 [SMILES: CCN(CC)[C@@H](C)CNC(=O)c1cc(-c2cnn3ccc(-c4cccs4)nc23)nc(N2CC(C)(O)C2)c1]

Compound 226 was synthesized as shown in the Example 141, starting from commercially available 3-methylazetidin-3-ol, as a TFA salt. LC/MS (M+H): 520.2; $^1$H NMR (MeOD, 400 MHz): δ 8.99 (d, 1H), 8.76 (s, 1H), 8.04 (dd, 1H), 7.98 (s, 1H), 7.80 (dd, 1H), 7.67 (d, 1H), 7.28 (dd, 1H), 6.85 (d, 1H), 4.35-4.25 (m, 4H), 3.94 (dd, 1H), 3.85 (q, 1H), 3.57-3.46 (m, 2H), 3.37 (q, 2H), 3.22 (dd, 1H), 1.64 (s, 3H), 1.49-1.35 (m, 9H).

Example 227

(S)—N-(2-(diethylamino)propyl)-2-(3-methoxy-3-methylazetidin-1-yl)-6-(5-(thiophen-2-yl)pyrazolo[1,5-a]pyrimidin-3-yl)isonicotinamide

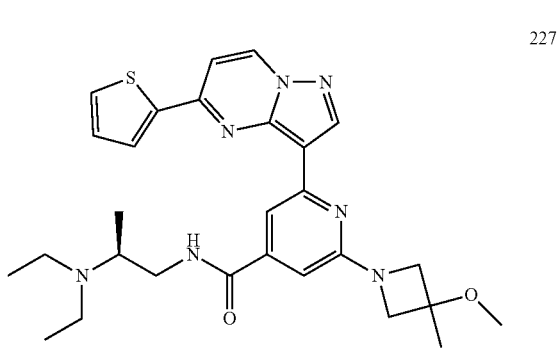 [SMILES: CCN(CC)[C@@H](C)CNC(=O)c1cc(-c2cnn3ccc(-c4cccs4)nc23)nc(N2CC(C)(OC)C2)c1]

Compound 227 was synthesized as shown in the Example 141, starting from commercially available 3-methoxy-3-methylazetidine, as a TFA salt. LC/MS (M+H): 534.3; $^1$H NMR (MeOD, 400 MHz): δ 8.98 (d, 1H), 8.76 (s, 1H), 8.04 (dd, 1H), 8.00 (s, 1H), 7.81 (dd, 1H), 7.66 (d, 1H), 7.28 (dd, 1H), 6.84 (d, 1H), 4.34 (d, 2H), 4.21 (d, 2H), 3.94 (dd, 1H), 3.85 (q, 1H), 3.57-3.47 (m, 2H), 3.37 (s, 5H), 3.22 (dd, 1H), 1.64 (s, 3H), 1.47-1.37 (m, 9H).

Example 228

(S)—N-(2-(diethylamino)propyl)-2-(methylamino)-6-(5-(thiophen-2-yl)pyrazolo[1,5-a]pyrimidin-3-yl)isonicotinamide

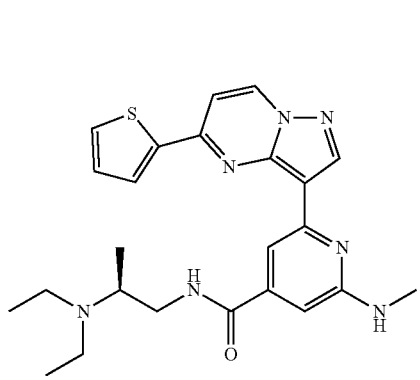

Compound 228 was synthesized as shown in the Example 141, starting from commercially available methylamine, as a TFA salt. LC/MS (M+H): 464.2; $^1$H NMR (MeOD, 400 MHz): δ 9.02 (d, 1H), 8.77 (s, 1H), 8.05 (d, 1H), 7.90 (bs, 1H), 7.80 (d, 1H), 7.69 (d, 1H), 7.28 (dd, 1H), 7.1 (bs, 1H), 3.80-4.00 (m, 3H), 3.10-3.60 (m, 7H), 1.37-1.48 (m, 9H).

Example 229

(S)—N-(2-(diethylamino)propyl)-2-((2-hydroxyethyl)amino)-6-(5-(thiophen-2-yl)pyrazolo[1,5-a]pyrimidin-3-yl)isonicotinamide

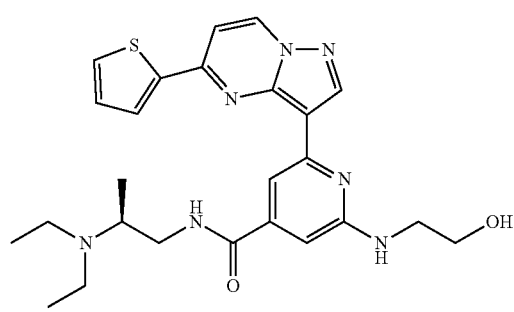

Compound 229 was synthesized as shown in the Example 141, starting from commercially available 2-aminoethan-1-ol, as a TFA salt. LC/MS (M+H): 494.2; $^1$H NMR (MeOD, 400 MHz): δ 8.99 (d, 1H), 8.74 (s, 1H), 8.07-7.99 (m, 2H), 7.79 (d, 1H), 7.68 (d, 1H), 7.28-7.25 (m, 1H), 7.03 (s, 1H), 4.13 (t, 1H), 3.92-3.78 (m, 5H), 3.53 (dd, 2H), 3.37 (d, 2H), 3.23 (d, 1H), 1.47-1.39 (m, 9H).

Example 230

(S)—N-(2-(diethylamino)propyl)-2-(3,3,4,4-tetrafluoropyrrolidin-1-yl)-6-(5-(thiophen-2-yl)pyrazolo[1,5-a]pyrimidin-3-yl)isonicotinamide

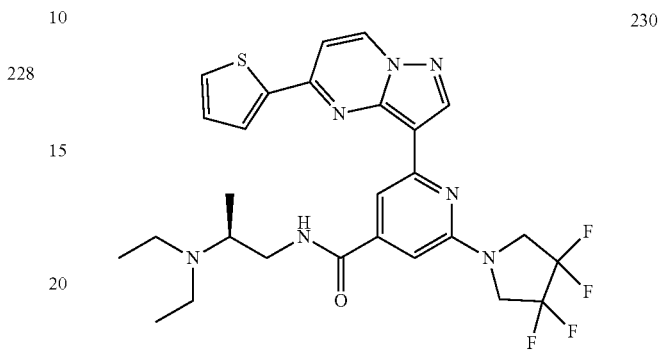

Compound 230 was synthesized as shown in the Example 141, starting from commercially available 3,3,4,4-tetrafluoropyrrolidine, as a TFA salt. LC/MS (M+H): 576.2; $^1$H NMR (MeOD, 400 MHz): δ 8.90 (d, 1H), 8.78 (s, 1H), 8.42 (s, 1H), 7.96 (d, 1H), 7.70 (d, 1H), 7.55 (d, 1H), 7.24 (dd, 1H), 6.73 (s, 1H), 4.56 (s, 1H), 4.15-4.25 (m, 4H), 3.70-3.90 (m, 2H), 3.46 (bs, 2H), 3.12 (bs, 2H), 1.27-1.43 (m, 9H).

Example 231

(S)-2-((1H-pyrazol-4-yl)amino)-N-(2-(diethylamino)propyl)-6-(5-(thiophen-2-yl)pyrazolo[1,5-a]pyrimidin-3-yl)isonicotinamide

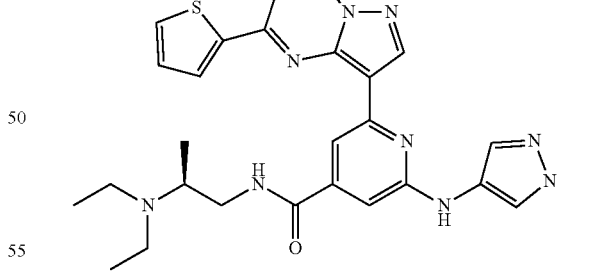

Compound 231 was synthesized as shown in the Example 141, starting from commercially available 4-aminopyrazole, as a TFA salt. LC/MS (M+H): 516.2; $^1$H NMR (MeOD, 400 MHz): δ 8.92 (d, 1H), 8.87 (d, 1H), 8.83 (s, 1H), 8.14 (s, 1H), 8.06-7.90 (m, 2H), 7.78 (d, 1H), 7.76-7.72 (m, 1H), 7.57 (d, 1H), 7.27-7.23 (m, 1H), 4.02-3.96 (m, 1H), 3.59-3.52 (m, 2H), 3.38 (d, 1H), 3.23 (d, 1H), 3.10-3.14 (m, 1H), 2.98 (s, 1H), 2.85 (s, 1H), 1.48 (d, 5H), 1.41 (t, 3H).

Example 232

(S)—N-(2-(diethylamino)propyl)-2-(3,3-difluoropyrrolidin-1-yl)-6-(5-(thiophen-2-yl)pyrazolo[1,5-a]pyrimidin-3-yl)isonicotinamide

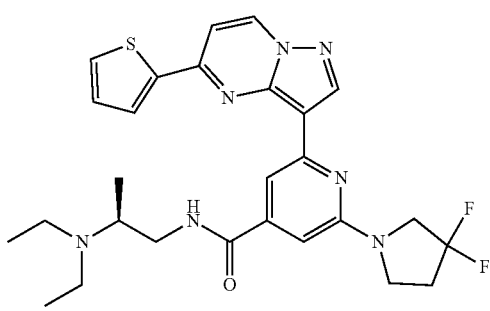

Compound 232 was synthesized as shown in the Example 141, starting from commercially available 3,3-difluoropyrrolidine, as a TFA salt. LC/MS (M+H): 540.2

Example 233

(S)—N-(2-(diethylamino)propyl)-2-(2-oxa-6-azaspiro[3.4]octan-6-yl)-6-(5-(thiophen-2-yl)pyrazolo[1,5-a]pyrimidin-3-yl)isonicotinamide

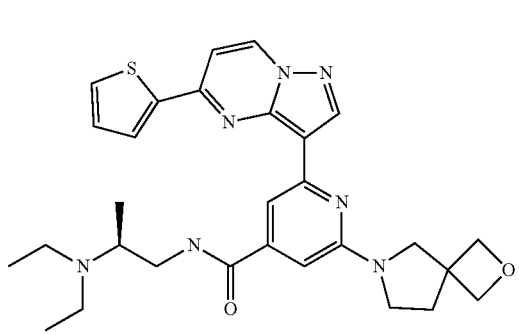

Compound 233 was synthesized as shown in the Example 141, starting from commercially available 2-oxa-6-azaspiro[3.4]octane, as a TFA salt. LC/MS (M+H): 546.3; $^1$H NMR (MeOD, 400 MHz): δ8.91 (d, 1H), 8.74 (s, 1H), 8.15 (s, 1H), 7.95 (d, 1H), 7.73 (d, 1H), 7.55 (d, 1H), 7.24 (dd, 1H), 6.72 (s, 1H), 4.61 (t, 1H), 4.15 (d, 1H), 3.75-3.96 (m, 4H), 3.10-3.60 (m, 11H), 1.35-1.50 (m, 9H).

Example 234

(S)—N-(2-(diethylamino)propyl)-2-(6-oxa-1-azaspiro[3.3]heptan-1-yl)-6-(5-(thiophen-2-yl)pyrazolo[1,5-a]pyrimidin-3-yl)isonicotinamide

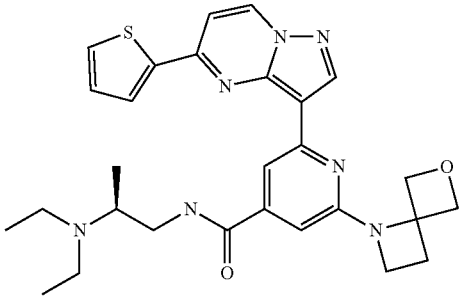

Compound 234 was synthesized as shown in the Example 141, starting from commercially available 6-oxa-1-azaspiro[3.3]heptane, as a TFA salt. LC/MS (M+H): 532.2; $^1$H NMR (MeOD, 400 MHz): $^1$H NMR (MeOD, 400 MHz): δ 8.90 (d, 1H), 8.74 (s, 1H), 8.21 (s, 1H), 7.94 (d, 1H), 7.73 (d, 1H), 7.55 (d, 1H), 7.24 (dd, 1H), 6.72 (s, 1H), 4.61 (t, 1H), 4.13 (bs, 1H), 3.75-3.96 (m, 4H), 3.10-3.60 (m, 9H), 1.35-1.50 (m, 9H).

Example 235

2-(((R)-1-amino-1-oxopropan-2-yl)amino)-N—((S)-2-(diethylamino)propyl)-6-(5-(thiophen-2-yl)pyrazolo[1,5-a]pyrimidin-3-yl)isonicotinamide

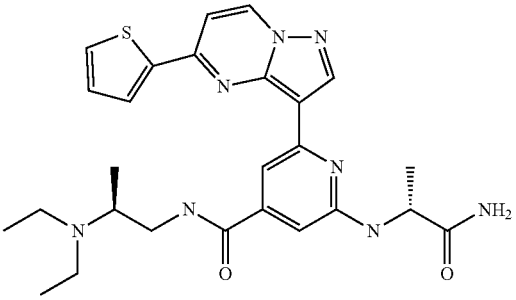

Compound 235 was synthesized as shown in the Example 141, starting from commercially available (R)-2-aminopropanamide, as a TFA salt. LC/MS (M+H): 521.2

Example 236

2-(((S)-1-amino-1-oxopropan-2-yl)amino)-N—((S)-2-(diethylamino)propyl)-6-(5-(thiophen-2-yl)pyrazolo[1,5-a]pyrimidin-3-yl)isonicotinamide

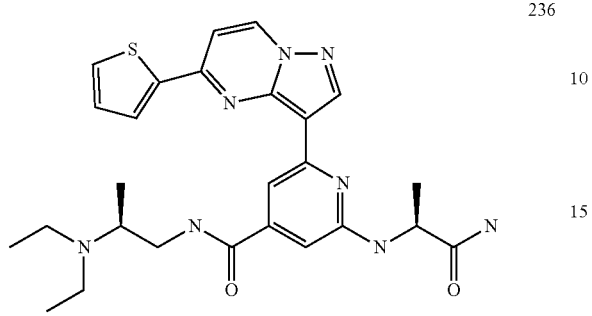

Compound 236 was synthesized as shown in the Example 141, starting from commercially available (S)-2-aminopropanamide, as a TFA salt. LC/MS (M+H): 521.2

Example 237

(S)-2-(((1H-imidazol-2-yl)methyl)amino)-N-(2-(diethylamino)propyl)-6-(5-(thiophen-2-yl)pyrazolo[1,5-a]pyrimidin-3-yl)isonicotinamide

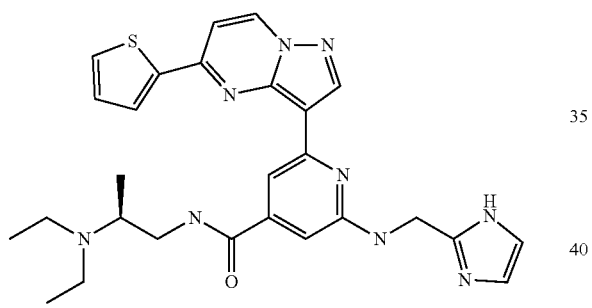

Compound 237 was synthesized as shown in the Example 141, starting from commercially available (1H-imidazol-2-yl)methanamine, as a TFA salt. LC/MS (M+H): 530.2

Example 238

(S)-2-((2-amino-2-oxoethyl)amino)-N-(2-(diethylamino)propyl)-6-(5-(thiophen-2-yl)pyrazolo[1,5-a]pyrimidin-3-yl)isonicotinamide

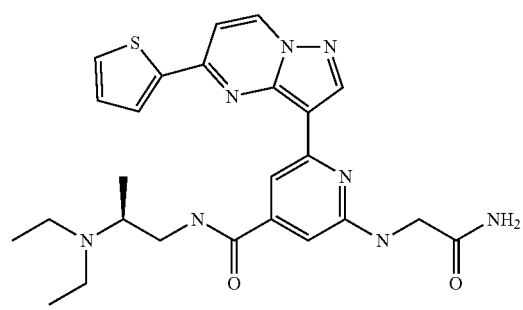

Compound 238 was synthesized as shown in the Example 141, starting from commercially available 2 aminoacetamide, as a TFA salt. LC/MS (M+H): 507.2

Example 239

N—((S)-2-(diethylamino)propyl)-2-(((R)-1-(methylamino)-1-oxopropan-2-yl)amino)-6-(5-(thiophen-2-yl)pyrazolo[1,5-a]pyrimidin-3-yl)isonicotinamide

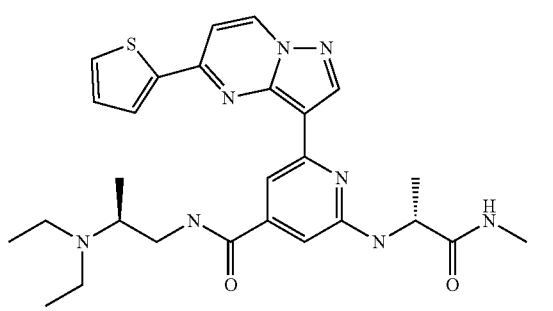

Compound 239 was synthesized as shown in the Example 141, starting from commercially available (R)-2-amino-N-methylpropanamide, as a TFA salt. LC/MS (M+H): 535.3

Example 240

N—((S)-2-(diethylamino)propyl)-2-(((S)-1-(methylamino)-1-oxopropan-2-yl)amino)-6-(5-(thiophen-2-yl)pyrazolo[1,5-a]pyrimidin-3-yl)isonicotinamide

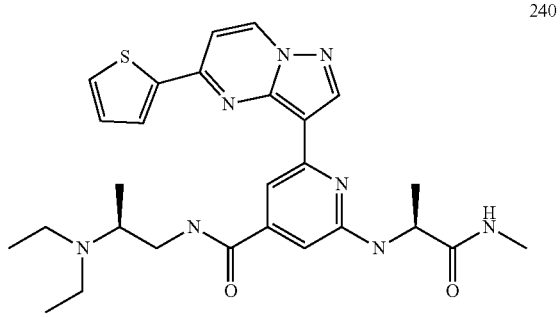 [SMILES: CCN(CC)[C@@H](C)CNC(=O)c1cc(N[C@@H](C)C(=O)NC)nc(-c2cnn3ccc(-c4cccs4)nc23)c1]

Compound 240 was synthesized as shown in the Example 141, starting from commercially available (S)-2-amino-N-methylpropanamide, as a TFA salt. LC/MS (M+H): 535.3

Example 241

(S)-2-((1H-imidazol-2-yl)amino)-N-(2-(diethyl-amino)propyl)-6-(5-(thiophen-2-yl)pyrazolo[1,5-a]pyrimidin-3-yl)isonicotinamide

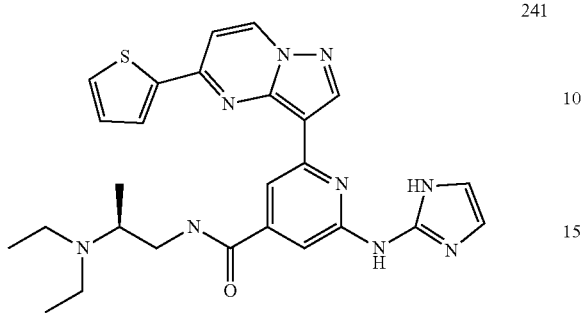

241

Compound 241 was synthesized as shown in the Example 141, starting from commercially available 1H-imidazol-2-amine, as a TFA salt. LC/MS (M+H): 516.2

Example 242

(S)—N-(2-(diethylamino)propyl)-2-((2-sulfamoyl-ethyl)amino)-6-(5-(thiophen-2-yl)pyrazolo[1,5-a]pyrimidin-3-yl)isonicotinamide

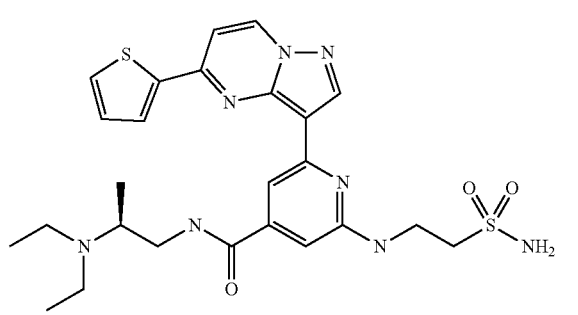

242

Compound 242 was synthesized as shown in the Example 141, starting from commercially available 2-aminoethane-1-sulfonamide, as a TFA salt. LC/MS (M+H): 557.2

Example 243

N—((S)-2-(diethylamino)propyl)-2-((3S,4S)-3,4-dihydroxypyrrolidin-1-yl)-6-(5-(thiophen-2-yl)pyrazolo[1,5-a]pyrimidin-3-yl)isonicotinamide

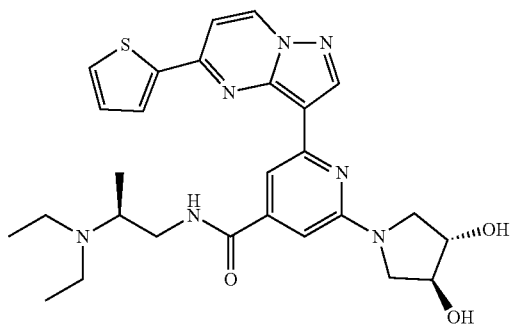

243

Compound 243 was synthesized as shown in the Example 141, starting from commercially available (3S,4S)-pyrrolidine-3,4-diol, as a TFA salt. LC/MS (M+H): 536.2

Example 244

(S)-2-(3,3-bis(hydroxymethyl)azetidin-1-yl)-N-(2-(diethylamino)propyl)-6-(5-(thiophen-2-yl)pyrazolo[1,5-a]pyrimidin-3-yl)isonicotinamide

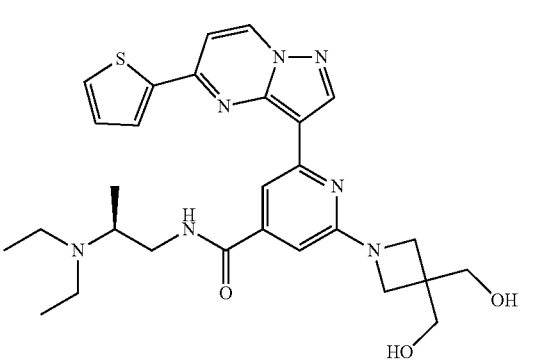

244

Compound 244 was synthesized as shown in the Example 141, starting from commercially available azetidine-3,3-diyldimethanol, as a TFA salt. LC/MS (M+H): 550.3

Example 245

(S)—N-(2-(ethylamino)propyl)-2-(3-hydroxy-3-methylazetidin-1-yl)-6-(5-(thiophen-2-yl)pyrazolo[1,5-a]pyrimidin-3-yl)isonicotinamide

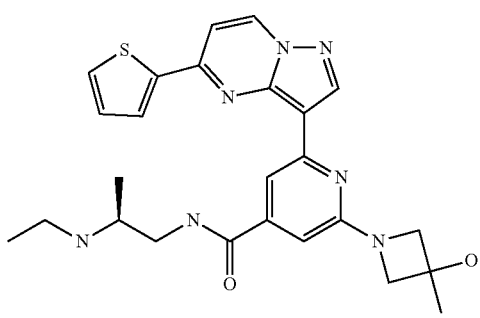

245

Compound 245 was synthesized as shown in the Example 141, starting from commercially available 3-methylazetidin-3-ol, as a TFA salt. LC/MS (M+H): 492.2

Example 246

(S)—N-(2-(diethylamino)propyl)-2-((2-(methyl-amino)-2-oxoethyl)amino)-6-(5-(thiophen-2-yl)pyrazolo[1,5-a]pyrimidin-3-yl)isonicotinamide

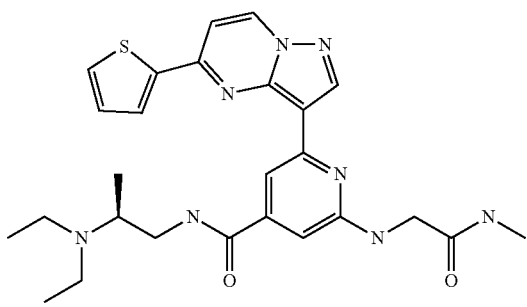

Compound 246 was synthesized as shown in the Example 141, starting from commercially available 2-amino-N-methylacetamide, as a TFA salt. LC/MS (M+H): 521.2

Example 247

(S)—N-(2-(diethylamino)propyl)-2-(4-methoxypiperidin-1-yl)-6-(5-(thiophen-2-yl)pyrazolo[1,5-a]pyrimidin-3-yl)isonicotinamide

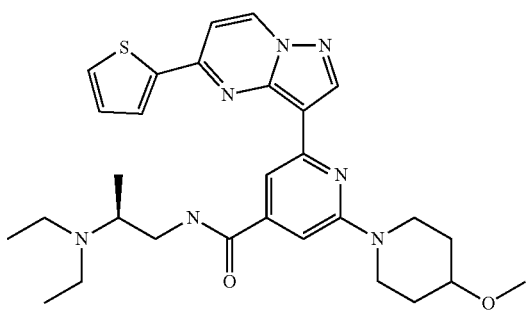

Compound 247 was synthesized as shown in the Example 141, starting from commercially available 4-methoxypiperidine, as a TFA salt. LC/MS (M+H): 548.3

Example 248

(S)—N-(2-(diethylamino)propyl)-2-(3-(dimethyl-amino)-3-methylazetidin-1-yl)-6-(5-(thiophen-2-yl)pyrazolo[1,5-a]pyrimidin-3-yl)isonicotinamide

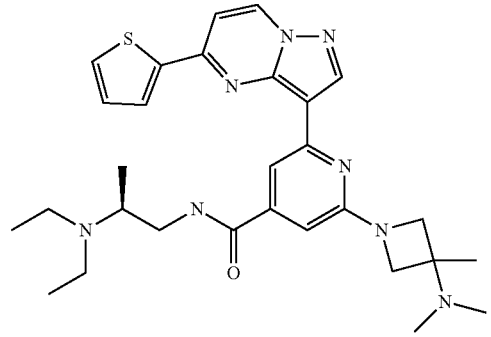

Compound 248 was synthesized as shown in the Example 141, starting from commercially available N,N,3-trimethylazetidin-3-amine, as a TFA salt. LC/MS (M+H): 547.3

Example 249

(S)—N-(2-(diethylamino)propyl)-2-(5,5-difluoro-2-azaspiro[3.3]heptan 2 yl)-6-(5-(thiophen-2-yl)pyrazolo[1,5-a]pyrimidin-3-yl)isonicotinamide

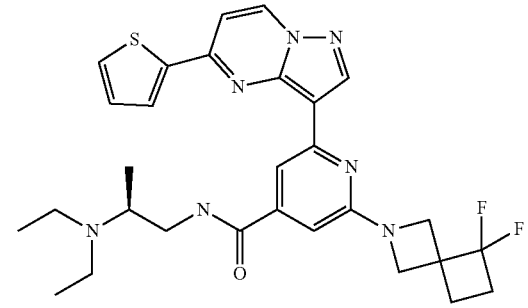

Compound 249 was synthesized as shown in the Example 141, starting from commercially available 5,5-difluoro-1-azaspiro[3.3]heptane, as a TFA salt. LC/MS (M+H): 566.2

Example 250

(S)—N-(2-(diethylamino)propyl)-2-(1-azaspiro[3.3]heptan-1-yl)-6-(5-(thiophen-2-yl)pyrazolo[1,5-a]pyrimidin-3-yl)isonicotinamide

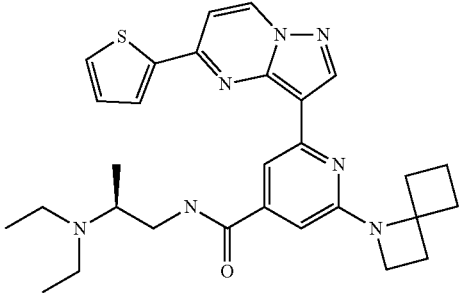

Compound 250 was synthesized as shown in the Example 141, starting from commercially available 1-azaspiro[3.3]heptane, as a TFA salt. LC/MS (M+H): 530.3

Example 251

N—((S)-2-(diethylamino)propyl)-2-(5-(thiophen-2-yl)pyrazolo[1,5-a]pyrimidin-3-yl)-6-((R)-2-(trifluoromethyl)pyrrolidin-1-yl)isonicotinamide

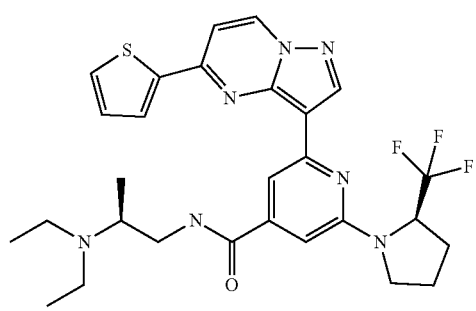

Compound 251 was synthesized as shown in the Example 141, starting from commercially available (R)-2-(trifluoromethyl)pyrrolidine, as a TFA salt. LC/MS (M+H): 572.2

Example 252

(S)—N-(2-(diethylamino)propyl)-2-(5-(thiophen-2-yl)pyrazolo[1,5-a]pyrimidin-3-yl)-6-(1H-1,2,4-triazol-1-yl)isonicotinamide

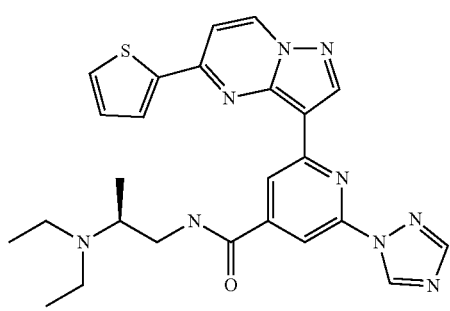

Compound 252 was synthesized as shown in the Example 141, starting from commercially available 1H-1,2,4-triazole, as a TFA salt. LC/MS (M+H): 502.2

Example 253

2-((1S,4S)-2-oxa-5-azabicyclo[2.2.1]heptan-5-yl)-N—((S)-2-(diethylamino)propyl)-6-(5-(thiophen-2-yl)pyrazolo[1,5-a]pyrimidin-3-yl)isonicotinamide

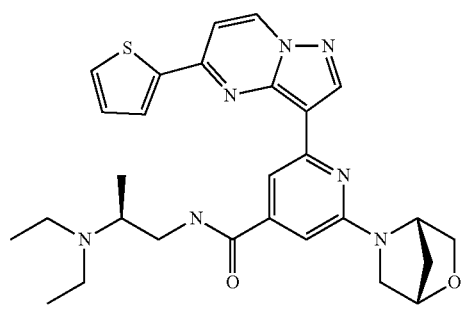

Compound 253 was synthesized as shown in the Example 141, starting from commercially available (1S,4S)-2-oxa-5-azabicyclo[2.2.1]heptane, as a TFA salt. LC/MS (M+H): 532.2

Example 254

N-(2-(diethylamino)ethyl)-2-(3-methoxyazetidin-1-yl)-6-(5-(thiophen-2-yl)pyrazolo[1,5-a]pyrimidin-3-yl)isonicotinamide

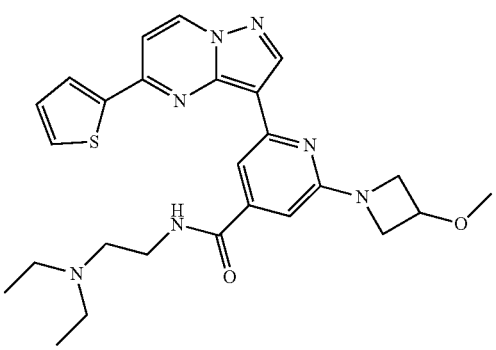

Compound 254 was synthesized as shown in the Example 141, coupling with commercially available N1,N1-diethylethane-1,2-diamine, as a TFA salt. LC/MS (M+H): 506.2; 1H NMR (400 MHz, Methanol-d4) δ 8.69 (d, J=7.3 Hz, 1H), 8.44 (s, 1H), 7.82 (d, J=3.7 Hz, 1H), 7.76-7.65 (m, 1H), 7.60 (s, 1H), 7.38 (d, J=7.4 Hz, 1H), 7.19 (dd, J=4.9, 3.7 Hz, 1H), 6.52 (s, 1H), 4.42 (d, J=5.7 Hz, 1H), 4.35 (t, J=7.8 Hz, 2H), 4.03 (dd, J=9.6, 3.6 Hz, 2H), 3.76 (d, J=6.5 Hz, 2H), 3.50-3.23 (m, 8H), 1.54-1.24 (m, 6H).

Example 255

(S)-2-(3-methoxyazetidin-1-yl)-N-(pyrrolidin-2-ylmethyl)-6-(5-(thiophen-2-yl)pyrazolo[1,5-a]pyrimidin-3-yl)isonicotinamide

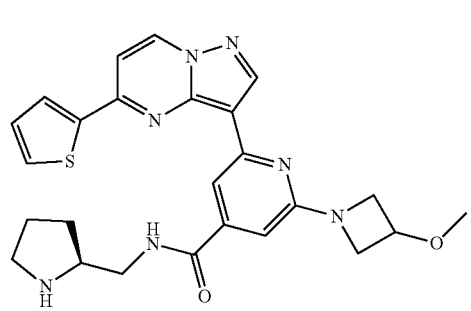

Compound 255 was synthesized as a TFA salt, as shown in the Example 141, coupling with commercially available tert-butyl (S)-2-(aminomethyl)pyrrolidine-1-carboxylate and by deprotecting with TFA. LC/MS (M+H): 490.2

Example 256

(S)—N-((1-ethylpyrrolidin-2-yl)methyl)-2-(3-methoxyazetidin-1-yl)-6-(5-(thiophen-2-yl)pyrazolo[1,5-a]pyrimidin-3-yl)isonicotinamide

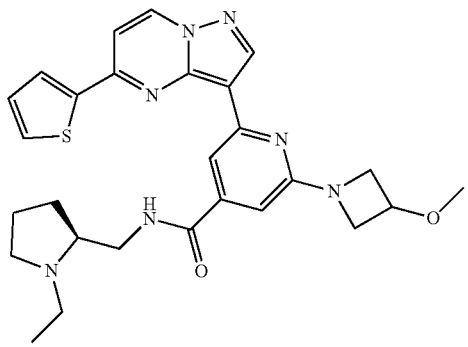

256

Compound 256 was synthesized by alkylating the compound 255 with ethyl iodide in DMF, in the presence of potassium carbonate, as a TFA salt. LC/MS (M+H): 518.2

Example 257

(S)-2-(3-methoxyazetidin-1-yl)-N-((1-methylpyrrolidin-2-yl)methyl)-6-(5-(thiophen-2-yl)pyrazolo[1,5-a]pyrimidin-3-yl)isonicotinamide

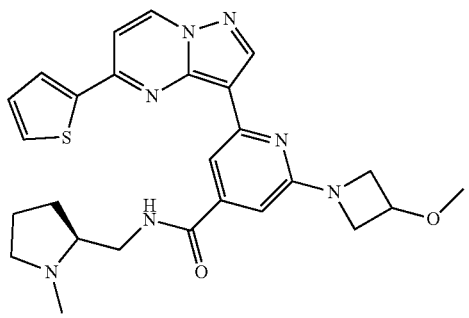

257

Compound 257 was synthesized by alkylating the compound 255 with methyl iodide in DMF, in the presence of potassium carbonate, as a TFA salt. LC/MS (M+H): 504.2

Example 258

N-(2-(diethylamino)ethyl)-2-(3-hydroxy-3-methylazetidin-1-yl)-6-(5-(thiophen-2-yl)pyrazolo[1,5-a]pyrimidin-3-yl)isonicotinamide

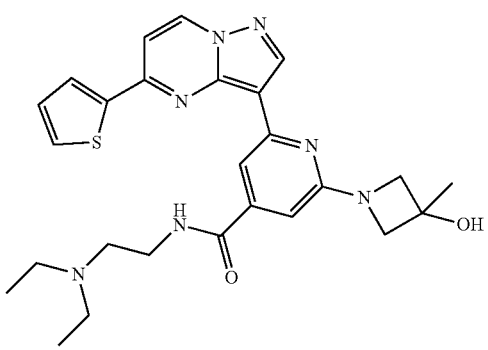

258

Compound 258 was synthesized as shown in the Example 141, starting with commercially available 3-methylazetidin-3-ol, and by coupling with commercially available N1,N1-diethylethane-1,2-diamine, as a TFA salt. LC/MS (M+H): 506.2; 1H NMR (400 MHz, Methanol-d4) δ 8.98 (d, J=7.4 Hz, 1H), 8.75 (s, 1H), 8.03 (dd, J=3.8, 1.1 Hz, 1H), 7.83 (dd, J=5.1, 1.1 Hz, 1H), 7.76 (d, J=1.4 Hz, 1H), 7.67 (d, J=7.4 Hz, 1H), 7.28 (dd, J=5.1, 3.8 Hz, 1H), 6.94 (d, J=1.4 Hz, 1H), 4.41 (q, J=9.2 Hz, 4H), 3.82 (t, J=6.4 Hz, 2H), 3.44 (t, J=6.4 Hz, 2H), 3.36 (dd, J=7.3, 3.7 Hz, 4H), 1.66 (s, 3H), 1.37 (t, J=7.3 Hz, 6H).

Example 259

N-(2-(diethylamino)ethyl)-2-((2-hydroxyethyl)amino)-6-(5-(thiophen-2-yl)pyrazolo[1,5-a]pyrimidin-3-yl)isonicotinamide

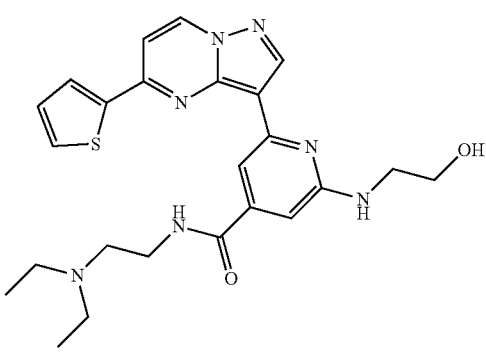

259

Compound 259 was synthesized as shown in the Example 141, starting with commercially available ethanolamine, and by coupling with commercially available N1,N1-diethylethane-1,2-diamine, as a TFA salt. LC/MS (M+H): 480.2

Example 260

(S)-2-(diethylamino)-N-(2-(diethylamino)propyl)-6-(5-(thiophen-2-yl)pyrazolo[1,5-a]pyrimidin-3-yl)isonicotinamide

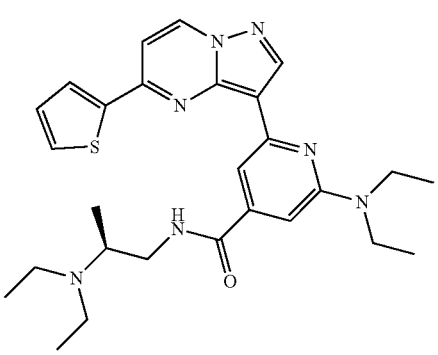

260

Compound 260 was synthesized as shown in the Example 141, starting with commercially available diethylamine, as a TFA salt. LC/MS (M+H): 506.2; 1H NMR (400 MHz, Methanol-d4) δ 9.01 (d, J=7.4 Hz, 1H), 8.79 (s, 1H), 8.02

(dd, J=3.8, 1.1 Hz, 1H), 7.83 (dd, J=5.0, 1.1 Hz, 1H), 7.73 (d, J=1.3 Hz, 1H), 7.68 (d, J=7.4 Hz, 1H), 7.29 (dd, J=5.0, 3.8 Hz, 1H), 7.24 (d, J=1.3 Hz, 1H), 4.30 (ddd, J=10.5, 4.1, 1.7 Hz, 1H), 4.23-4.08 (m, 1H), 3.91 (q, J=7.3 Hz, 4H), 3.60 (dd, J=13.8, 6.2 Hz, 1H), 3.55-3.42 (m, 1H), 3.47-3.35 (m, 1H), 3.28-3.14 (m, 1H), 2.41-2.23 (m, 1H), 2.11-1.93 (m, 2H), 1.51-1.36 (m, 14H), 1.28 (t, J=3.2 Hz, 5H).

Example 261

(S)—N-(2-(diethylamino)propyl)-2-(ethylamino)-6-(5-(thiophen-2-yl)pyrazolo[1,5-a]pyrimidin-3-yl)isonicotinamide

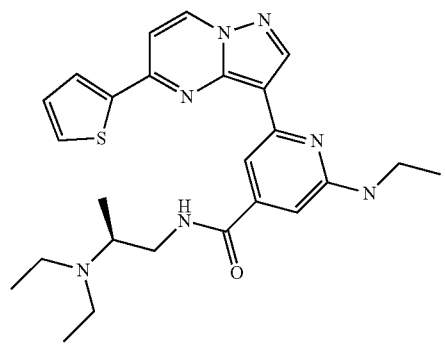

261

Compound 261 was synthesized as shown in the Example 141, starting with commercially available ethylamine, as a TFA salt. LC/MS (M+H): 478.2

Example 262

(S)—N-(2-(diethylamino)propyl)-2-(3-methoxyazetidin-1-yl)-6-(5-(pyridin-4-yl)pyrazolo[1,5-a]pyrimidin-3-yl)isonicotinamide

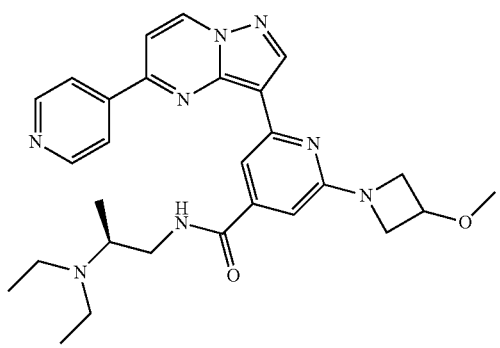

262

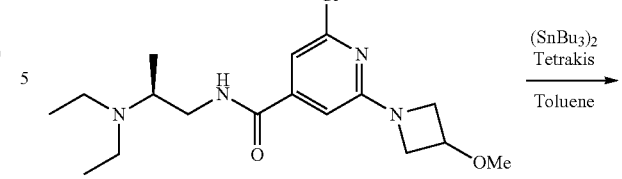

141D

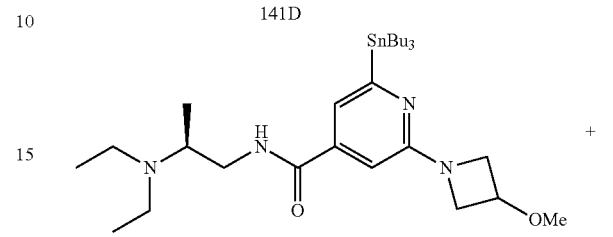

262A

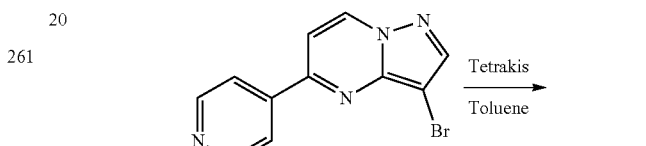

262B

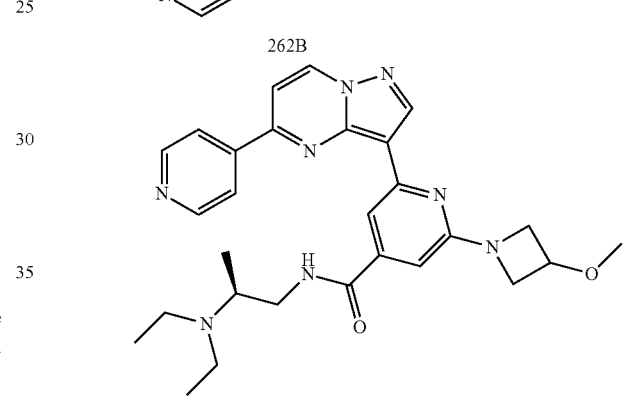

262

Synthesis of (S)—N-(2-(diethylamino)propyl)-2-(3-methoxyazetidin-1-yl)-6-(tributylstannyl)isonicotinamide (262A)

In a seal vessel, Compound 141D (94.8%, 281 mg, 0.75 mmol) and hexabutylditin (752.09 μl, 1.5 mmol) in 5 mL toluene were heated 150° C. for 16 hours. Reaction was concentrated and purified on silica eluting with ethyl acetate and hexanes. Compound 262B was synthesized similarly to Compound 1C in Example 1, using commercially available pyridin-4-ylboronic acid.

Synthesis of (S)—N-(2-(diethylamino)propyl)-2-(3-methoxyazetidin-1-yl)-6-(5-(pyridin-4-yl)pyrazolo[1,5-a]pyrimidin-3-yl)isonicotinamide (262)

Compound 262A (60 mg, 0.1 mmol), Compound 262B (32.5 mg, 0.12 mmol), and Tetrakis(triphenylphosphine)palladium(0) (11.38 mg, 0.01 mmol) in 2 mL toluene were microwaved at 120° C. for 15 minute. The reaction was concentrated and purified by reverse phase chromatography to afford the product as a TFA salt (2.5 mg)
LC/MS (M+H): 515.3

Example 263

(S)-2-(4-carbamoylpiperidin-1-yl)-N-(2-(diethylamino)propyl)-6-(5-(thiophen-2-yl)pyrazolo[1,5-a]pyrimidin-3-yl)isonicotinamide

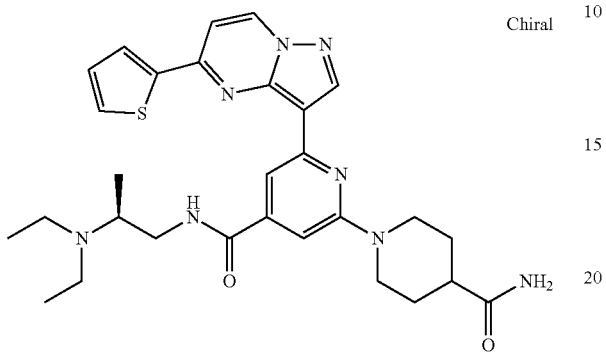

263
Chiral

Compound 263 was synthesized as shown in the Example 141, starting with commercially available piperidine-4-carboxamide, as a TFA salt. LC/MS (M+H): 561.335; 1H NMR (400 MHz, Methanol-d4) δ 8.92 (d, J=7.4 Hz, 1H), 8.74 (s, 1H), 8.10 (s, 1H), 7.99 (dd, J=3.8, 1.1 Hz, 1H), 7.76 (dd, J=5.0, 1.1 Hz, 1H), 7.59 (d, J=7.4 Hz, 1H), 7.26 (dd, J=5.0, 3.8 Hz, 1H), 7.13 (s, 1H), 4.62-4.53 (m, 2H), 3.95 (dd, J=14.2, 5.8 Hz, 1H), 3.86 (q, J=6.3 Hz, 1H), 3.53 (ddd, J=13.4, 10.0, 6.6 Hz, 2H), 3.44-3.34 (m, 3H), 3.28-3.12 (m, 3H), 2.01 (d, J=12.5 Hz, 2H), 1.84 (qd, J=12.2, 4.1 Hz, 2H), 1.47 (t, J=7.2 Hz, 6H), 1.41 (t, J=7.3 Hz, 3H).

Example 264

N—((S)-2-(diethylamino)propyl)-2-((S)-2-(hydroxymethyl)morpholino)-6-(5-(thiophen-2-yl)pyrazolo[1,5-a]pyrimidin-3-yl)isonicotinamide

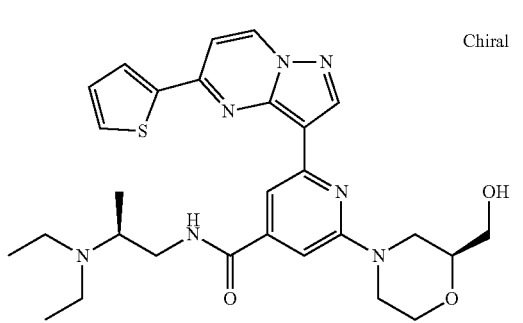

264
Chiral

Compound 263 was synthesized as shown in the Example 141, starting with commercially available (S)-morpholin-2-ylmethanol, as a TFA salt. LC/MS (M+H): 550.367; 1H NMR (400 MHz, Methanol-d4) δ 8.81 (d, J=7.4 Hz, 1H), 7.98-7.88 (m, 1H), 7.76-7.70 (m, 1H), 7.47 (d, J=7.4 Hz, 1H), 7.23 (dd, J=5.0, 3.7 Hz, 1H), 7.00 (d, J=5.4 Hz, 1H), 4.24 (dd, J=30.3, 12.8 Hz, 2H), 4.11 (d, J=10.6 Hz, 1H), 3.94 (dd, J=14.0, 5.6 Hz, 1H), 3.86 (q, J=6.4 Hz, 1H), 3.82-3.72 (m, 1H), 3.69 (s, 3H), 3.53 (ddd, J=22.1, 12.1, 6.5 Hz, 2H), 3.46-3.33 (m, 2H), 3.22 (dq, J=14.2, 7.2 Hz, 1H), 3.11 (dd, J=13.1, 9.8 Hz, 1H), 2.87 (t, J=11.0 Hz, 1H), 1.47 (t, J=7.1 Hz, 6H), 1.41 (t, J=7.2 Hz, 3H).

Example 265

N—((S)-2-(diethylamino)propyl)-2-((S)-2-(methoxymethyl)azetidin-1-yl)-6-(5-(thiophen-2-yl)pyrazolo[1,5-a]pyrimidin-3-yl)isonicotinamide

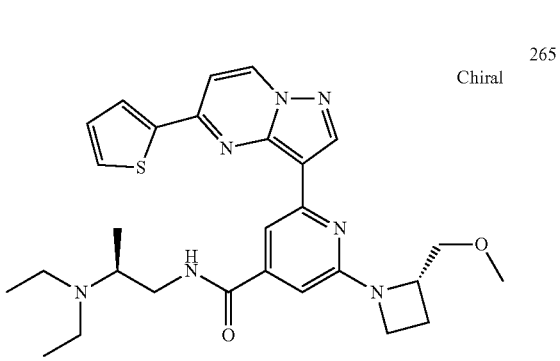 [SMILES: CCN(CC)[C@@H](C)CNC(=O)c1cc(-c2cnn3ccc(-c4cccs4)nc23)nc(N2CC[C@H]2COC)c1]

265
Chiral

Compound 265 was synthesized as shown in the Example 141, starting with commercially available (S)-2-(methoxymethyl)azetidine, as a TFA salt. LC/MS (M+H): 534.249; 1H NMR (400 MHz, Methanol-d4) δ 9.03 (d, J=7.4 Hz, 1H), 8.72 (s, 1H), 8.08 (dd, J=3.9, 1.1 Hz, 1H), 7.85 (dd, J=5.0, 1.0 Hz, 1H), 7.83 (d, J=1.4 Hz, 1H), 7.74 (d, J=7.5 Hz, 1H), 7.29 (dd, J=5.0, 3.8 Hz, 1H), 7.03 (s, 1H), 5.23 (s, 1H), 4.47-4.33 (m, 2H), 3.99-3.79 (m, 4H), 3.60 (ddd, J=14.0, 6.5, 2.7 Hz, 1H), 3.50 (dq, J=14.5, 7.5 Hz, 1H), 3.42-3.33 (m, 2H), 3.28-3.15 (m, 5H), 2.79-2.68 (m, 1H), 2.42-2.32 (m, 1H), 1.49-1.36 (m, 9H).

Example 266

N—((S)-2-(diethylamino)propyl)-2-((R)-2-(methoxymethyl)azetidin-1-yl)-6-(5-(thiophen-2-yl)pyrazolo[1,5-a]pyrimidin-3-yl)isonicotinamide

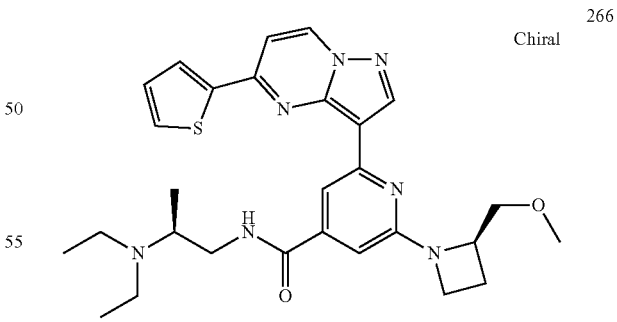

266
Chiral

Compound 266 was synthesized as shown in the Example 141, starting with commercially available (R)-2-(methoxymethyl)azetidine, as a TFA salt. LC/MS (M+H): 534.215; 1H NMR (400 MHz, Methanol-d4) δ 9.04 (d, J=7.4 Hz, 1H), 8.73 (s, 1H), 8.08 (dd, J=3.8, 1.0 Hz, 1H), 7.88-7.83 (m, 2H), 7.75 (d, J=7.4 Hz, 1H), 4.47-4.33 (m, 2H), 3.99-3.81 (m, 4H), 3.58 (ddd, J=14.1, 6.6, 2.3 Hz, 1H), 3.49 (dt, J=14.5, 7.3 Hz, 1H), 3.38 (dd, J=8.1, 6.3 Hz, 2H), 3.21

(s, 4H), 2.78-2.68 (m, 1H), 2.43-2.33 (m, 1H), 1.44 (dd, J=7.3, 5.5 Hz, 7H), 1.40 (t, J=7.2 Hz, 3H).

Example 267

N—((S)-2-(diethylamino)propyl)-2-((R)-2-(hydroxymethyl)azetidin-1-yl)-6-(5-(thiophen-2-yl)pyrazolo[1,5-a]pyrimidin-3-yl)isonicotinamide

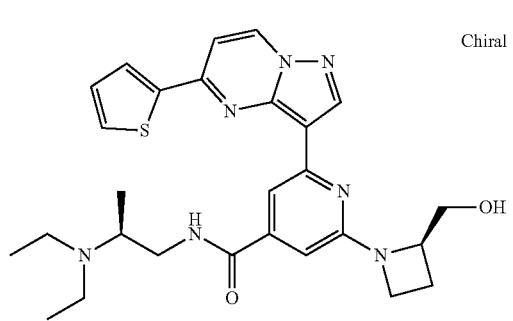

Compound 267 was synthesized as shown in the Example 141, starting with commercially available (R)-azetidin-2-ylmethanol, as a TFA salt. LC/MS (M+H): 520.169; 1H NMR (400 MHz, Methanol-d4) δ 8.98 (d, J=7.4 Hz, 1H), 8.60 (s, 1H), 8.21 (s, 1H), 8.04 (dd, J=3.8, 1.1 Hz, 1H), 7.80 (dd, J=5.1, 1.1 Hz, 1H), 7.68 (d, J=7.4 Hz, 1H), 7.27 (dd, J=5.0, 3.8 Hz, 1H), 6.92 (d, J=1.5 Hz, 1H), 4.94 (d, J=8.5 Hz, 2H), 4.28 (t, J=8.0 Hz, 2H), 4.04-3.92 (m, 3H), 3.87 (h, J=6.5 Hz, 1H), 3.55 (ddd, J=26.9, 14.0, 6.9 Hz, 3H), 3.38 (d, J=6.5 Hz, 3H), 3.23 (dd, J=13.5, 7.0 Hz, 1H), 2.64-2.53 (m, 1H), 2.42-2.31 (m, 1H), 1.45 (dd, J=7.2, 3.6 Hz, 7H), 1.40 (t, J=7.2 Hz, 4H).

Example 268

N—((S)-2-(diethylamino)propyl)-2-((S)-2-(hydroxymethyl)azetidin-1-yl)-6-(5-(thiophen-2-yl)pyrazolo[1,5-a]pyrimidin-3-yl)isonicotinamide

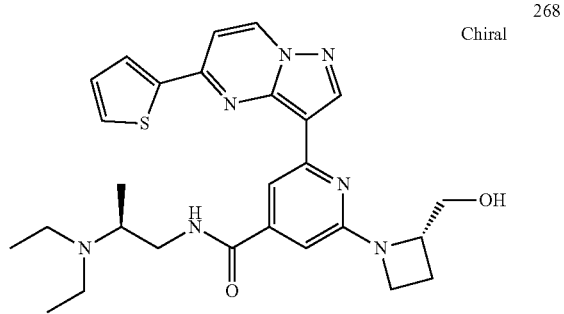 [SMILES: CCN(CC)[C@@H](C)CNC(=O)c1cc(-c2cnn3ccc(-c4cccs4)nc23)nc(N2CC[C@H]2CO)c1]

Compound 268 was synthesized as shown in the Example 141, starting with commercially available (S)-azetidin-2-ylmethanol, as a TFA salt. LC/MS (M+H): 520.181; 1H NMR (400 MHz, Methanol-d4) δ 8.98 (d, J=7.4 Hz, 1H), 8.61 (s, 1H), 8.22 (s, 1H), 8.04 (dd, J=3.8, 1.1 Hz, 1H), 7.80 (dd, J=5.0, 1.1 Hz, 1H), 7.69 (d, J=7.4 Hz, 1H), 7.27 (dd, J=5.0, 3.8 Hz, 1H), 6.92 (d, J=1.4 Hz, 1H), 4.94 (d, J=8.8 Hz, 1H), 4.28 (t, J=7.8 Hz, 2H), 4.04-3.92 (m, 3H), 3.86 (dt, J=12.8, 6.5 Hz, 1H), 3.58 (dd, J=14.0, 6.4 Hz, 1H), 3.55-3.45 (m, 1H), 3.43-3.34 (m, 2H), 3.22 (dt, J=14.4, 7.2 Hz, 1H), 2.64-2.53 (m, 1H), 2.42-2.31 (m, 1H), 1.46 (dd, J=7.1, 4.8 Hz, 6H), 1.40 (t, J=7.3 Hz, 3H).

Example 269

2-((R)-2-carbamoylpyrrolidin-1-yl)-N—((S)-2-(diethylamino)propyl)-6-(5-(thiophen-2-yl)pyrazolo[1,5-a]pyrimidin-3-yl)isonicotinamide

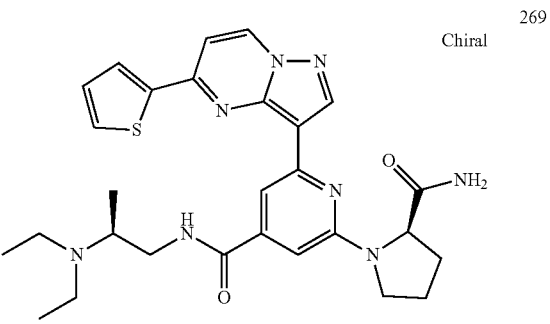 [SMILES: CCN(CC)[C@@H](C)CNC(=O)c1cc(-c2cnn3ccc(-c4cccs4)nc23)nc(N2CCC[C@@H]2C(N)=O)c1]

Compound 269 was synthesized as shown in the Example 141, starting with commercially available (R)-pyrrolidine-2-carboxamide, as a TFA salt. LC/MS (M+H): 547.379; 1H NMR (400 MHz, Methanol-d4) δ 8.78 (d, J=7.4 Hz, 1H), 8.66 (s, 1H), 8.03 (s, 1H), 7.89 (dd, J=3.9, 1.2 Hz, 1H), 7.71 (dd, J=5.0, 1.0 Hz, 1H), 7.45 (d, J=7.4 Hz, 1H), 7.22 (dd, J=5.0, 3.8 Hz, 1H), 6.73 (d, J=1.4 Hz, 1H), 4.60 (dd, J=8.5, 2.9 Hz, 1H), 3.96 (dd, J=14.2, 5.8 Hz, 1H), 3.87 (p, J=7.3, 6.4 Hz, 2H), 3.69-3.58 (m, 1H), 3.53 (dt, J=14.7, 7.3 Hz, 2H), 3.44-3.34 (m, 2H), 3.23 (dq, J=14.0, 7.1 Hz, 1H), 2.50-2.36 (m, 1H), 2.30-2.10 (m, 3H), 1.47 (t, J=6.7 Hz, 6H), 1.41 (t, J=7.2 Hz, 3H).

Example 270

2-((S)-2-carbamoylpyrrolidin-1-yl)-N—((S)-2-(diethylamino)propyl)-6-(5-(thiophen-2-yl)pyrazolo[1,5-a]pyrimidin-3-yl)isonicotinamide

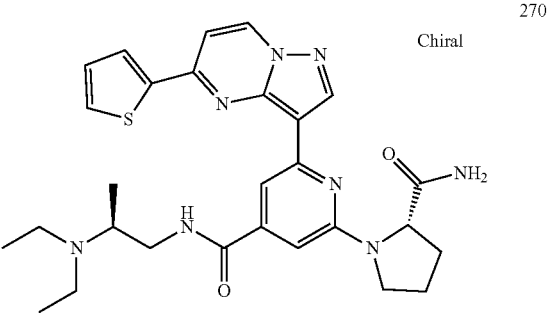 [SMILES: CCN(CC)[C@@H](C)CNC(=O)c1cc(-c2cnn3ccc(-c4cccs4)nc23)nc(N2CCC[C@H]2C(N)=O)c1]

Compound 270 was synthesized as shown in the Example 141, starting with commercially available (S)-pyrrolidine-2-carboxamide, as a TFA salt. LC/MS (M+H): 547.388; 1H NMR (400 MHz, Methanol-d4) δ 8.82 (s, 1H), 8.12 (s, 1H), 7.92 (s, 1H), 7.72 (d, J=4.7 Hz, 1H), 7.48 (s, 1H), 7.30-7.18 (m, 1H), 6.74 (s, 1H), 4.60 (d, J=9.3 Hz, 1H), 4.00-3.79 (m, 3H), 3.69-3.47 (m, 3H), 3.37 (dt, J=8.9, 4.5 Hz, 2H), 3.23 (dq, J=14.3, 7.1 Hz, 1H), 2.41 (d, J=10.6 Hz, 1H), 1.46 (d, J=6.7 Hz, 6H), 1.41 (t, J=7.2 Hz, 3H).

Example 271

N—((S)-2-(diethylamino)propyl)-2-((S)-2-(hydroxymethyl)pyrrolidin-1-yl)-6-(5-(thiophen-2-yl)pyrazolo[1,5-a]pyrimidin-3-yl)isonicotinamide

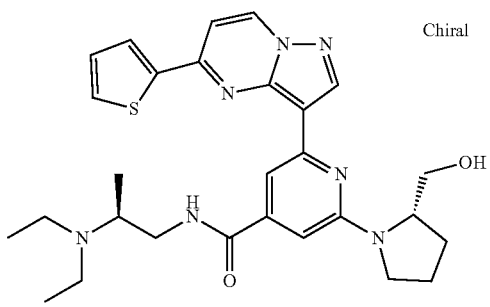

Compound 271 was synthesized as shown in the Example 141, starting with commercially available (S)-pyrrolidin-2-ylmethanol, as a TFA salt. LC/MS (M+H): 534.352; 1H NMR (400 MHz, Methanol-d4) δ 8.97 (d, J=7.4 Hz, 1H), 8.72 (s, 1H), 8.03 (dd, J=3.8, 1.1 Hz, 1H), 7.98 (s, 1H), 7.82 (dd, J=5.0, 1.1 Hz, 1H), 7.68 (d, J=7.4 Hz, 1H), 7.28 (dd, J=5.0, 3.8 Hz, 1H), 7.19 (s, 1H), 4.61 (s, 1H), 4.00-3.72 (m, 6H), 3.66-3.57 (m, 1H), 3.44-3.34 (m, 2H), 3.22 (dt, J=14.0, 7.1 Hz, 1H), 2.35-2.16 (m, 3H), 2.05 (d, J=8.4 Hz, 1H), 1.50-1.36 (m, 9H).

Example 272

N—((S)-2-(diethylamino)propyl)-2-((R)-2-(hydroxymethyl)pyrrolidin-1-yl)-6-(5-(thiophen-2-yl)pyrazolo[1,5-a]pyrimidin-3-yl)isonicotinamide

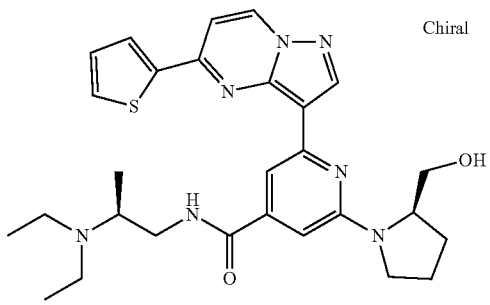

Compound 272 was synthesized as shown in the Example 141, starting with commercially available (R)-pyrrolidin-2-ylmethanol, as a TFA salt. LC/MS (M+H): 534.337; 1H NMR (400 MHz, Methanol-d4) δ 8.97 (d, J=7.4 Hz, 1H), 8.72 (s, 1H), 8.03 (dd, J=3.8, 1.1 Hz, 1H), 7.99 (s, 1H), 7.82 (dd, J=5.0, 1.1 Hz, 1H), 7.67 (d, J=7.4 Hz, 1H), 7.27 (dd, J=5.0, 3.8 Hz, 1H), 7.17 (s, 1H), 4.60 (s, 1H), 4.00-3.69 (m, 6H), 3.59 (dd, J=14.0, 6.3 Hz, 1H), 3.50 (dd, J=13.7, 7.2 Hz, 1H), 3.37 (s, 2H), 2.26 (dq, J=26.7, 6.9, 4.7 Hz, 3H), 2.04 (d, J=8.6 Hz, 1H), 1.43 (dd, J=18.1, 6.9 Hz, 9H).

Example 273

N—((S)-2-(diethylamino)propyl)-2-((R)-2-(methoxymethyl)pyrrolidin-1-yl)-6-(5-(thiophen-2-yl)pyrazolo[1,5-a]pyrimidin-3-yl)isonicotinamide

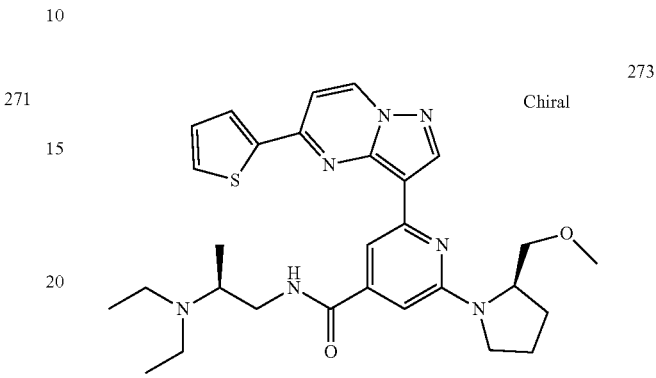

Compound 273 was synthesized as shown in the Example 141, starting with commercially available (R)-2-(methoxymethyl)pyrrolidine, as a TFA salt. LC/MS (M+H): 548.370; 1H NMR (400 MHz, Methanol-d4) δ 9.02 (d, J=7.4 Hz, 1H), 8.78 (s, 1H), 8.07 (dd, J=3.8, 1.1 Hz, 1H), 7.89-7.83 (m, 2H), 7.72 (d, J=7.4 Hz, 1H), 7.30 (dd, J=5.1, 3.8 Hz, 1H), 7.19 (s, 1H), 3.92 (ddt, J=29.1, 12.8, 6.0 Hz, 3H), 3.82-3.65 (m, 3H), 3.63-3.56 (m, 1H), 3.50 (dt, J=14.3, 7.1 Hz, 1H), 3.37 (tt, J=7.0, 3.2 Hz, 2H), 3.21 (d, J=19.9 Hz, 4H), 2.36-2.20 (m, 3H), 2.18-2.06 (m, 1H), 1.51-1.36 (m, 10H).

Example 274

N—((S)-2-(diethylamino)propyl)-2-((S)-2-(methoxymethyl)pyrrolidin-1-yl)-6-(5-(thiophen-2-yl)pyrazolo[1,5-a]pyrimidin-3-yl)isonicotinamide

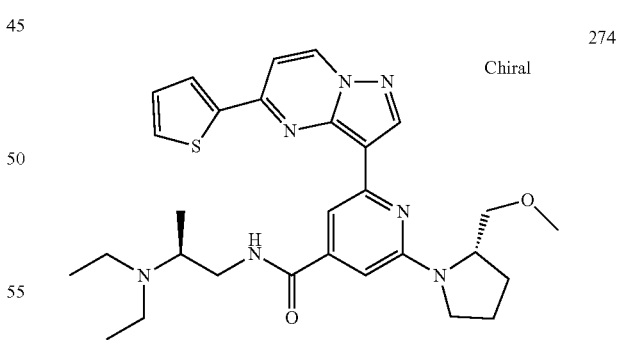

Compound 274 was synthesized as shown in the Example 141, starting with commercially available (S)-2-(methoxymethyl)pyrrolidine, as a TFA salt. LC/MS (M+H): 548.225; 1H NMR (400 MHz, Methanol-d4) δ 9.04 (d, J=7.4 Hz, 1H), 8.79 (s, 1H), 8.08 (d, J=3.8 Hz, 1H), 7.87 (dd, J=5.0, 1.0 Hz, 1H), 7.85 (s, 1H), 7.74 (d, J=7.4 Hz, 1H), 7.31 (dd, J=5.0, 3.8 Hz, 1H), 7.23 (s, 1H), 4.82 (d, J=10.9 Hz, 1H), 3.92 (ddd, J=27.9, 13.4, 6.0 Hz, 3H), 3.85-3.65 (m, 4H), 3.61 (dd, J=13.8, 6.3 Hz, 1H), 3.49 (dt, J=14.4, 7.2 Hz, 1H), 3.38 (dd, J=7.3, 3.3 Hz, 2H), 3.28-3.10 (m, 5H), 2.11 (d, J=6.4 Hz, 1H), 1.44 (t, J=6.9 Hz, 6H), 1.40 (t, J=7.2 Hz, 3H).

Example 275

N—((S)-2-(diethylamino)propyl)-2-((S)-2-(methylcarbamoyl)azetidin-1-yl)-6-(5-(thiophen-2-yl)pyrazolo[1,5-a]pyrimidin-3-yl)isonicotinamide

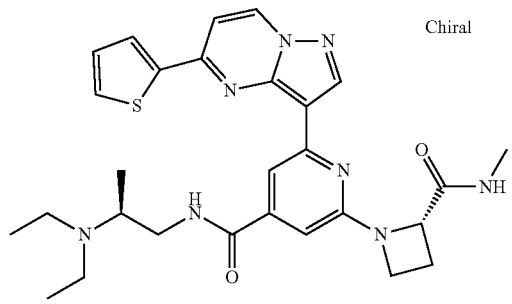

Synthesis of (S)-2,6-dichloro-N-(2-(diethylamino)propyl)isonicotinamide (275B)

Synthesis of 2-chloro-N—((S)-2-(diethylamino)propyl)-6-((S)-2-(methylcarbamoyl)azetidin-1-yl)isonicotinamide (275D)

Dichloroarene, K₂CO₃, and L-azetidine carboxylic acid were taken up in 1 mL of NMP in a microwave vial. The vial headspace was purged with argon, sealed and the vial heated to 120 C (to avoid decarboxylation) for 30 minutes. The reaction mixture was then diluted with DMF (1 mL) and the requisite as a TFA salt, DIPEA, and HATU were added sequentially. After 5 minutes, LCMS showed full conversion of carboxylic acid to desired amide product.

Synthesis of Final Product 275

Product 275D was coupled with boronic ester 1D as shown in Example 1 to provide the product 275, as a TFA salt. LC/MS (M+H): 547.364; 1H NMR (400 MHz, Methanol-d4) δ 8.90 (d, J=7.4 Hz, 1H), 8.64 (s, 1H), 8.35 (d, J=1.3 Hz, 1H), 8.00-7.96 (m, 1H), 7.73 (dd, J=5.0, 1.1 Hz, 1H), 7.56 (d, J=7.4 Hz, 1H), 7.25 (dd, J=5.1, 3.8 Hz, 1H), 6.68 (s, 1H), 4.16 (t, J=4.4 Hz, 1H), 4.08 (d, J=8.0 Hz, 1H), 3.95 (dd, J=14.2, 5.7 Hz, 1H), 3.86 (d, J=6.2 Hz, 1H), 3.53 (dt, J=13.6,

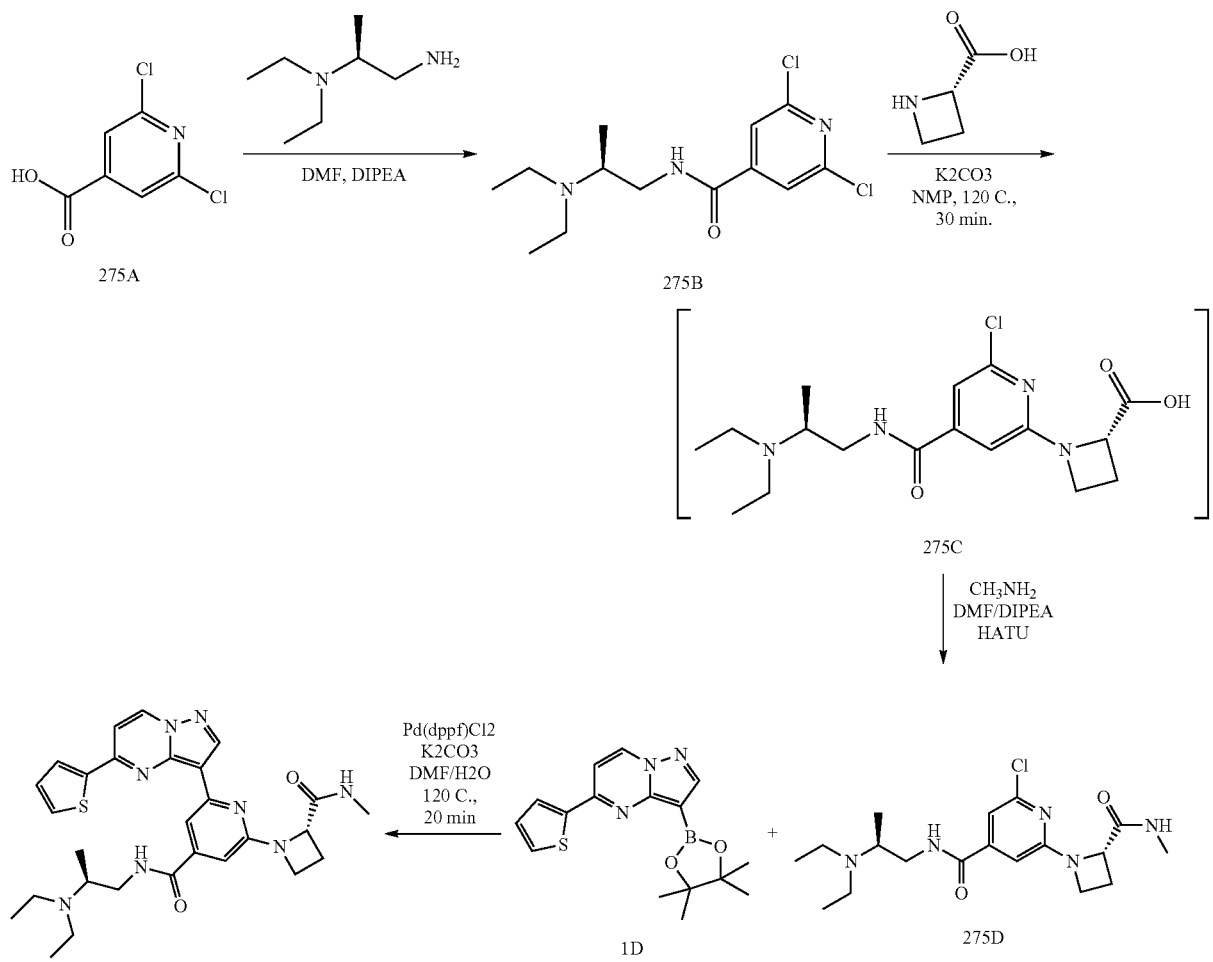

6.9 Hz, 2H), 3.38 (dd, J=7.2, 2.8 Hz, 2H), 3.22 (dd, J=13.4, 7.0 Hz, 2H), 2.82 (s, 3H), 2.73-2.63 (m, 1H), 2.59 (d, J=8.6 Hz, 1H), 1.47 (t, J=7.3 Hz, 6H), 1.41 (t, J=7.3 Hz, 3H).

Example 275B

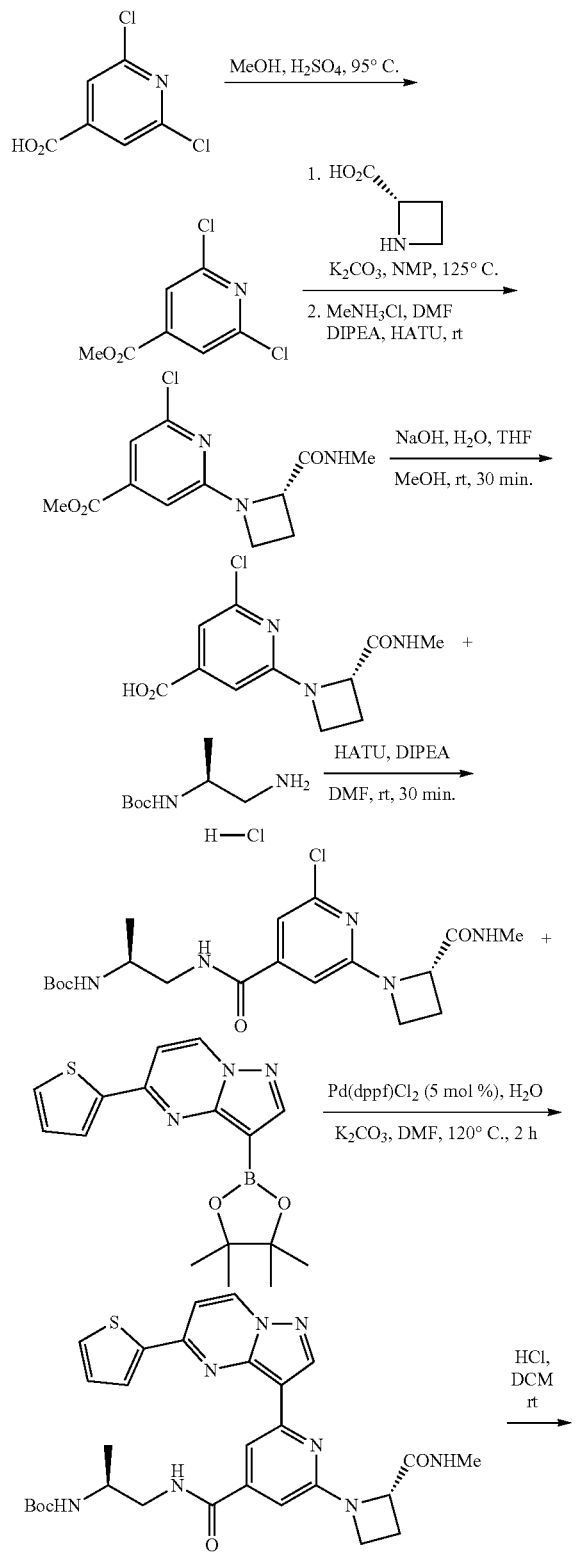

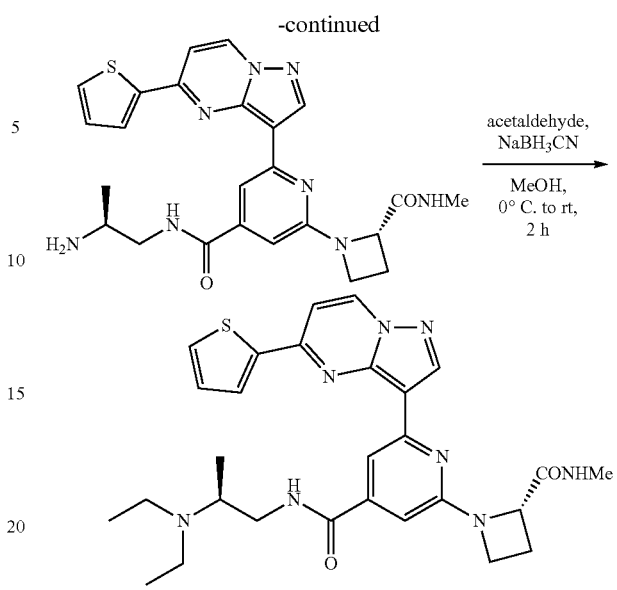

To a round bottom flask (rbf) was added carboxylic acid (15.0 g, 78.9 mmol) in MeOH (250 mL, 0.32M) at rt. To the vessel was added concentrated sulfuric acid (10.0 mL, 189.4 mmol, 2.4 equiv.), and the mixture was refluxed for 2 hours. Upon completion by LCMS, the contents of the flask were cooled to rt and concentrated under vacuum. The residue was added to a separatory funnel containing saturated sodium bicarbonate. The mixture was then extracted ×3 with ethyl acetate. The combined organics were washed ×1 with brine, dried over magnesium sulfate, filtered, and concentrated. The off-white solid was used without further purification.

To a rbf (round bottom flask) was added ester (3.77 g, 18.3 mmol) and NMP (37 mL, 0.5M) at rt. To the vessel was added potassium carbonate (5.06 g, 36.6 mmol, 2.0 equiv.) and (S)-azetidine-2-carboxylic acid (1.94 g, 19.2 mmol, 1.05 equiv.). The mixture was heated to 125° C. for 2 hours, until completed by LCMS. The vessel was cooled to rt, and DMF (37 mL), methylamine HCl (2.47 g, 36.6 mmol, 2.0 equiv.), and DIPEA (6.4 mL, 36.6 mmol, 2.0 equiv.) were added. Finally, HATU (8.35 g, 22.0 mmol, 1.2 equiv.) was added, and the mixture was stirred at rt for 15-30 minutes, until completed by LCMS. The mixture was diluted with saturated sodium bicarbonate (37 mL) and water (260 mL). The aqueous mixture was then extracted ×3 with ethyl acetate, until the aqueous layer showed to only possess minimal desired product by LCMS. The combined organics were washed ×1 with water and ×1 with brine, dried over magnesium sulfate, filtered, and partially concentrated.

Upon removal of the majority of ethyl acetate, some of the desired product precipitated from the solution. The slurry was filtered, and the white solid was washed with ether. The solid was collected and used without further purification. The filtrate was diluted with ether and, which precipitated more product. After filtration of the slurry, the solid was collected. The filtrate was concentrated and purified by silica gel chromatography. Any additional desired product was added to the solids from the earlier filtrations.

To a rbf was added ester (1.5 g, 5.3 mmol) in a mixture of THF (5.0 mL), MeOH (2.5 mL), and water (2.5 mL) at rt. The mixture was cooled to 0° C., and NaOH (0.44 g, 11.1 mmol, 2.1 equiv.) was added. The mixture was warmed to rt and stirred vigorously for 15-30 minutes, until completed by LCMS. The pH was adjusted to pH=7 with 4N HCl(aq) (2.5 mL), and the organics were removed under vacuum. The aqueous mixture was then diluted with water (5.0 mL) and acidified with 4N HCl(aq) until pH=2-3. The resulting slurry was filtered, and the solid was washed with water. The desired product was collected by transferring the wet solid to a rbf with rinsing of the funnel and spatula with methanol. The methanol slurry was then diluted with toluene, and the mixture was slowly concentrated under vacuum. The residue was then dried overnight under vacuum and used without further purification.

To a rbf was added acid (980 mg, 3.6 mmol) in DMF (14.5 mL, 0.25 M) at rt. The vessel was cooled to 0° C. and tert-butyl-(S)-(1-aminopropan-2-yl)carbamate hydrochloride (919 mg, 4.36 mmol, 1.2 equiv.) and DIPEA (2.0 mL, 11.6 mmol, 3.2 equiv.) were added. Finally, HATU (2.9 g, 3.8 mmol, 1.05 equiv.) was added, and the mixture was slowly warmed to rt. After 30 minutes at rt, the reaction was completed by LCMS, and the mixture was diluted with water (65 mL). The white slurry was filter, and the solid was washed with water. The solid was then collected, dried overnight under vacuum, and triturated with ether. The ether mixture was filtered, and the solid was collected.

To a rbf was added carbamate (600 mg, 1.4 mmol) and DMF (19 mL, 0.075 M) at rt. To the vessel was added potassium carbonate (584 mg, 4.2 mmol, 3.0 equiv.) and boronic ester (690 mg, 2.1 mmol, 1.5 equiv.). Water (1.4 mL) was added, and the mixture was degassed with nitrogen for 10 minutes. Finally, Pd(dppf)Cl$_2$ (58 mg, 0.07 mmol, 5 mol %) was added, and the mixture was heated to 120° C. under nitrogen for 1 hour. Upon completion by LCMS, the mixture was cooled to rt and filtered. The solid was washed with DMF then water then acetone. The solid was collected and dried under vacuum.

To a rbf was added carbamate (340 mg, 0.58 mmol) and DCM (11.5 mL, 0.05M) at rt. The vessel was cooled to 0° C., and 4N HCl in dioxane (1.45 mL, 5.8 mmol, 10.0 equiv.) was added dropwise. After slowly warming to rt, the mixture was vigorously stirred for 30 minutes, until complete by LCMS. The mixture was filtered through celite, and the sticky solid was washed with DCM. The filtrate was discarded. The sticky solid was then dissolved in water and basified to pH>11 with 4N NaOH(aq), until no more yellow solid precipitated from the solution. The mixture was filtered, and the solid was washed with water. The solid was collected and dried overnight under vacuum.

To a rbf was added the amine (490 mg, 0.87 mmol) in DCM (3.1 mL) and MeOH (6.2 mL, 0.1M total). The vessel was cooled to 0° C., and acetic acid (0.06 mL, 1.0 mmol, 1.2 equiv.) was added. After 5 minutes, sodium cyanoborohydride (232 mg, 3.7 mmol, 4.0 equiv.) was added, followed by the addition of acetaldehyde (0.52 mL, 9.3 mmol, 10.0 equiv.). The vessel was sealed using a septum containing a non-inflated balloon. The mixture was then warmed to rt and stirred for 2 hours. The mixture was diluted with saturated sodium bicarbonate (10 mL) and water (30 mL). The aqueous solution was then extracted ×3 with DCM. The combined organics were washed ×1 with brine, dried over magnesium sulfate, filtered, and concentrated to give the desired product. The crude residue was purified by silica gel chromatography.

Example 276

N—((S)-2-(diethylamino)propyl)-2-((S)-2-(ethylcarbamoyl)azetidin-1-yl)-6-(5-(thiophen-2-yl)pyrazolo[1,5-a]pyrimidin-3-yl)isonicotinamide

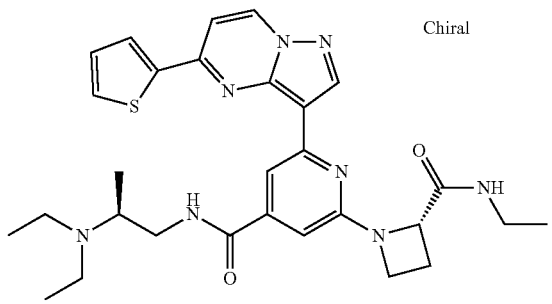

Compound 276 was synthesized following the Example 275, starting from commercially available ethyl amine, as a TFA salt. LC/MS (M+H): 561.447; $^1$H NMR (400 MHz, Methanol-d$_4$) δ 8.88 (d, J=7.4 Hz, 1H), 8.64 (s, 1H), 8.23 (d, J=1.4 Hz, 1H), 7.96 (dd, J=3.8, 1.1 Hz, 1H), 7.73 (dd, J=5.1, 1.1 Hz, 1H), 7.55 (d, J=7.4 Hz, 1H), 7.24 (dd, J=5.0, 3.8 Hz, 1H), 6.71 (d, J=1.4 Hz, 1H), 5.01 (t, J=8.1 Hz, 1H), 4.23-4.08 (m, 2H), 3.90 (ddd, J=30.2, 13.4, 6.1 Hz, 2H), 3.61-3.46 (m, 2H), 3.37 (dt, J=9.0, 4.5 Hz, 2H), 3.30-3.17 (m, 3H), 2.76-2.56 (m, 2H), 1.47 (t, J=6.5 Hz, 6H), 1.41 (t, J=7.2 Hz, 3H), 1.12 (t, J=7.2 Hz, 3H).

Example 277

2-((S)-2-(cyclopropylcarbamoyl)azetidin-1-yl)-N—((S)-2-(diethylamino)propyl)-6-(5-(thiophen-2-yl)pyrazolo[1,5-a]pyrimidin-3-yl)isonicotinamide

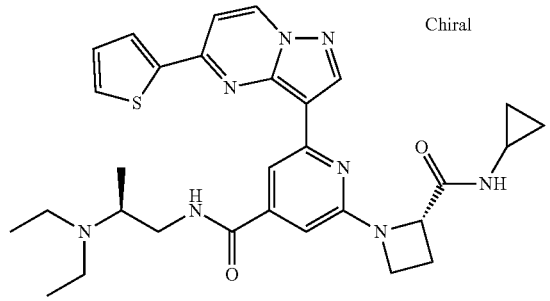

Compound 277 was synthesized following the Example 275, starting from commercially available cyclopropyl amine, as a TFA salt. LC/MS (M+H): 573.482; 1H NMR (400 MHz, Methanol-d4) δ 8.87 (d, J=7.4 Hz, 0H), 8.61 (s, 0H), 8.08 (d, J=1.3 Hz, 0H), 7.94 (d, J=3.7 Hz, 0H), 7.74 (dd, J=5.0, 1.0 Hz, 0H), 7.55 (d, J=7.4 Hz, 0H), 7.24 (dd, J=5.0, 3.8 Hz, 1H), 6.72 (d, J=1.4 Hz, 0H), 5.09 (t, J=8.0 Hz, 1H), 4.18 (dq, J=24.3, 7.7 Hz, 1H), 3.89 (ddd, J=25.6, 13.3, 6.1 Hz, 1H), 3.58 (dd, J=13.7, 6.1 Hz, 0H), 3.54-3.44 (m, 0H), 3.37 (d, J=7.4 Hz, 1H), 3.23 (dd, J=13.6, 7.0 Hz, 0H), 2.67 (dtt, J=22.4, 10.1, 6.1 Hz, 1H), 2.04 (s, 1H), 1.55-1.32 (m, 5H), 0.71 (qd, J=7.1, 3.5 Hz, 1H), 0.59-0.36 (m, 1H).

Example 278

2-((S)-2-((cyclopropylmethyl)carbamoyl)azetidin-1-yl)-N—((S)-2-(diethylamino)propyl)-6-(5-(thiophen-2-yl)pyrazolo[1,5-a]pyrimidin-3-yl)isonicotinamide

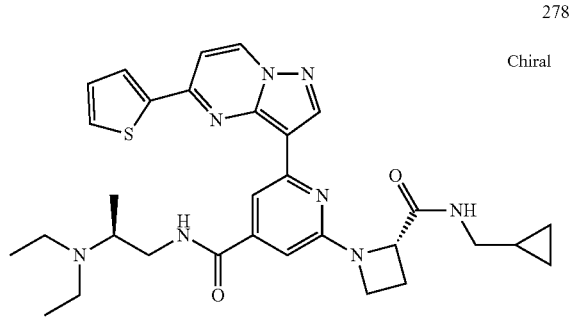 [SMILES: CCN(CC)[C@@H](C)CNC(=O)c1cc(-c2cnn3ccc(-c4cccs4)nc23)nc(N2CC[C@H]2C(=O)NCC2CC2)c1]

Compound 278 was synthesized following the Example 275, starting from commercially available cyclopropylmethanamine, as a TFA salt. LC/MS (M+H): 587.710; 1H NMR (400 MHz, Methanol-d4) δ 8.88 (d, J=7.4 Hz, 1H), 8.67 (s, 1H), 8.20 (d, J=1.3 Hz, 1H), 7.96 (dd, J=3.8, 1.1 Hz, 1H), 7.74 (dd, J=5.1, 1.1 Hz, 1H), 7.56 (d, J=7.4 Hz, 1H), 7.24 (dd, J=5.0, 3.8 Hz, 1H), 6.74 (d, J=1.4 Hz, 1H), 5.09 (t, J=8.1 Hz, 1H), 4.24-4.10 (m, 2H), 3.90 (ddd, J=29.2, 13.3, 6.1 Hz, 2H), 3.54 (ddd, J=25.0, 13.8, 6.7 Hz, 2H), 3.37 (tt, J=7.3, 4.2 Hz, 2H), 3.23 (dq, J=14.2, 7.1 Hz, 1H), 3.17-3.05 (m, 2H), 2.78-2.60 (m, 2H), 1.47 (dd, J=7.0, 5.0 Hz, 7H), 1.40 (t, J=7.2 Hz, 4H), 1.02-0.91 (m, 1H), 0.44 (ddt, J=8.0, 6.7, 1.9 Hz, 2H), 0.23-0.14 (m, 2H).

Example 279

N—((S)-2-(diethylamino)propyl)-2-((S)-2-(dimethylcarbamoyl)azetidin-1-yl)-6-(5-(thiophen-2-yl)pyrazolo[1,5-a]pyrimidin-3-yl)isonicotinamide

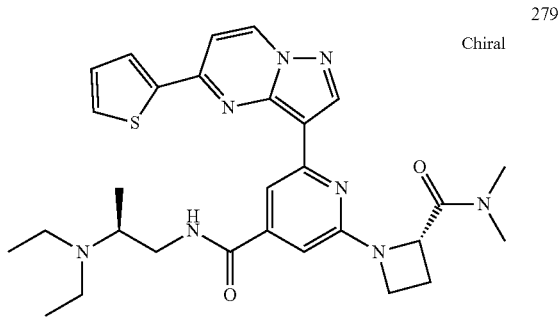 [SMILES: CCN(CC)[C@@H](C)CNC(=O)c1cc(-c2cnn3ccc(-c4cccs4)nc23)nc(N2CC[C@H]2C(=O)N(C)C)c1]

Compound 279 was synthesized following the Example 275, starting from commercially available dimethylamine, as a TFA salt. LC/MS (M+H): 561.409; 1H NMR (400 MHz, Methanol-d4) δ 8.90 (d, J=7.4 Hz, 1H), 8.62 (s, 1H), 8.06 (d, J=1.3 Hz, 1H), 7.97 (dd, J=3.8, 1.1 Hz, 1H), 7.76 (dd, J=5.1, 1.1 Hz, 1H), 7.56 (d, J=7.4 Hz, 1H), 7.26 (dd, J=5.1, 3.8 Hz, 1H), 6.74 (d, J=1.4 Hz, 1H), 5.53 (t, J=7.9 Hz, 1H), 4.26 (t, J=7.5 Hz, 2H), 3.89 (ddd, J=28.9, 13.4, 6.0 Hz, 2H), 3.53 (ddd, J=23.6, 14.0, 6.6 Hz, 2H), 3.37 (dd, J=7.3, 3.0 Hz, 2H), 3.22 (dt, J=14.2, 7.1 Hz, 1H), 3.09 (s, 3H), 2.96 (s, 4H), 2.61 (s, 1H), 1.46 (t, J=6.9 Hz, 6H), 1.40 (t, J=7.2 Hz, 3H).

Example 280

N—((S)-2-(diethylamino)propyl)-2-((S)-2-(diethylcarbamoyl)azetidin-1-yl)-6-(5-(thiophen-2-yl)pyrazolo[1,5-a]pyrimidin-3-yl)isonicotinamide

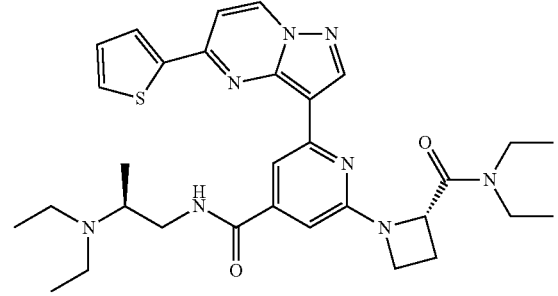

Compound 280 was synthesized following the Example 275, starting from commercially available diethylamine, as a TFA salt. LC/MS (M+H): 589.542; 1H NMR (400 MHz, Methanol-d4) δ 8.87 (dd, J=7.4, 1.4 Hz, 1H), 8.56 (s, 1H), 8.03 (d, J=1.4 Hz, 1H), 7.95 (dd, J=3.8, 1.1 Hz, 1H), 7.75 (dd, J=5.0, 1.1 Hz, 1H), 7.54 (dd, J=7.5, 1.9 Hz, 1H), 7.24 (dd, J=5.0, 3.8 Hz, 1H), 6.70 (d, J=1.4 Hz, 1H), 5.52 (t, J=7.8 Hz, 1H), 4.27 (dt, J=15.0, 7.0 Hz, 2H), 3.88 (ddd, J=25.3, 13.3, 6.0 Hz, 2H), 3.62-3.33 (m, 9H), 3.23 (dq, J=14.2, 7.1 Hz, 1H), 2.90 (s, 1H), 2.58 (s, 1H), 1.46 (t, J=6.4 Hz, 7H), 1.40 (t, J=7.2 Hz, 4H), 1.35-1.27 (m, 4H), 1.12 (t, J=7.1 Hz, 3H).

Example 281

N—((S)-2-(diethylamino)propyl)-2-((S)-2-((2-fluoroethyl)carbamoyl)azetidin-1-yl)-6-(5-(thiophen-2-yl)pyrazolo[1,5-a]pyrimidin-3-yl)isonicotinamide

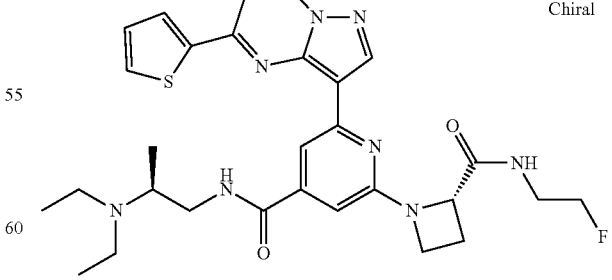

Compound 281 was synthesized following the Example 275, starting from commercially available 2-fluoroethan-1-amine, as a TFA salt. LC/MS (M+H): 579.409; 1H NMR (400 MHz, Methanol-d4) δ 8.87 (d, J=7.4 Hz, 1H), 8.65 (s, 1H), 8.28 (d, J=1.3 Hz, 1H), 7.96 (dd, J=3.8, 1.1 Hz, 1H), 7.73 (dd, J=5.1, 1.0 Hz, 1H), 7.54 (d, J=7.4 Hz, 1H), 7.24 (dd, J=5.0, 3.8 Hz, 1H), 6.70 (d, J=1.3 Hz, 1H), 4.98 (t, J=8.1 Hz, 1H), 4.58-4.49 (m, 1H), 4.46-4.37 (m, 1H), 4.22-4.14 (m, 1H), 4.10 (q, J=7.8 Hz, 1H), 3.94 (dd, J=14.1, 5.7 Hz, 1H), 3.86 (h, J=6.4 Hz, 1H), 3.55 (qd, J=14.2, 13.0, 6.6 Hz, 4H), 3.38 (dd, J=7.2, 2.8 Hz, 2H), 3.23 (dq, J=14.2, 7.2 Hz, 1H), 2.76-2.57 (m, 2H), 1.47 (t, J=7.1 Hz, 6H), 1.41 (t, J=7.3 Hz, 3H).

Example 282

N—((S)-2-(diethylamino)propyl)-2-((S)-2-((2,2-difluoroethyl)carbamoyl)azetidin-1-yl)-6-(5-(thiophen-2-yl)pyrazolo[1,5-a]pyrimidin-3-yl)isonicotinamide

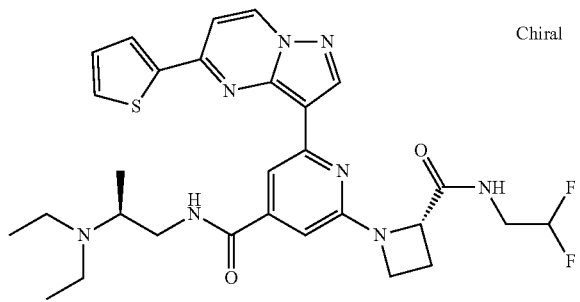

Compound 282 was synthesized following the Example 275, starting from commercially available 2,2-difluoroethan-1-amine, as a TFA salt. LC/MS (M+H): 597.398; 1H NMR (400 MHz, Methanol-d4) δ 8.88 (d, J=7.4 Hz, 1H), 8.64 (s, 1H), 8.33 (d, J=1.3 Hz, 1H), 7.96 (dd, J=3.8, 1.1 Hz, 1H), 7.73 (dd, J=5.1, 1.1 Hz, 1H), 7.54 (d, J=7.4 Hz, 1H), 7.24 (dd, J=5.0, 3.8 Hz, 1H), 6.68 (d, J=1.3 Hz, 1H), 4.94 (t, J=8.0 Hz, 1H), 4.18 (td, J=8.1, 4.2 Hz, 1H), 4.07 (q, J=7.8 Hz, 1H), 3.95 (dd, J=14.2, 5.7 Hz, 1H), 3.86 (q, J=6.3 Hz, 1H), 3.64 (tt, J=15.2, 3.9 Hz, 2H), 3.58-3.48 (m, 2H), 3.43-3.34 (m, 2H), 3.22 (dq, J=14.1, 7.2 Hz, 1H), 2.75-2.55 (m, 2H), 1.47 (t, J=7.2 Hz, 6H), 1.41 (t, J=7.2 Hz, 3H).

Example 283

N—((S)-2-(diethylamino)propyl)-2-(5-(thiophen-2-yl)pyrazolo[1,5-a]pyrimidin-3-yl)-6-((S)-2-((2,2,2-trifluoroethyl)carbamoyl)azetidin-1-yl)isonicotinamide

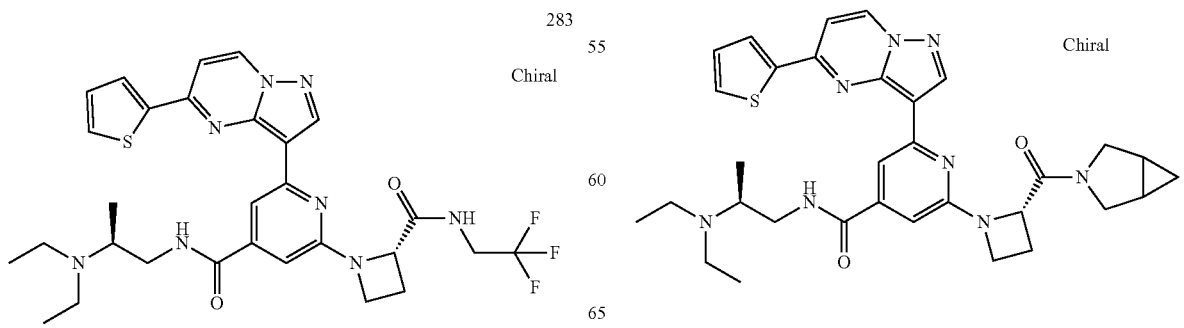

Compound 283 was synthesized following the Example 275, starting from commercially available 2,2,2-trifluoroethan-1-amine, as a TFA salt. LC/MS (M+H): 615.331; 1H NMR (400 MHz, Methanol-d$_4$) δ 8.88 (d, J=7.4 Hz, 1H), 8.63 (s, 1H), 8.39 (d, J=1.3 Hz, 1H), 7.97 (dd, J=3.8, 1.1 Hz, 1H), 7.72 (dd, J=5.1, 1.1 Hz, 1H), 7.55 (d, J=7.4 Hz, 1H), 7.24 (dd, J=5.1, 3.8 Hz, 1H), 6.67 (d, J=1.3 Hz, 1H), 4.93-4.88 (m, 2H), 4.17 (td, J=8.1, 4.2 Hz, 1H), 4.09-3.90 (m, 4H), 3.86 (q, J=6.3 Hz, 1H), 3.58-3.49 (m, 2H), 3.43-3.34 (m, 2H), 3.22 (dq, J=14.1, 7.2 Hz, 2H), 2.67 (dd, J=12.1, 8.0 Hz, 1H), 2.64-2.53 (m, 1H), 1.47 (t, J=7.4 Hz, 6H), 1.41 (t, J=7.3 Hz, 4H).

Example 284

N—((S)-2-(diethylamino)propyl)-2-((S)-2-(3-fluoroazetidine-1-carbonyl)azetidin-1-yl)-6-(5-(thiophen-2-yl)pyrazolo[1,5-a]pyrimidin-3-yl)isonicotinamide

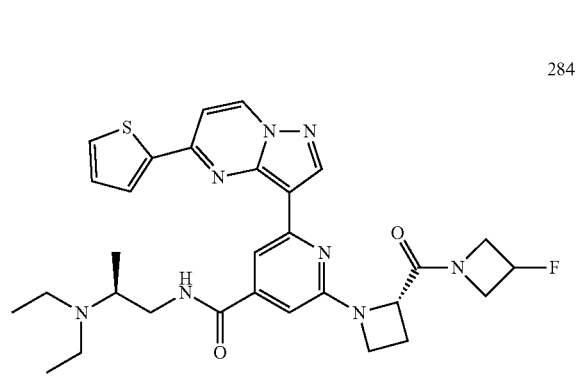 [SMILES: CCN(CC)[C@@H](C)CNC(=O)c1cc(-c2cnn3ccc(-c4cccs4)nc23)nc(N2CC[C@H]2C(=O)N2CC(F)C2)c1]

Compound 284 was synthesized following the Example 275, starting from commercially available 3-fluoroazetidine, as a TFA salt. LC/MS (M+H): 591.3; 1H NMR (MeOD, 400 MHz): δ 8.87 (d, 1H), 8.63 (d, 1H), 8.39 (s, 1H), 7.97 (d, 1H), 7.71 (d, 1H), 7.54 (d, 1H), 7.27-7.19 (m, 1H), 6.59 (s, 1H), 4.17-3.82 (m, 7H), 3.51 (s, 4H), 3.10-3.40 (m, 5H), 2.40-2.70 (m, 2H), 1.42 (d, 8H).

Example 285

2-((2S)-2-(3-azabicyclo[3.1.0]hexane-3-carbonyl)azetidin-1-yl)-N—((S)-2-(diethylamino)propyl)-6-(5-(thiophen-2-yl)pyrazolo[1,5-a]pyrimidin-3-yl)isonicotinamide Compound 285 was synthesized following the Example 275, starting from commercially available 3-azabicyclo

[3.1.0]hexane, as a TFA salt. LC/MS (M+H): 599.432; 1H NMR (400 MHz, Methanol-d4) δ 8.90 (dd, J=7.4, 2.8 Hz, 1H), 8.59 (d, J=3.2 Hz, 1H), 8.19-8.15 (m, 1H), 7.98 (dt, J=3.9, 1.2 Hz, 1H), 7.75 (ddd, J=5.1, 3.0, 1.1 Hz, 1H), 7.57 (d, J=7.4 Hz, 1H), 7.25 (ddd, J=5.0, 3.8, 1.2 Hz, 1H), 6.68-6.65 (m, 1H), 5.25 (dt, J=16.6, 7.8 Hz, 1H), 4.29-4.14 (m, 2H), 3.98-3.72 (m, 5H), 3.65-3.34 (m, 7H), 3.22 (dq, J=14.1, 7.1 Hz, 1H), 2.82 (ddd, J=24.8, 15.2, 5.5 Hz, 1H), 2.52 (dt, J=29.4, 9.6 Hz, 1H), 1.74 (dp, J=11.0, 3.7 Hz, 1H), 1.64 (tt, J=7.6, 4.1 Hz, 1H), 1.46 (t, J=7.5 Hz, 7H), 1.40 (t, J=7.2 Hz, 3H), 0.17 (q, J=4.4 Hz, 1H).

Example 286

N—((S)-2-(diethylamino)propyl)-2-((S)-2-(3-(methylsulfonamido)azetidine-1-carbonyl)azetidin-1-yl)-6-(5-(thiophen-2-yl)pyrazolo[1,5-a]pyrimidin-3-yl)isonicotinamide

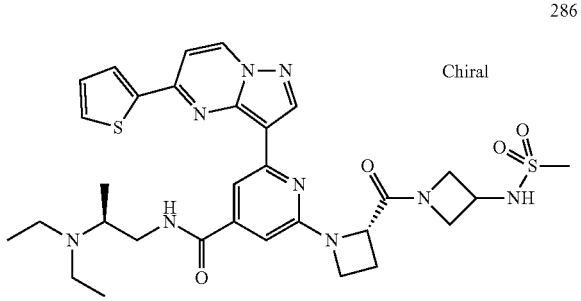 [SMILES: CCN(CC)[C@@H](C)CNC(=O)c1cc(-c2cnn3ccc(-c4cccs4)nc23)nc(N2CC[C@H]2C(=O)N2CC(NS(C)(=O)=O)C2)c1]

286

Chiral

Compound 286 was synthesized following the Example 275, starting from commercially available N-(azetidin-3-yl)methanesulfonamide, as a TFA salt. LC/MS (M+H): 666.427; 1H NMR (400 MHz, Methanol-d4) δ 8.87 (dd, J=7.4, 6.3 Hz, 1H), 8.63 (d, J=6.9 Hz, 1H), 8.26-8.20 (m, 1H), 7.96 (dd, J=5.1, 3.7 Hz, 1H), 7.78-7.72 (m, 1H), 7.53 (t, J=7.8 Hz, 1H), 7.28-7.22 (m, 1H), 6.68-6.62 (m, 1H), 5.03 (dt, J=26.1, 7.8 Hz, 1H), 4.45-4.32 (m, 3H), 4.25-4.06 (m, 3H), 4.06-3.81 (m, 3H), 3.60-3.46 (m, 2H), 3.38 (dd, J=7.2, 2.9 Hz, 2H), 3.23 (dq, J=14.0, 7.1 Hz, 1H), 2.96 (d, J=12.2 Hz, 3H), 2.72 (s, 1H), 2.65-2.52 (m, 1H), 1.46 (d, J=6.7 Hz, 7H), 1.41 (t, J=7.2 Hz, 3H).

Example 287

N—((S)-2-(diethylamino)propyl)-2-((S)-2-(methoxy(methyl)carbamoyl)azetidin-1-yl)-6-(5-(thiophen-2-yl)pyrazolo[1,5-a]pyrimidin-3-yl)isonicotinamide

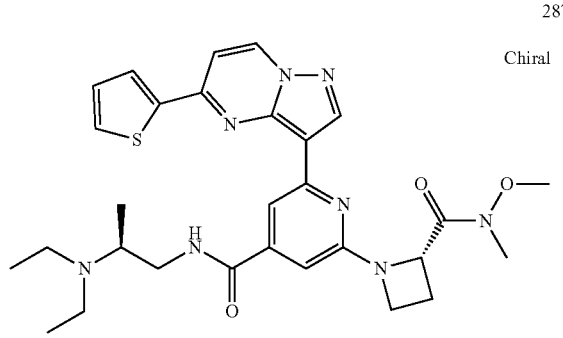

287

Chiral

Compound 287 was synthesized following the Example 275, starting from commercially available N,O-dimethylhydroxylamine, as a TFA salt. LC/MS (M+H): 577.467; 1H NMR (400 MHz, Methanol-d4) δ 8.89 (d, J=7.4 Hz, 1H), 8.63 (s, 1H), 8.20 (s, 1H), 7.97 (dd, J=3.8, 1.1 Hz, 1H), 7.74 (dd, J=5.1, 1.1 Hz, 1H), 7.55 (d, J=7.4 Hz, 1H), 7.25 (dd, J=5.0, 3.8 Hz, 1H), 6.67 (d, J=1.4 Hz, 1H), 5.49 (s, 1H), 4.22 (dq, J=31.5, 7.7 Hz, 2H), 3.99-3.81 (m, 6H), 3.54 (dt, J=13.3, 6.5 Hz, 3H), 3.38 (dd, J=7.3, 3.2 Hz, 3H), 3.29-3.17 (m, 4H), 2.57 (s, 1H), 1.46 (t, J=7.3 Hz, 7H), 1.40 (t, J=7.2 Hz, 4H).

Example 288

N—((S)-2-(diethylamino)propyl)-2-((S)-2-(pyrrolidine-1-carbonyl)azetidin-1-yl)-6-(5-(thiophen-2-yl)pyrazolo[1,5-a]pyrimidin-3-yl)isonicotinamide

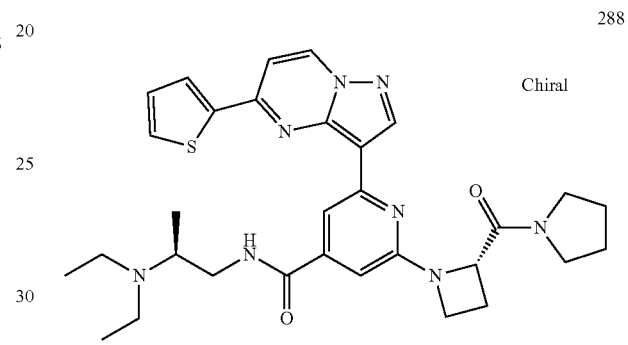

288

Chiral

Compound 288 was synthesized following the Example 275, starting from commercially available pyrrolidine, as a TFA salt. LC/MS (M+H): 587.547; 1H NMR (400 MHz, Methanol-d4) δ 8.92 (d, J=7.4 Hz, 1H), 8.60 (s, 1H), 8.18 (s, 1H), 7.99 (dd, J=3.9, 1.1 Hz, 1H), 7.75 (dd, J=5.0, 1.1 Hz, 1H), 7.58 (d, J=7.4 Hz, 1H), 7.26 (dd, J=5.0, 3.8 Hz, 1H), 6.71 (s, 1H), 5.35 (t, J=7.9 Hz, 1H), 4.29-4.16 (m, 2H), 3.94 (dd, J=14.1, 6.0 Hz, 1H), 3.85 (h, J=6.5 Hz, 1H), 3.75 (dd, J=10.9, 5.6 Hz, 1H), 3.59-3.34 (m, 9H), 3.22 (dq, J=13.9, 7.1 Hz, 1H), 2.82 (p, J=9.2, 8.8 Hz, 1H), 2.60 (p, J=8.7, 8.2 Hz, 1H), 2.06 (td, J=6.8, 2.9 Hz, 2H), 1.93 (q, J=6.9 Hz, 2H), 1.46 (t, J=7.4 Hz, 7H), 1.40 (t, J=7.2 Hz, 3H).

Example 289

N—((S)-2-(diethylamino)propyl)-2-((S)-2-(methoxycarbamoyl)azetidin-1-yl)-6-(5-(thiophen-2-yl)pyrazolo[1,5-a]pyrimidin-3-yl)isonicotinamide

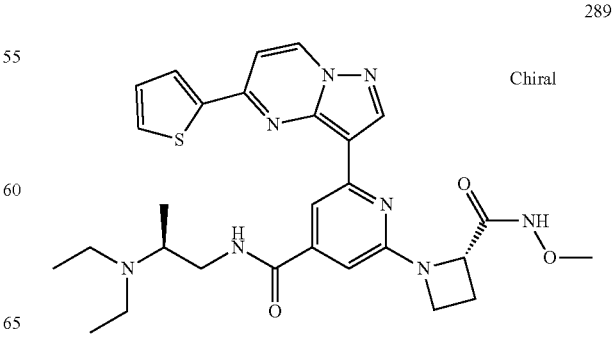

289

Chiral

Compound 289 was synthesized following the Example 275, starting from commercially available O-methylhydroxylamine, as a TFA salt. LC/MS (M+H): 563.371; 1H NMR (400 MHz, Methanol-d4) δ 8.88 (d, J=7.4 Hz, 1H), 8.68 (s, 1H), 8.37 (d, J=1.3 Hz, 1H), 7.97 (dd, J=3.8, 1.1 Hz, 1H), 7.72 (dd, J=5.0, 1.1 Hz, 1H), 7.54 (d, J=7.4 Hz, 1H), 7.24 (dd, J=5.0, 3.8 Hz, 1H), 6.65 (d, J=1.3 Hz, 1H), 4.82-4.76 (m, 2H), 4.21-4.14 (m, 1H), 4.05 (q, J=7.6 Hz, 1H), 3.95 (dd, J=14.2, 5.8 Hz, 1H), 3.87 (p, J=6.4 Hz, 1H), 3.74 (s, 3H), 3.53 (dt, J=12.6, 6.3 Hz, 2H), 3.43-3.34 (m, 2H), 3.27-3.16 (m, 2H), 2.72-2.54 (m, 2H), 1.47 (dd, J=8.2, 7.0 Hz, 7H), 1.41 (t, J=7.2 Hz, 4H).

Example 290

N—((S)-2-(diethylamino)propyl)-2-((R)-2-(methylcarbamoyl)azetidin-1-yl)-6-(5-(thiophen-2-yl)pyrazolo[1,5-a]pyrimidin-3-yl)isonicotinamide

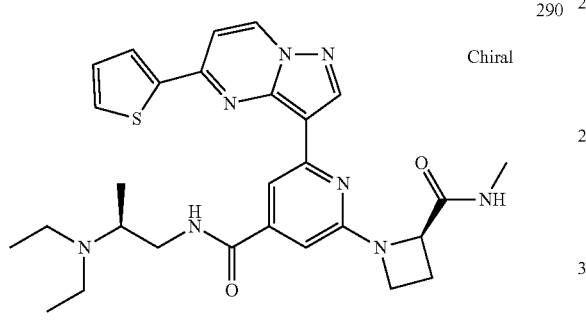

290

Chiral

Compound 290 was synthesized following the Example 275, starting from commercially available (R)-azetidine-2-carboxylic acid, and coupling with methyl amine, as a TFA salt.
LC/MS (M+H): 547.379; ¹H NMR (400 MHz, Methanol-d₄) δ 8.89 (d, J=7.4 Hz, 1H), 8.64 (s, 1H), 8.28 (t, J=1.2 Hz, 1H), 7.97 (dd, J=3.8, 1.1 Hz, 1H), 7.73 (dd, J=5.0, 1.1 Hz, 1H), 7.56 (d, J=7.4 Hz, 1H), 7.24 (dd, J=5.1, 3.8 Hz, 1H), 6.70 (d, J=1.4 Hz, 1H), 4.96 (t, J=8.0 Hz, 1H), 4.22-4.05 (m, 2H), 3.95 (dd, J=14.2, 5.7 Hz, 1H), 3.85 (q, J=6.4 Hz, 1H), 3.59-3.45 (m, 2H), 3.43-3.33 (m, 2H), 3.22 (dq, J=14.2, 7.2 Hz, 1H), 2.80 (s, 3H), 2.60 (t, J=9.3 Hz, 2H), 1.46 (t, J=7.1 Hz, 6H), 1.40 (t, J=7.2 Hz, 3H).

Example 291

N—((S)-2-(diethylamino)propyl)-2-((S)-2-(thiazol-2-ylcarbamoyl)azetidin-1-yl)-6-(5-(thiophen-2-yl)pyrazolo[1,5-a]pyrimidin-3-yl)isonicotinamide

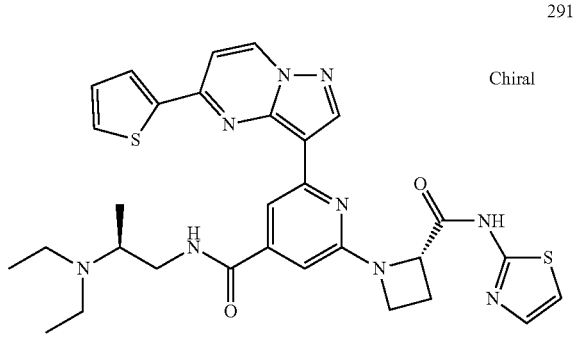 [SMILES: CCN(CC)[C@@H](C)CNC(=O)c1cc(-c2cnn3ccc(-c4cccs4)nc23)nc(N2CC[C@H]2C(=O)Nc2nccs2)c1]

291

Chiral

Compound 291 was synthesized following the Example 275, starting from commercially available 2-aminothiazole, as a TFA salt. LC/MS (M+H): 616.383; 1H NMR (400 MHz, Methanol-d4) δ 8.82 (d, J=7.4 Hz, 1H), 8.68 (s, 1H), 8.32 (d, J=1.2 Hz, 1H), 7.86 (d, J=3.7 Hz, 1H), 7.68 (d, J=5.0 Hz, 1H), 7.47 (d, J=7.4 Hz, 1H), 7.32 (d, J=3.6 Hz, 1H), 7.19 (dd, J=5.1, 3.8 Hz, 1H), 7.09 (d, J=3.5 Hz, 1H), 6.71 (d, J=2.0 Hz, 1H), 5.18 (t, J=8.0 Hz, 1H), 4.27-3.71 (m, 4H), 3.55 (dd, J=13.6, 6.7 Hz, 1H), 2.98-2.49 (m, 2H), 1.52-1.38 (m, 15H).

Example 292

N—((S)-2-(diethylamino)propyl)-2-((S)-2-(3,3-dimethylazetidine-1-carbonyl)azetidin-1-yl)-6-(5-(thiophen-2-yl)pyrazolo[1,5-a]pyrimidin-3-yl)isonicotinamide

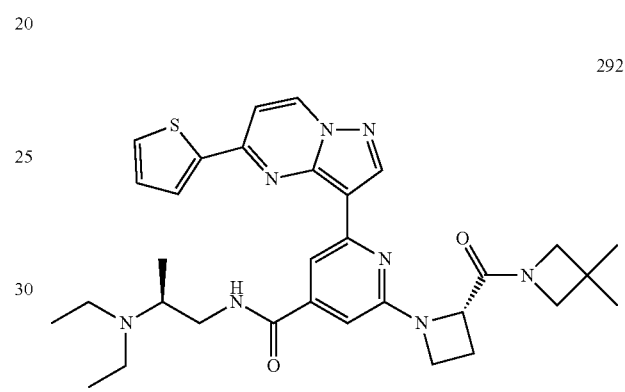

292

Compound 292 was synthesized following the Example 275, starting from commercially available 3,3-dimethylazetidine, as a TFA salt. LC/MS (M+H): 601.3

Example 293

N—((S)-2-(diethylamino)propyl)-2-((S)-2-(morpholine-4-carbonyl)azetidin-1-yl)-6-(5-(thiophen-2-yl)pyrazolo[1,5-a]pyrimidin-3-yl)isonicotinamide

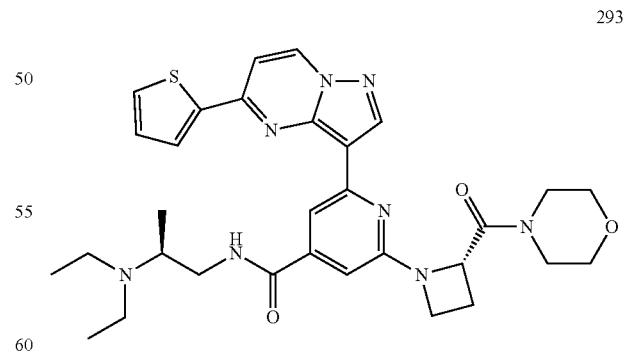

293

Compound 293 was synthesized following the Example 275, starting from commercially available morpholine, as a TFA salt. LC/MS (M+H): 603.3; ¹H NMR (MeOD, 400 MHz): δ 8.92 (d, 1H), 8.65 (s, 1H), 8.18 (s, 1H), 7.99 (d, 1H), 7.74 (d, 1H), 7.58 (d, 1H), 7.25 (dd, 1H), 6.70 (s, 1H), 5.42 (d, 1H), 4.23 (dd, 2H), 3.93 (dd, 1H), 3.87-3.81 (m, 1H), 3.68 (d, 5H), 3.54 (bs, 5H), 3.25-3.19 (m, 1H), 2.85 (s, 1H), 2.57 (s, 1H), 1.46 (t, 5H), 1.39 (t, 3H).

Example 294

N—((S)-2-(diethylamino)propyl)-2-((S)-2-(3,3-difluoroazetidine-1-carbonyl)azetidin-1-yl)-6-(5-(thiophen-2-yl)pyrazolo[1,5-a]pyrimidin-3-yl)isonicotinamide

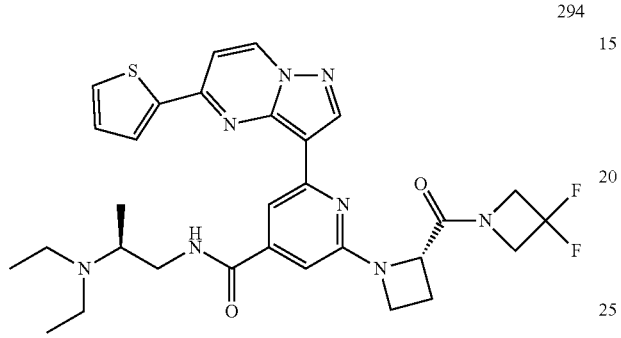

Compound 294 was synthesized following the Example 275, starting from commercially available 3,3-difluoroazetidine, as a TFA salt. LC/MS (M+H): 609.3; $^1$H NMR (MeOD, 400 MHz): δ 8.89 (d, 1H), 8.60 (s, 1H), 8.39 (s, 1H), 7.98 (d, 1H), 7.72 (d, 1H), 7.55 (d, 1H), 7.24-7.25 (m, 1H), 6.63 (s, 1H), 4.89-4.93 (m, 2H), 4.41-4.46 (m, 2H), 3.80-4.20 (m, 5H), 3.42-3.52 (m, 2H), 3.30-3.39 (m, 4H), 3.15 (d, 1H), 2.55-2.75 (m, 2H), 1.35-1.50 (m, 7H).

Example 295

N—((S)-2-(diethylamino)propyl)-2-((S)-2-(3-methoxyazetidine-1-carbonyl)azetidin-1-yl)-6-(5-(thiophen-2-yl)pyrazolo[1,5-a]pyrimidin-3-yl)isonicotinamide

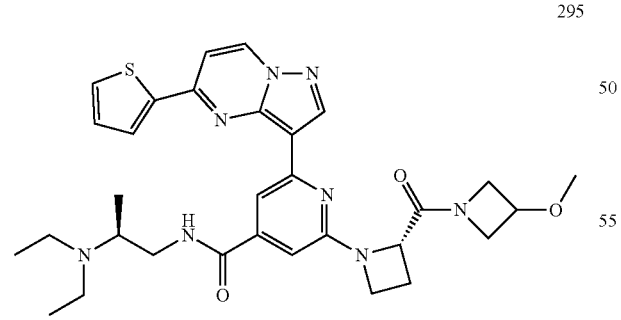

Compound 295 was synthesized following the Example 275, starting from commercially available 3-methoxyazetidine, as a TFA salt. LC/MS (M+H): 603.3; $^1$H NMR (MeOD, 400 MHz): δ 8.90 (d, 1H), 8.61 (d, 1H), 8.40 (s, 1H), 7.88 (d, 1H), 7.71 (d, 1H), 7.54 (d, 1H), 7.27-7.18 (m, 1H), 6.60 (s, 1H), 4.17-3.77 (m, 7H), 3.51 (s, 4H), 3.40 (s, 3H), 3.00-3.33 (m, 3H), 1.40 (d, 9H).

Example 296

(S)-1-(4-(((S)-2-(diethylamino)propyl)carbamoyl)-6-(5-(thiophen-2-yl)pyrazolo[1,5-a]pyrimidin-3-yl)pyridin-2-yl)azetidine-2-carboxylic Acid

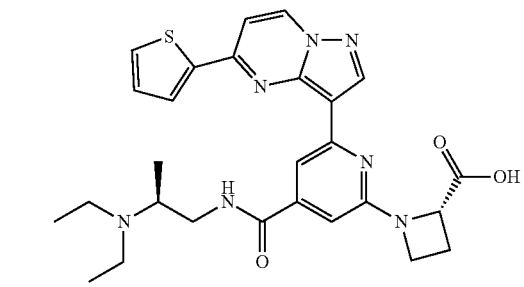

Compound 296 was synthesized following the Example 275, coupling the intermediate acid with the boronic ester 1D, as a TFA salt. LC/MS (M+H): 534.2; $^1$H NMR (MeOD, 400 MHz): δ 8.85 (d, 1H), 8.61 (s, 1H), 8.32 (s, 1H), 7.95 (d, 1H), 7.72 (d, 1H), 7.53 (d, 1H), 7.27-7.20 (m, 1H), 6.66 (s, 1H), 4.95 (t, 1H), 4.16-4.06 (m, 2H), 3.97-3.82 (m, 3H), 3.56-3.48 (m, 2H), 3.38 (s, 1H), 3.10-3.30 (m, 1H), 2.64 (d, 2H), 1.46 (d, 9H).

Example 297

N—((S)-2-(diethylamino)propyl)-2-((S)-2-((2-hydroxyethyl)carbamoyl)azetidin-1-yl)-6-(5-(thiophen-2-yl)pyrazolo[1,5-a]pyrimidin-3-yl)isonicotinamide

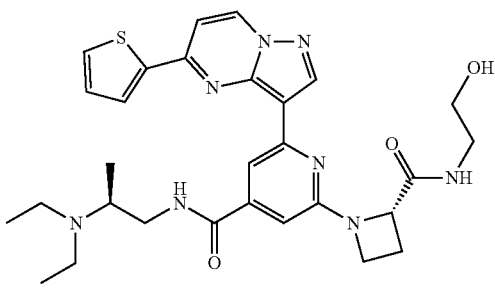

Compound 297 was synthesized following the Example 275, starting from commercially available 2-aminoethan-1-ol, as a TFA salt. LC/MS (M+H): 576.3; $^1$H NMR (MeOD, 400 MHz): δ 8.90 (d, 1H), 8.68 (s, 1H), 8.38 (s, 1H), 7.95 (d, 1H), 7.70 (d, 1H), 7.53 (d, 1H), 7.27-7.20 (m, 1H), 6.62 (s, 1H), 4.95 (t, 1H), 4.16-4.06 (m, 2H), 4.00-3.82 (m, 3H), 3.55-3.48 (m, 2H), 3.39-3.45 (m, 3H), 3.37 (s, 1H), 3.12-3.15 (m, 2H), 2.64 (d, 2H), 1.35 (br s, 9H).

Example 298

N—((S)-2-(diethylamino)propyl)-2-((S)-2-(hydroxy (methyl)carbamoyl)azetidin-1-yl)-6-(5-(thiophen-2-yl)pyrazolo[1,5-a]pyrimidin-3-yl)isonicotinamide

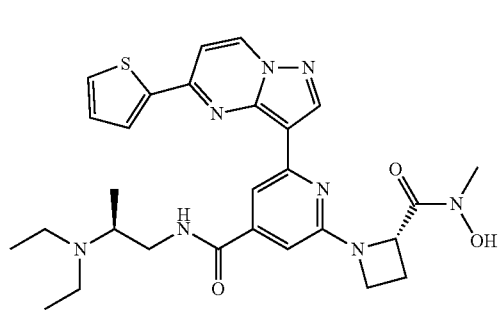

Compound 298 was synthesized following the Example 275, starting from commercially available N-methylhydroxylamine, as a TFA salt. LC/MS (M+H): 563.3; $^1$H NMR (MeOD, 400 MHz): δ 8.88 (d, 1H), 8.68 (s, 1H), 8.27 (s, 1H), 7.96 (d, 1H), 7.72 (d, 1H), 7.54 (d, 1H), 7.24 (s, 1H), 6.61 (s, 1H), 5.49 (s, 1H), 4.02-4.20 (m, 2H), 4.00-3.77 (m, 4H), 3.53 (bs, 3H), 3.37 (bs, 2H), 3.09 (d, 3H), 2.40-2.80 (2H), 1.43 (dt, 7H).

Example 299

2-((S)-2-carbamoylazetidin-1-yl)-N—((S)-2-(diethylamino)propyl)-6-(5-(thiophen-2-yl)pyrazolo[1,5-a]pyrimidin-3-yl)isonicotinamide

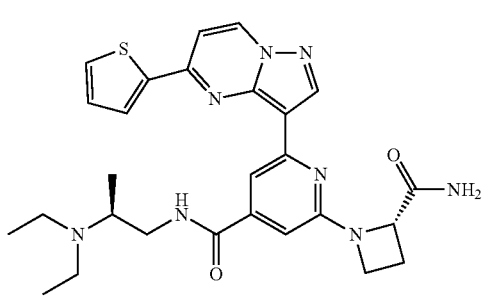

Compound 299 was synthesized following the Example 275, starting from commercially available ammonia, as a TFA salt. LC/MS (M+H): 533.2; $^1$H NMR (MeOD, 400 MHz): δ 8.88 (d, 1H), 8.66 (s, 1H), 8.41 (d, 1H), 7.97 (d, 1H), 7.71 (d, 1H), 7.54 (d, 1H), 7.27-7.20 (m, 1H), 6.64 (s, 1H), 3.80-4.18 (m, 5H), 3.52 (dd, 2H), 3.42-3.35 (m, 2H), 3.09-3.25 (m, 2H), 2.50-2.70 (m, 2H), 1.50-1.36 (m, 8H).

Example 300

2-((S)-2-((cyanomethyl)carbamoyl)azetidin-1-yl)-N—((S)-2-(diethylamino)propyl)-6-(5-(thiophen-2-yl)pyrazolo[1,5-a]pyrimidin-3-yl)isonicotinamide

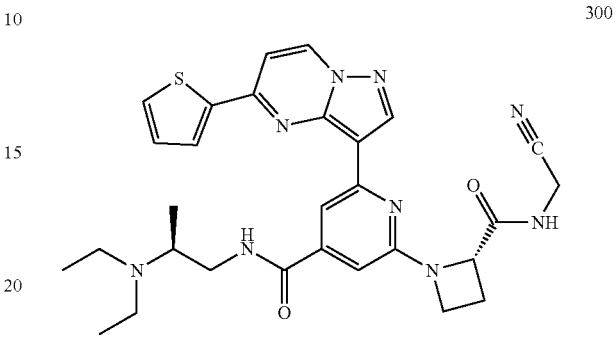

Compound 300 was synthesized following the Example 275, starting from commercially available 2-aminoacetonitrile, as a TFA salt. LC/MS (M+H): 572.3; $^1$H NMR (MeOD, 400 MHz): δ 8.88 (d, 1H), 8.66 (s, 1H), 8.41 (s, 1H), 7.97 (d, 1H), 7.71 (d, 1H), 7.54 (d, 1H), 7.23 (dd, 1H), 6.65 (s, 1H), 4.22 (d, 2H), 3.80-4.20 (m, 5H), 3.40-3.50 (m, 3H), 3.10 (bs, 3H), 2.50-2.70 (m, 2H), 1.47-1.37 (m, 8H).

Example 301

N—((S)-2-(diethylamino)propyl)-2-((S)-2-((2-methoxyethyl)carbamoyl)azetidin-1-yl)-6-(5-(thiophen-2-yl)pyrazolo[1,5-a]pyrimidin-3-yl)isonicotinamide

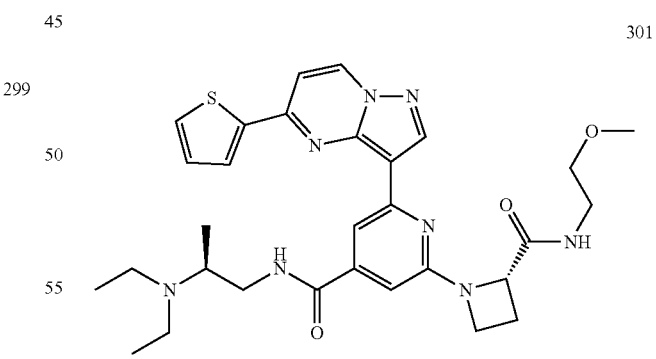

Compound 301 was synthesized following the Example 275, starting from commercially available 2-methoxyethan-1-amine, as a TFA salt. LC/MS (M+H): 591.3; $^1$H NMR (MeOD, 400 MHz): δ 8.89 (d, 1H), 8.69 (s, 1H), 8.29 (d, 1H), 7.96 (dd, 1H), 7.72 (dd, 1H), 7.55 (d, 1H), 7.24 (dd, 1H), 6.70 (d, 1H), 4.99 (t, 1H), 4.18 (q, 1H), 4.08 (q, 1H), 3.94 (dd, 1H), 3.85 (q, 1H), 3.57-3.33 (m, 8H), 3.24 (s, 4H), 2.70-2.59 (m, 2H), 1.55-1.32 (m, 9H).

Example 302

N—((S)-2-(diethylamino)propyl)-2-((S)-2-(3-(methylsulfonyl)azetidine-1-carbonyl)azetidin-1-yl)-6-(5-(thiophen-2-yl)pyrazolo[1,5-a]pyrimidin-3-yl)isonicotinamide

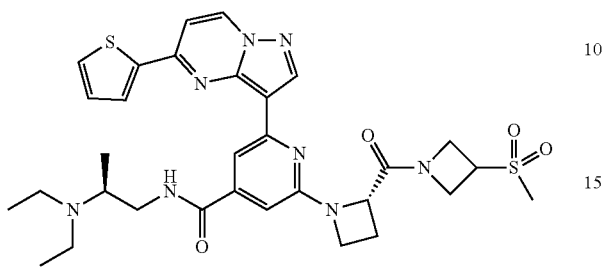

Compound 302 was synthesized following the Example 275, starting from commercially available 3-(methylsulfonyl)azetidine, as a TFA salt. LC/MS (M+H): 651.3

Example 303

N—((S)-2-(diethylamino)propyl)-2-((S)-2-(1,1-dioxidothiomorpholine-4-carbonyl)azetidin-1-yl)-6-(5-(thiophen-2-yl)pyrazolo[1,5-a]pyrimidin-3-yl)isonicotinamide

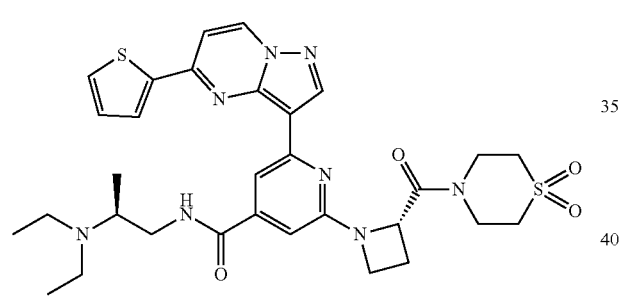

Compound 303 was synthesized following the Example 275, starting from commercially available thiomorpholine 1,1-dioxide, as a TFA salt. LC/MS (M+H): 651.3

Example 304

N—((S)-2-(diethylamino)propyl)-2-((S)-2-(3-hydroxyazetidine-1-carbonyl)azetidin-1-yl)-6-(5-(thiophen-2-yl)pyrazolo[1,5-a]pyrimidin-3-yl)isonicotinamide

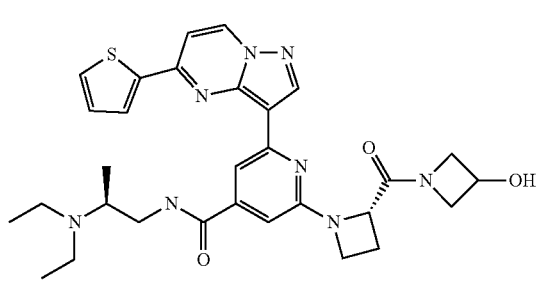

Compound 304 was synthesized following the Example 275, starting from commercially available 3-hydroxy azetidine, as a TFA salt. LC/MS (M+H): 589.3

Example 305

N—((S)-2-aminopropyl)-2-((S)-2-(methylcarbamoyl)azetidin-1-yl)-6-(5-(thiophen-2-yl)pyrazolo[1,5-a]pyrimidin-3-yl)isonicotinamide

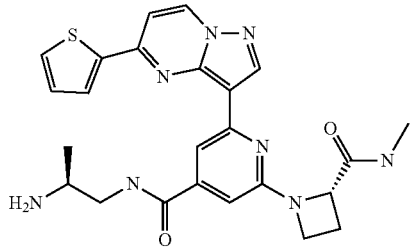

Compound 305 was synthesized following the Example 275, starting by coupling with commercially available tert-butyl (S)-(1-aminopropan-2-yl)carbamate and by deprotection with TFA, as a TFA salt. LC/MS (M+H): 491.2

Example 306

N—((S)-2-(ethylamino)propyl)-2-((S)-2-(methylcarbamoyl)azetidin-1-yl)-6-(5-(thiophen-2-yl)pyrazolo[1,5-a]pyrimidin-3-yl)isonicotinamide

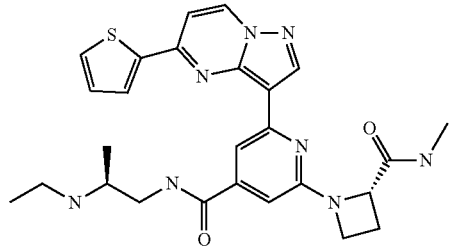

Compound 306 was synthesized following the Example 275, starting by coupling with commercially available tert-butyl (S)-(1-aminopropan-2-yl)(ethyl)carbamate and by deprotection with TFA, as a TFA salt. LC/MS (M+H): 519.2

Example 307

N—((S)-2-(diethylamino)propyl)-2-(5-(isothiazol-5-yl)pyrazolo[1,5-a]pyrimidin-3-yl)-6-((S)-2-(methylcarbamoyl)azetidin-1-yl)isonicotinamide

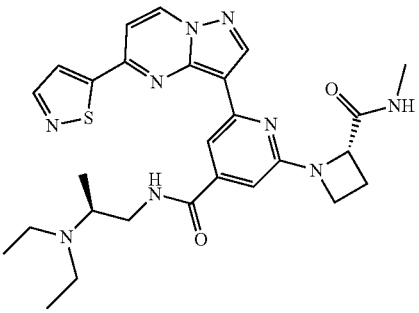

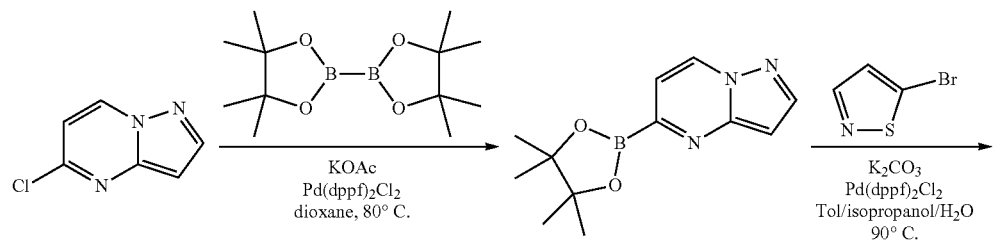
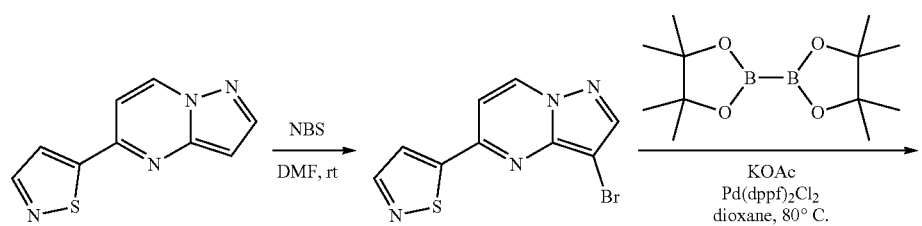
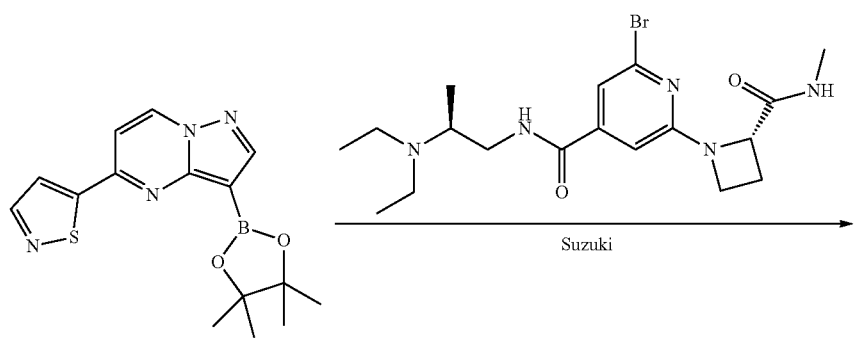
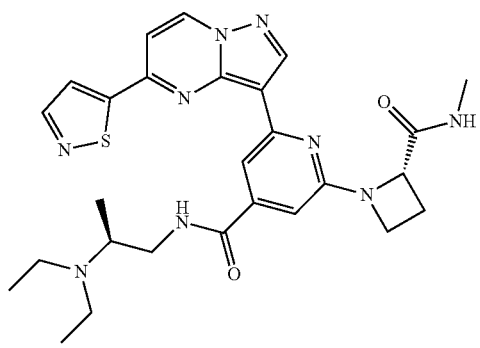
Compound 307 was synthesized following the Examples 1 and 5 starting from the corresponding commercially available starting materials. LC/MS (M+H): 548.2; $^1$H-NMR (CD$_3$OD) δ 9.08 (d, 1H, J=7.2 Hz), 8.72 (s, 1H), 8.63 (d, 1H, J=2.0 Hz), 8.28 (d, 1H, J=1.2 Hz), 8.05 (d, 1H, J=2.0 Hz), 7.63 (d, 1H, J=7.2 Hz), 6.75 (d, 1H, J=1.2 Hz), 4.97 (t, 1H, J=8.0 Hz), 4.09-4.20 (m, 2H), 3.95 (dd, 1H, J=14.0, 5.6 Hz), 3.82-3.90 (m, 1H), 3.48-3.57 (m, 2H), 3.33-3.43 (m, 2H), 3.16-3.27 (m, 1H), 2.82 (s, 3H), 2.56-2.78 (m, 2H), 1.46-1.49 (m, 6H), 1.41 (t, 3H, J=7.2 Hz);

Example 308

N—((S)-2-(diethylamino)propyl)-2-((S)-2-(3-methyl-1,2,4-oxadiazol-5-yl)azetidin-1-yl)-6-(5-(thiophen-2-yl)pyrazolo[1,5-a]pyrimidin-3-yl)isonicotinamide

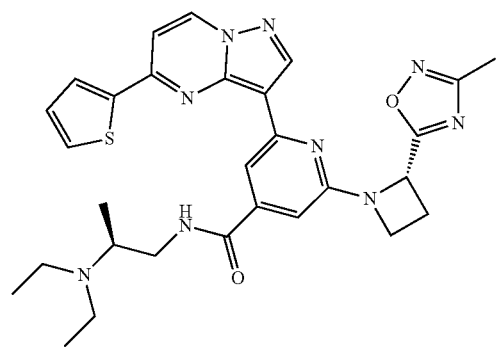

308

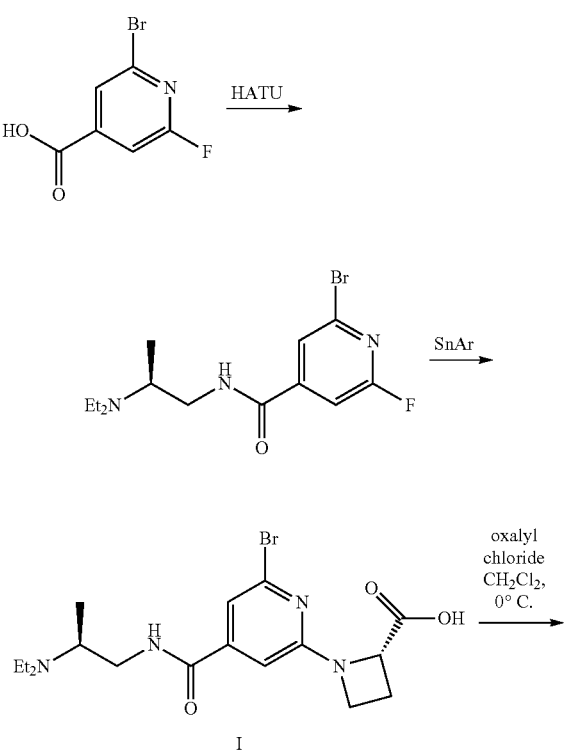

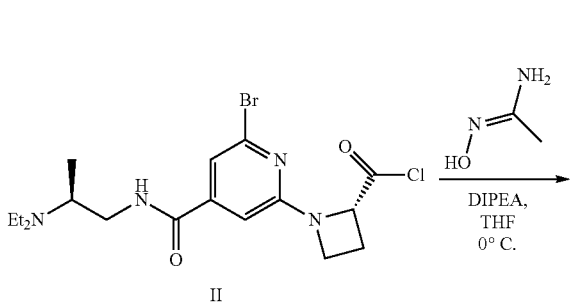

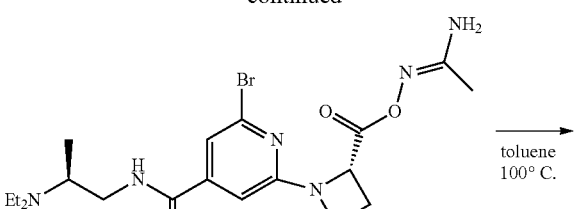

III

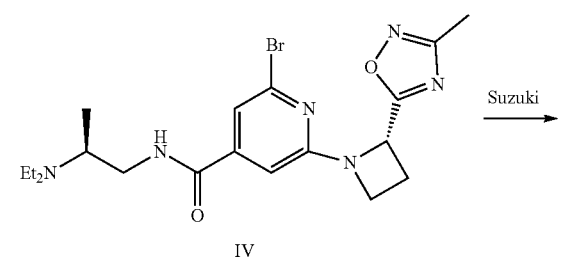

IV

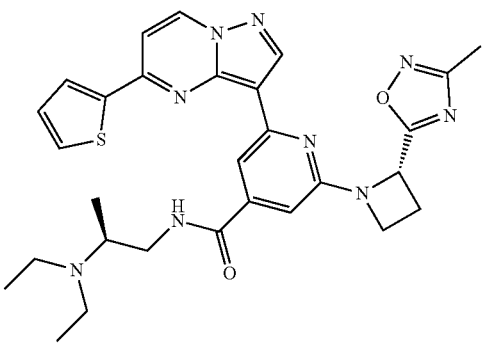

Step I-II:

To as stirred solution of I (27.2 mg, 0.066 mmol) in CH$_2$Cl$_2$ ((2 mL) was added oxalyl chloride (1 mL) slowly in an ice bath. The resulting mixture was stirred at 0° C. for 1 h and concentrated. The white crude product was used directly for next step.

Step II-III:

A mixture of II (28.50 mg, 0.066 mmol), N'-hydroxyacetimidamide (14.67 mg, 0.198 mmol), and DIPEA (25.59 mg, 0.198 mmol) were stirred in THF at 0° C. for 1 h. After concentration, the crude white product was used directly for next step.

Step III-IV:

Crude product from previous step was stirred in toluene (4 mL) at 100° C. for 1 h. After concentration, the residue was purified with prep-HPLC to get product (6.5 mg).

LC/MS (M+H): 572.2; $^1$H-NMR (CD$_3$OD) δ 8.83 (d, 1H, J=7.2 Hz), 8.47-8.54 (m, 1H), 8.31 (d, 1H, J=1.6 Hz), 7.94 (dd, 1H, J=3.8, 1.0 Hz), 7.70 (dd, 1H, J=5.0, 1.0 Hz), 7.49 (d, 1H, J=7.6 Hz), 7.21 (dd, 1H, J=5.0, 3.8 Hz), 6.60-6.65 (m, 1H), 5.57-5.60 (m, 1H), 4.26-4.31 (m, 1H), 4.11-4.17 (m, 1H), 3.43-3.47 (m, 2H), 3.33-3.38 (m, 2H), 3.18-3.23 (m, 1H), 2.55-2.91 (m, 4H), 2.39 (s, 3H), 1.08-1.18 (m, 9H);

Example 309

N—((S)-2-(diethylamino)propyl)-2-((S)-2-(methyl-carbamoyl)azetidin-1-yl)-6-(5-phenylpyrazolo[1,5-a]pyrimidin-3-yl)isonicotinamide

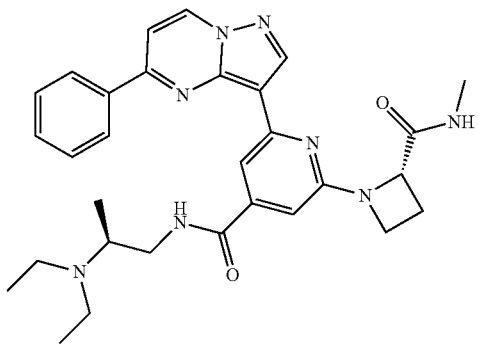

309

Compound 309 was synthesized following the Example 275, coupling with the boronic ester 5-phenyl-3-(4,4,5,5-tetramethyl-1,3,2-dioxaborolan-2-yl)pyrazolo[1,5-a]pyrimidine (37C), as a TFA salt. LC/MS (M+H): 541.2

Example 310

N—((S)-2-(diethylamino)propyl)-2-((S)-3-(methyl-carbamoyl)pyrrolidin-1-yl)-6-(5-(thiophen-2-yl)pyrazolo[1,5-a]pyrimidin-3-yl)isonicotinamide

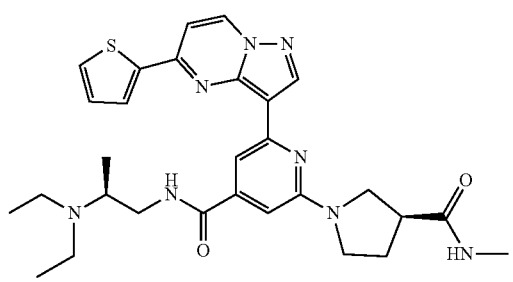

310

Compound 310 was synthesized following the Example 275, starting from commercially available (S)-pyrrolidine-3-carboxylic acid, as a TFA salt. LC/MS (M+H): 561.3; $^1$H NMR (MeOD, 400 MHz): δ 8.92 (d, 1H), 8.73 (s, 1H), 7.95-8.00 (m, 2H), 7.74 (d, 1H), 7.60 (d, 1H), 7.26 (t, 1H), 6.85 (s, 1H), 3.80-4.00 (m, 4H), 3.66-3.72 (m, 1H), 3.45-3.55 (m, 3H), 3.35-3.40 (m, 2H), 3.16-3.25 (m, 2H), 2.80 (s, 3H), 2.30-2.45 (m, 2H), 1.36-1.50 (m, 9H).

Example 311

N—((S)-2-(diethylamino)propyl)-2-((R)-3-(methyl-carbamoyl)pyrrolidin-1-yl)-6-(5-(thiophen-2-yl)pyrazolo[1,5-a]pyrimidin-3-yl)isonicotinamide

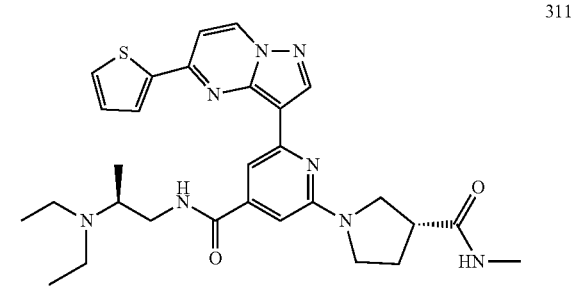 [SMILES: CCN(CC)[C@@H](C)CNC(=O)c1cc(-c2cnn3ccc(-c4cccs4)nc23)nc(N2CC[C@@H](C(=O)NC)C2)c1]

311

Compound 311 was synthesized following the Example 275, starting from commercially available (R)-pyrrolidine-3-carboxylic acid, as a TFA salt. LC/MS (M+H): 561.3; $^1$H NMR (MeOD, 400 MHz): δ 8.99 (d, 1H), 8.78 (s, 1H), 8.05-7.99 (m, 1H), 7.87 (s, 1H), 7.78 (d, 1H), 7.67 (d, 1H), 7.31-7.24 (m, 1H), 7.00 (s, 1H), 4.11-3.75 (m, 6H), 3.58-3.46 (m, 2H), 3.36 (t, 3H), 3.27-3.10 (m, 1H), 2.81 (s, 3H), 2.45 (s, 2H), 1.53-1.33 (m, 9H).

Example 312

2-((R)-3-cyanopyrrolidin-1-yl)-N—((S)-2-(diethyl-amino)propyl)-6-(5-(thiophen-2-yl)pyrazolo[1,5-a]pyrimidin-3-yl)isonicotinamide

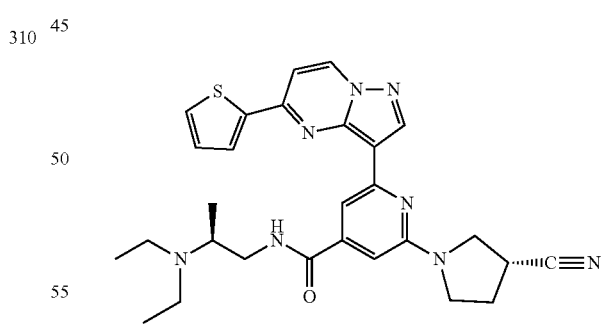

312

Compound 312 was synthesized following the Example 141, starting from commercially available (R)-pyrrolidine-3-carbonitrile, as a TFA salt. LC/MS (M+H): 529.2; $^1$H NMR (MeOD, 400 MHz): δ 8.91 (d, 1H), 8.75 (s, 1H), 8.12 (s, 1H), 7.99 (dd, 1H), 7.75 (dd, 1H), 7.58 (d, 1H), 7.26 (dd, 1H), 6.81 (s, 1H), 4.08-3.91 (m, 3H), 3.86 (q, 2H), 3.79-3.70 (m, 1H), 3.55 (ddd, 3H), 3.38 (dd, 2H), 3.22 (dd, 1H), 2.55 (q, 1H), 2.45 (dt, 1H), 1.44 (dt, 9H).

Example 313

2-((S)-3-cyanopyrrolidin-1-yl)-N—((S)-2-(diethyl-amino)propyl)-6-(5-(thiophen-2-yl)pyrazolo[1,5-a]pyrimidin-3-yl)isonicotinamide

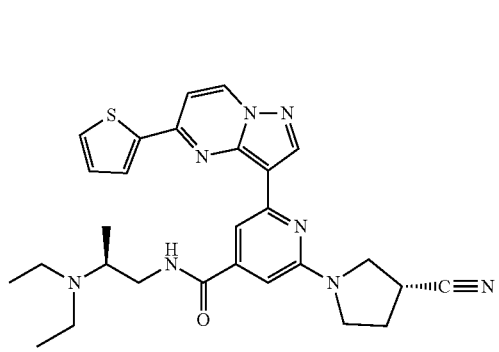

Compound 313 was synthesized following the Example 141, starting from commercially available (S)-pyrrolidine-3-carbonitrile, as a TFA salt. LC/MS (M+H): 529.2; $^1$H NMR (MeOD, 400 MHz): δ 8.93 (d, 1H), 8.76 (s, 1H), 8.20 (s, 1H), 7.98 (dd, 1H), 7.73 (dd, 1H), 7.58 (d, 1H), 7.26 (dd, 1H), 6.76 (s, 1H), 4.08-3.91 (m, 3H), 3.86 (q, 2H), 3.79-3.70 (m, 1H), 3.55 (ddd, 3H), 3.38 (dd, 2H), 3.22 (dd, 1H), 2.55 (q, 1H), 2.45 (dt, 1H), 1.44 (dt, 9H).

Example 314

(S)—N-(2-(diethylamino)propyl)-2-(3-oxopiperazin-1-yl)-6-(5-(thiophen-2-yl)pyrazolo[1,5-a]pyrimidin-3-yl)isonicotinamide

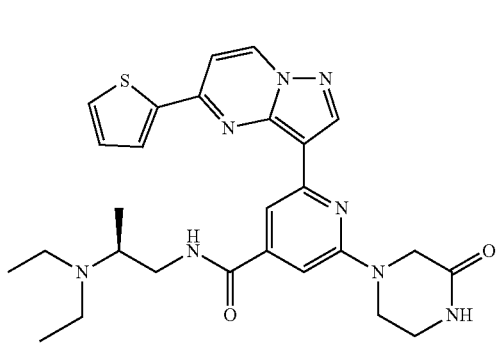

Compound 314 was synthesized following the Example 141, starting from commercially available piperazin-2-one, as a TFA salt. LC/MS (M+H): 533.2; $^1$H NMR (MeOD, 400 MHz): δ 8.86 (d, 1H), 8.74 (s, 1H), 8.31 (d, 1H), 7.95 (dd, 1H), 7.72 (dd, 1H), 7.52 (d, 1H), 7.24 (dd, 1H), 6.94 (d, 1H), 4.28 (s, 2H), 4.02-3.93 (m, 3H), 3.87 (q, 1H), 3.58-3.46 (m, 4H), 3.42-3.34 (m, 2H), 3.22 (dd, 1H), 1.53-1.44 (m, 6H), 1.41 (t, 3H).

Example 315

N—((S)-2-(diethylamino)propyl)-2-((S)-3-hydroxy-pyrrolidin-1-yl)-6-(5-(thiophen-2-yl)pyrazolo[1,5-a]pyrimidin-3-yl)isonicotinamide

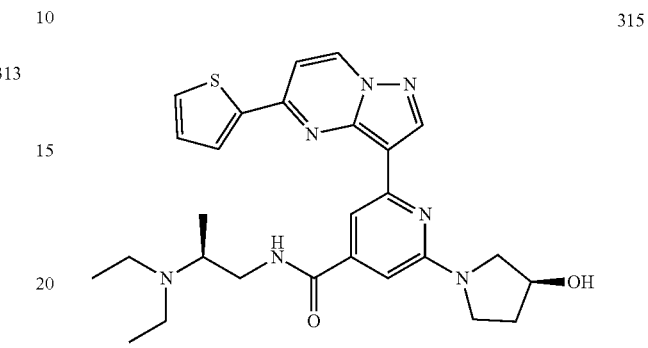

Compound 315 was synthesized following the Example 141, starting from commercially available (S)-pyrrolidin-3-ol, as a TFA salt. LC/MS (M+H): 520.2; $^1$H NMR (MeOD, 400 MHz): δ 8.86 (d, 1H), 8.74 (s, 1H), 8.31 (d, 1H), 7.95 (dd, 1H), 7.72 (dd, 1H), 7.52 (d, 1H), 7.24 (dd, 1H), 6.94 (d, 1H), 4.72 (bs, 1H), 4.28 (s, 2H), 4.02-3.93 (m, 3H), 3.87 (q, 1H), 3.58-3.46 (m, 2H), 3.42-3.34 (m, 2H), 3.22 (dd, 1H), 2.20-2.40 (m, 2H), 1.53-1.44 (m, 6H), 1.41 (t, 3H).

Example 316

N—((S)-2-(diethylamino)propyl)-2-((R)-3-hydroxy-pyrrolidin-1-yl)-6-(5-(thiophen-2-yl)pyrazolo[1,5-a]pyrimidin-3-yl)isonicotinamide

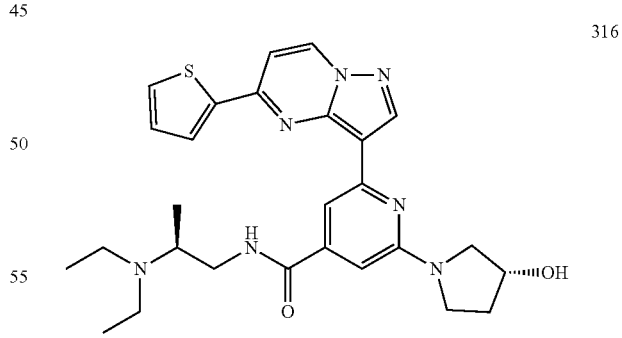

Compound 316 was synthesized following the Example 141, starting from commercially available (R)-pyrrolidin-3-ol, as a TFA salt. LC/MS (M+H): 520.2; $^1$H NMR (MeOD, 400 MHz): δ 8.76 (d, 1H), 8.70 (s, 1H), 8.30 (d, 1H), 7.95 (dd, 1H), 7.72 (dd, 1H), 7.52 (d, 1H), 7.20 (dd, 1H), 6.94 (d, 1H), 4.72 (bs, 1H), 4.28 (s, 2H), 4.02-3.93 (m, 3H), 3.87 (q, 1H), 3.58-3.46 (m, 2H), 3.42-3.34 (m, 2H), 3.22 (dd, 1H), 2.20-2.40 (m, 2H), 1.53-1.44 (m, 6H), 1.41 (t, 3H).

Example 317

2-((S)-3-aminopyrrolidin-1-yl)-N—((S)-2-(diethyl-amino)propyl)-6-(5-(thiophen-2-yl)pyrazolo[1,5-a]pyrimidin-3-yl)isonicotinamide

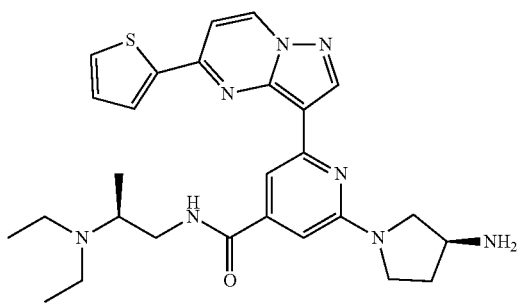

317

Compound 317 was synthesized following the Example 141, starting from commercially available (S)-pyrrolidin-3-amine, as a TFA salt. LC/MS (M+H): 519.3; $^1$H NMR (MeOD, 400 MHz): δ 8.91 (d, 1H), 8.75 (s, 1H), 8.30 (d, 1H), 8.01-7.95 (m, 1H), 7.75-7.71 (m, 1H), 7.56 (d, 1H), 7.28-7.23 (m, 1H), 6.74 (s, 1H), 4.10 (s, 1H), 4.01-3.94 (m, 2H), 3.84 (dd, 3H), 3.73 (s, 1H), 3.54 (dd, 3H), 3.40-3.35 (m, 2H), 3.23 (dd, 1H), 2.53-2.59 (m, 1H), 2.26 (s, 1H), 1 47 (dd, 5H), 1.41 (t, 3H).

Example 318

2-((R)-3-aminopyrrolidin-1-yl)-N—((S)-2-(diethyl-amino)propyl)-6-(5-(thiophen-2-yl)pyrazolo[1,5-a]pyrimidin-3-yl)isonicotinamide

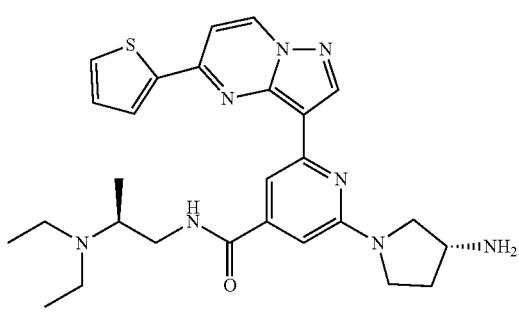

318

Compound 318 was synthesized following the Example 141, starting from commercially available (R)-pyrrolidin-3-amine, as a TFA salt. LC/MS (M+H): 519.3; $^1$H NMR (MeOD, 400 MHz): δ 8.89 (d, 1H), 8.74 (s, 1H), 8.30 (d, 1H), 8.02-7.93 (m, 1H), 7.75-7.71 (m, 1H), 7.56 (d, 1H), 7.28-7.23 (m, 1H), 6.68 (s, 1H), 4.10 (s, 1H), 4.00-3.94 (m, 2H), 3.84 (dd, 3H), 3.73 (s, 1H), 3.54 (dd, 3H), 3.40-3.35 (m, 2H), 3.18 (dd, 1H), 2.53-2.59 (m, 1H), 2.26 (s, 1H), 1.47 (dd, 5H), 1.41 (t, 3H).

Example 319

N—((S)-2-(diethylamino)propyl)-2-((S)-2-(methyl-carbamoyl)pyrrolidin-1-yl)-6-(5-(thiophen-2-yl)pyrazolo[1,5-a]pyrimidin-3-yl)isonicotinamide

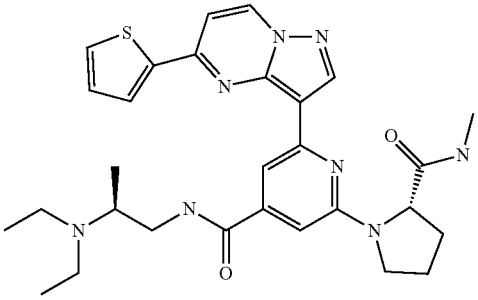

319

Compound 319 was synthesized following the Example 275, starting from commercially available L-proline, as a TFA salt. LC/MS (M+H): 561.3

Example 320

N—((S)-2-(diethylamino)propyl)-2-((R)-2-(methyl-carbamoyl)pyrrolidin-1-yl)-6-(5-(thiophen-2-yl)pyrazolo[1,5-a]pyrimidin-3-yl)isonicotinamide

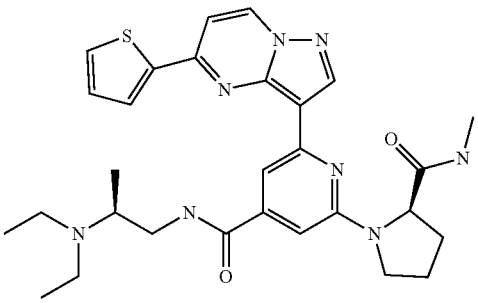

320

Compound 320 was synthesized following the Example 275, starting from commercially available L-proline, as a TFA salt. LC/MS (M+H): 561.3

Example 321

(2-((2-(1H-imidazol-1-yl)ethyl)(methyl)amino)-6-(5-(thiophen-2-yl)pyrazolo[1,5-a]pyrimidin-3-yl)pyridin-4-yl)(-3,6-diazabicyclo[3.2.2]nonan-3-yl)methanone

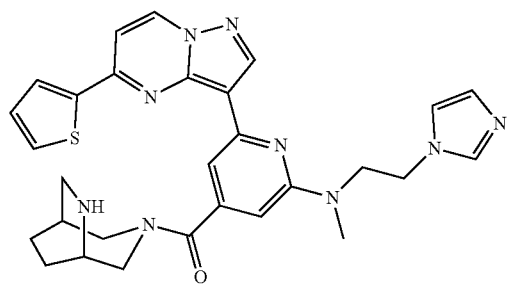

321

Compound 321 was synthesized following the Example 141, starting from commercially available 2-(1H-imidazol- 1-yl)-N-methylethan-1-amine, and coupling with tert-butyl-3,6-diazabicyclo[3.2.2]nonane-6-carboxylate and removing the BOC group by treating with TFA/CH$_2$Cl$_2$, as a TFA salt. LC/MS (M+H): 504.2

Example 322

(-3,6-diazabicyclo[3.2.2]nonan-3-yl)(2-((2-hydroxy-2-methylpropyl)amino)-6-(5-(thiophen-2-yl)pyrazolo[1,5-a]pyrimidin-3-yl)pyridin-4-yl)methanone

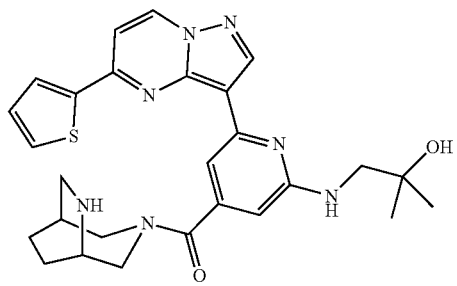

Compound 322 was synthesized following the Example 141, starting from commercially available 1-amino-2-methylpropan-2-ol, and coupling with tert-butyl-3,6-diazabicyclo[3.2.2]nonane-6-carboxylate and removing the BOC group by treating with TFA/CH$_2$Cl$_2$, as a TFA salt. LC/MS (M+H): 518.2

Example 323

(-3,6-diazabicyclo[3.2.2]nonan-3-yl)(2-((2-methoxyethyl)amino)-6-(5-(thiophen-2-yl)pyrazolo[1,5-a]pyrimidin-3-yl)pyridin-4-yl)methanone

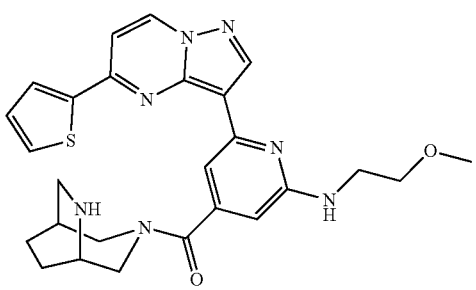

Compound 323 was synthesized following the Example 141, starting from commercially available 2-methoxyethan-1-amine, and coupling with tert-butyl-3,6-diazabicyclo[3.2.2]nonane-6-carboxylate and removing the BOC group by treating with TFA/CH$_2$Cl$_2$, as a TFA salt. LC/MS (M+H): 504.2

Example 324

(-3,6-diazabicyclo[3.2.2]nonan-3-yl)(2-(4-(oxetan-3-yl)piperazin-1-yl)-6-(5-(thiophen-2-yl)pyrazolo[1,5-a]pyrimidin-3-yl)pyridin-4-yl)methanone

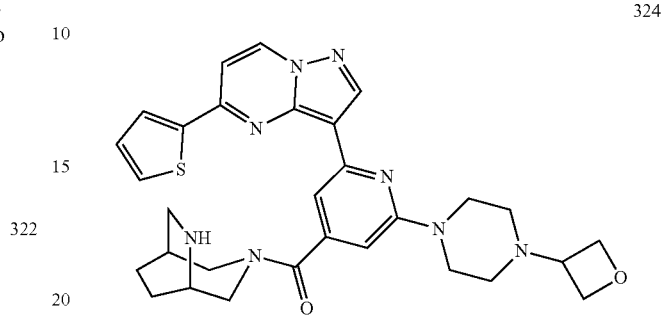

Compound 324 was synthesized following the Example 141, starting from commercially available 1-(oxetan-3-yl)piperazine, and coupling with tert-butyl-3,6-diazabicyclo[3.2.2]nonane-6-carboxylate and removing the BOC group by treating with TFA/CH$_2$Cl$_2$, as a TFA salt. LC/MS (M+H): 571.2; 1H NMR (400 MHz, Methanol-d4) δ 8.94 (d, J=7.4 Hz, 1H), 8.82 (s, 1H), 8.13 (s, 1H), 8.00 (dd, J=3.8, 1.1 Hz, 1H), 7.77 (d, J=4.8 Hz, 1H), 7.61 (d, J=7.4 Hz, 1H), 7.29 (dd, J=5.1, 3.8 Hz, 1H), 6.85 (s, 1H), 5.16 (m, 1H), 5.03-4.90 (m, 4H), 4.60-4.45 (m, 1H), 4.06 (m, 5H), 3.89-3.60 (m, 1H), 3.58-3.39 (m, 8H), 2.26-1.80 (m, 4H).

Example 325

(-3,6-diazabicyclo[3.2.2]nonan-3-yl)(2-(3-methoxyazetidin-1-yl)-6-(5-(thiophen-2-yl)pyrazolo[1,5-a]pyrimidin-3-yl)pyridin-4-yl)methanone

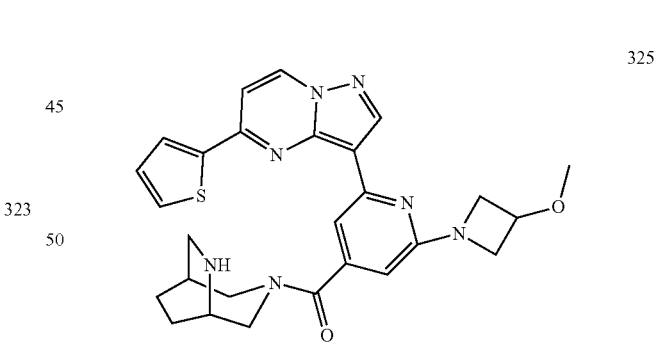

Compound 325 was synthesized following the Example 141, starting from commercially available 3-methoxy azetidine, and coupling with tert-butyl-3,6-diazabicyclo[3.2.2]nonane-6-carboxylate and removing the BOC group by treating with TFA/CH$_2$Cl$_2$, as a TFA salt. LC/MS (M+H): 516.2; 1H NMR (400 MHz, Methanol-d4) δ 8.97 (d, J=7.4 Hz, 1H), 8.76 (d, J=2.3 Hz, 1H), 8.02 (d, J=3.8 Hz, 1H), 7.80 (dd, J=5.1, 1.1 Hz, 1H), 7.75-7.58 (m, 3H), 7.27 (dd, J=5.1, 3.8 Hz, 1H), 6.53 (d, J=9.1 Hz, 1H), 4.66-4.42 (m, 3H), 4.23 (d, J=8.6 Hz, 3H), 4.08-3.90 (m, 1H), 3.76 (d, J=16.0 Hz, 1H), 3.60 (d, J=14.0 Hz, 1H), 3.42 (s, 5H), 2.30 (s, 1H), 2.18-1.78 (m, 5H).

Example 326

((1S,6R)-3,9-diazabicyclo[4.2.1]nonan-9-yl)(2-(3-methoxyazetidin-1-yl)-6-(5-(thiophen-2-yl)pyrazolo[1,5-a]pyrimidin-3-yl)pyridin-4-yl)methanone

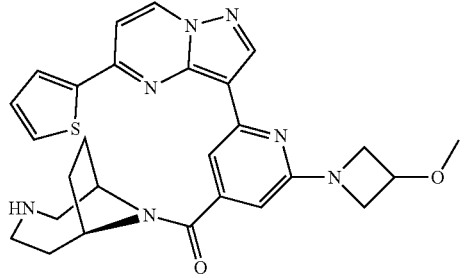

326

Compound 326 was synthesized following the Example 141, starting from commercially available 3-methoxy azetidine, and coupling with tert-butyl (1S,6R)-3,9-diazabicyclo[4.2.1]nonane-3-carboxylate and removing the BOC group by treating with TFA/CH$_2$Cl$_2$, as a TFA salt. LC/MS (M+H): 516.2

Example 327

(S)-(3-aminopyrrolidin-1-yl)(2-(3-methoxyazetidin-1-yl)-6-(5-(thiophen-2-yl)pyrazolo[1,5-a]pyrimidin-3-yl)pyridin-4-yl)methanone

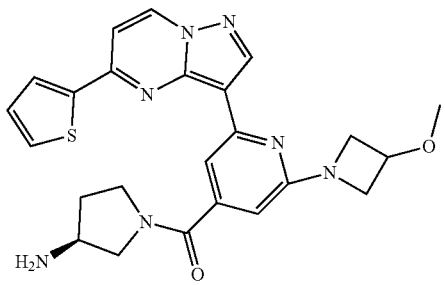

327

Compound 327 was synthesized following the Example 141, starting from commercially available 3-methoxy azetidine, and coupling with tert-butyl (S)-pyrrolidin-3-ylcarbamate and removing the BOC group by treating with TFA/CH$_2$Cl$_2$, as a TFA salt. LC/MS (M+H): 576.2

Example 328

(S)-(3-aminopyrrolidin-1-yl)(2-(3-methoxyazetidin-1-yl)-6-(5-phenylpyrazolo[1,5-a]pyrimidin-3-yl)pyridin-4-yl)methanone

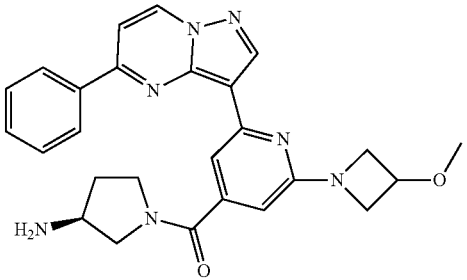

328

Compound 328 was synthesized following the Example 159, starting from commercially available 3-methoxy azetidine, and coupling with tert-butyl (S)-pyrrolidin-3-ylcarbamate and removing the BOC group by treating with TFA/CH$_2$Cl$_2$, as a TFA salt. LC/MS (M+H): 470.2

Example 329

(-3,6-diazabicyclo[3.2.2]nonan-3-yl)(2-(3-methoxyazetidin-1-yl)-6-(5-phenylpyrazolo[1,5-a]pyrimidin-3-yl)pyridin-4-yl)methanone

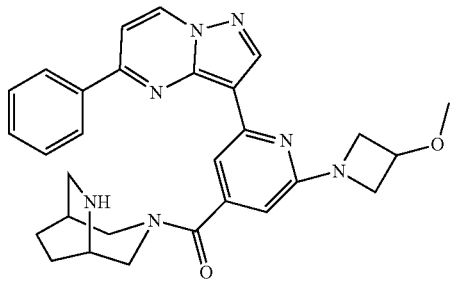

329

Compound 329 was synthesized following the Example 159, starting from commercially available 3-methoxy azetidine, and coupling with tert-butyl-3,6-diazabicyclo[3.2.2]nonane-6-carboxylate and removing the BOC group by treating with TFA/CH$_2$Cl$_2$, as a TFA salt. LC/MS (M+H): 510.3

Example 330

(-3,9-diazabicyclo[4.2.1]nonan-9-yl)(2-(3-methoxyazetidin-1-yl)-6-(5-phenylpyrazolo[1,5-a]pyrimidin-3-yl)pyridin-4-yl)methanone

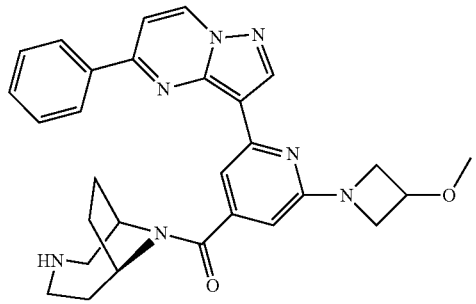

330

Compound 330 was synthesized following the Example 159, starting from commercially available 3-methoxy azetidine, and coupling with tert-butyl-3,9-diazabicyclo[4.2.1]nonane-3-carboxylate and removing the BOC group by treating with TFA/CH$_2$Cl$_2$, as a TFA salt. LC/MS (M+H): 510.2

Example 331

(S)—N-(2-(diethylamino)propyl)-2-(1-methyl-1H-pyrazol-4-yl)-6-(5-(thiophen-2-yl)pyrazolo[1,5-a]pyrimidin-3-yl)isonicotinamide

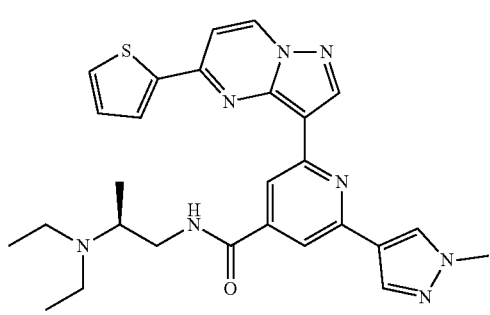

331

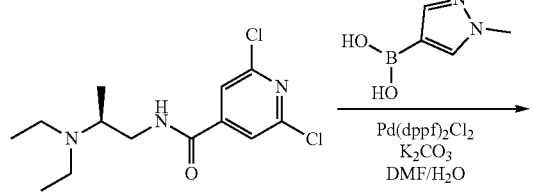

267B

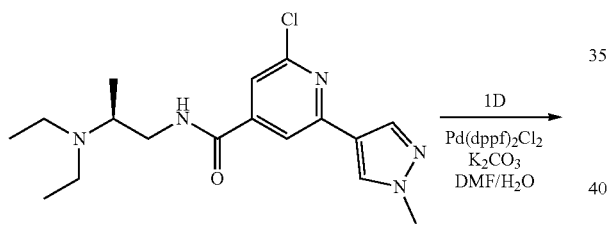

331A

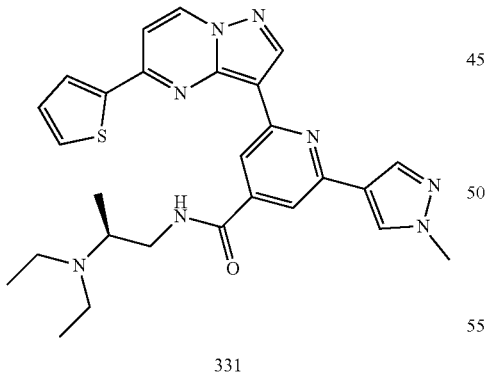

331

Synthesis of (S)-2-chloro-N-(2-(diethylamino)propyl)-6-(1-methyl-1H-pyrazol-4-yl)isonicotinamide (331A)

To a vial was added (S)-2,6-dichloro-N-(2-(diethylamino)propyl) isonicotinamide 257B (50 mg, 0.164 mmol), DMF (1.0 mL), potassium carbonate (68 mg, 0.493 mmol, 3.0 equiv.), Pd(dppf)Cl$_2$ (6 mg, 0.008 mmol, 5 mol %), and 1-methyl-4-(4,4,5,5-tetramethyl-1,3,2-dioxaborolan-2-yl)-1H-pyrazole (35 mg, 0.165 mmol, 1.0 equiv.) at rt. The vessel was purged with nitrogen and heated to 140° C. for 30 min. The mixture was cooled and purified by prep HPLC to yield (S)-2-chloro-N-(2-(diethylamino)propyl)-6-(1-methyl-1H-pyrazol-4-yl)isonicotinamide 331A in 52% isolated yield.

Synthesis of (S)—N-(2-(diethylamino)propyl)-2-(1-methyl-1H-pyrazol-4-yl)-6-(5-(thiophen-2-yl)pyrazolo[1,5-a]pyrimidin-3-yl)isonicotinamide (331)

To a vial was added (S)-2-chloro-N-(2-(diethylamino) propyl)-6-(1-methyl-1H-pyrazol-4-yl)isonicotinamide 331A (30 mg, 0.086 mmol), DMF (1.0 mL), water (0.2 mL), potassium carbonate (36 mg, 0.257 mmol, 3.0 equiv.), Pd(dppf)Cl$_2$ (3 mg, 0.004 mmol, 5 mol %), and 3-(4,4,5,5-tetramethyl-1,3,2-dioxaborolan-2-yl)-5-(thiophen-2-yl)pyrazolo[1,5-a]pyrimidine 1D (56 mg, 0.171 mmol, 2.0 equiv.) at rt. The vessel was purged with nitrogen and heated to 120° C. for 30 min. The mixture was cooled to rt and purified by prep HPLC to yield the desired product 331, as TFA salt in 23% isolated yield. LC/MS (M+H): 515.2; $^1$H NMR (MeOD, 400 MHz): δ 8.93 (s, 1H), 8.91 (d, 1H), 8.86 (d, 1H), 8.33 (s, 1H), 8.14 (s, 1H), 7.99 (d, 1H), 7.77 (d, 1H), 7.74 (d, 1H), 7.57 (d, 1H), 7.28-7.22 (m, 1H), 4.00 (s, 3H), 3.85-3.90 (m, 2H), 3.56 (dt, 2H), 3.43-3.36 (m, 2H), 3.20-3.30 (m, 2H), 1.48 (t, 5H), 1.41 (t, 3H).

Example 332

(S)—N-(2-(diethylamino)propyl)-2-(3,5-dimethyl-1H-pyrazol-4-yl)-6-(5-(thiophen-2-yl)pyrazolo[1,5-a]pyrimidin-3-yl)isonicotinamide

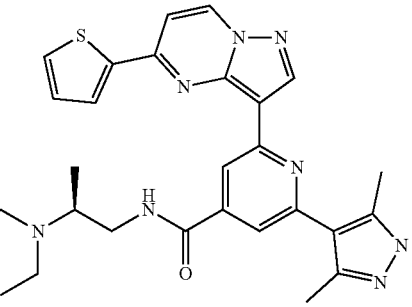

332

Compound 332 was synthesized following the Example 331, starting from commercially available (3,5-dimethyl-1H-pyrazol-4-yl)boronic acid, as a TFA salt. LC/MS (M+H): 529.2; $^1$H NMR (MeOD, 400 MHz): δ 8.99-8.87 (m, 2H), 8.81 (s, 1H), 8.01 (d, 1H), 7.75 (dd, 1H), 7.65-7.54 (m, 2H), 7.29-7.23 (m, 1H), 4.01 (dd, 1H), 3.89 (q, 1H), 3.60-3.50 (m, 2H), 3.43-3.34 (m, 2H), 3.23 (dd, 1H), 3.10-3.15 (m, 1H), 2.55 (s, 6H), 1.51-1.45 (m, 5H), 1.41 (t, 3H).

Example 333

(S)—N-(2-(diethylamino)propyl)-2-(3-methyl-1H-pyrazol-4-yl)-6-(5-(thiophen-2-yl)pyrazolo[1,5-a]pyrimidin-3-yl)isonicotinamide

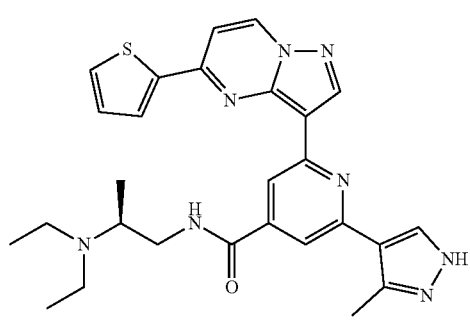

333

Compound 333 was synthesized following the Example 331, starting from commercially available (3-methyl-1H-pyrazol-4-yl)boronic acid, as a TFA salt. LC/MS (M+H): 515.2; $^1$H NMR (MeOD, 400 MHz): δ 9.00 (d, 1H), 8.91 (s, 1H), 8.83 (s, 1H), 8.13 (d, 1H), 8.02 (d, 1H), 7.81 (s, 1H), 7.76 (d, 1H), 7.62 (d, 1H), 7.30-7.23 (m, 1H), 3.95-4.01 (m, 1H), 3.89 (s, 1H), 3.58 (dd, 2H), 3.45-3.50 (m, 2H), 3.39 (s, 3H), 3.10-3.15 (m, 1H), 1.45 (dd, 9H).

Example 334

(S)—N-(2-(diethylamino)propyl)-2-(5-(thiophen-2-yl)pyrazolo[1,5-a]pyrimidin-3-yl)-6-(3-(trifluoromethyl)-1H-pyrazol-4-yl)isonicotinamide

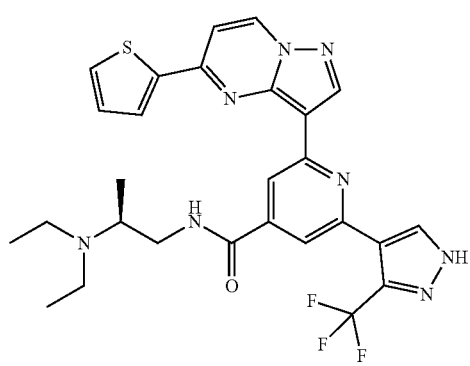

334

Compound 334 was synthesized following the Example 331, starting from commercially available 3-(trifluoromethyl)-1H-pyrazol-4-yl)boronic acid, as a TFA salt. LC/MS (M+H): 569.2; $^1$H NMR (MeOD, 400 MHz): δ 8.95 (d, 1H), 8.91 (d, 1H), 8.86 (s, 1H), 8.39 (s, 1H), 7.99 (dd, 1H), 7.78 (d, 1H), 7.74 (dd, 1H), 7.56 (d, 1H), 7.25 (dd, 1H), 4.00 (dd, 1H), 3.88 (q, 1H), 3.55 (ddd, 2H), 3.39 (q, 2H), 3.23 (dd, 2H), 1.50-1.46 (m, 5H), 1.41 (t, 3H).

Example 335

(S)—N-(2-(diethylamino)propyl)-2-(isoxazol-4-yl)-6-(5-(thiophen-2-yl)pyrazolo[1,5-a]pyrimidin-3-yl)isonicotinamide

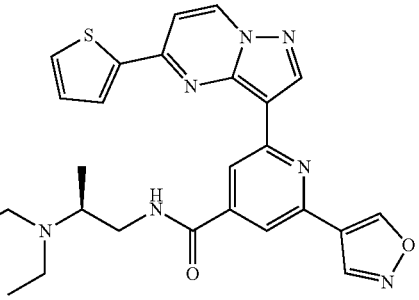

335

Compound 335 was synthesized following the Example 331, starting from commercially available isoxazol-4-ylboronic acid, as a TFA salt. LC/MS (M+H): 502.2; $^1$H NMR (MeOD, 400 MHz): δ 9.06 (s, 1H), 8.98 (d, 1H), 8.68 (s, 1H), 8.35 (d, 1H), 8.17 (d, 1H), 7.78 (d, 1H), 7.66 (d, 1H), 7.43 (d, 1H), 7.28-7.23 (m, 1H), 3.97-3.85 (m, 2H), 3.55 (td, 3H), 3.38 (t, 2H), 3.24 (dd, 1H), 1.43 (dd, 8H).

Example 336

(S)—N-(2-(diethylamino)propyl)-2-(1H-pyrazol-3-yl)-6-(5-(thiophen-2-yl)pyrazolo[1,5-a]pyrimidin-3-yl)isonicotinamide

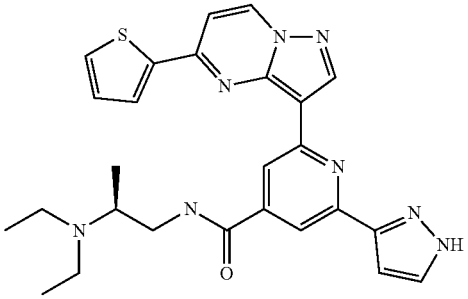

336

Compound 336 was synthesized following the Example 331, starting from commercially available (1H-pyrazol-3-yl)boronic acid, as a TFA salt. C/MS (M+H): 501.2; $^1$H NMR (MeOD, 400 MHz): δ 9.02 (s, 1H), 8.93 (dd, 2H), 8.10-8.00 (m, 2H), 7.78 (dd, 2H), 7.59 (d, 1H), 7.30-7.23 (m, 1H), 7.09 (d, 1H), 3.99 (dd, 1H), 3.89 (q, 1H), 3.57 (ddd, 2H), 3.39 (dd, 2H), 3.25-3.19 (m, 1H), 1.53-1.33 (m, 9H).

Example 337

(S)—N-(2-(diethylamino)propyl)-2,6-bis(5-(thiophen-2-yl)pyrazolo[1,5-a]pyrimidin-3-yl)isonicotinamide

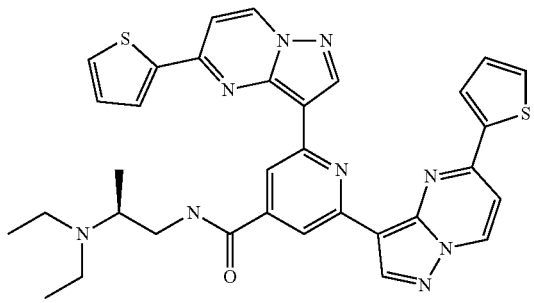

337

Compound 337 was synthesized following the Example 331, starting from 3-(4,4,5,5-tetramethyl-1,3,2-dioxaborolan-2-yl)-5-(thiophen-2-yl)pyrazolo[1,5-a]pyrimidine 1D, as a TFA salt. LC/MS (M+H): 634.2

Example 338

(S)—N-(2-(diethylamino)propyl)-2-(thiazol-2-yl)-6-(5-(thiophen-2-yl)pyrazolo[1,5-a]pyrimidin-3-yl)isonicotinamide

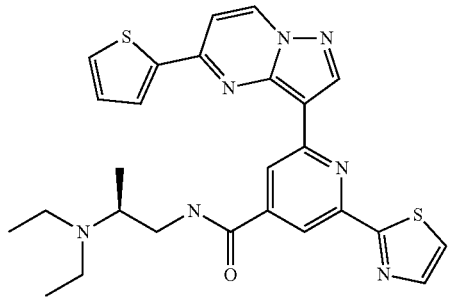

338

Compound 338 was synthesized following the Example 331, starting from commercially available thiazol-2-ylboronic acid, as a TFA salt. LC/MS (M+H): 518.2

Example 339

(S)—N-(2-(diethylamino)propyl)-2-(oxazol-2-yl)-6-(5-(thiophen-2-yl)pyrazolo[1,5-a]pyrimidin-3-yl)isonicotinamide

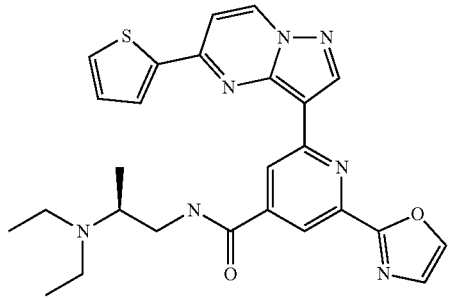

339

Compound 339 was synthesized following the Example 331, starting from commercially available oxazol-2-ylboronic acid, as a TFA salt. LC/MS (M+H): 502.2

Example 340

(S)—N-(2-(diethylamino)propyl)-2-(1H-pyrazol-4-yl)-6-(5-(thiophen-2-yl)pyrazolo[1,5-a]pyrimidin-3-yl)isonicotinamide

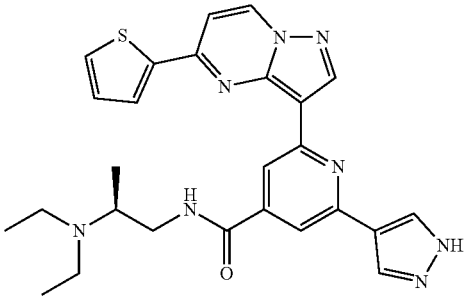

340

Compound 340 was synthesized following the Example 331, starting from commercially available 1H-pyrazol-4-yl boronic acid, as a TFA salt. LC/MS (M+H): 501.2; $^1$H NMR (MeOD, 400 MHz): δ 8.86-8.95 (m, 3H), 8.32 (s, 2H), 8.00 (d, 1H), 7.81 (s, 1H), 7.72 (d, 1H), 7.56 (d, 1H), 7.24 (dd, 1H), 3.85-4.04 (m, 2H), 3.44-3.60 (m, 3H), 3.11-3.43 (m, 3H), 1.47 (t, 5H), 1.42 (t, 3H).

Example 341

(S)-2-(1-(2-cyanoethyl)-1H-pyrazol-4-yl)-N-(2-(diethylamino)propyl)-6-(5-(thiophen-2-yl)pyrazolo[1,5-a]pyrimidin-3-yl)isonicotinamide

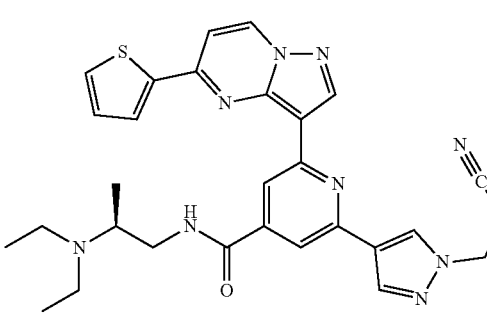

341

Compound 341 was synthesized following the Example 331, starting from commercially available (1-(2-cyanoethyl)-1H-pyrazol-4-yl)boronic acid, as a TFA salt. LC/MS (M+H): 554.2

Example 342

(S)—N-(2-(diethylamino)propyl)-2-(1-(oxetan-3-yl)-1H-pyrazol-4-yl)-6-(5-(thiophen-2-yl)pyrazolo[1,5-a]pyrimidin-3-yl)isonicotinamide

Example 343

N—((S)-2-(diethylamino)propyl)-2-(((R)-tetrahydrofuran-2-yl)methoxy)-6-(5-(thiophen-2-yl)pyrazolo[1,5-a]pyrimidin-3-yl)isonicotinamide

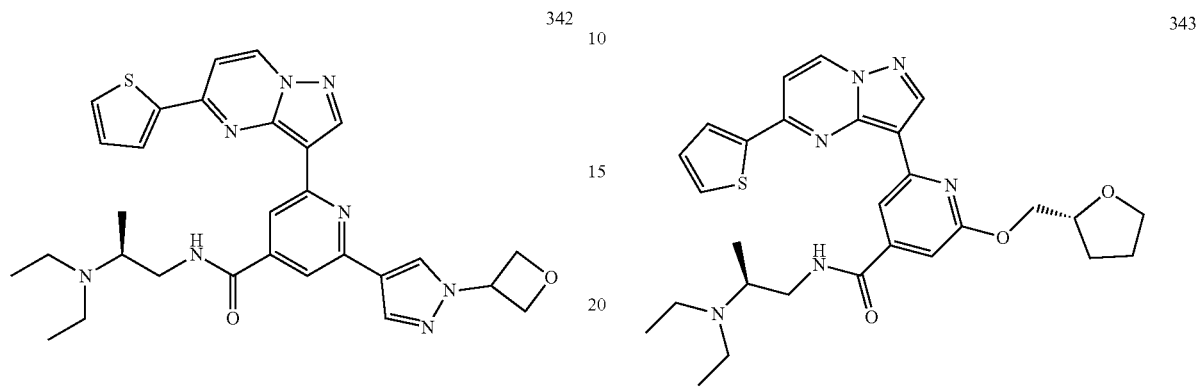

Compound 342 was synthesized following the Example 331, starting from commercially available (1-(oxetan-3-yl)-1H-pyrazol-4-yl)boronic acid, as a TFA salt. LC/MS (M+H): 557.2; $^1$H NMR (MeOD, 400 MHz): δ 8.90 (t, 2H), 8.84 (d, 1H), 8.51 (s, 1H), 8.27 (s, 1H), 8.00-7.95 (m, 1H), 7.80 (d, 1H), 7.74 (dd, 1H), 7.56 (d, 1H), 7.25 (dd, 1H), 5.65 (q, 1H), 5.11 (d, 4H), 4.02-3.97 (m, 1H), 3.88 (q, 1H), 3.61-3.45 (m, 3H), 3.39 (dd, 2H), 3.23 (dd, 1H), 1.49 (t, 5H), 1.41 (t, 3H).

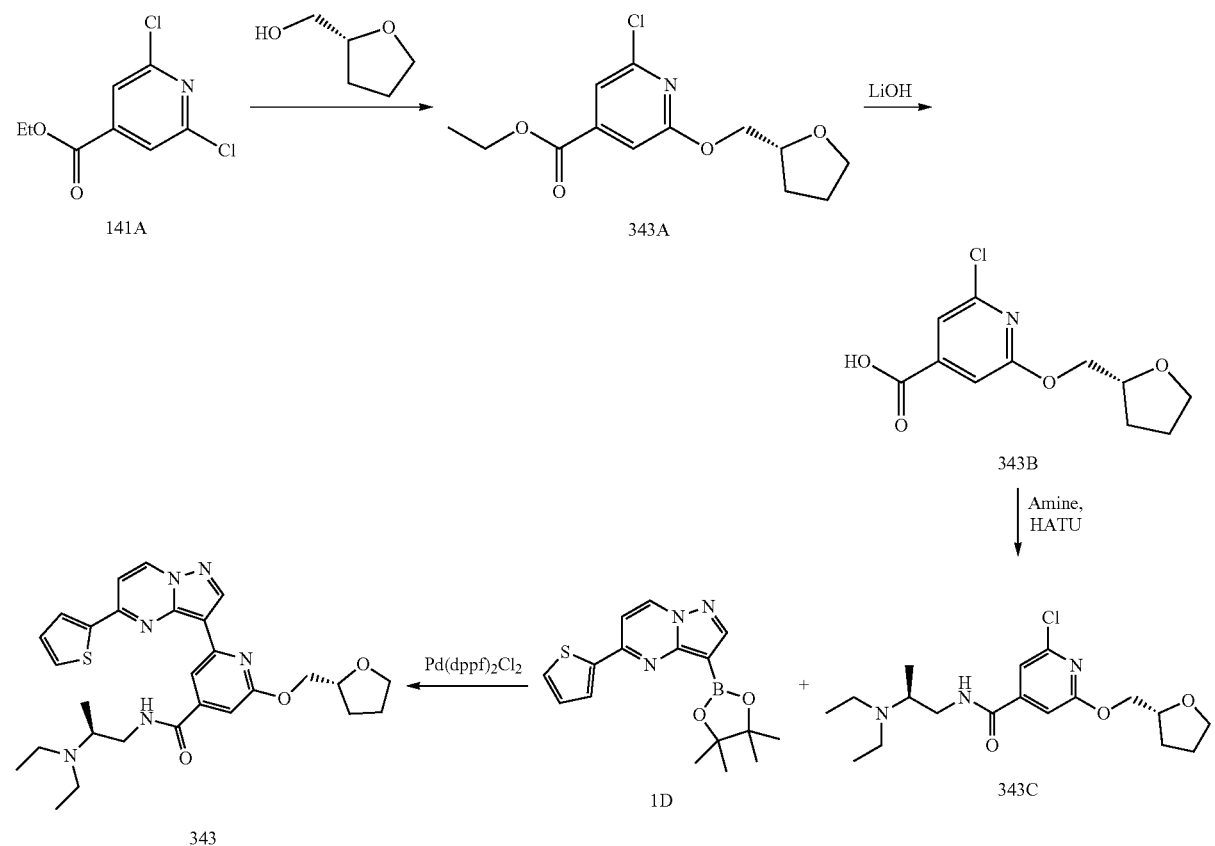

Compound 343 was synthesized as shown above, following the Example 141, starting from commercially available (R)-(tetrahydrofuran-2-yl)methanol, as a TFA salt. LC/MS (M+H): 535.2; $^1$H-NMR (CD$_3$OD) δ 8.90 (dd, 1H, J=7.0, 1.4 Hz), 8.76 (d, 1H, J=1.2 Hz), 8.61 (d, 1H, J=1.2 Hz), 7.98 (d, 1H, J=4.0 Hz), 7.73 (d, 1H, J=4.8 Hz), 7.56 (d, 1H, J=7.6 Hz), 7.23-7.26 (m, 1H), 6.97 (d, 1H, J=1.2 Hz), 4.54 (dd, 1H, J=12.0, 4.0 Hz), 4.44 (dd, 1H, J=11.2, 6.4 Hz), 4.33-4.39 (m, 1H), 3.93-3.98 (m, 2H), 3.82-3.90 (m, 2H), 3.48-3.57 (m, 2H), 3.34-3.43 (m, 2H), 3.17-3.25 (m, 1H), 2.10-2.19 (m, 1H), 1.93-2.06 (m, 2H), 1.81-1.89 (m, 1H), 1.44-1.49 (m, 6H), 1.40 (t, 3H, J=7.2 Hz);

Example 344

N—((S)-2-(diethylamino)propyl)-2-((S)-2-methoxy-propoxy)-6-(5-(thiophen-2-yl)pyrazolo[1,5-a]pyrimidin-3-yl)isonicotinamide

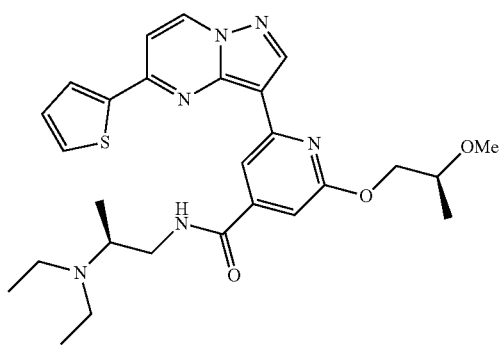

344

Compound 344 was synthesized following the Example 343, starting from commercially available (S)-2-methoxy-propan-1-ol, as a TFA salt. LC/MS (M+H): 523.2; $^1$H-NMR (CD$_3$OD) δ 8.90 (dd, 1H, J=7.2, 1.2 Hz), 8.75 (d, 1H, J=0.8 Hz), 8.61 (d, 1H, J=1.2 Hz), 7.98 (d, 1H, J=3.6 Hz), 7.73 (d, 1H, J=4.8 Hz), 7.56 (d, 1H, J=7.6 Hz), 7.24-7.26 (m, 1H), 6.97 (d, 1H, J=1.2 Hz), 4.52 (dd, 1H, J=11.6, 4.0 Hz), 4.44 (dd, 1H, J=11.4, 5.8 Hz), 3.95 (dd, 1H, J=14.4, 6.0 Hz), 3.82-3.88 (m, 2H), 3.50-3.56 (m, 2H), 3.46 (d, 3H, J=0.8 Hz), 3.34-3.41 (m, 2H), 3.17-3.25 (m, 1H), 1.44-1.49 (m, 6H), 1.40 (t, 3H, J=7.2 Hz), 1.31 (d, 3H, J=6.0 Hz);

Example 345

N—((S)-2-(diethylamino)propyl)-2-(((S)-tetrahydro-furan-3-yl)oxy)-6-(5-(thiophen-2-yl)pyrazolo[1,5-a]pyrimidin-3-yl)isonicotinamide

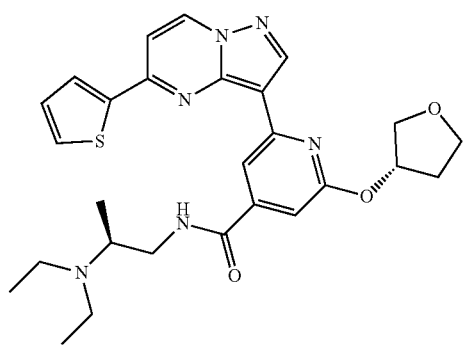

345

Compound 345 was synthesized following the Example 343, starting from commercially available (S)-tetrahydro-furan-2-ol, as a TFA salt. LC/MS (M+H): 521.2; $^1$H-NMR (CD$_3$OD) δ 8.90 (d, 1H, J=7.6 Hz), 8.75 (s, 1H), 8.61 (d, 1H, J=1.2 Hz), 7.98 (dd, 1H, J=4.0, 1.2 Hz), 7.73 (dd, 1H, J=5.0, 1.0 Hz), 7.56 (d, 1H, J=3.6 Hz), 7.25 (dd, 1H, J=5.0, 3.8 Hz), 6.95 (d, 1H, J=1.2 Hz), 5.77-5.80 (m, 1H), 4.15 (dd, 1H, J=10.4, 4.8 Hz), 3.90-4.03 (m, 4H), 3.81-3.88 (m, 1H), 3.48-3.57 (m, 2H), 3.34-3.41 (m, 2H), 3.17-3.26 (m, 1H), 2.36-2.45 (m, 1H), 2.18-2.22 (m, 1H), 1.42-1.49 (m, 6H), 1.40 (t, 3H, J=7.2 Hz);

Example 346

N—((S)-2-(diethylamino)propyl)-2-(((R)-tetrahydro-furan-3-yl)oxy)-6-(5-(thiophen-2-yl)pyrazolo[1,5-a]pyrimidin-3-yl)isonicotinamide

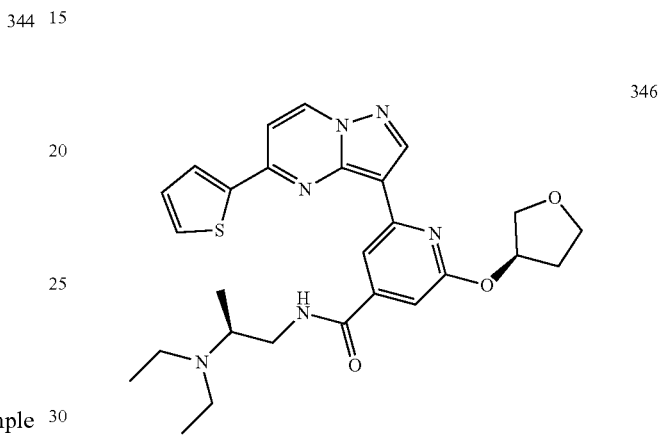

346

Compound 346 was synthesized following the Example 343, starting from commercially available (R)-tetrahydro-furan-2-ol, as a TFA salt. LC/MS (M+H): 521.2; $^1$H-NMR (CD$_3$OD) δ 8.91 (d, 1H, J=7.6 Hz), 8.76 (s, 1H), 8.62 (d, 1H, J=1.2 Hz), 7.98 (dd, 1H, J=3.6, 1.2 Hz), 7.73 (dd, 1H, J=5.2, 1.2 Hz), 7.56 (d, 1H, J=7.2 Hz), 7.25 (dd, 1H, J=5.0, 3.8 Hz), 6.95 (d, 1H, J=1.6 Hz), 5.78-5.81 (m, 1H), 4.16 (dd, 1H, J=10.4, 4.8 Hz), 3.91-4.03 (m, 4H), 3.83-3.90 (m, 1H), 3.48-3.55 (m, 2H), 3.34-3.42 (m, 2H), 3.19-3.26 (m, 1H), 2.38-2.43 (m, 1H), 2.18-2.22 (m, 1H), 1.44-1.49 (m, 6H), 1.40 (t, 3H, J=7.2 Hz);

Example 374

(S)—N-(2-(diethylamino)propyl)-2-(2-(diethyl-amino)ethoxy)-6-(5-(thiophen-2-yl)pyrazolo[1,5-a]pyrimidin-3-yl)isonicotinamide

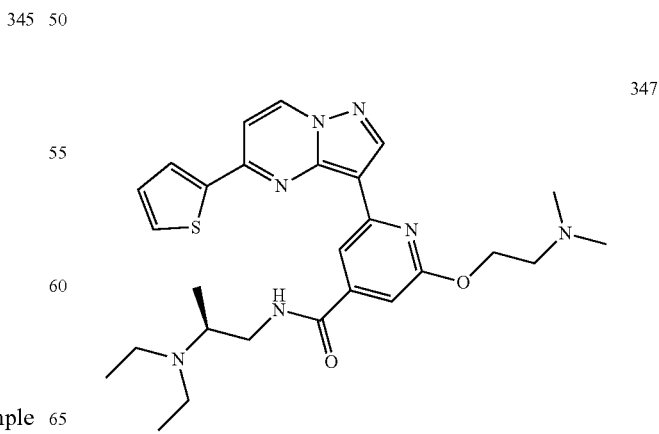

347

Compound 347 was synthesized following the Example 343, starting from commercially available 2-(dimethylamino)ethan-1-ol, as a TFA salt. LC/MS (M+H): 522.2

Example 348

(S)—N-(2-(diethylamino)propyl)-2-(2-methoxyethoxy)-6-(5-(thiophen-2-yl)pyrazolo[1,5-a]pyrimidin-3-yl)isonicotinamide

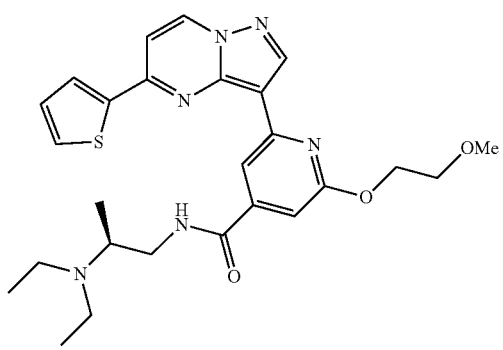

348

Compound 348 was synthesized following the Example 343, starting from commercially available 2-methoxyethan-1-ol, as a TFA salt. LC/MS (M+H): 509.2; $^1$H-NMR (CD$_3$OD) δ 8.89 (d, 1H, J=7.6 Hz), 8.75 (s, 1H), 8.60 (d, 1H, J=1.2 Hz), 7.98 (d, 1H, J=3.6 Hz), 7.73 (d, 1H, J=4.8 Hz), 7.55 (d, 1H, J=7.2 Hz), 7.24 (dd, 1H, J=5.0, 3.8 Hz), 6.96 (d, 1H, J=1.2 Hz), 4.62-4.64 (m, 2H), 3.95 (dd, 1H, J=14.0, 6.0 Hz), 3.82-3.90 (m, 3H), 3.50-3.56 (m, 2H), 3.45 (s, 3H), 3.35-3.42 (m, 2H), 3.17-3.26 (m, 1H), 1.44-1.49 (m, 6H), 1.40 (t, 1H, J=7.2 Hz);

Example 349

(S)—N-(2-(diethylamino)propyl)-2-((3-methyloxetan-3-yl)methoxy)-6-(5-(thiophen-2-yl)pyrazolo[1,5-a]pyrimidin-3-yl)isonicotinamide

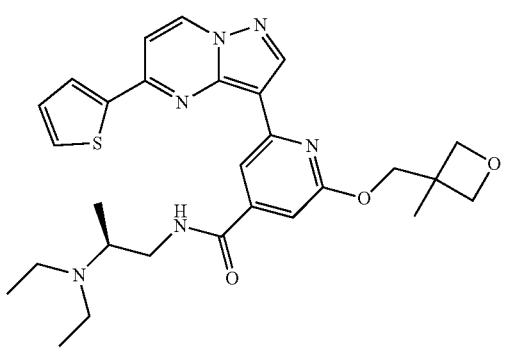

349

Compound 349 was synthesized following the Example 343, starting from commercially available (3-methyloxetan-3-yl)methanol, as a TFA salt. LC/MS (M+H): 535.2; $^1$H-NMR (CD$_3$OD) δ 8.89 (d, 1H, J=7.2 Hz), 8.78 (s, 1H), 8.61 (d, 1H, J=1.2 Hz), 7.97 (dd, 1H, J=4.0, 1.2 Hz), 7.72 (dd, 1H, J=5.0, 1.0 Hz), 7.55 (d, 1H, J=7.2 Hz), 7.23-7.26 (m, 1H), 7.01 (d, 1H, J=1.2 Hz), 4.73 (d, 2H, J=6.0 Hz), 4.58 (s, 2H), 4.48 (d, 2H, J=5.6 Hz), 3.95 (dd, 1H, J=14.0, 6.0 Hz), 3.81-3.89 (m, 1H), 3.47-3.56 (m, 2H), 3.34-3.42 (m, 2H), 3.17-3.26 (m, 1H), 1.44-1.48 (m, 9H), 1.40 (t, 3H, J=7.2 Hz);

Example 350

(S)—N-(2-(diethylamino)propyl)-2-(2-(pyrazin-2-yl)ethoxy)-6-(5-(thiophen-2-yl)pyrazolo[1,5-a]pyrimidin-3-yl)isonicotinamide

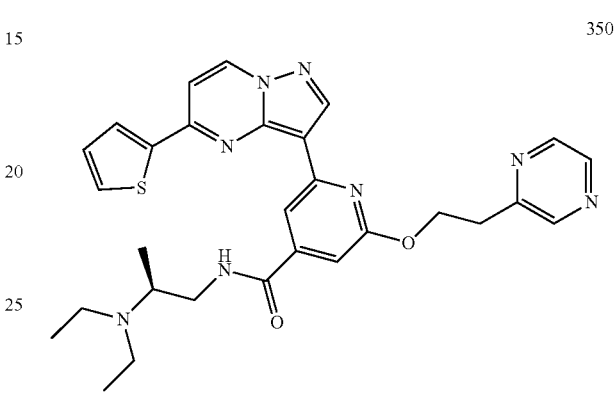

350

Compound 350 was synthesized following the Example 343, starting from commercially available 2-(pyrazin-2-yl)ethan-1-ol, as a TFA salt. LC/MS (M+H): 557.2; $^1$H-NMR (CD$_3$OD) δ 8.89 (d, 1H, J=7.6 Hz), 8.77 (s, 1H), 8.62 (d, 1H, J=1.2 Hz), 8.58 (d, 1H, J=1.2 Hz), 8.55-8.56 (m, 1H), 8.43 (d, 1H, J=2.8 Hz), 7.97 (dd, 1H, J=3.6, 1.2 Hz), 7.71 (dd, 1H, J=5.0, 1 0 Hz), 7.55 (d, 1H, J=7.6 Hz), 7.23 (dd, 1H, J=5.0, 3.8 Hz), 6.88 (d, 1H, J=1.2 Hz), 4.91 (t, 2H, J=6.2 Hz), 3.92 (dd, 1H, J=14.0, 6.0 Hz), 3.81-3.85 (m, 1H), 3.48-3.53 (m, 2H), 3.35-3.40 (m, 4H), 3.17-3.22 (m, 1H), 1.42-1.47 (m, 6H), 1.39 (t, 3H, J=7.2 Hz);

Example 351

(S)—N-(2-(diethylamino)propyl)-2-(3-methoxypropoxy)-6-(5-(thiophen-2-yl)pyrazolo[1,5-a]pyrimidin-3-yl)isonicotinamide

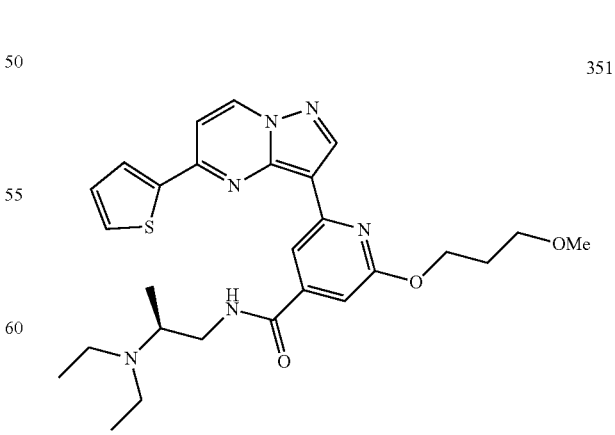

351

Compound 351 was synthesized following the Example 343, starting from commercially available 3-methoxy-propan-1-ol, as a TFA salt. LC/MS (M+H): 523.2; ¹H-NMR (CD₃OD) δ 8.88 (d, 1H, J=7.2 Hz), 8.75 (s, 1H), 8.58 (d, 1H, J=1.2 Hz), 7.97 (dd, 1H, J=4.0, 1.2 Hz), 7.72 (dd, 1H, J=5.2, 1.2 Hz), 7.54 (d, 1H, J=7.2 Hz), 7.24 (dd, 1H, J=5.0, 3.8 Hz), 6.93 (d, 1H, J=1.6 Hz), 4.55 (t, 2H, J=6.4 Hz), 3.94 (dd, 1H, J=14.0, 6.0 Hz), 3.81-3.89 (m, 1H), 3.60 (t, 2H, J=6.4 Hz), 3.47-3.55 (m, 2H), 3.37 (s, 3H), 3.35-3.41 (m, 2H), 3.19-3.24 (m, 1H), 2.07-2.13 (m, 2H), 1.35-1.46 (m, 9H);

Example 352

(S)—N-(2-(diethylamino)propyl)-2-(2-morpholinoethoxy)-6-(5-(thiophen-2-yl)pyrazolo[1,5-a]pyrimidin-3-yl)isonicotinamide

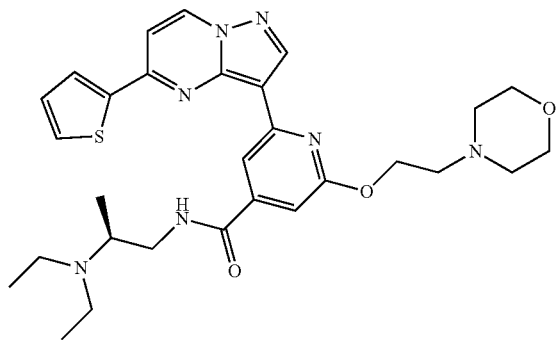

352

Compound 352 was synthesized following the Example 343, starting from commercially available 2-morpholinoethan-1-ol, as a TFA salt. LC/MS (M+H): 564.2; ¹H-NMR (CD₃OD) δ 8.92 (d, 1H, J=7.6 Hz), 8.80 (s, 1H), 8.65 (d, 1H, J=1.6 Hz), 7.99 (dd, 1H, J=4.0, 1.2 Hz), 7.74 (dd, 1H, J=5.0, 1.0 Hz), 7.58 (d, 1H, J=7.2 Hz), 7.25 (dd, 1H, J=5.0, 3.8 Hz), 7.06 (d, 1H, J=1.6 Hz), 4.91-4.94 (m, 2H), 3.83-3.98 (m, 6H), 3.72-3.74 (m, 2H), 3.35-3.58 (m, 8H), 3.18-3.27 (m, 1H), 1.44-1.48 (m, 6H), 1.40 (t, 3H, J=7.4 Hz);

Example 353

(S)—N-(2-(diethylamino)propyl)-2-(2-hydroxy-2-methylpropoxy)-6-(5-(thiophen-2-yl)pyrazolo[1,5-a]pyrimidin-3-yl)isonicotinamide

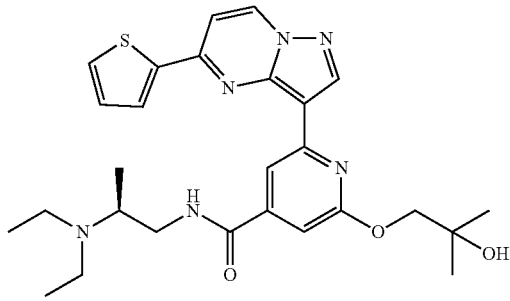

353

Compound 353 was synthesized following the Example 343, starting from commercially available 2-methylpropane-1,2-diol, as a TFA salt. LC/MS (M+H): 523.2

Example 354

(S)—N-(2-(diethylamino)propyl)-2-(pyridin-3-ylmethoxy)-6-(5-(thiophen-2-yl)pyrazolo[1,5-a]pyrimidin-3-yl)isonicotinamide

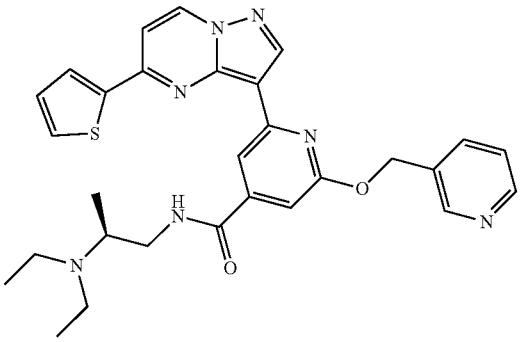

354

Compound 354 was synthesized following the Example 343, starting from commercially available pyridin-3-ylmethanol, as a TFA salt. LC/MS (M+H): 542.2; ¹H-NMR (CD₃OD) δ 8.96 (s, 1H), 8.90 (d, 1H, J=7.2 Hz), 8.76 (s, 1H), 8.65-8.67 (m, 1H), 8.62 (d, 1H, J=1.2 Hz), 8.47 (d, 1H, J=8.0 Hz), 7.98 (d, 1H, J=3.6 Hz), 7.81-7.84 (m, 1H), 7.72 (d, 1H, J=5.2 Hz), 7.57 (d, 1H, J=7.2 Hz), 7.23-7.25 (m, 1H), 7.07-7.08 (m, 1H), 5.75 (s, 2H), 3.95 (dd, 1H, J=14.0, 2.0 Hz), 3.83-3.88 (m, 1H), 3.49-3.57 (m, 2H), 3.36-3.38 (m, 2H), 3.19-3.24 (m, 1H), 1.43-1.48 (m, 6H), 1.38-1.42 (m, 3H);

Example 355

(S)-3-(((4-((2-(diethylamino)propyl)carbamoyl)-6-(5-(thiophen-2-yl)pyrazolo[1,5-a]pyrimidin-3-yl)pyridin-2-yl)oxy)methyl)pyridine 1-oxide

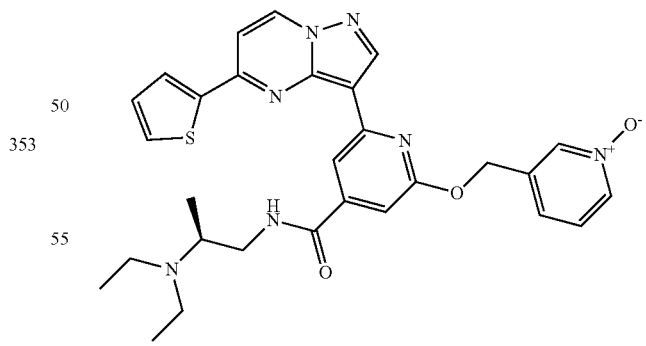

355

Compound 355 was synthesized following the Example 343, starting from commercially available 3-(hydroxymethyl)pyridine 1-oxide, as a TFA salt. LC/MS (M+H): 558.2; ¹H-NMR (CD₃OD) δ 8.89 (d, 1H, J=7.6 Hz), 8.74 (s, 1H), 8.63 (d, 1H, J=1.2 Hz), 8.53 (s, 1H), 8.28 (d, 1H, J=6.4 Hz), 7.97 (dd, 1H, J=3.8, 1.0 Hz), 7.80 (d, 1H, J=8.0 Hz), 7.72 (dd, 1H, J=5.2, 1.2 Hz), 7.55-7.59 (m, 2H), 7.24 (dd, 1H, J=5.0, 3.8 Hz), 7.07 (d, 1H, J=1.6 Hz), 5.66 (s, 2H), 3.95 (dd, 1H, J=14.4, 6.0 Hz), 3.83-3.88 (m, 1H), 3.48-3.56 (m, 2H), 3.35-3.41 (m, 2H), 3.17-3.26 (m, 1H), 1.44-1.48 (m, 6H), 1.40 (t, 3H, J=7.2 Hz).
Example 356
N-(2-(diethylamino)butyl)-2-((S)-2-(methylcarbamoyl)azetidin-1-yl)-6-(5-(thiophen-2-yl)pyrazolo[1,5-a]pyrimidin-3-yl)isonicotinamide
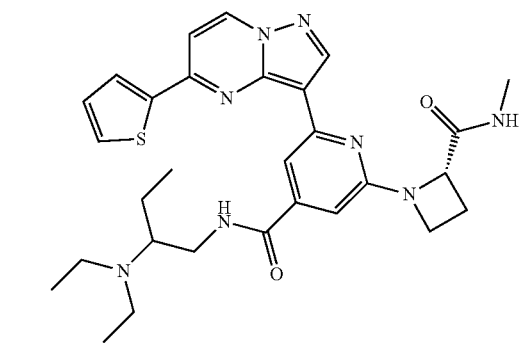
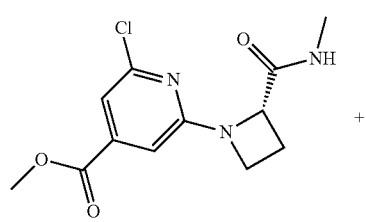
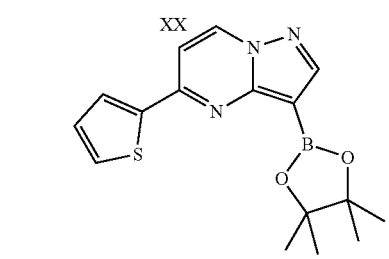
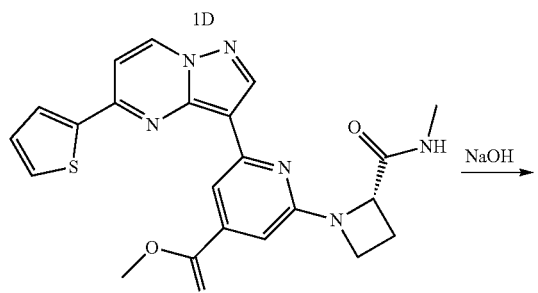
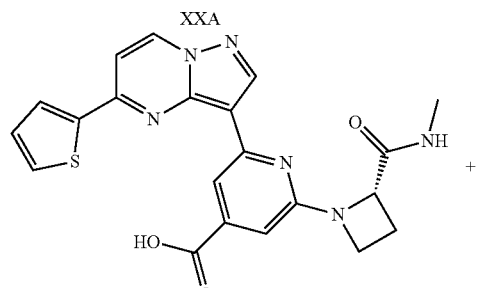
-continued
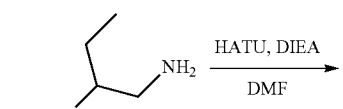
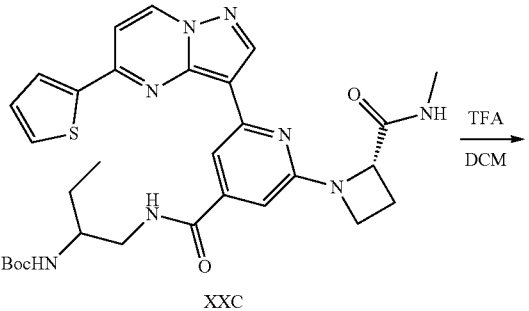
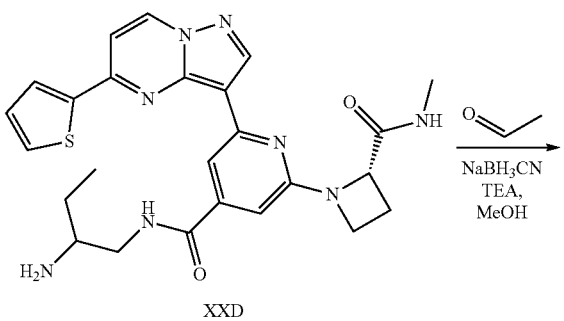
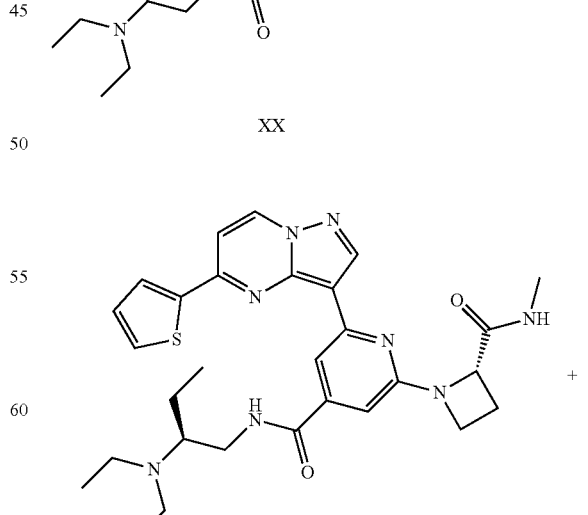

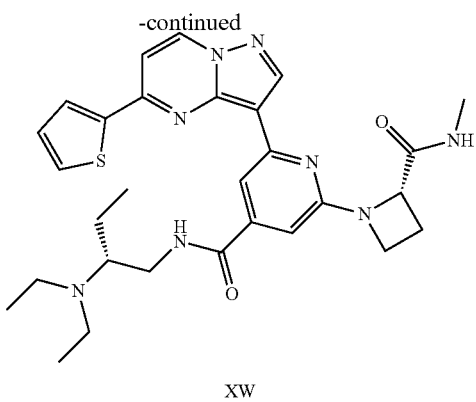

XW

Synthesis of methyl (S)-2-(2-(methylcarbamoyl)azetidin-1-yl)-6-(5-(thiophen-2-yl)pyrazolo[1,5-a]pyrimidin-3-yl)isonicotinate (XXA)

To a solution of Compound 1D (864.99 mg, 2.64 mmol), XX (500 mg, 1.76 mmol), Dichloro 1,1-bis(diphenylphosphino)ferrocene palladium(II) (64.48 mg, 0.09 mmol), and potassium carbonate (487.13 mg, 3.52 mmol) in 14 mL 9:1 DMF water was heated to 120° C. After 30 minutes a precipitate formed. The reaction was cooled and 30 mL of EA was added and the filtered. The filter cake was washed with EA. The filter cake was then suspended in water, filtered, and then dried under hi-vac to afford 570 mg of product.

Synthesis (S)-2-(2-(methylcarbamoyl)azetidin-1-yl)-6-(5-(thiophen-2-yl)pyrazolo[1,5-a]pyrimidin-3-yl)isonicotinic Acid (XXB)

To a suspension of Compound XXA (270 mg, 0.6 mmol) in 10 mL 1:1 DMF water:THF was added Sodium hydroxide (130 mg, 3.25 mmol). The reaction was stirred for 4 days. Added 6M HCl, 6N aq (541.8 µl) to solution. The solution was concentrated to 428 mg of product.

tert-butyl (1-(2-((S)-2-(methylcarbamoyl)azetidin-1-yl)-6-(5-(thiophen-2-yl)pyrazolo[1,5-a]pyrimidin-3-yl)isonicotinamido)butan-2-yl)carbamate (XXC)

Compound XXC synthesized following the same process as shown in Example 1 and using commercially available tert-butyl (1-aminobutan-2-yl)carbamate HCl as its TFA salt.

tert-butyl (1-(2-((S)-2-(methylcarbamoyl)azetidin-1-yl)-6-(5-(thiophen-2-yl)pyrazolo[1,5-a]pyrimidin-3-yl)isonicotinamido)butan-2-yl)carbamate (XXC)

Compound XXC synthesized following the same process as shown in Example 5 as its TFA salt.

N-(2-(diethylamino)butyl)-2-((S)-2-(methylcarbamoyl)azetidin-1-yl)-6-(5-(thiophen-2-yl)pyrazolo[1,5-a]pyrimidin-3-yl)isonicotinamide (XX) (356)

Compound 356 synthesized following the same process as shown in Example 31 and using commercially available acetaldehyde as its TFA salt. LC/MS (M+H): 561.2; $^1$H-NMR (CD$_3$OD) δ 8.86 (d, J=7.4 Hz, 1H), 8.63-8.51 (m, 1H), 8.27 (s, 0H), 7.99-7.88 (m, 1H), 7.72 (dd, J=5.1, 1.1 Hz, 1H), 7.53 (d, J=7.4 Hz, 1H), 7.23 (dd, J=5.0, 3.8 Hz, 1H), 6.69 (t, J=1.3 Hz, 1H), 4.25-4.04 (m, 2H), 4.01-3.86 (m, 1H), 3.69-3.47 (m, 3H), 3.36 (dt, J=13.7, 6.9 Hz, 2H), 3.21 (dd, J=13.4, 7.0 Hz, 1H), 2.80 (d, J=1.5 Hz, 3H), 2.69 (dd, J=9.8, 3.3 Hz, 1H), 2.61 (d, J=8.6 Hz, 1H), 1.90 (td, J=7.0, 3.3 Hz, 1H), 1.87-1.70 (m, 1H), 1.49 (t, J=7.2 Hz, 3H), 1.38 (t, J=7.2 Hz, 3H), 1.17 (t, J=7.4 Hz, 3H).

Example 356A

N—((S)-2-(diethylamino)butyl)-2-((S)-2-(methylcarbamoyl)azetidin-1-yl)-6-(5-(thiophen-2-yl)pyrazolo[1,5-a]pyrimidin-3-yl)isonicotinamide

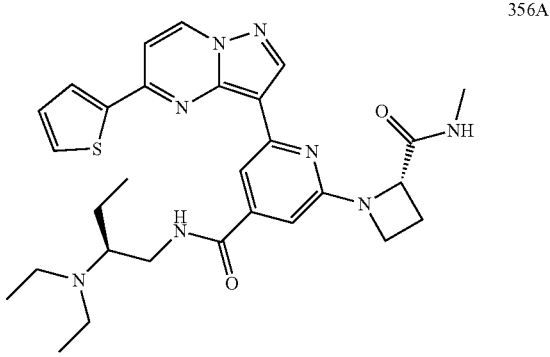 [SMILES: CC[C@@H](CNC(=O)c1cc(-c2cnn3ccc(-c4cccs4)nc23)nc(N2CC[C@H]2C(=O)NC)c1)N(CC)CC]

356A

Compound 356A was synthesized by SFC (supercritical fluid chromatography) separation of Compound XX, stereochemistry was arbitrarily assigned. LC/MS (M+H): 561.2

Example 356B

N—((R)-2-(diethylamino)butyl)-2-((S)-2-(methylcarbamoyl)azetidin-1-yl)-6-(5-(thiophen-2-yl)pyrazolo[1,5-a]pyrimidin-3-yl)isonicotinamide

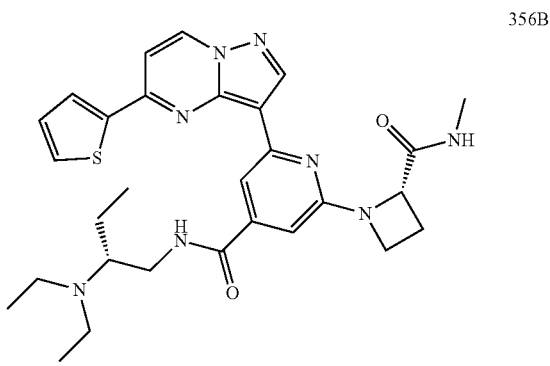 [SMILES: CC[C@H](CNC(=O)c1cc(-c2cnn3ccc(-c4cccs4)nc23)nc(N2CC[C@H]2C(=O)NC)c1)N(CC)CC]

356B

Compound XW was synthesized by SFC separation of Compound 356, stereochemistry was arbitrarily assigned. LC/MS (M+H): 561.2

Example 357

N—((S)-2-(ethyl(propyl)amino)propyl)-2-((S)-2-(methylcarbamyl)azetidin-1-yl)-6-(5-(thiophen-2-yl)pyrazolo[1,5-a]pyrimidin-3-yl)isonicotinamide

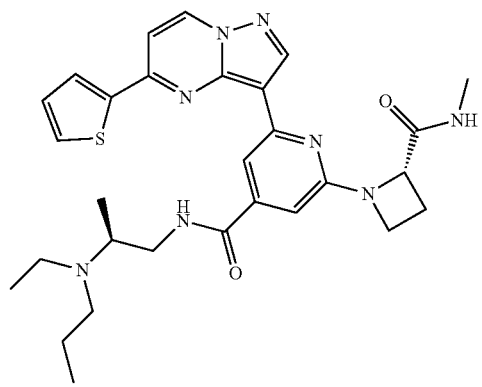

357

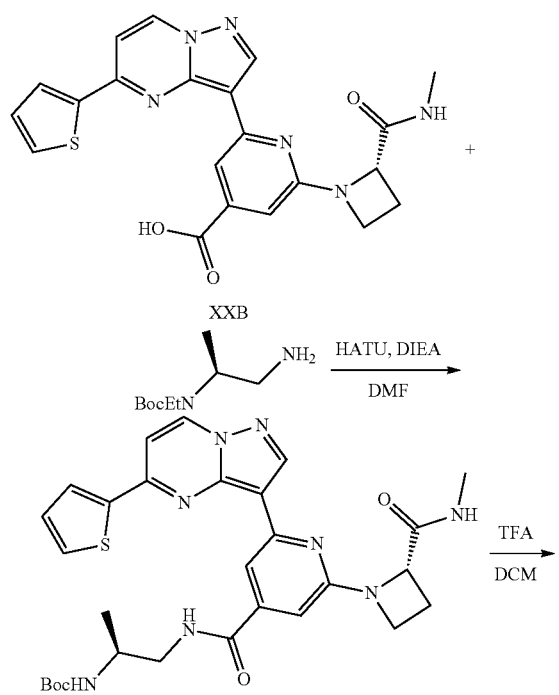

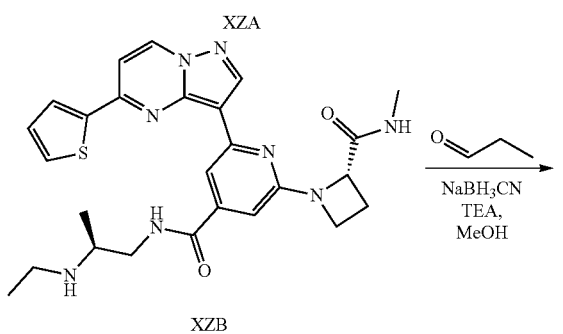

XZB

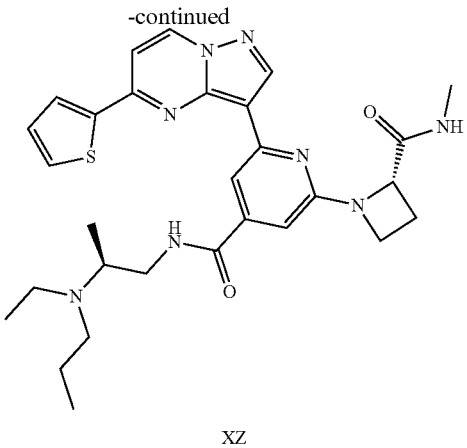

XZ

Synthesis N—((S)-2-(ethylamino)propyl)-2-((S)-2-(methylcarbamoyl)azetidin-1-yl)-6-(5-(thiophen-2-yl)pyrazolo[1,5-a]pyrimidin-3-yl)isonicotinamide (XZB)

Compound XZB was synthesized following the same process as shown in Example XXD and using commercially available tert-butyl (S)-(1-aminopropan-2-yl)(ethyl)carbamate as its TFA salt.

N—((S)-2-(ethyl(propyl)amino)propyl)-2-((S)-2-(methylcarbamoyl)azetidin-1-yl)-6-(5-(thiophen-2-yl)pyrazolo[1,5-a]pyrimidin-3-yl)isonicotinamide (357) (XZ)

Compound XZB WAS synthesized following the same process as shown in Example 31 and using commercially available propionaldehyde as its TFA salt. LC/MS (M+H): 561.2; $^1$H-NMR (CD$_3$OD) δ 8.88 (d, J=7.4 Hz, 1H), 8.63 (s, 1H), 8.26 (s, 1H), 7.96 (dd, J=3.8, 1.1 Hz, 1H), 7.73 (dd, J=5.1, 1.0 Hz, 1H), 7.55 (d, J=7.4 Hz, 1H), 7.24 (dd, J=5.1, 3.8 Hz, 1H), 6.71 (s, 1H), 4.28-4.07 (m, 2H), 3.95 (dd, J=14.2, 5.8 Hz, 1H), 3.56-346 (m, 2H), 3.42-3.32 (m, 2H), 3.44-3.33 (m, 1H), 3.23 (d, J=8.8 Hz, 1H), 3.13-3.04 (m, 1H), 2.80 (s, 3H), 2.75-2.54 (m, 1H), 1.84 (dd, J=31.5, 7.9 Hz, 1H), 1.47 (dd, J=11.7, 6.9 Hz, 3H), 1.39 (t, J=7.2 Hz, 3H), 1.07 (dt, J=19.3, 7.3 Hz, 3H).

Example 358

N—((R)-2-(diethylamino)-3-hydroxypropyl)-2-((S)-2-(methylcarbamoyl)azetidin-1-yl)-6-(5-(thiophen-2-yl)pyrazolo[1,5-a]pyrimidin-3-yl)isonicotinamide

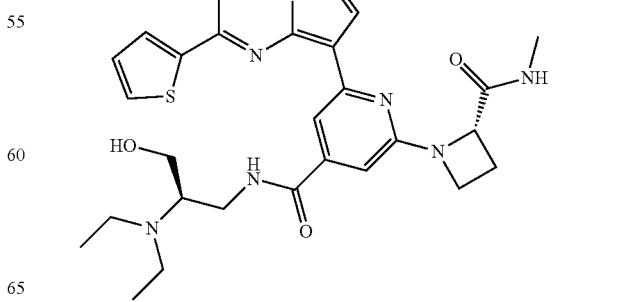

358

Compound 358 synthesized following the same process as shown in Example 356 using commercially available tert-butyl (R)-(1-amino-3-hydroxypropan-2-yl)carbamate as its TFA salt. LC/MS (M+H): 563.2; $^1$H-NMR (CD$_3$OD) δ 8.88 (d, J=7.4 Hz, 1H), 8.62 (s, 1H), 8.27 (d, J=1.3 Hz, 1H), 7.96 (dd, J=3.9, 1.1 Hz, 1H), 7.73 (dd, J=5.1, 1.1 Hz, 1H), 7.55 (d, J=7.4 Hz, 1H), 7.24 (dd, J=5.0, 3.8 Hz, 1H), 6.66 (d, J=1.4 Hz, 1H), 4.23-4.13 (m, 1H), 4.13-4.04 (m, 1H), 4.04-3.89 (m, 3H), 3.83-3.74 (m, 1H), 3.66-3.49 (m, 3H), 3.52-3.39 (m, 1H), 3.38-3.31 (m, 1H), 2.83 (d, J=18.2 Hz, 3H), 2.75-2.64 (m, 1H), 2.59 (d, J=8.3 Hz, 1H), 1.45 (dt, J=19.4, 7.2 Hz, 6H).

Example 359

N—((R)-2-(diethylamino)-3-hydroxypropyl)-2-((S)-2-(methylcarbamoyl)azetidin-1-yl)-6-(5-(thiophen-2-yl)pyrazolo[1,5-a]pyrimidin-3-yl)isonicotinamide

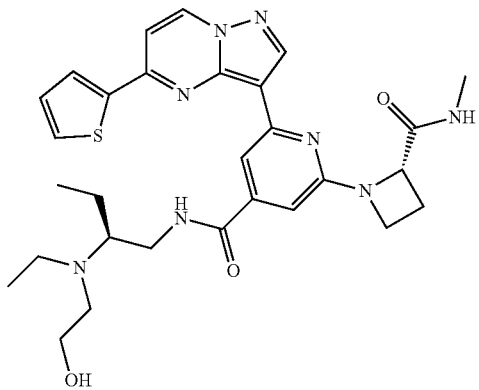 [SMILES: CC[C@@H](CNC(=O)c1cc(-c2cnn3ccc(-c4cccs4)nc23)nc(N2CC[C@H]2C(=O)NC)c1)N(CC)CCO]

359 was synthesized following the same process as shown in Example 356 using Compound XXB as its TFA salt. LC/MS (M+H): 563.2; $^1$H-NMR (CD$_3$OD) δ 8.85 (d, J=7.4 Hz, 1H), 8.59 (s, 1H), 8.23 (s, 1H), 7.93 (dd, J=3.8, 1.1 Hz, 1H), 7.72 (dd, J=5.1, 1.1 Hz, 1H), 7.52 (d, J=7.4 Hz, 1H), 7.23 (dd, J=5.0, 3.8 Hz, 1H), 6.68 (d, J=1.4 Hz, 1H), 4.20-4.01 (m, 2H), 4.01-3.78 (m, 2H), 3.66-3.49 (m, 1H), 3.49-3.35 (m, 2H), 3.28-3.20 (m, 1H), 2.80 (s, 3H), 2.76-2.53 (m, 2H), 1.52 (t, J=7.1 Hz, 1H), 1.46 (d, J=6.8 Hz, 4H).

Example 360

(S)—N-(2-(diethylamino)ethyl)-2-(2-(methylcarbamoyl)azetidin-1-yl)-6-(5-(thiophen-2-yl)pyrazolo[1,5-a]pyrimidin-3-yl)isonicotinamide

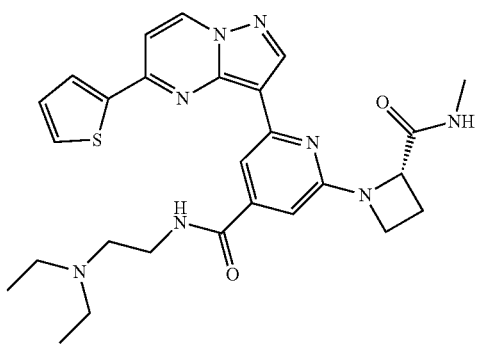

Compound 360 synthesized following the same process as shown in Example 356 using Compound XXB and commercially available N1,N1-diethylethane 1,2 diamine as its TFA salt. LC/MS (M+H): 533.2; $^1$H-NMR (CD$_3$OD) δ 8.87 (d, J=7.4 Hz, 1H), 8.61 (s, 1H), 8.29 (s, 1H), 7.95 (dd, J=3.8, 1.1 Hz, 1H), 7.72 (dd, J=5.0, 1.1 Hz, 1H), 7.54 (d, J=7.4 Hz, 1H), 7.23 (dd, J=5.0, 3.8 Hz, 1H), 6.66 (d, J=1.4 Hz, 1H), 4.22-4.01 (m, 2H), 3.81 (t, J=6.3 Hz, 3H), 3.44 (t, J=6.3 Hz, 2H), 3.37 (dd, J=7.3, 4.0 Hz, 4H), 2.80 (s, 3H), 2.72-2.52 (m, 1H), 1.39 (t, J=7.3 Hz, 6H).

Example 361

N—((S)-2-(diethylamino)propyl)-2-(5-(5-fluorothiophen-2-yl)pyrazolo[1,5-a]pyrimidin-3-yl)-6-((S)-2-(methylcarbamoyl)azetidin-1-yl)isonicotinamide

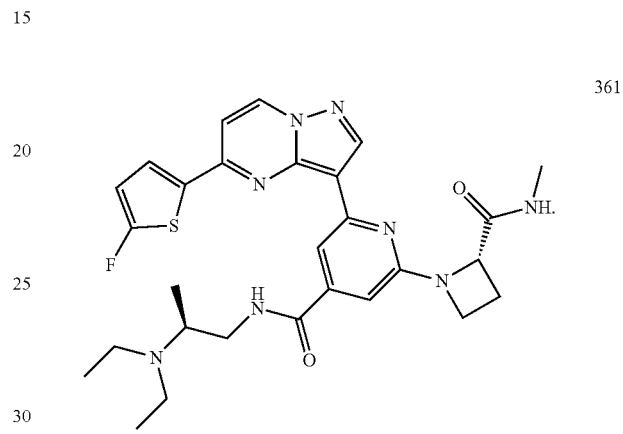

Compound 361 synthesized following the same process as shown in Example 275 using commercially available (5-fluorothiophen-2-yl)boronic acid as its TFA salt. LC/MS (M+H): 565.2; $^1$H-NMR (CD$_3$OD) δ 8.86 (d, 1H, J=7.6 Hz), 8.61 (s, 1H), 8.29 (d, 1H, J=1.2 Hz), 7.67 (t, 1H, J=4.0 Hz), 7.51 (d, 1H, J=7.2 Hz), 6.72 (dd, 1H, J=4.2, 1.8 Hz), 6.68 (d, 1H, J=1.6 Hz), 4.87-4.90 (m, 1H), 4.12-4.187 (m, 1H), 4.07 (dd, 1H, J=16.0, 8.0 Hz), 3.92-3.98 (m, 1H), 3.81-3.89 (m, 1H), 3.47-3.56 (m, 2H), 3.34-3.43 (m, 2H), 3.17-3.25 (m, 1H), 2.83 (s, 3H), 2.53-2.72 (m, 2H), 1.44-1.48 (m, 6H), 1.40 (t, 3H, J=7.2 Hz)

Example 362

(S)—N-(2-(diethylamino)propyl)-5-(5-(thiophen-2-yl)pyrazolo[1,5-a]pyrimidin-3-yl)nicotinamide

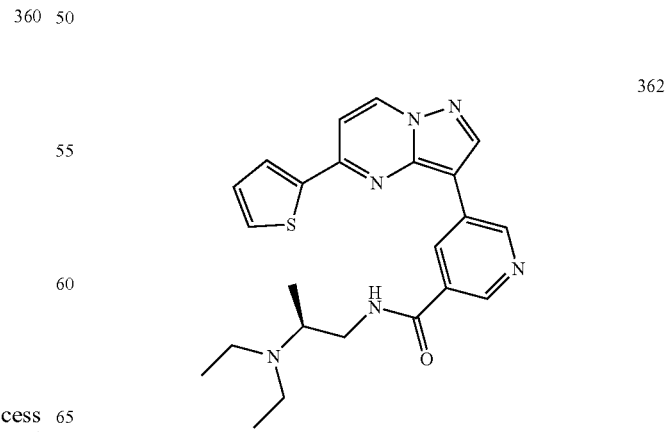

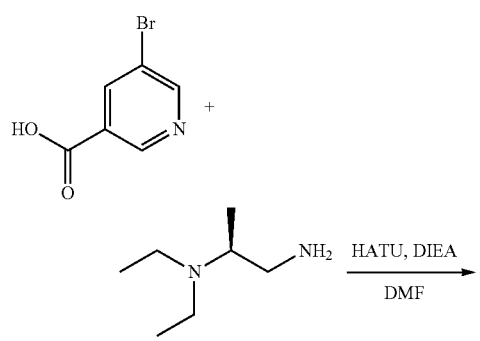

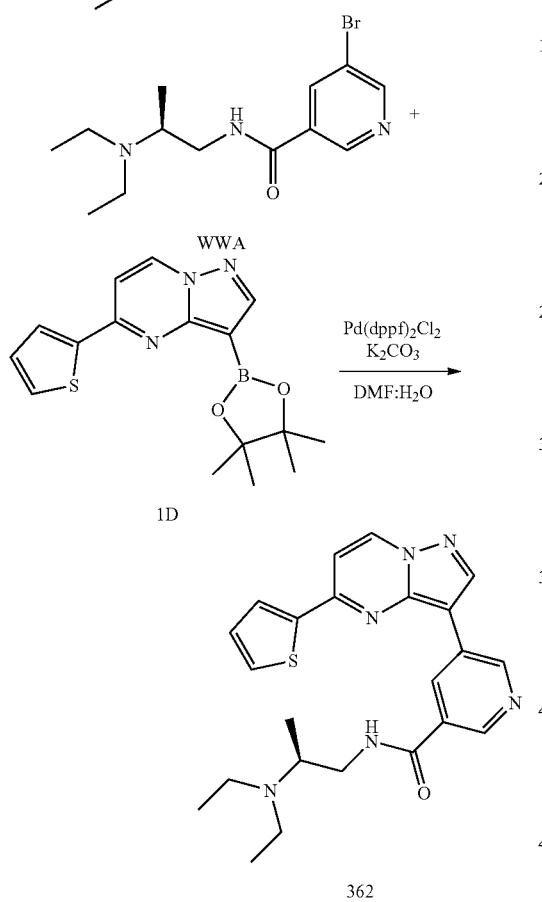

Synthesis of (S)-5-bromo-N-(2-(diethylamino)propyl)nicotinamide (WWA)

Stirred 5-bromonicotinic acid (125 mg, 0.62 mmol), (S)—N2,N2-diethylpropane-1,2-diamine (120.88 mg, 0.93 mmol), HATU (282.17 mg, 0.74 mmol), and N,N-diisopropylethylamine (215.56 µl, 1.24 mmol) in 2 mL DMF at RT. After 1 h, reaction was done. The reaction mixture was purified by reverse-phase chromatography. Product was isolated as a TFA salt (110 mg).

Synthesis of (S)—N-(2-(diethylamino)propyl)-5-(5-(thiophen-2-yl)pyrazolo[1,5-a]pyrimidin-3-yl)nicotinamide (362)

WWA (110 mg, 0.26 mmol), 1D (126.07 mg, 0.39 mmol), Dichloro 1,1-bis(diphenylphosphino)ferrocene palladium (II) dichloromethane (0.01 g, 0.01 mmol), and potassium carbonate (0.11 g, 0.77 mmol) in 2 mL DMF with 0.2 mL water was microwaved for 10 m at 120° C. The reaction mixture was purified by reverse-phase chromatography. Product was isolated as its TFA salt (50 mg). LC/MS (M+H): 435.2; $^1$H-NMR (CD$_3$OD) δ 9.45 (d, J=2.0 Hz, 1H), 9.04 (t, J=2.0 Hz, 1H), 8.82 (d, J=1.9 Hz, 1H), 8.69 (d, J=7.3 Hz, 1H), 8.54 (s, 1H), 7.78 (dd, J=3.8, 1.1 Hz, 1H), 7.64 (dd, J=5.1, 1.1 Hz, 1H), 7.36 (d, J=7.4 Hz, 1H), 7.13 (dd, J=5.0, 3.8 Hz, 1H), 3.96 (dd, J=14.1, 5.9 Hz, 1H), 3.88 (q, J=6.4 Hz, 1H), 3.60 (dd, J=14.1, 6.0 Hz, 1H), 3.56-3.45 (m, 1H), 3.45-3.32 (m, 1H), 3.22 (dd, J=13.5, 7.0 Hz, 1H), 1.54-1.33 (m, 7H).

Example 363

(S)—N-(2-(diethylamino)propyl)-4-(5-(thiophen-2-yl)pyrazolo[1,5-a]pyrimidin-3-yl)picolinamide

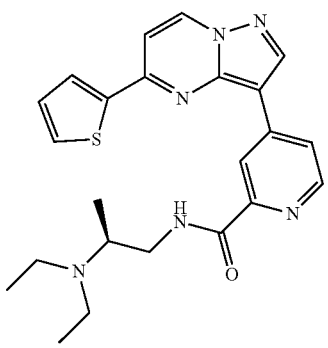

Compound 363 was synthesized following the same process as shown in Example 362 using commercially available 4-chloropicolinic acid as its TFA salt. LC/MS (M+H): 435.2; $^1$H-NMR (CD$_3$OD) δ 8.89 (dd, J=1.8, 0.8 Hz, 1H), 8.81 (d, J=7.4 Hz, 1H), 8.64 (s, 1H), 8.57 (dd, J=5.3, 0.8 Hz, 1H), 8.30 (dd, J=5.3, 1.8 Hz, 1H), 7.90 (dd, J=3.8, 1.1 Hz, 1H), 7.70 (dd, J=5.1, 1.1 Hz, 1H), 7.49 (d, J=7.4 Hz, 1H), 7.20 (dd, J=5.0, 3.8 Hz, 1H), 4.02-3.82 (m, 2H), 3.68-3.58 (m, 1H), 3.57-3.47 (m, 1H), 3.40 (t, J=6.9 Hz, 1H), 3.17 (dd, J=13.4, 6.9 Hz, 1H), 1.61-1.29 (m, 7H).

Example 364

(S)—N-(2-(diethylamino)propyl)-6-(5-(thiophen-2-yl)pyrazolo[1,5-a]pyrimidin-3-yl)picolinamide

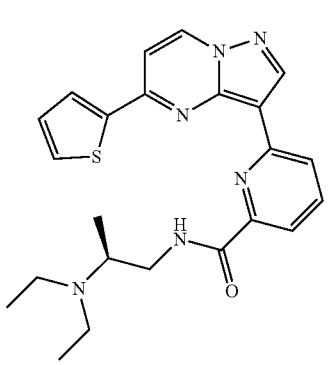

Compound 364 synthesized following the same process as shown in Example 362 using commercially available 6-chloropicolinic acid as its TFA salt. LC/MS (M+H): 435.2.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Formulation Example 2

A tablet Formula Is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

Formulation Example 5

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 6

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Formulation Example 7

A subcutaneous formulation may be prepared as follows:

| Ingredient | Quantity |
| --- | --- |
| Active Ingredient | 5.0 mg |
| Corn Oil | 1.0 mL |

Formulation Example 8

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Formulation Example 9

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients and water then added q.s. 100 g.

Formulation Example 10

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this disclosure are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Biological Assays

Activity testing is conducted in the Examples below using methods described herein and those well known in the art.

Assay Example 1: In Vitro CaMK 2 Delta Assay

CaMKIIδ Biochemical Assay

The biochemical activity of recombinant CaMKIIδ was measured by monitoring the phosphorylation of a target peptide using Homogenous Time Resolved Fluorescence (HTRF) technology from CisBio Bioassays. 10 pM CaM-KIS (Life Technologie Corporation) was incubated for 1 hour with 110 nM calmodulin (EMD Millipore), 1 µM Biotin-STK1 (target peptide, CisBio Bioassays) and 12 µM ATP (Sigma-Aldrich) in a buffer containing 20 mM Hepes pH7.2, 10 mM $MgCl_2$ and 1 mM $CaCl_2$ as well as the compound to be tested or DMSO at a final concentration of 0.6%. The reaction was stopped with the addition of the detection buffer (containing EDTA) with Eu-cryptate labeled anti-phospho-STK1 antibody (CisBio Bioassays) and 125 nM XL665 labeled streptavidin (CisBio Bioassays). After a 1 hour incubation, fluorescence at 620 nm and 665 nm was read using an EnVision Multilabel Reader (Perkin Elmer) and the ratio of signal at 665 nm and 620 nm (665/620) was calculated and plotted against compound concentration to determine compound $IC_{50}$.

CaMKII Cell-Based Activity

CaMKII activity in neonatal rat ventricular myocytes (NRVM) was measured by monitoring the phosphorylation level of phospholamban using high-content imaging. NRVMs were plated in a clear bottom 384-well plate in medium supplemented with 10% fetal bovine serum (FBS) and incubated at 37° C., 5% $CO_2$ overnight. The medium was changed to a serum-free medium and compounds were dosed to the cells. The cells were incubated at 37° C., 5% $CO_2$ for 4 hours and were then treated with 100 nM ATX-II (Alomone Labs) to activate CaMKII. 10 minutes after the addition of ATX-II, the cells were fixed with 4% formaldehyde followed by permeabilization with 0.1% triton X100. The fixed cells were stained with an anti-phospho-phospholamban primary antibody (Santa Cruz Biotechnology) and an Alexa488-labeled anti-rabbit IgG secondary antibody (Life Technologies Corporation) as well as Hoechst 33342 (Life Technologies Corporation). The cells were imaged using an ArrayScan VTI (Cellomics) and analyzed for cells containing a positive fluorescent signal at 485 nm, reported as % responder. The % responders were plotted against the compound concentration to determine the compounds $EC_{50}$.

| Compound Example | CAMKIID-HTRF-384V2 ($IC_{50}$ - nM) | EC50-PPLN-NRVM-ATX ($EC_{50}$ - nM) |
|---|---|---|
| 1 | 1.62 | 17.13 |
| 2 | 0.41 | 35.43 |
| 3 | 5.55 | 41.54 |
| 4 | 0.09 | 21.37 |
| 5 | 12.65 | 385.71 |
| 6 | 7.07 | 53.35 |
| 7 | 6.05 | 131.72 |
| 8 | 10.01 | 125.71 |
| 9 | 26.03 | 115.65 |
| 10 | 9.80 | 99.17 |
| 11 | 10.71 | 128.69 |
| 12 | 14.88 | 141.55 |
| 13 | 153.17 | 517.80 |
| 14 | 23.84 | 442.73 |
| 15 | 8.34 | 197.31 |
| 16 | 59.97 | 346.87 |
| 17 | 7.47 | 65.96 |
| 18 | 6.51 | 66.94 |
| 19 | 89.33 | 288.40 |
| 20 | 4.97 | 32.95 |
| 21 | 27.82 | 300.89 |
| 22 | 13.91 | 62.22 |
| 23 | 14.60 | 65.24 |
| 24 | 7.88 | 95.24 |
| 25 | 8.62 | 22.86 |
| 26 | 10.68 | 15.05 |
| 27 | 18.43 | 149.42 |
| 28 | 53.37 | 717.24 |
| 29 | 7.72 | 39.79 |
| 30 | 3.67 | 43.26 |
| 31 | 12.11 | 60.02 |
| 32 | 18.03 | 165.54 |
| 33 | 8.44 | 34.83 |
| 34 | 12.38 | 124.93 |
| 35 | 95.55 | 173.14 |
| 36 | 3.44 | 82.45 |
| 37 | 7.03 | 102.52 |
| 38 | 2.08 | 29.00 |
| 39 | 136.81 | 320.26 |
| 40 | 268.04 | 955.12 |
| 41 | 119.31 | 166.44 |
| 42 | 14.42 | 56.06 |
| 43 | 27.68 | 143.42 |
| 44 | 43.08 | |
| 45 | 77.37 | 25.31 |
| 46 | 23.66 | 80.92 |
| 47 | 35.32 | 44.10 |
| 48 | 25.69 | 11.76 |
| 49 | 391.23 | 779.13 |
| 50 | 8.52 | 76.66 |
| 51 | 9.61 | 8.15 |
| 52 | 4.98 | 88.83 |
| 53 | 4.79 | 42.89 |
| 54 | 13.41 | 46.78 |
| 55 | 12.04 | 106.60 |
| 56 | 192.72 | 287.21 |
| 57 | 26.48 | 334.07 |
| 58 | 3.35 | 61.92 |
| 59 | 5.34 | 242.89 |
| 60 | 2.35 | 31.25 |
| 61 | 3.60 | 37.20 |
| 62 | 215.88 | 174.96 |
| 63 | 217.96 | 225.76 |
| 64 | 99.91 | 109.64 |
| 65 | 12.56 | 168.92 |
| 66 | 204.61 | 146.58 |
| 67 | 101.99 | 67.43 |
| 68 | 26.33 | 45.28 |
| 69 | 91.07 | 45.85 |
| 70 | 30.07 | 47.27 |
| 71 | 547.06 | 259.20 |
| 72 | 106.29 | 302.69 |
| 73 | 31.86 | 152.21 |
| 74 | 34.17 | 73.14 |
| 75 | 39.27 | 278.76 |
| 76 | 3.47 | 95.38 |
| 77 | 2.70 | 54.31 |
| 78 | 9.44 | 315.51 |
| 79 | 2.85 | 58.33 |
| 80 | 3.47 | 95.38 |
| 81 | 7.33 | 259.00 |
| 82 | 6.14 | 187.00 |
| 83 | 18.82 | 217.06 |
| 84 | 17.50 | 207.52 |
| 85 | 4.80 | 171.90 |
| 86 | 0.99 | 14.10 |
| 87 | 45.24 | 199.98 |
| 88 | 50.30 | 74.01 |
| 89 | 13.64 | 88.13 |
| 90 | 58.47 | 45.65 |
| 91 | 32.78 | 51.57 |
| 92 | 32.14 | 48.55 |
| 93 | 27.82 | 6.81 |
| 94 | 7.00 | 23.00 |
| 95 | 390.33 | 65.60 |
| 96 | 12.73 | 41.67 |
| 97 | 215.61 | 8.20 |
| 98 | 7.36 | 71.66 |
| 99 | 6.98 | 61.95 |
| 100 | 29.84 | |
| 101 | 9.54 | 80.81 |
| 102 | 0.04 | 10.49 |
| 103 | 0.52 | 69.31 |
| 104 | 3.96 | 80.44 |
| 105 | 0.92 | 59.67 |
| 106 | 1.59 | 48.99 |
| 107 | 5.62 | 102.24 |
| 108 | 0.23 | 40.75 |
| 109 | 20.75 | 212.06 |
| 110 | 7.60 | 145.07 |
| 111 | 0.05 | 23.73 |
| 112 | 0.14 | 13.90 |
| 113 | 41.92 | 242.88 |
| 114 | 0.50 | 24.97 |
| 115 | 1.41 | 52.80 |
| 116 | 5.89 | 65.16 |
| 117 | 8.08 | 29.18 |
| 118 | 5.29 | 53.24 |
| 119 | 71.00 | 170.16 |
| 120 | 41.80 | 283.64 |
| 121 | 15.70 | 112.60 |
| 122 | 4.61 | 19.49 |
| 123 | 94.73 | 15.26 |
| 124 | 17.12 | 13.85 |
| 125 | 266.55 | 841.43 |
| 126 | 65.59 | 470.74 |
| 127 | 0.22 | 33.74 |
| 128 | 27.83 | 605.76 |
| 129 | 1.55 | 111.25 |
| 130 | 266.39 | 46.57 |
| 131 | 56.06 | 211.39 |
| 132 | 32.74 | 316.30 |
| 133 | 162.91 | 212.60 |
| 134 | 303.00 | 288.09 |
| 135 | 760.74 | 417.76 |
| 136 | 0.84 | 33.26 |
| 137 | 1.82 | 35.21 |
| 138 | 0.40 | 23.31 |
| 139 | 0.87 | 21.77 |
| 140 | 1.91 | 66.36 |
| 141 | 0.10 | 13.71 |
| 142 | 0.10 | 9.07 |
| 143 | 0.17 | 9.45 |
| 144 | 0.18 | 19.95 |
| 145 | 0.10 | 17.73 |
| 146 | 0.19 | 40.17 |
| 147 | 0.34 | 54.43 |
| 148 | 0.21 | 17.31 |
| 149 | 0.14 | 31.32 |

-continued

| Compound Example | CAMKIID-HTRF-384V2 ($IC_{50}$ - nM) | EC50-PPLN-NRVM-ATX ($EC_{50}$ - nM) |
|---|---|---|
| 150 | 0.20 | 50.50 |
| 151 | 0.32 | 51.04 |
| 152 | 0.59 | 93.77 |
| 153 | 0.13 | 20.53 |
| 154 | 0.28 | 28.08 |
| 155 | 0.32 | 121.39 |
| 156 | 0.85 | 65.46 |
| 157 | 0.07 | 59.05 |
| 158 | 0.56 | 31.89 |
| 159 | 84.63 | 39.29 |
| 160 | 1.15 | 16.87 |
| 161 | 104.88 | 69.56 |
| 162 | 0.23 | 46.59 |
| 163 | 0.18 | 46.03 |
| 164 | 0.38 | 232.06 |
| 165 | 0.13 | 14.93 |
| 166 | 26.00 | 518.88 |
| 167 | 0.16 | 11.17 |
| 168 | 18.11 | 2477.19 |
| 169 | 9.11 | 603.98 |
| 170 | 19.85 | 156.03 |
| 171 | 18.77 | 139.37 |
| 172 | 85.28 | 121.95 |
| 173 | 13.03 | 90.49 |
| 174 | 35.17 | 145.26 |
| 175 | 0.24 | 27.01 |
| 176 | 0.29 | 13.86 |
| 177 | 0.80 | 9.60 |
| 178 | 1.25 | 114.69 |
| 179 | 0.72 | 126.34 |
| 180 | 0.47 | 95.94 |
| 181 | 0.64 | 106.75 |
| 182 | 0.16 | 25.71 |
| 183 | 0.26 | 31.50 |
| 184 | 1.16 | 150.27 |
| 185 | 0.11 | 9.83 |
| 186 | 0.23 | 143.36 |
| 187 | 0.27 | 39.78 |
| 188 | 0.43 | 48.76 |
| 189 | 0.45 | 20.47 |
| 190 | 0.16 | 27.41 |
| 191 | 0.20 | 23.43 |
| 192 | 141.21 | 13641.20 |
| 193 | 83.20 | 7289.75 |
| 194 | 0.19 | 7.80 |
| 195 | 0.28 | 22.64 |
| 196 | 0.22 | 3.75 |
| 197 | 0.09 | 26.36 |
| 198 | 0.15 | 28.35 |
| 199 | 0.32 | 75.17 |
| 200 | 0.16 | 34.01 |
| 201 | 0.11 | 27.08 |
| 202 | 0.14 | 32.72 |
| 203 | 0.18 | 29.92 |
| 204 | 0.28 | 43.62 |
| 205 | 0.10 | 69.89 |
| 206 | 0.10 | 168.23 |
| 207 | 0.21 | 67.05 |
| 208 | 0.07 | 71.39 |
| 209 | 0.17 | |
| 210 | 18.21 | |
| 211 | 0.30 | |
| 212 | 0.30 | 54.27 |
| 213 | 0.18 | 30.61 |
| 214 | 0.18 | 24.68 |
| 215 | 0.22 | 57.25 |
| 216 | 0.10 | 21.64 |
| 217 | 0.18 | 56.72 |
| 218 | 0.17 | 31.91 |
| 219 | 0.21 | 26.50 |
| 220 | 0.11 | 49.41 |
| 221 | 0.13 | 22.31 |
| 222 | 0.17 | 24.17 |
| 223 | 0.14 | 27.52 |
| 224 | 0.21 | 45.56 |
| 225 | 0.08 | 43.74 |

-continued

| Compound Example | CAMKIID-HTRF-384V2 ($IC_{50}$ - nM) | EC50-PPLN-NRVM-ATX ($EC_{50}$ - nM) |
|---|---|---|
| 226 | 0.10 | 21.43 |
| 227 | 0.07 | 8.28 |
| 228 | 0.05 | 21.15 |
| 229 | 0.10 | 34.61 |
| 230 | 1.80 | 61.46 |
| 231 | 0.06 | 9.87 |
| 232 | 0.28 | 28.09 |
| 233 | 0.18 | 18.21 |
| 234 | 1.28 | 54.52 |
| 235 | 1.83 | 354.80 |
| 236 | 0.83 | 148.43 |
| 237 | 0.13 | 148.18 |
| 238 | 0.28 | 306.40 |
| 239 | 3.66 | 146.72 |
| 240 | 1.07 | 128.61 |
| 241 | 1.87 | 246.93 |
| 242 | 0.07 | 231.86 |
| 243 | 0.14 | 250.05 |
| 244 | 0.16 | 106.66 |
| 245 | 9.25 | 367.87 |
| 246 | 0.17 | 108.43 |
| 247 | 0.46 | 110.36 |
| 248 | 0.21 | |
| 249 | 0.20 | |
| 250 | 1.61 | |
| 251 | 2.05 | |
| 252 | 1.87 | |
| 253 | 0.38 | 514.43 |
| 254 | 0.86 | 90.90 |
| 255 | 33.94 | 260.99 |
| 256 | 2.42 | 180.87 |
| 257 | 284.38 | 326.21 |
| 258 | 1.07 | 53.68 |
| 259 | 1.02 | 135.52 |
| 260 | 1.71 | 40.42 |
| 261 | 0.54 | 97.82 |
| 262 | 6.97 | 606.70 |
| 263 | 0.51 | 115.07 |
| 264 | 0.20 | 43.46 |
| 265 | 0.42 | 78.39 |
| 266 | 0.46 | 80.07 |
| 267 | 0.28 | |
| 268 | 0.06 | |
| 269 | 6.05 | 165.50 |
| 270 | 1.91 | 258.61 |
| 271 | 0.31 | 112.25 |
| 272 | 0.14 | 45.87 |
| 273 | 1.43 | 260.34 |
| 274 | 0.63 | |
| 275 | 0.20 | 24.34 |
| 276 | 0.22 | 28.49 |
| 277 | 0.51 | 28.04 |
| 278 | 0.41 | 33.42 |
| 279 | 0.17 | 10.74 |
| 280 | 0.45 | 25.18 |
| 281 | 0.46 | 52.97 |
| 282 | 0.47 | 27.48 |
| 283 | 1.37 | 41.56 |
| 284 | 0.18 | 16.20 |
| 285 | 0.42 | 33.93 |
| 286 | 0.16 | 146.85 |
| 287 | 0.33 | 28.56 |
| 288 | 0.29 | 22.34 |
| 289 | 0.65 | 84.22 |
| 290 | 14.10 | 300.98 |
| 291 | 3.55 | 126.78 |
| 292 | 0.58 | 78.99 |
| 293 | 0.16 | 21.30 |
| 294 | 0.22 | 29.41 |
| 295 | 0.25 | 32.52 |
| 296 | 1.93 | 89.30 |
| 297 | 0.33 | 84.94 |
| 298 | 0.23 | 25.62 |
| 299 | 0.22 | 35.99 |
| 300 | 0.58 | 65.32 |
| 301 | 0.48 | 47.10 |

| Compound Example | CAMKIID-HTRF-384V2 (IC$_{50}$ - nM) | EC50-PPLN-NRVM-ATX (EC$_{50}$ - nM) |
|---|---|---|
| 302 | 0.20 | 280.85 |
| 303 | 0.16 | 118.22 |
| 304 | 0.17 | 152.00 |
| 305 | 51.71 | 6741.86 |
| 306 | 10.64 | 653.77 |
| 307 | 0.27 | 32.68 |
| 308 | 0.71 | 9.53 |
| 309 | 2.16 | 146.36 |
| 310 | 0.25 | 69.29 |
| 311 | 0.23 | 46.88 |
| 312 | 0.21 | 63.56 |
| 313 | 0.18 | 41.52 |
| 314 | 0.14 | 96.05 |
| 315 | 0.07 | 42.19 |
| 316 | 0.06 | 32.57 |
| 317 | 0.07 | 68.73 |
| 318 | 0.05 | 68.77 |
| 319 | 3.02 | 113.74 |
| 320 | 32.77 | 814.76 |
| 321 | 9.11 | 448.59 |
| 322 | 5.01 | 405.55 |
| 323 | 3.22 | 124.22 |
| 324 | 3.59 | 81.83 |
| 325 | 2.19 | 63.59 |
| 326 | 3.29 | 148.34 |
| 327 | 9.25 | 154.31 |
| 328 | 91.90 | 42.91 |
| 329 | 14.13 | 95.61 |
| 330 | 44.63 | 271.56 |
| 331 | 0.08 | 8.24 |
| 332 | 0.24 | 9.37 |
| 333 | 0.22 | 70.37 |
| 334 | 0.19 | 20.34 |
| 335 | 0.29 | 29.66 |
| 336 | 0.10 | 14.51 |
| 337 | 0.33 | 794.22 |
| 338 | 0.86 | |
| 339 | 0.35 | |
| 340 | 0.05 | 13.52 |
| 341 | 0.15 | 12.80 |
| 342 | 0.13 | 12.32 |
| 343 | 0.26 | 27.75 |
| 344 | 0.56 | 48.38 |
| 345 | 1.22 | 57.08 |
| 346 | 1.07 | 66.15 |
| 347 | 0.10 | 114.55 |
| 348 | 0.28 | 32.02 |
| 349 | 0.56 | 55.34 |
| 350 | 0.31 | 64.25 |
| 351 | 0.34 | 37.81 |
| 352 | 0.21 | 86.77 |
| 353 | 0.10 | 38.39 |
| 354 | 1.05 | 56.10 |
| 355 | 0.54 | 68.45 |
| 356 | 0.70 | 36.77 |
| 356A | 0.31 | 37.81 |
| 356B | 3.04 | 34.27 |
| 357 | 0.27 | 13.57 |
| 358 | 0.46 | 72.93 |
| 359 | 0.35 | 57.56 |
| 360 | 2.98 | 34.68 |
| 361 | 0.15 | 10 |
| 362 | 0.52 | 22 |
| 363 | 1.3 | 18 |
| 364 | 715 | 103 |

Assay Example 2: Kinome Selectivity

Compounds 4, 141, 145, and 275 were tested at Carna Biosciences, Inc. (Kobe, Japan) for selectivity against 319 kinases at 100 nM concentration with ATP concentration in all assays ~1×K$_m$ for each kinase: ABL, ACK, ALK, EML4-ALK, NPM1-ALK, ARG, AXL, BLK, BMX, BRK, BTK, CSK, DDR1, DDR2, EGFR, EPHA1, EPHA2, EPHA3, EPHA4, EPHA5, EPHA6, EPHA7, EPHA8, EPHB1, EPHB2, EPHB3, EPHB4, FAK, FER, FES, FGFR1, FGFR2, FGFR3, FGFR4, FGR, FLT1, FLT3, FLT4, FMS, FRK, FYN, HCK, HER2, HER4, IGF1R, INSR, IRR, ITK, JAK1, JAK2, JAK3, KDR, KIT, LCK, LTK, LYNa, LYNb, MER, MET, MUSK, PDGFRα, PDGFRβ, PYK2, RET, RON, ROS, SRC, SRM, SYK, TEC, TIE2, TNK1, TRKA, TRKB, TRKC, TXK, TYK2, TYRO3, YES, ZAP70, AKT1, AKT2, AKT3, AMPKα1/β1/γ1, AMPKα2/β1/γ1, AurA, AurA/TPX2, AurB, AurC, BMPR1A, BRAF, BRSK1, BRSK2, CaMK1α, CaMK1δ, CaMK2α, CaMK2β, CaMK2γ, CaMK4, CDC2/CycB1, CDC7/ASK, CDK2/CycA2, CDK2/CycE1, CDK3/CycE1, CDK4/CycD3, CDK5/p25, CDK6/CycD3, CDK7/CycH/MAT1, CDK9/CycT1, CGK2, CHK1, CHK2, CK1α, CK1γ1, CK1γ2, CK1γ3, CK1ε, CK2α1/β, CK2α2/β, CLK1, CLK2, CLK3, COT, CRIK, DAPK1, DCAMKL2, DLK, DYRK1A, DYRK1B, DYRK2, DYRK3, EEF2K, Erk1, Erk2, Erk5, GSK3α, GSK3β, Haspin, HGK, HIPK1, HIPK2, HIPK3, HIPK4, IKKα, IKKβ, IKKε, IRAK1, IRAK4, JNK1, JNK2, JNK3, LATS2, LIMK1, LKB1, LOK, MAP2K1, MAP2K2, MAP2K3, MAP2K4, MAP2K5, MAP2K6, MAP2K7, MAP3K1, MAP3K2, MAP3K3, MAP3K4, MAP3K5, MAP4K2, MAPKAPK2, MAPKAPK3, MAPKAPK5, MARK1, MARK2, MARK3, MARK4, MELK, MGC42105, MINK, MLK1, MLK2, MLK3, MNK1, MNK2, MOS, MRCKα, MRCKβ, MSK1, MSK2, MSSK1, MST1, MST2, MST3, MST4, NDR1, NDR2, NEK1, NEK2, NEK4, NEK6, NEK7, NEK9, NuaK1, NuaK2, p38α, p38β, p38γ, p38δ, p70S6K, p70S6Kβ, PAK1, PAK2, PAK3, PAK4, PAK5, PAK6, PASK, PBK, PDHK2, PDHK4, PDK1, PEK, PGK, PHKG1, PHKG2, PIM1, PIM2, PIM3, PKACα, PKACβ, PKACγ, PKCα, PKCβ1, PKCβ2, PKCγ, PKCδ, PKCε, PKCζ, PKCη, PKC0, PKCι, PKD1, PKD2, PKD3, PKN1, PKR, PLK1, PLK2, PLK3, PLK4, PRKX, QIK, RAF1, ROCK1, ROCK2, RSK1, RSK2, RSK3, RSK4, SGK, SGK2, SGK3, SIK, skMLCK, SLK, SRPK1, SRPK2, TAK1-TAB1, TAOK2, TBK1, TNIK, TSSK1, TSSK2, TSSK3, TTK, WEE1, WNK1, WNK2, WNK3, PIK3CA/PIK3R1, SPHK1, SPHK2.

In cases where inhibition exceeded 70% full dose-response curves were acquired. Potency for inhibiting each kinase was divided by potency numbers against CamKIIδ acquired with in-house assays to generate selectivity values. Data for all selectivities that were found to be <50-fold are listed below in Table 1.

TABLE 1

Kinome selectivity data for compounds of examples 141, 145, 275 and 4.

| CamKIIδ | Ex. 141 0.28 nM | Ex. 145 0.32 nM | Ex. 275 0.43 nM | Ex. 4 0.22 nM |
|---|---|---|---|---|
| CamKIIγ | 2.8x | 2.5x | 2.8x | 2.4x |
| CamKIIβ | 12.2x | 10.0x | 19.6x | 11.3x |
| CamKIIα | 5.8x | 4.7x | 6.2x | 4.1x |
| PHKG1 | 6.4x | 7.3x | 14.4 | 4.6x |
| FLT3 | 3.2x | 4.4x | 25.8x | 10.5x |
| TRKA | 1.9x | 2.9x | 29.4x | 3.5x |
| TRKB | 3.1x | 4.1x | | 4.7x |
| TRKC | 3.5x | 3.6x | | 4.8x |
| PDGFRα | | | 43.2x | |
| DDR1 | 22.2x | 37.9x | | 43.0x |
| DDR2 | 10.4x | 13.7x | | 12.1x |
| MUSK | 16x | 22.3x | | 30.4x |
| PKN1 | 5.6x | 11.0x | | |

303

Data Analysis

Data were expressed as mean±SEM and analyzed using one-way ANOVA with Newman-Keuls tests. All statistical analyses were performed using GraphPad Prism. Differences were considered significant when p<0.05.

Assay Example 3: ATX Assay

Both late $I_{Na}$ and CaMKII have been implicated in cardiac arrhythmias and heart failure. An increased late $I_{Na}$ contributes to action potential prolongation, the generation of arrhythmias, and diastolic dysfunction in heart failure. Increases in CaMKII expression and phosphorylation are also found in human failing hearts and atrial myocardium of patients with atrial fibrillation. An activated CaMKII also associates with and phosphorylates cardiac Na$^+$ channels, thereby enhancing late $I_{Na}$. In this assay, we use ATX-II to increase late $I_{Na}$ and activate CaMKII to recapitulate the pathophysiology of human cardiac arrhythmias, atrial fibrillation and heart failure. Therefore, CaMKII inhibitors identified as potent by this assay present potential new therapies for the treatment of human cardiac arrhythmias, atrial and ventricular fibrillation, diastolic dysfunction, systolic and diastolic heart failure and ischemic heart disease.

Materials and Methods

1. Animals

Male Sprague-Dawley rats (300-350 g) were purchased from Charles River Laboratories (Wilmington, Mass.). The use of animals in this study was approved by the Animal Care and Use Committee of Gilead Sciences, Inc., and conforms to the Guide for the Care and Use of Laboratory Animals published by the US National Institutes of Health.

2. Recording of Right Atrial Contractile and Electrical Activity

Rats were anesthetized by intraperitoneal injection of 60 mg/kg ketamine and 8 mg/kg xylazine. The heart was rapidly removed and immersed in oxygenated Krebs-Henseleit buffer (in mmol/L: 118 NaCl, 4.8 KCl, 1.2 KH$_2$PO$_4$, 2.5 CaCl$_2$, 1.2, MgSO$_4$, 2 pyruvic acid, 5.5 glucose, 0.5 Na$_2$EDTA, and 25 NaHCO$_3$, pH 7.4). Rat right atria were quickly excised and suspended in a chamber of the Danish Myo Technologies (DMT) myograph containing 8 mL of oxygenated Krebs-Henseleit buffer. Mechanical and electrical changes were measured simultaneously in spontaneously beating atria. Isometric tension was recorded by a force transducer connected to a PowerLab data acquisition system (ADInstruments, Colorado Springs, Colo.). A bipolar electrode was attached to the surface of the atrium to record an electrogram. After stabilization, the atria were preincubated with varying concentrations of testing articles for 30 min, and then treated with 50 nmol/L ATX-II to enhance late $I_{Na}$ and activate CaMKII.

3. Quantification of Arrhythmias in Isolated Right Atria

Isolated right atria beat spontaneously at a rate of 298±12 bpm. ATX-II induced premature beats, tachyarrhythmia and fibrillation in rat isolated right atria. Arrhythmias were quantified for 30 min following ATX-II treatment using an arbitrary numerical grading of perceived severity as described in Table 1.

Arrhythmia Scores:
Score Type of arrhythmias
0 <0-10 premature atrial beats (PABs)
1 10-100 PABs
2 >100 PABs or 1-3 episodes of atrial tachycardia (AT) or both
3 3-10 episodes of AT

304

4 >10 episodes of AT, or 1-2 episodes of AF (duration <10 s) or both
5 3-5 episodes of AF or >10 s duration of AF
6 6-10 episodes of AF or >30 s duration of AF
7 >10 episodes of AF or >60 s duration of AF
8 Stop beating Results:

| Example # | ATX-AF (nM) |
|---|---|
| 275 | 103 |
| 145 | 45 |
| 141 | 19 |
| 139 | 84 |
| 42 | 127 |
| 38 | 126 |
| 79 | 159 |
| 3 | 89 |
| 1 | 48.4 |

What is claimed is:

1. A compound of formula I:

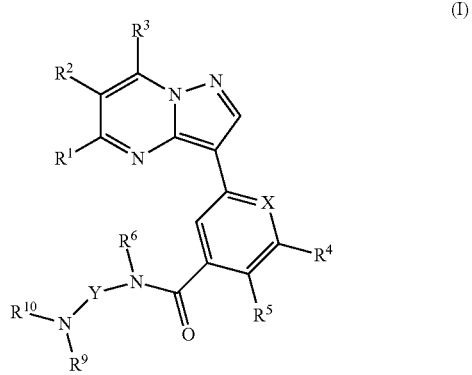

wherein

R$^1$ is aryl, heteroaryl or heterocyclic; wherein the aryl, heteroaryl or heterocyclic group is optionally substituted with one, two or three groups independently selected from the group consisting of halo, hydroxy, C$_1$-C$_6$ alkyl, C$_1$-C$_6$ haloalkyl, C$_1$-C$_6$ alkoxy, —OC$_1$-C$_6$ haloalkyl, —SC$_1$-C$_6$ alkyl, —NHSO$_2$R$^a$, and C$_0$-C$_6$ alkylene-NR$^a$R$^b$;

R$^2$ and R$^3$ are each independently selected from the group consisting of H, halo and C$_1$-C$_6$ alkyl;

X is CH or N;

R$^4$ is is H, halo, cyano, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ haloalkoxy, C$_1$-C$_6$ alkylC$_3$-C$_6$ cycloalkyl, —NR$^a$R$^b$, C$_1$-C$_6$ alkylNR$^a$R$^b$, C$_1$-C$_6$ alkyl-O—C$_1$-C$_6$ alkylNR$^a$R$^b$, —OC$_2$-C$_6$ alkylNR$^a$R$^b$, —C(O)NR$^a$R$^b$, —NR$^a$C(O)NR$^a$R$^b$, —NR$^a$C(O)R$^a$, —NR$^a$C(O)OR$^a$, aryl, heteroaryl, mono, bicyclic, bridged or spirocyclic carbocyclic or heterocyclic group, —O—C$_0$-C$_3$ alkylheterocyclic, or C$_1$-C$_6$ alkylheterocyclic, wherein the alkyl, cycloalkyl, aryl, heteroaryl, carbocyclic or heterocyclic group is optionally substituted with one to four groups independently selected from —OH, oxo, halo, cyano, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —OC$_1$-C$_6$ haloalkyl, C$_1$-C$_6$ alkyl C$_3$-C$_8$ cycloalkyl, C$_1$-C$_6$ alkyl-O—C$_1$-C$_6$ alkyl, C$_0$-C$_3$ alkylNR$^a$CHR$^a$C(O)NHR$^a$, —C(O)R$^a$, —COOR$^a$, —NHC(O)NHR$^a$, —NHC(O)

$R^a$, —NHC(O)OR$^a$, C(O)NR$^a$R$^b$, —NR$^a$R$^b$, —NHC$_1$-C$_3$alkylNR$^a$R$^b$, SO$_2$R$^a$, —NHSO$_2$R$^a$, SO$_2$NR$^a$R$^b$, aryl, heteroaryl, mono, bicyclic, bridged or spirocyclic carbocyclic or heterocyclic group, and C$_1$-C$_6$ alkylheterocyclic; or two substituents on the aryl, heteroaryl, mono, bicyclic, bridged or spirocyclic carbocyclic or heterocyclic group combine to form a mono, bicyclic, spirocyclic, or bridged carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, C$_1$-C$_6$ alkyl, C$_3$-C$_8$ cycloalkyl, C$_1$-C$_6$ haloalkyl, C$_1$-C$_6$ alkylOH, —OC$_1$-C$_6$ alkyl, —OC$_1$-C$_6$ haloalkyl, C$_1$-C$_6$ alkyl C$_3$-C$_6$ cycloalkyl, C$_1$-C$_6$ alkyl-O—C$_1$-C$_6$ alkyl, C$_0$-C$_3$ alkylNR$^a$CHR$^a$C(O)NHR$^a$, C(O)NR$^a$R$^b$, —SO$_2$R$^a$, and SO$_2$NR$^a$R$^b$;

R$^a$ and R$^b$ are each independently H, OH, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —C(O)C$_1$-C$_6$ alkyl, —C(O)OC$_1$-C$_6$ alkyl, C$_0$-C$_3$ alkylNR$^c$R$^d$, C$_1$-C$_3$alkylC(O)NH$_2$, C$_1$-C$_3$alkylC(O)NHC$_1$-C$_3$alkyl, C$_1$-C$_6$ alkylC$_3$-C$_6$ cycloalkyl, SO$_2$C$_1$-C$_3$alkyl, SO$_2$C$_3$-C$_6$cycloalkyl, —C$_1$-C$_3$ alkylSO$_2$NR$^c$R$^d$, aryl, heteroaryl, heterocyclic, C$_1$-C$_6$ alkylheterocyclic, wherein the cycloalkyl, aryl, heteroaryl or heterocyclic group is optionally substituted with one to four groups independently selected from —OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, C$_1$-C$_6$ alkyl-O—C$_1$-C$_6$ alkyl, and heterocyclyl; or R$^a$ and R$^b$ combine with a nitrogen atom to which they are attached to form a mono, bicyclic, bridged or spirocyclic heterocyclic group optionally substituted with one to four groups independently selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^c$R$^d$, —SO$_2$R$^c$, SO$_2$NR$^c$R$^d$ and C$_1$-C$_6$ alkyl-O—C$_1$-C$_6$ alkyl;

R$^c$ and R$^d$ are independently selected from H, C$_1$-C$_6$ alkyl, C$_3$-C$_8$ cycloalkyl, C$_2$-C$_6$ haloalkyl, C$_2$-C$_6$ alkylOH, C$_1$-C$_6$ alkylC$_3$-C$_6$ cycloalkyl, SO$_2$C$_1$-C$_6$ alkyl, and C$_1$-C$_6$ alkyl-O—C$_1$-C$_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^e$R$^f$, —SO$_2$R$^e$, SO$_2$NR$^e$R$^f$ and C$_1$-C$_6$ alkyl-O—C$_1$-C$_6$ alkyl;

R$^e$ and R$^f$ are at each occurrence independently selected from the group consisting of: C$_1$-C$_6$ alkyl, C$_3$-C$_8$ cycloalkyl, C$_2$-C$_6$ haloalkyl, C$_1$-C$_6$ haloalkyl, —OC$_1$-C$_6$ haloalkyl, and C$_1$-C$_6$ alkylOH;

R$^5$ is H, halo, cyano, NH$_2$, NHC$_1$-C$_6$ alkyl, N(C$_1$-C$_6$ alkyl)$_2$, C$_1$-C$_6$ alkyl, C$_3$-C$_8$ cycloalkyl, C$_1$-C$_6$ alkylC$_3$-C$_8$ cycloalkyl, C$_1$-C$_6$ haloalkyl, —OC$_1$-C$_6$ haloalkyl, C$_1$-C$_6$ alkyl-OH, or C$_1$-C$_6$ alkoxy;

R$^6$ is H, C$_1$-C$_6$ alkyl, C$_3$-C$_8$ cycloalkyl, C$_2$-C$_6$ haloalkyl, C$_2$-C$_6$ alkyl-OH, or C$_1$-C$_6$ alkoxy; or R$^6$ combines with Y, R$^9$, or R$^{10}$ to form an optionally substituted 4-8 membered nitrogen containing heterocyclic group;

Y is —(CR$^7$R$^8$)$_n$ wherein n is 2 or 3;

each R$^7$ or R$^8$ is independently selected from H, C$_1$-C$_6$ alkyl, C$_1$-C$_3$ alkylOH, C$_1$-C$_3$ alkylNH$_2$ and C$_1$-C$_3$alkyl-O-heterocyclic; or one R$^7$ or R$^8$ group combines with the R$^6$ group to form an optionally substituted nitrogen containing heterocyclic group; or one R$^7$ group combines with another R$^7$ or an R$^8$ group to form an optionally substituted monocyclic or bicyclic, bridged or spirocyclic ring system having from 4 to 10 carbon atoms in the ring; wherein the optional substituents include 1 or 2 groups independently selected from halo, —OH, NH$_2$, cyano, C$_1$-C$_6$ alkyl, C$_1$-C$_6$ haloalkyl, C$_1$-C$_6$ alkylOH, and C$_3$-C$_8$ cycloalkyl;

each R$^9$ and R$^{10}$ is independently H, C$_1$-C$_6$ alkyl, C$_2$-C$_6$ haloalkyl, C$_2$-C$_6$ alkylOH, C$_3$-C$_8$ cycloalkyl, C$_1$-C$_6$ alkylC$_3$-C$_8$ cycloalkyl, —C(O)OR$^{13}$, —C(O)NR$^{13}$R$^{14}$ or heterocyclic, wherein the alkyl, cycloalkyl or heterocyclic group is optionally substituted with one or two groups independently selected from the group consisting of halo, C$_1$-C$_6$ alkyl, C$_1$-C$_6$ haloalkyl, C$_1$-C$_6$ alkylOH, C$_3$-C$_8$ cycloalkyl, —OR$^{12}$, —NR$^{13}$R$^{14}$, —C(O)NR$^{13}$R$^{14}$, —NR$^{13}$COR$^{14}$, —SO$_2$NR$^{13}$R$^{14}$, —NR$^{13}$SO$_2$R$^{14}$, —NR$^{12}$SO$_2$NR$^{13}$R$^{14}$, —NR$^{12}$C(O)NR$^{13}$R$^{14}$, —NR$^{13}$CO$_2$R$^{14}$, and —OC(O)NR$^{13}$R$^{14}$; or R$^9$ and R$^{10}$ together with the nitrogen atom to which they are attached form a mono, bicyclic, bridged or spirocyclic heterocyclic ring optionally substituted with one or two groups independently selected from the group consisting of halo, —OH, —NH$_2$, —NH—C$_1$-C$_6$ alkyl, —C$_1$-C$_6$ alkyl, —C$_1$-C$_6$ alkylOH, C$_3$-C$_8$ cycloalkyl, aryl, and heterocyclic; wherein the cycloalkyl, aryl or heterocyclic group is optionally substituted with halo, —OH, —NH$_2$, —NH—C$_1$-C$_6$ alkyl, —C$_1$-C$_6$ alkyl, and —C$_1$-C$_6$ alkylOH; or R$^9$ and/or R$^{10}$ combines with Y to form a mono, bicyclic, bridged or spirocyclic nitrogen containing heterocycle optionally substituted with one or two groups independently selected from the group consisting of —C$_1$-C$_6$ alkyl, —C$_1$-C$_6$ alkylOH, C$_3$-C$_8$ cycloalkyl, —OH, —NH$_2$, and —NH—C$_1$-C$_6$ alkyl;

each R$^{12}$, R$^{13}$ and R$^{14}$ is independently H, C$_1$-C$_6$ alkyl, C$_3$-C$_8$ cycloalkyl, or heterocyclic, wherein the C$_1$-C$_6$ alkyl, C$_3$-C$_8$ cycloalkyl group, or heterocyclic, group is optionally substituted with one or two groups independently selected from the group consisting of —OH, —NH$_2$, —N(CH$_3$)$_2$, C$_1$-C$_6$ haloalkyl; or R$^{13}$ and R$^{14}$ together with the atom to which they are attached form a heterocyclic ring;

or a pharmaceutically acceptable salt, stereoisomer or mixture of stereoisomer thereof.

2. The compound of claim 1, wherein R$^4$ is H.

3. The compound of claim 1, wherein R$^5$ is H.

4. The compound of claim 1, wherein R$^1$ is phenyl, isothiazolyl, pyridine, pyrimidine or thienyl.

5. The compound of claim 1 wherein R$^1$ is phenyl or thienyl.

6. The compound of claim 1 wherein X is N.

7. The compound of claim 1 wherein R$^6$ is H.

8. A compound of formula (IV):

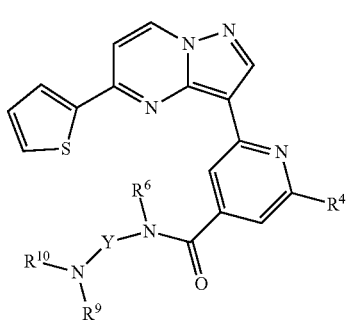

(IV)

wherein
$R^4$ is H, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkyl$C_3$-$C_6$ cycloalkyl, —$NR^aR^b$, $C_1$-$C_6$ alkyl$NR^aR^b$, $C_1$-$C_6$alkyl-O—$C_1$-$C_6$ alkyl$NR^aR^b$, —O$C_2$-$C_6$ alkyl$NR^aR^b$, —C(O)$NR^aR^b$, —$NR^a$C(O)$NR^aR^b$, —$NR^a$C(O)$R^a$, —$NR^a$C(O)O$R^a$, aryl, heteroaryl, mono, bicyclic, bridged or spirocyclic carbocyclic or heterocyclic group, —O—$C_0$-$C_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —O$C_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkyl$NR^a$CH$R^a$C(O)NH$R^a$, —C(O)$R^a$, —COO$R^a$, —NHC(O)NH$R^a$, —NHC(O) $R^a$, —NHC(O)O$R^a$, C(O)$NR^aR^b$, —$NR^aR^b$, —NH$C_1$-$C_3$alkyl$NR^aR^b$, SO$_2R^a$, —NHSO$_2R^a$, SO$_2NR^aR^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group combines to form a mono, bicyclic, bridged or spirocyclic carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, $C_1$-$C_6$ alkyl, $C_3$-$C_8$ cycloalkyl, $C_1$-$C_6$ haloalkyl, $C_1$-$C_6$ alkylOH, —O$C_1$-$C_6$ alkyl, —O$C_1$-$C_6$ haloalkyl, $C_1$-$C_6$ alkyl $C_3$-$C_6$ cycloalkyl, $C_1$-$C_6$ alkyl-O—$C_1$-$C_6$ alkyl, $C_0$-$C_3$ alkyl$NR^a$CH$R^a$C(O)NH$R^a$, C(O)$NR^aR^b$, —SO$_2R^a$, and SO$_2NR^aR^b$;
$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkyl$NR^cR^d$, $C_1$-$C_3$alkylC(O)NH$_2$, $C_1$-$C_3$alkylC(O)NH$C_1$-$C_3$alkyl, $C_1$-$C_6$ alkyl$C_3$-$C_6$ cycloalkyl, SO$_2C_1$-$C_3$alkyl, SO$_2C_3$-$C_6$cycloalkyl, aryl, heterocyclic, or $C_1$-$C_6$ alkylheterocyclic; wherein the cycloalkyl, aryl or heterocyclic group is optionally substituted with one to four groups independently selected from —OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a monocyclic, bicyclic, bridged or spirocyclic heterocyclic group optionally substituted with a group selected from OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^cR^d$, —SO$_2R^c$, SO$_2NR^cR^d$ and $C_1$-$C_6$ alkyl-O—$C_1$-$C_6$ alkyl;
$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, SO$_2C_1$-$C_6$ alkyl, and $C_1$-$C_6$ alkyl-O—$C_1$-$C_6$ alkyl; or $R^c$ and $R^d$ combine to form mono or bicyclic, bridged or spirocyclic heterocycle optionally substituted with a group selected from OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^eR^f$, —SO$_2R^e$, SO$_2NR^eR^f$ and $C_1$-$C_6$ alkyl-O—$C_1$-$C_6$ alkyl; wherein $R^e$ and $R^f$ are independently selected from $C_1$-$C_6$ alkyl, $C_1$-$C_6$ alkylOH, and $C_1$-$C_6$ alkyl aryl;
$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —O$C_1$-$C_6$ haloalkyl, and $C_1$-$C_6$ alkylOH;
$R^6$ is H, $C_1$-$C_6$ alkyl, $C_3$-$C_8$ cycloalkyl, $C_2$-$C_6$ haloalkyl, $C_2$-$C_6$ alkyl-OH, or $C_1$-$C_6$ alkoxy; or $R^6$ combines with Y to form a 4-8 membered nitrogen containing heterocyclic group;
Y is —(CR$^7R^8$)$_n$ wherein n is 2 or 3;
each $R^7$ or $R^8$ is independently selected from H, $C_1$-$C_6$ alkyl, $C_1$-$C_6$ alkylOH, $C_1$-$C_3$ alkyl-O-heteroaryl, $C_1$-$C_3$ alkyl-O-heterocyclyl, $C_1$-$C_3$ alkyl-O-aryl, $C_1$-$C_3$ alkylNH$_2$; or one $R^7$ or $R^8$ group combines with the $R^6$ group to form a nitrogen containing heterocyclic group; or one $R^7$ group combines with an another $R^7$ or $R^8$ group to form an optionally substituted monocyclic or bicyclic ring system having from 4 to 10 carbon atoms in the ring;
each $R^9$ and $R^{10}$ is independently H, $C_1$-$C_6$ alkyl, $C_3$-$C_8$ cycloalkyl, or heterocyclic, wherein the alkyl, cycloalkyl or heterocyclic group is optionally substituted with one or two groups independently selected from the group consisting of halo, $C_1$-$C_6$ alkyl, $C_1$-$C_6$ haloalkyl, $C_1$-$C_6$ alkylOH, $C_3$-$C_8$ cycloalkyl, —OR$^{12}$, —NR$^{13}$R$^{14}$, —C(O)NR$^{13}$R$^{14}$, —NR$^{13}$COR$^{14}$, —SO$_2$NR$^{13}$R$^{14}$, —NR$^{13}$SO$_2$R$^{14}$, —NR$^{12}$SO$_2$NR$^{13}$R$^{14}$, —NR$^{12}$C(O)NR$^{13}$R$^{14}$, —NR$^{13}$CO$_2$R$^{14}$, and —OC(O)NR$^{13}$R$^{14}$; or $R^9$ and $R^{10}$ together with the nitrogen atom to which they are attached form a mono, bicyclic bridged or spirocyclic heterocyclic ring optionally substituted with one or two groups independently selected from the group consisting of halo, —OH, —NH$_2$, —NH—$C_1$-$C_6$ alkyl, —$C_1$-$C_6$ alkyl, —$C_1$-$C_6$ alkylOH, $C_3$-$C_8$ cycloalkyl, aryl, and heterocyclic; wherein the cycloalkyl, aryl or heterocyclic group is optionally substituted with halo, —OH, —NH$_2$, —NH—$C_1$-$C_6$ alkyl, —$C_1$-$C_6$ alkyl, and —$C_1$-$C_6$ alkylOH; or $R^9$ and/or $R^{10}$ combines with Y to form a monocyclic, bicyclic, bridged or spirocyclic nitrogen containing heterocycle optionally substituted with one or two groups independently selected from the group consisting of —$C_1$-$C_6$ alkyl, —$C_1$-$C_6$ alkylOH, $C_3$-$C_8$ cycloalkyl, —OH, —NH$_2$, and —NH—$C_1$-$C_6$ alkyl;
each $R^{12}$, $R^{13}$ and $R^{14}$ is independently H, $C_1$-$C_6$ alkyl, $C_3$-$C_8$ cycloalkyl, or heterocyclic, wherein the $C_1$-$C_6$ alkyl, $C_3$-$C_8$ cycloalkyl group, or heterocyclic, is optionally substituted with one or two groups independently selected from the group consisting of —OH, —$NH_2$, —$N(CH_3)_2$, $C_1$-$C_6$ haloalkyl; or $R^{13}$ and $R^{14}$ together with the atom to which they are attached form a heterocyclic ring;

or a pharmaceutically acceptable salt, stereoisomer or mixture of stereoisomer thereof.

9. The compound according to claim 8 wherein:

$R^4$ is H, $NR^aR^b$, —$OC_2$-$C_6$ alkyl$NR^aR^b$, $C_1$-$C_6$ alkylN-$R^aR^b$, —$C(O)NR^aR^b$, or $NR^aC(O)NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$C(O)C_1$-$C_6$ alkyl, —$C(O)OC_1$-$C_6$ alkyl, $C_0$-$C_3$ alkyl$NR^cR^d$, $C_1$-$C_3$alkyl$C(O)NH_2$, $C_1$-$C_3$alkyl$C(O)NHC_1$-$C_3$alkyl, $C_1$-$C_6$ alkyl$C_3$-$C_6$ cycloalkyl, $SO_2C_1$-$C_3$alkyl, $SO_2C_3$-$C_6$cycloalkyl, —$C_1$-$C_3$ alkyl$SO_2NR^cR^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^eR^f$, —$SO_2R^e$, $SO_2NR^eR^f$ and $C_1$-$C_6$ alkyl-O—$C_1$-$C_6$ alkyl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH;

$R^6$ is H, $C_1$-$C_6$ alkyl, or $C_3$-$C_8$ cycloalkyl; or $R^6$ combines with Y, $R^9$, or $R^{10}$ to form an optionally substituted 4-8 membered nitrogen containing heterocyclic group.

10. The compound according to claim 8 wherein:

$R^4$ is H, $NR^aR^b$, $C_1$-$C_6$ alkyl$NR^aR^b$, —$C(O)NR^aR^b$, or $NR^aC(O)NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$C(O)C_1$-$C_6$ alkyl, —$C(O)OC_1$-$C_6$ alkyl, $C_0$-$C_3$ alkyl$NR^cR^d$, $C_1$-$C_3$alkyl$C(O)NH_2$, $C_1$-$C_3$alkyl$C(O)NHC_1$-$C_3$alkyl, $C_1$-$C_6$ alkyl$C_3$-$C_6$ cycloalkyl, $SO_2C_1$-$C_3$alkyl, $SO_2C_3$-$C_6$cycloalkyl, —$C_1$-$C_3$ alkyl$SO_2NR^cR^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^eR^f$, —$SO_2R^e$, $SO_2NR^eR^f$ and $C_1$-$C_6$ alkyl-O—$C_1$-$C_6$ alkyl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH; and $R^6$ is H.

11. The compound of claim 8 wherein:

$R^4$ is $NR^aR^b$, $C_1$-$C_6$ alkyl$NR^aR^b$, —$C(O)NR^aR^b$, or $NR^aC(O)NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —$C(O)C_1$-$C_6$ alkyl, —$C(O)OC_1$-$C_6$ alkyl, $C_0$-$C_3$ alkyl$NR^cR^d$, $C_1$-$C_3$alkyl$C(O)NH_2$, $C_1$-$C_3$alkyl$C(O)NHC_1$-$C_3$alkyl, $C_1$-$C_6$ alkyl$C_3$-$C_6$ cycloalkyl, $SO_2C_1$-$C_3$alkyl, $SO_2C_3$-$C_6$cycloalkyl, —$C_1$-$C_3$ alkyl$SO_2NR^cR^d$, aryl, heteroaryl, heterocyclic, or $C_1$-$C_6$ alkylheterocyclic; wherein the cycloalkyl, aryl, heteroaryl or heterocyclic group is optionally substituted with one to four groups independently selected from —OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a mono, bicyclic, bridged, or spirocyclic heterocyclic group optionally substituted with one to four groups independently selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —$C(O)NR^eR^f$, —$SO_2R^e$, $SO_2NR^eR^f$ and $C_1$-$C_6$ alkyl-O—$C_1$-$C_6$ alkyl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH; and $R^6$ is H.

12. A compound selected from the group consisting of:
N-(2-(diethylamino)ethyl)-2-(5-(thiophen-2-yl)pyrazolo[1,5-a]pyrimidin-3-yl)isonicotinamide,
N-(2-(diethylamino)propyl)-2-(5-(thiophen-2-yl)pyrazolo[1,5-a]pyrimidin-3-yl)isonicotinamide,
N-((hexahydro-1H-pyrrolizin-7a-yl)methyl)-2-(5-(thiophen-2-yl)pyrazolo[1,5-a]pyrimidin-3-yl)isonicotinamide,
(S)—N-(2-(diethylamino)propyl)-2-(5-(thiophen-2-yl)pyrazolo[1,5-a]pyrimidin-3-yl)isonicotinamide,
N-(((2S,4S)-4-fluoropyrrolidin-2-yl)methyl)-2-(5-(thiophen-2-yl)pyrazolo[1,5-a]pyrimidin-3-yl)isonicotinamide,
(S)—N-(azetidin-2-ylmethyl)-2-(5-(thiophen-2-yl)pyrazolo[1,5-a]pyrimidin-3-yl)isonicotinamide,
(R)—N-(azetidin-2-ylmethyl)-2-(5-(thiophen-2-yl)pyrazolo[1,5-a]pyrimidin-3-yl)isonicotinamide,
N-(2-(dimethylamino)ethyl)-2-(5-(thiophen-2-yl)pyrazolo[1,5-a]pyrimidin-3-yl)isonicotinamide,
(S)—N-((2-propylpyrrolidin-2-yl)methyl)-2-(5-(thiophen-2-yl)pyrazolo[1,5-a]pyrimidin-3-yl)isonicotinamide,
(S)—N-((2-ethylpyrrolidin-2-yl)methyl)-2-(5-(thiophen-2-yl)pyrazolo[1,5-a]pyrimidin-3-yl)isonicotinamide,
(S)—N-((2-methylpyrrolidin-2-yl)methyl)-2-(5-(thiophen-2-yl)pyrazolo[1,5-a]pyrimidin-3-yl)isonicotinamide,
N—((R)-1-((S)-pyrrolidin-2-yl)ethyl)-2-(5-(thiophen-2-yl)pyrazolo[1,5-a]pyrimidin-3-yl)isonicotinamide,
(S)—N-(2-((2,2-difluoroethyl)(ethyl)amino)propyl)-2-(5-(thiophen-2-yl)pyrazolo[1,5-a]pyrimidin-3-yl)isonicotinamide,
(S)—N-(2-((2,2-difluoroethyl)amino)propyl)-2-(5-(thiophen-2-yl)pyrazolo[1,5-a]pyrimidin-3-yl)isonicotinamide,
N-(azepan-2-ylmethyl)-2-(5-(thiophen-2-yl)pyrazolo[1,5-a]pyrimidin-3-yl)isonicotinamide,
(R)—N-((2-isobutylpyrrolidin-2-yl)methyl)-2-(5-(thiophen-2-yl)pyrazolo[1,5-a]pyrimidin-3-yl)isonicotinamide,
(R)—N-((2-(cyclopropylmethyl)pyrrolidin-2-yl)methyl)-2-(5-(thiophen-2-yl)pyrazolo[1,5-a]pyrimidin-3-yl)isonicotinamide,
N-(piperidin-2-ylmethyl)-2-(5-(thiophen-2-yl)pyrazolo[1,5-a]pyrimidin-3-yl)isonicotinamide,
(S)—N-(2-(ethylamino)propyl)-2-(5-(thiophen-2-yl)pyrazolo[1,5-a]pyrimidin-3-yl)isonicotinamide,
(S)—N-(2-((2-hydroxyethyl)amino)propyl)-2-(5-(thiophen-2-yl)pyrazolo[1,5-a]pyrimidin-3-yl)isonicotinamide,
(S)—N-(2-aminopropyl)-2-(5-(thiophen-2-yl)pyrazolo[1,5-a]pyrimidin-3-yl)isonicotinamide,
(S)—N-(2-(propylamino)propyl)-2-(5-(thiophen-2-yl)pyrazolo[1,5-a]pyrimidin-3-yl)isonicotinamide,
(S)—N-(2-((2-fluoroethyl)amino)propyl)-2-(5-(thiophen-2-yl)pyrazolo[1,5-a]pyrimidin-3-yl)isonicotinamide,
N-(2-aminobutyl)-2-(5-(thiophen-2-yl)pyrazolo[1,5-a]pyrimidin-3-yl)isonicotinamide,
(S)—N-(2-((cyclopropylmethyl)amino)propyl)-2-(5-(thiophen-2-yl)pyrazolo[1,5-a]pyrimidin-3-yl)isonicotinamide,
(S)—N-(2-((2,2-difluoroethyl)amino)propyl)-2-(5-(thiophen-2-yl)pyrazolo[1,5-a]pyrimidin-3-yl)isonicotinamide,
(S)-2-(5-(thiophen-2-yl)pyrazolo[1,5-a]pyrimidin-3-yl)-N-(2-((2,2,2-trifluoroethyl)amino)propyl)isonicotinamide,
(R)—N-(2-(ethylamino)butyl)-2-(5-(thiophen-2-yl)pyrazolo[1,5-a]pyrimidin-3-yl)isonicotinamide,
(S)—N-(2-(ethylamino)butyl)-2-(5-(thiophen-2-yl)pyrazolo[1,5-a]pyrimidin-3-yl)isonicotinamide,
N-(2-(isopropylamino)butyl)-2-(5-(thiophen-2-yl)pyrazolo[1,5-a]pyrimidin-3-yl)isonicotinamide,
(S)—N-(2-(isopropylamino)propyl)-2-(5-(thiophen-2-yl)pyrazolo[1,5-a]pyrimidin-3-yl)isonicotinamide,
(R)—N-(2-(ethylamino)propyl)-2-(5-(thiophen-2-yl)pyrazolo[1,5-a]pyrimidin-3-yl)isonicotinamide,
(S)—N-(pyrrolidin-2-ylmethyl)-2-(5-(thiophen-2-yl)pyrazolo[1,5-a]pyrimidin-3-yl)isonicotinamide,
(S)—N-((1-methylpyrrolidin-2-yl)methyl)-2-(5-(thiophen-2-yl)pyrazolo[1,5-a]pyrimidin-3-yl)isonicotinamide,
(S)—N-((1-ethylpyrrolidin-2-yl)methyl)-2-(5-(thiophen-2-yl)pyrazolo[1,5-a]pyrimidin-3-yl)isonicotinamide,
((5S)-3,6-diazabicyclo[3.2.2]nonan-3-yl)(2-(5-(thiophen-2-yl)pyrazolo[1,5-a]pyrimidin-3-yl)pyridin-4-yl)methanone,
((1S)-3,9-diazabicyclo[3.3.2]decan-3-yl)(2-(5-(thiophen-2-yl)pyrazolo[1,5-a]pyrimidin-3-yl)pyridin-4-yl)methanone,
(S)-(2-(aminomethyl)-4,4-difluoropyrrolidin-1-yl)(2-(5-(thiophen-2-yl)pyrazolo[1,5-a]pyrimidin-3-yl)pyridin-4-yl)methanone,
(R)-(2-(aminomethyl)pyrrolidin-1-yl)(2-(5-(thiophen-2-yl)pyrazolo[1,5-a]pyrimidin-3-yl)pyridin-4-yl)methanone,
((5S)-3,6-diazabicyclo[3.2.2]nonan-3-yl)(2-(5-(thiophen-2-yl)pyrazolo[1,5-a]pyrimidin-3-yl)pyridin-4-yl)methanone,
((1R)-3-oxa-7,9-diazabicyclo[3.3.2]decan-7-yl)(2-(5-(thiophen-2-yl)pyrazolo[1,5-a]pyrimidin-3-yl)pyridin-4-yl)methanone,
((1R,6S)-3,9-diazabicyclo[4.2.1]nonan-9-yl)(2-(5-(thiophen-2-yl)pyrazolo[1,5-a]pyrimidin-3-yl)pyridin-4-yl)methanone,
(S)-(3-aminopiperidin-1-yl)(2-(5-(thiophen-2-yl)pyrazolo[1,5-a]pyrimidin-3-yl)pyridin-4-yl)methanone,
(R)-(2-methylpiperazin-1-yl)(2-(5-(thiophen-2-yl)pyrazolo[1,5-a]pyrimidin-3-yl)pyridin-4-yl)methanone,
(S)-(3-aminopyrrolidin-1-yl)(2-(5-(thiophen-2-yl)pyrazolo[1,5-a]pyrimidin-3-yl)pyridin-4-yl)methanone,
((4aR,8R,8aS)-8-aminooctahydroquinolin-1(2H)-yl)(2-(5-(thiophen-2-yl)pyrazolo[1,5-a]pyrimidin-3-yl)pyridin-4-yl)methanone,
((4aR,8aR)-octahydro-1,7-naphthyridin-1(2H)-yl)(2-(5-(thiophen-2-yl)pyrazolo[1,5-a]pyrimidin-3-yl)pyridin-4-yl)methanone,
(S)-2-amino-N-(2-(diethylamino)propyl)-6-(5-(thiophen-2-yl)pyrazolo[1,5-a]pyrimidin-3-yl)isonicotinamide,
(S)-2-chloro-N-(2-(diethylamino)propyl)-6-(5-(thiophen-2-yl)pyrazolo[1,5-a]pyrimidin-3-yl)isonicotinamide,
(S)—N-(2-(diethylamino)propyl)-2-isopropyl-6-(5-(thiophen-2-yl)pyrazolo[1,5-a]pyrimidin-3-yl)isonicotinamide,
(S)—N-(2-(diethylamino)propyl)-2-ethyl-6-(5-(thiophen-2-yl)pyrazolo[1,5-a]pyrimidin-3-yl)isonicotinamide,
(R)-(2-(aminomethyl)piperidin-1-yl)(2-(dimethylamino)-6-(5-(thiophen-2-yl)pyrazolo[1,5-a]pyrimidin-3-yl)pyridin-4-yl)methanone,
(S)—N-(2-(diethylamino)propyl)-2-(5-(thiophen-2-yl)pyrazolo[1,5-a]pyrimidin-3-yl)-6-(trifluoromethyl)isonicotinamide, (S)—N-(2-(diethylamino)propyl)-2-(dimethylamino)-6-(5-(thiophen-2-yl)pyrazolo[1,5-a]pyrimidin-3-yl)isonicotinamide, (S)-(3-aminopyrrolidin-1-yl)(2-(dimethylamino)-6-(5-(thiophen-2-yl)pyrazolo[1,5-a]pyrimidin-3-yl)pyridin-4-yl)methanone, (S)-(3-aminopyrrolidin-1-yl)(2-methoxy-6-(5-(thiophen-2-yl)pyrazolo[1,5-a]pyrimidin-3-yl)pyridin-4-yl)methanone, (R)-(2-(aminomethyl)piperidin-1-yl)(2-chloro-6-(5-(thiophen-2-yl)pyrazolo[1,5-a]pyrimidin-3-yl)pyridin-4-yl)methanone, (S)—N-(2-(diethylamino)propyl)-2-methoxy-6-(5-(thiophen-2-yl)pyrazolo[1,5-a]pyrimidin-3-yl)isonicotinamide, (S)-(2-(aminomethyl)piperidin-1-yl)(2-chloro-6-(5-(thiophen-2-yl)pyrazolo[1,5-a]pyrimidin-3-yl)pyridin-4-yl)methanone, (2-amino-6-(5-(thiophen-2-yl)pyrazolo[1,5-a]pyrimidin-3-yl)pyridin-4-yl)((1S,6R)-3,9-diazabicyclo[4.2.1]nonan-9-yl)methanone, (S)—N-(2-(diethylamino)propyl)-2-(3-methoxyazetidin-1-yl)-6-(5-(thiophen-2-yl)pyrazolo[1,5-a]pyrimidin-3-yl)isonicotinamide, (S)-2-(3-cyanoazetidin-1-yl)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-(3-ethoxyazetidin-1-yl)-6-(5-(thiophen-2-yl)pyrazolo[1,5-a]pyrimidin-3-yl)isonicotinamide, (S)—N-(2-(diethylamino)propyl)-2-(3-(difluoromethoxy)azetidin-1-yl)-6-(5-(thiophen-2-yl)pyrazolo[1,5-a]pyrimidin-3-yl)isonicotinamide, (S)—N-(2-(diethylamino)propyl)-2-(3-hydroxyazetidin-1-yl)-6-(5-(thiophen-2-yl)pyrazolo[1,5-a]pyrimidin-3-yl)isonicotinamide, (S)-2-(azetidin-1-yl)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-(5-(thiophen-2-yl)pyrazolo[1,5-a]pyrimidin-3-yl)-6-(3-(trifluoromethyl)azetidin-1-yl)isonicotinamide, (S)—N-(2-(diethylamino)propyl)-2-(3,3-difluoroazetidin-1-yl)-6-(5-(thiophen-2-yl)pyrazolo[1,5-a]pyrimidin-3-yl)isonicotinamide, (S)—N-(2-(diethylamino)propyl)-2-(3-(methylsulfonyl)azetidin-1-yl)-6-(5-(thiophen-2-yl)pyrazolo[1,5-a]pyrimidin-3-yl)isonicotinamide, (S)—N-(2-(diethylamino)propyl)-2-(3-(N-methylsulfamoyl)azetidin-1-yl)-6-(5-(thiophen-2-yl)pyrazolo[1,5-a]pyrimidin-3-yl)isonicotinamide, (S)-2-(3-(N-cyclopropylsulfamoyl)azetidin-1-yl)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-(3,3-dimethylazetidin-1-yl)-6-(5-(thiophen-2-yl)pyrazolo[1,5-a]pyrimidin-3-yl)isonicotinamide, (S)—N-(2-(diethylamino)propyl)-2-(3-fluoroazetidin-1-yl)-6-(5-(thiophen-2-yl)pyrazolo[1,5-a]pyrimidin-3-yl)isonicotinamide, (S)-2-(3-(cyclopropanesulfonamido)azetidin-1-yl)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-(5,6-dihydroimidazo[1,2-a]pyrazin-7(8H)-yl)-6-(5-(thiophen-2-yl)pyrazolo[1,5-a]pyrimidin-3-yl)isonicotinamide, N—((S)-2-(diethylamino)propyl)-2-(3,3-difluoro-4-hydroxypiperidin-1-yl)-6-(5-(thiophen-2-yl)pyrazolo[1,5-a]pyrimidin-3-yl)isonicotinamide, (S)—N-(2-(diethylamino)propyl)-2-((2-(dimethylamino)ethyl)amino)-6-(5-(thiophen-2-yl)pyrazolo[1,5-a]pyrimidin-3-yl)isonicotinamide, (S)—N-(2-(diethylamino)propyl)-2-(4-hydroxypiperidin-1-yl)-6-(5-(thiophen-2-yl)pyrazolo[1,5-a]pyrimidin-3-yl)isonicotinamide, (S)—N-(2-(diethylamino)propyl)-2-(4-hydroxy-4-methylpiperidin-1-yl)-6-(5-(thiophen-2-yl)pyrazolo[1,5-a]pyrimidin-3-yl)isonicotinamide, (S)—N-(2-(diethylamino)propyl)-2-(((3-(pyrrolidin-1-yl)oxetan-3-yl)methyl)amino)-6-(5-(thiophen-2-yl)pyrazolo[1,5-a]pyrimidin-3-yl)isonicotinamide, (S)—N-(2-(diethylamino)propyl)-2-(1,1-dioxidoisothiazolidin-2-yl)-6-(5-(thiophen-2-yl)pyrazolo[1,5-a]pyrimidin-3-yl)isonicotinamide, (S)—N-(2-aminopropyl)-2-(3-hydroxyazetidin-1-yl)-6-(5-(thiophen-2-yl)pyrazolo[1,5-a]pyrimidin-3-yl)isonicotinamide, (S)—N-(2-(ethylamino)propyl)-2-(3-hydroxyazetidin-1-yl)-6-(5-(thiophen-2-yl)pyrazolo[1,5-a]pyrimidin-3-yl)isonicotinamide, N-((1-aminocyclobutyl)methyl)-2-(3-methoxyazetidin-1-yl)-6-(5-(thiophen-2-yl)pyrazolo[1,5-a]pyrimidin-3-yl)isonicotinamide, (S)—N-(2-aminopropyl)-2-(3-methoxyazetidin-1-yl)-6-(5-(thiophen-2-yl)pyrazolo[1,5-a]pyrimidin-3-yl)isonicotinamide, (S)—N-(2-(ethylamino)propyl)-2-(3-methoxyazetidin-1-yl)-6-(5-(thiophen-2-yl)pyrazolo[1,5-a]pyrimidin-3-yl)isonicotinamide, (S)—N-(2-(diethylamino)propyl)-2-(3-((isoxazol-3-ylmethyl)sulfonamido)azetidin-1-yl)-6-(5-(thiophen-2-yl)pyrazolo[1,5-a]pyrimidin-3-yl)isonicotinamide, (S)—N-(2-(diethylamino)propyl)-2-((N-methylmethyl)sulfonamido)-6-(5-(thiophen-2-yl)pyrazolo[1,5-a]pyrimidin-3-yl)isonicotinamide, (S)—N-(2-(diethylamino)propyl)-2-((1-methylethyl)sulfonamido)-6-(5-(thiophen-2-yl)pyrazolo[1,5-a]pyrimidin-3-yl)isonicotinamide, (S)—N-(2-(diethylamino)propyl)-2-(ethylsulfonamido)-6-(5-(thiophen-2-yl)pyrazolo[1,5-a]pyrimidin-3-yl)isonicotinamide, (S)-2-(cyclopropanesulfonamido)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-(methylsulfonamido)-6-(5-(thiophen-2-yl)pyrazolo[1,5-a]pyrimidin-3-yl)isonicotinamide, (S)—N-(2-(diethylamino)propyl)-2-(3-(ethylsulfonamido)azetidin-1-yl)-6-(5-(thiophen-2-yl)pyrazolo[1,5-a]pyrimidin-3-yl)isonicotinamide, (S)—N-(2-(diethylamino)propyl)-2-(3-((1-methylethyl)sulfonamido)azetidin-1-yl)-6-(5-(thiophen-2-yl)pyrazolo[1,5-a]pyrimidin-3-yl)isonicotinamide, (S)—N-(2-(diethylamino)propyl)-2-(2-oxoimidazolidin-1-yl)-6-(5-(thiophen-2-yl)pyrazolo[1,5-a]pyrimidin-3-yl)isonicotinamide, (S)—N-(2-(diethylamino)propyl)-2-(3-ethylureido)-6-(5-(thiophen-2-yl)pyrazolo[1,5-a]pyrimidin-3-yl)isonicotinamide, (S)-ethyl (4-((2-(diethylamino)propyl)carbamoyl)-6-(5-(thiophen-2-yl)pyrazolo[1,5-a]pyrimidin-3-yl)pyridin-2-yl)carbamate, (S)-isopropyl (4-((2-(diethylamino)propyl)carbamoyl)-6-(5-(thiophen-2-yl)pyrazolo[1,5-a]pyrimidin-3-yl)pyridin-2-yl)carbamate, (S)—N-(2-(diethylamino)propyl)-2-propionamido-6-(5-(thiophen-2-yl)pyrazolo[1,5-a]pyrimidin-3-yl)isonicotinamide, (S)—N-(2-(diethylamino)propyl)-2-isobutyramido-6-(5-(thiophen-2-yl)pyrazolo[1,5-a]pyrimidin-3-yl)isonicotinamide, (S)-2-(cyclopropanecarboxamido)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-(((3-methyloxetan-3-yl)methyl)amino)-6-(5-(thiophen-2-yl)pyrazolo[1,5-a]pyrimidin-3-yl)isonicotinamide, (S)—N-(2-(diethylamino)propyl)-2-((oxetan-3-ylmethyl)amino)-6-(5-(thiophen-2-yl)pyrazolo[1,5-a]pyrimidin-3-yl)isonicotinamide, (S)—N-(2-(diethylamino)propyl)-2-(oxetan-3-ylamino)-6-(5-(thiophen-2-yl)pyrazolo[1,5-a]pyrimidin-3-yl)isonicotinamide, (S)—N-(1-(4-((2-(diethylamino)propyl)carbamoyl)-6-(5-(thiophen-2-yl)pyrazolo[1,5-a]pyrimidin-3-yl)pyridin-2-yl)azetidin-3-yl)oxazole-2-carboxamide, (S)—N-(2-(diethylamino)propyl)-2-(3-(3,3-dimethylureido)azetidin-1-yl)-6-(5-(thiophen-2-yl)pyrazolo[1,5-a]pyrimidin-3-yl)isonicotinamide, (S)-2-(3-(cyclopropanecarboxamido)azetidin-1-yl)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-(3-(methylsulfonamido)azetidin-1-yl)-6-(5-(thiophen-2-yl)pyrazolo[1,5-a]pyrimidin-3-yl)isonicotinamide, (S)-2-(3-acetamidoazetidin-1-yl)-N-(2-(diethylamino)propyl)-6-(5-(thiophen-2-yl)pyrazolo[1,5-a]pyrimidin-3-yl)isonicotinamide, N—((S)-2-(diethylamino)propyl)-2-(((R)-1-hydroxypropan-2-yl)amino)-6-(5-(thiophen-2-yl)pyrazolo[1,5-a]pyrimidin-3-yl)isonicotinamide, N—((S)-2-(diethylamino)propyl)-2-(((S)-1-hydroxypropan-2-yl)amino)-6-(5-(thiophen-2-yl)pyrazolo[1,5-a]pyrimidin-3-yl)isonicotinamide, N—((S)-2-(diethylamino)propyl)-2-(((S)-2-hydroxypropyl)amino)-6-(5-(thiophen-2-yl)pyrazolo[1,5-a]pyrimidin-3-yl)isonicotinamide, N—((S)-2-(diethylamino)propyl)-2-(((R)-2-hydroxypropyl)amino)-6-(5-(thiophen-2-yl)pyrazolo[1,5-a]pyrimidin-3-yl)isonicotinamide, N—((S)-2-(diethylamino)propyl)-2-(((S)-tetrahydrofuran-3-yl)amino)-6-(5-(thiophen-2-yl)pyrazolo[1,5-a]pyrimidin-3-yl)isonicotinamide, (S)-2-(4-acetylpiperazin-1-yl)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-(3-(methylamino)azetidin-1-yl)-6-(5-(thiophen-2-yl)pyrazolo[1,5-a]pyrimidin-3-yl)isonicotinamide, (S)—N-(2-(diethylamino)propyl)-2-(3-(dimethylamino)azetidin-1-yl)-6-(5-(thiophen-2-yl)pyrazolo[1,5-a]pyrimidin-3-yl)isonicotinamide, (S)—N-(2-(diethylamino)propyl)-2-(piperazin-1-yl)-6-(5-(thiophen-2-yl)pyrazolo[1,5-a]pyrimidin-3-yl)isonicotinamide, (S)-2-(3-carbamoylazetidin-1-yl)-N-(2-(diethylamino)propyl)-6-(5-(thiophen-2-yl)pyrazolo[1,5-a]pyrimidin-3-yl)isonicotinamide, N—((S)-2-(diethylamino)propyl)-2-((S)-3-methoxypyrrolidin-1-yl)-6-(5-(thiophen-2-yl)pyrazolo[1,5-a]pyrimidin-3-yl)isonicotinamide, (S)—N-(2-(diethylamino)propyl)-2-(3-(4-fluorophenoxy)azetidin-1-yl)-6-(5-(thiophen-2-yl)pyrazolo[1,5-a]pyrimidin-3-yl)isonicotinamide, (S)—N-(2-(diethylamino)propyl)-2-morpholino-6-(5-(thiophen-2-yl)pyrazolo[1,5-a]pyrimidin-3-yl)isonicotinamide, (S)-2-(((1H-pyrazol-3-yl)methyl)amino)-N-(2-(diethylamino)propyl)-6-(5-(thiophen-2-yl)pyrazolo[1,5-a]pyrimidin-3-yl)isonicotinamide, (S)-2-(cyclopropylamino)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-(3-ethyl-3-hydroxyazetidin-1-yl)-6-(5-(thiophen-2-yl)pyrazolo[1,5-a]pyrimidin-3-yl)isonicotinamide, (S)—N-(2-(diethylamino)propyl)-2-(3-(2-hydroxypropan-2-yl)azetidin-1-yl)-6-(5-(thiophen-2-yl)pyrazolo[1,5-a]pyrimidin-3-yl)isonicotinamide, (S)—N-(2-(diethylamino)propyl)-2-(3-(hydroxymethyl)azetidin-1-yl)-6-(5-(thiophen-2-yl)pyrazolo[1,5-a]pyrimidin-3-yl)isonicotinamide, (S)-2-(3-cyclopropyl-3-hydroxyazetidin-1-yl)-N-(2-(diethylamino)propyl)-6-(5-(thiophen-2-yl)pyrazolo[1,5-a]pyrimidin-3-yl)isonicotinamide, (S)—N-(2-(diethylamino)propyl)-2-((3-methoxypropyl)amino)-6-(5-(thiophen-2-yl)pyrazolo[1,5-a]pyrimidin-3-yl)isonicotinamide, (S)—N-(2-(diethylamino)propyl)-2-(3-hydroxy-3-(trifluoromethyl)azetidin-1-yl)-6-(5-(thiophen-2-yl)pyrazolo[1,5-a]pyrimidin-3-yl)isonicotinamide, (S)—N-(2-(diethylamino)propyl)-2-((3-hydroxypropyl)amino)-6-(5-(thiophen-2-yl)pyrazolo[1,5-a]pyrimidin-3-yl)isonicotinamide, (S)—N-(2-(diethylamino)propyl)-2-((3-hydroxy-3-methylbutyl)amino)-6-(5-(thiophen-2-yl)pyrazolo[1,5-a]pyrimidin-3-yl)isonicotinamide, (S)—N-(2-(diethylamino)propyl)-2-((tetrahydro-2H-pyran-4-yl)amino)-6-(5-(thiophen-2-yl)pyrazolo[1,5-a]pyrimidin-3-yl)isonicotinamide, (S)—N-(2-(diethylamino)propyl)-2-((2-morpholinoethyl)amino)-6-(5-(thiophen-2-yl)pyrazolo[1,5-a]pyrimidin-3-yl)isonicotinamide, (S)—N-(2-(diethylamino)propyl)-2-((2-(3,3-difluoroazetidin-1-yl)ethyl)amino)-6-(5-(thiophen-2-yl)pyrazolo[1,5-a]pyrimidin-3-yl)isonicotinamide, (S)—N-(2-(diethylamino)propyl)-2-((2-methoxyethyl)amino)-6-(5-(thiophen-2-yl)pyrazolo[1,5-a]pyrimidin-3-yl)isonicotinamide, (S)—N-(2-(diethylamino)propyl)-2-(3-hydroxy-3-methylazetidin-1-yl)-6-(5-(thiophen-2-yl)pyrazolo[1,5-a]pyrimidin-3-yl)isonicotinamide, (S)—N-(2-(diethylamino)propyl)-2-(3-methoxy-3-methylazetidin-1-yl)-6-(5-(thiophen-2-yl)pyrazolo[1,5-a]pyrimidin-3-yl)isonicotinamide, (S)—N-(2-(diethylamino)propyl)-2-(methylamino)-6-(5-(thiophen-2-yl)pyrazolo[1,5-a]pyrimidin-3-yl)isonicotinamide, (S)—N-(2-(diethylamino)propyl)-2-((2-hydroxyethyl)amino)-6-(5-(thiophen-2-yl)pyrazolo[1,5-a]pyrimidin-3-yl)isonicotinamide, (S)—N-(2-(diethylamino)propyl)-2-(3,3,4,4-tetrafluoropyrrolidin-1-yl)-6-(5-(thiophen-2-yl)pyrazolo[1,5-a]pyrimidin-3-yl)isonicotinamide,

- (S)-2-((1H-pyrazol-4-yl)amino)-N-(2-(diethylamino)propyl)-6-(5-(thiophen-2-yl)pyrazolo[1,5-a]pyrimidin-3-yl)isonicotinamide,
- (S)—N-(2-(diethylamino)propyl)-2-(3,3-difluoropyrrolidin-1-yl)-6-(5-(thiophen-2-yl)pyrazolo[1,5-a]pyrimidin-3-yl)isonicotinamide,
- (S)—N-(2-(diethylamino)propyl)-2-(2-oxa-6-azaspiro[3.4]octan-6-yl)-6-(5-(thiophen-2-yl)pyrazolo[1,5-a]pyrimidin-3-yl)isonicotinamide,
- (S)—N-(2-(diethylamino)propyl)-2-(6-oxa-1-azaspiro[3.3]heptan-1-yl)-6-(5-(thiophen-2-yl)pyrazolo[1,5-a]pyrimidin-3-yl)isonicotinamide,
- 2-(((R)-1-amino-1-oxopropan-2-yl)amino)-N—((S)-2-(diethylamino)propyl)-6-(5-(thiophen-2-yl)pyrazolo[1,5-a]pyrimidin-3-yl)isonicotinamide,
- 2-(((S)-1-amino-1-oxopropan-2-yl)amino)-N—((S)-2-(diethylamino)propyl)-6-(5-(thiophen-2-yl)pyrazolo[1,5-a]pyrimidin-3-yl)isonicotinamide,
- (S)-2-(((1H-imidazol-2-yl)methyl)amino)-N-(2-(diethylamino)propyl)-6-(5-(thiophen-2-yl)pyrazolo[1,5-a]pyrimidin-3-yl)isonicotinamide,
- (S)-2-((2-amino-2-oxoethyl)amino)-N-(2-(diethylamino)propyl)-6-(5-(thiophen-2-yl)pyrazolo[1,5-a]pyrimidin-3-yl)isonicotinamide,
- N—((S)-2-(diethylamino)propyl)-2-(((R)-1-(methylamino)-1-oxopropan-2-yl)amino)-6-(5-(thiophen-2-yl)pyrazolo[1,5-a]pyrimidin-3-yl)isonicotinamide,
- N—((S)-2-(diethylamino)propyl)-2-(((S)-1-(methylamino)-1-oxopropan-2-yl)amino)-6-(5-(thiophen-2-yl)pyrazolo[1,5-a]pyrimidin-3-yl)isonicotinamide,
- (S)-2-((1H-imidazol-2-yl)amino)-N-(2-(diethylamino)propyl)-6-(5-(thiophen-2-yl)pyrazolo[1,5-a]pyrimidin-3-yl)isonicotinamide,
- (S)—N-(2-(diethylamino)propyl)-2-((2-sulfamoylethyl)amino)-6-(5-(thiophen-2-yl)pyrazolo[1,5-a]pyrimidin-3-yl)isonicotinamide,
- N—((S)-2-(diethylamino)propyl)-2-((3S,4S)-3,4-dihydroxypyrrolidin-1-yl)-6-(5-(thiophen-2-yl)pyrazolo[1,5-a]pyrimidin-3-yl)isonicotinamide,
- (S)-2-(3,3-bis(hydroxymethyl)azetidin-1-yl)-N-(2-(diethylamino)propyl)-6-(5-(thiophen-2-yl)pyrazolo[1,5-a]pyrimidin-3-yl)isonicotinamide,
- (S)—N-(2-(ethylamino)propyl)-2-(3-hydroxy-3-methylazetidin-1-yl)-6-(5-(thiophen-2-yl)pyrazolo[1,5-a]pyrimidin-3-yl)isonicotinamide,
- (S)—N-(2-(diethylamino)propyl)-2-((2-(methylamino)-2-oxoethyl)amino)-6-(5-(thiophen-2-yl)pyrazolo[1,5-a]pyrimidin-3-yl)isonicotinamide,
- (S)—N-(2-(diethylamino)propyl)-2-(4-methoxypiperidin-1-yl)-6-(5-(thiophen-2-yl)pyrazolo[1,5-a]pyrimidin-3-yl)isonicotinamide,
- (S)—N-(2-(diethylamino)propyl)-2-(3-(dimethylamino)-3-methylazetidin-1-yl)-6-(5-(thiophen-2-yl)pyrazolo[1,5-a]pyrimidin-3-yl)isonicotinamide,
- (S)—N-(2-(diethylamino)propyl)-2-(5,5-difluoro-2-azaspiro[3.3]heptan-2-yl)-6-(5-(thiophen-2-yl)pyrazolo[1,5-a]pyrimidin-3-yl)isonicotinamide,
- (S)—N-(2-(diethylamino)propyl)-2-(1-azaspiro[3.3]heptan-1-yl)-6-(5-(thiophen-2-yl)pyrazolo[1,5-a]pyrimidin-3-yl)isonicotinamide,
- N—((S)-2-(diethylamino)propyl)-2-(5-(thiophen-2-yl)pyrazolo[1,5-a]pyrimidin-3-yl)-6-((R)-2-(trifluoromethyl)pyrrolidin-1-yl)isonicotinamide,
- (S)—N-(2-(diethylamino)propyl)-2-(5-(thiophen-2-yl)pyrazolo[1,5-a]pyrimidin-3-yl)-6-(1H-1,2,4-triazol-1-yl)isonicotinamide,
- 2-((1S,4S)-2-oxa-5-azabicyclo[2.2.1]heptan-5-yl)-N—((S)-2-(diethylamino)propyl)-6-(5-(thiophen-2-yl)pyrazolo[1,5-a]pyrimidin-3-yl)isonicotinamide,
- N-(2-(diethylamino)ethyl)-2-(3-methoxyazetidin-1-yl)-6-(5-(thiophen-2-yl)pyrazolo[1,5-a]pyrimidin-3-yl)isonicotinamide,
- (S)-2-(3-methoxyazetidin-1-yl)-N-(pyrrolidin-2-ylmethyl)-6-(5-(thiophen-2-yl)pyrazolo[1,5-a]pyrimidin-3-yl)isonicotinamide,
- (S)—N-((1-ethylpyrrolidin-2-yl)methyl)-2-(3-methoxyazetidin-1-yl)-6-(5-(thiophen-2-yl)pyrazolo[1,5-a]pyrimidin-3-yl)isonicotinamide,
- (S)-2-(3-methoxyazetidin-1-yl)-N-((1-methylpyrrolidin-2-yl)methyl)-6-(5-(thiophen-2-yl)pyrazolo[1,5-a]pyrimidin-3-yl)isonicotinamide,
- N-(2-(diethylamino)ethyl)-2-(3-hydroxy-3-methylazetidin-1-yl)-6-(5-(thiophen-2-yl)pyrazolo[1,5-a]pyrimidin-3-yl)isonicotinamide,
- N-(2-(diethylamino)ethyl)-2-((2-hydroxyethyl)amino)-6-(5-(thiophen-2-yl)pyrazolo[1,5-a]pyrimidin-3-yl)isonicotinamide,
- (S)-2-(diethylamino)-N-(2-(diethylamino)propyl)-6-(5-(thiophen-2-yl)pyrazolo[1,5-a]pyrimidin-3-yl)isonicotinamide,
- (S)—N-(2-(diethylamino)propyl)-2-(ethylamino)-6-(5-(thiophen-2-yl)pyrazolo[1,5-a]pyrimidin-3-yl)isonicotinamide,
- (S)-2-(4-carbamoylpiperidin-1-yl)-N-(2-(diethylamino)propyl)-6-(5-(thiophen-2-yl)pyrazolo[1,5-a]pyrimidin-3-yl)isonicotinamide,
- N—((S)-2-(diethylamino)propyl)-2-((S)-2-(hydroxymethyl)morpholino)-6-(5-(thiophen-2-yl)pyrazolo[1,5-a]pyrimidin-3-yl)isonicotinamide,
- N—((S)-2-(diethylamino)propyl)-2-((S)-2-(methoxymethyl)azetidin-1-yl)-6-(5-(thiophen-2-yl)pyrazolo[1,5-a]pyrimidin-3-yl)isonicotinamide,
- N—((S)-2-(diethylamino)propyl)-2-((R)-2-(methoxymethyl)azetidin-1-yl)-6-(5-(thiophen-2-yl)pyrazolo[1,5-a]pyrimidin-3-yl)isonicotinamide,
- N—((S)-2-(diethylamino)propyl)-2-((R)-2-(hydroxymethyl)azetidin-1-yl)-6-(5-(thiophen-2-yl)pyrazolo[1,5-a]pyrimidin-3-yl)isonicotinamide,
- N—((S)-2-(diethylamino)propyl)-2-((S)-2-(hydroxymethyl)azetidin-1-yl)-6-(5-(thiophen-2-yl)pyrazolo[1,5-a]pyrimidin-3-yl)isonicotinamide,
- 2-((R)-2-carbamoylpyrrolidin-1-yl)-N—((S)-2-(diethylamino)propyl)-6-(5-(thiophen-2-yl)pyrazolo[1,5-a]pyrimidin-3-yl)isonicotinamide,
- 2-((S)-2-carbamoylpyrrolidin-1-yl)-N—((S)-2-(diethylamino)propyl)-6-(5-(thiophen-2-yl)pyrazolo[1,5-a]pyrimidin-3-yl)isonicotinamide,
- N—((S)-2-(diethylamino)propyl)-2-((S)-2-(hydroxymethyl)pyrrolidin-1-yl)-6-(5-(thiophen-2-yl)pyrazolo[1,5-a]pyrimidin-3-yl)isonicotinamide,
- N—((S)-2-(diethylamino)propyl)-2-((R)-2-(hydroxymethyl)pyrrolidin-1-yl)-6-(5-(thiophen-2-yl)pyrazolo[1,5-a]pyrimidin-3-yl)isonicotinamide,
- N—((S)-2-(diethylamino)propyl)-2-((R)-2-(methoxymethyl)pyrrolidin-1-yl)-6-(5-(thiophen-2-yl)pyrazolo[1,5-a]pyrimidin-3-yl)isonicotinamide,
- N—((S)-2-(diethylamino)propyl)-2-((S)-2-(methoxymethyl)pyrrolidin-1-yl)-6-(5-(thiophen-2-yl)pyrazolo[1,5-a]pyrimidin-3-yl)isonicotinamide,
- N—((S)-2-(diethylamino)propyl)-2-((S)-2-(methylcarbamoyl)azetidin-1-yl)-6-(5-(thiophen-2-yl)pyrazolo[1,5-a]pyrimidin-3-yl)isonicotinamide, N—((S)-2-(diethylamino)propyl)-2-((S)-2-(ethylcarbamoyl)azetidin-1-yl)-6-(5-(thiophen-2-yl)pyrazolo[1,5-a]pyrimidin-3-yl)isonicotinamide,
2-((S)-2-(cyclopropylcarbamoyl)azetidin-1-yl)-N—((S)-2-(diethylamino)propyl)-6-(5-(thiophen-2-yl)pyrazolo[1,5-a]pyrimidin-3-yl)isonicotinamide,
2-((S)-2-((cyclopropylmethyl)carbamoyl)azetidin-1-yl)-N—((S)-2-(diethylamino)propyl)-6-(5-(thiophen-2-yl)pyrazolo[1,5-a]pyrimidin-3-yl)isonicotinamide,
N—((S)-2-(diethylamino)propyl)-2-((S)-2-(dimethylcarbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(diethylcarbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-((2-fluoroethyl)carbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-((2,2-difluoroethyl)carbamoyl)azetidin-1-yl)-6-(5-(thiophen-2-yl)pyrazolo[1,5-a]pyrimidin-3-yl)isonicotinamide,
N—((S)-2-(diethylamino)propyl)-2-(5-(thiophen-2-yl)pyrazolo[1,5-a]pyrimidin-3-yl)-6-((S)-2-((2,2,2-trifluoroethyl)carbamoyl)azetidin-1-yl)isonicotinamide,
N—((S)-2-(diethylamino)propyl)-2-((S)-2-(3-fluoroazetidine-1-carbonyl)azetidin-1-yl)-6-(5-(thiophen-2-yl)pyrazolo[1,5-a]pyrimidin-3-yl)isonicotinamide,
2-((2S)-2-(3-azabicyclo[3.1.0]hexane-3-carbonyl)azetidin-1-yl)-N—((S)-2-(diethylamino)propyl)-6-(5-(thiophen-2-yl)pyrazolo[1,5-a]pyrimidin-3-yl)isonicotinamide,
N—((S)-2-(diethylamino)propyl)-2-((S)-2-(3-(methylsulfonamido)azetidine-1-carbonyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(methoxy(methyl)carbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(pyrrolidine-1-carbonyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(methoxycarbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((R)-2-(methylcarbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(thiazol-2-ylcarbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(3,3-dimethylazetidine-1-carbonyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(morpholine-4-carbonyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(3,3-difluoroazetidine-1-carbonyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(3-methoxyazetidine-1-carbonyl)azetidin-1-yl)-6-(5-(thiophen-2-yl)pyrazolo[1,5-a]pyrimidin-3-yl)isonicotinamide,
(S)-1-(4-(((S)-2-(diethylamino)propyl)carbamoyl)-6-(5-(thiophen-2-yl)pyrazolo[1,5-a]pyrimidin-3-yl)pyridin-2-yl)azetidine-2-carboxylic acid,
N—((S)-2-(diethylamino)propyl)-2-((S)-2-((2-hydroxyethyl)carbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(hydroxy(methyl)carbamoyl)azetidin-1-yl)-6-(5-(thiophen-2-yl)pyrazolo[1,5-a]pyrimidin-3-yl)isonicotinamide,
2-((S)-2-carbamoylazetidin-1-yl)-N—((S)-2-(diethylamino)propyl)-6-(5-(thiophen-2-yl)pyrazolo[1,5-a]pyrimidin-3-yl)isonicotinamide,
2-((S)-2-((cyanomethyl)carbamoyl)azetidin-1-yl)-N—((S)-2-(diethylamino)propyl)-6-(5-(thiophen-2-yl)pyrazolo[1,5-a]pyrimidin-3-yl)isonicotinamide,
N—((S)-2-(diethylamino)propyl)-2-((S)-2-((2-methoxyethyl)carbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(3-(methylsulfonyl)azetidine-1-carbonyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(1,1-dioxidothiomorpholine-4-carbonyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(3-hydroxyazetidine-1-carbonyl)azetidin-1-yl)-6-(5-(thiophen-2-yl)pyrazolo[1,5-a]pyrimidin-3-yl)isonicotinamide,
N—((S)-2-aminopropyl)-2-((S)-2-(methylcarbamoyl)azetidin-1-yl)-6-(5-(thiophen-2-yl)pyrazolo[1,5-a]pyrimidin-3-yl)isonicotinamide,
N—((S)-2-(ethylamino)propyl)-2-((S)-2-(methylcarbamoyl)azetidin-1-yl)-6-(5-(thiophen-2-yl)pyrazolo[1,5-a]pyrimidin-3-yl)isonicotinamide,
N—((S)-2-(diethylamino)propyl)-2-((S)-2-(3-methyl-1,2,4-oxadiazol-5-yl)azetidin-1-yl)-6-(5-(thiophen-2-yl)pyrazolo[1,5-a]pyrimidin-3-yl)isonicotinamide,
N—((S)-2-(diethylamino)propyl)-2-((S)-3-(methylcarbamoyl)pyrrolidin-1-yl)-6-(5-(thiophen-2-yl)pyrazolo[1,5-a]pyrimidin-3-yl)isonicotinamide,
N—((S)-2-(diethylamino)propyl)-2-((R)-3-(methylcarbamoyl)pyrrolidin-1-yl)-6-(5-(thiophen-2-yl)pyrazolo[1,5-a]pyrimidin-3-yl)isonicotinamide,
2-((R)-3-cyanopyrrolidin-1-yl)-N—((S)-2-(diethylamino)propyl)-6-(5-(thiophen-2-yl)pyrazolo[1,5-a]pyrimidin-3-yl)isonicotinamide,
2-((S)-3-cyanopyrrolidin-1-yl)-N—((S)-2-(diethylamino)propyl)-6-(5-(thiophen-2-yl)pyrazolo[1,5-a]pyrimidin-3-yl)isonicotinamide,
(S)—N-(2-(diethylamino)propyl)-2-(3-oxopiperazin-1-yl)-6-(5-(thiophen-2-yl)pyrazolo[1,5-a]pyrimidin-3-yl)isonicotinamide,
N—((S)-2-(diethylamino)propyl)-2-((S)-3-hydroxypyrrolidin-1-yl)-6-(5-(thiophen-2-yl)pyrazolo[1,5-a]pyrimidin-3-yl)isonicotinamide,
N—((S)-2-(diethylamino)propyl)-2-((R)-3-hydroxypyrrolidin-1-yl)-6-(5-(thiophen-2-yl)pyrazolo[1,5-a]pyrimidin-3-yl)isonicotinamide,
2-((S)-3-aminopyrrolidin-1-yl)-N—((S)-2-(diethylamino)propyl)-6-(5-(thiophen-2-yl)pyrazolo[1,5-a]pyrimidin-3-yl)isonicotinamide,
2-((R)-3-aminopyrrolidin-1-yl)-N—((S)-2-(diethylamino)propyl)-6-(5-(thiophen-2-yl)pyrazolo[1,5-a]pyrimidin-3-yl)isonicotinamide,
N—((S)-2-(diethylamino)propyl)-2-((S)-2-(methylcarbamoyl)pyrrolidin-1-yl)-6-(5-(thiophen-2-yl)pyrazolo[1,5-a]pyrimidin-3-yl)isonicotinamide, N—((S)-2-(diethylamino)propyl)-2-((R)-2-(methylcarbamoyl)pyrrolidin-1-yl)-6-(5-(thiophen-2-yl)pyrazolo[1,5-a]pyrimidin-3-yl)isonicotinamide,
(2-((2-(1H-imidazol-1-yl)ethyl)(methyl)amino)-6-(5-(thiophen-2-yl)pyrazolo[1,5-a]pyrimidin-3-yl)pyridin-4-yl)((1S,5S)-3,6-diazabicyclo[3.2.2]nonan-3-yl)methanone,
((1S,5S)-3,6-diazabicyclo[3.2.2]nonan-3-yl)(2-((2-hydroxy-2-methylpropyl)amino)-6-(5-(thiophen-2-yl)pyrazolo[1,5-a]pyrimidin-3-yl)pyridin-4-yl)methanone,
((1S,5S)-3,6-diazabicyclo[3.2.2]nonan-3-yl)(2-((2-methoxyethyl)amino)-6-(5-(thiophen-2-yl)pyrazolo[1,5-a]pyrimidin-3-yl)pyridin-4-yl)methanone,
((1S,5S)-3,6-diazabicyclo[3.2.2]nonan-3-yl)(2-(4-(oxetan-3-yl)piperazin-1-yl)-6-(5-(thiophen-2-yl)pyrazolo[1,5-a]pyrimidin-3-yl)pyridin-4-yl)methanone,
((1S,5S)-3,6-diazabicyclo[3.2.2]nonan-3-yl)(2-(3-methoxyazetidin-1-yl)-6-(5-(thiophen-2-yl)pyrazolo[1,5-a]pyrimidin-3-yl)pyridin-4-yl)methanone,
((1S,6R)-3,9-diazabicyclo[4.2.1]nonan-9-yl)(2-(3-methoxyazetidin-1-yl)-6-(5-(thiophen-2-yl)pyrazolo[1,5-a]pyrimidin-3-yl)pyridin-4-yl)methanone,
(S)-(3-aminopyrrolidin-1-yl)(2-(3-methoxyazetidin-1-yl)-6-(5-(thiophen-2-yl)pyrazolo[1,5-a]pyrimidin-3-yl)pyridin-4-yl)methanone,
(S)—N-(2-(diethylamino)propyl)-2-(1-methyl-1H-pyrazol-4-yl)-6-(5-(thiophen-2-yl)pyrazolo[1,5-a]pyrimidin-3-yl)isonicotinamide,
(S)—N-(2-(diethylamino)propyl)-2-(3,5-dimethyl-1H-pyrazol-4-yl)-6-(5-(thiophen-2-yl)pyrazolo[1,5-a]pyrimidin-3-yl)isonicotinamide,
(S)—N-(2-(diethylamino)propyl)-2-(3-methyl-1H-pyrazol-4-yl)-6-(5-(thiophen-2-yl)pyrazolo[1,5-a]pyrimidin-3-yl)isonicotinamide,
(S)—N-(2-(diethylamino)propyl)-2-(5-(thiophen-2-yl)pyrazolo[1,5-a]pyrimidin-3-yl)-6-(3-(trifluoromethyl)-1H-pyrazol-4-yl)isonicotinamide,
(S)—N-(2-(diethylamino)propyl)-2-(isoxazol-4-yl)-6-(5-(thiophen-2-yl)pyrazolo[1,5-a]pyrimidin-3-yl)isonicotinamide,
(S)—N-(2-(diethylamino)propyl)-2-(1H-pyrazol-3-yl)-6-(5-(thiophen-2-yl)pyrazolo[1,5-a]pyrimidin-3-yl)isonicotinamide,
(S)—N-(2-(diethylamino)propyl)-2,6-bis(5-(thiophen-2-yl)pyrazolo[1,5-a]pyrimidin-3-yl)isonicotinamide,
(S)—N-(2-(diethylamino)propyl)-2-(thiazol-2-yl)-6-(5-(thiophen-2-yl)pyrazolo[1,5-a]pyrimidin-3-yl)isonicotinamide,
(S)—N-(2-(diethylamino)propyl)-2-(oxazol-2-yl)-6-(5-(thiophen-2-yl)pyrazolo[1,5-a]pyrimidin-3-yl)isonicotinamide,
(S)—N-(2-(diethylamino)propyl)-2-(1H-pyrazol-4-yl)-6-(5-(thiophen-2-yl)pyrazolo[1,5-a]pyrimidin-3-yl)isonicotinamide,
(S)-2-(1-(2-cyanoethyl)-1H-pyrazol-4-yl)-N-(2-(diethylamino)propyl)-6-(5-(thiophen-2-yl)pyrazolo[1,5-a]pyrimidin-3-yl)isonicotinamide,
(S)—N-(2-(diethylamino)propyl)-2-(1-(oxetan-3-yl)-1H-pyrazol-4-yl)-6-(5-(thiophen-2-yl)pyrazolo[1,5-a]pyrimidin-3-yl)isonicotinamide,
N—((S)-2-(diethylamino)propyl)-2-(((R)-tetrahydrofuran-2-yl)methoxy)-6-(5-(thiophen-2-yl)pyrazolo[1,5-a]pyrimidin-3-yl)isonicotinamide,
N—((S)-2-(diethylamino)propyl)-2-((S)-2-methoxypropoxy)-6-(5-(thiophen-2-yl)pyrazolo[1,5-a]pyrimidin-3-yl)isonicotinamide,
N—((S)-2-(diethylamino)propyl)-2-(((S)-tetrahydrofuran-3-yl)oxy)-6-(5-(thiophen-2-yl)pyrazolo[1,5-a]pyrimidin-3-yl)isonicotinamide,
N—((S)-2-(diethylamino)propyl)-2-(((R)-tetrahydrofuran-3-yl)oxy)-6-(5-(thiophen-2-yl)pyrazolo[1,5-a]pyrimidin-3-yl)isonicotinamide,
(S)—N-(2-(diethylamino)propyl)-2-(2-(dimethylamino)ethoxy)-6-(5-(thiophen-2-yl)pyrazolo[1,5-a]pyrimidin-3-yl)isonicotinamide,
(S)—N-(2-(diethylamino)propyl)-2-(2-methoxyethoxy)-6-(5-(thiophen-2-yl)pyrazolo[1,5-a]pyrimidin-3-yl)isonicotinamide,
(S)—N-(2-(diethylamino)propyl)-2-((3-methyloxetan-3-yl)methoxy)-6-(5-(thiophen-2-yl)pyrazolo[1,5-a]pyrimidin-3-yl)isonicotinamide,
(S)—N-(2-(diethylamino)propyl)-2-(2-(pyrazin-2-yl)ethoxy)-6-(5-(thiophen-2-yl)pyrazolo[1,5-a]pyrimidin-3-yl)isonicotinamide,
(S)—N-(2-(diethylamino)propyl)-2-(3-methoxypropoxy)-6-(5-(thiophen-2-yl)pyrazolo[1,5-a]pyrimidin-3-yl)isonicotinamide,
(S)—N-(2-(diethylamino)propyl)-2-(2-morpholinoethoxy)-6-(5-(thiophen-2-yl)pyrazolo[1,5-a]pyrimidin-3-yl)isonicotinamide,
(S)—N-(2-(diethylamino)propyl)-2-(2-hydroxy-2-methylpropoxy)-6-(5-(thiophen-2-yl)pyrazolo[1,5-a]pyrimidin-3-yl)isonicotinamide,
(S)—N-(2-(diethylamino)propyl)-2-(pyridin-3-ylmethoxy)-6-(5-(thiophen-2-yl)pyrazolo[1,5-a]pyrimidin-3-yl)isonicotinamide,
(S)-3-(((4-((2-(diethylamino)propyl)carbamoyl)-6-(5-(thiophen-2-yl)pyrazolo[1,5-a]pyrimidin-3-yl)pyridin-2-yl)oxy)methyl)pyridine 1-oxide,
N-(2-(diethylamino)butyl)-2-((S)-2-(methylcarbamoyl)azetidin-1-yl)-6-(5-(thiophen-2-yl)pyrazolo[1,5-a]pyrimidin-3-yl)isonicotinamide,
N—((S)-2-(diethylamino)butyl)-2-((S)-2-(methylcarbamoyl)azetidin-1-yl)-6-(5-(thiophen-2-yl)pyrazolo[1,5-a]pyrimidin-3-yl)isonicotinamide,
N—((R)-2-(diethylamino)butyl)-2-((S)-2-(methylcarbamoyl)azetidin-1-yl)-6-(5-(thiophen-2-yl)pyrazolo[1,5-a]pyrimidin-3-yl)isonicotinamide,
N—((S)-2-(ethyl(propyl)amino)propyl)-2-((S)-2-(methylcarbamoyl)azetidin-1-yl)-6-(5-(thiophen-2-yl)pyrazolo[1,5-a]pyrimidin-3-yl)isonicotinamide,
N—((R)-2-(diethylamino)-3-hydroxypropyl)-2-((S)-2-(methylcarbamoyl)azetidin-1-yl)-6-(5-(thiophen-2-yl)pyrazolo[1,5-a]pyrimidin-3-yl)isonicotinamide,
N—((S)-2-(ethyl(2-hydroxyethyl)amino)propyl)-2-((S)-2-(methylcarbamoyl)azetidin-1-yl)-6-(5-(thiophen-2-yl)pyrazolo[1,5-a]pyrimidin-3-yl)isonicotinamide, and
(S)—N-(2-(diethylamino)ethyl)-2-(2-(methylcarbamoyl)azetidin-1-yl)-6-(5-(thiophen-2-yl)pyrazolo[1,5-a]pyrimidin-3-yl)isonicotinamide or a pharmaceutically acceptable salt, stereoisomer or mixture of stereoisomer thereof.

13. A compound of formula (VI):

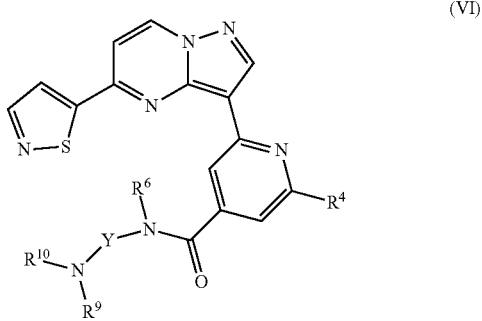

(VI)

wherein $R^4$ is H, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkyl$C_3$-$C_6$ cycloalkyl, —$NR^aR^b$, $C_1$-$C_6$ alkyl$NR^aR^b$, $C_1$-$C_6$alkyl-O—$C_1$-$C_6$ alkylN$R^aR^b$, —O$C_2$-$C_6$ alkyl$NR^aR^b$, —C(O)$NR^aR^b$, —$NR^aC(O)NR^aR^b$, —$NR^aC(O)R^a$, —$NR^aC(O)OR^a$, aryl, heteroaryl, mono, bicyclic, bridged or spirocyclic carbocyclic or heterocyclic group, —O—$C_0$-$C_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —O$C_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkyl$NR^aCHR^aC(O)NHR^a$, —C(O)$R^a$, —COO$R^a$, —NHC(O)NH$R^a$, —NHC(O) $R^a$, —NHC(O)O$R^a$, C(O)$NR^aR^b$, —$NR^aR^b$, —NH$C_1$-$C_3$alkyl$NR^aR^b$, SO$_2R^a$, —NHSO$_2R^a$, SO$_2NR^aR^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group combines to form a mono, bicyclic, bridged or spirocyclic carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, $C_1$-$C_6$ alkyl, $C_3$-$C_8$ cycloalkyl, $C_1$-$C_6$ haloalkyl, $C_1$-$C_6$ alkylOH, —O$C_1$-$C_6$ alkyl, —O$C_1$-$C_6$ haloalkyl, $C_1$-$C_6$ alkyl $C_3$-$C_6$ cycloalkyl, $C_1$-$C_6$ alkyl-O—$C_1$-$C_6$ alkyl, $C_0$-$C_3$ alkyl$NR^aCHR^aC(O)NHR^a$, C(O)$NR^aR^b$, —SO$_2R^a$, and SO$_2NR^aR^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)$C_1$-$C_6$ alkyl, —C(O)O$C_1$-$C_6$ alkyl, $C_0$-$C_3$ alkyl$NR^cR^d$, $C_1$-$C_3$alkylC(O)NH$_2$, $C_1$-$C_3$alkylC(O)NH$C_1$-$C_3$alkyl, $C_1$-$C_6$ alkyl$C_3$-$C_6$ cycloalkyl, SO$_2C_1$-$C_3$alkyl, SO$_2C_3$-$C_6$cycloalkyl, aryl, heterocyclic, or $C_1$-$C_6$ alkylheterocyclic; wherein the cycloalkyl, aryl or heterocyclic group is optionally substituted with one to four groups independently selected from —OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a monocyclic, bicyclic, bridged or spirocyclic heterocyclic group optionally substituted with a group selected from OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^cR^d$, —SO$_2R^c$, SO$_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, SO$_2C_1$-$C_6$ alkyl, and $C_1$-$C_6$ alkyl-O—$C_1$-$C_6$ alkyl; or $R^c$ and $R^d$ combine to form mono or bicyclic, bridged or spirocyclic heterocycle optionally substituted with a group selected from OH, oxo, halo, cyano, NH$_2$, NH$C_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^eR^f$, —SO$_2R^e$, SO$_2NR^eR^f$ and $C_1$-$C_6$ alkyl-O—$C_1$-$C_6$ alkyl; wherein $R^e$ and $R^f$ are independently selected from $C_1$-$C_6$ alkyl, $C_1$-$C_6$ alkylOH, and $C_1$-$C_6$ alkyl aryl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —O$C_1$-$C_6$ haloalkyl, and $C_1$-$C_6$ alkylOH;

$R^6$ is H, $C_1$-$C_6$ alkyl, $C_3$-$C_8$ cycloalkyl, $C_1$-$C_6$ haloalkyl, $C_1$-$C_6$ alkyl-OH, or $C_1$-$C_6$ alkoxy; or $R^6$ combines with Y to form a 4-8 membered nitrogen containing heterocyclic group;

Y is —(CR$^7$R$^8$)$_n$ wherein n is 0, 1, 2 or 3;

each $R^7$ or $R^8$ is independently selected from H, $C_1$-$C_6$ alkyl, $C_1$-$C_6$ alkylOH, $C_1$-$C_3$ alkyl-O-heteroaryl, $C_1$-$C_3$ alkyl-O-heterocyclyl, $C_1$-$C_3$ alkyl-O-aryl, $C_1$-$C_3$ alkylNH$_2$; or one $R^7$ or $R^8$ group combines with the $R^6$ group to form a nitrogen containing heterocyclic group; or one $R^7$ group combines with an another $R^7$ or $R^8$ group to form an optionally substituted monocyclic or bicyclic ring system having from 4 to 10 carbon atoms in the ring;

each $R^9$ and $R^{10}$ is independently H, $C_1$-$C_6$ alkyl, $C_3$-$C_8$ cycloalkyl, or heterocyclic, wherein the alkyl, cycloalkyl or heterocyclic group is optionally substituted with one or two groups independently selected from the group consisting of halo, $C_1$-$C_6$ alkyl, $C_1$-$C_6$ haloalkyl, $C_1$-$C_6$ alkylOH, $C_3$-$C_8$ cycloalkyl, —OR$^{12}$, —NR$^{13}$R$^{14}$, —C(O)NR$^{13}$R$^{14}$, —NR$^{13}$COR$^{14}$, —SO$_2$NR$^{13}$R$^{14}$, —NR$^{13}$SO$_2$R$^{14}$, —NR$^{12}$SO$_2$NR$^{13}$R$^{14}$, —NR$^{12}$C(O)NR$^{13}$R$^{14}$, —NR$^{13}$CO$_2$R$^{14}$, and —OC(O)NR$^{13}$R$^{14}$; or $R^9$ and $R^{10}$ together with the nitrogen atom to which they are attached form a mono, bicyclic bridged or spirocyclic heterocyclic ring optionally substituted with one or two groups independently selected from the group consisting of halo, —OH, —NH$_2$, —NH—$C_1$-$C_6$ alkyl, —$C_1$-$C_6$ alkyl, —$C_1$-$C_6$ alkylOH, $C_3$-$C_8$ cycloalkyl, aryl, and heterocyclic; wherein the cycloalkyl, aryl or heterocyclic group is optionally substituted with halo, —OH, —NH$_2$, —NH—$C_1$-$C_6$ alkyl, —$C_1$-$C_6$ alkyl, and —$C_1$-$C_6$ alkylOH; or $R^9$ and/or $R^{10}$ combines with Y to form a monocyclic, bicyclic, bridged or spirocyclic nitrogen containing heterocycle optionally substituted with one or two groups independently selected from the group consisting of —$C_1$-$C_6$ alkyl, —$C_1$-$C_6$ alkylOH, $C_3$-$C_8$ cycloalkyl, —OH, —NH$_2$, and —NH—$C_1$-$C_6$ alkyl;

each $R^{12}$, $R^{13}$ and $R^{14}$ is independently H, $C_1$-$C_6$ alkyl, $C_3$-$C_8$ cycloalkyl, or heterocyclic, wherein the $C_1$-$C_6$ alkyl, $C_3$-$C_8$ cycloalkyl group, or heterocyclic, is optionally substituted with one or two groups independently selected from the group consisting of —OH, —NH$_2$, —N(CH$_3$)$_2$, C$_1$-C$_6$ haloalkyl; or R$^{13}$ and R$^{14}$ together with the atom to which they are attached form a heterocyclic ring;

or a pharmaceutically acceptable salt, stereoisomer or mixture of stereoisomer thereof.

14. The compound according to claim 13 wherein:

R$^4$ is H, NR$^a$R$^b$, —OC$_2$-C$_6$ alkylNR$^a$R$^b$, C$_1$-C$_6$ alkylNR$^a$R$^b$, —C(O)NR$^a$R$^b$, or NR$^a$C(O)NR$^a$R$^b$;

R$^a$ and R$^b$ are each independently H, OH, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —C(O)C$_1$-C$_6$ alkyl, —C(O)OC$_1$-C$_6$ alkyl, C$_0$-C$_3$ alkylNR$^c$R$^d$, C$_1$-C$_3$alkylC(O)NH$_2$, C$_1$-C$_3$alkylC(O)NHC$_1$-C$_3$alkyl, C$_1$-C$_6$ alkylC$_3$-C$_6$ cycloalkyl, SO$_2$C$_1$-C$_3$alkyl, SO$_2$C$_3$-C$_6$cycloalkyl, —C$_1$-C$_3$ alkylSO$_2$NR$^c$R$^d$, aryl, heteroaryl, heterocyclic, or C$_1$-C$_6$ alkylheterocyclic; wherein the cycloalkyl, aryl, heteroaryl or heterocyclic group is optionally substituted with one to four groups independently selected from —OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, C$_1$-C$_6$ alkyl-O—C$_1$-C$_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^c$R$^d$, —SO$_2$R$^c$, SO$_2$NR$^c$R$^d$ and C$_1$-C$_6$ alkyl-O—C$_1$-C$_6$ alkyl;

R$^c$ and R$^d$ are independently selected from H, C$_1$-C$_6$ alkyl, C$_3$-C$_8$ cycloalkyl, C$_2$-C$_6$ haloalkyl, C$_2$-C$_6$ alkylOH, C$_1$-C$_6$ alkylC$_3$-C$_6$ cycloalkyl, SO$_2$C$_1$-C$_6$ alkyl, and C$_1$-C$_6$ alkyl-O—C$_1$-C$_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^e$R$^f$, —SO$_2$R$^e$, SO$_2$NR$^e$R$^f$ and C$_1$-C$_6$ alkyl-O—C$_1$-C$_6$ alkyl;

R$^e$ and R$^f$ are at each occurrence independently selected from the group consisting of: C$_1$-C$_6$ alkyl, C$_3$-C$_8$ cycloalkyl, C$_2$-C$_6$ haloalkyl, C$_1$-C$_6$ haloalkyl, —OC$_1$-C$_6$ haloalkyl, and C$_1$-C$_6$ alkylOH;

R$^6$ is H, C$_1$-C$_6$ alkyl, or C$_3$-C$_8$ cycloalkyl; or R$^6$ combines with Y, R$^9$, or R$^{10}$ to form an optionally substituted 4-8 membered nitrogen containing heterocyclic group.

15. The compound according to claim 13 wherein:

R$^4$ is H, NR$^a$R$^b$, C$_1$-C$_6$ alkylNR$^a$R$^b$, —C(O)NR$^a$R$^b$, or NR$^a$C(O)NR$^a$R$^b$;

R$^a$ and R$^b$ are each independently H, OH, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —C(O)C$_1$-C$_6$ alkyl, —C(O)OC$_1$-C$_6$ alkyl, C$_0$-C$_3$ alkylNR$^c$R$^d$, C$_1$-C$_3$alkylC(O)NH$_2$, C$_1$-C$_3$alkylC(O)NHC$_1$-C$_3$alkyl, C$_1$-C$_6$ alkylC$_3$-C$_6$ cycloalkyl, SO$_2$C$_1$-C$_3$alkyl, SO$_2$C$_3$-C$_6$cycloalkyl, —C$_1$-C$_3$ alkylSO$_2$NR$^c$R$^d$, aryl, heteroaryl, heterocyclic, or C$_1$-C$_6$ alkylheterocyclic; wherein the cycloalkyl, aryl, heteroaryl or heterocyclic group is optionally substituted with one to four groups independently selected from —OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, C$_1$-C$_6$ alkyl-O—C$_1$-C$_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^c$R$^d$, —SO$_2$R$^c$, SO$_2$NR$^c$R$^d$ and C$_1$-C$_6$ alkyl-O—C$_1$-C$_6$ alkyl;

R$^c$ and R$^d$ are independently selected from H, C$_1$-C$_6$ alkyl, C$_3$-C$_8$ cycloalkyl, C$_2$-C$_6$ haloalkyl, C$_2$-C$_6$ alkylOH, C$_1$-C$_6$ alkylC$_3$-C$_6$ cycloalkyl, SO$_2$C$_1$-C$_6$ alkyl, and C$_1$-C$_6$ alkyl-O—C$_1$-C$_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^e$R$^f$, —SO$_2$R$^e$, SO$_2$NR$^e$R$^f$ and C$_1$-C$_6$ alkyl-O—C$_1$-C$_6$ alkyl;

R$^e$ and R$^f$ are at each occurrence independently selected from the group consisting of: C$_1$-C$_6$ alkyl, C$_3$-C$_8$ cycloalkyl, C$_2$-C$_6$ haloalkyl, C$_1$-C$_6$ haloalkyl, —OC$_1$-C$_6$ haloalkyl, and C$_1$-C$_6$ alkylOH; and R$^6$ is H.

16. The compound of claim 13 wherein:

R$^4$ is NR$^a$R$^b$, C$_1$-C$_6$ alkylNR$^a$R$^b$, —C(O)NR$^a$R$^b$, or NR$^a$C(O)NR$^a$R$^b$;

R$^a$ and R$^b$ are each independently H, OH, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, —C(O)C$_1$-C$_6$ alkyl, —C(O)OC$_1$-C$_6$ alkyl, C$_0$-C$_3$ alkylNR$^c$R$^d$, C$_1$-C$_3$alkylC(O)NH$_2$, C$_1$-C$_3$alkylC(O)NHC$_1$-C$_3$alkyl, C$_1$-C$_6$ alkylC$_3$-C$_6$ cycloalkyl, SO$_2$C$_1$-C$_3$alkyl, SO$_2$C$_3$-C$_6$cycloalkyl, —C$_1$-C$_3$ alkylSO$_2$NR$^c$R$^d$, aryl, heteroaryl, heterocyclic, or C$_1$-C$_6$ alkylheterocyclic; wherein the cycloalkyl, aryl, heteroaryl or heterocyclic group is optionally substituted with one to four groups independently selected from —OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, C$_1$-C$_6$ alkyl-O—C$_1$-C$_6$ alkyl, and heterocyclyl; or R$^a$ and R$^b$ combine with a nitrogen atom to which they are attached to form a mono, bicyclic, bridged, or spirocyclic heterocyclic group optionally substituted with one to four groups independently selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^c$R$^d$, —SO$_2$R$^c$, SO$_2$NR$^c$R$^d$ and C$_1$-C$_6$ alkyl-O—C$_1$-C$_6$ alkyl;

R$^c$ and R$^d$ are independently selected from H, C$_1$-C$_6$ alkyl, C$_3$-C$_8$ cycloalkyl, C$_2$-C$_6$ haloalkyl, C$_2$-C$_6$ alkylOH, C$_1$-C$_6$ alkylC$_3$-C$_6$ cycloalkyl, SO$_2$C$_1$-C$_6$ alkyl, and C$_1$-C$_6$ alkyl-O—C$_1$-C$_6$ alkyl; or R$^c$ and R$^d$ combine to form mono, bicyclic, bridged or spirocyclic heterocyclic group optionally substituted with a group selected from OH, oxo, halo, cyano, NH$_2$, NHC$_1$-C$_3$ alkyl, C$_1$-C$_6$ alkyl, C$_3$-C$_8$ cycloalkyl, C$_1$-C$_6$ haloalkyl, C$_1$-C$_6$ alkylOH, C$_1$-C$_6$ alkoxy, C$_1$-C$_6$ alkylC$_3$-C$_6$ cycloalkyl, —C(O)NR$^e$R$^f$, —SO$_2$R$^e$, SO$_2$NR$^e$R$^f$ and C$_1$-C$_6$ alkyl-O—C$_1$-C$_6$ alkyl;

R$^e$ and R$^f$ are at each occurrence independently selected from the group consisting of: C$_1$-C$_6$ alkyl, C$_3$-C$_8$ cycloalkyl, C$_2$-C$_6$ haloalkyl, C$_1$-C$_6$ haloalkyl, —OC$_1$-C$_6$ haloalkyl, and C$_1$-C$_6$ alkylOH; and R$^6$ is H.

17. The compound of claim 13 wherein $R^6$ is H, halo, —$OR^9$, or —$NR^{10}R^{11}$.

18. The compound of claim 13 wherein $R^6$ is H.

19. A compound selected from the group consisting of:
(S)—N-(2-(diethylamino)propyl)-2-(5-(isothiazol-5-yl)pyrazolo[1,5-a]pyrimidin-3-yl)-6-(3-methoxyazetidin-1-yl)isonicotinamide, or
N—((S)-2-(diethylamino)propyl)-2-(5-(isothiazol-5-yl)pyrazolo[1,5-a]pyrimidin-3-yl)-6-((S)-2-(methylcarbamoyl)azetidin-1-yl)isonicotinamide, or a pharmaceutically or a pharmaceutically acceptable salt, stereoisomer or mixture of stereoisomer thereof.

20. The compound of claim 1 wherein $R^4$ is H, chloro,

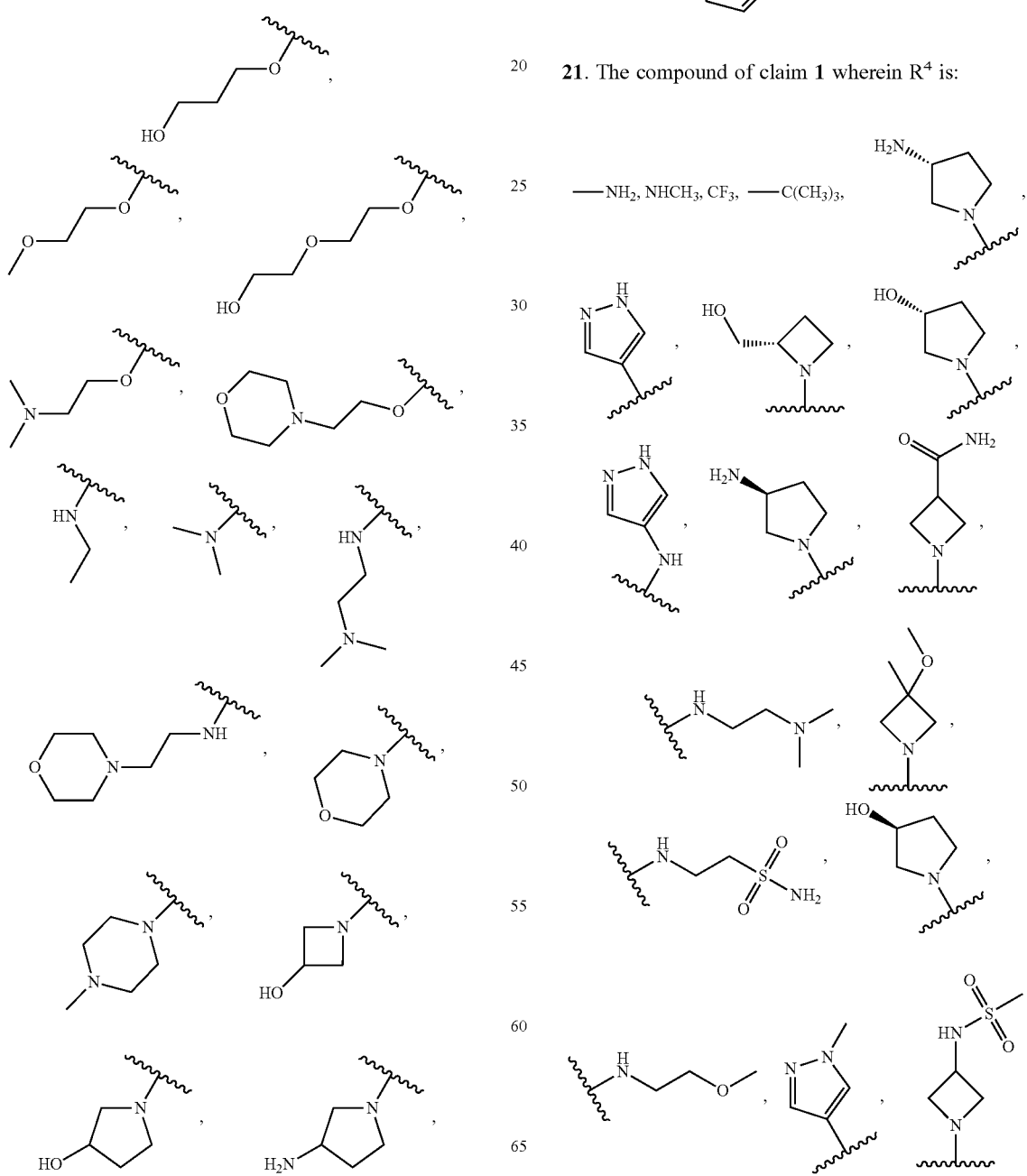

21. The compound of claim 1 wherein $R^4$ is:

—$NH_2$, $NHCH_3$, $CF_3$, —$C(CH_3)_3$,

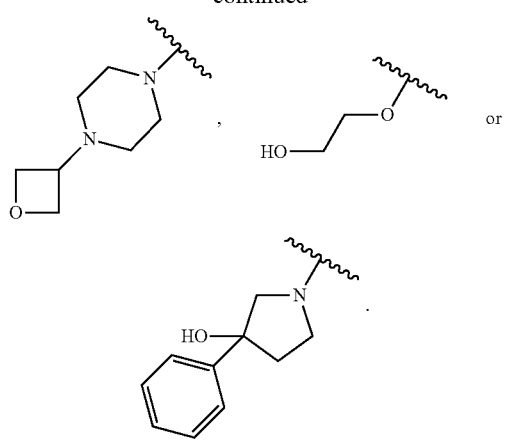

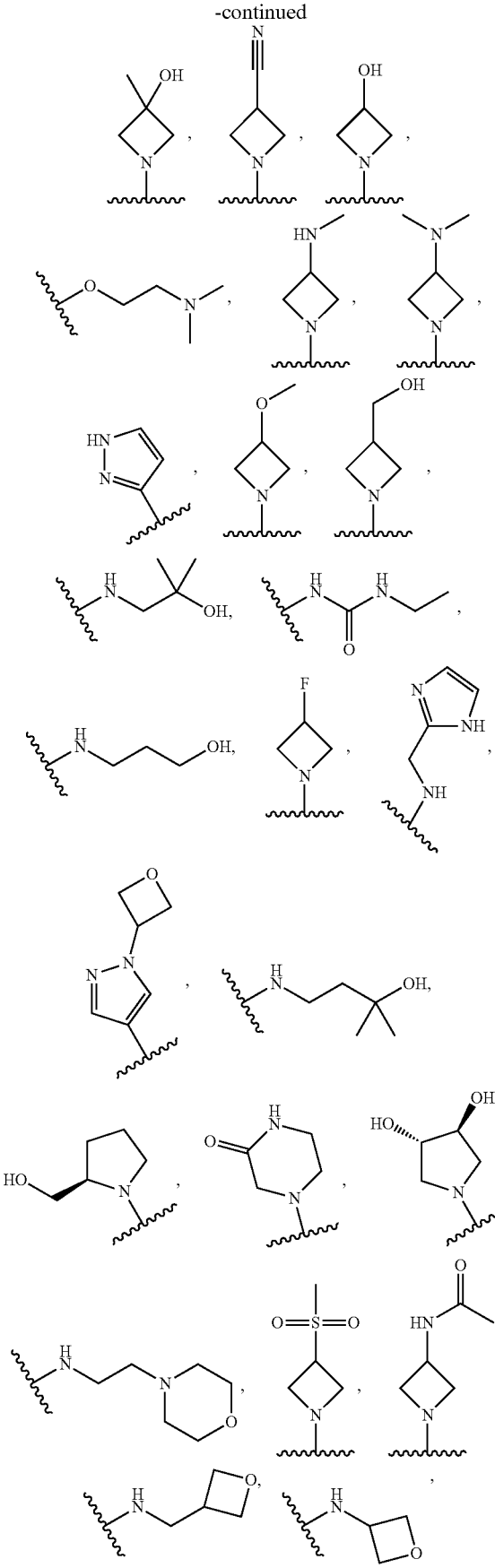
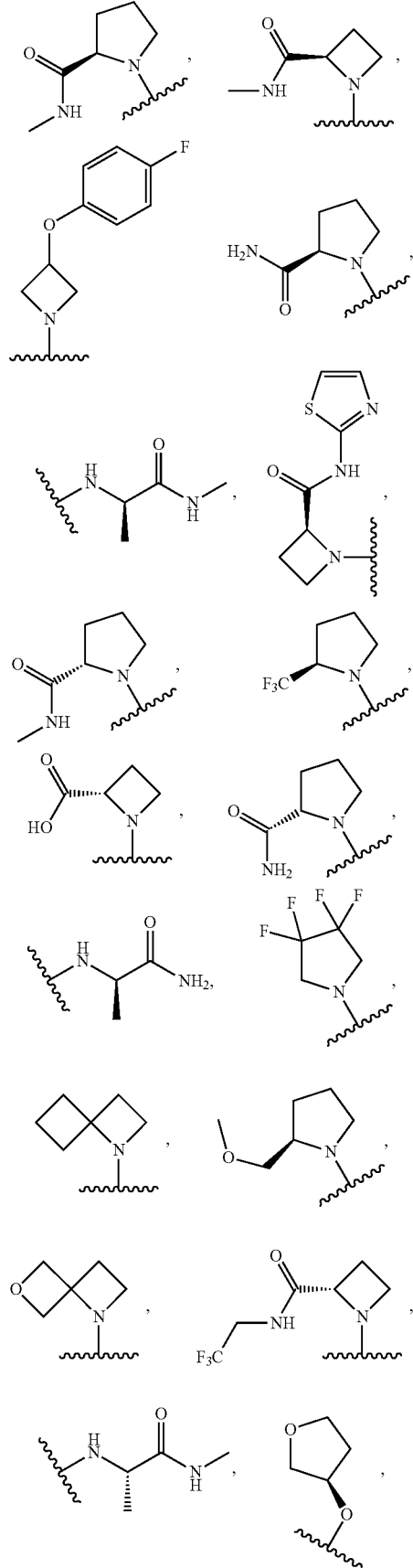

-continued

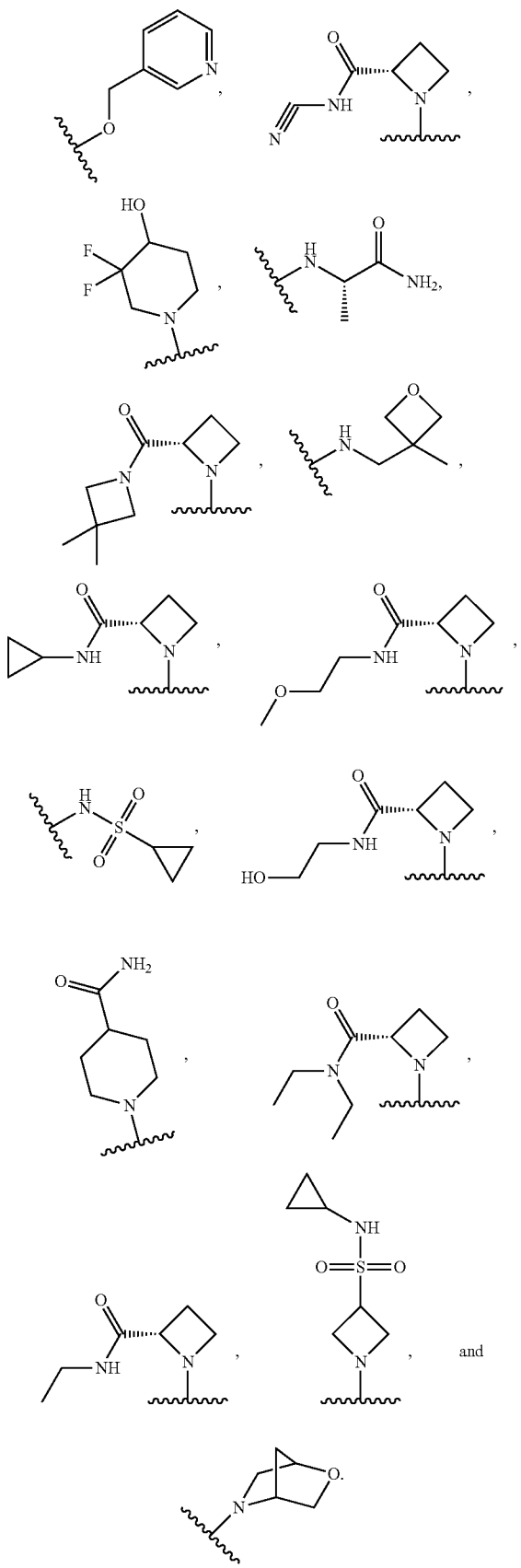

22. A compound of formula (V):

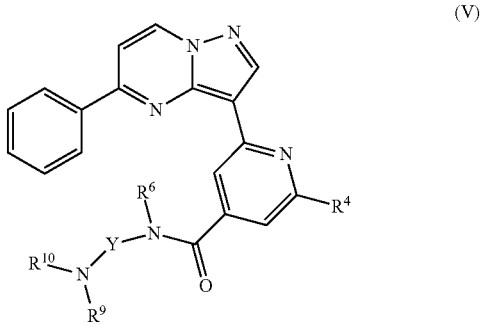

(V)

wherein:

$R^4$ is H, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ haloalkoxy, $C_1$-$C_6$ alkyl$C_3$-$C_6$ cycloalkyl, —NR$^a$R$^b$, $C_1$-$C_6$ alkylNR$^a$R$^b$, $C_1$-$C_6$alkyl-O—$C_1$-$C_6$ alkylNR$^a$R$^b$, —OC$_2$-$C_6$ alkylNR$^a$R$^b$, —C(O)NR$^a$R$^b$, —NR$^a$C(O)NR$^a$R$^b$, —NR$^a$C(O)R$^a$, —NR$^a$C(O)OR$^a$, aryl, heteroaryl, mono, bicyclic, bridged or spirocyclic carbocyclic or heterocyclic group, —O—$C_0$-$C_3$ alkylheterocyclyl, or $C_1$-$C_6$ alkylheterocyclic; wherein the alkyl, cycloalkyl, aryl, heteroaryl, carbocyclic or heterocyclic group is optionally substituted with one to four groups independently selected from —OH, oxo, halo, cyano, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —OC$_1$-$C_6$ haloalkyl, $C_1$-$C_6$ alkyl $C_3$-$C_8$ cycloalkyl, $C_1$-$C_6$ alkyl-O—$C_1$-$C_6$ alkyl, $C_0$-$C_3$ alkylNR$^a$CHR$^a$C(O)NHR$^a$, —C(O)R$^a$, —COOR$^a$, —NHC(O)NHR$^a$, —NHC(O)R$^a$, —NHC(O)OR$^a$, C(O)NR$^a$R$^b$, —NR$^a$R$^b$, —NHC$_1$-C$_3$alkylNR$^a$R$^b$, SO$_2$R$^a$, —NHSO$_2$R$^a$, SO$_2$NR$^a$R$^b$, aryl, heteroaryl, mono, bicyclic, bridged or spirocyclic carbocyclic or heterocyclic group, and $C_1$-$C_6$ alkylheterocyclic; or two substituents on the aryl, heteroaryl, mono, bicyclic, bridged or spirocyclic carbocyclic or heterocyclic group combines to form a mono, bicyclic, bridged or spirocyclic carbocyclic or heterocyclic ring; wherein said heteroaryl, mono, bicyclic, bridged or spirocyclic carbocyclic or heterocyclic ring is optionally substituted with one to four groups independently selected from the group consisting of OH, oxo, halo, cyano, $C_1$-$C_6$ alkyl, $C_3$-$C_8$ cycloalkyl, $C_1$-$C_6$ haloalkyl, $C_1$-$C_6$ alkylOH, —OC$_1$-$C_6$ alkyl, —OC$_1$-$C_6$ haloalkyl, $C_1$-$C_6$ alkyl $C_3$-$C_6$ cycloalkyl, $C_1$-$C_6$ alkyl-O—$C_1$-$C_6$ alkyl, $C_0$-$C_3$ alkylNR$^a$CHR$^a$C(O)NHR$^a$, C(O)NR$^a$R$^b$, —SO$_2$R$^a$, and SO$_2$NR$^a$R$^b$;

$R^a$ and $R^b$ are each independently H, OH, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, —C(O)C$_1$-$C_6$ alkyl, —C(O)OC$_1$-$C_6$ alkyl, $C_0$-$C_3$ alkylNR$^c$R$^d$, $C_1$-$C_3$alkylC(O)NH$_2$, $C_1$-$C_3$alkylC(O)NHC$_1$-$C_3$alkyl, $C_1$-$C_6$ alkylC$_3$-$C_6$ cycloalkyl, SO$_2$C$_1$-$C_3$alkyl, SO$_2$C$_3$-$C_6$cycloalkyl, aryl, heterocyclic, $C_1$-$C_6$ alkylheterocyclic, wherein the cycloalkyl, aryl or heterocyclic group is optionally substituted with one to four groups independently selected from —OH, oxo, halo, cyano, NH$_2$, NHC$_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkylC$_3$-$C_6$ cycloalkyl, $C_1$-$C_6$ alkyl-O—$C_1$-$C_6$ alkyl, and heterocyclyl; or $R^a$ and $R^b$ combine with a nitrogen atom to which they are attached to form a monocyclic, bicyclic, bridged or spirocyclic heterocyclic group optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^cR^d$, —$SO_2R^c$, $SO_2NR^cR^d$ and $C_1$-$C_6$ alkyl-O—$C_1$-$C_6$ alkyl;

$R^c$ and $R^d$ are independently selected from H, $C_1$-$C_6$ alkyl, $C_3$-$C_8$ cycloalkyl, $C_2$-$C_6$ haloalkyl, $C_2$-$C_6$ alkylOH, $C_1$-$C_6$ alkyl$C_3$-$C_6$ cycloalkyl, $SO_2C_1$-$C_6$ alkyl, and $C_1$-$C_6$ alkyl-O—$C_1$-$C_6$ alkyl; or $R^c$ and $R^d$ combine to form mono or bicyclic, bridged or spirocyclic heterocycle optionally substituted with a group selected from OH, oxo, halo, cyano, $NH_2$, $NHC_1$-$C_3$ alkyl, $C_1$-$C_6$ alkyl, $C_3$-$C_8$ cycloalkyl, $C_1$-$C_6$ haloalkyl, $C_1$-$C_6$ alkylOH, $C_1$-$C_6$ alkoxy, $C_1$-$C_6$ alkyl$C_3$-$C_6$ cycloalkyl, —C(O)$NR^eR^f$, —$SO_2R^e$, $SO_2NR^eR^f$ and $C_1$-$C_6$ alkyl-O—$C_1$-$C_6$ alkyl; wherein $R^e$ and $R^f$ are independently selected from $C_1$-$C_6$ alkyl, $C_1$-$C_6$ alkylOH, and $C_1$-$C_6$ alkyl aryl;

$R^e$ and $R^f$ are at each occurrence independently selected from the group consisting of: $C_1$-$C_6$ alkyl, $C_3$-$C_8$ cycloalkyl, $C_2$-$C_6$ haloalkyl, $C_1$-$C_6$ haloalkyl, —$OC_1$-$C_6$ haloalkyl, and $C_1$-$C_6$ alkylOH;

$R^6$ is H, $C_1$-$C_6$ alkyl, $C_3$-$C_8$ cycloalkyl, $C_1$-$C_6$ haloalkyl, $C_1$-$C_6$ alkyl-OH, or $C_1$-$C_6$ alkoxy; or $R^6$ combines with Y to form a 4-8 membered nitrogen containing heterocyclic group;

Y is —$(CR^7R^8)_n$ wherein n is 2 or 3;

each $R^7$ or $R^8$ is independently selected from H, $C_1$-$C_6$ alkyl, $C_1$-$C_6$ alkylOH, $C_1$-$C_3$ alkyl-O-heteroaryl, $C_1$-$C_3$ alkyl-O-heterocyclyl, $C_1$-$C_3$ alkyl-O-aryl, $C_1$-$C_3$ alkyl$NH_2$; or one $R^7$ or $R^8$ group combines with the $R^6$ group to form a nitrogen containing heterocyclic group; or one $R^7$ group combines with an another $R^7$ or $R^8$ group to form an optionally substituted monocyclic or bicyclic ring system having from 4 to 10 carbon atoms in the ring;

each $R^9$ and $R^{10}$ is independently H, $C_1$-$C_6$ alkyl, $C_3$-$C_8$ cycloalkyl, or heterocyclic, wherein the alkyl, cycloalkyl or heterocyclic group is optionally substituted with one or two groups independently selected from the group consisting of halo, $C_1$-$C_6$ alkyl, $C_1$-$C_6$ haloalkyl, $C_1$-$C_6$ alkylOH, $C_3$-$C_8$ cycloalkyl, —$OR^{12}$, —$NR^{13}R^{14}$, —C(O)$NR^{13}R^{14}$, —$NR^{13}COR^{14}$, —$SO_2NR^{13}R^{14}$, —$NR^{13}SO_2R^{14}$, —$NR^{12}SO_2NR^{13}R^{14}$, —$NR^{12}C(O)NR^{13}R^{14}$, —$NR^{13}CO_2R^{14}$, and —OC(O)$NR^{13}R^{14}$; or $R^9$ and $R^{10}$ together with the nitrogen atom to which they are attached form a mono, bicyclic bridged or spirocyclic heterocyclic ring optionally substituted with one or two groups independently selected from the group consisting of halo, —OH, —$NH_2$, —NH—$C_1$-$C_6$ alkyl, —$C_1$-$C_6$ alkyl, —$C_1$-$C_6$ alkylOH, $C_3$-$C_8$ cycloalkyl, aryl, and heterocyclic; wherein the cycloalkyl, aryl or heterocyclic group is optionally substituted with halo, —OH, —$NH_2$, —NH—$C_1$-$C_6$ alkyl, —$C_1$-$C_6$ alkyl, and —$C_1$-$C_6$ alkylOH; or $R^9$ and/or $R^{10}$ combines with Y to form a monocyclic, bicyclic, bridged or spirocyclic nitrogen containing heterocycle optionally substituted with one or two groups independently selected from the group consisting of —$C_1$-$C_6$ alkyl, —$C_1$-$C_6$ alkylOH, $C_3$-$C_8$ cycloalkyl, —OH, —$NH_2$, and —NH—$C_1$-$C_6$ alkyl;

each $R^{12}$, $R^{13}$ and $R^{14}$ is independently H, $C_1$-$C_6$ alkyl, $C_3$-$C_8$ cycloalkyl, or heterocyclic, wherein the $C_1$-$C_6$ alkyl, $C_3$-$C_8$ cycloalkyl group, or heterocyclic, is optionally substituted with one or two groups independently selected from the group consisting of —OH, —$NH_2$, —$N(CH_3)_2$, $C_1$-$C_6$ haloalkyl; or $R^{13}$ and $R^{14}$ together with the atom to which they are attached form a heterocyclic ring;

or a pharmaceutically acceptable salt, stereoisomer or mixture of stereoisomer thereof.

23. The compound of claim 22 wherein $R^6$ is H, halo, —$OR^9$, or —$NR^{10}R^{11}$.

24. The compound of claim 22 wherein $R^6$ is H.

25. A compound selected from the group consisting of:
N-(2-(diethylamino)propyl)-2-(5-phenylpyrazolo[1,5-a]pyrimidin-3-yl)isonicotinamide,
(S)—N-(2-(diethylamino)propyl)-2-(5-phenylpyrazolo[1,5-a]pyrimidin-3-yl)isonicotinamide,
N-(2-(dimethylamino)ethyl)-2-(5-phenylpyrazolo[1,5-a]pyrimidin-3-yl)isonicotinamide,
2-(5-phenylpyrazolo[1,5-a]pyrimidin-3-yl)-N-(piperidin-2-ylmethyl)isonicotinamide,
N-((3,3-dimethylazetidin-2-yl)methyl)-2-(5-phenylpyrazolo[1,5-a]pyrimidin-3-yl)isonicotinamide,
(S)—N-(2-(ethylamino)propyl)-2-(5-phenylpyrazolo[1,5-a]pyrimidin-3-yl)isonicotinamide,
(R)—N-((2-ethylpyrrolidin-2-yl)methyl)-2-(5-phenylpyrazolo[1,5-a]pyrimidin-3-yl)isonicotinamide,
(S)—N-(2-aminopropyl)-2-(5-phenylpyrazolo[1,5-a]pyrimidin-3-yl)isonicotinamide,
N-((2S)-2-(sec-butylamino)propyl)-2-(5-phenylpyrazolo[1,5-a]pyrimidin-3-yl)isonicotinamide,
N-(2-aminobutyl)-2-(5-phenylpyrazolo[1,5-a]pyrimidin-3-yl)isonicotinamide,
N-(2-amino-3-methylbutyl)-2-(5-phenylpyrazolo[1,5-a]pyrimidin-3-yl)isonicotinamide,
N-(2-aminopentyl)-2-(5-phenylpyrazolo[1,5-a]pyrimidin-3-yl)isonicotinamide,
(S)-2-(5-phenylpyrazolo[1,5-a]pyrimidin-3-yl)-N-(2-((pyrimidin-2-ylmethyl)amino)propyl)isonicotinamide,
N-(2-((cyclopropylmethyl)amino)butyl)-2-(5-phenylpyrazolo[1,5-a]pyrimidin-3-yl)isonicotinamide,
2-(5-phenylpyrazolo[1,5-a]pyrimidin-3-yl)-N-(2-(propylamino)butyl)isonicotinamide,
N-(2-((cyclopropylmethyl)amino)-3-methylbutyl)-2-(5-phenylpyrazolo[1,5-a]pyrimidin-3-yl)isonicotinamide,
N-(3-methyl-2-(propylamino)butyl)-2-(5-phenylpyrazolo[1,5-a]pyrimidin-3-yl)isonicotinamide,
N-(2-(ethylamino)butyl)-2-(5-phenylpyrazolo[1,5-a]pyrimidin-3-yl)isonicotinamide,
N-(2-(ethylamino)-3-methylbutyl)-2-(5-phenylpyrazolo[1,5-a]pyrimidin-3-yl)isonicotinamide,
N-((1S,2S)-2-aminocyclopentyl)-2-(5-phenylpyrazolo[1,5-a]pyrimidin-3-yl)isonicotinamide,
(R)—N-(2-amino-3-hydroxypropyl)-2-(5-phenylpyrazolo[1,5-a]pyrimidin-3-yl)isonicotinamide,
(R)—N-(2-(diethylamino)-3-hydroxypropyl)-2-(5-phenylpyrazolo[1,5-a]pyrimidin-3-yl)isonicotinamide,
(R)—N-(2-(ethylamino)-3-hydroxypropyl)-2-(5-phenylpyrazolo[1,5-a]pyrimidin-3-yl)isonicotinamide,
N-(2-(diethylamino)pentyl)-2-(5-phenylpyrazolo[1,5-a]pyrimidin-3-yl)isonicotinamide,
N-(2-(diethylamino)-3-methylbutyl)-2-(5-phenylpyrazolo[1,5-a]pyrimidin-3-yl)isonicotinamide,
N-(1-aminopropan-2-yl)-2-(5-phenylpyrazolo[1,5-a]pyrimidin-3-yl)isonicotinamide,
N-((1R,2S)-2-aminocyclopentyl)-2-(5-phenylpyrazolo[1,5-a]pyrimidin-3-yl)isonicotinamide,
N-(2-amino-2-methylpropyl)-2-(5-phenylpyrazolo[1,5-a]pyrimidin-3-yl)isonicotinamide, N-(2-aminoethyl)-N-ethyl-2-(5-phenylpyrazolo[1,5-a]pyrimidin-3-yl)isonicotinamide,
(R)—N-(2-amino-3-(pyrimidin-2-yloxy)propyl)-2-(5-phenylpyrazolo[1,5-a]pyrimidin-3-yl)isonicotinamide,
N-(2-(ethylamino)-2-methylpropyl)-2-(5-phenylpyrazolo[1,5-a]pyrimidin-3-yl)isonicotinamide,
(2-(5-phenylpyrazolo[1,5-a]pyrimidin-3-yl)pyridin-4-yl)(1,8-diazaspiro[5.5]undecan-1-yl)methanone,
(R)—N-(2-(ethylamino)-3-(pyrimidin-2-yloxy)propyl)-2-(5-phenylpyrazolo[1,5-a]pyrimidin-3-yl)isonicotinamide,
(R)—N-(2-(diethylamino)-3-(pyrimidin-2-yloxy)propyl)-2-(5-phenylpyrazolo[1,5-a]pyrimidin-3-yl)isonicotinamide,
N-((1R,2R)-2-aminocyclopentyl)-2-(5-phenylpyrazolo[1,5-a]pyrimidin-3-yl)isonicotinamide,
N-((1S,2R)-2-aminocyclopentyl)-2-(5-phenylpyrazolo[1,5-a]pyrimidin-3-yl)isonicotinamide,
N-(2-(isopropylamino)-3-methylbutyl)-2-(5-phenylpyrazolo[1,5-a]pyrimidin-3-yl)isonicotinamide,
(R)—N-(2-(ethylamino)propyl)-2-(5-phenylpyrazolo[1,5-a]pyrimidin-3-yl)isonicotinamide,
(S)—N-((2-ethylpyrrolidin-2-yl)methyl)-2-(5-phenylpyrazolo[1,5-a]pyrimidin-3-yl)isonicotinamide,
(S)-(3-aminopyrrolidin-1-yl)(2-(5-phenylpyrazolo[1,5-a]pyrimidin-3-yl)pyridin-4-yl)methanone,
((1S,5R,6S)-6-amino-8-azabicyclo[3.2.1]octan-8-yl)(2-(5-phenylpyrazolo[1,5-a]pyrimidin-3-yl)pyridin-4-yl)methanone,
(2-(5-phenylpyrazolo[1,5-a]pyrimidin-3-yl)pyridin-4-yl)(2,6-diazaspiro[4.5]decan-6-yl)methanone,
((S)-2-((S)-1-aminoethyl)piperidin-1-yl)(2-(5-phenylpyrazolo[1,5-a]pyrimidin-3-yl)pyridin-4-yl)methanone,
((1S,6R)-3,10-diazabicyclo[4.3.1]decan-10-yl)(2-(5-phenylpyrazolo[1,5-a]pyrimidin-3-yl)pyridin-4-yl)methanone,
(hexahydropyrrolo[3,4-b]pyrrol-1(2H)-yl)(2-(5-phenylpyrazolo[1,5-a]pyrimidin-3-yl)pyridin-4-yl)methanone,
(2-(5-phenylpyrazolo[1,5-a]pyrimidin-3-yl)pyridin-4-yl)((R)-2-((S)-pyrrolidin-2-yl)piperidin-1-yl)methanone,
((4aR,7S,7aR)-7-aminooctahydro-1H-cyclopenta[b]pyridin-1-yl)(2-(5-phenylpyrazolo[1,5-a]pyrimidin-3-yl)pyridin-4-yl)methanone,
(octahydro-1H-pyrrolo[2,3-c]pyridin-1-yl)(2-(5-phenylpyrazolo[1,5-a]pyrimidin-3-yl)pyridin-4-yl)methanone,
((4aR,7R,7aR)-7-aminooctahydro-1H-cyclopenta[b]pyridin-1-yl)(2-(5-phenylpyrazolo[1,5-a]pyrimidin-3-yl)pyridin-4-yl)methanone,
(2-(5-phenylpyrazolo[1,5-a]pyrimidin-3-yl)pyridin-4-yl)(1,7-diazaspiro[4.5]decan-1-yl)methanone,
((4aS,8R,8aR)-8-aminooctahydroquinolin-1(2H)-yl)(2-(5-phenylpyrazolo[1,5-a]pyrimidin-3-yl)pyridin-4-yl)methanone,
((4aS,7S,7aS)-7-aminooctahydro-1H-cyclopenta[b]pyridin-1-yl)(2-(5-phenylpyrazolo[1,5-a]pyrimidin-3-yl)pyridin-4-yl)methanone,
((1R,5S)-3,8-diazabicyclo[3.2.1]octan-3-yl)(2-(5-phenylpyrazolo[1,5-a]pyrimidin-3-yl)pyridin-4-yl)methanone,
(S)-2-amino-N-(2-(diethylamino)propyl)-6-(5-phenylpyrazolo[1,5-a]pyrimidin-3-yl)isonicotinamide,
(R)-(2-(aminomethyl)piperidin-1-yl)(2-methyl-6-(5-phenylpyrazolo[1,5-a]pyrimidin-3-yl)pyridin-4-yl)methanone,
(R)-(2-(aminomethyl)piperidin-1-yl)(2-(5-phenylpyrazolo[1,5-a]pyrimidin-3-yl)-6-(trifluoromethyl)pyridin-4-yl)methanone,
(R)-(2-(aminomethyl)piperidin-1-yl)(2-cyclopropyl-6-(5-phenylpyrazolo[1,5-a]pyrimidin-3-yl)pyridin-4-yl)methanone,
(R)-(2-(aminomethyl)piperidin-1-yl)(2-(dimethylamino)-6-(5-phenylpyrazolo[1,5-a]pyrimidin-3-yl)pyridin-4-yl)methanone,
(S)-2-ethyl-N-(2-(ethylamino)propyl)-6-(5-phenylpyrazolo[1,5-a]pyrimidin-3-yl)isonicotinamide,
(S)—N-(2-(ethylamino)propyl)-2-methyl-6-(5-phenylpyrazolo[1,5-a]pyrimidin-3-yl)isonicotinamide,
(S)-2-amino-N-(2-(ethylamino)propyl)-6-(5-phenylpyrazolo[1,5-a]pyrimidin-3-yl)isonicotinamide,
(S)—N-(2-(ethylamino)propyl)-2-isopropyl-6-(5-phenylpyrazolo[1,5-a]pyrimidin-3-yl)isonicotinamide,
(S)-2-cyclopropyl-N-(2-(ethylamino)propyl)-6-(5-phenylpyrazolo[1,5-a]pyrimidin-3-yl)isonicotinamide,
(S)-2-chloro-N-(2-(ethylamino)propyl)-6-(5-phenylpyrazolo[1,5-a]pyrimidin-3-yl)isonicotinamide,
(S)-(3-aminopyrrolidin-1-yl)(2-(dimethylamino)-6-(5-phenylpyrazolo[1,5-a]pyrimidin-3-yl)pyridin-4-yl)methanone,
(S)-(3-aminopyrrolidin-1-yl)(2-methoxy-6-(5-phenylpyrazolo[1,5-a]pyrimidin-3-yl)pyridin-4-yl)methanone,
(R)-(2-(aminomethyl)piperidin-1-yl)(2-chloro-6-(5-phenylpyrazolo[1,5-a]pyrimidin-3-yl)pyridin-4-yl)methanone,
(2-amino-6-(5-phenylpyrazolo[1,5-a]pyrimidin-3-yl)pyridin-4-yl)((1S,6R)-3,9-diazabicyclo[4.2.1]nonan-9-yl)methanone,
(R)-(2-(aminomethyl)piperidin-1-yl)(2-(tert-butyl)-6-(5-phenylpyrazolo[1,5-a]pyrimidin-3-yl)pyridin-4-yl)methanone,
(R)-(2-(aminomethyl)pyrrolidin-1-yl)(2-methyl-6-(5-phenylpyrazolo[1,5-a]pyrimidin-3-yl)pyridin-4-yl)methanone,
(R)-(2-(aminomethyl)piperidin-1-yl)(2-methoxy-6-(5-phenylpyrazolo[1,5-a]pyrimidin-3-yl)pyridin-4-yl)methanone,
(S)-(2-(aminomethyl)piperidin-1-yl)(2-chloro-6-(5-phenylpyrazolo[1,5-a]pyrimidin-3-yl)pyridin-4-yl)methanone,
(S)-(2-(aminomethyl)piperidin-1-yl)(2-methoxy-6-(5-phenylpyrazolo[1,5-a]pyrimidin-3-yl)pyridin-4-yl)methanone,
(S)-(2-(aminomethyl)piperidin-1-yl)(2-(dimethylamino)-6-(5-phenylpyrazolo[1,5-a]pyrimidin-3-yl)pyridin-4-yl)methanone,
(R)-(2-(aminomethyl)piperidin-1-yl)(5-methyl-2-(5-phenylpyrazolo[1,5-a]pyrimidin-3-yl)pyridin-4-yl)methanone,
(R)-(2-(aminomethyl)piperidin-1-yl)(5-chloro-2-(5-phenylpyrazolo[1,5-a]pyrimidin-3-yl)pyridin-4-yl)methanone,
(R)-(5-amino-2-(5-phenylpyrazolo[1,5-a]pyrimidin-3-yl)pyridin-4-yl)(2-(aminomethyl)piperidin-1-yl)methanone,
(R)-(2-(aminomethyl)piperidin-1-yl)(5-(methylamino)-2-(5-phenylpyrazolo[1,5-a]pyrimidin-3-yl)pyridin-4-yl)methanone,
((R)-2-((R)-1-aminoethyl)piperidin-1-yl)(5-methyl-2-(5-phenylpyrazolo[1,5-a]pyrimidin-3-yl)pyridin-4-yl)methanone, (S)—N-(2-(diethylamino)propyl)-2-((2-(dimethylamino)ethyl)amino)-6-(5-phenylpyrazolo[1,5-a]pyrimidin-3-yl)isonicotinamide, N-((1-aminocyclobutyl)methyl)-2-(3-methoxyazetidin-1-yl)-6-(5-phenylpyrazolo[1,5-a]pyrimidin-3-yl)isonicotinamide, (S)—N-(2-(diethylamino)propyl)-2-(3-methoxyazetidin-1-yl)-6-(5-phenylpyrazolo[1,5-a]pyrimidin-3-yl)isonicotinamide, N-((hexahydro-1H-pyrrolizin-7a-yl)methyl)-2-(3-methoxyazetidin-1-yl)-6-(5-phenylpyrazolo[1,5-a]pyrimidin-3-yl)isonicotinamide, (S)—N-(2-aminopropyl)-2-(3-methoxyazetidin-1-yl)-6-(5-phenylpyrazolo[1,5-a]pyrimidin-3-yl)isonicotinamide, (S)—N-(2-(ethylamino)propyl)-2-(3-methoxyazetidin-1-yl)-6-(5-phenylpyrazolo[1,5-a]pyrimidin-3-yl)isonicotinamide, N—((S)-2-(diethylamino)propyl)-2-((S)-2-(methylcarbamoyl)azetidin-1-yl)-6-(5-phenylpyrazolo[1,5-a]pyrimidin-3-yl)isonicotinamide, (S)-(3-aminopyrrolidin-1-yl)(2-(3-methoxyazetidin-1-yl)-6-(5-phenylpyrazolo[1,5-a]pyrimidin-3-yl)pyridin-4-yl)methanone, ((1S,5S)-3,6-diazabicyclo[3.2.2]nonan-3-yl)(2-(3-methoxyazetidin-1-yl)-6-(5-phenylpyrazolo[1,5-a]pyrimidin-3-yl)pyridin-4-yl)methanone, and ((1S,6R)-3,9-diazabicyclo[4.2.1]nonan-9-yl)(2-(3-methoxyazetidin-1-yl)-6-(5-phenylpyrazolo[1,5-a]pyrimidin-3-yl)pyridin-4-yl)methanone, and a pharmaceutically acceptable salt, stereoisomer or mixture of stereoisomer thereof.

26. A compound selected from the group consisting of:

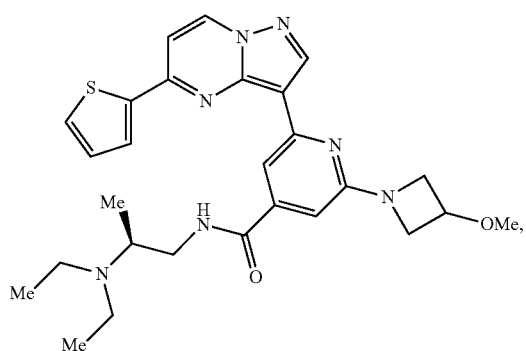

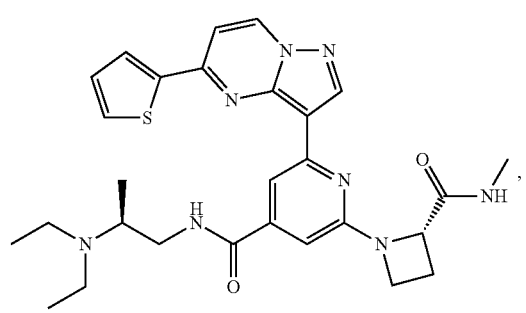

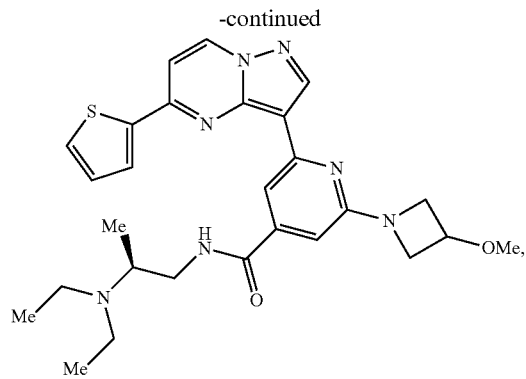

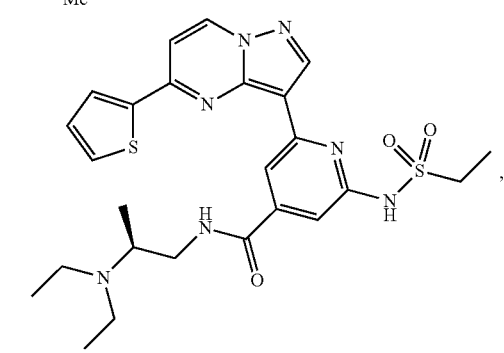

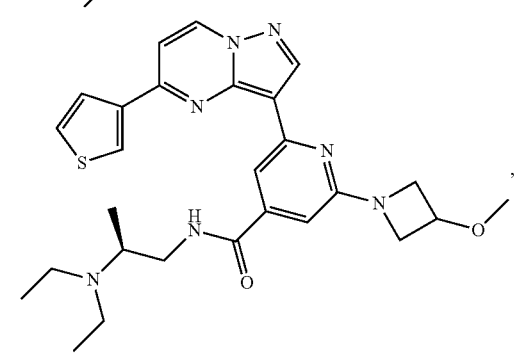

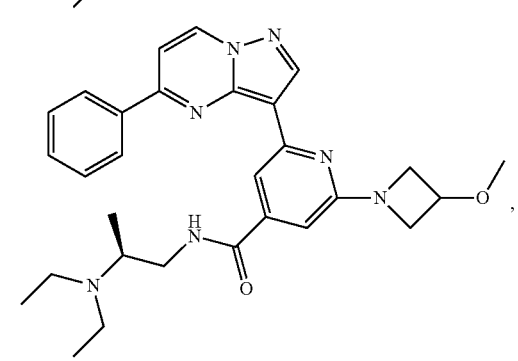

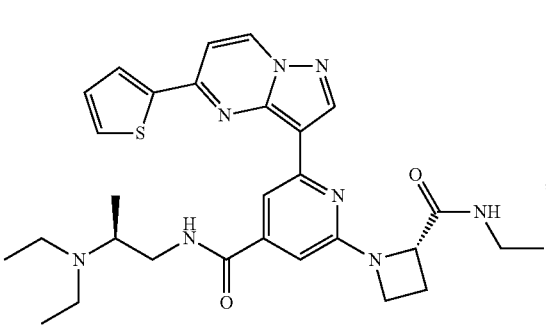

339
-continued
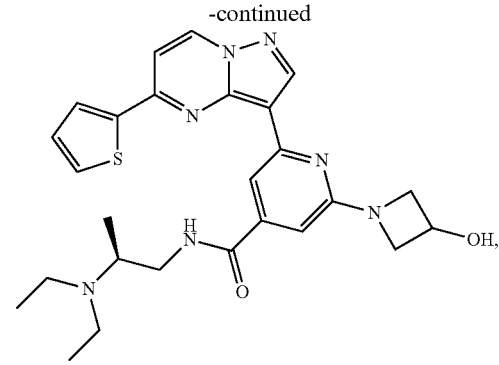
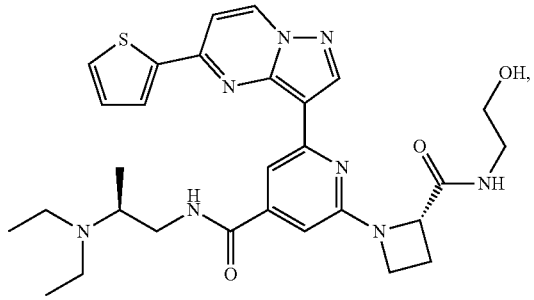
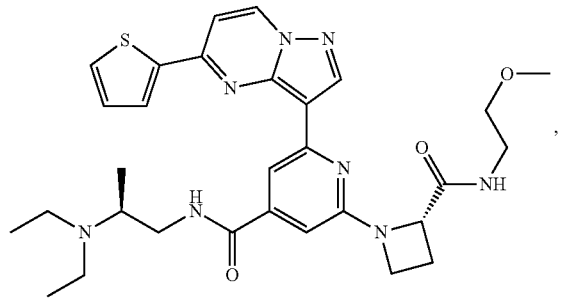
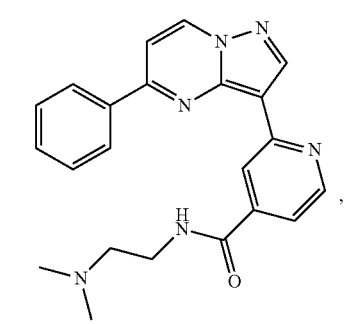
340
-continued
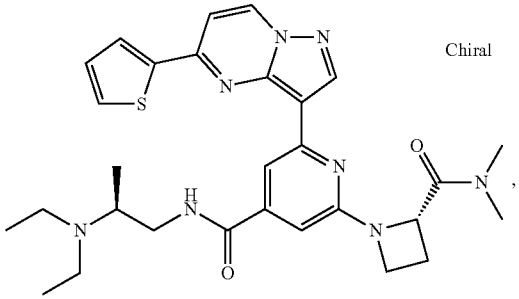
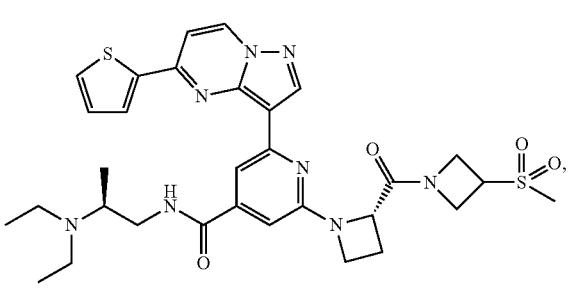
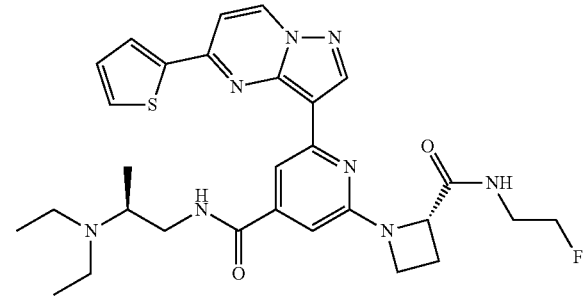
and
or a pharmaceutically acceptable salt, stereoisomer or mixture of stereoisomer thereof.
27. The compound
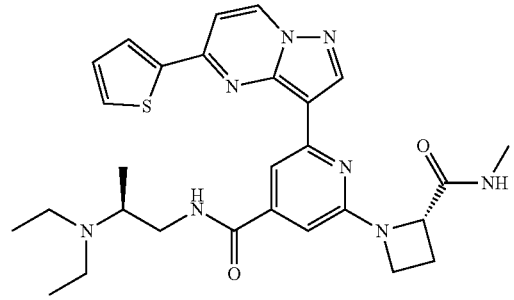 [SMILES: CCN(CC)[C@@H](C)CNC(=O)c1cc(-c2cnn3ccc(-c4cccs4)nc23)nc(N2CC[C@H]2C(=O)NC)c1]
or a pharmaceutically acceptable salt thereof.

28. The compound

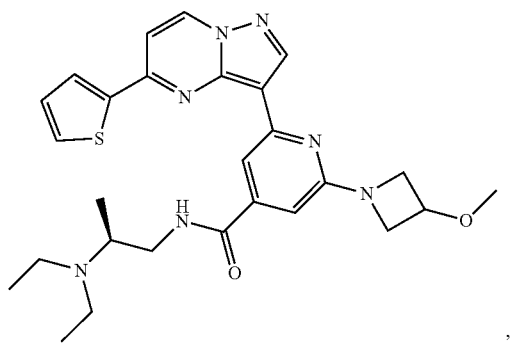 [SMILES: CCN(CC)[C@@H](C)CNC(=O)c1cc(-c2cnn3ccc(-c4cccs4)nc23)nc(N2CC(OC)C2)c1]

or a pharmaceutically acceptable salt thereof.

29. The compound

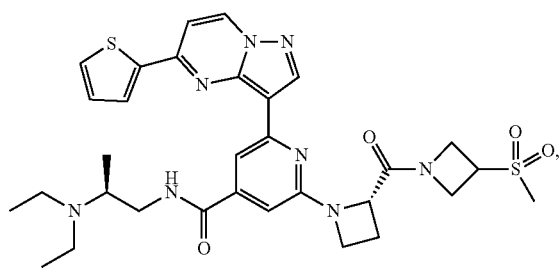 [SMILES: CCN(CC)[C@@H](C)CNC(=O)c1cc(-c2cnn3ccc(-c4cccs4)nc23)nc(N2CC[C@H]2C(=O)N2CC(S(C)(=O)=O)C2)c1]

or a pharmaceutically acceptable salt thereof.

30. The compound

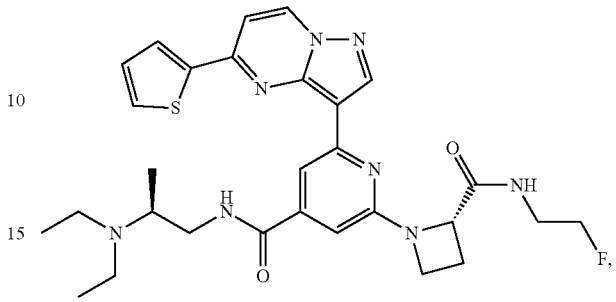

or a pharmaceutically acceptable salt thereof.

31. A pharmaceutical composition comprising a pharmaceutically acceptable excipient and a therapeutically effective amount of a compound of claim 1 or a pharmaceutically acceptable salt, thereof.

32. A method for treating arrhythmia in a human subject comprising administering a compound of claim 1 or the pharmaceutical acceptable salt or stereoisomer thereof.

33. A method for treating atrial fibrillation in a human subject comprising administering a compound of claim 1 or the pharmaceutical acceptable salt or stereoisomer thereof.

* * * * *